(12) United States Patent
Palmer et al.

(10) Patent No.: US 9,181,234 B2
(45) Date of Patent: Nov. 10, 2015

(54) ANTIBACTERIAL COMPOUNDS

(75) Inventors: James T Palmer, Notting Hill (AU); Christopher James Lunnis, Notting Hill (AU); Daniel A Offermann, Notting Hill (AU); Lorraine Claire Axford, Notting Hill (AU); Michael Blair, Notting Hill (AU); Dale Mitchell, Essex (GB); Nicholas Palmer, Essex (GB); Christopher Steele, Essex (GB); John Atherall, Essex (GB); David Watson, Essex (GB); David Haydon, Yarnton (GB); Lloyd Czaplewski, Yarnton (GB); David Davies, Yarnton (GB); Ian Collins, Yarnton (GB); Edward Malcolm Tyndall, NottingHill (AU); Laura Andrau, Notting Hill (AU); Gary Robert William Pitt, Notting Hill (AU)

(73) Assignee: Biota Europe Ltd., Yarnton, Oxfordshire (GB)

( * ) Notice: Subject to any disclaimer, the term of this patent is extended or adjusted under 35 U.S.C. 154(b) by 922 days.

(21) Appl. No.: 13/268,154

(22) Filed: Oct. 7, 2011

(65) Prior Publication Data

US 2012/0088750 A1    Apr. 12, 2012

Related U.S. Application Data

(60) Provisional application No. 61/391,163, filed on Oct. 8, 2010.

(51) Int. Cl.
| | | |
|---|---|---|
| *C07D 417/14* | (2006.01) | |
| *C07D 491/04* | (2006.01) | |
| *C07D 513/04* | (2006.01) | |
| *A01N 47/36* | (2006.01) | |

(52) U.S. Cl.
CPC .............. *C07D 417/14* (2013.01); *A01N 47/36* (2013.01); *C07D 491/04* (2013.01); *C07D 513/04* (2013.01)

(58) Field of Classification Search
CPC ..... A61K 31/506; A01N 43/54; C07D 417/14
See application file for complete search history.

(56) References Cited

U.S. PATENT DOCUMENTS

| 7,569,591 | B2 * | 8/2009 | Charifson et al. ............. 514/338 |
|---|---|---|---|
| 8,299,065 | B2 * | 10/2012 | Haydon et al. ............. 514/230.5 |
| 8,404,852 | B2 * | 3/2013 | Charifson et al. ......... 546/273.4 |
| 2005/0038247 | A1 * | 2/2005 | Charifson et al. ............ 544/295 |
| 2006/0025424 | A1 | 2/2006 | Charifson et al. |
| 2011/0166088 | A1 * | 7/2011 | Sattigeri et al. ................. 514/27 |

FOREIGN PATENT DOCUMENTS

| WO | 02-060879 | | 8/2002 | |
|---|---|---|---|---|
| WO | 2009-074812 | | 6/2009 | |
| WO | 2009-156966 | | 12/2009 | |
| WO | WO2010100144 | * | 9/2010 | ............. C07D 43/54 |

OTHER PUBLICATIONS

CAS Registry No. 1202854-83-8, entered STN: Jan. 22, 2010.
CAS Registry No. 1202854-75-8, entered STN: Jan. 22, 2010.
CAS Registry No. 1202854-62-3, entered STN: Jan. 22, 2010.
CAS Registry No. 1202854-57-6, entered STN: Jan. 22, 2010.
CAS Registry No. 1202854-51-0, entered STN: Jan. 22, 2010.
PCT International Search Report and Written Opinion for corresponding International Application No. PCT/AU2011/001284 dated Nov. 18, 2011.

* cited by examiner

*Primary Examiner* — Paul V Ward
(74) *Attorney, Agent, or Firm* — Banner & Witcoff, Ltd.

(57) ABSTRACT

The present invention provides a compound of the following formula and salts thereof:

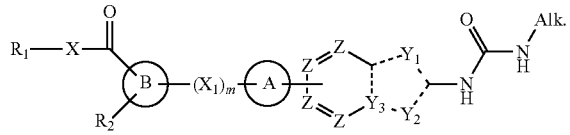

Also provided is the use of these compounds as antibacterials, compositions comprising them and processes for their manufacture.

17 Claims, 8 Drawing Sheets

Compound A

Compound B

A

B

A

B

A

B

A

B

A

A

B

A

B

ANTIBACTERIAL COMPOUNDS

CROSS-REFERENCE TO RELATED APPLICATIONS

The present application claims priority to U.S. Provisional Application No. 61/391,163, filed Oct. 8, 2010, and entitled "Antibacterial Compounds," the entire disclosure of which is hereby incorporated by reference in its entirety.

FIELD OF THE INVENTION

The present invention relates to a novel class of compounds, their use as antibacterials, compositions comprising them and processes for their manufacture.

BACKGROUND

Type II topoisomerases catalyse the interconversion of DNA topoisomers by transporting one DNA segment through another. Bacteria encode two type II topoisomerase enzymes, DNA gyrase and DNA topoisomerase IV. Gyrase controls DNA supercoiling and relieves topological stress. Topoisomerase IV decatenates daughter chromosomes following replication and can also relax supercoiled DNA.

Bacterial type II topoisomerases form a heterotetrameric complex composed of two subunits. Gyrase forms an $A_2B_2$ complex comprised of GyrA and GyrB whereas topoisomerase forms a $C_2E_2$ complex comprised of ParC and ParE. In contrast eukaryotic type II topoisomerases are homodimers. Ideally, an antibiotic based on the inhibition of bacterial type II topoisomerases would be selective for the bacterial enzymes and be relatively inactive against the eukaryotic type II isomerases.

The type II topoisomerases are highly conserved enzymes allowing the design of broad-spectrum inhibitors. Furthermore, the GyrB and ParE subunits are functionally similar, having an ATPase domain in the N-terminal domain and a C-terminal domain that interacts with the other subunit (GyrA and ParC respectively) and the DNA. The conservation between the gyrase and topoisomerase IV active sites suggests that inhibitors of the sites might simultaneously target both type II topoisomerases. Such dual-targeting inhibitors are attractive because they have the potential to reduce the development of target-based resistance.

Type II topoisomerases are the target of a number of antibacterial agents. The most prominent of these agents are the quinolones. The original quinolone antibiotics included nalidixic acid, cinoxacin and oxolinic acid. The addition of fluorine yielded a new class of drugs, the fluoroquinolones, which have a broader antimicrobial spectrum and improved pharmacokinetic properties. The fluoroquinolones include norfloxacin, ciprofloxacin, and fourth generation quinolones gatifloxacin and moxifloxacin. The coumarins and the cyclothialidines are further classes of antibiotics that inhibit type II topoisomerases, however they are not widely used because of poor permeability in bacteria, eukaryotic toxicity, and low water solubility. Examples of such antibiotics include novobiocin and coumermycin A1, cyclothialidine, cinodine, and clerocidin. However, the continuous emergence of antibiotic resistance demands that novel classes of antibiotics continue to be developed and alternative compounds that inhibit bacterial topoisomerases are required.

WO2007/148093 and WO2009/074812 describe compounds that inhibit bacterial gyrase activity. The applicant has now identified a class of related compounds that includes a carbocyclic or heterocyclic ring comprising an α-substituted carboxylate or amide. Compounds of this class appear to possess a number of advantages including enhanced solubilities at physiologically acceptable pH, in particular, advantageous solubilities for intraveneous (IV) administration and/or advantageous pharmacokinetic properties.

SUMMARY

According to a first aspect there is provided a compound of the following general formula or salt thereof:

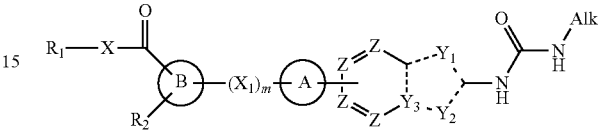

wherein
$R_1$ is selected from H, $C_{1-6}$alkyl, $C_{2-6}$alkenyl, $C_{2-6}$alkynyl, $S(O)_2OH$, $S(O)_2$—$C_{1-6}$alkyl, and M where M represents a monovalent or divalent cation;
$R_2$ is joined to the same ring B atom as the —C(=O)—X—$R_1$ moiety and is selected from $C_{1-6}$alkyl, $C_{2-6}$alkenyl, $C_{2-6}$alkynyl, $(C_{1-6}$alkyl)$_r$$C_{3-7}$cycloalkyl, $(C_{1-6}$alkyl)$_r$aryl, $(C_{1-6}$alkyl)$_r$heterocyclyl, $(C_{1-6}$alkyl)$_r$heteroaryl, $NH_2$, $NH(C_{1-6}$alkyl), $N(C_{1-6}$alkyl)$_2$, CN, OH, $C_{1-6}$alkoxy, $SO_2H$, $SO_2C_{1-6}$alkyl, SH, $SC_{1-6}$alkyl, halo, halo$C_{1-6}$alkyl, —NH(C=O)O$C_{1-6}$alkyl, —NH(C=O)OC($C_{1-3}$alkyl)$_3$, and wherein $C_{1-3}$alkyl, $C_{1-6}$alkyl, $C_{2-6}$alkenyl, $C_{2-6}$alkynyl, $C_{3-7}$cycloalkyl, aryl and heterocyclyl in each case may be further optionally substituted, in particular, with one or more substituents selected from $NH_2$, $NH(C_{1-6}$alkyl), $N(C_{1-6}$alkyl)$_2$, CN, OH, $C_{1-6}$alkoxy, $SO_2H$, $SO_2C_{1-6}$alkyl, SH, $SC_{1-6}$alkyl and halo or $R_2$ is a chain of 3 or 4 carbon atoms or carbon and heteroatoms which joins with an adjacent B ring atom to form a fused carbocyclylic or heterocycylic ring which is optionally further substituted;
ring "A" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered-heterocyclyl, $C_{6-10}$aryl and 5-10 membered heteroaryl;
ring "B" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-12 membered heterocyclyl, $C_{6-10}$aryl, 5-10 membered heteroaryl, and a spiro bicyclic 8-12 membered heterocyclic ring system;
or ring "A" and ring "B" may join together to form a saturated or unsaturated fused bicyclic $C_{8-10}$cycloalkyl, a saturated or unsaturated fused bicyclic 8-10 membered heterocyclyl and a spiro bicyclic 8-12 membered heterocyclic ring system;
Each Z is independently selected from C—H, C—$C_{1-3}$alkyl, C—OH, C—O$C_{1-3}$alkyl, C-halo, C-halo$C_{1-3}$alkyl, C—CN, N or C—(X$_2$)$_n$R$_3$ wherein $R_3$ is H, halo, OH, CN, $C_{1-6}$alkyl, $C_{1-6}$alkoxy, halo$C_{1-6}$alkyl, $C_{2-6}$alkenyl, $C_{2-6}$alkenyl, saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl wherein each $R_3$ may be optionally substituted; provided that one Z is C substituted with ring "A";

X is O, NH or N(C$_{1-6}$alkyl);

m, n and t are each independently an integer 0 or 1;

X$_1$ is a covalent bond, a spiro ring centre, or a fused ring bond when m is 0 or when m is 1 is selected from optionally substituted C$_{1-3}$alkylene, optionally substituted C$_{2-3}$alkenylene and optionally substituted C$_{2-3}$alkynylene and wherein each carbon atom in C$_{1-3}$alkylene may be optionally replaced by an oxygen or nitrogen heteroatom or C(=O);

X$_2$ is a covalent bond when n is 0 or when n is 1 is selected from optionally substituted C$_{1-4}$alkylene, optionally substituted C$_{2-3}$alkenylene and optionally substituted C$_{2-3}$alkynylene and wherein each carbon atom in C$_{1-3}$alkylene and C$_{2-3}$alkenylene may be optionally replaced by an oxygen or nitrogen heteroatom (wherein the nitrogen atom may be substituted with H or C$_{1-3}$alkyl) or C(=O);

Y$_1$ and Y$_2$ are each independently selected from C, N, O or S;

Y$_3$ is selected from C or N;

------ indicates a double or a single bond as the case may be; and

Alk is C$_{1-6}$alkyl, C$_{2-6}$alkenyl, C$_{2-6}$alkynyl, C$_{3-6}$cycloalkyl.

In one embodiment the compound is of Formula I or a salt thereof

Formula I

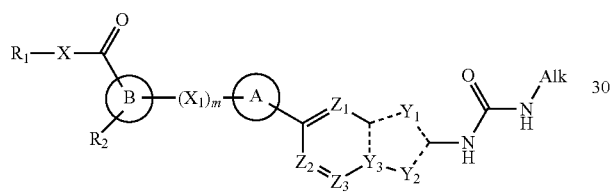

wherein

Z$_1$, Z$_2$ and Z$_3$ are each independently selected from C—H, C—C$_{1-3}$alkyl, C—OH, C—OC$_{1-3}$alkyl, C-halo, C-haloC$_{1-3}$alkyl, C—CN, N or C—(X$_2$)$_n$R$_3$ wherein R$_3$ is H, halo, OH, CN, C$_{1-6}$alkyl, C$_{1-6}$alkoxy, haloC$_{1-6}$alkyl, C$_{2-6}$alkenyl, C$_{2-6}$alkenyl, saturated or unsaturated monocyclic C$_{3-7}$cycloalkyl, saturated or unsaturated monocyclic 3-7 membered heterocycle, saturated or unsaturated fused bicyclic C$_{8-10}$cycloalkyl, saturated or unsaturated fused bicyclic 8-10 membered heterocyclyl, C$_{6-10}$aryl and 5-10 membered heteroaryl wherein each R$_3$ may be optionally substituted;

and wherein R$_1$, R$_2$, ring "A", ring "B", X, Y$_1$, Y$_2$, Y$_3$, m, ------ and Alk are as previously defined in accordance with the general formula.

According to a second aspect there is provided a method for the treatment of a bacterial infection comprising administration of a compound of Formula I or a pharmaceutically acceptable salt thereof to a subject suffering from said infection. In a preferred embodiment the administration is intravenous administration, oral administration or a combination thereof.

According to a third aspect there is provided a compound of Formula I or a pharmaceutically acceptable salt thereof for use in the treatment of a bacterial infection.

According to a fourth aspect there is provided an antibacterial agent comprising a compound of Formula I or a pharmaceutically acceptable salt thereof.

According to a fifth aspect there is provided a composition comprising a compound of Formula I or a salt thereof. In one embodiment the composition is a pharmaceutical composition and the salt is a pharmaceutically acceptable salt.

According to a sixth aspect there is provided a compound of Formula I or a pharmaceutically acceptable salt thereof for use as a gyrase inhibitor.

According to a seventh aspect there is provided a process for the manufacture of a compound of Formula I comprising the step of coupling an intermediate of Formula IIa with an L-(X$_2$)$_n$—R$_3$ precursor moiety;

Formula IIa or alternatively comprising the step of coupling an intermediate of Formula IIb Formula IIb with a precursor moiety of general formula to form a compound of Formula I;

wherein R$_1$, X, R$_2$, (X$_1$)$_m$, ring A, ring B, Z$_1$, Z$_2$, Y$_1$, Y$_2$, Alk, (X$_2$)$_n$ and R$_3$ are as defined for Formula I and L is a suitable reactive group. In one embodiment the process further comprises the step of forming a salt thereof.

According to an eighth aspect, there is provided a provided a process for the manufacture of a compound of Formula I comprising the step of coupling a precursor of Formula IIIa with a boronic acid intermediate of Formula IVa Formula IIIa Formula IVa

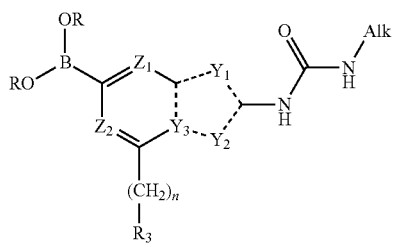

or alternatively comprising the step of coupling a boronic acid intermediate of Formula IVb with a halo-$(X_2)_n$—$R_3$ precursor moiety Formula IVb

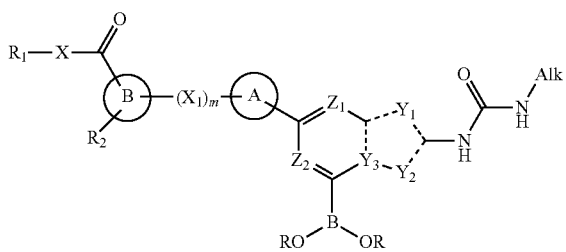

to form a compound of Formula I;
wherein $R_1$, X, $R_2$, $(X_1)_m$ ring A, ring B, $Z_1$, $Z_2$, $Y_1$, $Y_2$, Alk, $(X_2)_n$ and $R_3$ are as defined for Formula I and $B(OR)_2$ is a boronic acid ($B(OH)_2$) or a pinacolborane. In one embodiment the process further comprises the step of forming a salt thereof.

According to a ninth aspect, there is provided a method of treating bacterial contamination of a substrate comprising applying to the site of such contamination an amount of a compound of Formula I or pharmaceutically acceptable salt thereof sufficient to inhibit bacterial growth.

BRIEF DESCRIPTION OF THE FIGURES

FIG. 1: Shows the IV and oral pharmacokinetic profile of two alpha-unsubstituted comparator compounds A and B in a mouse assay.

FIG. 2: Shows the IV and oral pharmacokinetic profile of (A) compound 1 and (B) compound 4 in a rat assay.

FIG. 3: Shows the IV and oral pharmacokinetic profile of (A) compound 29 and (B) compound 98 in the rat assay.

FIG. 4: Shows the IV and oral pharmacokinetic profile of (A) compound 103 and (B) compound 136 in the rat assay.

FIG. 5: Shows the IV and oral pharmacokinetic profile of (A) compound 141 and (B) compound 143 in the rat assay.

FIG. 6: Shows the IV and oral pharmacokinetic profile of (A) compound 161 in the rat assay.

FIG. 7: Shows the IV and oral pharmacokinetic profile of (A) compound 4 and (B) compound 88 in the mouse assay.

FIG. 8: Shows the IV and oral pharmacokinetic profile of (A) compound 98 and (B) compound 136 in the mouse assay.

DETAILED DESCRIPTION

Figure 1:
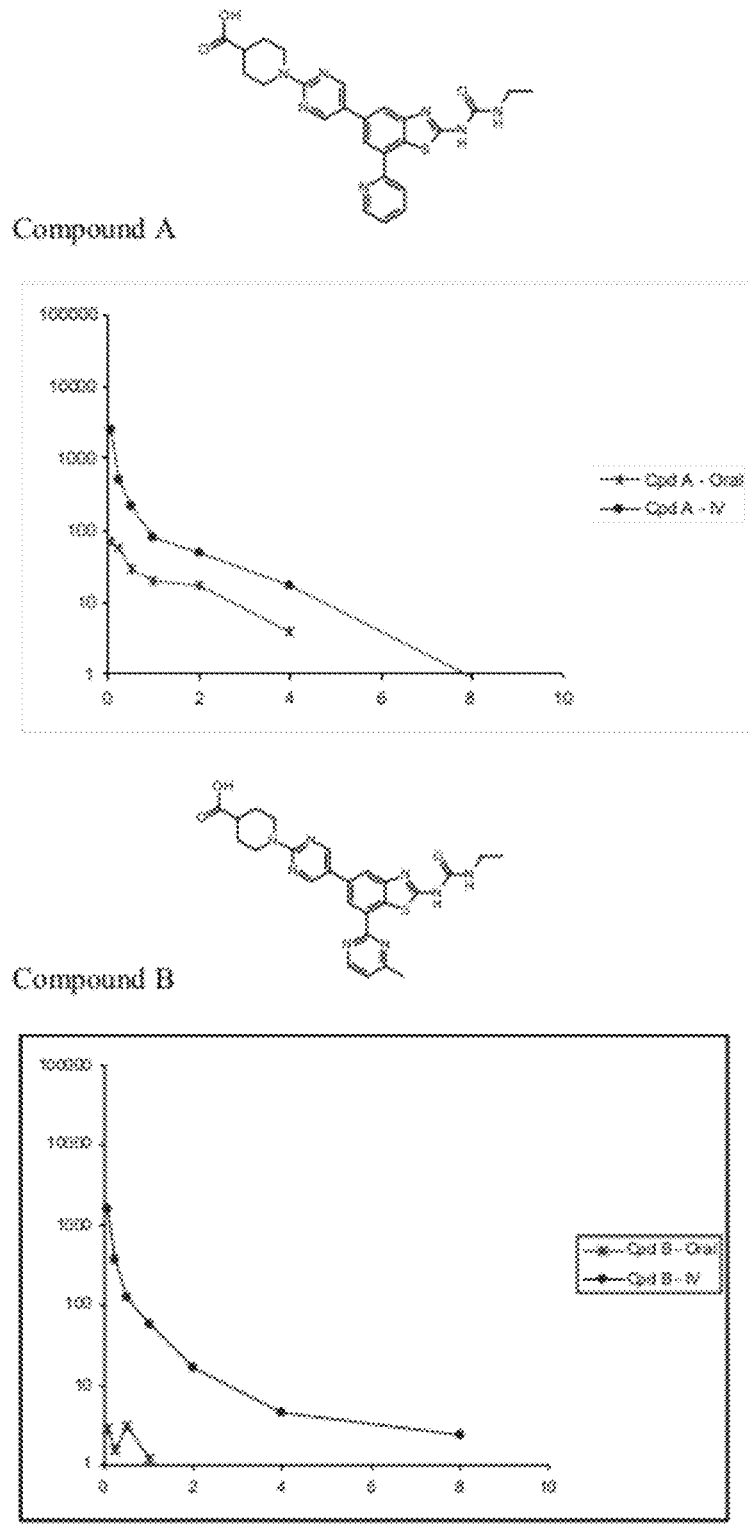
In FIGS. 1 to 8 the X axis denotes the time (hours) and the Y axis denotes the plasma concentration (ng/mL).
Figure 2:
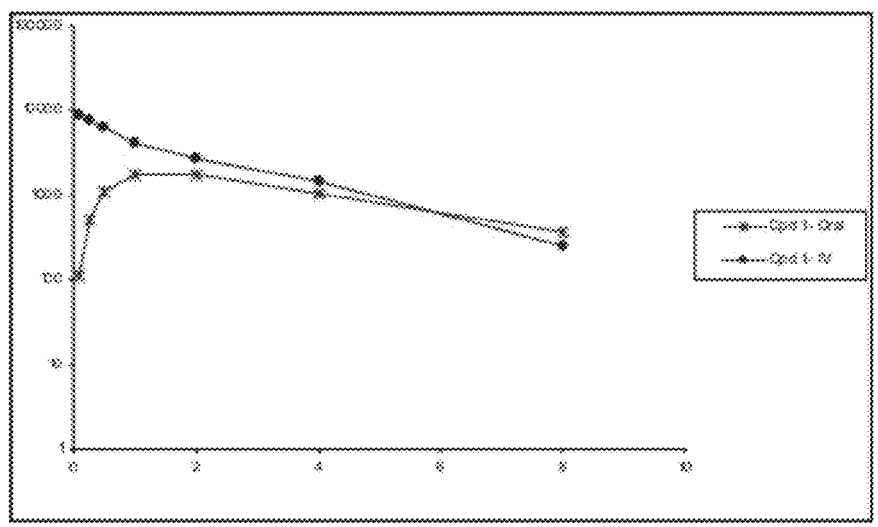
Figure 2:
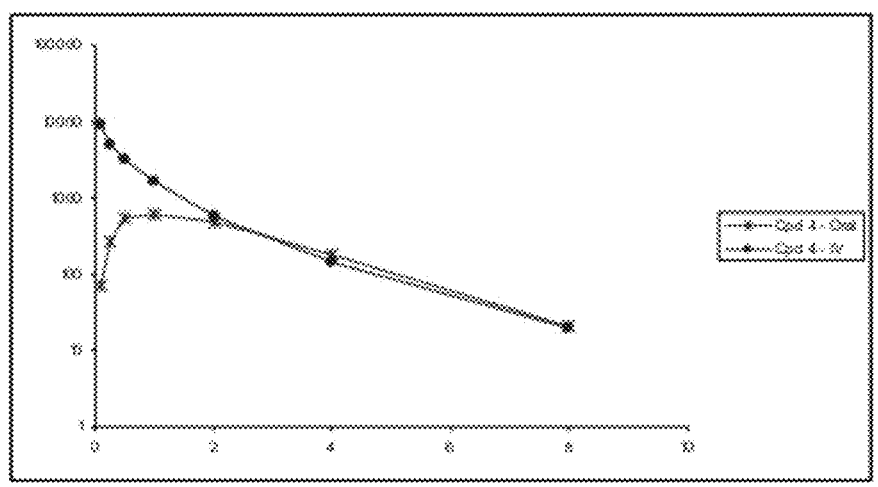
Figure 3:
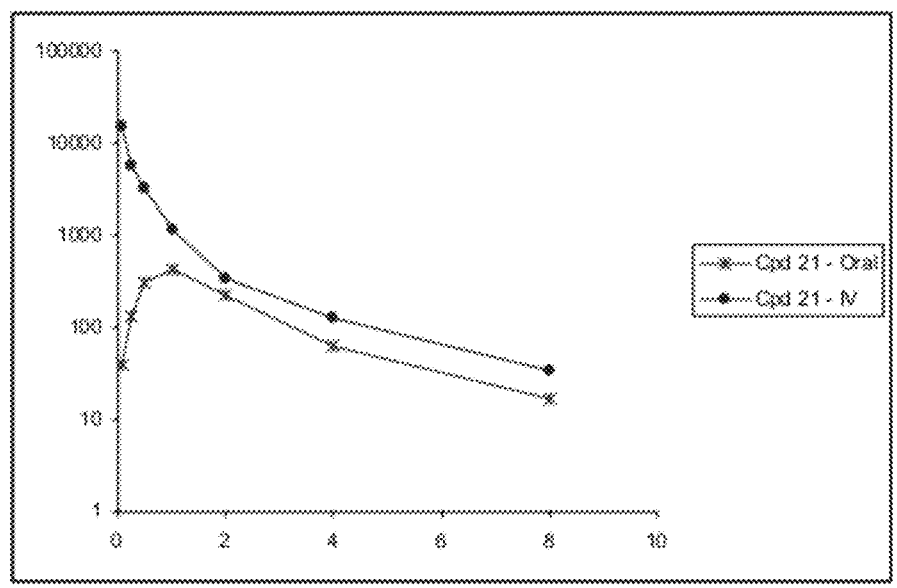
Figure 3:
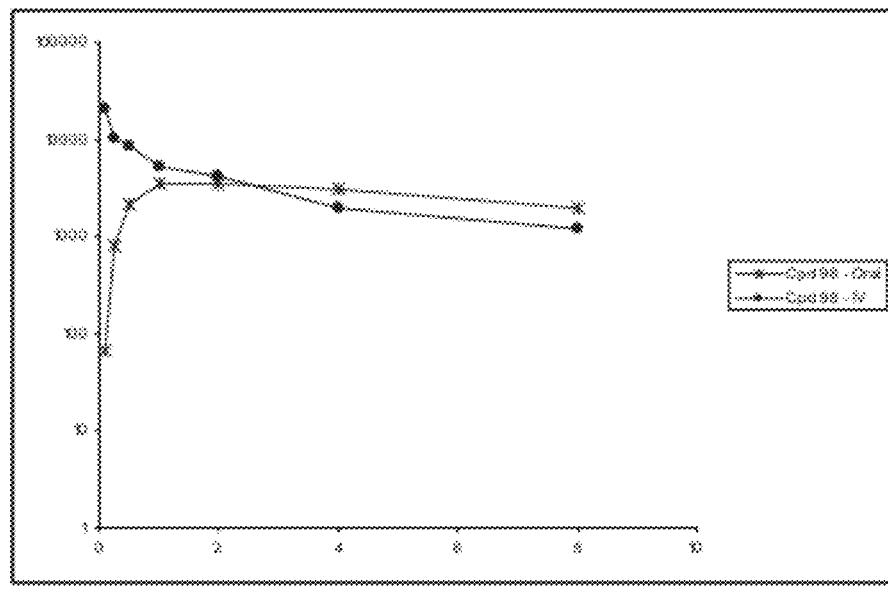
Figure 4:
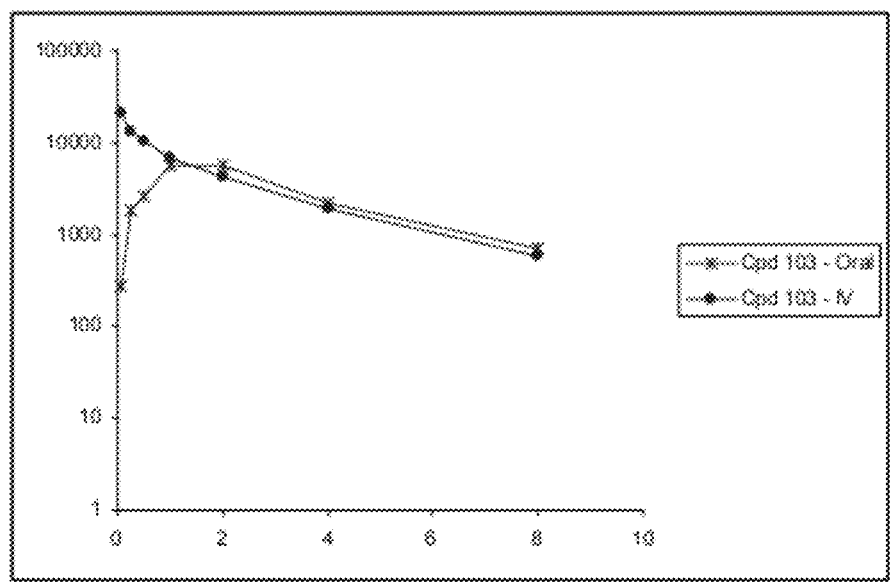
Figure 4:
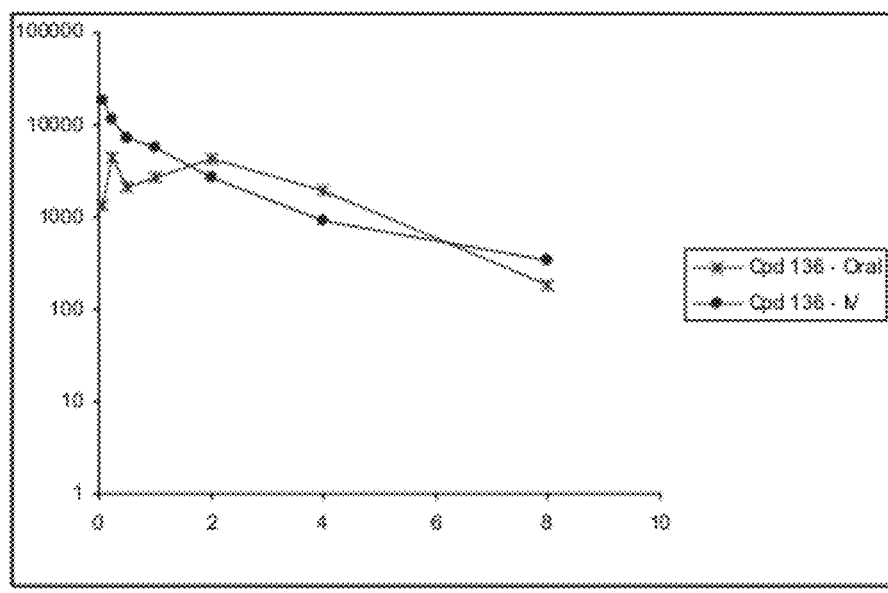
Figure 5:
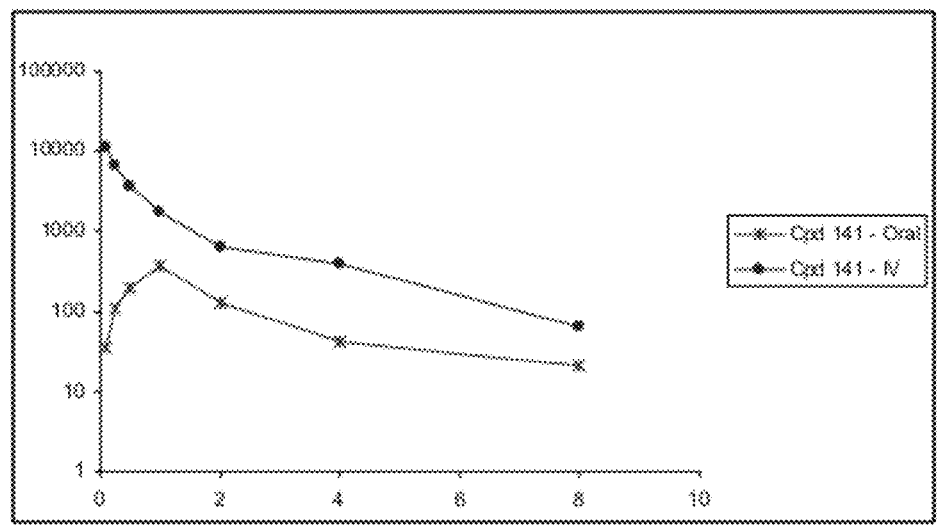
Figure 5:
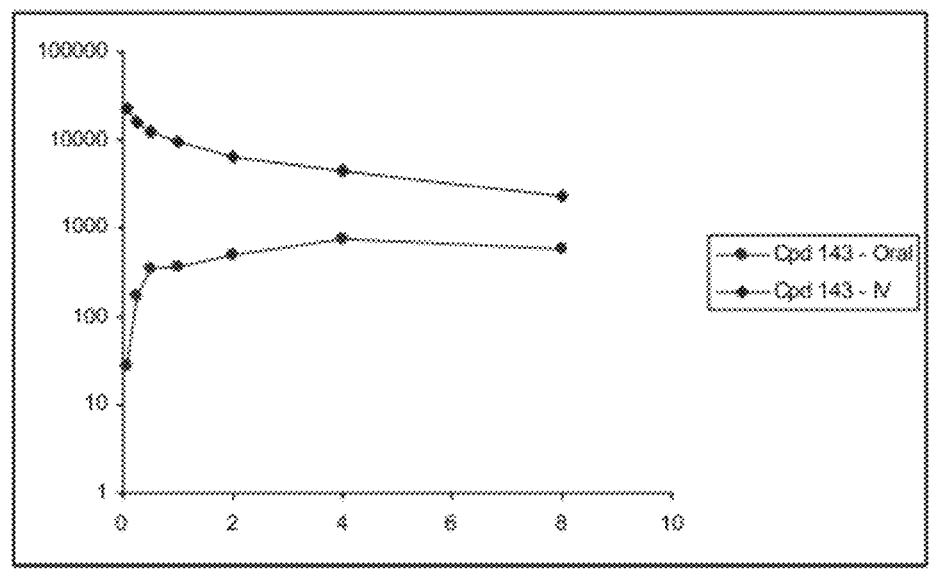
Figure 6:
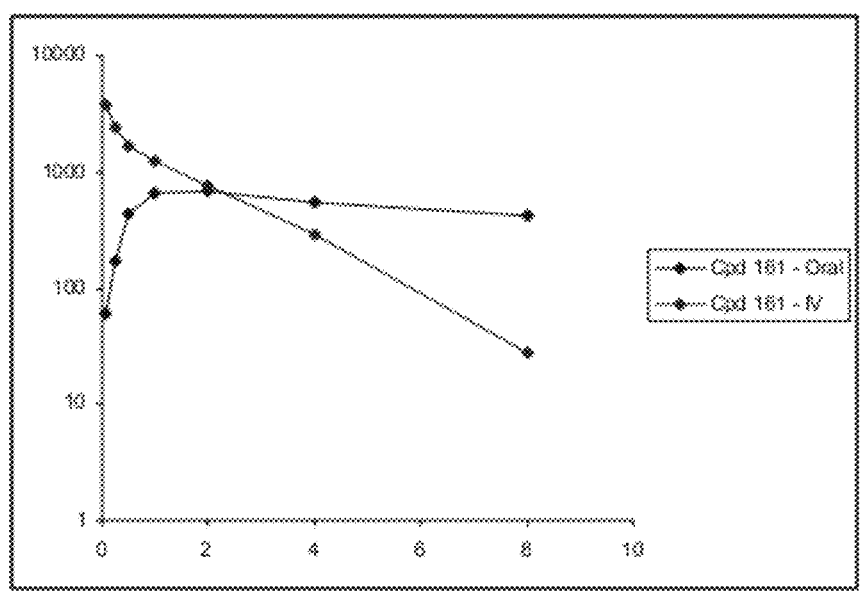
Figure 7:
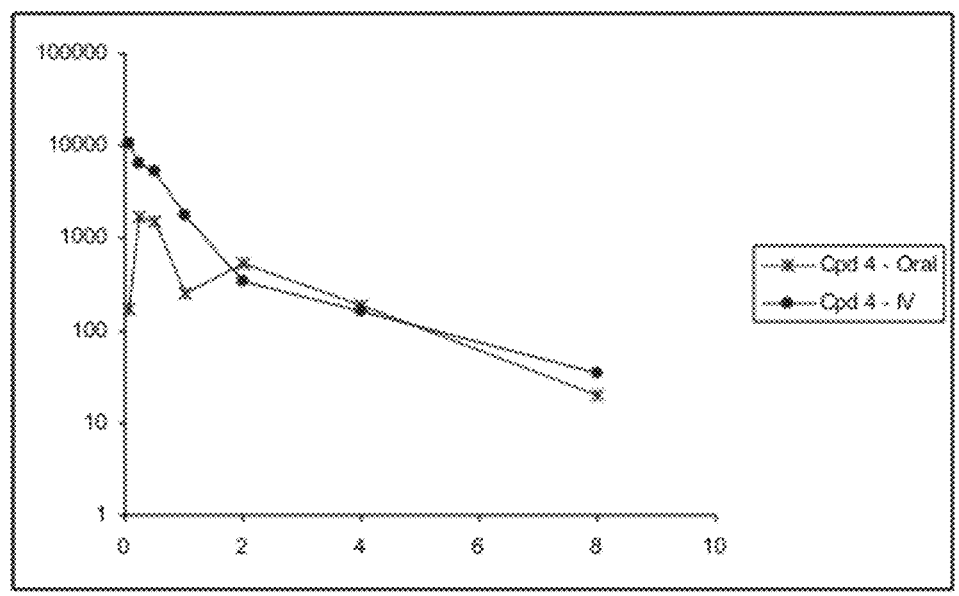
Figure 7:
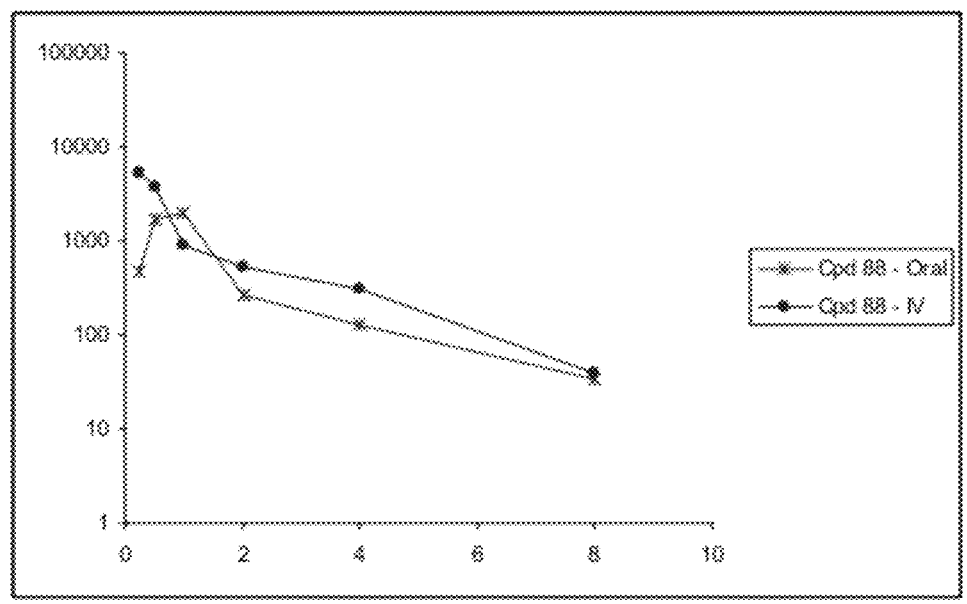
Figure 8:
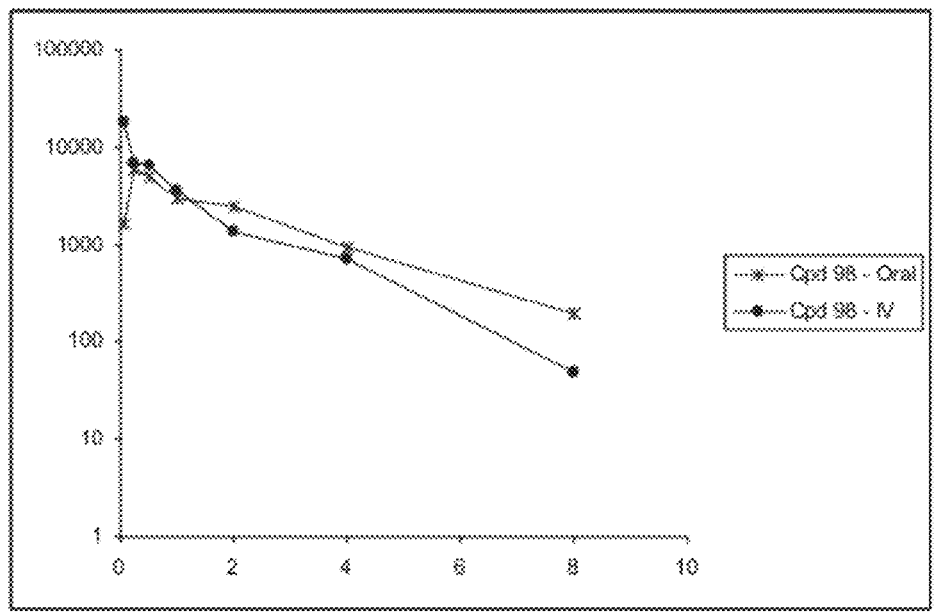
Figure 8:
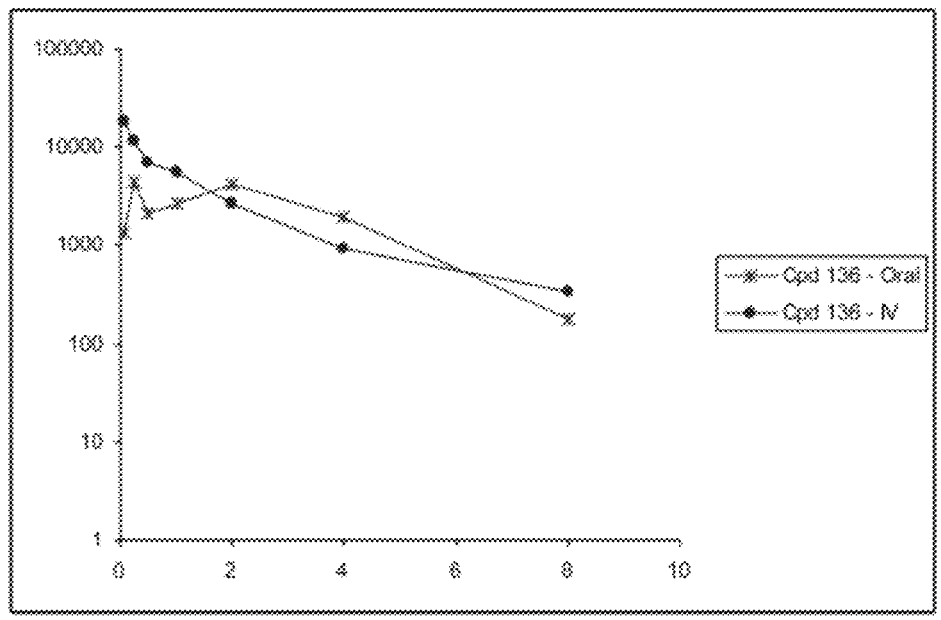

The present invention is predicated on the discovery of a new class of compounds that demonstrate one or more advantageous pharmaceutical properties. More particularly, compounds of this class have shown on-target gyrase enzyme activity. Accordingly, in one embodiment the compounds of Formula I are useful in modulating the activity of gyrase, more particularly as gyrase inhibitors.

Compounds of this class also exhibit antibacterial activity more particularly antibacterial activity against strains of Gram-positive and/or Gram-negative classes, such as staphylococci, enterococci, streptococci and haemophili for example *Staphylococcus aureus, Enterococcus faecalis, Streptococcus pyogenes* and *Haemophilus influenzae*. The compounds with which the invention is concerned are therefore useful for the treatment of bacterial infection or contamination, for example in the treatment of, inter alia, Gram-positive infections and community acquired pneumonias. Accordingly, in one embodiment the compounds of Formula (I) are useful in the treatment of bacterial infections caused by gram positive bacterial strains. In another embodiment, the compounds of Formula (I) are useful in the treatment of bacterial infections caused by gram negative bacterial strains.

The development of antibacterial resistance is particularly common in a hospital setting. Hospital patients are therefore especially at risk of infection by resistant strains of bacteria. In a hospital setting IV administration of an antibacterial agent is often the preferred or required form of administration. Thus compound solubility of an antibacterial agent is of particular importance in developing an antibacterial for IV administration. Good demonstrated bioavailability of the antibacterial agent and pharmacokinetic (PK) profile are also important considerations amongst others, in particular to facilitate alternative modes of administration, such as for example, an IV to oral switch. Compounds which demonstrate similar IV and oral PK profiles are therefore advantageous in that the same dose of active ingredient can be administered by both routs of administration. This type of PK profile is ideal for an IV/oral switch therapy to enable patients to benefit from IV dosing in controlling their bacterial infection in the first 1-3 days or so, followed by oral dosing to complete the course of treatment.

It has been found that compounds of Formula I demonstrate high to very high solubility. This is so particularly so when compared to compounds without the feature of an α-substituted carboxylate or amide, more particularly an α-substituted carboxylic acid. Compounds of Formula (I) have also demonstrated good bioavailability and an advantageous pharmacokinetic profile.

As used herein, the term "halo" or "halogen" refers to fluorine (fluoro), chlorine (chloro), bromine (bromo) or iodine (iodo).

As used herein, the term "alkyl" either used alone or in compound terms such as NH(alkyl) or N(alkyl)$_2$, refers to monovalent straight chain or branched hydrocarbon groups, having 1 to 3, 1 to 6, or 1 to 10 carbon atoms as appropriate. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

The term "haloalkyl" refers to an alkyl group which has one or more halo substituents. One, two or three halo substituents are particularly preferred. For instance, $CF_3$ is a haloalkyl group as is $CHF_2$.

The term "alkoxyl", including $C_{1-6}$alkoxyl, refers to a an alkyl group having an oxygen atom either connecting the alkyl group to the remainder of the compound or located along the hydrocarbon chain.

The term "carboxylate" includes carboxylic acids and carboxylate esters where the term "ester" refers to a carboxylic acid group having the hydrogen replaced with, for example, a $C_{1-6}$alkyl, aryl or alkaryl group.

As used herein, the term "alkenyl", including $C_{2-6}$alkenyl, refers to a straight chain or branched hydrocarbon groups having one or more double bonds between carbon atoms. Suitable alkenyl groups include, but are not limited to, ethenyl, allyl, propenyl, iso-propenyl, butenyl, pentenyl and hexenyl.

The term "alkynyl", including $C_{2-6}$alkynyl, as used herein, refers to straight chain or branched hydrocarbon groups containing one or more triple bonds. Suitable alkynyl groups include, but are not limited to ethynyl, propynyl, butynyl, pentynyl and hexenyl.

The terms "cycloalkyl", "carbocyclic" and "carbocyclyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The terms "heterocycle", "heterocyclic" and "heterocyclyl" when used alone or in compound words includes monocyclic, polycyclic, fused or conjugated hydrocarbon residues wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include O, N and S. Where two or more carbon atoms are replaced, this may be by two or more of the same heteroatom or by different heteroatoms. Suitable examples of heterocyclic groups may include azetidine, pyrrolidinyl, piperidyl, piperazinyl, azepane, morpholino, quinolinyl, isoquinolinyl, thiomorpholino, dioxanyl, 2,2'-dimethyl-[1,3]-dioxolanyl, tetrahydrofuranyl, tetrahydropyranyl, tetrahydropyrrolyl, cyclic sulfonamides such as sultams etc.

The term "heteroaryl" includes but is not limited to a 5- or 6-membered heteroaromatic ring containing one or more heteroatoms selected from O, N and S. Suitable examples of heteroaryl groups include furanyl, thiophenyl, tetrazolyl, 1,2,3-triazolyl, 1,2,4-triazolyl, imidazolyl, pyrazolyl, pyridinyl, pyrimidinyl, pyrazinyl, pyridazinyl, oxazolyl, oxadiazolyl, thioazolyl, thiodiazolyl etc. The heteroaromatic ring may be fused to a 5- or 6-membered aromatic or heteroaromatic ring to form a 9- or 10-membered bicyclic aromatic ring system eg benzofuran, pyrollopyrimidine, furopyridine etc.

Unless otherwise stated, each alkyl, alkenyl, alkynyl, alkoxy, cycloalkyl, alkylaryl, aryl, heterocyclyl, or heteroaryl group may be optionally substituted with one or more of $C_1$-$C_3$alkyl, $C_{2-3}$alkenyl, $C_{2-3}$alkynyl, $C_3$-$C_6$cycloalkyl, $C_6$aryl, heterocyclyl, heteroaryl, $C_1$-$C_3$alkylheterocyclyl, $C_1$-$C_3$alkylheteroaryl, $C_1$-$C_3$alkylOH, alkylaryl, OH, $OC_1$-$C_3$alkyl, halo, CN, $NO_2$, $CO_2H$, $CO_2C_1$-$C_3$alkyl, $CONH_2$, $CONH(C_1$-$C_3$alkyl), $C(O)N(C_1$-$C_3$alkyl)$_2$, halo$C_{1-3}$alkyl such as $CF_3$ and $CHF_2$, halo$C_{1-3}$alkoxy such as $OCHCF_2$ and $OCF_3$, =O, $C(O)C_{1-3}$alkyl, $C(O)$halo$C_{1-3}$alkyl, $NH_2$, $NH(C_1$-$C_3$alkyl) or $N(C_1$-$C_3$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted. For example, heterocyclyl and heteroaryl groups containing a nitrogen heteroatom when optionally substituted with an alkyl group such as a $C_{1-3}$alkyl the alkyl group may be on any available carbon atom and/or nitrogen ring atom (e.g. N-methyl).

Examples of optional substituents also include suitable oxygen and nitrogen protecting groups (see "Protective Groups in Organic Synthesis" Theodora Greene and Peter Wuts, third edition, Wiley Interscience, 1999).

Embodiments will now be described.

In one embodiment the compound is of Formula I or salt thereof

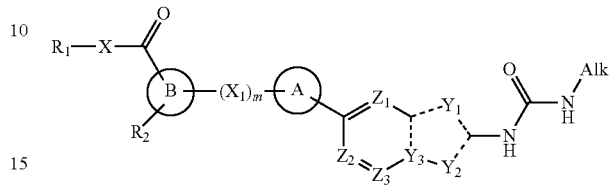

Formula I wherein
$R_1$, $R_2$, ring "A", ring "B", X, $X_1$, $X_2$, $Y_1$, $Y_2$, $Y_3$, m, n, t, ------, and Alk are as previously defined in accordance with the general formula; and
$Z_1$, $Z_2$ and $Z_3$ are each independently selected from C—H, C—$C_{1-3}$alkyl, C—OH, C—$OC_{1-3}$alkyl, C-halo, C-halo$C_{1-3}$alkyl, C—CN, N or C—$(X_2)_n R_3$ wherein $R_3$ is H, halo, OH, CN, $C_{1-6}$alkyl, $C_{1-6}$alkoxy, halo$C_{1-6}$alkyl, $C_{2-6}$alkenyl, $C_{2-6}$alkenyl, saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl wherein each $R_3$ may be optionally substituted.

In one embodiment, M is selected from the group comprising pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine.

In one embodiment $R_1$ is H or $C_{1-3}$alkyl selected from methyl, ethyl, propyl and iso-propyl, preferably H.

In another embodiment $R_2$ is $C_{1-6}$alkyl or $C_{3-7}$cycloalkyl, preferably $C_{1-3}$alkyl or cyclopropyl, more preferably methyl, ethyl, n-propyl and iso-propyl, most preferably methyl or ethyl.

In one embodiment X is O. In another embodiment X is NH. Preferably X is O.

In one embodiment $Y_1$ and $Y_2$ are each independently N or S, preferably one is N and the other S, more preferably $Y_1$ is N and $Y_2$ is S.

In another embodiment $Y_1$ and $Y_2$ are each independently N or O, preferably one is N and the other O, more preferably $Y_1$ is N and $Y_2$ is O.

In another embodiment $Y_1$ and $Y_2$ are each independently N.

In yet another embodiment $Y_1$ is N and $Y_2$ is CH.

In one embodiment $Y_3$ is C. In an alternative embodiment $Y_3$ is N. Preferably $Y_3$ is C.

In yet another embodiment Alk is $C_{1-6}$alkyl, preferably $C_{1-3}$alkyl, most preferably ethyl.

In still another embodiment m is 0 and $X_1$ is a covalent bond or a fused ring bond. In a preferred embodiment $X_1$ is a covalent bond when m is 0.

In a further embodiment when $X_1$ is a covalent bond, ring "B" is an optionally substituted 5- or 6-membered heterocyclic or heteroaryl group preferably containing a nitrogen heteroatom which, in the case of 5- or 6-membered heterocyclic groups is preferably the point of attachment to $X_1$.

In another embodiment m is 1 and $X_1$ is selected from the group consisting of —C(O)NH— or —NHC(O)—, —NH—, —CH$_2$NH—, —NHCH$_2$—, —N(CH$_3$)—, —CH$_2$N(CH$_3$)—, —N(CH$_3$)CH$_2$—, methylene, ethylene, propylene and C=O. Preferably X$_1$ is selected from methylene, NH, N(CH$_3$) and C(=O). When X$_1$ is —NH— or —N(CH$_3$)—, most preferably —NH—, ring "B" is preferably an optionally substituted C$_{3-7}$cycloalkyl or optionally substituted C$_6$aryl, preferably an optionally substituted cyclohexyl.

In one embodiment one of Z$_1$, Z$_2$ and Z$_3$ is C—(X$_2$)$_n$R$_3$, preferably Z$_2$ and/or Z$_3$, most preferably Z$_3$. In a further embodiment C—(X$_2$)$_n$R$_3$ is not C—H.

In one embodiment n is 0 and X$_2$ is a covalent bond.

In another embodiment n is 1 and X$_2$ is selected from O, C(=O), C$_{1-6}$alkylene preferably C$_{1-3}$alkylene most preferably —CH$_2$—, C$_{1-6}$alkylO— preferably C$_{1-3}$alkylO— most preferably —CH$_2$O—, C$_{1-6}$alkylNH— preferably C$_{1-3}$alkylNH— most preferably —CH$_2$NH—, C$_{1-6}$alkylN(C$_{1-3}$alkyl)- preferably C$_{1-3}$alkylN(C$_{1-3}$alkyl)- most preferably —CH$_2$N(Me)-, C$_{2-6}$alkenylene preferably C$_{2-3}$alkenylene, C$_{2-6}$alkynylene preferably C$_{2-3}$alkynylene, —CH$_2$N(C$_{1-3}$alkyl)-, NH, N(C$_{1-3}$alkyl) preferably N(Me), —C(O)NH—, —C(O)N(C$_{1-3}$alkyl)- preferably —C(O)N(Me)-, —NHC(O)—, —C(C$_{1-3}$alkyl)=N—O— (preferably —C(Et)=N—O— or —C(Me)=N—O—) and —CH=N—O—.

In one embodiment, R$_3$ is selected from the group consisting of optionally substituted C$_{3-7}$cycloalkyl preferably C$_{3-6}$cycloalkyl, optionally substituted 5-6 membered heterocycles, optionally substituted 5-6 membered heteroaryl and optionally substituted 9 membered heterocycles.

Preferred optionally substituted C$_{3-6}$cycloalkyl includes cyclopropyl, cyclobutyl, cyclopentyl and cyclohexyl. Preferred optionally substituted 5-6 membered heterocycles includes tetrahydropyran, piperidinyl, morpholinyl and dihydroisoxazolyl. Preferred optionally substituted 5-6 membered heteroaryl includes pyrrolyl, pyridinyl, pyrimidinyl, pyrazinyl, pyridazinyl, oxazolyl, thiazolyl, thiadiazolyl, imidazolyl pyrazolyl, triazolyl. Preferred optionally substituted 9 membered heterocycles includes pyrrolopyrimidine and furopyridine.

In a particularly preferred embodiment R$_3$ is an optionally substituted 5-6-membered heteroaryl. In an even more preferred embodiment R$_3$ is an optionally substituted 6-membered heteroaryl selected from pyridinyl (preferably 2-pyridyl), pyrimidinyl (preferably 2- or 4-pyrimidinyl) and pyrazinyl (preferably 2-pyrazinyl). Most preferred is optionally substituted 2- or 4-pyrimidinyl.

In another embodiment, R$_3$ is selected from H, halo, OH, CN, optionally substituted C$_{1-6}$alkoxyl (preferably C$_{1-3}$alkoxyl more preferably C$_{1-2}$alkoxyl), optionally substituted C$_{1-6}$alkyl (preferably C$_{1-3}$alkyl more preferably C$_{1-2}$alkyl) and C$_{1-3}$haloalkyl preferably C$_{1-2}$haloalkyl including CF$_3$ and CHF$_2$.

In one embodiment X$_2$ is —C(C$_{1-3}$alkyl)=N—O— (preferably —C(Et)=N—O— or —C(Me)=N—O—) or —CH=N—O— and R$_3$ is H or an optionally substituted C$_{1-6}$alkyl (preferably C$_{1-3}$alkyl more preferably C$_{1-2}$alkyl).

In another embodiment n is 0 and X$_2$ is absent.

In yet another embodiment R$_3$ may be optionally substituted with one or more, preferably 1 or two independently selected optional substituents. Suitable optional substituents on R$_3$ include but are not limited to C$_{1-6}$alkyl (preferably C$_{1-3}$alkyl selected from methyl, ethyl, n-propyl and iso-propyl), halo (particularly Br, F and I), C$_{1-6}$haloalkyl (preferably C$_{1-2}$haloalkyl most preferably CF$_3$ and CHF$_2$), CN, OH, C$_{1-6}$alkoxy (preferably C$_{1-3}$alkoxy selected from methoxy, ethoxy, n-propoxy and iso-propoxy, most preferably methoxy), amino groups (including NH$_2$, NH(C$_{1-3}$alkyl) and N(C$_{1-3}$alkyl)$_2$), phenyl, =O, CO$_2$H, CO$_2$C$_{1-3}$alkyl, NHCOC$_{1-3}$alkyl, OSO$_2$C$_{1-3}$alkyl, 5-6-membered heteroaryl and 5-6-membered heterocyclyl (including morpholino and piperidinyl) where each optional substituent may be further optionally substituted.

In another embodiment R$_3$ is unsubstituted.

In one embodiment, ring "A" is an optionally substituted 6-membered aryl or an optionally substituted 5- or 6-membered heteroaryl group. In a further embodiment, ring "A" is an optionally substituted 5- or 6-membered heteroaryl group preferably containing nitrogen and even more particularly is selected from thiazolyl, thiadiazolyl, pyridyl, pyradizinyl, pyrimidinyl and pyrazinyl. In a particularly preferred embodiment ring "A" is an optionally substituted pyridyl, pyrimidinyl and pyrazinyl more preferred pyridyl and pyrimidinyl and most preferred pyrimidinyl.

In another embodiment, ring "B" is an optionally substituted C$_{3-7}$cycloalkyl or an optionally substituted 4-, 5-, 6- or 7-membered heterocyclic group, preferably an optionally substituted C$_{5-6}$cycloalkyl preferably cyclohexyl or an optionally substituted 5- or 6-membered heterocyclic group preferably 6-membered. In a further embodiment, ring "B" is a heterocylic group containing nitrogen and/or oxygen and includes dioxane, piperidinyl, pyrrolidinyl, azepane, isoxazolyl and morpholinyl and even more particularly is selected from piperidinyl, pyrrolidinyl, azepane, isoxazolyl and morpholinyl. Piperidinyl is particularly preferred.

In one embodiment ring "A" and/or ring "B" may be optionally substituted with one or more, preferably 1 or two optional substituents independently selected from C$_{1-3}$alkyl (preferably methyl), OH, =O, halo (preferably F) and C$_{1-3}$alkoxy, preferably methoxy.

In one embodiment ring "B" is substituted with the R$_1$XC(=O)/R$_2$ moiety in the para-position.

In a particular embodiment the group (R$_1$XC(=O)/R$_2$)-ring B—(X$_1$)$_m$-ring A- is of the formula:

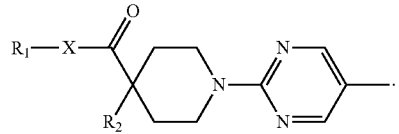

In a preferred embodiment X is O, R$_1$ is H and R$_2$ is C$_{1-6}$alkyl, preferably C$_{1-3}$alkyl selected from methyl, ethyl, n-propyl and iso-propyl, most preferably methyl.

In one embodiment there is provided a compound of Formula Ia or a salt thereof.

Formula Ia

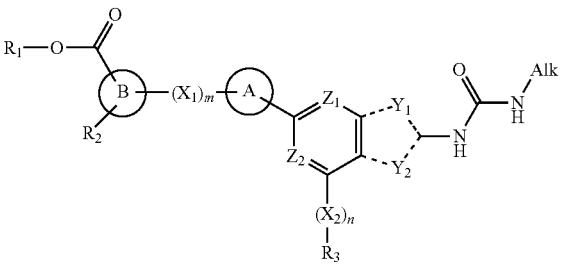

wherein R$_1$, R$_2$, R$_3$, X$_1$, X$_2$, Z$_1$, Z$_2$, Y$_1$, Y$_2$, ring A, ring B, Alk, m and n are as defined in Formula I.

In a further embodiment there is provided a compound of Formula Ia and salts thereof wherein R$_1$ is selected from H, C$_{1-6}$alkyl, C$_{2-6}$alkenyl C$_{2-6}$alkynyl, and M, more preferably R$_1$ is selected from H, C$_{1-3}$alkyl, C$_{2-3}$alkenyl and M, most preferably R$_1$ is H;

ring "A" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl, more preferably ring "A" is optionally substituted and is selected from saturated or unsaturated monocyclic $C_{3-7}$cycloalkyl, saturated or unsaturated monocyclic 3-7 membered heterocycle, $C_6$aryl and 5-6 membered heteroaryl;

ring "B" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl, more preferably ring "B" is optionally substituted and is selected from saturated or unsaturated monocyclic $C_{3-7}$cycloalkyl, saturated or unsaturated monocyclic 3-7 membered heterocycle, $C_6$aryl and 5-6 membered heteroaryl;

or ring "A" and ring "B" may join together to form a saturated or unsaturated fused bicyclic $C_{8-10}$cycloalkyl or saturated or unsaturated fused bicyclic 8-10 membered heterocyclyl;

$C_{2-3}$alkynylene (preferably $C_2$alkynyl), NH, N($C_{1-3}$alkyl), —C(O)NH—, —NHC(O)—, —C($C_{1-3}$alkyl)=N—O— (preferably —C(Me)=N—O—), and —CH=N—O—.

In one embodiment, there is provided a compound of Formula Ia wherein $R_3$ is selected from the group consisting of optionally substituted $C_{3-6}$cycloalkyl, optionally substituted 5-6 membered heterocycles (including tetrahydropyran, piperidinyl, morpholinyl and dihydroisoxazoyl), optionally substituted 5-6 membered heteroaryl (including pyrrolyl, pyridinyl, pyrimidinyl, pyrazinyl, oxazolyl, thiazolyl, thiadiazolyl, imidazolyl pyrazolyl, triazolyl) and optionally substituted 9 membered heterocycles (including pyrrolopyrimidine and furopyridine).

In another embodiment, there is provided a compound of Formula Ia wherein $R_3$ is selected from H, $C_{1-2}$alkyl, and $C_{1-2}$haloalkyl.

In a further embodiment there is provided a compound of Formula Ia-(i) or a salt thereof Formula Ia-(i)

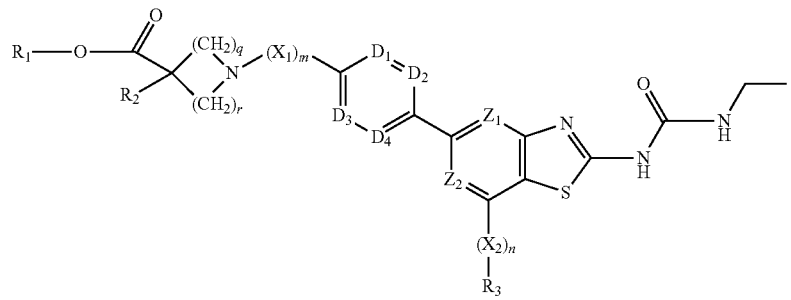

$Z_1$ and $Z_2$ are each independently selected from C—H, C—$C_{1-3}$alkyl, C—O$C_{1-3}$alkyl, C-halo, C-halo$C_{1-3}$alkyl, C—CN, or N, more preferably $Z_1$ and $Z_2$ are each independently selected from C—H, C-halo, C—OCH$_3$ or N;

$Y_1$ and $Y_2$ are each independently selected from N, O or S, more preferably N or S most preferably where $Y_1$ is N and $Y_2$ is S;

m is 0 and $X_1$ is a covalent bond or a fused ring bond preferably a covalent bond or when m is 1 then $X_1$ is preferably selected from CH$_2$, C(=O), NH or N(Me);

Alk is $C_{1-6}$alkyl, $C_{2-6}$alkenyl, $C_{2-6}$alkenyl, preferably $C_{1-6}$alkyl, more preferably $C_{1-3}$alkyl and most preferably ethyl; and —($X_2$)$_n$—$R_3$ is as previously defined.

In one embodiment, there is provided a compound of Formula Ia wherein $X_2$ is selected from —CH$_2$N($C_{1-3}$)alkyl-, wherein D1, D2, D3 and D4 are each independently selected from C—H, C—C1-3alkyl, C—C1-3alkoxy, C-halo and N;

each —(CH2)- moiety is optionally substituted with one or more substituents independently selected from C1-3alkyl, C1-3alkoxy, halo, haloC1-3alkoxy, haloC1-3alkyl, OH and =O;

q and r are each an integer independently selected from 0, 1, 2, 3, 4 and 5 provided that q and r together are at least 1 and no more than 6; and R1, R2, R3, X1, X2, Z1, Z2, m and n are as defined in Formula I or Ia.

In still another embodiment there is provided a compound of Formula Ia-(ii) or a salt thereof Formula Ia-(ii)

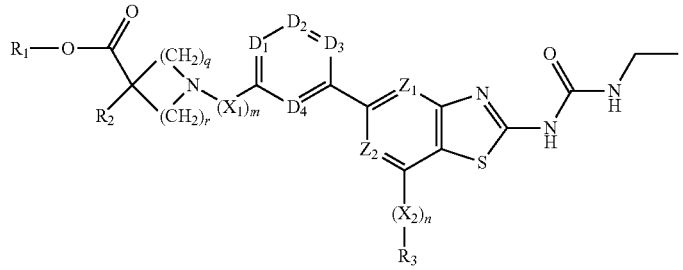

wherein
$D_1$, $D_2$, $D_3$ and $D_4$ are each independently selected from C—H, C—$C_{1-3}$alkyl, $C_{1-3}$alkoxy, C-halo and N;
each —($CH_2$)— moiety is optionally substituted with one or more substituents selected from $C_{1-3}$alkyl, $C_{1-3}$alkoxy, halo, halo$C_{1-3}$alkoxy, halo$C_{1-3}$alkyl, OH and =O;
q and r are each an integer independently selected from 0, 1, 2, 3, 4 and 5 provided that q and r together are at least 1 and no more than 6; and
$R_1$, $R_2$, $R_3$, $X_1$, $X_2$, $Z_1$, $Z_2$, m and n are as defined in Formula I or Ia.

In yet another embodiment there is provided a compound of Formula Ia-(iii) and salts thereof Formula Ia-(iii)

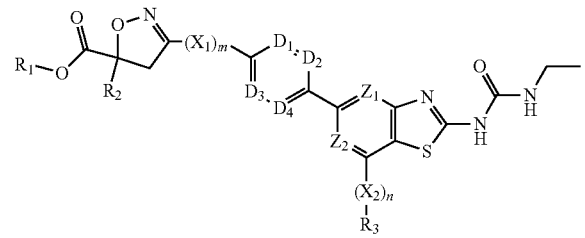

wherein
$D_1$, $D_2$, $D_3$ and $D_4$ are each independently selected from C—H, C—$C_{1-3}$alkyl, $C_{1-3}$alkoxy, C-halo and N; and
$R_1$, $R_2$, $R_3$, $X_1$, $X_2$, $Z_1$, $Z_2$, m and n are as defined in Formula I or Ia.

In yet another embodiment there is provided a compound of formula Ia-(iv) and salts thereof Formula Ia-(iv)

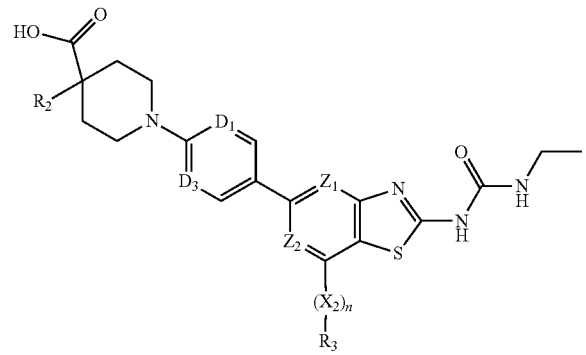

wherein $R_2$, $R_3$, $Z_1$, $Z_2$, $X_2$, n, $D_1$ and $D_2$ are as previously defined.

In a preferred embodiment $D_1$ and $D_2$ are independently N or CH, preferably at least one of $D_1$ or $D_2$ are N or both $D_1$ and $D_2$ are N.

In another preferred embodiment $R_2$ is $C_{1-3}$alkyl preferably methyl or ethyl.

In one embodiment, there is provided a compound of Formulae Ia, Ia-(i), Ia-(ii), Ia-(iii), Ia-(iv) or salts thereof wherein $R_1$ is H or $C_{1-6}$alkyl preferably $C_{1-3}$alkyl, most preferably $R_1$ is H;
$R_2$ is selected from $C_{1-6}$alkyl, preferably $C_{1-3}$alkyl most preferably methyl; $C_{2-6}$alkenyl, preferably $C_3$alkenyl; ($C_{1-6}$alkyl)$_r$$C_{3-7}$cycloalkyl, preferably ($C_{1-3}$alkyl)$_r$$C_{3-6}$cycloalkyl; ($C_{1-6}$alkyl)$_r$aryl, preferably ($C_{1-3}$alkyl)$_r$aryl, more preferably ($C_{1-3}$alkyl)$_r$phenyl; ($C_{1-6}$alkyl)$_r$heterocyclyl, preferably ($C_{1-3}$alkyl)$_r$heterocyclyl; $NH_2$; NH($C_{1-6}$alkyl), preferably NH($C_{1-3}$alkyl); N($C_{1-6}$alkyl)$_2$, preferably N($C_{1-3}$alkyl)$_2$; CN; OH; $C_{1-6}$alkoxy, preferably $C_{1-3}$alkoxy; $SO_2$H; $SO_2$$C_{1-6}$alkyl, preferably $SO_2$$C_{1-3}$alkyl; SH; S$C_{1-6}$alkyl, preferably S$C_{1-3}$alkyl; halo; halo$C_{1-6}$alkyl, preferably halo$C_{1-3}$alkyl, more preferably halo$C_{1-2}$alkyl; and wherein each alkyl, alkenyl, cycloalkyl, aryl and heterocyclyl is further optionally substituted with one or more substituents selected from $NH_2$, NH($C_{1-6}$alkyl), N($C_{1-6}$alkyl)$_2$, CN, OH, $C_{1-6}$alkoxy, $SO_2$H, $SO_2$$C_{1-6}$alkyl, SH, S$C_{1-6}$alkyl and halo;

$R_3$ is selected from an optionally substituted saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl, more preferably $R_3$ is selected from an optionally substituted saturated or unsaturated monocyclic 3-7 membered heterocycle, $C_6$aryl and 5-6 membered heteroaryl, most preferably $R_3$ is an optionally substituted 5-6 membered heteroaryl;

$D_1$, $D_2$, $D_3$ and $D_4$ are each independently selected from C—H or N, preferably one or two of any one of $D_1$, $D_2$, $D_3$ and $D_4$ are N and the remaining are C—H and even more preferably in the case of compounds of formulae Ia-(i), Ia-(iii) and Ia-(iv) $D_1$ and/or $D_3$ are/is preferably N and in the case of compounds of formula Ia-(ii) $D_1$ and/or $D_4$ are/is preferably N;

q and r are each an integer independently selected from 0, 1, 2, 3, 4 or 5 provided that q and r together are 3, 4 or 5, preferably q and r together are 4;

m is 0 and $X_1$ is a covalent bond or m is 1 and $X_1$ is selected from the group consisting of —C(O)NH— or —NHC(O)—, —NH—, —$CH_2$NH—, —NH$CH_2$—, —N($CH_3$)—, —$CH_2$N($CH_3$)—, —N($CH_3$)$CH_2$—, methylene, ethylene, propylene and C=O; preferably $X_1$ is selected from methylene, NH, N($CH_3$) and C(=O); and n is 0 and $X_2$ is a covalent bond or n is 1 and $X_2$ is selected from O, C(=O), $C_{1-6}$alkylene preferably $C_{1-3}$alkylene most preferably —$CH_2$—, $C_{1-6}$alkylO— preferably $C_{1-3}$alkylO— most preferably —$CH_2$O—, $C_{1-6}$alkylNH— preferably $C_{1-3}$alkylNH— most preferably —$CH_2$NH—, $C_{1-6}$alkylN($C_{1-3}$alkyl)- preferably $C_{1-3}$alkylN($C_{1-3}$alkyl)- most preferably —$CH_2$N(Me)-, $C_{2-6}$alkenylene preferably $C_{2-3}$alkenylene, $C_{2-6}$alkynylene preferably $C_{2-3}$alkynylene, —$CH_2$N($C_{1-3}$alkyl)-, NH, N($C_{1-3}$alkyl) preferably N(Me), —C(O)NH—, —C(O)N($C_{1-3}$alkyl)- preferably —C(O)N(Me)-, —NHC(O)—, —C($C_{1-3}$alkyl)=N—O— (preferably —C(Et)=N—O— or —C(Me)=N—O—) and —CH=N—O—; preferably $X_2$ is —C($C_{1-3}$alkyl)=N—O— (preferably —C(Et)=N—O— or —C(Me)=N—O—) or —CH=N—O— and $R_3$ is H or an optionally substituted $C_{1-6}$alkyl (preferably $C_{1-3}$alkyl more preferably $C_{1-2}$alkyl).

In one embodiment $Z_1$ and $Z_2$ are independently selected from C—H and N. In another embodiment $Z_1$ and $Z_2$ are each C—H. In yet another embodiment one of $Z_1$ or $Z_2$ is N and the other is C—H. In still another embodiment $Z_1$ and $Z_2$ are each independently selected from C—H, C-halo and C—$C_{1-3}$alkoxy (preferably methoxy) more preferably one of $Z_1$ or $Z_2$ is C—H and the other is C-halo more preferably C—F or C—$C_{1-3}$alkoxy preferably methoxy.

In another embodiment there is provided a compound of Formula Ib and salts thereof

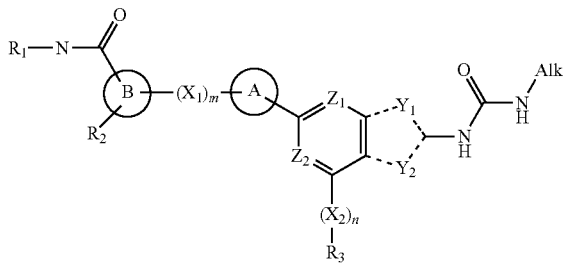

Formula Ib wherein $R_1, R_2, R_3, X_1, X_2, Z_1, Z_2, Y_1, Y_2$, ring A, ring B, Alk, m and n are as defined in Formula I.

In a further embodiment there is provided a compound of Formula Ib and salts thereof wherein
R1 is selected from H; C1-6alkyl, preferably C1-3alkyl; S(O)2OH or S(O)2-C1-6alkyl, preferably S(O)2-C1-3alkyl;
ring "A" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl, more preferably ring "A" is optionally substituted and is selected from saturated or unsaturated monocyclic $C_{3-7}$cycloalkyl, saturated or unsaturated monocyclic 3-7 membered heterocycle, $C_6$aryl and 5-6 membered heteroaryl;
ring "B" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl, more preferably ring "B" is optionally substituted and is selected from saturated or unsaturated monocyclic $C_{3-7}$cycloalkyl, saturated or unsaturated monocyclic 3-7 membered heterocycle, $C_6$aryl and 5-6 membered heteroaryl;
or ring "A" and ring "B" may join together to form a saturated or unsaturated fused bicyclic $C_{8-10}$cycloalkyl or saturated or unsaturated fused bicyclic 8-10 membered heterocyclyl;
$Z_1$ and $Z_2$ are each independently selected from C—H, C—$C_{1-3}$alkyl, C—O$C_{1-3}$alkyl, C-halo, C-halo$C_{1-3}$alkyl, C—CN, or N, more preferably $Z_1$ and $Z_2$ are each independently selected from C—H, C-halo or N;

$Y_1$ and $Y_2$ are each independently selected from N, O or S, more preferably N or S;
m is 0 and $X_1$ is a covalent bond or a fused ring bond; and
Alk is $C_{1-6}$alkyl, $C_{2-6}$alkenyl, $C_{2-6}$alkenyl, preferably $C_{1-6}$alkyl, more preferably $C_{1-3}$alkyl and most preferably ethyl.

In one embodiment, there is provided a compound of formula Ib wherein $X_2$ is —$CH_2N(C_{1-3})$alkyl-, $C_{2-3}$alkynylene (preferably $C_2$alkynyl), NH, N($C_{1-3}$alkyl), —C(O)NH—, —NHC(O)—, —C($C_{1-3}$alkyl)=N—O— (preferably —C(Me)=N—O—), or —CH=N—O—.

In one embodiment, there is provided a compound of formula Ib wherein
$R_3$ is selected from the group consisting of optionally substituted $C_{5-6}$cycloalkyl, optionally substituted 5-6 membered heterocycles including tetrahydropyran, piperidinyl and morpholinyl, optionally substituted 5-6 membered heteroaryl including pyridinyl, pyrimidinyl, pyrazinyl, oxazolyl, thiazolyl, thiadiazolyl, imidazolyl pyrazolyl, triazolyl, and optionally substituted 9 membered heterocycles including pyrrolopyrimidine and furopyridine.

In another embodiment, there is provided a compound of formula Ib wherein $R_3$ is selected from H, $C_{1-2}$alkyl, $C_{1-2}$haloalkyl, In another embodiment there is provided a compound of Formula Ib-(i) or a salt thereof

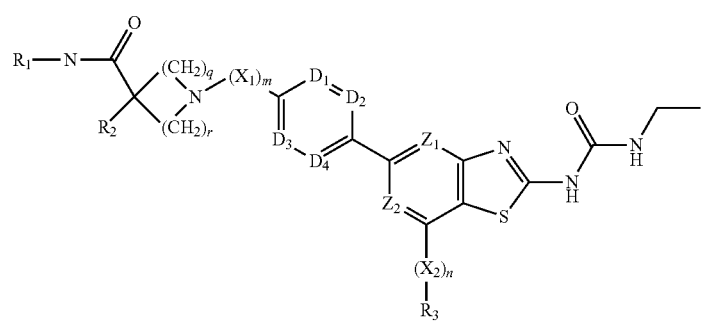

Formula Ib-(i)

wherein
$D_1, D_2, D_3$ and $D_4$ are each independently selected from C—H, C—$C_{1-3}$alkyl, C-halo or N;
each —(CH$_2$)— moiety is optionally substituted with one or more substituents selected from $C_{1-3}$alkyl, $C_{1-3}$alkoxy, halo, halo$C_{1-3}$alkoxy, halo$C_{1-3}$alkyl, OH and =O;
q and r are each an integer independently selected from 0, 1, 2, 3, 4 and 5 provided that q and r together are at least 1 and no more than 6; and
$R_1, R_2, R_3, X_1, X_2, Z_1, Z_2$, m and n are as defined for Formula I or Ib.

In one embodiment, there is provided compounds of Formula Ib-(i) wherein
$R_1$ is H; $C_{1-6}$alkyl, preferably $C_{1-3}$alkyl; S(O)$_2$OH or S(O)$_2$—$C_{1-6}$alkyl, preferably S(O)$_2$—$C_{1-3}$alkyl;
$R_2$ is selected from $C_{1-6}$alkyl, preferably $C_{1-3}$alkyl; $C_{2-6}$alkenyl, preferably $C_3$alkenyl; ($C_{1-6}$alkyl)$_t$$C_{3-7}$cycloalkyl, preferably ($C_{1-3}$alkyl)$_t$$C_{3-6}$cycloalkyl; ($C_{1-6}$alkyl)$_t$aryl, preferably ($C_{1-3}$alkyl)$_t$aryl, more preferably ($C_{1-3}$alkyl)$_t$phenyl; ($C_{1-6}$alkyl)$_t$heterocyclyl, preferably ($C_{1-3}$alkyl)$_t$heterocyclyl; NH$_2$; NH($C_{1-6}$alkyl), preferably NH($C_{1-3}$alkyl); N($C_{1-6}$alkyl)$_2$, preferably N($C_{1-3}$alkyl)$_2$; CN; OH; $C_{1-6}$alkoxy, preferably $C_{1-3}$alkoxy; SO$_2$H; SO$_2$$C_{1-6}$alkyl, preferably SO$_2$$C_{1-3}$alkyl; SH; S$C_{1-6}$alkyl, preferably S$C_{1-3}$alkyl; halo; halo$C_{1-6}$ alkyl, preferably haloC$_{1-3}$alkyl, more preferably haloC$_{1-2}$ alkyl; wherein t is an integer 0 or 1 and wherein each alkyl, alkenyl, cycloalkyl, aryl and heterocyclyl is further optionally substituted with one or more substituents selected from NH$_2$, NH(C$_{1-6}$alkyl), N(C$_{1-6}$alkyl)$_2$, CN, OH, C$_{1-6}$alkoxy, SO$_2$H, SO$_2$C$_{1-6}$alkyl, SH, SC$_{1-6}$alkyl and halo;

R$_3$ is selected from an optionally substituted saturated or unsaturated monocyclic C$_{3-7}$cycloalkyl, saturated or unsaturated monocyclic 3-7 membered heterocycle, saturated or unsaturated fused bicyclic C$_{8-10}$cycloalkyl, saturated or unsaturated fused bicyclic 8-10 membered heterocyclyl, C$_{6-10}$aryl and 5-10 membered heteroaryl, more preferably R$_3$ is selected from an optionally substituted saturated or unsaturated monocyclic 3-7 membered heterocycle, C$_6$aryl and 5-6 membered heteroaryl, most preferably R$_3$ is an optionally substituted 5-6 membered heteroaryl;

D$_1$, D$_2$, D$_3$ and D$_4$ are each independently selected from C—H or N, preferably one or two of any one of D$_1$, D$_2$, D$_3$ and D$_4$ are N and the remaining are C—H;

q and r are each an integer independently selected from 0, 1, 2, 3, 4 or 5 provided that q and r together are 3, 4 or 5, preferably q and r together are 4;

m is 0 and X$_1$ is a covalent bond; and n is 0 and X$_2$ is a covalent bond.

In one embodiment Z$_1$ and Z$_2$ are selected from C—H and N. In another embodiment Z$_1$ and Z$_2$ are each C—H. In yet another embodiment one of Z$_1$ or Z$_2$ is N and the other is C—H. In still another embodiment Z$_1$ and Z$_2$ are selected from C—H and C-halo, preferably one of Z$_1$ or Z$_2$ is C—H and the other is C-halo more preferably C—F.

In another embodiment of the compounds of any one of formulae I, Ia, Ia-(i), Ia-(ii), Ia-(iii), Ia-(iv), Ib, and Ib-(i), (X$_2$)$_n$—R$_3$ is a 5-6 membered N-containing heteroaryl or an oxime group (ie where X$_2$ is selected from —C(C$_{1-3}$alkyl)=N—O— and —CH=N—O— and n is one) in which at least one nitrogen of the heteroaryl group or oxime group is adjacent to the point of attachment to the six membered ring. For example, if (X$_2$)$_n$—R$_3$ is a pyridine then the nitrogen of the pyridine is ortho to the carbon attached to the six membered ring.

In another embodiment the compound of Formula I is a compound or salt thereof selected from the group consisting of any one of compound examples 1 to 234.

In another embodiment, the compounds of Formula I demonstrate enhanced solubility, including high (H) to very high (VH) solubility at physiological pH 7.4. In a particularly preferred embodiment the solubility of the compounds is very high (VH) at physiological pH 7.4. The solubility of illustrative compounds of the invention is provided in the following table.

TABLE 1

Compound Solubility at pH 7.4

| Compound No. | Solubility (pH 7.4) | Solubility Range |
|---|---|---|
| 171, 174, 178 | 3.125 | L |
| 2, 16, 71, 92, 169, 170, 179, 180, 184, 185, 191 | 6.25 | L |
| 60, 65, 100, 104, 127, 129, 167, 172, 177 | 12.5 | M |
| 35, 42, 53, 58, 75, 112, 128, 168, 175, 216 | 25 | M |
| 34, 36, 125, 146, 173, 196, 220 | 50 | M |
| 8, 10, 13, 46, 90, 113, 121, 126, 131, 134, 152, 153, 176, 183, 203, 207, 208, 223, 229 | 100 | M |
| 33, 57, 77, 81, 82, 83, 84, 85, 130, 154, 162, 182, 209, 210, 218, 228 | 200 | M |
| 3, 6, 7, 32, 43, 48, 55, 63, 73, 78, 80, 103, 114, 115, 117, 118, 119, 120, 132, 135, 137, 144, 151, 155, 159, 190, 205, 213, 214, 215, 217, 227 | 400 | H |

TABLE 1-continued

Compound Solubility at pH 7.4

| Compound No. | Solubility (pH 7.4) | Solubility Range |
|---|---|---|
| 1, 4, 5, 9, 11, 12, 14, 15, 17, 18, 19, 20, 21, 22, 23, 24, 25, 26, 27, 28, 29, 30, 31, 38, 40, 41, 44, 45, 47, 49, 50, 51, 52, 54, 56, 59, 61, 62, 64, 66, 67, 68, 69, 70, 72, 74, 76, 79, 86, 87, 88, 89, 91, 93, 94, 95, 96, 97, 98, 99, 101, 102, 105, 106, 107, 108, 109, 110, 116, 122, 123, 124, 133, 136, 138, 139, 140, 141, 142, 143, 145, 147, 148, 149, 150, 156, 157, 158, 160, 161, 163, 164, 165, 166, 181, 186, 187, 188, 189, 192, 193, 194, 195, 197, 198, 199, 200, 201, 202, 204, 206, 211, 212, 219, 221, 222, 224, 225, 226 | ≥800 | VH |

L = "Low" solubility <12.5 µg/mL;
M = "Moderate" solubility ≥12.5 µg/mL to <400 µg/mL;
H = "High" solubility ≥400 µg/mL to <800 µg/mL; and
VH = "Very High" solubility ≥800 µg/mL.

For comparative purposes, the inventors determined the solubility of the most active compounds, that is those showing "A" range activity (MIC activity against *E. faecalis* of <0.25 µg/mL) in applicant's earlier filed related applications, WO2007/148093 and WO2009/074812. In each case, those compounds only demonstrated low to moderate solubility at pH7.4 as shown in the following table.

TABLE 2

Comparator Compound Solubility at pH 7.4

| PCT Publication No. | Compound No. | Solubility Range (pH 7.4) |
|---|---|---|
| WO2007/148093 | 95, 130, 161, 176 | Low |
| WO2007/148093 | 10, 27, 33, 34, 35, 36, 41, 51, 58, 59, 69, 70, 71, 88, 89, 91, 92, 96, 99, 100, 101, 103, 104, 107, 110, 111, 112, 113, 114, 115, 116, 117, 118, 119, 121, 122, 123, 124, 125, 126, 127, 131, 133, 134, 136, 138, 139, 142, 154, 163, 167, 174, 175, 176, 177, 179 | Moderate |
| WO2009/074812 | 79 | Low |
| WO2009/074812 | 44 | Moderate |

L = "Low" solubility <12.5 µg/mL;
M = "Moderate" solubility ≥12.5 µg/mL to <400 µg/mL;
H = "High" solubility ≥400 µg/mL to <800 µg/mL; and
VH = "Very High" solubility ≥800 µg/mL.

Selected compounds of the invention were also tested to determine their maximum solubilities in the physiologically acceptable pH range of pH 4 to pH 9. The solubilities of each compound was measured at pH 4, 7.4 and 9 and the maximum solubility (µg/mL) is set out in the table together with the pH at which this solubility was demonstrated.

TABLE 3

Maximum solubilities at physiologically acceptable pH of compounds according to the present invention

| Compound No. | Max Solubility (µg/mL) | pH | Solubility Range |
|---|---|---|---|
| 178 | 6.25 | 4/9 | L |
| 191 | 6.25 | 7.4/9 | L |
| 92, 179 | 12.5 | 4/9 | M |
| 65 | 12.5 | 7.4 | M |
| 127 | 25 | 9 | M |
| 58 | 50 | 9 | M |

TABLE 3-continued

Maximum solubilities at physiogically acceptable pH
of compounds according to the present invention

| Compound No. | Max Solubility (μg/mL) | pH | Solubility Range |
|---|---|---|---|
| 71, 216 | 50 | 4 | M |
| 34, 42, 75, 112 | 100 | 9 | M |
| 90, 113 | 100 | 7.4/9 | M |
| 196 | 100 | 9 | M |
| 210, 228 | 200 | 7.4/9 | M |
| 208, 229 | 200 | 9 | M |
| 80, 114, 227 | 400 | 7.4 | H |
| 36, 46, 57, 60, 77, 81, 153, 154, 162, 207, 209, 220, 223 | 400 | 9 | H |
| 32, 159, 190 | 400 | 7.4/9 | H |
| 95, 96, 122, 186 | ≥800 | 7.4 | VH |
| 33, 35, 43, 48, 53, 55, 63, 73, 78, 82, 83, 84, 85, 103, 115, 118, 119, 120, 121, 125, 126, 151, 152, 155, 182, 187, 203, 205, 213, 214, 215, 217, 218, | ≥800 | 9 | VH |
| 1, 4, 18, 31, 38, 40, 41, 44, 45, 47, 49, 50, 51, 52, 54, 56, 59, 61, 62, 64, 66, 67, 68, 69, 70, 72, 74, 76, 79, 86, 87, 88, 89, 91, 93, 94, 97, 105, 106, 107, 108, 109, 110, 116, 123, 124, 136, 140, 141, 142, 143, 148, 149, 150, 156, 157, 158, 160, 161, 163, 166, 181, 188, 189, 190, 192, 193, 194, 195, 197, 198, 199, 200, 201, 202, 204, 206, 211, 212, 219, 221, 222, 224, 225, 226 | ≥800 | 7.4/9 | VH |

L = "Low" solubility <12.5 μg/mL;
M = "Moderate" solubility ≥12.5 μg/mL to <400 μg/mL;
H = "High" solubility ≥400 μg/mL to <800 μg/mL; and
VH = "Very High" solubility ≥800 μg/mL.

Without wishing to be bound by theory, it is believed that the alpha-substituted carboxylate or amide moiety on ring "B" provides compounds with enhanced solubility and/or an advantageous pharmacokinetic profile. The pharmacokinetic IV and oral profile of selected illustrative compounds was determined in an animal model (mouse and/or rat assay) including non-alpha substituted comparator compounds A and B (FIG. 1).

As shown in FIGS. 2 to 8, alpha-substituted compounds of Formula (I) show an advantageous pharmacokinetic profile as demonstrated by their increased bioavailability and decreased clearance rates. The compounds also demonstrate similar IV and oral pharmacokinetic profiles thereby offering the potential for efficacious IV-oral dosing.

Accordingly, in one embodiment the compounds are administered intravenously or orally or by a combination thereof. In another embodiment the compounds are formulated for intravenous (IV) administration. In still another embodiment the compounds are formulated for oral administration.

In another embodiment the compound of Formula I may be in the form of a salt including pharmaceutically acceptable salts.

Illustrative examples of salt forms are provided in the following table.

TABLE 4

Salt forms of Compound No 4

| Cpd No | $R_1$ | Solubility Range (pH 7.4) |
|---|---|---|
| 4 | H | VH |
| 4 | $NH_4$ | M |
| 4 | K | VH |
| 4 | Na | VH |

The salts of the compound of Formula I are preferably pharmaceutically acceptable, but it will be appreciated that non-pharmaceutically acceptable salts also fall within the scope of the present invention, since these are useful as intermediates in the preparation of pharmaceutically acceptable salts.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, $1^{st}$ edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid.

It will be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

This invention also encompasses prodrugs of compounds of formula I. Compounds of formula I having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

The present invention provides a method for the treatment of a bacterial infection comprising administration of a compound of Formula I or a pharmaceutically acceptable salt thereof to a subject suffering from said infection.

The compounds of the present invention may be administered by any suitable means, for example, orally, parenterally, such as by subcutaneous, intravenous, intramuscular, or intracisternal injection or infusion techniques (e.g., as sterile injectable aqueous or non-aqueous solutions or suspensions).

In a preferred embodiment the administration is intravenous administration, oral administration or a combination thereof.

The present invention also provides compound of Formula I or a pharmaceutically acceptable salt thereof for use in the treatment of a bacterial infection.

There is also provided a composition comprising a compound of Formula I or a salt thereof. Preferably, the composition further comprises a pharmaceutically acceptable carrier, diluent or excipient.

The compositions of the present invention may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

The term "effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In the treatment or prevention of bacterial infections, an appropriate dosage level will generally be about 0.01 to 500 mg per kg patient body weight per day which can be administered in single or multiple doses. For oral administration, the compositions are preferably provided in the form of tablets containing 1.0 to 1000 milligrams of the active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the invention may be generally prepared by coupling an intermediate of Formula IIa with an L—(X$_2$)$_n$—R$_3$ precursor moiety to form compounds of Formula I

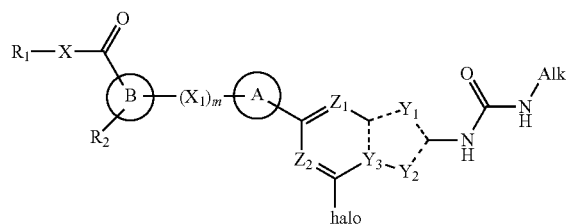

Formula IIa or alternatively coupling an intermediate of Formula IIb

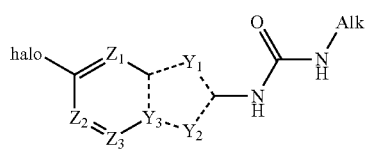

Formula IIb with a precursor moiety of general formula

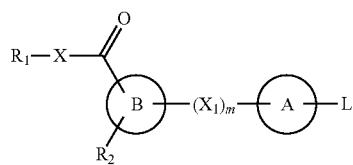

to form compounds of Formula I;

wherein R$_1$, X, R$_2$, (X$_1$)$_m$, ring A, ring B, Z$_1$, Z$_2$, Y$_1$, Y$_2$, Alk, (X$_2$)$_n$ and R$_3$ are as defined for Formula I and L is a reactive group.

While those skilled in the art will be familiar with suitable coupling conditions and selection of moiety L, particularly suitable coupling conditions include Suzuki and Stille coupling conditions. It will also be understood that compounds of Formula I having X—R$_1$ is OH may be formed via an ester protected intermediate i.e. X—R$_1$ is O-alkyl or other suitable protecting group and subsequently deprotected.

Compounds of the invention may also be generally prepared by coupling a precursor of Formula IIIa with a boronic acid intermediate of Formula IVa under suitable coupling conditions to form compounds of Formula I

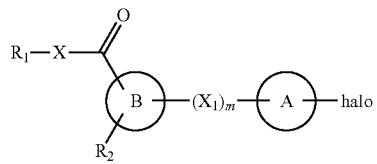

Formula IIIa

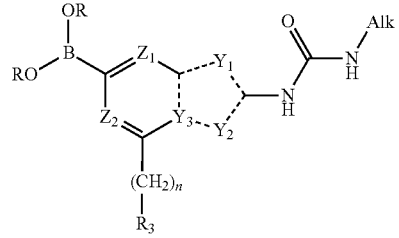

Formula IVa or alternatively comprising the step of coupling a boronic acid intermediate of Formula IVb with a halo-(X$_2$)$_n$—R$_3$ precursor moiety

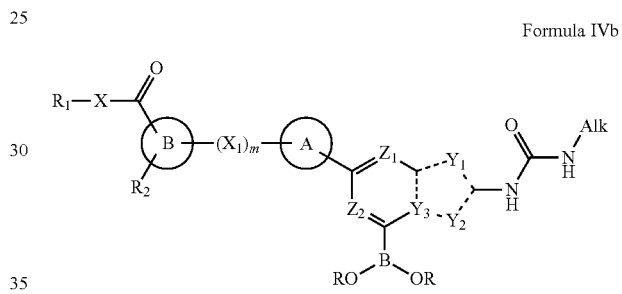

Formula IVb to form a compound of Formula I;

wherein R$_1$, X, R$_2$, (X$_1$)$_m$, ring A, ring B, Z$_1$, Z$_2$, Y$_1$, Y$_2$, Alk, (X$_2$)$_n$ and R$_3$ are as defined for Formula I and B(OR)$_2$ is a boronic acid (B(OH)$_2$) or a pinacolborane.

Suitable coupling conditions and reactive groups L will be familiar to those skilled in the art though they may include Suzuki coupling and Stille coupling conditions. Suitable reactive groups L under Suzuki coupling conditions include boronic acid moieties B(OR)$_2$ such as boronic acid B(OH)$_2$ and pinacolborane. Suitable reactive groups L under Stille coupling conditions include stannylated moieties such as Sn(Bu)$_3$.

The skilled addressee will appreciate that the halo moiety functions as a leaving group under the coupling conditions particularly described and may therefore be interchanged with suitable alternative leaving groups such as triflate (CF$_3$SO$_3$—).

The skilled addressee will also understand that the leaving group such as halo and the reactive group L may be present on either the precursor or intermediate. That is, when the intermediate comprises a leaving group such as halo, the reactive group will be present on the precursor moiety to which the intermediate is being coupled and in the alternative, when the precursor comprises a leaving group, the reactive group will be present on the intermediate such that the precursor and intermediate may be coupled under suitable conditions such as those previously described.

In one embodiment there is provided an intermediate selected from Formulae IIa, IIb, IVa and IVb.

In one embodiment there is provided a precursor of Formula IIIa or of general formula

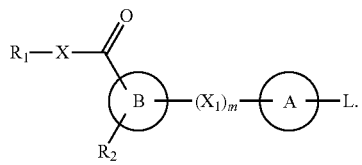

In another embodiment the compound of Formula I is formed by coupling a precursor selected from the group consisting of any one of precursor examples 1 to 32 with an intermediate selected from the group consisting of any one of intermediate examples 1 to 17 under coupling conditions.

In yet another embodiment there is provided an intermediate selected from the group consisting of any one of intermediate examples 1 to 17.

In still another embodiment there is provided a precursor selected from the group consisting of any one of precursor examples 1 to 32.

Examples

Those skilled in the art will appreciate that the invention described herein is susceptible to variations and modifications other than those specifically described. The invention will now be described without limitation by reference to the examples which follow.

Compound Synthesis $^1$H NMR spectra were recorded on either a Brüker Avance DRX 400, AC 200 or AM 300 spectrometer. Spectra were recorded in deuterated solvents (CDCl$_3$, MeOD, DMSO, CD$_3$CN, or Acetone) using the residual solvent peak as a reference. Chemical shifts are reported on the δ scale in parts per million (ppm) using the following conventions to assign the multiplicity: s (singlet), d (doublet), t (triplet), q (quartet), p (pentet), m (multiplet) and prefixed br (broad). Mass spectra (ESI) were recorded on either a Micromass Platform QMS or Thermo Finnigan LCQ Advantage spectrometer. Flash chromatography was performed on 40-63 µm silica gel 60 (Merck No. 9385). Automated flash chromatography was performed either on a Combi-Flash™ purification system using Combi-Flash™ silica gel columns or on a Biotage SP4 purification system using either GraceResolv™ silica gel cartridges, Grace Reveleris™ C-18 reverse phase silica gel cartridges or Biotage SNAP™ C-18 reverse phase silica gel cartridges. Preparative HPLC was carried out using either a Gilson 322 pump with a Gilson 215 liquid handler and a HP1100 PDA detector or an Agilent 1200 Series mass detected preparative LCMS using a Varian XRs C-18 100×21.2 mm column. Unless otherwise specified, the HPLC systems employed Phenomenex C8(2) columns using either acetonitrile or acetonitrile containing 0.06% TFA in water, water containing 0.1% TFA or water containing 0.1% formic acid.

During the reactions a number of the moieties may need to be protected. Suitable protecting groups are well known in industry and have been described in many references such as Protecting Groups in Organic Synthesis, Greene T W, Wiley-Interscience, New York, 1981.

The abbreviations used in the Examples are as follows unless indicated otherwise:

| | |
|---|---|
| Ac: | acetyl |
| ACN: | acetonitrile |
| AIBN: | 2-[(E)-(1-cyano-1-methyl-ethyl)azo]-2-methyl-propanenitrile) |
| CEM: | CEM Corporation |
| conc.: | concentrated |
| DCM: | dichloromethane |
| DIPEA: | N,N-diisopropylethylamine |
| DIEA: | N,N-diisopropylethylamine |
| DMAP: | N,N-dimethylpyridin-4-amine |
| DMF: | N,N-dimethylformamide |
| DMSO: | dimethylsulfoxide |
| EtOAc: | ethyl Acetate |
| Et2O: | diethylether |
| EtOH: | ethanol |
| ESI: | electrospray ionisation |
| h: | hour(s) |
| HATU: | 2-(7-Aza-1H-benzotriazole-1-yl)-1,1,3,3-tetramethyluronium hexafluorophosphate |
| HPLC: | high performance liquid chromatography |
| IPA: | propan-2-ol |
| LCMS: | liquid chromatography coupled mass spectrometry |
| LDA: | lithium diisopropylamide |
| LHMDS: | lithium bis(trimethylsilyl)amide |
| min. | minute(s) |
| MeCN: | methylcyanide |
| MeI: | methyliodide |
| MeOH: | methanol |
| MS: | mass spectrometry |
| NBS: | N-bromosuccinimide |
| NMR: | nuclear magnetic resonance |
| NOE: | nuclear overhauser effect |
| PTFE: | poly(tetrafluoroethylene) |
| s: | second(s) |
| rt: | room temperature |
| THF: | tetrahydrofuran |
| TLC: | thin-layer chromatography |
| TMEDA: | N,N,N',N'-tetramethylethylenediamine |

Preparation of Intermediates

Intermediate 1: [2-(ethylcarbamoylamino)-7-(2-pyridyl)-1,3-benzothiazol-5-yl]boronic acid

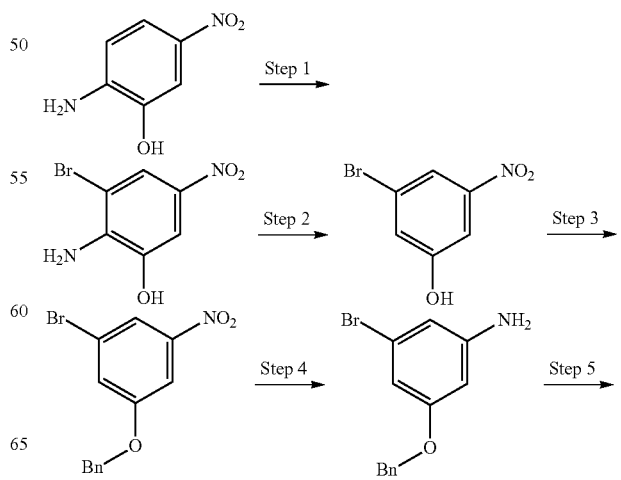

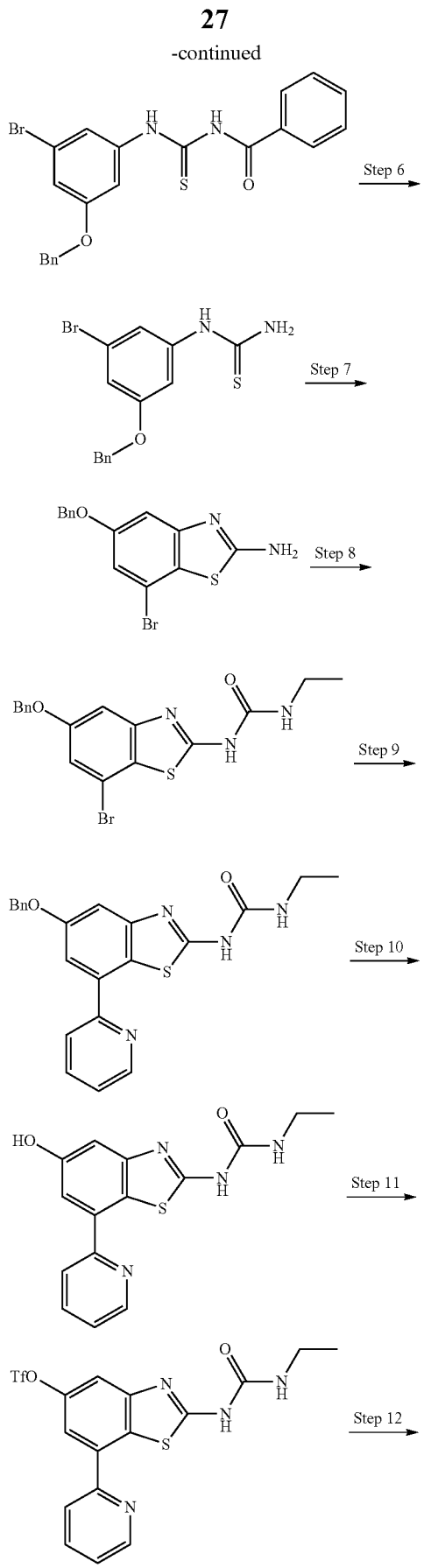

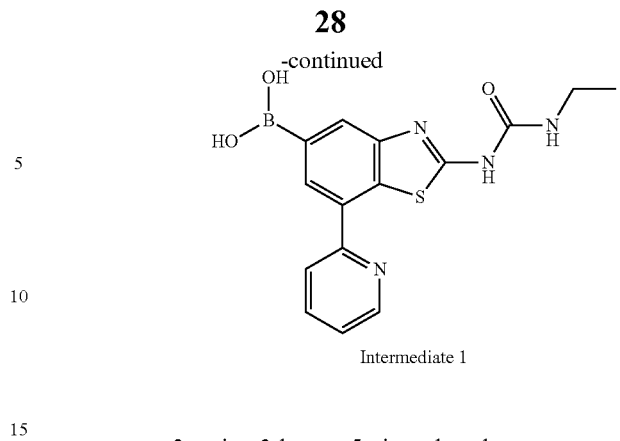

Intermediate 1

2-amino-3-bromo-5-nitro-phenol

To a solution of 2-amino-5-nitro-phenol (500 g, 3.24 mol) in ACN (12 L) was added bromine (290 mL, 5.63 mol) drop wise over a period of 30 min under stirring. The resulting mixture was stirred at 30-35° C. for 1 h. After the completion of the reaction (by TLC), solvent was evaporated till dryness. Hexane was added (2 L) and the mixture evaporated to remove solvent traces. Hexane (5 L) was added again to the residue and the mixture stirred for 1 h then filtered. The resulting solid (1102 g) was washed with hexane (2 L). The residue was added to ice-cold water (2.5 L) followed by addition of a saturated solution of sodium thiosulfate (2.5 L) and extraction with EtOAc (2×10 L). The combined organic layers were washed with brine, dried ($Na_2SO_4$), filtered and concentrated at 40-45° C. under reduced pressure to obtain the desired product (643 g crude yield 85%).

3-bromo-5-nitro-phenol

To a cooled solution (−10° C.) of 2-amino-3-bromo-5-nitro-phenol (643 g, 2.76 mol) in EtOH (13 L) was added conc. $H_2SO_4$ (515 mL, 9.97 mol) over a period of 35 min at −10 to −2° C. The reaction mixture was allowed to warm to rt then heated to 50-55° C. followed by portion-wise addition of $NaNO_2$ (671 g, 9.72 mol) over 30 min then heated at reflux for 3 h. After completion of reaction (by TLC), the mixture was concentrated to 3 L and cooled to 0° C. followed by the addition of chilled water (5 L) and extraction with EtOAc (3×6 L). The combined organic layers were washed with brine, dried over anhydrous $Na_2SO_4$, filtered and concentrated under reduced pressure to give a semi-solid residue. The residue was treated with 25% ether-hexane mixture (6 L) and stirred for 1 h. The solid was filtered and washed with hexane (3 L) to obtain the desired product (505 g, 84%).

1-benzyloxy-3-bromo-5-nitro-benzene

To a solution of 3-bromo-5-nitro-phenol (770 g, 3.53 mol) in acetone (10 L) was added pulverized $K_2CO_3$ (2.45 kg, 17.75 mol) in one portion at rt followed by addition of benzyl bromide (632 mL, 5.32 mol) over a period of 30 min. The resulting reaction mixture was stirred for 15 min then heated at reflux for 3 h. After reaction completion (by TLC), the reaction mixture was filtered through celite and the acetone distilled off. The crude residue thus obtained was purified over silica gel (60-120 M) using EtOAc:hexane (5:95) to obtain the desired product (551 g, 51%).

3-benzyloxy-5-bromo-aniline

To a solution of 1-benzyloxy-3-bromo-5-nitro-benzene (551 g, 1.78 mol) in THF (11 L) was added $SnCl_2.2H_2O$ (2.17 kg, 9.62 mol) in one portion at rt. The reaction mixture was refluxed for 3 h. After completion of reaction (by TLC) the reaction mixture was cooled to 0-5° C. and basified with saturated NaHCO$_3$ solution then extracted with EtOAc (4×5 L). The combined organic layers were washed with brine, dried over anhydrous Na$_2$SO$_4$, filtered and concentrated under reduced pressure to obtain a crude liquid product (480 g, 97%) that was carried forward to the next step without further purification.

N-[(3-benzyloxy-5-bromophenyl)carbamothioyl]benzamide

To a solution of 3-benzyloxy-5-bromo-aniline (480 g, 1.73 mol) in acetone (10 L) was added benzoylisothiocyanate (280 mL, 2.08 mol) at rt. After stirring the reaction mixture for 15 min, solid precipitated out and stirring was continued for 30 min at rt. After completion of reaction (by TLC), acetone was distilled off. Hexane (2 L) was added and again concentrated. To the concentrated solid was added hexane (4 L) heated to 40° C. for 30 min under stirring and the solid filtered. The solid was washed with hexane (2×2 L) to obtain the desired product (648 g, 85%).

(3-benzyloxy-5-bromo-phenyl)thiourea

To a solution of N-[(3-benzyloxy-5-bromo-phenyl)carbamothioyl]benzamide (648 g, 1.47 mol) in THF (12 L) was added NaOH solution (300 g, 7.5 mol in 3 L H$_2$O) at rt. The reaction mixture was heated up to 69 to 70° C. overnight. After completion of reaction (by TLC), the THF layer was decanted off and the aqueous layer extracted with EtOAc (3×2 L). The combined organic layer (THF+EtOAc) was washed with brine, dried over anhydrous Na$_2$SO$_4$, filtered and concentrated under reduced pressure. The crude residue was treated with mixture of Et$_2$O and hexane (5:95, 3.0 L), filtered, washed with hexane and dried under high vacuum to obtain the desired product (387 g, 78%).

5-benzyloxy-7-bromo-1,3-benzothiazol-2-amine

To an ice-cold suspension of (3-benzyloxy-5-bromo-phenyl)thiourea (372 g, 1.10 mol) in acetonitrile (6 L) was added dropwise a solution of bromine (65 mL 1.26 mol in 50 mL acetonitrile) over a period of 30 min. The reaction mixture was stirred for 30 min at 0-5° C. then slowly allowed to come to rt, whereby a solid precipitated out. The resulting mixture was stirred at rt for 1 h. After completion of reaction (by TLC), the solid was filtered off and washed extensively with hexane (2×3 L). The solid residue was taken up in ice water, basified with aq. NH$_3$ (pH 10-12) and stirred for 30 min at 5-10° C. The resulting solid was filtered off washed with water and dried under high vacuum to obtain the desired product (216 g, 59%). $^1$H-NMR (DMSO-d$_6$): δ 5.12 (s, 2H), 6.92 (d, J=2.40 Hz, 1H), 6.98 (d, J=2.0 Hz, 1H), 7.30-7.45 (m, 5H) and 7.69 (br s, 2H). LCMS: 334.79 [M+H]$^+$.

1-(5-benzyloxy-7-bromo-1,3-benzothiazol-2-yl)-3-ethyl-urea

To asuspension of 5-benzyloxy-7-bromo-1,3-benzothiazol-2-amine (216 g, 0.64 mol) in 1,4-dioxane (4 L) was added ethylisocyanate (380 mL, 4.81 mol). The reaction mixture was heated to 80-85° C. overnight. After completion of reaction (by TLC) 1,4-dioxane was distilled off and the residue was co-evaporated with hexane. The residue was treated with water at 78-80° C. for 3-5 h. The resulting solid was filtered off and again washed with hot water, dried under high vacuum to obtain an off-white solid that was washed with hexane to obtain the desired product (196 g, 75%). $^1$H-NMR (DMSO-d$_6$): δ 1.08 (t, J=7.20 Hz, 3H), 3.18 (q, J=6.80 Hz, 2H), 5.17 (s, 2H), 6.71 (br s, 1H), 7.15 (d, J=2.0 Hz, 1H), 7.26 (br s, 1H), 7.31-7.47 (m, 5H) and 10.82 (br s, 1H). LCMS: 405.90 [M+H]$^+$.

1-[5-benzyloxy-7-(2-pyridyl)-1,3-benzothiazol-2-yl]-3-ethyl-urea

To a stirred of 1-(5-benzyloxy-7-bromo-1,3-benzothiazol-2-yl)-3-ethyl-urea (110 g, 0.27 mol) in DMF (1.1 L) was added 2-tributylstannyl pyridine (298 g, 0.81 mol). The resulting solution was purged with N$_2$ for 15-20 min followed by addition of tetrakis(triphenylphosphine)palladium (0) (25.41 g, 0.022 mol). The resulting mixture was then heated to 100° C. under N$_2$ atmosphere for 15-16 h. The reaction mass was cooled to 40-45° C. then filtered through celite. The celite bed was washed with DMF (500 mL) and hot EtOAc (1.50 L) and the combined filtrate concentrated at 60-70° C. under reduced pressure. The residue was purified through silica gel (20% EtOAc-Hexanes to 100% EtOAc) to obtain the desired product (76 g, 70%). $^1$H-NMR (DMSO-d$_6$): δ 1.08 (t, J=7.20 Hz, 3H), 3.19 (q, J=6.80 Hz, 2H), 5.26 (s, 2H), 6.84 (br s, 1H), 7.32-7.43 (m, 5H), 7.51 (d, J=7.20 Hz, 2H), 7.69 (d, J=2.0 Hz, 1H), 7.95 (m, 1H), 8.25 (m, 1H), 8.78 (m, 1H) and 10.46 (br s, 1H). LCMS: 405.30 [M+H]$^+$.

1-ethyl-3-[5-hydroxy-7-(2-pyridyl)-1,3-benzothiazol-2-yl]urea

To a stirred solution of 1-[5-benzyloxy-7-(2-pyridyl)-1,3-benzothiazol-2-yl]-3-ethyl-urea (76 g, 0.187 mol) in DCM (1.7 L) was added methane sulfonic acid (270 mL, 4.17 mol) dropwise over 30 min. The reaction mixture was then stirred at rt for 3 h. After the completion of reaction (by TLC), the reaction mass was concentrated under reduced pressure. EtOAc (1 L) was added to the residue and the solution poured carefully onto crushed ice. The pH of the solution was maintained to 8-9 by addition of saturated NaHCO$_3$ solution followed by extraction with EtOAc (3×5 L). The combined organics were washed with water, brine, dried (anhydrous Na$_2$SO$_4$), filtered and concentrated under reduced pressure. The residue thus obtained was stirred in Et$_2$O (1.0 L) for 1 h at rt then filtered to obtain the desired product (57.0 g, 97%). $^1$H-NMR (DMSO-d$_6$): δ 1.08 (t, J=7.20 Hz, 3H), 3.20 (m, 2H), 6.86 (br s, 1H), 7.0 (s, 1H), 7.46 (s, 2H), 7.96 (m, 1H), 8.10 (m, 1H), 8.76 (m, 1H), 9.59 (br s, 1H) and 10.41 (br s, 1H). LCMS: 315.06 [M+H]$^+$.

[2-(ethylcarbamoylamino)-7-(2-pyridyl)-1,3-benzothiazol-5-yl]trifluoromethanesulfonate To a stirred solution of 1-ethyl-3-[5-hydroxy-7-(2-pyridyl)-1,3-benzothiazol-2-yl]urea (57 g, 0.181 mol) in DMF (1.7 L) was added N-phenylbis(trifluoromethane sulphonimide) (80.74 g, 0.226 mol) and DIPEA (28.04 g, 0.217 mol). The resulting reaction mixture was stirred at rt for 3 h. After the completion of reaction (by TLC), the reaction mixture was concentrated at 60-70° C. under reduced pressure. Et$_2$O was added to the residue and evaporated to dryness. The residue thus obtained was stirred with Et$_2$O (1.50 L) for 1 h and filtered to obtain the desired product (55.0 g, 68%). $^1$H-NMR (DMSO-d$_6$): δ 1.11 (t, J=7.20 Hz, 3H), 3.20 (m, 2H), 6.81 (br s, 1H), 7.50 (m, 1H), 7.78 (d, J=2.0 Hz, 1H), 8.01 (m, 1H), 8.12 (d, J=2.40 Hz, 1H), 8.35 (m, 1H), 8.84 (m, 1H) and 10.77 (br s, 1H). LCMS: 446.98 [M+H]⁺.

[2-(ethylcarbamoylamino)-7-(2-pyridyl)-1,3-benzothiazol-5-yl]boronic acid (Intermediate 1)

To a stirred solution of [2-(ethylcarbamoylamino)-7-(2-pyridyl)-1,3-benzothiazol-5-yl]trifluoromethanesulfonate (25 g, 56.1 mmol) in DMSO (250 mL) at rt was added bis(neopentylglycolato) diboron (25.20 g, 112.10 mmol) and potassium acetate (16.5 g, 168.2 mmol). The resulting reaction mixture was de-gassed by purging $N_2$ for 15-20 min followed by addition of [1,1'-bis(diphenylphosphino)ferrocene]dichloropalladium(II) DCM adduct (6.8 g, 8.4 mmol). The reaction mixture was again purged with $N_2$ for 15-20 min then heated to 80° C. for 90 min. After the completion of reaction (by TLC), the reaction mixture was poured onto saturated $NH_4Cl$ solution (1 L). The resulting precipitate was filtered and dried under vacuum. The solid cake was taken up in 2N NaOH (200 mL) and stirred for 45 min at rt. The solution was filtered and the filtrate acidified up to pH 5-6. The solid thus obtained was filtered and dried to obtain the desired product (17 g, 88%). $^1$H-NMR (DMSO-$d_6$): δ 1.10 (t, J=7.20 Hz, 3H), 3.20 (m, 2H), 6.84 (br s, 1H), 7.41 (m, 1H), 8.01 (m, 1H), 8.12 (s, 1H), 8.25 (m, 3H), 8.40 (s, 1H), 8.79 (d, J=4.0 Hz, 1H) and 10.57 (br s, 1H). MS: 343.25 [M+H]⁺.

Intermediate 2: 1-(7-bromo-5-iodo-1,3-benzothiazol-2-yl)-3-ethyl-urea

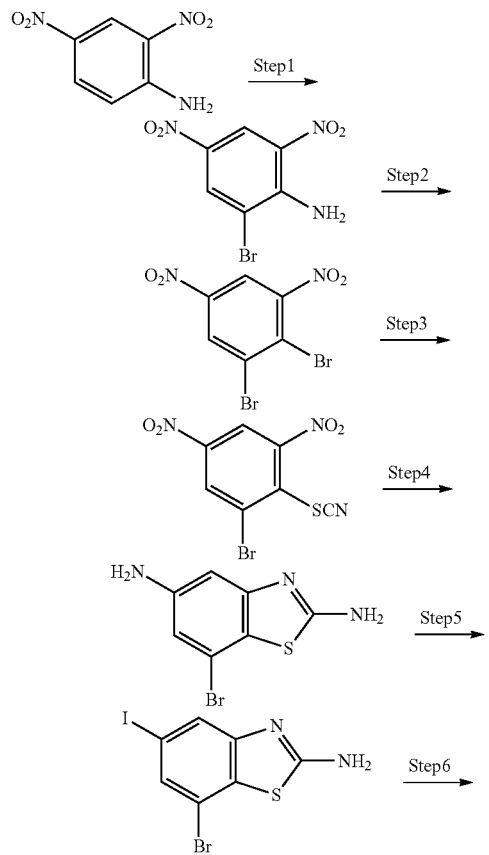

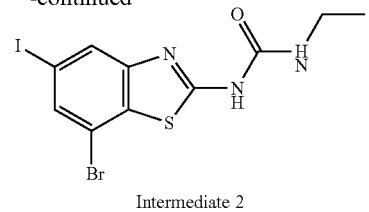

Intermediate 2

2-bromo-4,6-dinitroaniline

To a stirred mixture of water (3.75 L) and acetic acid (375 mL) at rt was added 2,4-dinitroaniline (500 g, 2.73 mol) followed by dropwise addition of bromine (210 mL, 4.09 mol) over 30 min. The reaction mixture was stirred at rt for 15 min then heated to 100° C. for 2 h. The reaction mixture was then cooled to rt poured onto ice-cold water (5-6 L) and basified (pH 8-10) with aqueous ammonia. The solid thus obtained was filtered, washed with cold water and dried under vacuum. The resulting solid was washed with n-pentane to give the desired product (600 g, 84%).

1,2-dibromo-3,5-dinitrobenzene

To a stirred solution of 2-bromo-4,6-dinitroaniline (600 g, 2.28 mol) in ACN (5 L) at rt was added tert-butylnitrite (680 mL, 5.7 mol) and cupric bromide (767 g, 3.43 mol). The resulting reaction mixture was heated to 70° C. for 1 h under nitrogen atmosphere. The reaction mixture was cooled to rt, acidified with 1N HCl solution, water added (4 L) and extracted with EtOAc (3×4 L). The combined organics were dried over anhydrous $Na_2SO_4$, filtered and concentrated under reduced pressure to obtain the desired product (723 g, 97%).

(2-bromo-4,6-dinitro-phenyl)thiocyanate

To a stirred solution of 1,2-dibromo-3,5-dinitrobenzene (723 g, 2.22 mol) in MeOH (7.5 L) at rt was added potassium thiocyanate (431 g, 4.44 mol) and the resulting reaction mixture stirred under a nitrogen atmosphere for 16 h. The reaction mixture was then filtered and washed with methanol. The filtrate was concentrated at 30-33° C. under reduced pressure. The residue thus obtained was purified over silica gel (2-6% EtOAc-hexane) to obtain the desired product (549 g, 81%).

7-bromobenzothiazole-2,5-diamine

To a stirred mixture of EtOH (8.37 L) and water (8.37 L) at rt was added (2-bromo-4,6-dinitro-phenyl)thiocyanate (549 g, 1.81 mol) followed by addition of Fe powder (2.02 kg, 36.11 mol) and drop wise addition of HCl (12N, 527 mL) over 30 min. The resulting reaction mixture was stirred at rt for 20 min then heated to 80° C. for 45 min. After completion of the reaction (by TLC) the reaction mixture was cooled to rt and basified to pH 8-10 by addition of aqueous ammonia solution. The resulting solution was passed through celite bed, washed with EtOAc and the combined filtrate evaporated under reduced pressure. To the resulting residue was added water (8 L) then extracted with EtOAc (2×4 L). The combined organics were washed with brine, dried (anhydrous $Na_2SO_4$), filtered and concentrated under reduced pressure to obtain the desired product (412 g, 93%). $^1$H NMR (DMSO-$d_6$): δ 5.16

(br s, 2H), 6.50 (d, J=2.0 Hz, 1H), 6.53 (d, J=1.60 Hz, 1H) and 7.44 (br s, 2H). LCMS: 243.86 [M+H]+.

7-bromo-5-iodobenzothiazol-2-amine

To THF (6 L) at −78° C. under N₂ atmosphere was added BF₃-etherate (50% assay, 708 mL, 2.81 mol) followed by slow addition of a solution of 7-bromobenzothiazole-2,5-diamine (275 g, 1.02 mol) in THF (500 mL) over 20 min. Tert-butyl nitrite (548 L, 4.61 mol) was then added to the solution at −78° C. The reaction mixture was stirred at the same temperature for 40 min then warmed to −5-0° C. Et₂O was added (at −5-0° C.) and stirring continued at the same temperature for 20 min. The precipitated solid was filtered then taken in acetone at 0° C. followed by sequential addition of potassium iodide (510 g, 3.07 mol) and iodine (519 g, 2.04 mol) and stirred at 0° C. for 30 min. After the completion of reaction the mixture was quenched with a saturated solution of sodium metabisulfite then extracted with EtOAc (3×5 L). The combined organics were dried over anhydrous Na₂SO₄, filtered and concentrated under reduced pressure at 45° C. The residue thus obtained was purified over basic alumina (30-35% EtOAc-hexane) to obtain the desired product (235 g, 65%) as a light brown solid. ¹H NMR (DMSO-d₆): δ 7.50 (d, J=1.20 Hz, 1H), 7.63 (d, J=1.20 Hz, 1H) and 7.91 (br s, 2H). LCMS: 354.90 [M+H]+.

1-(7-bromo-5-iodobenzothiazol-2-yl)-3-ethylurea (Intermediate 2)

To a stirred solution of 7-bromo-5-iodobenzothiazol-2-amine (250 g, 0.70 mol) in 1,4-dioxane at rt was added ethylisocyanate (278 mL, 3.52 mol). The resulting reaction mixture was heated to 80° C. for 10-12 h under N₂ atmosphere. After reaction completion (by TLC), the solvent was evaporated then n-hexane added and the evaporation procedure repeated. The resulting residue was stirred in hot water (2 L) at 60-65° C. for 30-40 min then filtered. The residue thus obtained was treated with a mixture of Et₂O and n-pentane and filtered to obtain the desired product (264 g, 88%). ¹H NMR (DMSO-d₆): δ 1.08 (t, J=7.20 Hz, 3H), 3.20 (q, J=6.80, 2H), 6.73 (br s, 1H), 7.72 (s, 1H), 7.96 (s, 1H) and 11.07 (br s, 1H). MS: 426.0 [M+H]+.

Intermediate 3: Ethyl 1-(5-bromopyrimidin-2-yl)-4-methyl-piperidine-4-carboxylate

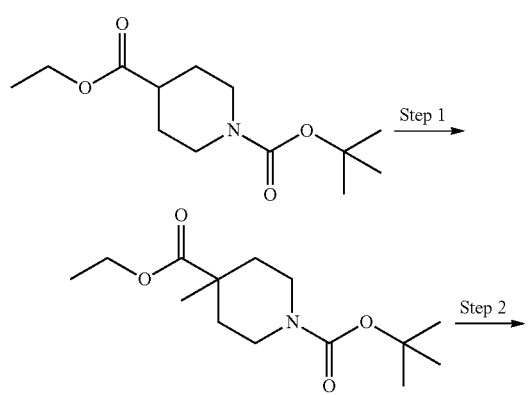

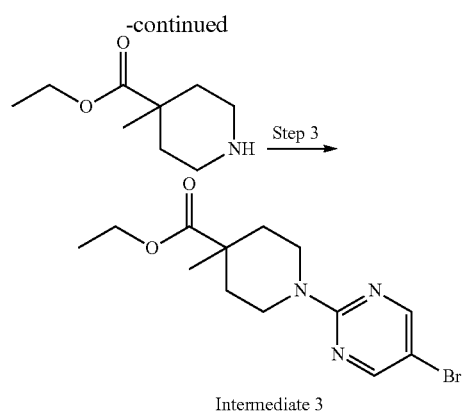

Intermediate 3

O1-tert-Butyl-O4-ethyl 4-methylpiperidine-1,4-dicarboxylate

A solution of O1-tert-butyl O4-ethyl piperidine-1,4-dicarboxylate (1.5 g, 5.84 mmol) in THF (25 mL) was cooled to −78° C. followed by dropwise addition of LDA (1.80 M in THF, 6.5 mL, 11.68 mmol) at −78° C. The resulting mixture was stirred at the same temperature for 45 minutes followed by addition of MeI (1.2 mL, 17.52 mmol) at −78° C. The temperature of the reaction mixture was slowly raised up to rt and left to stir at rt for 6 h. The reaction mixture was then cooled to 0° C., quenched by dropwise addition of saturated NH₄Cl solution (50 mL) and extracted with EtOAc (3×100 mL). The combined organics were washed with brine, dried (Na₂SO₄), filtered and concentrated under reduced pressure. The crude residue was purified over 100-200 M silica-gel by using 2% EtOAc:hexane to obtain the desired product as a liquid (1.0 g, 65%).

Ethyl 4-methylpiperidine-4-carboxylate hydrochloride

To an ice-cold solution of O1-tert-butyl O4-ethyl 4-methylpiperidine-1,4-dicarboxylate (1 g, 3.68 mmol) in 1,4-dioxane (10 mL) was added HCl-1,4-dioxane (4.0 M, 15 mL) solution. The mixture was stirred at rt for 30 minutes. After completion of reaction (by TLC), solvent was evaporated to obtain brown solid material (0.90 g) that was carried forward to the next step without purification. MS: 172.16 [M+H]+.

Ethyl 1-(5-bromopyrimidin-2-yl)-4-methylpiperidine-4-carboxylate (Intermediate 3)

To the solution of ethyl 4-methylpiperidine-4-carboxylate hydrochloride (0.9 g, 4.35 mmol) in EtOH (10 mL) was added DIPEA (2.30 mL, 13 mmol) at rt. The resulted mixture was stirred at rt for 10 minutes followed by addition of 5-bromo-2-chloropyrimidine (0.7 g, 3.6 mmol). The mixture was heated up to 70° C. for 1 h. After completion of reaction (by TLC), solvent was evaporated and the crude residue was purified over 100-200 M silica-gel by using 1.5% EtOAc: hexane to obtain the desired product as an off white solid compound (0.90 g, 75%). ¹H NMR (DMSO-d₆): δ 1.17 (s, 3H), 1.21 (t, J=7.20 Hz, 3H) 1.40 (m, 2H), 2.00 (m, 2H), 3.24 (m, 2H), 4.11 (m, 2H), 4.15 (q, J=7.20 Hz, 2H), 8.43 (s, 2H). MS: 328.08 [M+H]+.

Intermediate 4: Ethyl 1-[5-[7-bromo-2-(ethylcarbamoylamino)-1,3-benzothiazol-5-yl]pyrimidin-2-yl]-4-methyl-piperidine-4-carboxylate

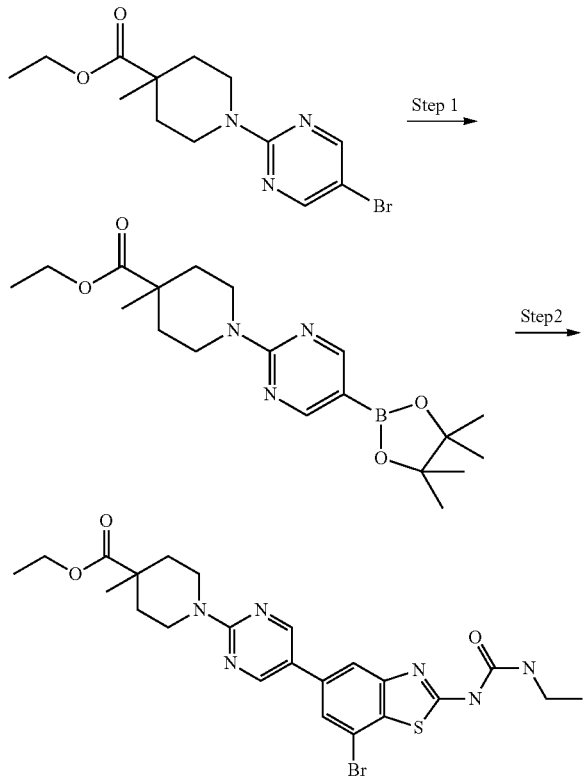

Ethyl 4-methyl-1-(5-(4,4,5,5-tetramethyl-1,3,2-dioxaborolan-2-yl)pyrimidin-2-yl)piperidine-4-carboxylate To the solution of ethyl 1-(5-bromopyrimidin-2-yl)-4-methylpiperidine-4-carboxylate (25 g, 76.2 mmol) in 1,4-dioxane (250 mL) was added potassium acetate (22.4 g, 228.6 mmol) and bis(pinacolato)diboron (38.7 g, 152.4 mmol) at rt. The resulting mixture was degassed for 15-20 min by purging N$_2$ followed by the addition of tris(dibenzylideneacetone)dipalladium(0) (4.0 g, 3.80 mmol) and tricyclohexyl phosphine (2.55 gm, 9.12 mmol). The reaction mixture was again degassed for another 15-20 min then heated up to 80° C. for 3 h. After completion of reaction (by TLC), the reaction was cooled to rt and diluted with 500 mL of EtOAc. The mixture was passed through celite and the filtrate was evaporated to obtain (20 g, 70%) of the crude material that was used for the next step without purification. MS: 376.30 [M+H]$^+$.

Ethyl 1-(5-(7-bromo-2-(3-ethylureido)benzothiazol-5-yl)pyrimidin-2-yl)-4-methylpiperidine-4-carboxylate (Intermediate 4)

To a solution of 1-(7-bromo-5-iodobenzo[d]thiazol-2-yl)-3-ethylurea (22.7 g, 53.20 mmol) and ethyl 4-methyl-1-(5-(4,4,5,5-tetramethyl-1,3,2-dioxaborolan-2-yl)pyrimidin-2-yl)piperidine-4-carboxylate (20 g, 53.2 mmol) in 1,4-dioxane: MeOH (300:180 mL) was added potassium phosphate (17 g, 79 mmol) at rt. The resulting mixture was degassed for 15-20 min by purging N$_2$ followed by addition of tetrakis(triphenylphosphine)palladium(0) (6.1 g, 5.32 mmol). The reaction mixture was again degassed for another 15-20 min then heated up to 80° C. or 5 h. After completion of reaction (by TLC), the reaction was cooled to rt, diluted with EtOAc (500 mL) and passed through celite. The filtrate was evaporated and the crude residue purified over 100-200 M silica-gel by using 1.50% MeOH: DCM to obtain the desired product as an off-white solid (12 g, 41%). $^1$H NMR (DMSO-d$_6$): δ 1.09 (t, J=7.20 Hz, 3H), 1.20 (m, 6H), 1.45 (m, 2H), 2.03 (m, 2H), 3.16 (m, 2H), 3.30 (q, J=7.20, 2H), 4.12 (q, J=6.80 Hz, 2H), 4.25 (m, 2H), 6.75 (br s, 1H), 7.69 (s, 1H), 7.86 (s, 1H); 8.75 (s, 2H) and 10.91 (br s, 1H). MS: 547.11 [M+H]$^+$.

Intermediate 5: 1-[5-[7-bromo-2-(ethylcarbamoylamino)-1,3-benzothiazol-5-yl]pyrimidin-2-yl]-4-methyl-piperidine-4-carboxylic acid

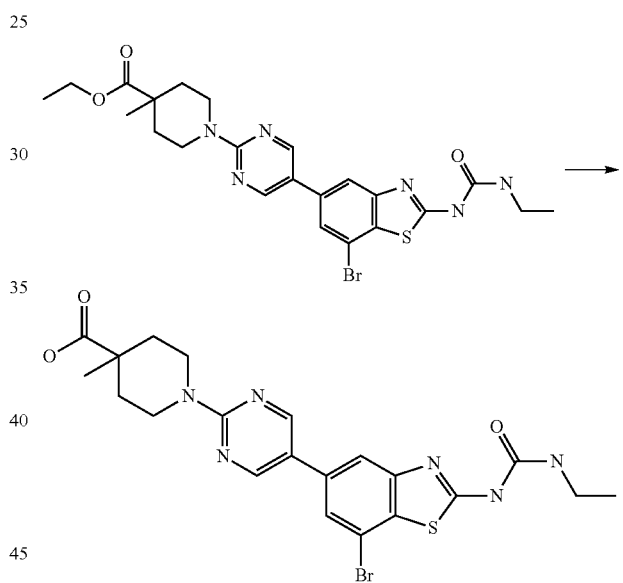

To an ice-cold solution of ethyl 1-(5-(7-bromo-2-(3-ethylureido)benzothiazol-5-yl)pyrimidin-2-yl)-4-methylpiperidine-4-carboxylate (25 g, 45.7 mmol) in DMSO (50 mL) was added potassium tert-butoxide (25.5 g, 228 mmol). The resulting mixture was stirred at rt for 1 h. After completion of reaction (by TLC), water (250 mL) was added followed by extraction with EtOAc (2×250 mL). The organic layer was discarded; the pH of the aqueous layer was adjusted up to 4-5 and then extracted with hot EtOAc (3×250 mL). The combined organic layer was dried over Na$_2$SO$_4$, filtered and evaporated under reduced pressure. The residue thus obtained was triturated with ether to obtain the desired product as off-white solid (21 g, 88%). $^1$H NMR (DMSO-d$_6$): δ 1.09 (t, J=7.20 Hz, 3H), 1.18 (s, 3H), 1.41 (m, 2H), 2.02 (m, 2H), 3.20 (m, 2H), 3.33 (m, 2H), 4.29 (m, 2H), 6.80 (br s, 1H), 7.70 (s, 1H), 7.87 (s, 1H), 8.76 (s, 2H), 10.95 (br s, 1H) and 12.46 (br, s, 1H). MS: 519.19 [M+H]$^+$.

Intermediate 6: 1-[5-(2-chloropyrimidin-5-yl)-7-(2-pyridyl)-1,3-benzothiazol-2-yl]-3-ethyl-urea

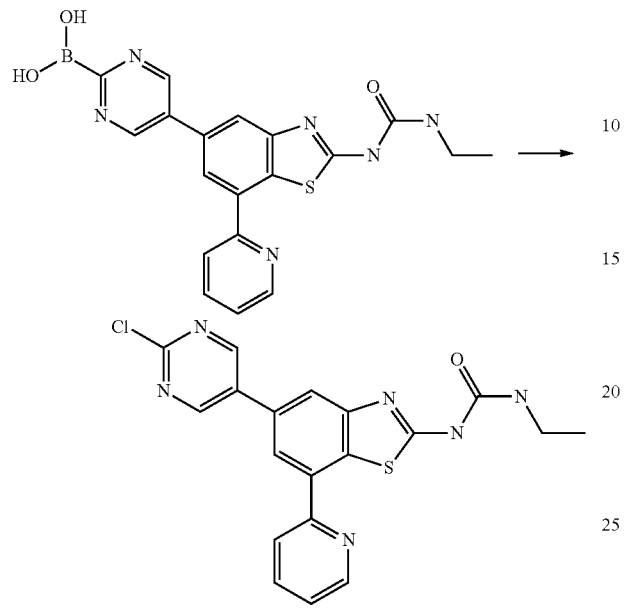

To a solution of 5-bromo-2-chloropyrimidine (6.80 g, 35.1 mmol) in DMF (40 mL) was added [5-[2-(ethylcarbamoylamino)-7-(2-pyridyl)-1,3-benzothiazol-5-yl]pyrimidin-2-yl]boronic acid (10 g, 29.24 mmol) and aqueous solution of $K_3PO_4$ (9.3 g, 43.86 mmol). The reaction mixture was degassed by purging $N_2$ for 15 min followed by addition of bis(triphenylphosphine)palladium (II) chloride (3.10 g, 4.4 mmol). The reaction mixture was again degassed for 10-15 min then heated up to 80° C. for 2 h. After completion of reaction (by TLC), solvent was evaporated under reduced pressure, 50 mL water added followed by extraction with EtOAc (3×200 mL). The combined organics were washed with brine, dried over anhydrous $Na_2SO_4$, filtered and evaporated under reduced pressure. The crude residue was purified over 60-120 M silica-gel by using 5% MeOH: DCM to obtain an off white solid compound that was triturated with ether (4.80 g). Further product was obtained by repeating the extraction (1.20 g) giving a combined total product yield of 6.0 g (50%). $^1$H NMR (DMSO-$d_6$): δ 1.12 (t, J=7.20 Hz, 3H), 3.20 (m, 2H), 6.83 (br s, 1H), 7.46 (m, 1H), 8.0 (m, 1H), 8.17 (s, 1H), 8.40 (s, 1H), 8.50 (d, J=8.0 Hz, 1H), 8.82 (d, J=4.0 Hz, 1H), 9.35 (s, 2H) and 10.61 (br s, 1H). MS: 411.16 [M+H]$^+$.

Intermediate 7: 1-(5-bromo-4-fluoro-7-(pyridin-2-yl)benzothiazol-2-yl)-3-ethylurea

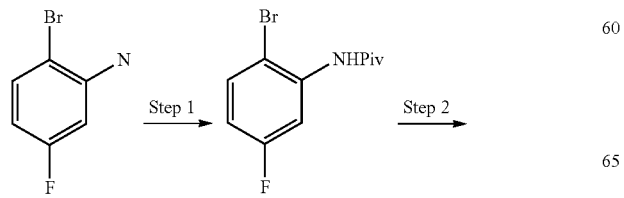

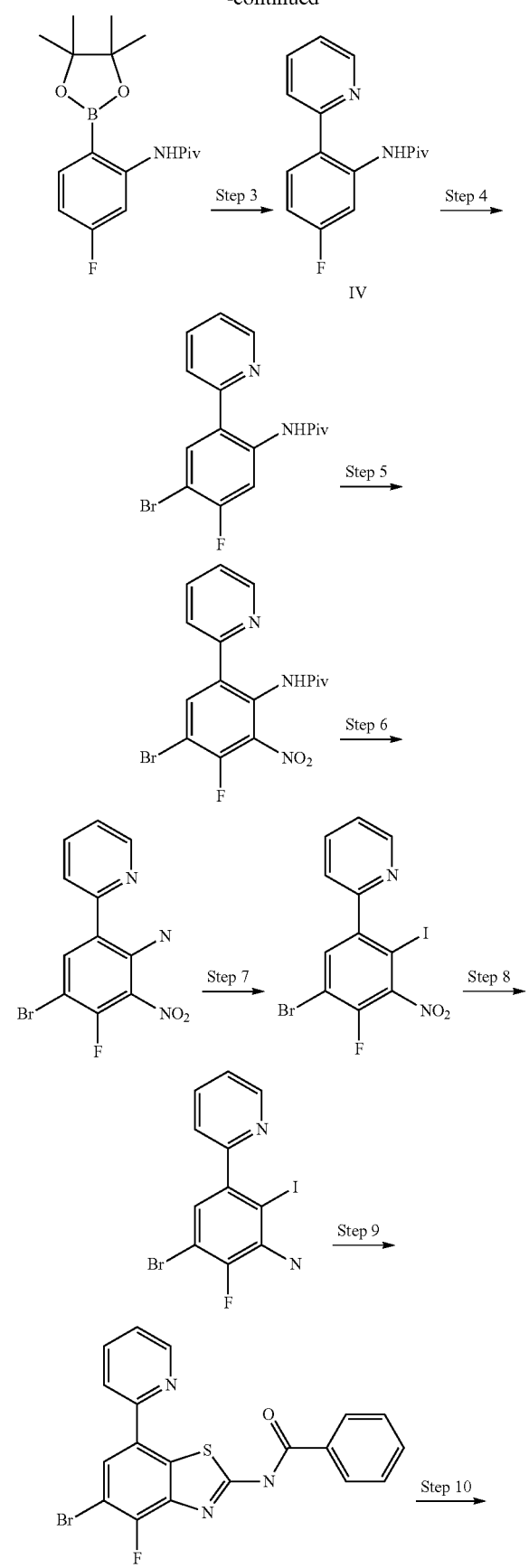

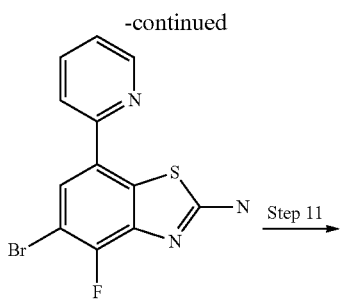

Step 11

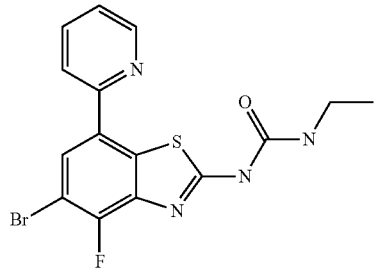

N-(2-bromo-5-fluorophenyl)pivalamide

To an ice-cold solution of 2-bromo-5-fluoroaniline (50.0 g, 263.14 mmol) in DCM (400 mL) was added triethyl amine (48.0 mL, 342.10 mmol). The resulting mixture was stirred at 0° C. for 10 min followed by addition of pivaloyl chloride (36.0 mL, 289.50 mmol) then stirred at rt for 3 h. After completion of reaction (by TLC), the reaction mixture was diluted with DCM and washed with saturated solution of NaHCO$_3$. The organic layer was washed with brine, dried over anhydrous Na$_2$SO$_4$, filtered and evaporated under reduced pressure. The crude residue was purified over 100-200 M silica-gel by using 1.0% EtOAc:hexane to obtain the product as an off white solid (66.0 g, 92% yield).

N-(5-fluoro-2-(4,4,5,5-tetramethyl-1,3,2-dioxaborolan-2-yl)phenyl)pivalamide To a solution of N-(2-bromo-5-fluorophenyl)pivalamide (20.0 g, 72.97 mmol) in 1,4-dioxane (200 mL) was added potassium acetate (35.80 g, 364.85 mmol) and bispinacolatodiboron (37.10 g, 145.93 mmol) at rt. The resulting mixture was degassed for 15-20 min by purging N$_2$ followed by the addition of (1,1-bis (diphenylphosphino)ferrocene)dichloropalladium(II) DCM adduct (6.0 gm, 7.30 mmol). The reaction mixture was again degassed for 15-20 min then heated up to 100° C. for 2 h. After completion of reaction (by TLC), the reaction was cooled to rt and diluted with 500 mL EtOAc. The resulting solution was passed through celite. The filtrate was evaporated to obtain the crude material (23.40 g), which was carried forward to the next step without further purification. MS: 322.24 [M+H]$^+$.

N-(5-fluoro-2-(pyridin-2-yl)phenyl)pivalamide

To a solution of N-(5-fluoro-2-(4,4,5,5-tetramethyl-1,3,2-dioxaborolan-2-yl)phenyl)pivalamide (23.4 g, 72.97 mmol) in acetonitrile (280 mL) was added 2-bromopyridine (16.14 g, 102.12 mmol) and aqueous solution of K$_2$CO$_3$ (50.40 g, 364.90 mmol). The reaction mixture was degassed by purging N$_2$ for 15 min followed by addition of tetrakis(triphenylphosphine)palladium(0) (8.40 g, 7.30 mmol). The mixture was again degassed for 10-15 min then heated up to 80° C. for 8 h. After completion of reaction (by TLC), the mixture was poured into 100 mL of ice-cold water and extracted with EtOAc (3×250 mL). The combined organics were washed with brine, dried over anhydrous Na$_2$SO$_4$, filtered and evaporated under reduced pressure. The crude residue was purified over 100-200 M silica-gel by using 2.0% EtOAc:hexane to obtain the desired product as a colourless liquid (19.0 g, 96% yield).

N-(4-bromo-5-fluoro-2-(pyridin-2-yl)phenyl)pivalamide

To a solution of N-(5-fluoro-2-(pyridin-2-yl)phenyl)pivalamide (19.0 g, 69.83 mmol) in acetic acid (140.0 mL) was added NBS (24.86 g, 139.66 mmol) at 0° C. The resulted mixture was stirred at 50° C. for 1 h. After completion of reaction (by TLC), the mixture was poured onto 100 mL of crushed ice and extracted with EtOAc (3×100 mL). The combined organic layer was washed with brine, dried over anhydrous Na$_2$SO$_4$ and solvent evaporated under reduced pressure. The crude residue was purified over 100-200 M silica-gel by using 2% EtOAc:hexane to obtain the desired product as an off white solid (17.50 g, 72%).

N-(4-bromo-3-fluoro-2-nitro-6-(pyridin-2-yl)phenyl)pivalamide

To an ice-cold solution of N-(4-bromo-5-fluoro-2-(pyridin-2-yl)phenyl)pivalamide (17.5 g, 50.0 mmol) in conc. H$_2$SO$_4$ (50.0 mL) was added drop wise fuming HNO$_3$ (10.0 mL). The resulting mixture was stirred at 0-10° C. for 1 h. After completion of reaction (by TLC), the mixture was poured onto 500 mL of crushed ice and stirred for 30 min followed by extraction with EtOAc (3×500 mL). The combined organic layer was washed with brine, dried over anhydrous Na$_2$SO$_4$ and evaporated under reduced pressure. The crude was triturated with Et$_2$O to obtain the desired product as a yellow solid (15.0 g, 76%). MS: 396.23 [M+H]$^+$.

4-bromo-3-fluoro-2-nitro-6-(pyridin-2-yl)aniline

A solution of N-(4-bromo-3-fluoro-2-nitro-6-(pyridin-2-yl)phenyl)pivalamide (7.50 g, 18.93 mmol) in 70% aqueous solution of H$_2$SO$_4$ (31.2 mL) was heated up to 80° C. for 30 min. After completion of reaction (by TLC), the mixture was poured onto 100 mL of crushed ice and basified up to pH 6 to 7 by 20% NaOH solution. Precipitated solid was filtered and dried under vacuum to obtain the desired product as a yellow solid (4.96 g, 84%).

2-(5-bromo-4-fluoro-2-iodo-3-nitrophenyl)pyridine

To an ice-cold solution of 4-bromo-3-fluoro-2-nitro-6-(pyridin-2-yl)aniline (4.0 g, 12.81 mmol) in chloroform (50 mL) was added iodine (18.21 g, 71.77 mmol) and the resulting mixture was stirred at 0° C. for 10 min followed by addition of isoamyl nitrile (3.44 mL, 25.63 mmol). The mixture was then heated up to 65° C. for 5 h. After completion of reaction (by TLC), the reaction was diluted with 10% sodium bisulfite and extracted with DCM (3×100 mL). The combined organic layer was washed with brine, dried over anhydrous Na$_2$SO$_4$ and evaporated under reduced pressure. The crude residue was purified over 100-200 M silica-gel by using 20% EtOAc:hexane to obtain the desired product as an off white solid (2.0 g, 37%).

3-bromo-2-fluoro-6-iodo-5-(pyridin-2-yl)aniline

To a solution of 2-(5-bromo-4-fluoro-2-iodo-3-nitrophenyl)pyridine (1.0 g, 2.36 mmol) in MeOH (25 mL) was added Fe powder (0.66 mL, 11.82 mmol) at 0° C. The mixture was stirred at rt for 10 min followed by addition of aqueous solution of NH₄Cl (0.63 g, 11.82 mmol). The mixture was then heated up to 80° C. for 2 h. After completion of reaction (by TLC), the mixture was poured onto 100 mL of ice cold water and extracted with EtOAc (3×100 mL). The combined organic layer was washed with brine, dried over anhydrous Na₂SO₄ and solvent evaporated under reduced pressure. The crude residue was purified over 100-200 M silica-gel by using 6% EtOAc:hexane to obtain the desired product as a white solid (0.90 g, 97%).

N-(5-bromo-4-fluoro-7-(pyridin-2-ylbenzothiazol-2-yl)benzamide

To a solution of 3-bromo-2-fluoro-6-iodo-5-(pyridin-2-yl) aniline (1.60 g, 4.07 mmol) in acetone (30 mL) was added benzoylisothiocyanate (2.70 mL, 20.35 mmol) at rt. The mixture was stirred rt for 16 h. After completion of reaction (by TLC), solvent was evaporated under reduced pressure. The crude residue was triturated with hexane to obtain the desired product as a yellow solid (2.10 g) which was used in the next step without further purification. MS: 428.07 [M+H]⁺.

5-bromo-4-fluoro-7-(pyridin-2-yl)benzothiazol-2-amine

To a solution of N-(5-bromo-4-fluoro-7-(pyridin-2-ylbenzothiazol-2-yl)benzamide (2.30 g, 5.37 mmol) in MeOH (25 mL) was added 2N aqueous solution of NaOH (3.01 g, 75.41 mmol) at 0° C. The reaction mixture was heated up to 80° C. for 16 h. After completion of reaction (by TLC), the reaction was poured into 100 mL of ice cold water and extracted with EtOAc (3×100 mL). The combined organic layer was washed with brine, dried over anhydrous Na₂SO₄ and solvent evaporated under reduced pressure to obtain the desired product as a white solid (1.20 g, 70%).

1-(5-bromo-4-fluoro-7-(pyridin-2-ylbenzothiazol-2-yl)-3-ethylurea

To a solution of 5-bromo-4-fluoro-7-(pyridin-2-yl)benzothiazol-2-amine (0.15 g, 0.46 mmol) in 1,4-dioxane (5.0 mL) was added ethylisocyanate (0.19 mL, 2.31 mmol) at rt. The reaction mixture was heated up to 80° C. for 6 h. After completion of reaction (by TLC), solvent was evaporated under reduced pressure. 20 mL of water was added to the residue and extracted with hot EtOAc (3×20 mL). The combined organic layer was washed with brine, dried over anhydrous Na₂SO₄ and the solvent evaporated under reduced pressure to obtain a white solid compound which was triturated with ether to obtain the desired product (0.095 g, 50%).

Intermediate 8: 1-(4,6-dibromothiazolo[5,4-c]pyridin-2-yl)-3-ethylurea

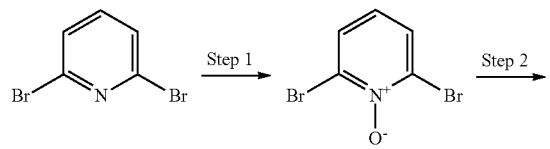

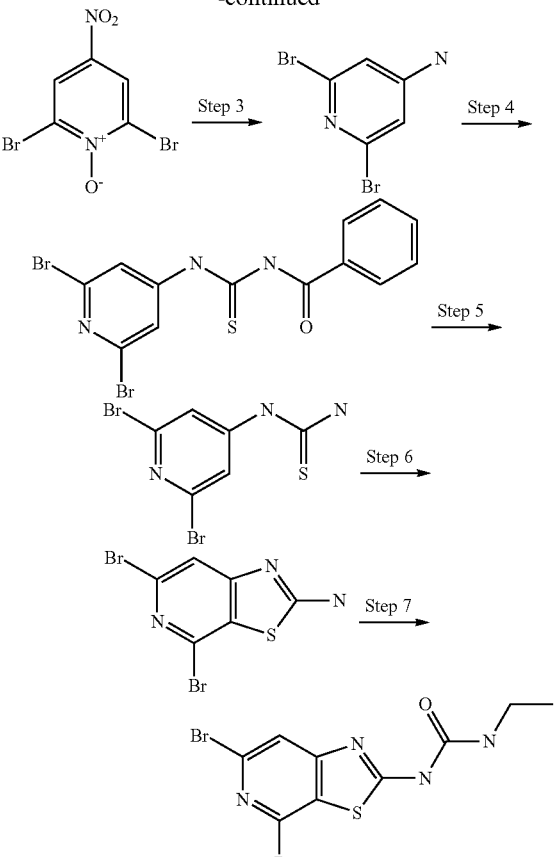

2,6-dibromopyridine 1-oxide

To an ice-cold solution of 2,6-dibromopyridine (50 g, 0.21 mol) in trifluoroacetic acid (250 mL) was added 30% H₂O₂ solution (70 mL) drop wise over 1 h. The reaction mixture was washed, heated to 100° C. for 16 h then cooled to rt, poured into 1.50 L of water and the precipitate filtered. The solid thus obtained (10 g) was the starting material (2,6-dibromopyridine). The filtrate was extracted with dichloromethane (3×1 L) and the combined organic layer was washed with 0.50 M K₂CO₃ solution (3×500 mL). The organic layer was then dried over anhydrous Na2SO4, filtered and concentrated under reduced pressure. The residue was treated with hexane then filtered to obtain the desired product as an off white solid (38.50 g, 72% and 90% yield based on the recovery of the starting material).

2,6-dibromo-4-nitropyridine 1-oxide

A solution of 2,6-dibromopyridine 1-oxide (34.0 g, 0.13 mol) in sulfuric acid (120 mL) was cooled to 0-5° C. followed by addition of nitric acid (60 mL). The reaction mixture was stirred at the same temperature for 10-15 min then heated to 60-65° C. for 20 h. The reaction was then cooled to rt, poured into ice-cold water and neutralized with aqueous ammonia solution. The resulting solution was stirred for 10 min at 0-5° C. then filtered and dried to obtain the desired product as a pale yellow solid (32 g, 83%).

2,6-dibromopyridin-4-amine

To a solution of 2,6-dibromo-4-nitropyridine 1-oxide (6.80 g, 22.82 mmol) in acetic acid (100 mL) at rt was added Fe powder (6.40 g, 114.13 mmol). The resulting reaction mixture was heated to 100° C. for 1 h. After completion of reaction (by TLC), acetic acid was distilled off under reduced pressure, the residue was basified with aqueous ammonia solution and extracted with EtOAc (3×250 mL). The combined organics were washed with brine, dried (Na$_2$SO$_4$), filtered and concentrated under reduced pressure. The residue thus obtained was treated with ether and hexane and filtered to obtain the desired product as an off white solid (5.40 g, 94%).

N-(2,6-dibromopyridin-4-ylcarbamothioyl)benzamide

To a solution of 2,6-dibromopyridin-4-amine in THF (250 mL) was added benzoylisothiocyanate (3.50 mL, 26.0 mmol)) and the resulting reaction mixture heated to 70° C. for 16 h. A further 1.50 mL (11.20 mmol) of benzoylisothiocyanate was added to complete the reaction and the reaction stirred at 70° C. for 16 h. After completion (by TLC), the solvent was distilled under reduced pressure, the residue treated with 10% MeOH-ether solution then filtered to obtain the desired product as a yellow solid (7.60 g, 85%).

1-(2,6-dibromopyridin-4-yl)thiourea

To a solution of N-(2,6-dibromopyridin-4-ylcarbamothioyl)benzamide (14.50 g, 34.93 mmol) in a mixture of THF (600 mL) and MeOH (200 mL) was added a solution of NaOH (7.0 g, 174.65 mmol) dissolved in 200 mL of water. The mixture was heated to 70° C. for 16-22 h. After reaction, the solvent wad distilled under reduced pressure, water added and extracted with EtOAc (3×500 mL). The combined organics were washed with brine, dried (Na$_2$SO$_4$), filtered and concentrated under reduced pressure. The residue thus obtained was treated with 20% EtOAc-hexane and finally filtered to obtain the desired product as an off-white solid (9.0 g, 83%).

4,6-dibromothiazolo[5,4-d]pyridin-2-amine

A solution of 1-(2,6-dibromopyridin-4-yl)thiourea (1.0 g, 3.22 mmol) in THF (250 mL) was cooled to –78° followed by drop wise addition of a solution of bromine (0.40 mL, 7.73 mmol) in THF (50 mL) over 30 min. The reaction was allowed to warm to rt and stirring continued for 20 h. The reaction was then cooled to 0° C., basified with aqueous ammonia and concentrated under reduced pressure. To the residue was added water followed by extraction with EtOAc (3×100 mL). The combined organics were washed with brine, dried (Na$_2$SO$_4$), filtered and concentrated. The residue was then purified over neutral alumina (70% acetone-hexane to 30% EtOAc-hexane) to obtain the desired product, which was finally triturated with hexane (0.38 g, 38%). $^1$H NMR (DMSO-d$_6$): δ 7.30 (s, 1H) and 8.59 (br s, 2H).

1-(4,6-dibromothiazolo[5,4-c]pyridin-2-yl)-3-ethylurea

To a solution of 4,6-dibromothiazolo[5,4-c]pyridin-2-amine (1.47 g, 56.74% as per LCMS, 2.70 mmol) in 1,4-dioxane (75 mL) was added ethylisocyanate (1.30 mL, 16.25 mmol) and the resulting reaction mixture was heated to 80° C. for 16 h. The solvent was distilled off under reduced pressure and the residue was then co-distilled with hexane (twice). The solid thus obtained was stirred in hot water at 80° C. for 30 min then filtered. The solid material was purified over silica gel (100-200 M, 30-40% EtOAc-hexane) to obtain the desired product as an off-white solid (0.85 g, 82%).

Intermediate 9: Ethyl 1-[5-[7-bromo-2-(3-ethyl-5-methyl-2-oxo-1,3,5-triazinan-1-yl)-1,3-benzothiazol-5-yl]pyrimidin-2-yl]-4-methyl-piperidine-4-carboxylate

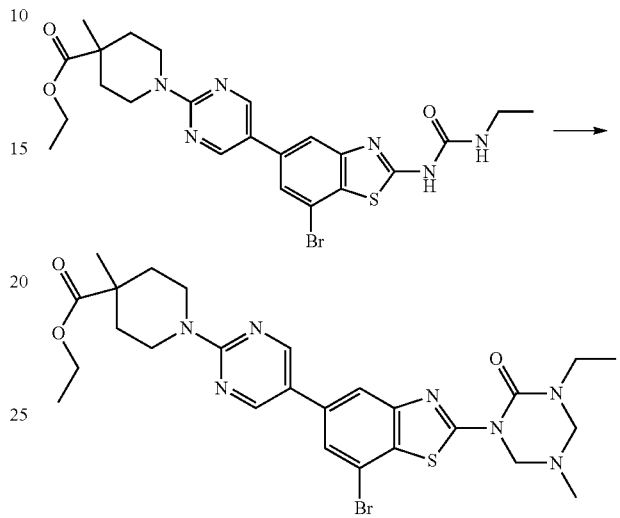

Ethyl 1-[5-[7-bromo-2-(ethylcarbamoylamino)-1,3-benzothiazol-5-yl]pyrimidin-2-yl]-4-methyl-piperidine-4-carboxylate (3.11 g, 5.68 mmol) was suspended in EtOH (120 mL). To the stirred suspension was added, NMM (3.1 mL, 28.4 mmol), aqueous formaldehyde (4.61 mL, 56.8 mmol) and methylamine solution (14.2 mL, 28.4 mmol). The reaction mixture was then stirred at 80° C. for 16 h. The reaction mixture was cooled to rt and filtered. The precipitate was washed with EtOH, Et$_2$O and dried to afford the desired compound (2.58 g, 75%) as an off-white solid. m/z=602.09 and 604.02 [M+H]$^+$.

Intermediate 10: 1-(5-(6-Bromopyridazin-4-yl)-7-(pyridin-2-yl)benzo[d]thiazol-2-yl)-3-ethylurea

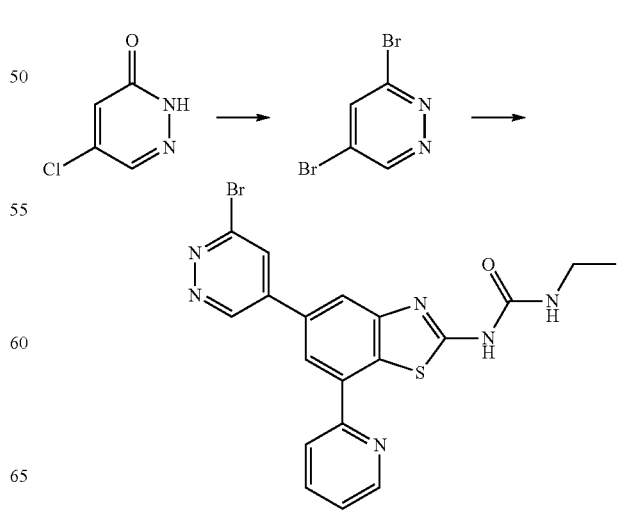

3,5-Dibromopyridazine

A solution of 5-chloropyridazin-3(2H)-one (0.20 g, 1.53 mmol) in POBr$_3$ (0.883 g, 3.07 mmol) was heated up to 90° C. for 4 h. After completion of reaction (by TLC), sat. NaHCO$_3$ solution was added up to pH 9-10 then extracted with EtOAc (3×150 mL). The combined organic layer was dried over Na$_2$SO$_4$, filtered and evaporated under reduced pressure. The residue thus obtained was triturated with ether to obtain the desired product as a solid (0.32 g, 88%). $^1$H NMR (CDCl$_3$): δ 9.14 (s, 1H) and 7.94 (s, 1H).

1-(5-(6-Bromopyridazin-4-yl)-7-(pyridin-2-yl)benzo[d]thiazol-2-yl)-3-ethylurea To a solution of 3,5-dibromopyridazine (0.32 g, 1.34 mmol) in DMF (5 mL) was added 2-(3-ethylureido)-7-(pyridin-2-yl)benzothiazol-5-ylboronic acid (0.46 g, 1.34 mmol) and aqueous solution of K$_3$PO$_4$ (0.43 g, 2.01 mmol). The reaction was degassed by purging N$_2$ for 15 min followed by addition of bis(triphenylphosphine)palladium (II) chloride (0.11 g, 0.13 mmol). The reaction mixture was again degassed for 10-15 min then heated up to 80° C. for 2-3 h. After reaction completion (by TLC), the mixture was poured onto crushed ice and extracted with EtOAc (3×50 mL). The combined organics were washed with brine, dried over anhydrous Na$_2$SO$_4$, filtered and evaporated under reduced pressure. The crude residue was purified over 100-200 M silica-gel by using 3% MeOH-DCM to obtain the desired product as off-white solid (0.52 g, 85%). $^1$H NMR (DMSO-d$_6$): δ 10.71 (s, 1H), 9.94 (m, 2H), 8.82 (m, 1H), 8.55 (d, J=8.0 Hz, 1H), 8.38 (s, 1H), 8.21 (s, 1H), 8.02 (t, J=8.0 Hz, 1H), 7.46 (m, 1H), 7.17 (br s, 1H), 3.22 (q, J=7.20 Hz, 2H), and 1.11 (t, J=7.20 Hz, 3H).

Intermediate 11: 1-(5-Bromo-6-methoxy-1,3-benzothiazol-2-yl)-3-ethyl-urea

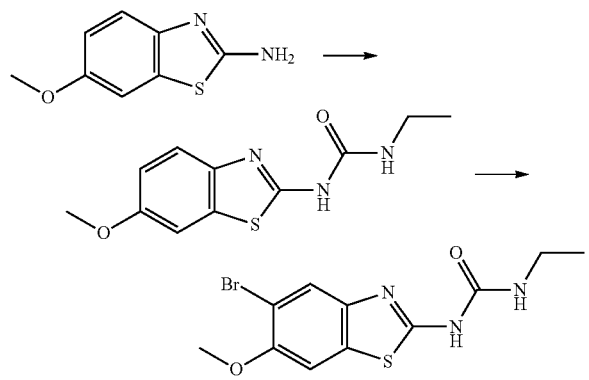

1-Ethyl-3-(6-methoxy-1,3-benzothiazol-2-yl)urea

6-Methoxy-1,3-benzothiazol-2-amine (5.00 g, 27.74 mmol) was dissolved in anhydrous DMSO (20 mL) and triethylamine (15.50 mL, 110.97 mmol) followed by ethyl isocyanate (4.39 mL, 55.49 mmol). The mixture was stirred at rt under N$_2$ for 4 h then quenched with water (~200 mL) and stirred for 1 h. A white solid formed, was collected by filtration, rinsed with water then washed with acetone (100 mL) and the filtrate collected separately to the aqueous filtrate. The solid was partially soluble in acetone so the filtrate was concentrated to dryness under reduced pressure and combined with the solid collected by filtration to obtain the desired compound as a white solid, 6.27 g (90%). m/z: 251.96 [M+H]$^+$.

1-(5-Bromo-6-methoxy-1,3-benzothiazol-2-yl)-3-ethyl-urea

1-Ethyl-3-(6-methoxy-1,3-benzothiazol-2-yl)urea (1.10 g, 4.38 mmol) was suspended in DCM (50 mL) and MeOH (5 mL). Bromine (0.34 mL, 6.60 mmol) was added and the mixture stirred at rt. The mixture was stirred for a total of 1.5 h then concentrated to dryness under reduced pressure. The desired compound was obtained as an orange solid, 2.17 g, and used without further purification, stating purity as 66 mass % in further reactions. m/z: 329.94/331.91 [M+H]$^+$.

Intermediate 12: [5-[2-(4-Ethoxycarbonyl-4-methyl-1-piperidyl)pyrimidin-5-yl]-2-(3-ethyl-5-methyl-2-oxo-1,3,5-triazinan-1-yl)-1,3-benzothiazol-7-yl]boronic acid

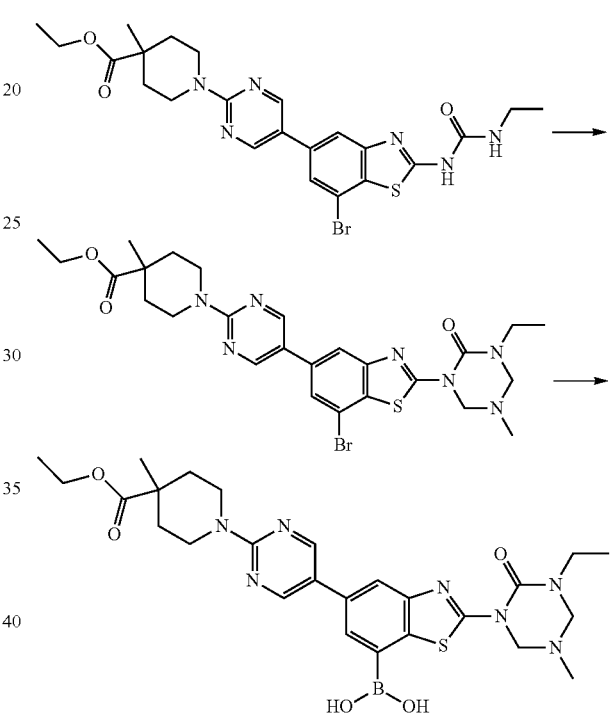

Ethyl 1-[5-[7-bromo-2-(3-ethyl-5-methyl-2-oxo-1,3,5-triazinan-1-yl)-1,3-benzothiazol-5-yl]pyrimidin-2-yl]-4-methyl-piperidine-4-carboxylate: Ethyl 1-[5-[7-bromo-2-(ethylcarbamoylamino)-1,3-benzothiazol-5-yl]pyrimidin-2-yl]-4-methyl-piperidine-4-carboxylate (Jubilant) (3.0 g, 5.48 mmol) was suspended in EtOH (120 mL). N-methylmorpholine (3.0 mL, 27.4 mmol), aqueous formaldehyde (4.45 mL, 54.8 mmol) and methylamine solution (2 M) (13.7 mL, 27.4 mmol) were added and the reaction mixture stirred at rt for 16 h, followed by a further 4 hrs at 80° C. The reaction mixture was cooled to rt and the resulting precipitate filtered. The precipitate was washed with EtOH, Et$_2$O and dried using a vacuum oven to afford the desired product (2.5 g, off white solid).

$^1$H NMR (MeOD/CDCl$_3$) δ 8.59 (s, 2H), 7.78 (d, J=1.5 Hz, 1H), 7.55 (d, J=1.5 Hz, 1H), 5.19 (s, 2H), 4.43-4.34 (m, 4H), 4.20 (q, J=7.1 Hz, 2H), 3.52-3.42 (m, 2H), 3.36-3.28 (m, 2H, obscured by solvent), 2.65 (s, 3H), 2.22-2.12 (m, 2H), 1.52-1.42 (m, 2H), 1.29 (t, J=7.1 Hz, 3H), 1.26-1.20 (m, 6H). m/z [M+H]$^+$ 602.0/604.0.

[5-[2-(4-Ethoxycarbonyl-4-methyl-1-piperidyl)pyrimidin-5-yl]-2-(3-ethyl-5-methyl-2-oxo-1,3,5-triazinan-1-yl)-1,3-benzothiazol-7-yl]boronic acid: Ethyl 1-[5-[7-bromo-2-(3-ethyl-5-methyl-2-oxo-1,3,5-triazinan-1-yl)-1,3- benzothiazol-5-yl]pyrimidin-2-yl]-4-methyl-piperidine-4-carboxylate (100 mg, 0.166 mmol), bis(neopentyl glycolato)diboron (75 mg, 0.33 mmol), Pd(dppf)Cl2.DCM (14 mg, 0.017 mmol), potassium acetate (49 mg, 0.50 mmol) and toluene (2 mL) were sealed in a microwave reaction vial under argon and heated at 130° C. for 40 min. The reaction mixture was diluted with n-hexane (10 mL) before being filtered to remove particulate palladium residues. The filtrate was concentrated to obtain desired product (118 mg, light brown solid). $^1$H NMR (MeOD) δ 8.63 (s, 2H), 7.91 (d, J=1.9 Hz, 1H), 7.82 (d, J=1.8 Hz, 1H), 5.20 (s, 2H), 4.44-4.34 (m, 4H), 4.21 (q, J=7.1 Hz, 2H), 3.50-3.42 (m, 2H), 3.33-3.28 (m, 2H, obscured by solvent), 2.65 (s, 3H), 2.21-2.13 (m, 2H), 1.69-1.38 (m, 2H), 1.33-1.19 (m, 9H). m/z [M+H]$^+$ 568.1.

Intermediate 13: 2-(3-Ethylureido)-7-propionylbenzo[d]thiazol-5-yl trifluoromethanesulfonate

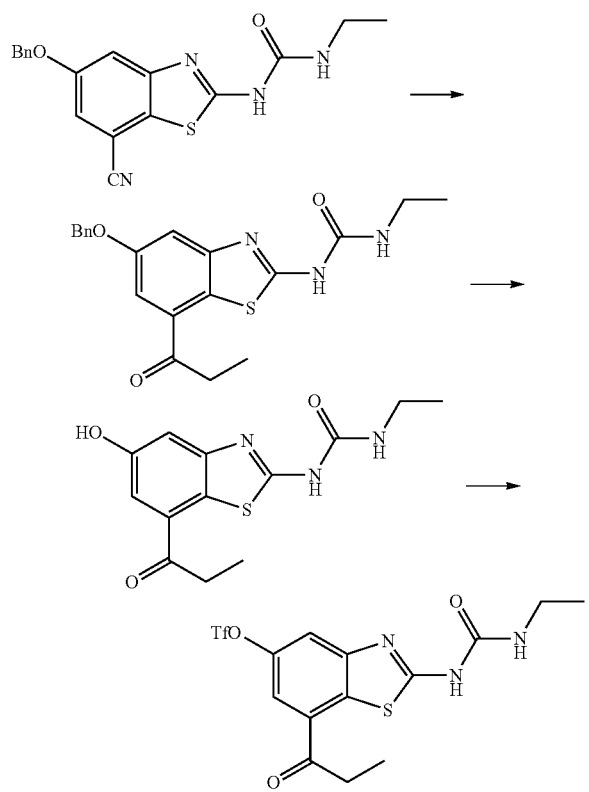

1-(5-(Benzyloxy)-7-propionylbenzo[d]thiazol-2-yl)-3-ethylurea: To a solution of ethyl magnesium bromide (3M in THF, 70 mL, 212.82 mmol) was added 1-(5-(benzyloxy)-7-cyanobenzo[d]thiazol-2-yl)-3-ethylurea (7.50 g, 21.28 mmol) at rt. The reaction was stirred for 4 h at rt. After reaction completion (by TLC), saturated aqueous ammonium chloride solution (250 ml) was added at 0° C. and extracted with EtOAc (8×200 mL). The combined organic layers were washed with brine, dried over anhydrous Na$_2$SO$_4$, filtered and concentrated under reduced pressure. The residue was purified by column chromatography on silica gel (100-200 M, 50% EtOAc-hexane) to obtain the desired product (7.50 gm, 91%). $^1$H NMR (DMSO-d$_6$): δ 10.62 (s, 1H), 7.68 (s, 1H), 7.56 (s, 1H), 7.50 (d, J=7.2 Hz, 2H), 7.39-7.43 (m, 2H), 7.32-7.36 (m, 1H), 6.78 (s, 1H), 5.21 (s, 2H), 3.16-3.21 (m, 4H), 1.05-1.22 (m, 6H). LCMS: 384.29 [M+H]$^+$.

1-Ethyl-3-(5-hydroxy-7-propionylbenzo[d]thiazol-2-yl)urea: To a solution of 1-(5-(benzyloxy)-7-propionylbenzo[d]thiazol-2-yl)-3-ethylurea (5.50 g, 14.34 mmol) in dichloromethane (50 mL) was added methanesulphonic acid (18.6 mL, 286.8 mmol) at rt. The mixture was stirred for 1 h at rt. After reaction completion (by TLC), was added ice-cold water (100 mL) at 0° C. followed by extraction with EtOAc (3×100 mL). The combined organic layers were washed with water, brine, dried over anhydrous Na$_2$SO$_4$, filtered and concentrated under reduced pressure. The residue was purified by column chromatography (silica gel 100-200 M, 5% MeOH-DCM) to obtain the desired product as an off white solid (4.30 g, 64%). $^1$H NMR (DMSO-d$_6$): δ 10.95 (br s, 1H), 9.80 (br s, 1H), 7.43 (s, 1H), 7.25 (s, 1H), 6.80 (br s, 1H), 3.15-3.20 (m, 2H), 3.08-3014 (m, 2H), 1.07-1.14 (m, 6H). LCMS: 294.20 [M+H]$^+$.

2-(3-Ethylureido)-7-propionylbenzo[d]thiazol-5-yl trifluoromethanesulfonate: To a solution of 1-ethyl-3-(5-hydroxy-7-propionylbenzo[d]thiazol-2-yl)urea (3.20 g, 10.9 mmol) in DMF (20 mL) was added DIPEA (3.80 mL, 21.80 mmol) at 0° C. and the mixture stirred at 0° C. for 15 min. N-Phenylbistrifluoromethanesulfonimide (5.80 g, 16.35 mmol) was added at 0° C. and the mixture slowly warmed to rt then stirred overnight. The reaction was quenched by addition of water and the aqueous layer extracted with EtOAc (3×100 mL). The combined organic layers were dried over anhydrous Na$_2$SO$_4$, filtered and concentrated under reduced pressure. The residue was purified by ether washing to obtain desired product as a beige solid (4.30 g, 93%). $^1$H NMR (DMSO-d$_6$): δ 10.95 (br s, 1H), 8.10-8.11 (d, J=2.0 Hz, 1H), 8.02-8.03 (d, J=1.6 Hz, 1H), 6.82 (br s, 1H), 3.17-3.32 (m, 4H), 1.13-1.16 (t, J=7.2 Hz, 3H), 1.08-1.12 (t, J=7.2 Hz, 3H). LCMS: 424.27 [M−H]$^-$.

Intermediate 14: 1-(5,7-Dibromo-6-methoxy-1,3-benzothiazol-2-yl)-3-ethyl-urea

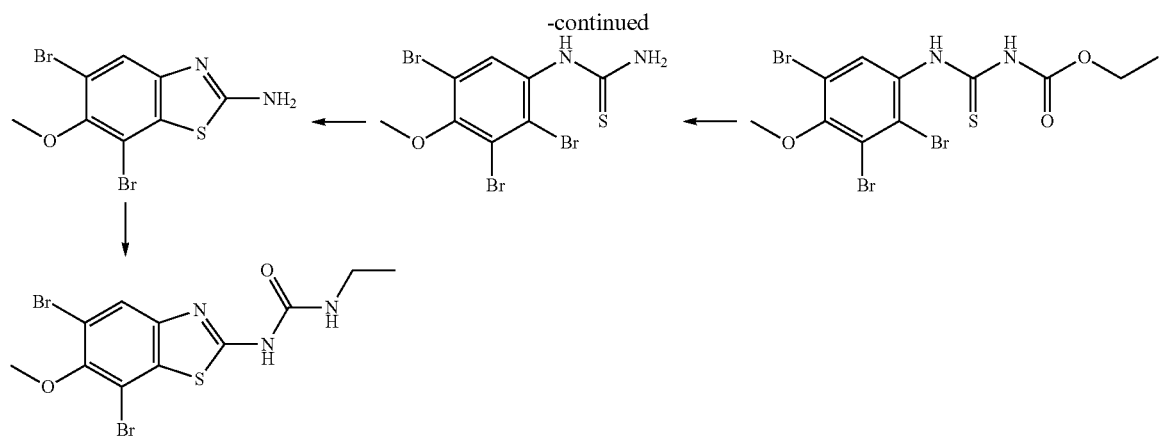

3,5-Dibromo-4-methoxy-aniline

4-Amino-2,6-dibromo-phenol (14.13 g, 52.9 mmol) was dissolved in acetone (425 mL) to give a dark brown solution. Potassium carbonate (21.95 g, 158.8 mmol) was added followed by iodomethane (3.46 mL, 55.6 mmol). The mixture was stirred at rt overnight. The acetone was removed under reduced pressure and the residue partitioned between EtOAc and water. Sodium metabisulphite and brine were added to aid separation of the layers. The mixture was extracted into EtOAc (4×150 mL). The combined organic layers were washed with sodium metabisuphite solution (saturated, aqueous) then brine, dried over $Na_2SO_4$ and concentrated under reduced pressure. A dark brown oil was obtained which crystallised upon standing. The mixture was purified by chromatography, Biotage SP4, 330 g Si cartridge, 20% EtOAc in cyclohexane. The relevant fractions were combined to give the desired compound as a brown solid, 11.31 g (76%). m/z: 280.03/282.00/284.02 $[M+H]^+$.

2,3,5-Tribromo-4-methoxy-aniline 3,5-Dibromo-4-methoxy-aniline (13.04 g, 46.42 mmol) was dissolved in DCM (500 mL) and a solution of bromine (2.38 mL, 46.42 mmol) in DCM (80 mL) was added dropwise. A thick, beige precipitate formed. After 45 minutes, the mixture was quenched with $NaHCO_3$ solution (saturated, aq) to pH 9, the layers separated and the aqueous layer extracted into DCM (3×50 mL). The combined organic phase was washed with brine, dried over $Na_2SO_4$ and concentrated to dryness under reduced pressure to give a brown solid. The mixture was purified by chromatography, Biotage SP4, 2×120 g Si cartridges in series, 10-50% EtOAc in cyclohexane. The relevant fractions were combined to give 2,3,5-tribromo-4-methoxy-aniline which was contaminated with some 2,3,5,6-tetrabromo-4-methoxy-aniline (12.64 g). The column was eluted further to give recovered starting material 3,5-dibromo-4-methoxy-aniline (2.84 g). The recovered starting material, 3,5-dibromo-4-methoxy-aniline (2.84 g, 10.11 mmol) was dissolved in DCM (100 mL) and a solution of bromine (0.52 mL, 10.11 mmol) in DCM (5 mL) was added dropwise. The mixture was stirred at rt for 2.5 h. The mixture was quenched with $NaHCO_3$ solution (saturated, aq) to pH 9, the layers separated and the aqueous layer extracted into DCM (3×50 mL). The combined organic phase was dried over $Na_2SO_4$ and concentrated to dryness under reduced pressure. This material was combined with the impure 2,3,5-tribromo-4-methoxy-aniline and purified by chromatography, Biotage SP4, 330 g Si cartridge, 10% EtOAc in cyclohexane. The relevant fractions were combined to give the desired compound as an orange oil, 9.95 g (60%). m/z: 357.93/359.89/361.90/363.84 $[M+H]^+$.

Ethyl N-[(2,3,5-tribromo-4-methoxy-phenyl)carbamothioyl]carbamate 2,3,5-Tribromo-4-methoxy-aniline (4.72 g, 13.1 mmol) was dissolved in acetone (150 mL) and ethoxycarbonyl isothiocyanate (1.63 mL, 14.4 mmol) was added. The solution was heated to 40° C. After 20 minutes a pale yellow precipitate had formed. The viscous mixture was cooled to rt and stirred at rt overnight. The solvent was removed under reduced pressure. Cyclohexane (~150 mL) was added to the residue and the suspension sonicated. The solid was collected by filtration through a PTFE filter to give an off-white fluffy solid which was dried in the vacuum oven (40° C.) to afford the desired compound as an off-white solid, 6.00 g (93%). m/z: 488.78/490.80/492.75/494.80 $[M+H]^+$.

(2,3,5-Tribromo-4-methoxy-phenyl)thiourea

Ethyl N-[(2,3,5-tribromo-4-methoxy-phenyl)carbamothioyl]carbamate (500 mg, 1.02 mmol) was dissolved in ethylamine solution (5.09 mL, 10.18 mmol, 2 M in THF) and stirred at rt overnight. The mixture was concentrated to dryness under reduced pressure to give the desired compound as an off white solid. The mixture was used with no further purification in the next step. m/z: 416.83/418.84/420.83/422.83 $[M+H]^+$.

5,7-Dibromo-6-methoxy-1,3-benzothiazol-2-amine

Anhydrous DMSO (2 mL) was added to a mixture of ethyl N-[(2,3,5-tribromo-4-methoxy-phenyl)carbamothioyl]carbamate (426 mg, 1.02 mmol), CuO (8 mg, 0.10 mmol) and potassium carbonate (211 mg, 1.53 mmol). The mixture was sonicated then heated to 90° C. in a pre-heated heating block under air. The mixture was cooled to rt after 55 minutes and diluted with water. The mixture was extracted into EtOAc (3×50 mL) and the combined organic layers were washed with water then brine. The organic layer was dried over $Na_2SO_4$ and the mixture filtered through a PTFE filter to remove copper salts, then the filtrate was concentrated to dryness under reduced pressure. The desired compound was obtained as an off-white solid, 208 mg (60% over 2 steps). m/z: 337.01/339.01/340.97 $[M+H]^+$.

1-(5,7-Dibromo-6-methoxy-1,3-benzothiazol-2-yl)-3-ethyl-urea 5,7-Dibromo-6-methoxy-1,3-benzothiazol-2-amine (208 mg, 0.62 mmol) was dissolved in anhydrous DMSO (1 mL) and triethylamine (0.189 mL, 1.35 mmol) followed by ethyl isocyanate (0.058 mL, 0.74 mmol). The mixture was stirred at rt. A further aliquot of ethyl isocyanate (0.058 mL, 0.74 mmol) was added after 3 h. After 3.75 h, the mixture was diluted with water and extracted into EtOAc (3×30 mL). The combined organic phases were washed with water and brine, dried over $Na_2SO_4$ and concentrated to dryness under reduced pressure. The desired compound was obtained as a pale yellow solid, 234 mg (93%). The material was used without further purification in the next step. m/z: 407.83/409.83/411.81 $[M+H]^+$.

Intermediate 15: 5,7-Dichloro[1,2,4]triazolo[1,5-a]pyridin-2-amine

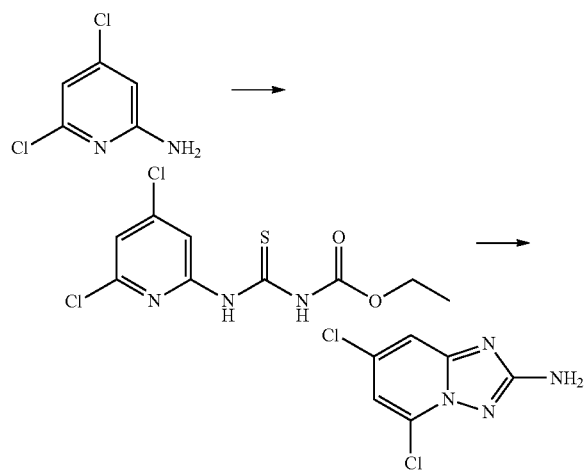

Ethyl [(4,6-dichloropyridin-2-yl)carbamothioyl]carbamate: Ethoxycarbonyl isothiocyanate (2 g, 16 mmol) was added to a solution of 4,6-dichloropyridin-2-amine (2.2 g, 13 mmol) in 1,4-dioxane (100 mL) and stirred at rt for 18 h. LCMS showed desired product. The reaction mixture was concentrated in vacuo and the residue azeotroped with EtOAc (3×20 mL) to give a cream solid, which was triturated with EtOAc to give the desired product as a white solid (2.9 g, 76%). $^1$H NMR (DMSO) δ 12.31 (s, 1H), 11.77 (s, 1H), 8.86 (d, J=1.1 Hz, 1H), 7.66 (d, J=1.5 Hz, 1H), 4.25 (q, J=7.1 Hz, 2H), 1.28 (t, J=7.1 Hz, 3H). m/z $[M+H]^+$=293.88

5,7-Dichloro[1,2,4]-triazolo[1,5-a]pyridin-2-amine

Ethyl [(4,6-dichloropyridin-2-yl)carbamothioyl]carbamate (2.9 g, 9.9 mmol) was added to a stirred suspension of hydroxylamine hydrochloride (1.1 g, 16 mmol) and DIEA (1.9 g, 15 mmol) in MeOH/EtOH (1:1, 40 mL) portion-wise as a solid. This mixture was stirred at rt for 2 h and then heated at 80° C. for 18 h. The reaction mixture was concentrated in vacuo and the resultant reside treated with water yielding a cream solid, which was filtered and dried in a vacuum oven at 40° C. for 18 h to give the desired product (1.2 g, 60%). $^1$H NMR (DMSO) δ 7.58 (d, J=2.0 Hz, 1H), 7.35 (d, J=2.0 Hz, 1H), 6.44 (s, 2H). m/z $[M+H]^+$=203.15.

Intermediate 16: Ethyl 7-bromo-5-chloro-imidazo[1,2-a]pyridine-2-carboxylate

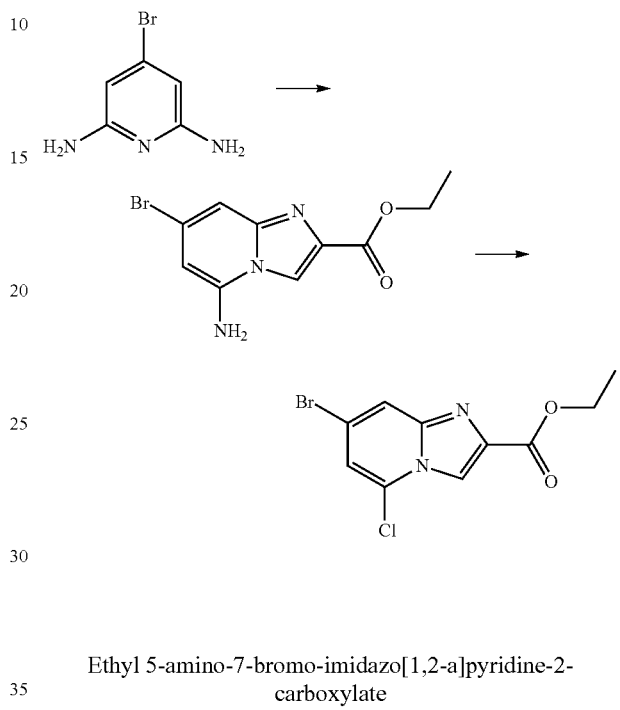

Ethyl 5-amino-7-bromo-imidazo[1,2-a]pyridine-2-carboxylate 4-bromopyridine-2,6-diamine (3 g, 15.96 mmol) was dissolved in EtOH (300 mL). Ethyl bromopyruvate (2.34 mL, 16.8 mmol, 90% tech grade) was added. The mixture was heated at reflux for 5 h. The solvent was evaporated under reduced pressure to give a dark tan foam which was triturated with 200 mL of saturated $NaHCO_3$ overnight. The solids were filtered, washed with 2×10 mL of saturated $NaHCO_3$, then triturated with EtOAc (100 mL) twice, filtered and air dried to give the desired product as a tan powder weighing 3.15 g (70%).

Ethyl 7-bromo-5-chloro-imidazo[1,2-a]pyridine-2-carboxylate 5-amino-7-bromo-imidazo[1,2-a]pyridine-2-carboxylate (3.15 g, 11.1 mmol) was suspended in 4M HCl (315 mL) and stirred vigorously overnight to form the HCl salt. This material was then cooled in an ice/MeOH bath and treated with sodium nitrite (1.1 g, 17 mmol). The mixture was stirred for 1 h then allowed to warm to ~5° C. where stirring was maintained for another 30 minutes. Urea (470 mg, 7.8 mmol) was added and stirred for another hour while warming to rt. Solid $NaHCO_3$ (~90 g) was added slowly in order to basify the mixture, which was then extracted with EtOAc (400 mL), concentrated, and plugged (0-50% EtOAc/heptane). The faster eluting material (TLC, 40% EtOAc/hexane, Rf~0.4) was concentrated to a gum (yield 0.867 g (26%)).

LCMS m/z $[M+1]^+$ 304.9.

Intermediate 17: 1-(5,7-dibromo-1,3-benzoxazol-2-yl)-3-ethylurea

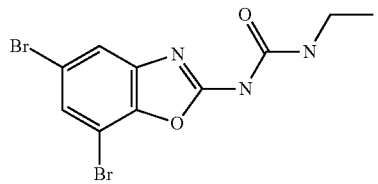 [SMILES: CCNC(=O)Nc1nc2cc(Br)cc(Br)c2o1]

A solution of 5,7-dibromo-1,3-benzoxazol-2-amine [1] (1050 mg; 3.60 mmol) in DMSO (0.7 mL) and dioxane (16 mL) was treated with triethylamine (980 mg, 9.7 mmol) and ethyl isocyanate (767 mg, 10.79 mmol). The reaction was stirred at 60° C. for 24 h. After that time an additional batch of ethyl isocyanate (400 mg, 6 mmol) and triethylamine (500 mg, 5 mmol) were added and the mixture stirred at 60° C. further 24 h. Water was then added and the solid formed was filtrated, rinsed with water and then triturated with EtOAc to give the desired product as a white-off solid (m=950 mg; yield: 73%). $^1$H NMR (DMSO) δ 11.25 (br s, 1H), 8.16-8.10 (m, 1H), 8.09 (s, 1H), 7.91 (s, 1H), 3.30-3.22 (m, 2H), 1.13 (t, J=7.2 Hz, 3H). ESI-MI m/z [M+H]$^+$: 293.1.

[1] Prepared according to the method described in *J. Pharm. Sci* (1964) Vol. 53 p 538-544.

Preparation of Coupling Precursors

Precursor 1: 1-(5-bromopyrimidin-2-yl)-2-methylpiperidine-2-carboxylic acid

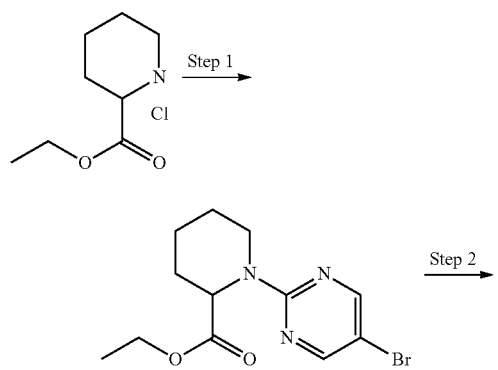

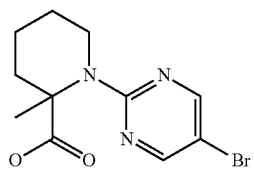

Ethyl 1-(5-bromopyrimidin-2-yl)piperidine-2-carboxylate

To a solution of ethyl piperidine-2-carboxylate hydrochloride (0.5 g, 2.58 mmol) in DMF (15 mL) was added potassium carbonate (1.77 g, 12.89 mmol) at rt. The mixture was stirred at rt for 10 min followed by addition of 5-bromo-2-chloropyrimidine (0.5 g, 2.58 mmol). The reaction was heated up to 80° C. for 3 h. After reaction completion (by TLC), the mixture was poured onto 100 mL ice-cold water and extracted with EtOAc (3×100 mL). The combined organic layer was washed with brine, dried over anhydrous Na$_2$SO$_4$ and evaporated under reduced pressure. The crude residue was purified over 100-200 M silica-gel by using 1.50% EtOAc: hexane to obtain the desired product as an off white solid (0.37 g, 46% yield). MS: 314.08 [M+H]$^+$.

1-(5-bromopyrimidin-2-yl)-2-methyl-piperidine-2-carboxylic acid (Precursor 1)

To an ice-cold solution of ethyl 1-(5-bromopyrimidin-2-yl)piperidine-2-carboxylate (0.37 g, 1.18 mmol) in THF (25 mL) was added NaH (60% dispersion in mineral oil, 0.06 g, 1.41 mmol) portion wise. The mixture was stirred at the same temperature for 45 min followed by addition of MeI (0.52 mL, 8.26 mmol) at 0° C. The temperature of the reaction was slowly raised up to rt and left to stir for 16 h. The reaction was then cooled to 0° C., quenched by drop wise addition of ice-cold water then extracted with EtOAc (3×100 mL). The combined organics were washed with brine, dried (Na$_2$SO$_4$), filtered and concentrated under reduced pressure. The crude residue was purified over 100-200 M silica-gel by using 2% EtOAc: hexane to obtain the desired product as off-white solid (0.115 g, 32% yield). MS: 300.09 [M+H]$^+$.

Precursor 2: Methyl 1-(5-bromopyrimidin-2-yl)-4-hydroxy-3-methyl-piperidine-3-carboxylate

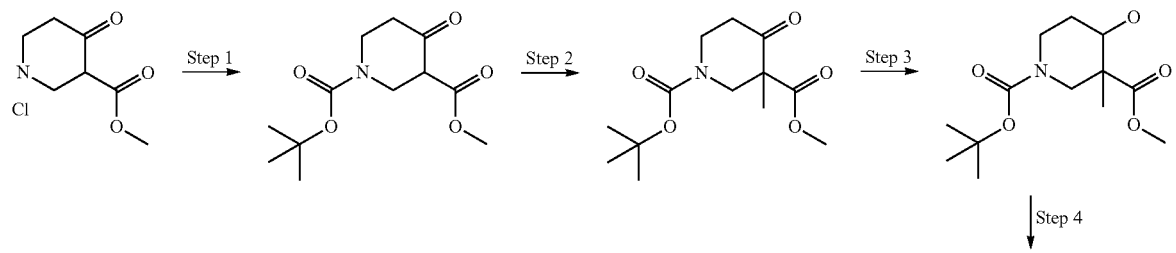

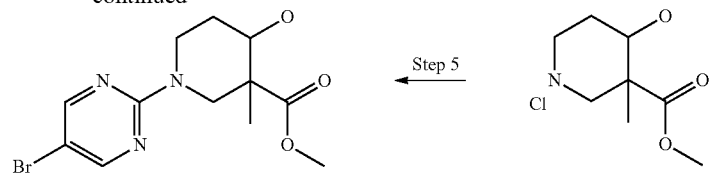

O1-tert-butyl O3-methyl 4-oxopiperidine-1,3-dicarboxylate

To an ice-cold solution of methyl 4-oxopiperidine-3-carboxylate hydrochloride (1 g, 5.18 mmol) in DCM (10 mL) was added DMAP (1.2 g, 10.36 mmol) followed by addition of Boc anhydride (1 mL, 5.18 mmol). The mixture was stirred at rt for 16 h. After completion of reaction (by TLC), DCM (75 mL) was added and the organic layer washed with water and brine then dried over anhydrous Na₂SO4, filtered and concentrated under reduced pressure. The crude residue was purified over 100-200 M silica-gel by using 10% EtOAc: hexane to obtain the product as a viscous liquid (1.30 g, 76% yield). MS: 258.32 [M+H]⁺.

O1-tert-butyl O3-methyl 3-methyl-4-oxo-piperidine-1,3-dicarboxylate

A solution of O1-tert-butyl O3-methyl 4-oxopiperidine-1,3-dicarboxylate (1 g, 3.88 mmol) in DMF (100 mL) was cooled to 0° C. followed by portion wise addition of NaH (60% dispersion of mineral oil, 0.16 g, 3.88 mmol). The resulting mixture was stirred at the same temperature for 15 min followed by addition of MeI (0.7 mL, 11.64 mmol) at 0° C. then stirred at rt for 44 h. After completion of reaction (by TLC), water (100 mL) was added and extracted with EtOAc (3×100 mL). The combined organics were washed with brine, dried (Na₂SO₄), filtered and concentrated under reduced pressure to obtain the product as a yellow oil (0.9 g). MS: 272.12 [M+H]⁺.

O1-tert-butyl O3-methyl 4-hydroxy-3-methyl-piperidine-1,3-dicarboxylate

To an ice-cold solution of O1-tert-butyl O3-methyl 3-methyl-4-oxo-piperidine-1,3-dicarboxylate (0.5 g, 1.85 mmol) in MeOH (10 mL) was added acetic acid (0.5 mL) followed by portion wise addition of sodium cyanoborohydride (0.12 g, 1.85 mmol). The mixture was stirred at rt for 4 h. After completion of reaction (by TLC), water (50 mL) was added and extracted with DCM (3×100 mL). The combined organic layer was washed with brine, dried over anhydrous Na₂SO₄, filtered and concentrated under reduced pressure to obtain the product as a viscous liquid (0.5 g). MS: 274.13 [M+H]⁺.

Methyl 4-hydroxy-3-methyl-piperidine-3-carboxylate hydrochloride

To an ice-cold solution of O1-tert-butyl O3-methyl 4-hydroxy-3-methyl-piperidine-1,3-dicarboxylate (0.5 g, 1.83 mmol) in 1,4-dioxane (10 mL) was added HCl-dioxane (4 M, 5 mL) solution. The resulting mixture was stirred at rt for 30 min. After reaction completion (by TLC), solvent was evaporated to obtain the desired product as a solid (0.4 g). MS: 174.13 [M+H]⁺.

Methyl 1-(5-bromopyrimidin-2-yl)-4-hydroxy-3-methyl-piperidine-3-carboxylate (Precursor 2)

To a solution of methyl 4-hydroxy-3-methyl-piperidine-3-carboxylate hydrochloride (0.4 g, 1.91 mmol) in EtOH (10 mL) was added DIPEA (1.7 mL, 9.55 mmol) at rt. The resulted mixture was stirred at rt for 10 min followed by addition of 5-bromo-2-chloropyrimidine (0.37 g, 1.91 mmol). The reaction mixture was heated up to 70° C. for 1 h. After completion of reaction (by TLC), solvent was evaporated and the crude residue was purified over 100-200 M silica-gel by using 25% EtOAc: hexane to obtain the product as an off white solid (0.345 g, 55%). MS: 330.12 [M+H]⁺.

Precursor 3: Ethyl 1-(5-bromopyrimidin-2-yl)-3,4-dimethyl-piperidine-4-carboxylate

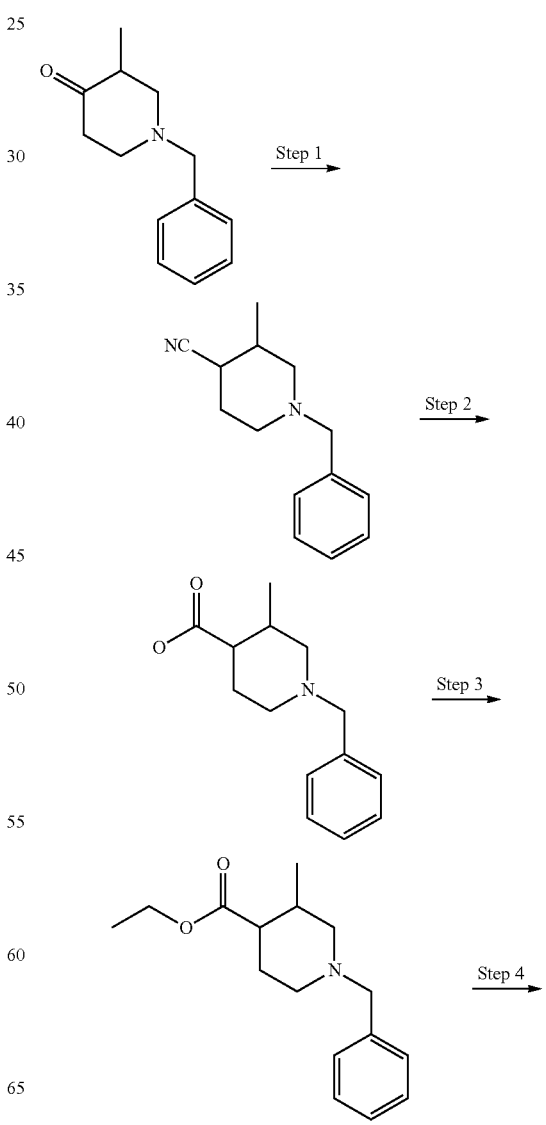

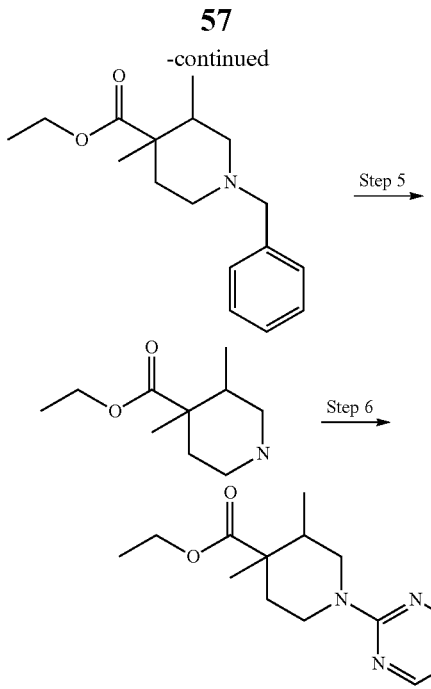

Step 1:

A solution of 1-benzyl-3-methylpiperidin-4-one (5 g, 24.6 mmol) in DMF (100 mL) was cooled to 0° C. followed by dropwise addition of potassium tert-butoxide (1M solution in THF) (73.8 mL, 73.82 mmol). The resulting mixture was stirred at the same temperature for 15 minutes followed by addition of p-toluene sulphonylmethyl isocyanide (7.2 g, 36.9 mmol) and EtOH (3.8 mL, 60 mmol) at 0° C. The mixture was stirred at 50° C. for 1 h and after completion of reaction (by TLC), water (100 mL) was added and extracted with EtOAc (3×100 mL). The combined organics were washed with brine, dried ($Na_2SO_4$), filtered and concentrated under reduced pressure. The crude residue was purified over 100-200 M silica-gel by using 10% EtOAc:hexane to obtain the desired product (2.60 g, 50% yield). MS: 215.15 [M+H]$^+$.

Step 2:

A solution of 1-benzyl-3-methylpiperidine-4-carbonitrile (2.6 g, 12.1 mmol) and conc. HCl (50 mL) was heated up to 110° C. and stirred at the same temperature for 48 h. After completion of reaction (by TLC), the solvent was concentrated, 10 mL water added, pH of the aqueous layer adjusted to 5-6 then extracted with hot EtOAc (3×100 mL). The combined organic layer was dried over $Na_2SO_4$ and solvent evaporated to obtain the desired product as a sticky solid (0.5 g, 18% yield). MS: 234.16 [M+H$^+$.

Step 3:

To a stirred solution of 1-benzyl-3-methylpiperidine-4-carboxylic acid (0.5 g, 2.14 mmol) in EtOH (10 mL) was added conc. $H_2SO_4$ (0.5 mL) at 0° C. The resulting mixture was heated up to 80° C. for 2 h. After completion of reaction (By TLC), the solvent was concentrated, added 10 mL of water to reaction mass and pH of the aqueous layer was neutralized by using NaHCO$_3$ followed by extraction with hot EtOAc (3×100 mL). The combined organic layer was dried over $Na_2SO_4$ and solvent was evaporated under reduced pressure. The crude residue was purified over 100-200 M silica-gel by using 5% EtOAc:hexane to obtain the yellow oil compound (0.5 g, 89% yield). MS: 262.25 [M+H]$^+$.

Step 4:

A solution of methyl 1-benzyl-3-methylpiperidine-4-carboxylate (0.5 g, 1.91 mmol) in THF (10 mL) was cooled to −78° C. followed by dropwise addition of LDA (1.80 M in THF, 2.4 mL, 3.82 mmol). The resulting mixture was stirred at the same temperature for 45 min followed by addition of MeI (0.36 mL, 5.73 mmol) at −78° C. The temperature of the reaction was slowly raised up to rt and left to stir for 6 h. The reaction was then cooled to 0° C. and quenched by drop wise addition of saturated NH$_4$Cl solution (25 mL). The reaction was then extracted with EtOA (3×75 mL), the combined organics washed with brine, dried ($Na_2SO_4$), filtered and concentrated under reduced pressure. The crude residue was purified over 100-200 M silica-gel by using 5% EtOAc:hexane to obtain the orange viscous liquid compound (0.33 g, 62% yield). MS: 276.22 [M+H]$^+$.

Step 5:

To a stirred solution of ethyl 1-benzyl-3,4-dimethylpiperidine-4-carboxylate (0.33 g, 1.2 mmol) in MeOH (10 mL) was added palladium hydroxide at rt. The mixture was stirred at rt for 6 h under H$_2$ atmosphere. After reaction completion (by TLC), the mixture was passed through celite and solvent evaporated. The crude (0.20 g) residue was carried forwarded without further purification. MS: 186.19 [M+H]$^+$.

Ethyl 1-(5-bromopyrimidin-2-yl)-3,4-dimethyl-piperidine-4-carboxylate (Precursor 3)

To a solution of ethyl 3,4-dimethylpiperidine-4-carboxylate (0.2 g, 1.08 mmol) in EtOH (7 mL) was added DIPEA (0.6 mL, 3.24 mmol) at rt. The mixture was stirred at rt for 10 min followed by addition of 5-bromo-2-chloropyrimidine (0.21 g, 1.08 mmol) then heated up to 70° C. for 1 h. After reaction completion (by TLC), solvent was evaporated and the crude residue was purified over 100-200 M silica-gel using 10% EtOAc:hexane to obtain the desired product as a yellow solid (0.33 g, 95% yield). MS: 341.03 [M+H]$^+$.

Precursor 4: Ethyl 1-(5-bromo-3-pyridyl)-4-methyl-piperidine-4-carboxylate

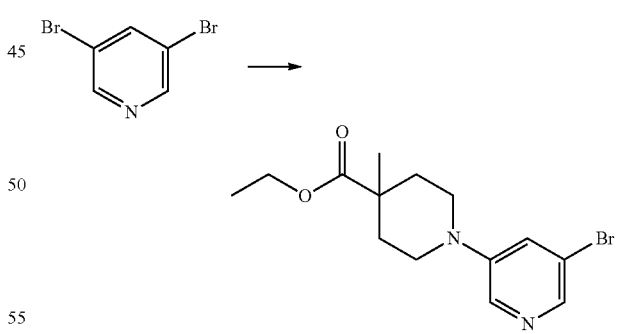

To a solution of 4-methylpiperidine-4-carboxylate hydrochloride (3.6 g, 21.10 mmol) in DMSO (5 mL) was added Cs$_2$CO$_3$ (1.63 g, 5 mmol) at rt. The resulting mixture was stirred at rt for 10 min followed by addition of 3,5-dibromopyridine (1.0 g, 4.20 mmol). The reaction was heated up to 150° C. for 48 h. After completion (by TLC), the reaction mixture was poured into 100 mL of ice-cold water and extracted with EtOAc (3×100 mL). The combined organics were washed with brine, dried over anhydrous Na$_2$SO$_4$, filtered and evaporated under reduced pressure. The crude residue was purified over 100-200 M silica-gel by using 20.0% EtOAc:hexane to obtain a viscous liquid product (0.2 g, 14% yield). MS: 327.08 [M+H]⁺.

Precursor 5: Ethyl 3-(5-bromo-2-pyridyl)-5-methyl-4H-isoxazole-5-carboxylate

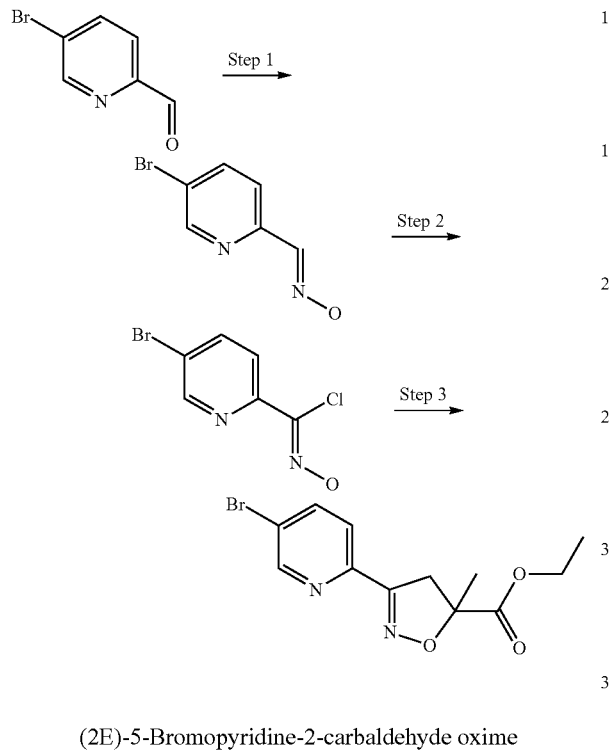

(2E)-5-Bromopyridine-2-carbaldehyde oxime

To a solution of 5-bromopyridine-2-carbaldehyde (0.5 g, 2.69 mmol) in MeOH (5.8 mL) was added water (5.8 mL) at 0° C. The mixture was stirred at same temperature for 10 min followed by addition of hydroxylamine hydrochloride (0.23 g, 3.38 mmol) and aqueous solution of $Na_2CO_3$ (0.17 g, 1.6 mmol). The reaction was then heated up to 60° C. for 1 h. After completion (by TLC), the mixture was poured into 25 mL of ice-cold water. The solid thus precipitated was filtered and dried under vacuum to obtain the product as a white solid (0.5 g, 93% yield). MS: 201.12 [M+H]⁺.

5-Bromo-N-hydroxy-pyridine-2-carboximidoyl chloride

To a solution of (2E)-5-bromopyridine-2-carbaldehyde oxime (0.5 g, 2.49 mmol) in DMF (1.50 mL) was added NCS (0.4 g, 2.97 mmol) at 0° C. The mixture was stirred at same temperature for 10 min then dry HCl (g) was purged for 20 min at 0° C. The reaction was then poured in 25 mL of ice-cold water and the precipitated solid filtered and dried under vacuum to obtain a white solid produce (0.5 g, 86% yield). MS: 234.93 [M+H]⁺.

Ethyl 3-(5-bromo-2-pyridyl)-5-methyl-4H-isoxazole-5-carboxylate (Precursor 5)

To the solution of 5-bromo-N-hydroxy-pyridine-2-carboximidoyl chloride (0.6 g, 2.56 mmol) in EtOAc (15 mL) was added ethyl methacrylate (1.5 mL, 13.33 mmol) at 0° C. The mixture was stirred at the same temperature for 10 min followed by addition of triethyl amine (0.35 mL, 2.82 mmol) then stirred at 0° C. for 1 h. After completion (by TLC), the residue was poured into 100 mL of ice-cold water followed by extraction with EtOAc (3×100 mL). The combined organics were washed with brine, dried over anhydrous $Na_2SO_4$, filtered and evaporated under reduced pressure. The crude residue was purified over 100-200 M silica-gel using 5.0% EtOAc:hexane to obtain a white solid product (0.70 g, 88% yield). ¹H NMR (DMSO-d₆): δ 1.19 (t, J=7.20 Hz, 3H), 1.60 (s, 3H), 3.41 (m, 1H), 3.86 (m, 1H), 4.16 (q, J=7.20 Hz, 2H), 7.87 (d, J=8.4 Hz, 1H), 8.14 (d, J=2.4 Hz, 1H) and 8.79 (s, 1H).

Precursor 6: 1-(5-bromopyrimidin-2-yl)-4-phenyl-piperidine-4-carboxylic acid

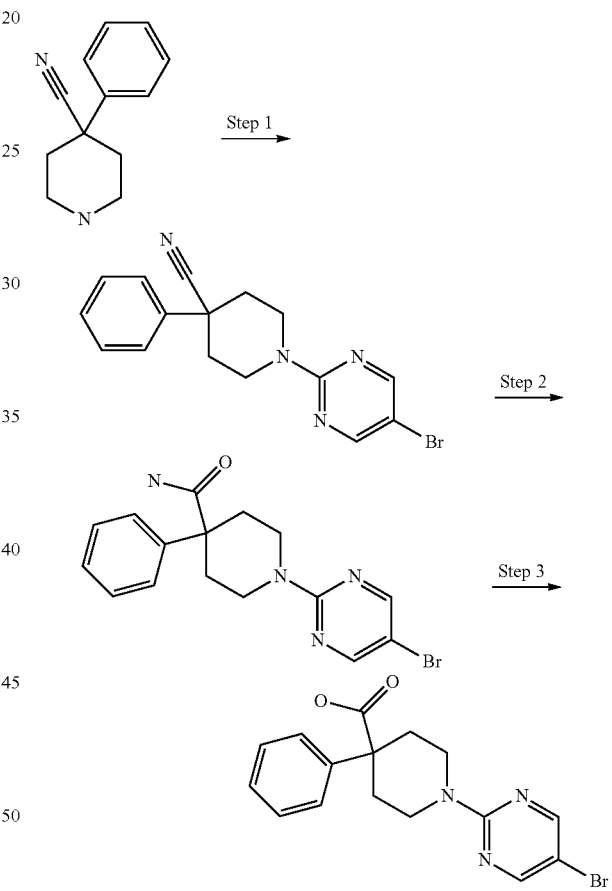

1-(5-Bromopyrimidin-2-yl)-4-phenyl-piperidine-4-carbonitrile

To a solution of 4-phenylpiperidine-4-carbonitrile (0.35 g, 1.55 mmol) in EtOH (5 mL) was added DIPEA (0.8 mL, 4.55 mmol) at rt. The mixture was stirred at rt for 10 min followed by addition of 5-bromo-2-chloropyrimidine (0.15 g, 1.3 mmol). The mixture was heated up to 70° C. for 1 h. After reaction completion (by TLC), solvent was evaporated and the crude residue purified over 100-200 M silica-gel using 10% EtOAc:hexane to obtain the product as a yellow solid (0.31 g, 70% yield). MS: 343.09 [M+H]⁺.

1-(5-Bromopyrimidin-2-yl)-4-phenyl-piperidine-4-carboxamide

A solution of 1-(5-bromopyrimidin-2-yl)-4-phenylpiperidine-4-carbonitrile (0.31 g, 0.9 mmol) in HBr-acetic acid (12 mL) was refluxed for 16 h. After completion of reaction (by TLC), the mixture was poured into 100 mL of ice cold water and extracted with EtOAc (3×150 mL). The combined organics were washed with brine, dried over anhydrous $Na_2SO_4$, filtered and evaporated to obtain the desired product as a white solid (0.12 g). MS: 361.15 $[M+H]^+$.

1-(5-Bromopyrimidin-2-yl)-4-phenyl-piperidine-4-carboxylic acid (Precursor 6)

A solution of 1-(5-bromopyrimidin-2-yl)-4-phenylpiperidine-4-carboxamide (0.10 g, 0.28 mmol) in 6N HCl (2.0 mL) was heated to 150° C. for 20 min under microwave irradiation. The reaction mixture was then poured into 100 mL of ice cold water and extracted with EtOAc (3×150 mL). The combined organics were washed with brine, dried over anhydrous $Na_2SO_4$, filtered and evaporated to obtain the desired product as a white solid (0.08 g, 80% yield). $^1$H NMR (DMSO-$d_6$): δ 1.78 (m, 2H), 2.44 (m, 2H), 3.16 (m, 2H), 4.42 (m, 2H), 7.24 to 7.40 (m, 5H), 8.44 (s, 2H) and 12.78 (br, s, 1H).

Precursor 7: Ethyl 1-(5-bromopyrimidin-2-yl)-4-cyano-piperidine-4-carboxylate

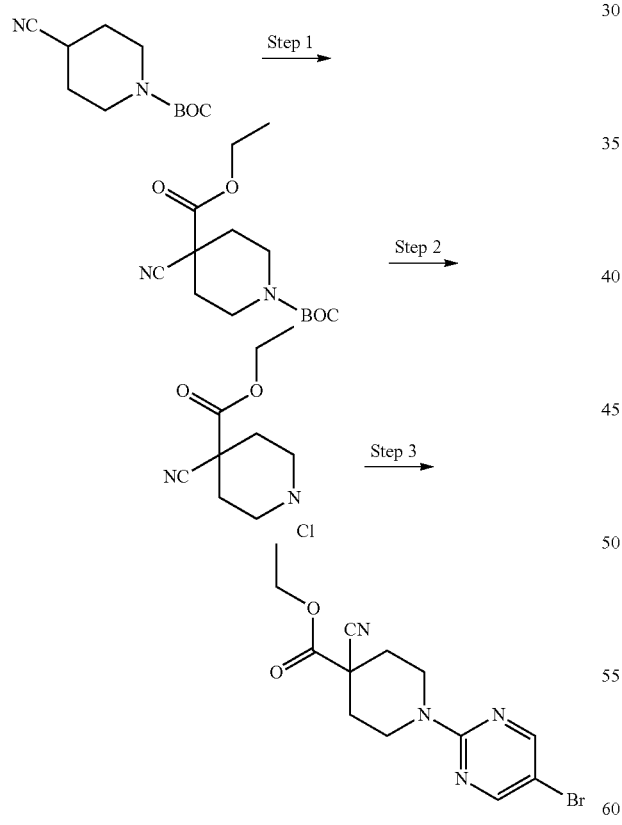

O1-tert-Butyl O4-ethyl 4-cyanopiperidine-1,4-dicarboxylate

A solution of tert-butyl 4-cyanopiperidine-1-carboxylate (0.75 g, 3.57 mmol) in THF (25.0 mL) was cooled to −78° C. followed by dropwise addition of LDA (1.8 M in THF, 6.0 mL, 5.35 mmol) and stirred at the same temperature (−78° C.) for 45 min followed by addition of ethyl chloroformate (0.46 g, 4.28 mmol). The temperature of the reaction was slowly raised to rt and left to stir for 6 h. The reaction was then cooled to 0° C. and quenched by drop wise addition of saturated $NH_4Cl$ solution (50 mL), extracted with EtOAc (3×100 mL) and the combined organics washed with brine, dried ($Na_2SO_4$), filtered and concentrated under reduced pressure. The crude residue was purified over 100-200 M silica-gel using 7% EtOAc:hexane to obtain the product as an orange viscous liquid (0.4 g, 48% yield). MS: 283.14 $[M+H]^+$.

Ethyl 4-cyanopiperidine-4-carboxylate hydrochloride

To an ice-cold solution of O1-tert-butyl O4-ethyl 4-cyanopiperidine-1,4-dicarboxylate (0.4 g, 1.41 mmol) in 1,4-dioxane (10 mL) was added HCl-dioxane (4 M, 5 mL) solution. The resulting mixture was stirred at rt for 30 minutes. After completion of reaction (by TLC), solvent was evaporated to obtain the product as a solid (0.28 g). MS: 183.27 $[M+H]^+$.

Ethyl 1-(5-bromopyrimidin-2-yl)-4-cyano-piperidine-4-carboxylate (Precursor 7)

To a solution of ethyl 4-cyanopiperidine-4-carboxylate hydrochloride (0.56 g, 2.6 mmol) in EtOH (10 mL) was added DIPEA (0.8 mL, 4.29 mmol) at rt and stirred at rt for 10 min followed by addition of 5-bromo-2-chloropyrimidine (0.33 g, 1.73 mmol). The reaction mixture was heated up to 70° C. for 1 h. After completion of reaction (by TLC), solvent was evaporated and the crude residue purified over 100-200 M silica-gel using 10% EtOAc:hexane to obtain the product as a yellow solid (0.4 g, 68% yield). $^1$H NMR (DMSO-$d_6$): δ 1.20 (t, J=7.20 Hz, 3H), 2.04 (m, 2H), 2.22 (m, 2H), 3.22 (m, 2H), 4.15 (q, J=7.20 Hz, 2H), 4.32 (m, 2H) and 8.50 (s, 2H).

Precursor 8: 1-(5-bromopyrimidin-2-yl)-4-hydroxy-piperidine-4-carboxylic acid

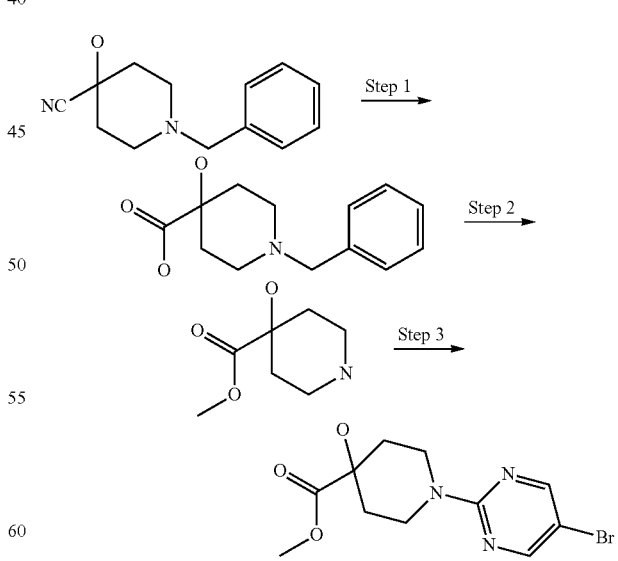

1-Benzyl-4-hydroxy-piperidine-4-carboxylic acid

A solution of 1-benzyl-4-hydroxypiperidine-4-carbonitrile (1 g, 4.60 mmol) in 6N HCl (5 mL) was heated to 120° C.

for 30 min under microwave irradiation. After completion of reaction (by TLC), solvent was concentrated under reduced pressure to give the desired product (1.5 g. MS: 236.16 [M+H]+.

Methyl 4-hydroxypiperidine-4-carboxylate

To a stirred solution of 1-benzyl-4-hydroxypiperidine-4-carboxylic acid (1.2 g, 5.10 mmol) in MeOH (15 mL) was added palladium hydroxide and the resulting mixture was stirred at rt for 6 h under $H_2$ atmosphere. After completion of reaction (by TLC), the reaction was passed through celite and the filtrate evaporated under reduced pressure to give the desired product (1 g). MS: 160.18 [M+H]+.

Methyl 1-(5-bromopyrimidin-2-yl)-4-hydroxy-piperidine-4-carboxylate (Precursor 8)

To a solution of methyl 4-hydroxypiperidine-4-carboxylate (0.4 g, 2.52 mmol) in EtOH (10 mL) was added DIPEA (2.2 mL, 12.57 mmol) and the resulting solution stirred at rt for 10 min followed by addition of 5-bromo-2-chloropyrimidine (0.49 g, 2.52 mmol). The reaction mixture was then heated up to 70° C. for 1 h. After completion of reaction (by TLC), solvent was evaporated and the crude residue purified over 100-200 M silica-gel using 10% EtOAc:hexane to obtain the product as a yellow solid (0.35 g, 44% yield). $^1$H NMR (DMSO-$d_6$): δ 1.64 (m, 2H), 1.82 (m, 2H), 3.20 (m, 2H), 3.64 (s, 3H), 4.27 (m, 2H), 5.60 (s, 1H) and 8.44 (s, 2H).

Precursor 9: 1-(5-bromopyrimidin-2-yl)-4-methoxy-piperidine-4-carboxylic acid

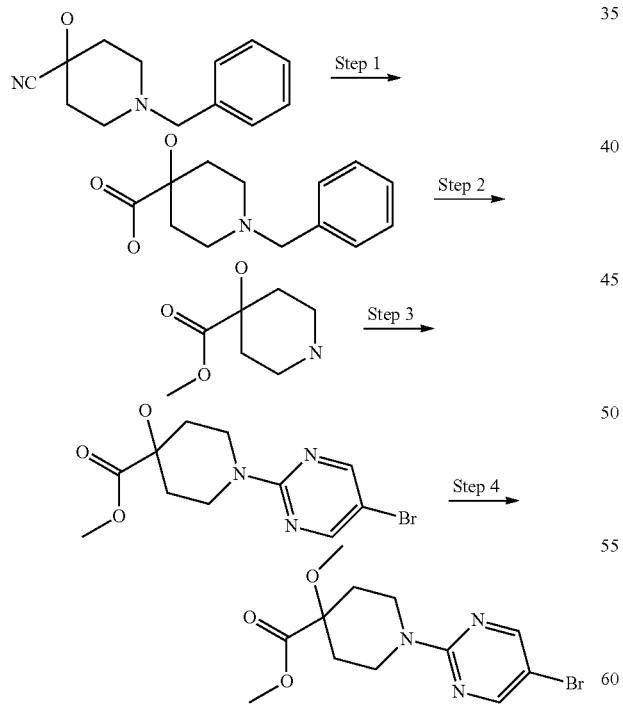

1-Benzyl-4-hydroxy-piperidine-4-carboxylic acid

A solution of 1-benzyl-4-hydroxypiperidine-4-carbonitrile (1 g, 4.6 mmol) in 6N HCl (5 mL) was heated to 120° C. for 30 min under microwave irradiation. After completion of reaction (by TLC), solvent was concentrated under reduced pressure to give the desired product (1.5 g). MS: 236.16 [M+H]+.

Methyl 4-hydroxypiperidine-4-carboxylate

To a stirred solution of 1-benzyl-4-hydroxypiperidine-4-carboxylic acid (1.2 g, 5.1 mmol) in MeOH (15 mL) was added palladium hydroxide and the resulting mixture was stirred at rt for 6 h under $H_2$ atmosphere. After completion (by TLC), the mixture was passed through celite and the filtrate evaporated under reduced pressure. The crude (1 g) residue was carried forward to the next step without further purification. MS: 160.18 [M+H]+.

Methyl 1-(5-bromopyrimidin-2-yl)-4-hydroxy-piperidine-4-carboxylate

To a solution of methyl 4-hydroxypiperidine-4-carboxylate (0.4 g, 2.52 mmol) in EtOH (10 mL) was added DIPEA (2.2 mL, 12.57 mmol) and the solution stirred at rt for 10 min followed by addition of 5-bromo-2-chloropyrimidine (0.49 g, 2.52 mmol). The mixture was then heated up to 70° C. for 1 h. After completion of reaction (by TLC), solvent was evaporated and the crude residue purified over 100-200 M silica-gel using 10% EtOAc:hexane to obtain the desired product as a yellow solid (0.35 g, 44% yield). $^1$H NMR (DMSO-$d_6$): δ 1.64 (m, 2H), 1.82 (m, 2H), 3.20 (m, 2H), 3.64 (s, 3H), 4.27 (m, 2H), 5.60 (s, 1H) and 8.44 (s, 2H).

1-(5-Bromopyrimidin-2-yl)-4-methoxy-piperidine-4-carboxylic acid (Precursor 9)

A solution of methyl 1-(5-bromopyrimidin-2-yl)-4-hydroxypiperidine-4-carboxylate (0.2 g, 0.63 mmol) in DMF (25 mL) was cooled to 0° C. followed by portion wise addition of NaH (60% dispersion in mineral oil, 0.05 g, 1.08 mmol) and the mixture stirred at 0° C. for 45 min followed by addition of MeI (0.20 mL, 3.16 mmol). The temperature of the reaction was slowly raised to rt and left to stir for 4 h. The reaction was then cooled to 0° C. and quenched by drop wise addition of saturated $NH_4Cl$ solution (50 mL), extracted with EtOAc (3×100 mL) and the combined organics washed with brine, dried ($Na_2SO_4$), filtered and concentrated under reduced pressure. The crude residue was purified over 100-200 M silica-gel using 3% EtOAc:hexane to obtain the product as an off-white solid (0.12 g, 57% yield). MS: 330.18 [M+H]+.

Precursor 10: Ethyl 1-(5-bromopyrimidin-2-yl)-4-methylsulfonyl-piperidine-4-carboxylate

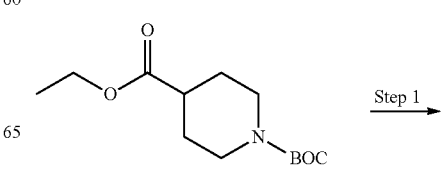

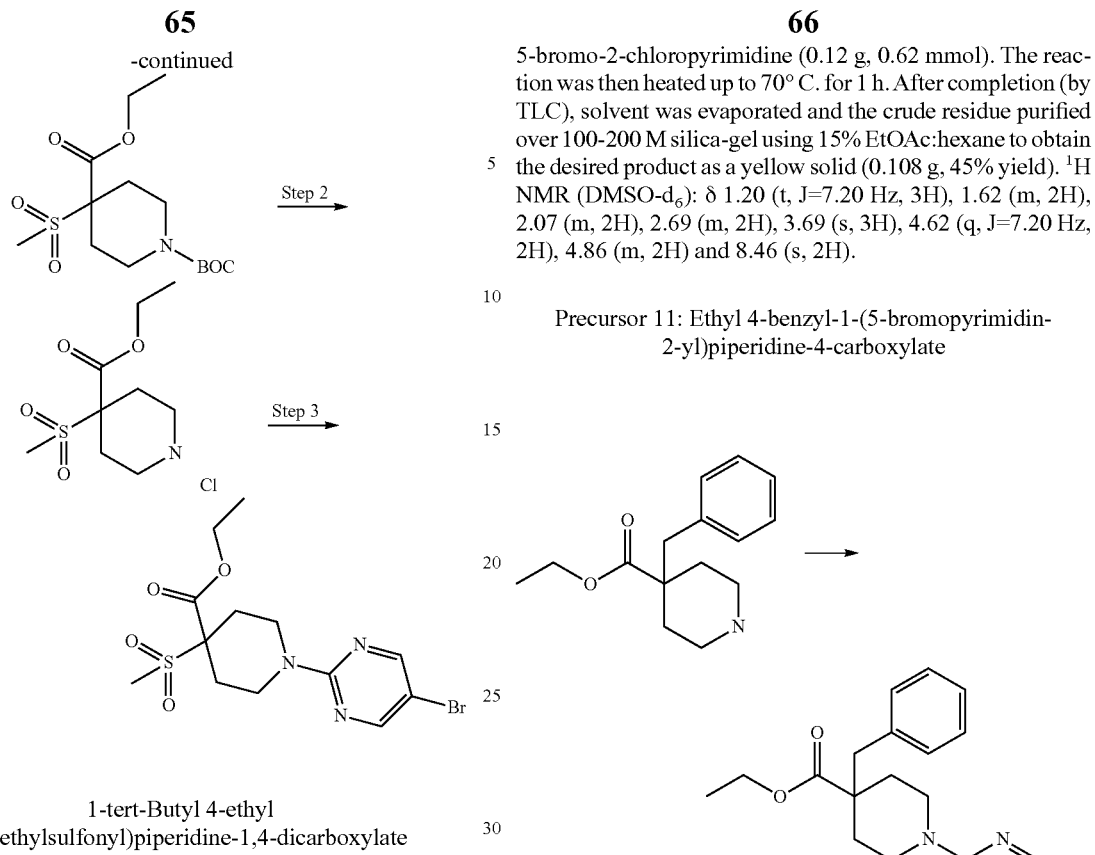

1-tert-Butyl 4-ethyl 4-(methylsulfonyl)piperidine-1,4-dicarboxylate

A solution of 1-tert-butyl 4-ethyl piperidine-1,4-dicarboxylate (2 g, 7.78 mmol) in THF (25 mL) was cooled to −78° C. followed by dropwise addition of LDA (1.8 M in THF, 8.8 mL, 15.56 mmol) and was stirred at the same temperature for 45 minutes followed by addition of methanesulfonyl chloride (1.3 g, 11.67 mmol) at −78° C. The temperature of the reaction was slowly raised to rt and left to stir for 6 h. The reaction was then cooled to 0° C. and quenched by drop wise addition of saturated $NH_4Cl$ solution (50 mL), extracted with EtOAc (3×100 mL) and the combined organics washed with brine, dried ($Na_2SO_4$), filtered and concentrated under reduced pressure. The crude residue was purified over 100-200 M silica-gel using 30% EtOAc:hexane to obtain the product as an orange viscous liquid (0.20 g, 8.0% yield). MS: 336.18 $[M+H]^+$.

Ethyl 4-(methylsulfonyl)piperidine-4-carboxylate hydrochloride

To an ice-cold solution of 1-tert-butyl 4-ethyl 4-(methylsulfonyl)piperidine-1,4-dicarboxylate (0.20 g, 0.60 mmol) in 1,4-dioxane (5.0 mL) was added HCl-dioxane (4.0 M, 1.0 mL) solution and the resulting mixture stirred at rt for 30 min. After completion of reaction (by TLC), solvent was evaporated to obtain a brownish solid material (0.20 g) that was carried forward to the next step without further purification. MS: 236.11 $[M+H]^+$.

Ethyl 1-(5-bromopyrimidin-2-yl)-4-methylsulfonyl-piperidine-4-carboxylate (Precursor 10)

To a solution of ethyl 4-(methylsulfonyl)piperidine-4-carboxylate hydrochloride (0.20 g, 0.74 mmol) in EtOH (7.0 mL) was added DIPEA (0.03 mL, 1.86 mmol) at rt and the mixture stirred at rt for 10 min followed by addition of 5-bromo-2-chloropyrimidine (0.12 g, 0.62 mmol). The reaction was then heated up to 70° C. for 1 h. After completion (by TLC), solvent was evaporated and the crude residue purified over 100-200 M silica-gel using 15% EtOAc:hexane to obtain the desired product as a yellow solid (0.108 g, 45% yield). $^1$H NMR (DMSO-$d_6$): δ 1.20 (t, J=7.20 Hz, 3H), 1.62 (m, 2H), 2.07 (m, 2H), 2.69 (m, 2H), 3.69 (s, 3H), 4.62 (q, J=7.20 Hz, 2H), 4.86 (m, 2H) and 8.46 (s, 2H).

Precursor 11: Ethyl 4-benzyl-1-(5-bromopyrimidin-2-yl)piperidine-4-carboxylate

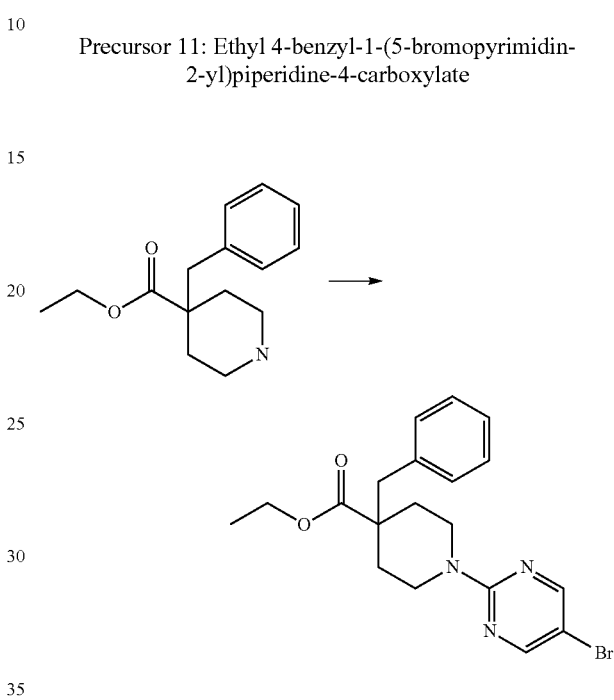

To a solution of ethyl 4-benzylpiperidine-4-carboxylate (0.46 g, 1.86 mmol) in EtOH (10.0 mL) was added DIPEA (0.80 mL, 4.65 mmol) at rt which was stirred at rt for 10 minutes followed by addition of 5-bromo-2-chloropyrimidine (0.30 g, 1.55 mmol). The reaction was heated up to 70° C. for 1 h. After completion of reaction (by TLC), solvent was evaporated and the crude residue purified over 100-200 M silica-gel using 4% EtOAc:hexane to obtain the desired product as a yellow solid (0.108 g, 45% yield). $^1$H NMR (DMSO-$d_6$): δ 1.16 (t, J=7.20 Hz, 3H), 1.47 (m, 2H), 2.00 (m, 2H), 2.80 (s, 2H), 2.97 (m, 2H), 4.08 (q, J=7.20 Hz, 2H), 4.40 (m, 2H), 7.02 to 7.27 (m, 5H) and 8.43 (s, 2H).

Precursor 12: Ethyl 1-(5-bromopyrimidin-2-yl)-4-fluoro-piperidine-4-carboxylate

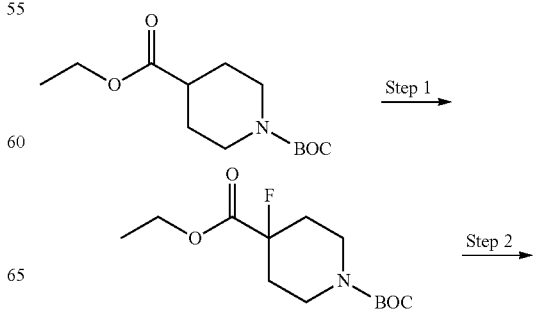

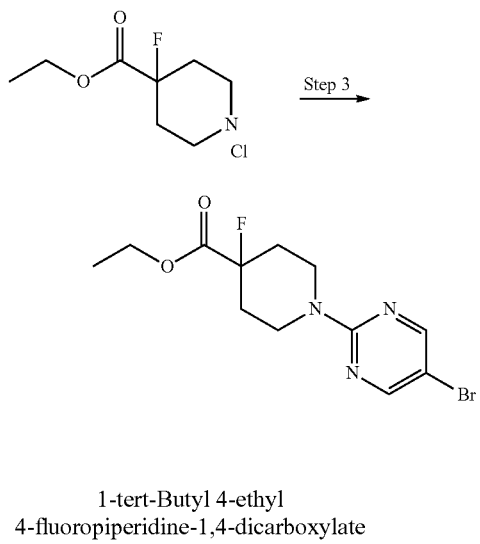

1-tert-Butyl 4-ethyl
4-fluoropiperidine-1,4-dicarboxylate

A solution of 1-tert-butyl 4-ethyl piperidine-1,4-dicarboxylate (1.50 g, 5.81 mmol) in THF (25.0 mL) was cooled to −78° C. followed by drop wise addition of LDA (1.80 M in THF, 6.50 mL, 11.62 mmol) and the mixture stirred at the same temperature for 45 min followed by addition of N-fluorobenzenesulphonimide (3.60 g, 11.62 mmol) at −78° C. The temperature of the reaction was slowly raised to rt and left to stir for 5-6 h. The reaction was then cooled to 0° C. and quenched by drop wise addition of saturated $NH_4Cl$ solution (50 mL), extracted with EtOAc (3×100 mL) and the combined organics was washed with brine, dried ($Na_2SO_4$), filtered and concentrated under reduced pressure. The crude residue was purified over 100-200 M silica-gel using 2% EtOAc:hexane to obtain the product as an orange viscous liquid (1.0 g, 63% yield). MS: 276.27 $[M+H]^+$.

Ethyl 4-fluoropiperidine-4-carboxylate
hydrochloride

To an ice-cold solution of 1-tert-butyl 4-ethyl 4-fluoropiperidine-1,4-dicarboxylate (1.0 g, 3.89 mmol) in 1,4-dioxane (10 mL) was added HCl-dioxane (4.0 M, 15 mL) solution and the mixture stirred at rt for 30 min. After completion of reaction (By TLC), solvent was evaporated to obtain brownish solid material (0.78 g) that was carried forward to the next step without purification. MS: 176.20 $[M+H]^+$.

Ethyl 1-(5-bromopyrimidin-2-yl)-4-fluoropiperidine-
4-carboxylate (Precursor 12)

To a solution of 4-fluoropiperidine-4-carboxylate hydrochloride (0.70 g, 4.34 mmol) in EtOH (10.0 mL) was added DIPEA (1.92 mL, 10.86 mmol) at rt and the mixture stirred at rt for 10 min followed by addition of 5-bromo-2-chloropyrimidine (0.70 g, 3.62 mmol). The reaction was then heated up to 70° C. for 1 h. After completion of reaction (by TLC), solvent was evaporated and the crude residue purified over 100-200 M silica-gel using 3.0% EtOAc:hexane to obtain the desired product as a yellow solid (0.50 g, 42% yield). MS: 332.12 $[M+H]^+$.

Precursor 13: Ethyl 4-allyl-1-(5-bromopyrimidin-2-
yl)piperidine-4-carboxylate

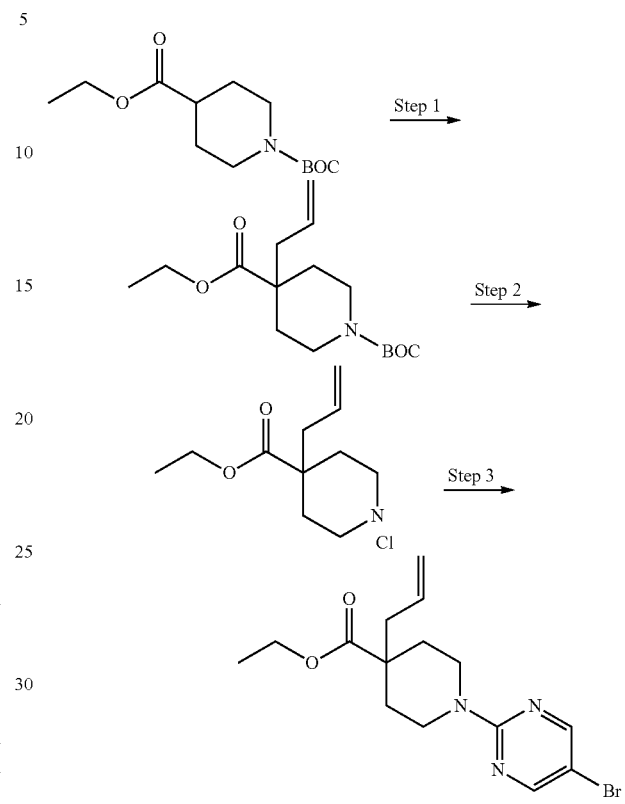

1-tert-Butyl 4-ethyl
4-allylpiperidine-1,4-dicarboxylate

A solution of 1-tert-butyl 4-ethyl piperidine-1,4-dicarboxylate (5 g, 19.37 mmol) in THF (50 mL) was cooled to −78° C. followed by drop wise addition of LDA (1.80 M in THF, 21.67 mL, 38.74 mmol) solution and was stirred at the same temperature for 45 min followed by addition of allyl bromide (5 mL, 58.14 mmol) at −78° C. The temperature of the reaction was slowly raised to rt and left to stir for 5-6 h. The reaction was then cooled to 0° C. and quenched by drop wise addition of saturated $NH_4Cl$ solution (50 mL), extracted with EtOAc (3×100 mL) and the combined organics washed with brine, dried ($Na_2SO_4$), filtered and concentrated under reduced pressure. The crude residue was purified over 100-200 M silica-gel using 1% EtOAc:hexane to obtain the product as an orange viscous liquid (5 g, 87% yield). MS: 298.19 $[M+H]^+$.

Ethyl 4-allylpiperidine-4-carboxylate hydrochloride

To an ice-cold solution of 1-tert-butyl 4-ethyl 4-allylpiperidine-1,4-dicarboxylate (2 g, 6.70 mmol) in 1,4-dioxane (10 mL) was added HCl-dioxane (4.0 M, 15 mL) solution and the mixture stirred at rt for 30 min. After completion of reaction (by TLC), the solvent was evaporated to obtain a brownish solid material (1.30 g) that was carried forward to the next step without further purification. MS: 198.28 $[M+H]^+$.

Ethyl 4-allyl-1-(5-bromopyrimidin-2-yl)piperidine-4-carboxylate (Precursor 13

To a solution of ethyl 4-allylpiperidine-4-carboxylate hydrochloride (1.30 g, 6.59 mmol) in EtOH (20.0 mL) was added DIPEA (3.0 mL, 16.47 mmol) and the mixture stirred at rt for 10 min followed by addition of 5-bromo-2-chloropyrimidine (1.06 g, 5.49 mmol). The reaction was then heated up to 70° C. for 1 h. After reaction completion (by TLC), solvent was evaporated and the crude residue purified over 100-200 M silica-gel using 2.0% EtOAc:hexane to obtain the desired product as a yellow solid (1.0 g, 56% yield). $^1$H NMR (DMSO-$d_6$): δ 1.19 (t, J=6.80 Hz, 3H), 1.44 (m, 2H), 2.02 (m, 2H), 2.27 (m, 2H), 3.10 (m, 2H), 4.13 (q, J=6.80 Hz, 2H), 4.29 (m, 2H), 5.06 (m, 2H), 5.66 (m, 1H) and 8.43 (s, 2H)

Precursor 14: Methyl 2-(5-bromopyrimidin-2-yl)-1,3,4,5,6,6a-hexahydrocyclopenta[c]pyrrole-3a-carboxylate

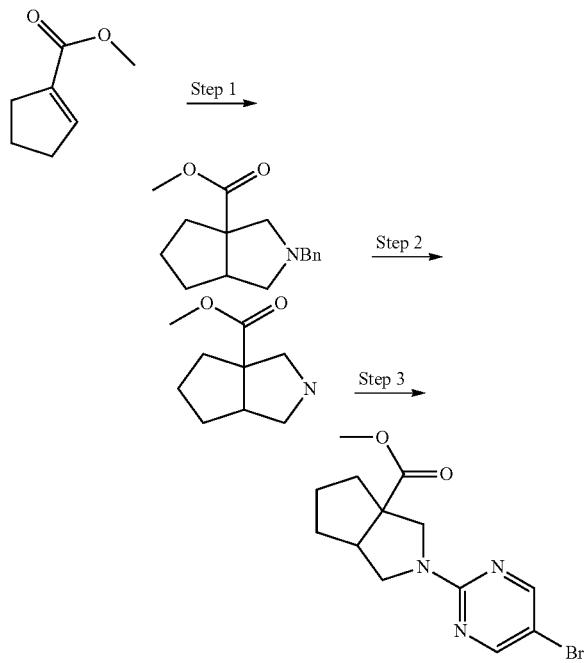

Methyl 2-benzyloctahydrocyclopenta[c]pyrrole-3a-carboxylate

To a stirred solution of methyl cyclopent-1-enecarboxylate (2.0 g, 15.89 mmol) in DCM (15.0 mL) was added (benzyl ((trimethylsilyl)methyl)amino) methyl methanesulfonate (4.0 mL, 15.88 mmol) at rt and the mixture stirred at 0° C. for 15 min followed by the drop wise addition of trifluoroacetic acid (0.50 mL). The mixture was then stirred for 16 h at rt. After completion of reaction (by TLC), solvent was evaporated, water added (50.0 mL) followed by extraction with EtOAc (3×100 mL) and the combined organic layer washed with brine, dried over anhydrous $Na_2SO_4$, filtered and evaporated under reduced pressure. The crude residue was purified over 100-200 M silica-gel using 7% EtOAc:hexane to obtain the product as a light yellow liquid (1.50 g, 75% yield). MS: 260.16 [M+H]$^+$.

Methyl octahydrocyclopenta[c]pyrrole-3a-carboxylate

To a stirred solution of methyl 2-benzyloctahydrocyclopenta[c]pyrrole-3a-carboxylate (2.0 g, 7.69 mmol) in MeOH (15.0 mL) was added palladium hydroxide (0.20 g, 10% w/w) and the mixture stirred at rt for 16 h under $H_2$ atmosphere. After completion of reaction (by TLC), the reaction mixture was passed through celite and the solvent evaporated. The crude (1.50 g) residue was carried forward for the next step without further purification. MS: 170.18 [M+H]$^+$.

Methyl 2-(5-bromopyrimidin-2-yl)octahydrocyclopenta[c]pyrrole-3a-carboxylate (Precursor 14)

To the solution of methyl octahydrocyclopenta[c]pyrrole-3a-carboxylate (1.0 g, 5.91 mmol) in EtOH (10.0 mL) was added DIPEA (2.80 mL, 16.12 mmol) at rt and the mixture stirred at rt for 10 min followed by addition of 5-bromo-2-chloropyrimidine (1.10 g, 5.37 mmol). The reaction was heated up to 70° C. for 2 h. After completion (by TLC), solvent was evaporated and the crude residue purified over 100-200 M silica-gel using 7.0% EtOAc:hexane to obtain the desired product as a white solid (0.80 g, 45%). MS: 326.19 [M+H]$^+$.

Precursor 15: ethyl 1-(5-bromopyrimidin-2-yl)-4-methylsulfanyl-piperidine-4-carboxylate

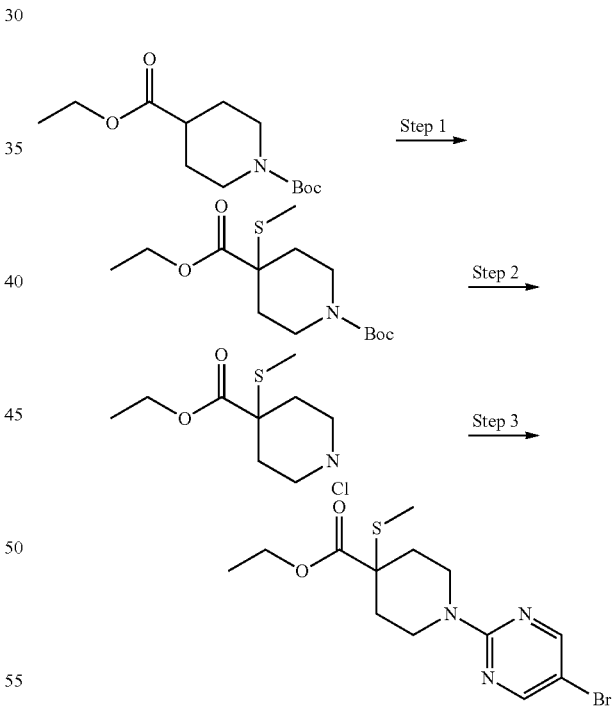

O1-tert-Butyl O4-ethyl 4-methylsulfanylpiperidine-1,4-dicarboxylate

A solution of 1-tert-butyl 4-ethyl piperidine-1,4-dicarboxylate (2.0 g, 7.75 mmol) in THF (100.0 mL) was cooled to −78° C. followed by drop wise addition of LDA (1.80 M in THF, 8.80 mL, 15.56 mmol) and the mixture stirred at the same temperature for 45 min followed by addition of dimethyl disulfide (2.21 mL, 23.25 mmol) at −78° C. The temperature of the reaction was slowly raised up to rt and left to stir for 6 h. The reaction was then cooled to 0° C. and quenched by drop wise addition of saturated NH₄Cl solution (50 mL), extracted with EtOAc (3×100 mL) and the combined organics washed with brine, dried (Na₂SO₄), filtered and concentrated under reduced pressure. The crude residue was purified over 100-200 M silica-gel using 5% EtOAc: hexane to obtain the product as an orange viscous liquid (1.90 g, 83% yield). MS: 304.19 [M+H]⁺.

Ethyl 4-methylsulfanylpiperidine-4-carboxylate hydrochloride

To an ice-cold solution of O1-tert-butyl O4-ethyl 4-methylsulfanylpiperidine-1,4-dicarboxylate (0.23 g, 7.75 mmol) in 1,4-dioxane (20 mL) was added HCl-dioxane (4 M, 15 mL) solution and the mixture stirred at rt for 30 min. After completion of reaction (by TLC), the solvent was evaporated to obtain a brownish solid material (0.17 g) that was carried forward to the next step without further purification. MS: 204.10 [M+H]⁺.

Ethyl 1-(5-bromopyrimidin-2-yl)-4-methylsulfanyl-piperidine-4-carboxylate (Precursor 15)

To a solution of ethyl 4-(methylthio)piperidine-4-carboxylate hydrochloride (0.17 g, 0.75 mmol) in EtOH (10.0 mL) was added DIPEA (0.60 mL, 3.75 mmol) at rt and the mixture stirred at rt for 10 min followed by addition of 5-bromo-2-chloropyrimidine (0.18 g, 0.90 mmol). The reaction was heated up to 70° C. for 1 h. After completion of reaction (by TLC), solvent was evaporated and the crude residue purified over 100-200 M silica-gel using 3.0% EtOAc:hexane to obtain the desired product as a white solid (0.16 g, 60% yield). ¹H NMR (DMSO-d₆): δ 1.18 (t, J=7.20 Hz, 3H), 1.70 (m, 2H), 2.04 (s, 3H), 2.14 (m, 2H), 3.50 (m, 2H), 4.00 (m, 2H), 4.20 (q, J=7.20 Hz, 2H), and 8.46 (s, 2H).

Precursor 16: Methyl 1-(5-bromopyrimidin-2-yl)-3-(trifluoromethyl)pyrrolidine-3-carboxylate

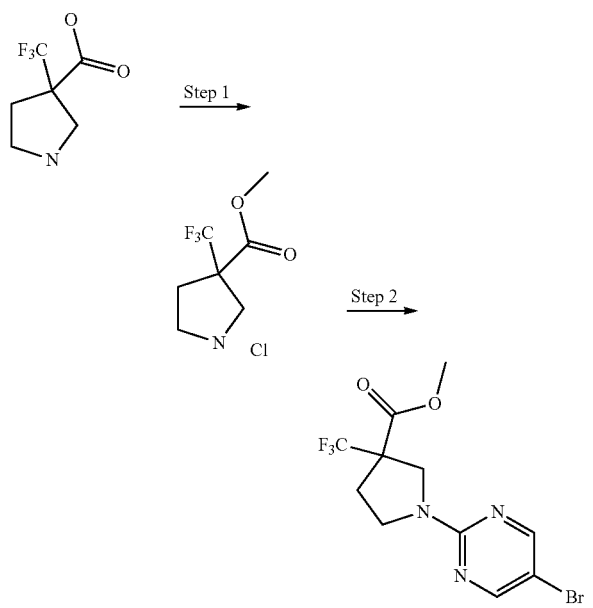

Methyl 3-(trifluoromethyl)pyrrolidine-3-carboxylate hydrochloride

To an ice-cold solution of 3-(trifluoromethyl)pyrrolidine-3-carboxylic acid (0.25 g, 1.36 mmol) in MeOH (5.0 mL) was purged dry-HCl (gas) for 10 minutes. The mixture was stirred at rt for 12 h. After reaction completion (by TLC), solvent was evaporated to obtain a brownish solid material (0.32 g) that was carried forward to the next step without purification. MS: 198.15 [M+H]⁺.

Methyl 1-(5-bromopyrimidin-2-yl)-3-(trifluoromethyl)pyrrolidine-3-carboxylate (Precursor 16)

To a solution of methyl 3-(trifluoromethyl)pyrrolidine-3-carboxylate hydrochloride (0.32 g, 1.36 mmol) in EtOH (10.0 mL) was added DIPEA (1.1 mL, 6.79 mmol) at rt and the mixture stirred at rt for 10 min followed by addition of 5-bromo-2-chloropyrimidine (0.26 g, 1.36 mmol). The reaction was heated up to 70° C. for 1 h. After reaction completion (by TLC), the solvent was evaporated and the crude residue purified over 60-120 M silica-gel using 10.0% EtOAc:hexane to obtain the desired product as a yellow solid (0.30 g, 63% yield). MS: 354.02 [M+H]⁺.

Precursor 17: Ethyl 1-[(5-bromopyrimidin-2-yl)methyl]-4-methyl-piperidine-4-carboxylate

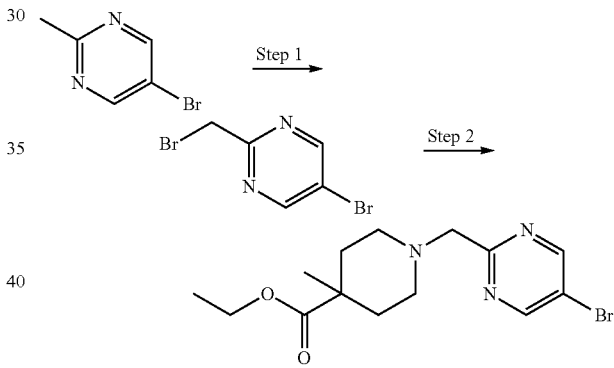

5-Bromo-2-(bromomethyl)pyrimidine

To an ice-cold solution of 5-bromo-2-methylpyrimidine (3.5 g, 20.23 mmol) in CCl₄ (20 mL) was added AIBN (0.14 g, 2.02 mmol) followed by portion wise addition of NBS (3.6 g, 20.23 mmol) and the mixture stirred at 70° C. for 30 h. After completion of reaction (by TLC), DCM (150 mL) was added and washed with water and brine. The organic layer was dried over anhydrous Na₂SO4, filtered and concentrated under reduced pressure. The crude residue was purified over 100-200 M silica-gel using 2% EtOAc:hexane to obtain the desired product (1.30 g, 25% yield). ¹H NMR (CDCl₃): δ 4.68 (s, 2H) and 9.03 (s, 2H).

Ethyl 1-[(5-bromopyrimidin-2-yl)methyl]-4-methyl-piperidine-4-carboxylate (Precursor 17)

To a solution of ethyl 4-methylpiperidine-4-carboxylate hydrochloride (0.08 g, 0.48 mmol) in EtOH (5.0 mL) was added DIPEA (0.22 mL, 1.20 mmol) at rt and the mixture stirred at rt for 10 minutes followed by addition of 5-bromo-2-(bromomethyl)pyrimidine (0.10 g, 0.40 mmol). The reaction was heated up to 70° C. for 1 h. After completion of reaction (by TLC), solvent was evaporated and the crude residue purified over 100-200 M silica-gel using 20% EtOAc: hexane to obtain the desired product as a yellow solid (0.10 g, 73% yield). ¹H NMR (DMSO-d₆): δ 1.09 (s, 3H), 1.13 (t, J=7.20 Hz, 3H), 1.45 (m, 2H), 2.00 (m, 2H), 3.12 (m, 2H), 3.32 (m, 2H), 3.62 (q, J=7.20 Hz, 2H), 4.08 (m, 2H) and 8.94 (s, 2H).

Precursor 18: Methyl 1-(5-bromo-3-fluoro-2-pyridyl)-4-methyl-piperidine-4-carboxylate

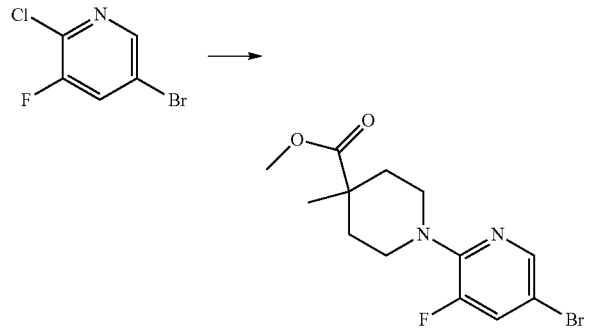

5-Bromo-2-chloro-3-fluoropyridine (100 mg, 0.475 mmol), ethyl 4-methyl-piperidine-4-carboxylate hydrochloride (118 mg, 0.57 mmol), ethyldiisopropylamine (248 uL, 1.426 mmol) and 1-methyl-pyrrolidin-2-one (0.5 mL) were transferred to a microwave reaction vial. The vial was sealed and heated at 210° C. for 15 minutes. A further portion of ethyl 4-methyl-piperidine-4-carboxylate hydrochloride (118 mg, 0.57 mmol) was added and the reaction mixture heated for a further 15 min at 210° C. The reaction mixture was diluted with water (25 mL), the pH adjusted to 3 using 1 M HCl, before extraction with DCM (3×25 mL). The organic fractions were combined, dried (cotton wool plug) and concentrated in vacuo to give a crude brown oil. Flash chromatography on silica gel, eluting with DCM (0-100% gradient) in n-hexane gave an impure mixture which was further purified using flash chromatography on silica gel, eluting with 0-4% EtOAc gradient, 4% isocratic, then 4-10% EtOAc in n-hexane to obtain the desired product (75 mg, clear oil). ¹H NMR (Acetone) δ 8.05 (dd, J=2.0, 1.1 Hz, 1H), 7.60 (dd, J=12.6, 2.0 Hz, 1H), 4.17 (q, J=7.1 Hz, 1H), 3.83-3.75 (m, 1H), 3.16-3.07 (m, 1H), 2.19-2.11 (m, 1H), 1.60-1.50 (m, 1H), 1.25 (t, J=7.1 Hz, 3H), 1.22 (s, 3H). m/z 345.0, 346.9 [M+H]⁺.

Precursor 19: Ethyl 1-(4-bromo-2-pyridyl)-4-methyl-piperidine-4-carboxylate

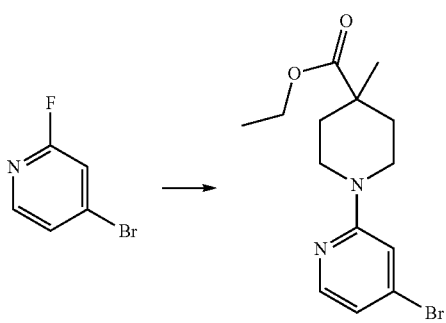 [SMILES: Fc1cc(Br)ccn1 ; CCOC(=O)C1(C)CCN(c2cc(Br)ccn2)CC1]

A suspension of the 4-bromo-2-fluoropyridine (500 mg, 2.84 mmol) and methyl piperidine ethyl ester (590 mg, 2.84 mmol) in anhydrous THF (4 mL) was treated with triethylamine (1.46 mL, 11.4 mmol) then heated in the microwave at 150° C. for 10 min. The reaction was concentrated, the crude residue (00801) suspended in DCM and purified by normal phase chromatography on silica, eluting with 0-20% EtOAc in hexane to give the desired product as a pale yellow oil (466 mg, 50% yield). m/z 327/329 [M+H]⁺.

Precursor 20: Ethyl 4-cyclopropylpiperidine-4-carboxylate hydrochloride

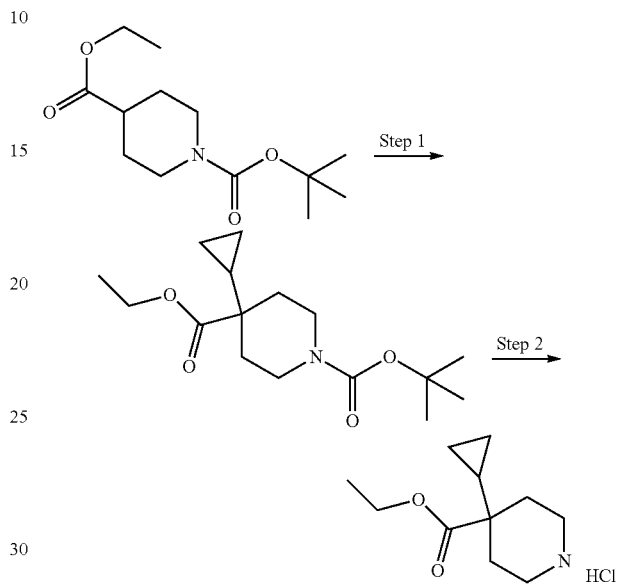

1-tert-Butyl 4-ethyl 4-cyclopropylpiperidine-1,4-dicarboxylate

LHMDS (1M THF solution; 2.4 mL, 2.4 mmol) was added to a −78° C. solution of 1-tert-butyl 4-ethyl piperidine-1,4-dicarboxylate (514 mg, 2 mmol) in anhydrous THF (5 mL) and the reaction was allowed to warm to 0° C. over the course of 30 mins, whilst under an inert atmosphere. This solution was added drop-wise to a solution of allylpalladium chloride dimer (365 mg, 1 mmol), TMEDA (302 uL, 2 mmol) in anhyrdous THF (2.5 mL) in an oven dried flask under an inert atmosphere at −60° C. A balloon of carbon monoxide was attached and the reaction stirred for 2.5 h at 0° C. Saturated ammonium chloride solution (10 mL) was added, the reaction mixture extracted with Et₂O (20 mL) and the organic phase washed with sat. brine (20 mL), dried (MgSO₄) and concentrated in vacuo. The desired product was isolated as an oil by normal phase chromatography (Grace 12 g, 25-75% hexane: EtOAc, gradient elution; visualised with permangenate stain) (164 mg, 28% yield). ¹H NMR (CDCl₃) δ 4.16 (q, J=7.1 Hz, 2H), 4.08-3.84 (m, 2H), 2.72 (s, 2H), 1.99 (dd, J=13.5, 2.0 Hz, 2H), 1.43 (s, 9H), 1.33-1.16 (m, 5H), 0.91 (tt, J=8.1, 5.8 Hz, 1H), 0.41-0.26 (m, 4H).

Ethyl 4-cyclopropylpiperidine-4-carboxylate hydrochloride (Precursor 20)

1-tert-Butyl 4-ethyl 4-cyclopropylpiperidine-1,4-dicarboxylate (164 mg, 0.55 mmol) was stirred at rt in 4M Hydrogen chloride in dioxane (2 mL, 8 mmol) for 35 minutes. The volatiles were removed and the residue dried under high vacuum to afford the desired product as a crystalline solid (129 mg). ¹H NMR (MeOD) δ 4.22 (q, J=7.1 Hz, 2H), 3.38 (dd, J=10.5, 2.7 Hz, 2H), 2.99-2.82 (m, 2H), 2.23 (dd, J=14.6, 2.2 Hz, 2H), 1.74 (td, J=14.3, 4.2 Hz, 2H), 1.29 (t, J=7.1 Hz, 3H), 1.11-0.96 (m, 1H), 0.50-0.43 (m, 2H), 0.43-0.36 (m, 2H).

Precursor 21: 1-(5-bromopyrimidin-2-yl)-4-methylpiperidine-4-carboxylic acid

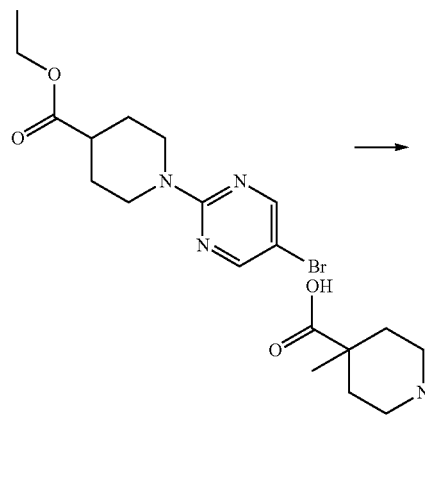

Ethyl 1-(5-bromopyrimidin-2-yl)-4-methylpiperidine-4-carboxylate (400 mg, 1.22 mmol) was stirred in dioxan (4 ml) and concentrated hydrochloric acid was added (2.8 ml). The reaction was stirred in a sealed tube at 100° C. for 5 h. LCMS indicated 90% conversion to the acid. The reaction was allowed to cool, diluted with a saturated aqueous solution of sodium hydrogen carbonate to adjust the pH to ~5 at which point a solid precipitated. The solid was collected by filtration and dried to afford the desired product as a yellow solid (270 mg, 90% purity by LCMS) (77%).

Precursor 22 Ethyl 4-allyl-1-(5-(4,4,5,5-tetramethyl-1,3,2-dioxaborolan-2-yl)pyrimidin-2-yl)piperidine-4-carboxylate

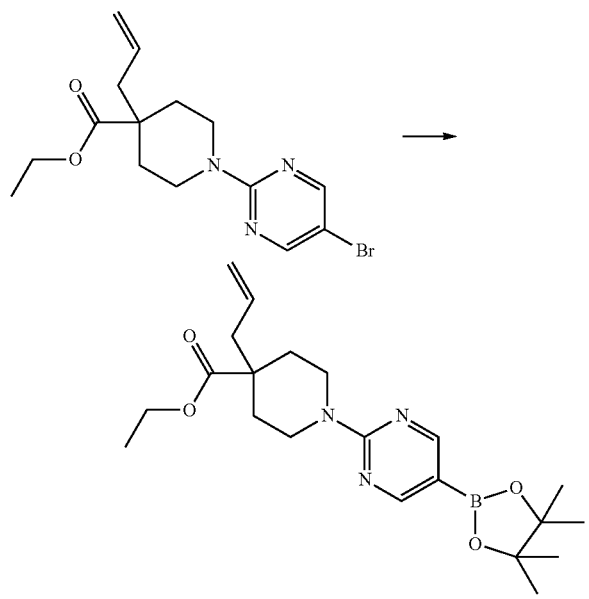

To a solution of ethyl 4-allyl-1-(5-bromopyrimidin-2-yl) piperidine-4-carboxylate (1.0 g, 2.80 mmol) in 1,4-dioxane (20 mL) was added potassium acetate (0.42 g, 4.20 mmol) and bispinacolatodiboron (0.78 g, 3.10 mmol) at rt and the mixture degassed for 15-20 min by purging $N_2$ followed by the addition of tris(dibenzylideneacetone)dipalladium(0) (0.144 g, 0.14 mmol) and tricyclohexylphosphine (0.09 gm, 0.33 mmol). The reaction mixture was again degassed for another 15-20 min then heated up to 80° C. for 3 h. After reaction completion (by TLC), the mixture was cooled to rt and diluted with 500 mL of EtOAc. The mixture was passed through celite and the solvent evaporated to obtain the crude material (0.80 g), which was carried forward to the next step (i.e. synthesis of Compound 139) without further purification. MS: 402.31 [M+H]$^+$.

Precursor 23: Ethyl 4-(trifluoromethyl)piperidine-4-carboxylate hydrochloride

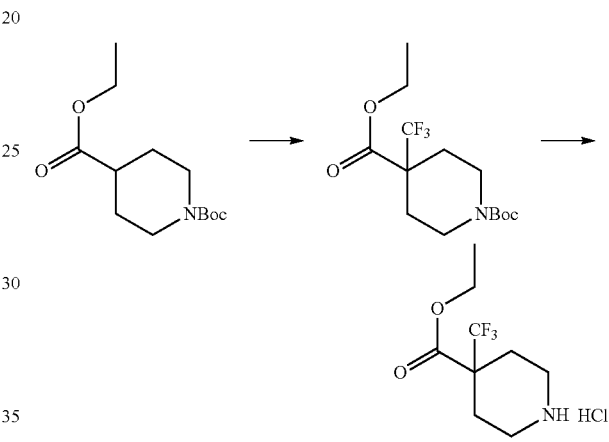

1-tert-Butyl 4-ethyl 4-(trifluoromethyl)piperidine-1,4-dicarboxylate

A solution of 1-tert-butyl 4-ethyl piperidine-1,4-dicarboxylate (0.5 g, 1.94 mmol) in THF (20 mL) was cooled to −78° C. followed by drop wise addition of LDA (1.80 M in THF, 2.15 mL, 3.88 mmol) and the mixture stirred at the same temperature for 45 min followed by addition of S-(Trifluoromethyl)dibenzothiophenium trifluoromethanesulphonate (1.56 g, 3.88 mmol) at −78° C. The temperature of the reaction was slowly raised to rt and stirred for 6 h. The reaction was then cooled to 0° C. and quenched by dropwise addition of saturated $NH_4Cl$ solution (50 mL), extracted with EtOAc (3×100 mL) and the combined organics washed with brine, dried ($Na_2SO_4$), filtered and concentrated under reduced pressure. The crude residue was purified over 100-200 M silica-gel using 2% EtOAc:hexane to obtain the product as a yellow solid (0.15 g, 23% yield). MS: 326.15 [M+H]$^+$.

Ethyl 4-(trifluoromethyl)piperidine-4-carboxylate hydrochloride

To an ice-cold solution of 1-tert-butyl 4-ethyl 4-(trifluoromethyl)piperidine-1,4-dicarboxylate (0.15 g, 0.19 mmol) in 1,4-dioxane (10 mL) was added HCl-1,4-dioxane (4.0 M, 15 mL) solution and the mixture stirred at rt for 30 min. After completion of reaction (by TLC), solvent was evaporated to obtain brownish solid material (0.12 g) that was carried forward to the next step (i.e. synthesis of Compound 142) without purification. MS: 226.12 [M+H]+.

Precursor 24: ethyl 7-bromo-2-methyl-3-oxo-3,4-dihydro-2H-pyrido[3,2-b][1,4]oxazine-2-carboxylate

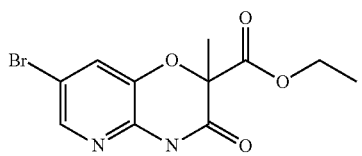 [SMILES: CCOC(=O)C1(C)Oc2cc(Br)cnc2NC1=O]

To an ice-cold solution of 2-amino-5-bromopyridin-3-ol (1 g, 5.29 mmol) in DMF (10 mL) was added KF (0.77 g, 13.23 mmol) followed by addition of diethyl 2-bromo-2-methylmalonate (1 mL, 5.29 mmol) and the mixture heated up to 60° C. for 4 h. After completion (by TLC), the reaction was cooled, quenched with water and extracted with EtOAc (3×100 mL). The combined organics were washed with brine, dried over anhydrous Na2SO4, filtered and concentrated under reduced pressure to obtain the desired product as an off-white solid (1 g, 60%).

Precursor 25: Ethyl 1-(4-bromothiazol-2-yl)-4-ethyl-piperidine-4-carboxylate

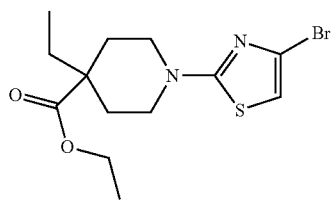 [SMILES: CCOC(=O)C1(CC)CCN(c2nc(Br)cs2)CC1]

To a solution of ethyl 4-ethylpiperidine-4-carboxylate hydrochloride (140 mg, 0.62 mmol) and 2,4-dibromothiazole (100 mg, 0.41 mmol) in DMF (0.3 mL) was added triethylamine (0.26 mL, 1.9 mmol) at rt and the mixture heated to 100° C. and stirred for 2 h. The mixture was cooled to rt then diluted with EtOAc (2 mL) and MeOH (2 mL) then evaporated to dryness under reduced pressure. The crude residue was purified over silica-gel using EtOAc: cyclohexane (10% to 60%) to obtain the desired product as viscous oil that solidified upon standing (127 mg, 89% yield). MS: 347.03, 349.01 [M+H]+.

Precursor 26: Ethyl 1-(5-bromothiazol-2-yl)-4-ethyl-piperidine-4-carboxylate

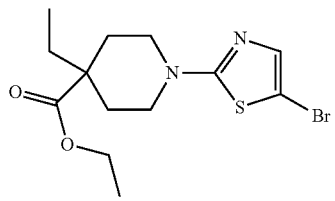 [SMILES: CCOC(=O)C1(CC)CCN(c2ncc(Br)s2)CC1]

To a solution of ethyl 4-ethylpiperidine-4-carboxylate hydrochloride (140 mg, 0.62 mmol) and 2,5-dibromothiazole (100 mg, 0.41 mmol) in DMF (0.3 mL) was added triethylamine (0.26 mL, 1.9 mmol) at rt and the mixture heated to 100° C. and stirred for 2 h. The mixture was cooled to rt, diluted with EtOAc (2 mL) and MeOH (2 mL). then evaporated to dryness under reduced pressure. The crude residue was purified over 12 g silica-gel using EtOAc: cyclohexane (10% to 60%) to obtain the desired product as viscous oil (110 mg, 77% yield). MS: 347.03, 349.01 [M+H]+.

Precursor 27: ethyl 1-(3-chloro-1,2,4-thiadiazol-5-yl)-4-ethylpiperidine-4-carboxylate

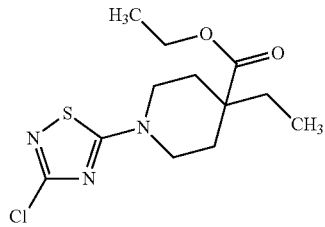 [SMILES: CCOC(=O)C1(CC)CCN(c2nc(Cl)ns2)CC1]

3,5-dichloro-1,2,4-thiadiazole (135 mg, 0.87 mmol) was added to a solution of ethyl 4-ethylpiperidine-4-carboxylate hydrochloride (190 mg, 0.87 mmol) and Triethylamine (264 mg, 2.61 mmol) in THF (9 mL) and stirred at rt for 1 h, giving a suspension, which was filtered, and the filtrate concentrated in vacuo to give ethyl 1-(3-chloro-1,2,4-thiadiazol-5-yl)-4-ethylpiperidine-4-carboxylate as a yellow oil (260 mg, 98%). ESI-MI m/z 304.2 [M+H]+.

Precursor 28: Ethyl 1-(5-bromopyrimidine-2-carbonyl)-4-methylpiperidine-4-carboxylate

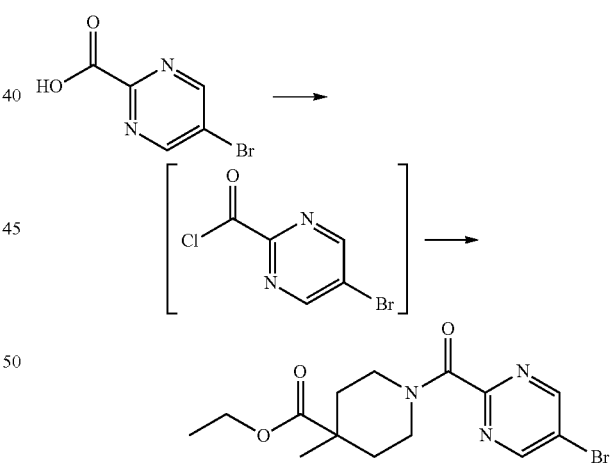

To a solution of 5-bromopyrimidine-2-carboxylic acid (0.150 g, 0.742 mmol) and DMF (1 drop, catalytic amount) in DCM (10 mL) was added dropwise oxalyl chloride (0.10 mL, 1.11 mmol.) at 0° C. under inert atmosphere and the mixture stirred at rt for 1 h. The solvent was evaporated under reduced pressure under an inert atmosphere and the residue taken up in THF (5 mL) followed by the addition of DIPEA (0.70 mL, 3.71 mmol) and ethyl 4-methylpiperidine-4-carboxylate hydrochloride (0.14 g, 0.89 mmol.) at 0° C. The resulting mixture was stirred at rt for 16 h. After completion of reaction (by TLC) the mixture was poured into ice cold water (100 mL), extracted with EtOAc (3×100 mL) and the combined organics washed with water and brine, dried over Na$_2$SO$_4$ and filtered. The solvent was evaporated under reduced pressure and the crude residue purified on silica-gel eluting with 40% EtOAc in hexane to obtain the desired product as an off white semi-solid (0.10 g, 37% yield). MS: 358.01 [M+H]$^+$.

Precursor 29: Ethyl 4-((5-bromopyrimidin-2-yl)-amino)-1-methylcyclohexanecarboxylate

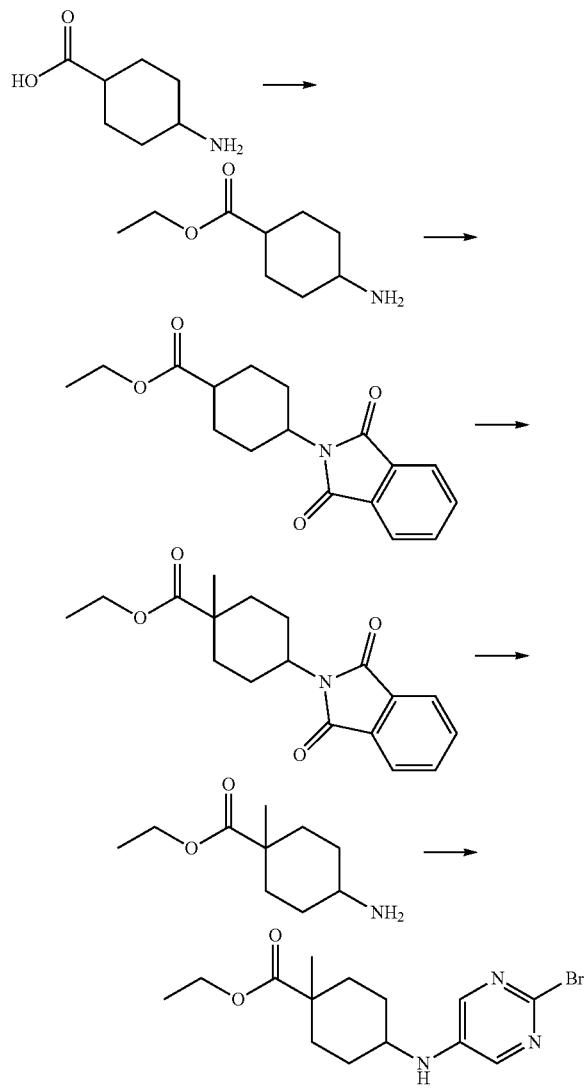

Ethyl 4-aminocyclohexanecarboxylate

To an ice-cold solution of 4-aminocyclohexanecarboxylic acid (5.0 g, 34.92 mmol) in ethanol (20 mL) was added thionyl chloride (7.60 ml, 104.76 mmol) and the mixture heated up to 80° C. for 2-3 h. After the completion of reaction (by TLC), the solvent was evaporated under reduced pressure to give the desired product in quantitative yield.

Ethyl 4-(1,3-dioxoisoindolin-2-yl)cyclohexanecarboxylate

A solution of ethyl 4-aminocyclohexanecarboxylate (0.50 g, 2.92 mmol) in toluene (10 mL) was added Et$_3$N (1.02 mL, 7.30 mmol) and phthalic anhydride (0.56 g, 3.80 mmol) and the mixture refluxed for 6-8 h using dean-stark apparatus to remove water. After completion of the reaction (by TLC), the solvent was evaporated under reduced pressure, water (50 mL) added and stirred for 30 min at rt. The solid material thus obtained was collected by filtration under vacuum and dried to obtain the desired product as off-white solid (0.30 g, 34%). $^1$H NMR (DMSO-d$_6$): δ 7.84 (s, 4H), 4.19 (q, J=7.20 Hz, 2H), 3.71 (m, 1H), 2.71 (m, 1H), 2.06 (m, 2H), 1.90 (m, 2H), 1.69 (m, 2H), 1.60 (m, 2H), and 1.23 (t, J=7.20 Hz, 3H).

Ethyl 4-(1,3-dioxoisoindolin-2-yl)-1-methylcyclohexanecarboxylate

A solution of ethyl 4-(1,3-dioxoisoindolin-2-yl)cyclohexanecarboxylate (0.30 g, 1.00 mmol) in THF (10 mL) was cooled to −78° C. followed by dropwise addition of LDA (1.60 M in THF, 1.88 mL, 3.00 mmol) at −78° C. The mixture was stirred at the same temperature for 30 minutes followed by addition of MeI (0.311 mL, 5.00 mmol) at −78° C. The temperature of the reaction was slowly raised up to rt and left to stir overnight. The reaction was then cooled to 0° C. and quenched by dropwise addition of saturated NH$_4$Cl solution (30 mL), extracted with EtOAc (3×50 mL) and the combined organics washed with brine, dried (Na$_2$SO$_4$), filtered and concentrated under reduced pressure to obtain the desired product as a viscous liquid (0.30 g, 97%). MS: 316.12 [M+H]$^+$.

Ethyl 4-amino-1-methylcyclohexanecarboxylate

To an ice-cold solution of ethyl 4-(1,3-dioxoisoindolin-2-yl)-1-methylcyclohexanecarboxylate (0.30 g, 0.95 mmol) in EtOH (20 mL) was added hydrazine hydrate (0.115 mL, 2.38 mmol) and the resulting mixture heated up to 80° C. for 2-3 h. After the completion of reaction (by TLC), solvent was evaporated under reduced pressure, water added (20 mL), extracted with EtOAc (3×50 mL) and the combined organics washed with brine, dried (Na$_2$SO$_4$), filtered and concentrated under reduced pressure to obtain the desired product as a viscous liquid (0.18 g, crude). MS: 186.20 [M+H]$^+$.

Ethyl 4-((5-bromopyrimidin-2-yl)amino)-1-methylcyclohexanecarboxylate

To an ice-cold solution of ethyl 4-amino-1-methylcyclohexanecarboxylate (0.18 g, 0.97 mmol) in EtOH (5.0 mL) was added DIPEA (0.52 mL, 2.91 mmol) followed by the addition of 5-bromo-2-chloropyrimidine (0.185 g, 0.97 mmol). The mixture was heated to 80° C. for 6-8 h after then cooled to rt, water added and extracted with EtOAc (3×100 mL). The combined organics were washed with brine, dried over anhydrous Na$_2$SO$_4$, filtered and evaporated under reduced pressure. The crude residue was purified over 100-200 M silica-gel by using 4% EtOAc:hexane to obtain the desired product (0.064 g, 19%). MS: 342.01 [M+H]$^+$.

Precursor 30: Ethyl 4-((5-bromopyrimidin-2-yl)(methyl)amino)-1-methylcyclohexanecarboxylate

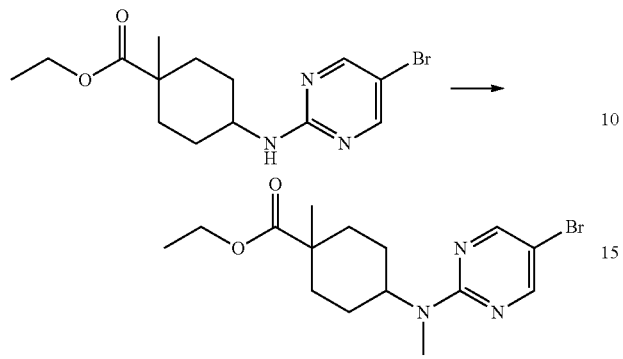

To an ice-cold solution of ethyl 4-(5-bromopyrimidin-2-ylamino)-1-methylcyclohexanecarboxylate (0.30 g, 0.88 mmol) in THF (10 mL) was added NaH (0.053 g, 1.32 mmol, 60% dispersion in mineral oil) portion wise and the mixture stirred at 0° C. for 10 min followed by drop wise addition of MeI (0.066 ml, 1.06 mmol). The mixture was heated up to 65° C. for 6-8 h. After completion (by TLC), the reaction was cooled up to 0° C. and quenched with ice-cold water (20 mL), extracted with EtOAc (2×50 mL) and the combined organics washed with water, brine and dried over $Na_2SO_4$. The crude residue was purified over 100-200 M silica-gel using 2% EtOAc:hexane to obtain the desired product as a yellow liquid (0.074 g, 24% yield). $^1$H NMR (DMSO-$d_6$): δ 8.42 (s, 2H), 4.51 (m, 1H), 4.15 (q, J=6.80 Hz, 2H), 2.85 (s, 3H), 2.15 (m, 2H), 1.52 (m, 4H), 1.36 (m, 2H), 1.29 (t, J=6.80 Hz, 3H) and 1.21 (s, 3H).

Precursor 31: Ethyl 1-(5-bromopyrimidin-2-yl)-4-ethoxypiperidine-4-carboxylate

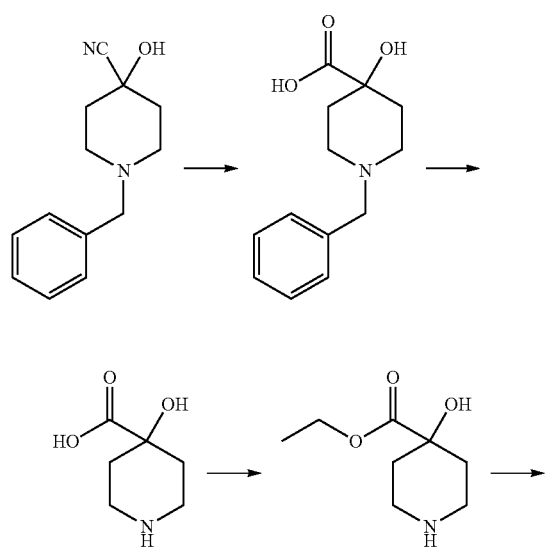

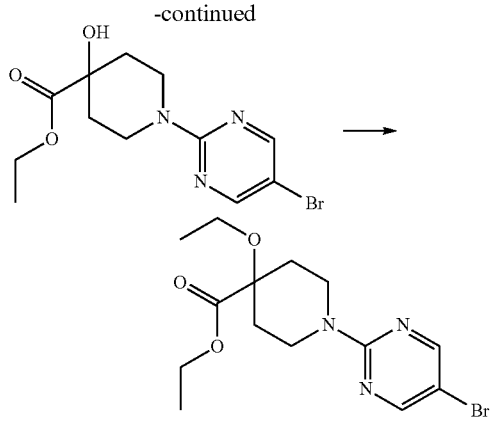

1-Benzyl-4-hydroxypiperidine-4-carboxylic acid

A solution of 1-benzyl-4-hydroxypiperidine-4-carbonitrile (2.5 g, 11.55 mmol) in 6N HCl (5.0 mL) was heated up to 100° C. for 2 h under microwave irradiation. After completion of reaction (by TLC) solvent was concentrated under reduced pressure and the crude residue (4.0 g) was carried forward for next step without further purification. MS: 236.16 [M+H]$^+$.

4-Hydroxypiperidine-4-carboxylic acid

To the solution of 1-benzyl-4-hydroxypiperidine-4-carboxylic acid (1.0 g, 4.25 mmol) in EtOH (15.0 mL) was added palladium hydroxide (0.40 g, 40% w/w) at rt and the mixture stirred at rt for 20 h under $H_2$ atmosphere. After completion of reaction (by TLC) the mixture was passed through celite and the solvent evaporated. The crude (0.70 g) residue was carried forward for next step without further purification. MS: 145.99 [M+H]$^+$.

Ethyl 4-hydroxypiperidine-4-carboxylate

To a solution of 4-hydroxypiperidine-4-carboxylic acid (1.20 g, 8.26 mmol) in EtOH (30 ml) was added conc. HCl (5 ml) at rt and the mixture heated up to 80° C. for 2-3 h. After completion (by TLC), solvent was evaporated under reduced pressure to obtain the desired product (1.20 g, crude) which was carried forward for next step without further purification. $^1$H NMR (D$_2$O): δ 4.20 (q, J=7.20 Hz, 2H), 3.28 (M, 4H), 2.22 (m, 2H), 1.91 (m, 2H), and 1.22 (t, J=7.20 Hz, 3H).

Ethyl 1-(5-bromopyrimidin-2-yl)-4-hydroxypiperidine-4-carboxylate

To an ice-cold solution of ethyl 4-hydroxypiperidine-4-carboxylate (0.60 g, 3.44 mmol) in EtOH (15 mL) was added DIPEA (2.95 mL, 17.24 mmol) followed by the addition of 5-bromo-2-chloropyrimidine (0.67 g, 3.44 mmol). The reaction was heated to 80° C. for 3 h then cooled to rt, water added and extracted with EtOAc (3×100 mL). The combined organics were washed with brine, dried over anhydrous $Na_2SO_4$, filtered and evaporated under reduced pressure. The crude residue was purified over 100-200 M silica-gel using 20% EtOAc:hexane to obtain the desired product as a yellow solid (0.57 g, 88%). $^1$H NMR (DMSO-$d_6$): δ 8.44 (s, 2H), 5.58 (s, 1H), 4.27 (m, 2H), 4.10 (q, J=7.20 Hz, 2H), 3.28 (m, 2H), 1.81 (m, 2H), 1.66 (m, 2H), and 1.18 (t, J=7.20 Hz, 3H).

Ethyl 1-(5-bromopyrimidin-2-yl)-4-ethoxypiperidine-4-carboxylate

To an ice-cold solution of ethyl 1-(5-bromopyrimidin-2-yl)-4-hydroxypiperidine-4-carboxylate (0.50 g, 1.51 mmol) in DMF (5 mL) was added NaH (0.066 g, 1.67 mmol, 60% dispersion in mineral oil) portion wiseand the mixture stirred at 0° C. for 10 minutes followed by drop wise addition of ethyl iodide (0.58 mL, 7.57 mmol). The reaction was stirred at 0° C. for 2 h. After completion of reaction (by TLC), the reaction was quenched with saturated $NH_4Cl$ solution (100 mL), extracted with EtOAc (3×100 mL) and the combined organics washed with water and brine and dried over $Na_2SO_4$. The crude residue was purified over 100-200 M silica-gel using 10% EtOAc:hexane to obtain the desired product as a yellow liquid (0.24 g, 44% yield). $^1$H NMR (DMSO-$d_6$): δ 8.27 (s, 2H), 4.31 (m, 2H), 4.22 (q, J=6.40 Hz, 2H), 3.44 (m, 4H), 1.96 (m, 4H), and 1.28 (m, 6H).

Precursor 32: ethyl 5-[(5-bromopyrimidin-2-yl)amino]-2-methyl-1,3-dioxane-2-carboxylate

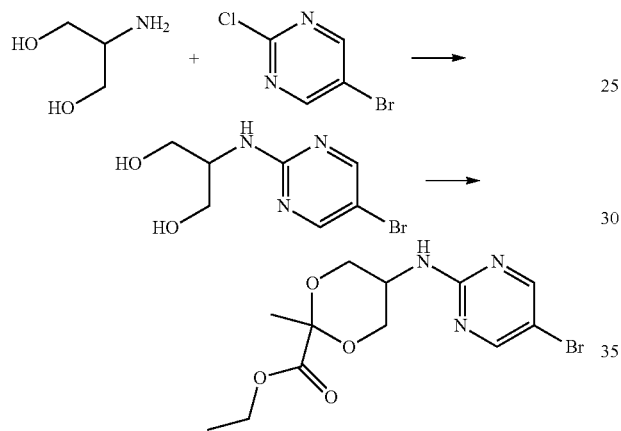

Ethyl 5-[(5-bromopyrimidin-2-yl)amino]-2-methyl-1,3-dioxane-2-carboxylate 5-bromo-2-chloro-pyrimidine (200 mg, 1.03 mmol), 2-aminopropane-1,3-diol (188 mg, 2.07 mmol), triethylamine (0.58 mL) and DMSO (2 mL) were combined and heated at 100 C for 3 hrs. The reaction mixture was diluted with water (25 mL) and the resulting precipitate filtered (filtrate discarded) to afford the desired product (227 mg, white solid). $^1$H NMR (MeOD/CDCl$_3$) δ 8.25 (s, 2H), 4.03-3.98 (m, 1H), 3.75-3.66 (m, 4H). m/z [M+H]$^+$ 248.0/250.0.

Ethyl 5-[(5-bromopyrimidin-2-yl)amino]-2-methyl-1,3-dioxane-2-carboxylate

2-[(5-bromopyrimidin-2-yl)amino]propane-1,3-diol (100 mg, 0.40 mmol), ethyl pyruvate (80 μL, 0.72 mmol) and acetonitrile (2 mL) were combined at rt. An aliquot of borontrifluoride etherate (100 μL, 0.80 mmol) was added to the reaction mixture and stirring was continued at rt for 24 hrs. A further portion of borontrifluoride etherate (100 μL, 0.80 mmol) was added to the reaction mixture, which was stirred at rt for a further 24 hrs. The reaction mixture was loaded directly onto a column for flash chromatography (12 g silica column), eluting with 0-100% EtOAc gradient in n-heptane, to give desired product (105 mg, light brown oil). m/z 345.9/347.9 [M+H]$^+$.

Compound 1: 1-[5-[2-(ethylcarbamoylamino)-7-(2-pyridyl)-1,3-benzothiazol-5-yl]pyrimidin-2-yl]-4-methyl-piperidine-4-carboxylic acid

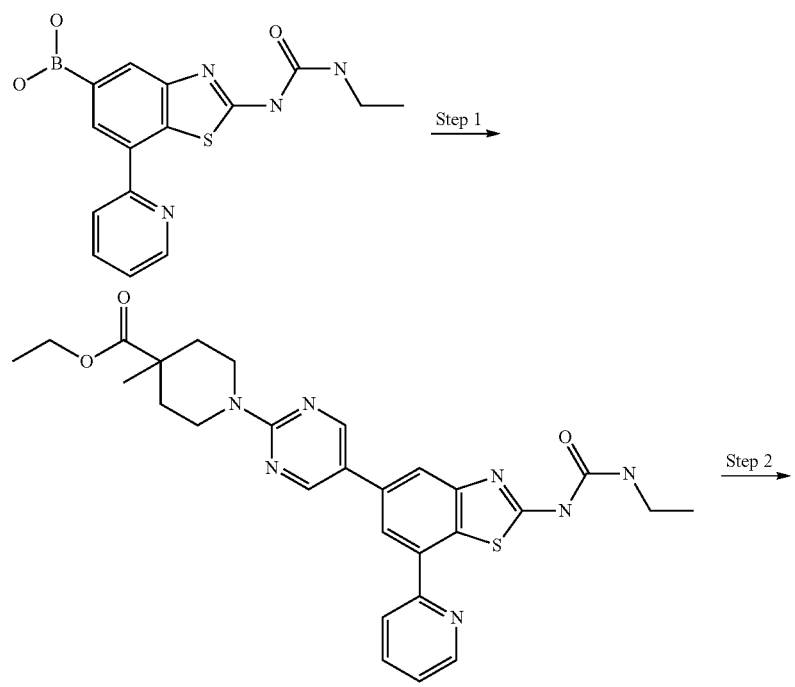

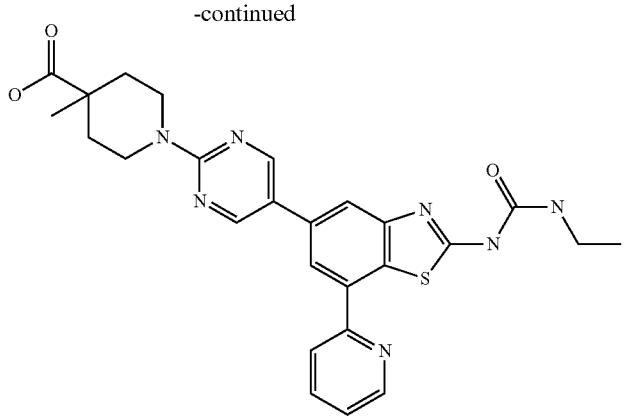

Ethyl 1-[5-[2-(ethylcarbamoylamino)-7-(2-pyridyl)-1,3-benzothiazol-5-yl]pyrimidin-2-yl]-4-methyl-piperidine-4-carboxylate To a solution of ethyl 1-(5-bromopyrimidin-2-yl)-4-methylpiperidine-4-carboxylate (0.50 g, 1.52 mmol) in EtOH (15 mL) was added [2-(ethylcarbamoylamino)-7-(2-pyridyl)-1,3-benzothiazol-5-yl]boronic acid (0.52 g, 1.52 mmol) and 2.0 M aqueous solution of $Na_2CO_3$ (0.24 g, 2.28 mmol). The reaction was degassed by purging $N_2$ for 15 min followed by addition of tetrakis(triphenylphosphine)palladium (0) (0.18 g, 0.15 mmol). The reaction was again degassed for 10-15 min then heated up to 80° C. for 2 h. The reaction mixture was then passed through celite and the solvent evaporated. The crude residue was purified over 100-200 M silica-gel using 1.50% MeOH: DCM to obtain the product as an off white solid that was finally triturated with ether (0.18 g, 22% yield). $^1$H NMR (DMSO-$d_6$): δ 1.15 (t, J=7.20 Hz, 3H), 1.20 (m, 6H), 1.45 (m, 2H), 2.06 (m, 2H), 2.54 (m, 2H), 3.21 (q, J=7.20, 2H), 4.15 (q, J=6.80 Hz, 2H), 4.32 (m, 2H), 6.86 (br s, 1H), 7.44 (m, 1H), 7.99 (m, 2H), 8.23 (s, 1H), 8.47 (m, 1H), 8.80 (m, 1H), 8.92 (s, 2H) and 10.55 (br s, 1H). MS: 546.12 [M+H]$^+$.

1-[5-[2-(Ethylcarbamoylamino)-7-(2-pyridyl)-1,3-benzothiazol-5-yl]pyrimidin-2-yl]-4-methyl-piperidine-4-carboxylic acid (1)

To an ice-cold solution of ethyl 1-[5-[2-(ethylcarbamoylamino)-7-(2-pyridyl)-1,3-benzothiazol-5-yl]pyrimidin-2-yl]-4-methyl-piperidine-4-carboxylate (0.18 g, 0.33 mmol) in DMSO (2 mL) was added potassium tert-butoxide (0.184 g, 1.65 mmol) and the mixture stirred at rt for 2 h. After completion of reaction (by TLC), water (10 mL) was added followed by extraction with EtOAc (2×50 mL). The organic layer was discarded and the pH of the aqueous layer was adjusted up to 4-5 then extracted with hot EtOAc (3×100 mL). The combined organic layer was dried over $Na_2SO_4$, filtered and evaporated under reduced pressure. The residue thus obtained was triturated with ether to afford the desired product as off-white solid (0.11 g, 65% yield). $^1$H NMR (DMSO-$d_6$): δ 1.10 (t, J=7.20 Hz, 3H), 1.19 (s, 3H), 1.40 (m, 2H), 2.04 (m, 2H), 3.22 (q, J=7.20, 2H), 3.39 (m, 2H), 4.30 (m, 2H), 6.87 (br s, 1H, $D_2O$ exchangeable), 7.44 (m, 1H), 7.92 (s, 1H), 7.99 (m, 1H), 8.18 (s, 1H), 8.42 (d, J=8.0 Hz, 1H), 8.78 (d, (J=4.40 Hz, 1H), 8.85 (s, 2H), 10.54 (br s, 1H, $D_2O$ exchangeable) and 12.45 (br s, 1H, $D_2O$ exchangeable). MS: 518.27 [M+H]$^+$.

The following compounds were similarly prepared from their respective precursors by coupling with Intermediate 1 and the appropriate aryl halide. The aryl halides may be made using methods described for the synthesis of Intermediate 3.

| Cpd No. | Structure | LCMS data [M + H]$^+$ | $^1$H NMR data |
|---|---|---|---|
| 2 | 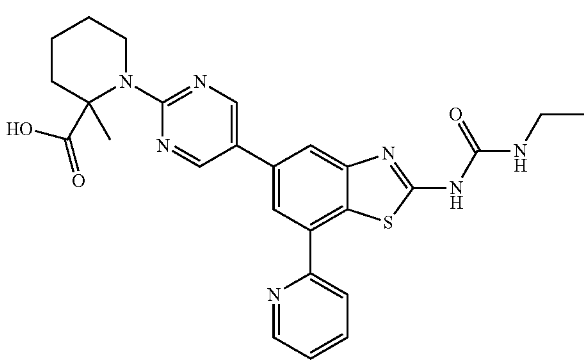 [SMILES: CCNC(=O)Nc1nc2cc(-c3cnc(N4CCCCC4(C)C(=O)O)nc3)cc(-c3ccccn3)c2s1] | 518.05 | δ 1.11 (m, 3H), 1.27-1.50 (m, 2H), 1.75 (m, 2H), 2.25 (m, 1H), 3.10 (m, 1H), 3.21 (m, 2H), 3.67 (s, 3H), 4.70 (m, 1H), 5.52 (m, 1H), 6.87 (br s, 1H), 7.44 (s, 1H), 7.98 (s, 2H), 8.25 (s, 1H), 8.50 (m, 1H), 8.81 (s, 1H), 8.95 (s, 2H) and 10.57 (br s, 1H) |

| Cpd No. | Structure | LCMS data [M + H]⁺ | ¹H NMR data |
|---|---|---|---|
| 3 | 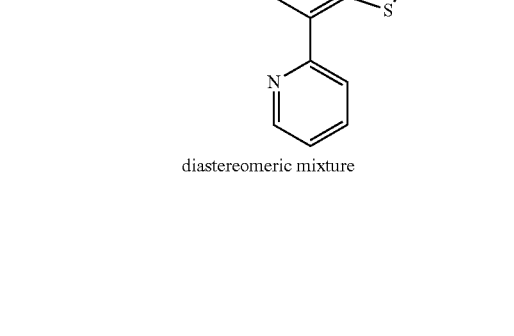<br>diastereomeric mixture | 534.22 | δ 1.10 (t, J = 7.20 Hz, 3H), 1.23 (m, 3H), 1.62 (m, 1H), 1.84 (m, 1H), 3.21 (m, 2H), 3.50-3.62 (m, 2H), 3.89 (m, 1H), 4.12 (m, 1H), 4.41 (m, 1H), 5.07 (br s, 1H), 7.20 (br s, 1H), 7.45 (m, 1H), 7.96-8.01 (m, 2H), 8.22 (s, 1H), 8.48 (m, 1H), 8.81 (m, 1H), 8.89 (s, 2H), 10.75 (br s, 1H) and 12.20 (br s, 1H) |
| 4 | 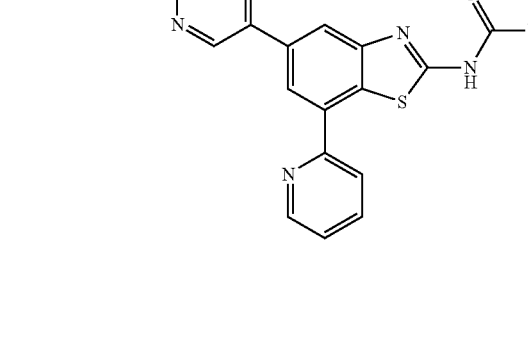 | 517.22 | δ 1.11 (t, J = 7.20 Hz, 3H), 1.18 (s, 3H), 1.42 (m, 2H), 2.0 (m, 2H), 3.15-3.22 (m, 4H), 4.0 (m, 2H), 6.87 (br s, 1H), 6.97 (d, J = 9.20 Hz, 1H), 7.45 (m, 1H), 7.91 (s, 1H), 7.97 (m, 1H), 8.05 (dd, J = 2.40 and 8.80 Hz, 1H), 8.20 (s, 1H), 8.45 (d, J = 8.40 Hz, 1H), 8.65 (m, 1H), 8.80 (d, J = 4.80 Hz, 1H), 10.56 (br s, 1H) and 12.43 (br s, 1H). |
| 5 | 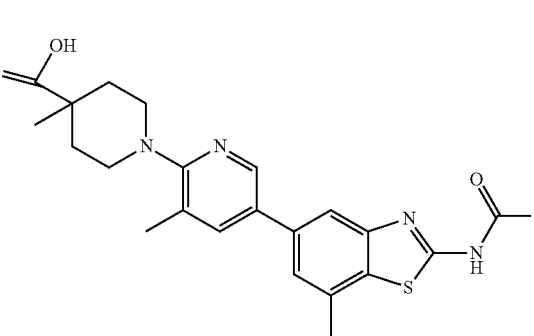 | 531.25 | δ 1.11 (t, J = 7.20 Hz, 3H), 1.21 (s, 3H), 1.56 (m, 2H), 2.10 (m, 2H), 2.34 (s, 3H), 2.92 (m, 2H), 3.19 (m, 2H), 3.30 (m, 2H), 6.89 (br s, 1H), 7.45 (m, 1H), 7.96 (s, 1H), 7.99-8.03 (m, 2H), 8.23 (s, 1H), 8.49 (m, 1H), 8.61 (s, 1H), 8.81 (m, 1H), 10.60 (br s, 1H) and 12.35 (br s, 1H). |

-continued

| Cpd No. | Structure | LCMS data [M + H]+ | 1H NMR data |
|---|---|---|---|
| 9 | 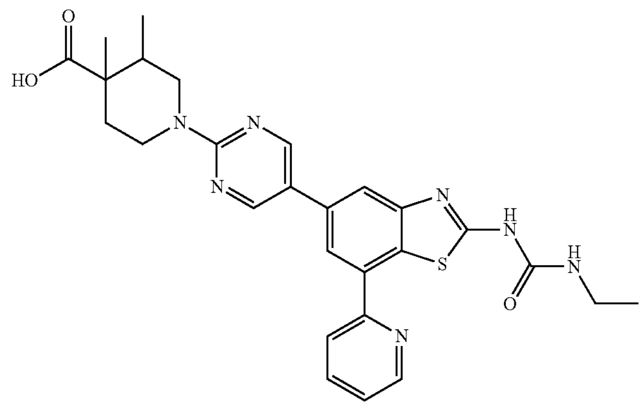 [SMILES: CCNC(=O)Nc1nc2cc(-c3cnc(N4CCC(C)(C(=O)O)C(C)C4)nc3)cc(-c3ccccn3)c2s1] | 532.25 | δ 0.97 (d, J = 6.80 Hz, 3H), 1.09 (t, J = 7.20 Hz, 3H), 1.22 (s, 3H), 1.44 (m, 1H), 1.70 (m, 1H), 1.99 (m, 1H), 3.19 (m, 2H), 3.67 (m, 1H), 3.81 (m, 1H), 4.05 (m, 2H), 6.91 (br s, 1H), 7.45 (m, 1H), 7.95 (s, 1H), 7.99-8.03 (m, 1H), 8.23 (s, 1H), 8.49 (d, J = 8.40 Hz, 1H), 8.81 (m, 1H), 8.89 (s, 2H), 10.60 (br s, 1H) and 12.40 (br s, 1H). |
| 40 | 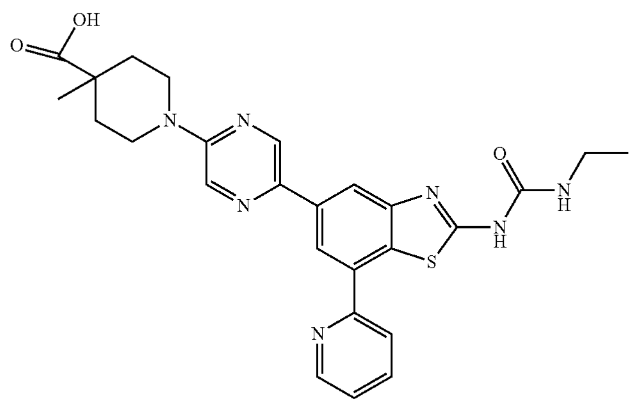 [SMILES: CCNC(=O)Nc1nc2cc(-c3cnc(N4CCC(C)(C(=O)O)CC4)cn3)cc(-c3ccccn3)c2s1] | 518.15 | δ 1.09 (t, J = 7.20 Hz, 3H), 1.19 (s, 3H), 1.49 (m, 2H), 2.03 (m, 2H), 3.16-3.29 (m, 4H), 4.08 (m, 2H), 6.87 (br s, 1H), 7.46 (m, 1H), 8.0 (t, J = 7.60 Hz, 1H), 8.27 (s, 1H), 8.40 (d, J = 8.0 Hz, 1H), 8.45 (s, 1H), 8.54 (s, 1H), 8.81 (m, 1H), 8.95 (s, 1H), 10.65 (br s, 1H) and 12.49 (br s, 1H). |
| 181 | 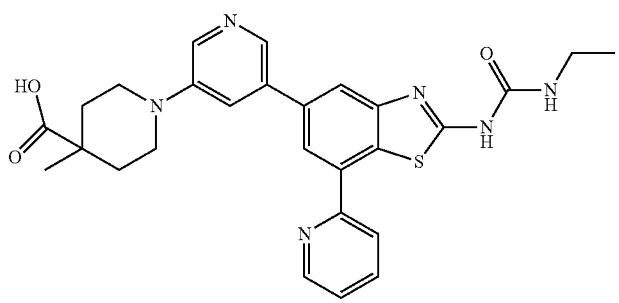 [SMILES: CCNC(=O)Nc1nc2cc(-c3cncc(N4CCC(C)(C(=O)O)CC4)c3)cc(-c3ccccn3)c2s1] | 517.14 | δ 1.09 (t, J = 7.20 Hz, 3H), 1.20 (s, 3H), 1.54 (m, 2H), 2.10 (m, 2H), 3.03 (m, 2H), 3.21 (m, 2H), 3.66 (m, 2H), 6.95 (br s, 1H), 7.45 (m, 1H), 7.70 (s, 1H), 8.0 (m, 2H), 8.25 (s, 1H), 8.33 (br s, 1H), 8.45 (br s, 1H), 8.50 (d, J = 8.0 Hz, 1H), 8.81 (m, 1H), 10.62 (br s, 1H) and 12.43 (br s, 1H) |
| 183 | 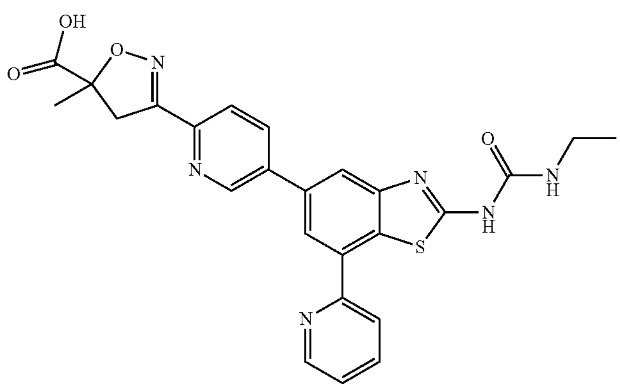 [SMILES: CCNC(=O)Nc1nc2cc(-c3ccc(C4=NOC(C)(C(=O)O)C4)nc3)cc(-c3ccccn3)c2s1] | 501.04 | δ 1.10 (t, J = 7.20 Hz, 3H), 1.60 (s, 3H), 3.20 (m, 2H), 3.45 (d, J = 19.20 Hz, 1H), 3.88 (d, J = 17.60 Hz, 1H), 6.90 (br s, 1H), 7.45 (m, 1H), 7.99-8.03 (m, 2H), 8.11 (s, 1H), 8.37 (s, 1H), 8.44 (d, J = 8.40 Hz, 1H), 8.53 (d, J = 8.0 Hz, 1H), 8.83 (d, J = 4.40 Hz, 1H), 9.21 (s, 1H), 10.67 (br s, 1H) and 13.28 (br s, 1H) |

-continued

| Cpd No. | Structure | LCMS data [M + H]+ | ¹H NMR data |
|---|---|---|---|
| 98 | 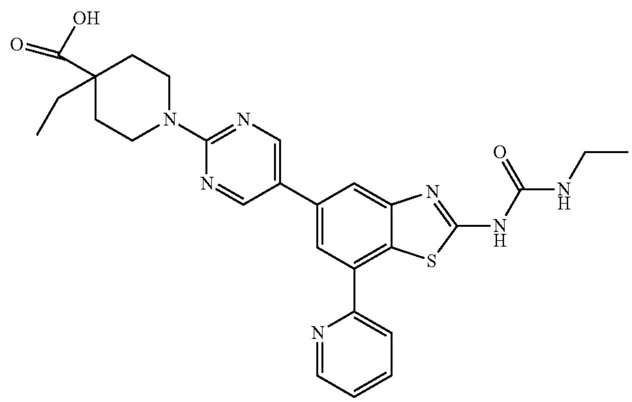 [SMILES: CCNC(=O)Nc1nc2cc(-c3cnc(N4CCC(CC)(C(=O)O)CC4)nc3)cc(-c3ccccn3)c2s1] | 532.20 | δ 0.83 (t, J = 7.60 Hz, 3H), 1.11 (t, J = 7.20 Hz, 3H), 1.35 (m, 2H), 1.55 (m, 2H), 2.05 (m, 2H), 3.13-3.24 (m, 4H), 4.46 (m, 2H), 6.92 (br s, 1H), 7.45 (m, 1H), 7.95 (s, 1H), 7.97-8.01 (m, 1H), 8.22 (s, 1H), 8.48 (d, J = 8.0 Hz, 1H), 8.80 (m, 1H), 8.90 (s, 2H), 10.60 (br s, 1H) and 12.50 (br s, 1H) |
| 108 | 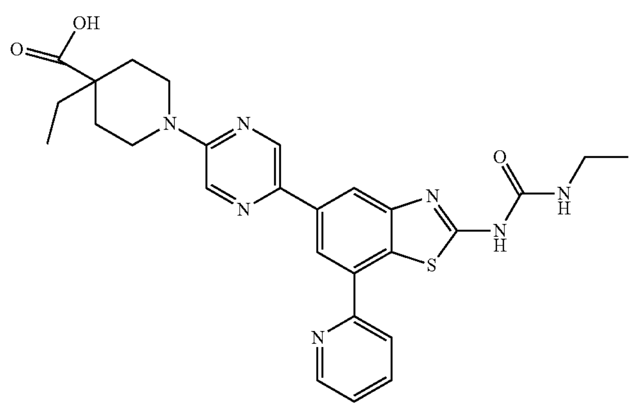 | 532.10 | δ 0.83 (t, J = 7.20 Hz, 3H), 1.10 (t, J = 7.20 Hz, 3H), 1.40 (m, 2H), 1.55 (m, 2H), 2.0 (m, 2H), 3.10 (m, 2H), 3.20 (m, 2H), 4.18 (m, 2H), 6.85 (br s, 1H), 7.45 (m, 1H), 8.0 (m, 1H), 8.27 (s, 1H), 8.40 (d, J = 8.40 Hz, 1H), 8.44 (s, 1H), 8.54 (s, 1H), 8.81 (m, 1H), 8.95 (s, 1H), 10.63 (br s, 1H) and 12.53 (br s, 1H) |
| 117 | 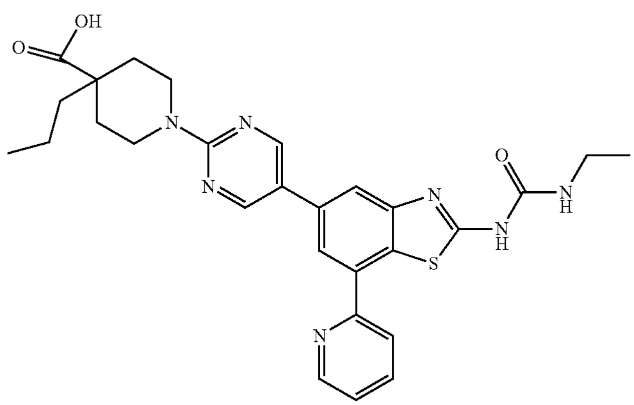 [SMILES: CCCC1(C(=O)O)CCN(c2ncc(-c3cc(-c4ccccn4)c4sc(NC(=O)NCC)nc4c3)cn2)CC1] | 546.29 | δ 0.85 (t, J = 7.20 Hz, 3H), 1.10 (t, J = 7.20 Hz, 3H), 1.22 (m, 2H), 1.37 (m, 2H), 1.49 (m, 2H), 2.0 (m, 2H), 3.12-3.22 (m, 4H), 4.48 (m, 2H), 6.93 (br s, 1H), 7.45 (m, 1H), 7.95 (s, 1H), 8.01 (m, 1H), 8.22 (s, 1H), 8.48 (d, J = 8.40 Hz, 1H), 8.81 (m, 1H), 8.90 (s, 2H), 10.61 (br s, 1H) and 12.53 (br s, 1H) |

-continued

| Cpd No. | Structure | LCMS data [M + H]+ | 1H NMR data |
|---|---|---|---|
| 129 | 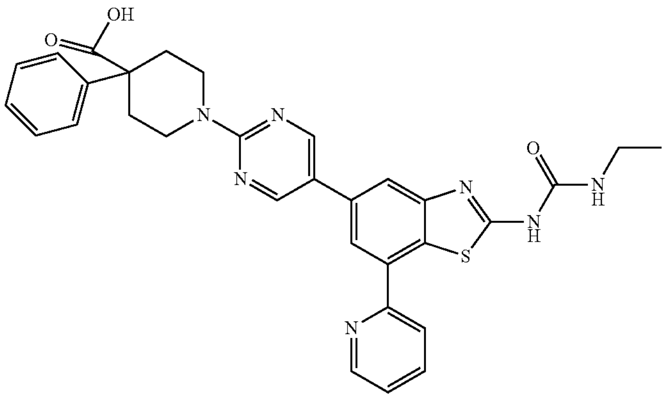 [SMILES: CCNC(=O)Nc1nc2cc(-c3cnc(N4CCC(C(=O)O)(c5ccccc5)CC4)nc3)cc(-c3ccccn3)c2s1] | 580.09 | (DMSO-d6): δ 1.11 (t, J = 7.20 Hz, 3H), 1.22 (m, 2H), 1.83 (m, 2H), 3.19-3.40 (m, 4H), 4.60 (m, 2H), 6.87 (br s, 1H), 7.25-7.45 (m, 5H), 7.96-8.01 (m, 2H), 8.23 (s, 1H), 8.49 (d, J = 8.40 Hz, 1H), 8.80 (d, J = 4.40 Hz, 1H), 8.92 (s, 2H), 10.57 (br s, 1H) and 12.79 (br s, 1H) |
| 130 | 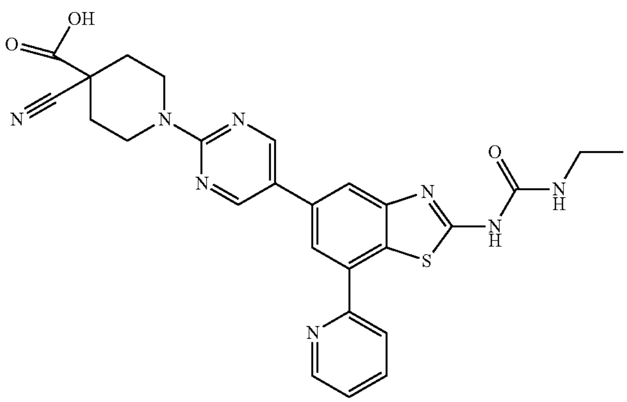 [SMILES: CCNC(=O)Nc1nc2cc(-c3cnc(N4CCC(C#N)(C(=O)O)CC4)nc3)cc(-c3ccccn3)c2s1] | 529.06 | (DMSO-d6): δ 1.11 (t, J = 7.20 Hz, 3H), 1.97 (m, 2H), 2.12 (m, 2H), 3.17-3.24 (m, 4H), 4.73 (m, 2H), 6.91 (br s, 1H), 7.44 (m, 1H), 7.99 (m, 2H), 8.25 (s, 1H), 8.49 (m, 1H), 8.81 (d, J = 4.80 Hz, 1H), 8.96 (s, 2H) and 10.60 (br s, 1H) |
| 131 | 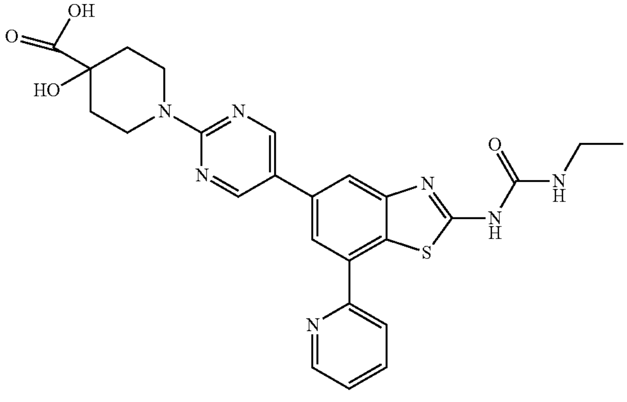 [SMILES: CCNC(=O)Nc1nc2cc(-c3cnc(N4CCC(O)(C(=O)O)CC4)nc3)cc(-c3ccccn3)c2s1] | 520.15 | (DMSO-d6): δ 1.11 (t, J = 7.20 Hz, 3H), 1.68 (m, 2H), 1.85 (m, 2H), 3.15-3.22 (m, 3H), 3.38 (m, 2H), 4.46 (m, 2H), 6.87 (br s, 1H), 7.44 (m, 1H), 7.99 (m, 2H), 8.24 (s, 1H), 8.49 (d, J = 8.80 Hz, 1H), 8.81 (d, J = 4.0 Hz, 1H), 8.91 (s, 2H), 10.56 (br s, 1H) and 12.60 (br s, 1H). |

| Cpd No. | Structure | LCMS data [M + H]⁺ | ¹H NMR data |
|---|---|---|---|
| 132 | 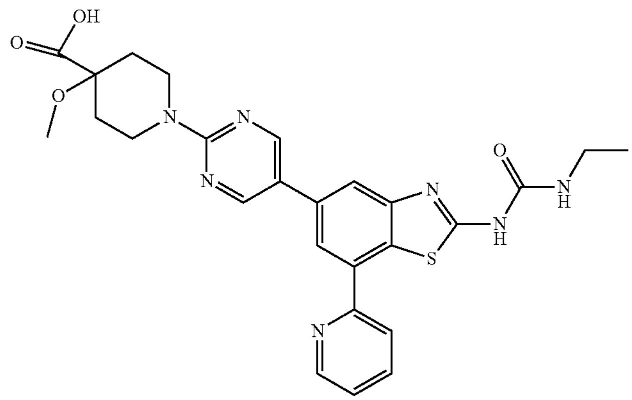 [SMILES: CCNC(=O)Nc1nc2cc(-c3cnc(N4CCC(OC)(C(=O)O)CC4)nc3)cc(-c3ccccn3)c2s1] | 532.24 [M − H]⁻ | (DMSO-d₆): δ 1.11 (t, J = 7.20 Hz, 3H), 1.82-1.90 (m, 4H), 3.19 (m, 2H), 3.24 (s, 3H), 3.41 (m, 2H), 4.36 (m, 2H), 6.90 (br s, 1H), 7.44 (m, 1H), 7.99 (m, 2H), 8.24 (s, 1H), 8.49 (d, J = 8.0 Hz, 1H), 8.81 (d, J = 4.40 Hz, 1H), 8.92 (s, 2H), 10.59 (br s, 1H) and 12.91 (br s, 1H). |
| 133 | 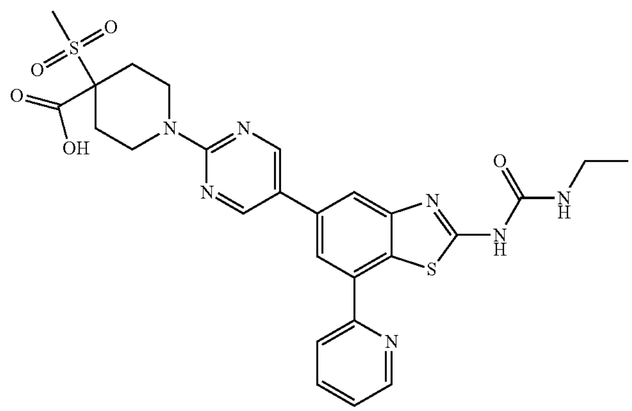 [SMILES: CCNC(=O)Nc1nc2cc(-c3cnc(N4CCC(C(=O)O)(S(C)(=O)=O)CC4)nc3)cc(-c3ccccn3)c2s1] | 582.26 | (DMSO-d₆) δ 1.11 (t, J = 7.20 Hz, 3H), 1.90 (m, 2H), 2.42 (m, 2H), 2.96 (m, 2H), 3.08 (s, 3H), 3.19 (m, 2H), 4.89 (m, 2H), 6.87 (br s, 1H), 7.44 (m, 1H), 8.01 (m, 2H), 8.25 (s, 1H), 8.49 (d, J = 8.0 Hz, 1H), 8.81 (d, J = 4.40 Hz, 1H), 8.95 (s, 2H), 10.56 (br s, 1H) and 14.20 (br s, 1H) |
| 134 | 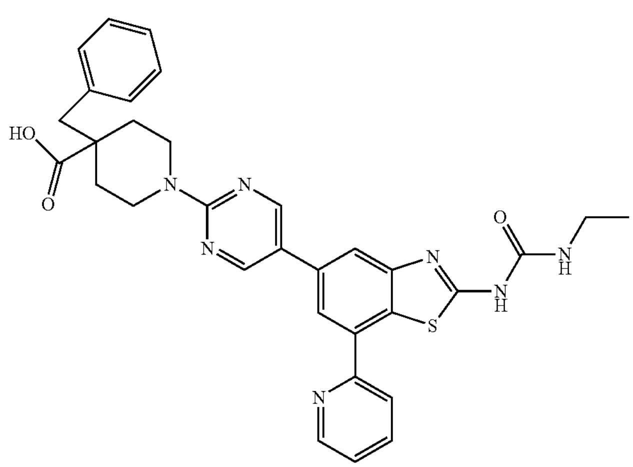 [SMILES: CCNC(=O)Nc1nc2cc(-c3cnc(N4CCC(Cc5ccccc5)(C(=O)O)CC4)nc3)cc(-c3ccccn3)c2s1] | 594.26 | (DMS0-d₆): δ 1.13 (t, J = 7.20 Hz, 3H), 1.50 (m, 2H), 2.01 (m, 2H), 2.84 (s, 2H), 3.14 (m, 2H), 3.21 (m, 2H), 4.56 (m, 2H), 6.87 (br s, 1H), 7.13 to 7.29 (m, 5H), 7.44 (m, 1H), 7.95 (s, 1H), 7.99 (m, 1H), 8.22 (s, 1H), 8.48 (d, J = 8.40 Hz, 1H), 8.80 (d, J = 4.80 Hz, 1H), 8.90 (s, 2H), 10.54 (br s, 1H) and 12.62 (br s, 1H). |

-continued

| Cpd No. | Structure | LCMS data [M + H]+ | ¹H NMR data |
|---|---|---|---|
| 135 | 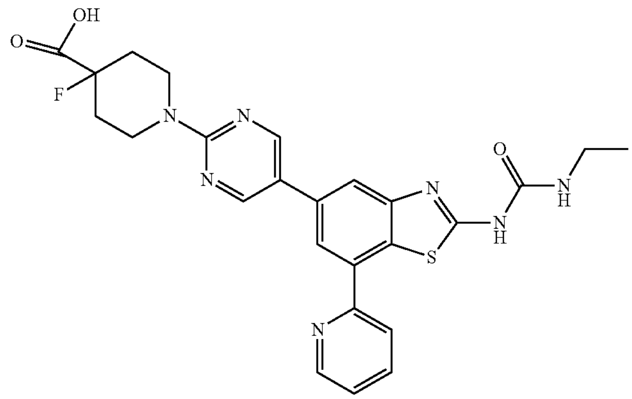 | 522.19 | (DMSO-d$_6$): δ 1.11 (t, J = 7.20 Hz, 3H), 1.92-2.05 (m, 4H), 3.17-3.22 (m, 4H), 4.59 (m, 2H), 7.24 (br s, 1H), 7.44 (m, 1H), 7.97-8.01 (m, 2H), 8.22 (s, 1H), 8.48 (d, J = 8.0 Hz, 1H), 8.81 (d, (J = 4.0 Hz, 1H), 8.93 (s, 2H) and 10.87 (br s, 1H) |
| 136 | 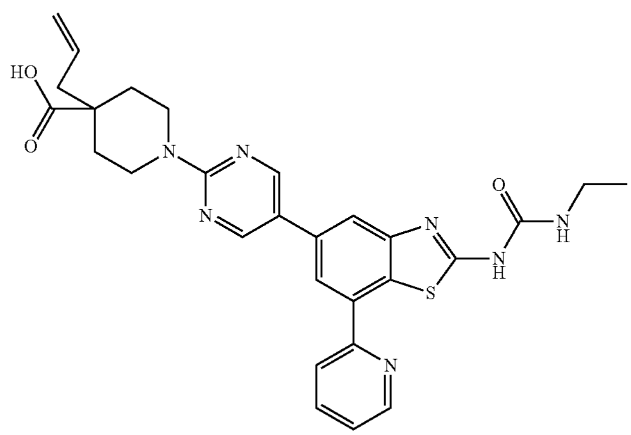 [SMILES: C=CCC1(C(=O)O)CCN(c2ncc(-c3cc(-c4ccccn4)c4sc(NC(=O)NCC)nc4c3)cn2)CC1] | 544.29 | (DMSO-d$_6$): δ 1.09 (t, J = 7.20 Hz, 3H), 1.42 (m, 2H), 2.05 (m, 2H), 2.29 (m, 2H), 3.19-3.22 (m, 4H), 4.45 (m, 2H), 5.07 (m, 2H), 5.75 (m, 1H), 6.92 (br s, 1H), 7.44 (m, 1H), 7.95-8.01 (m, 2H), 8.22 (s, 1H), 8.48 (d, J = 8.40 Hz, 1H), 8.81 (m, 1H), 8.90 (s, 2H), 10.67 (br s, 1H) and 12.58 (br s, 1H) |
| 165 | 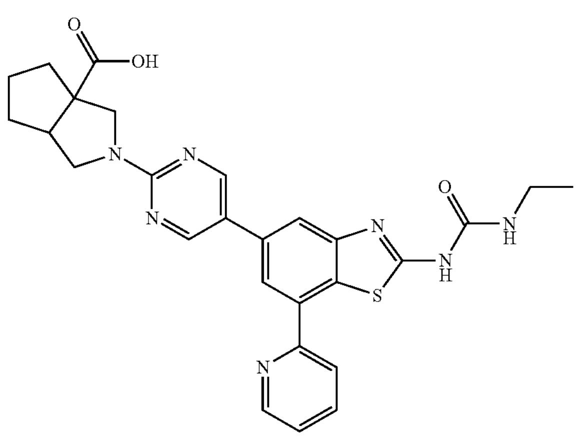 [SMILES: CCNC(=O)Nc1nc2cc(-c3cnc(N4CC5CCCC5(C(=O)O)C4)nc3)cc(-c3ccccn3)c2s1] | 530.24 | (DMSO-d$_6$): δ 1.11 (t, J = 7.20 Hz, 3H), 1.57 (m, 1H), 1.74 (m, 3H), 1.99 (m, 1H), 2.15 (m, 1H), 2.98 (m, 1H), 3.21 (m, 2H), 3.52 (m, 2H), 3.82 (m, 1H), 4.17 (m, 1H), 6.88 (br s, 1H), 7.44 (m, 1H), 7.95-8.01 (m, 2H), 8.22 (s, 1H), 8.48 (d, J = 7.60 Hz, 1H), 8.81 (m, 1H), 8.90 (s, 2H), 10.54 (brs, 1H) and 12.50 (br s, 1H) |

| Cpd No. | Structure | LCMS data [M + H]+ | 1H NMR data |
|---|---|---|---|
| 137 | 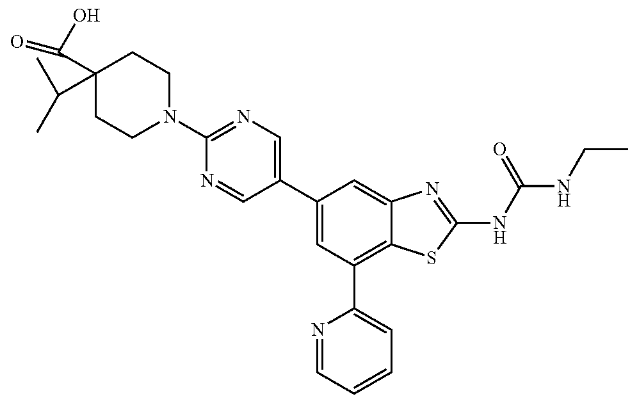 [SMILES: CCNC(=O)Nc1nc2cc(-c3cnc(N4CCC(C(=O)O)(C(C)C)CC4)nc3)cc(-c3ccccn3)c2s1] | 546.19 | (DMSO-d6): δ 0.86 (d, J = 6.80 Hz, 6H), 1.11 (t, J = 7.20 Hz, 3H), 1.39 (m, 2H), 1.71 (m, 1H), 2.0 (m, 2H), 2.92 (m, 2H), 3.20 (m, 2H), 4.71 (m, 2H), 6.66 (br s, 1H), 7.44 (m, 1H), 7.95-8.01 (m, 2H), 8.23 (s, 1H), 8.49 (d, J = 8.0 Hz, 1H), 8.80 (d, J = 4.40 Hz, 1H), 8.90 (s, 2H), 10.57 (br s, 1H) and 12.56 (br s, 1H) |
| 138 | 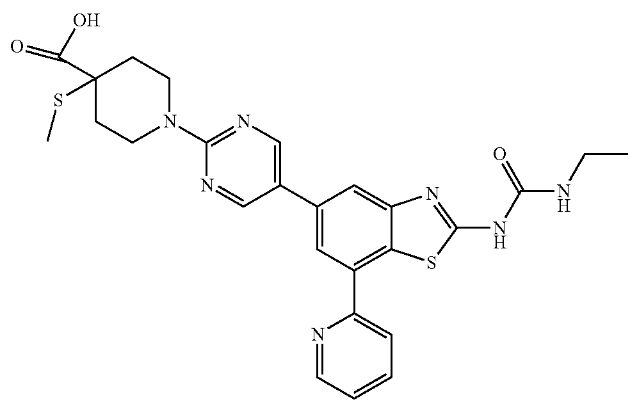 | 548.20 [M − H]− | (DMSO-d6): δ 1.11 (t, J = 7.20 Hz, 3H), 1.70 (m, 2H), 2.08 (s, 3H), 2.19 (m, 2H), 3.21 (q, J = 7.20, 2H), 3.55 (m, 2H), 4.20 (m, 2H), 6.91 (br s, 1H, D2O exchangeable), 7.44 (m, 1H), 7.96-8.01 (m, 2H), 8.23 (d, J = 1.20 Hz, 1H), 8.48 (d, J = 8.0 Hz, 1H), 8.81 (d, J = 4.40 Hz, 1H), 8.92 (s, 2H), 10.59 (br s, 1H, D2O exchangeable and 12.80 (br s, 1H, D2O exchangeable) |
| 140 | 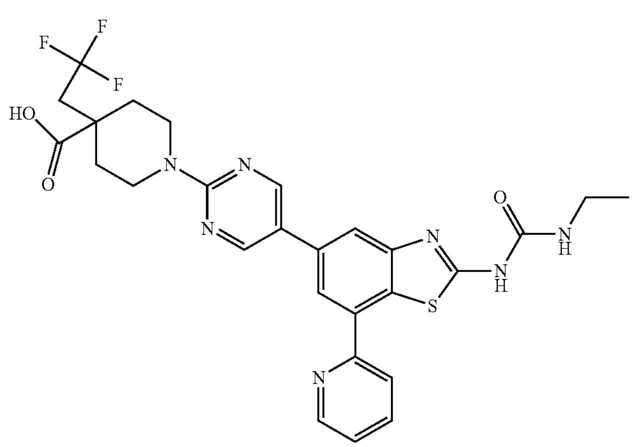 [SMILES: CCNC(=O)Nc1nc2cc(-c3cnc(N4CCC(CC(F)(F)F)(C(=O)O)CC4)nc3)cc(-c3ccccn3)c2s1] | 586.30 | (DMSO-d6): δ 1.11 (t, J = 7.20 Hz, 3H), 1.64 (m, 2H), 2.09 (m, 2H), 2.70 (m, 2H), 3.20 (m, 2H), 3.33 (m, 2H), 4.39 (m, 2H), 6.88 (br s, 1H), 7.44 (m, 1H), 7.96 (s, 1H), 8.01 (m, 1H), 8.23 (s, 1H), 8.49 (d, J = 8.40 Hz, 1H), 8.80 (d, J = 4.0 Hz, 1H), 8.93 (s, 2H), 10.57 (br s, 1H) and 13.0 (br s, 1H) |

-continued

| Cpd No. | Structure | LCMS data [M + H]+ | 1H NMR data |
|---|---|---|---|
| 141 | 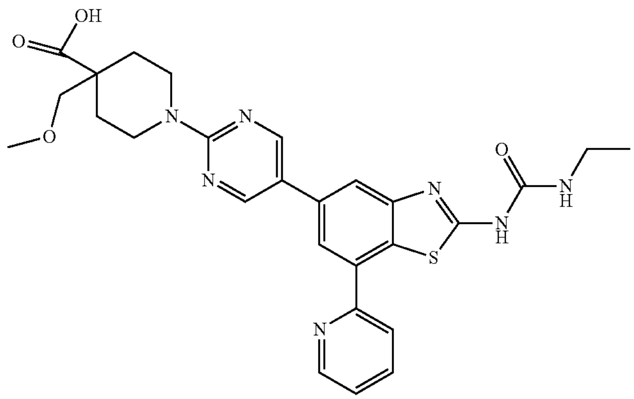 | 548.22 | (DMSO-d6): δ 1.11 (t, J = 7.20 Hz, 3H), 1.50 (m, 2H), 2.03 (m, 2H), 3.19 (m, 2H), 3.25 (s, 3H), 3.33 (m, 2H), 3.40 (s, 2H), 4.42 (m, 2H), 6.97 (br s, 1H), 7.44 (m, 1H), 7.95 (s, 1H), 8.0 (m, 1H), 8.22 (s, 1H), 8.48 (d, J = 8.0 Hz, 1H), 8.80 (d, J = 4.80 Hz, 1H), 8.90 (s, 2H), 10.63 (br s, 1H) and 12.54 (br s, 1H) |
| 164 | 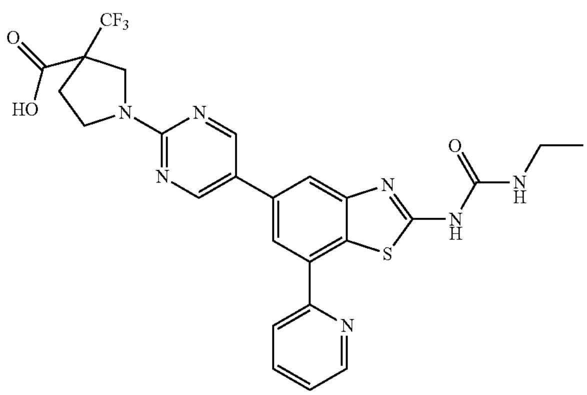 [SMILES: CCNC(=O)Nc1nc2cc(-c3cnc(N4CCC(C(=O)O)(C(F)(F)F)C4)nc3)cc(-c3ccccn3)c2s1] | 558.21 | (DMSO-d6): δ 1.11 (t, J = 7.20 Hz, 3H), 2.26 (m, 1H), 2.67 (m, 1H), 3.20 (m, 2H), 3.58 (m, 1H), 3.73 (m, 2H), 4.28 (m, 1H), 7.22 (br s, 1H), 7.43 (m, 1H), 7.95-8.0 (m, 2H), 8.21 (s, 1H), 8.48 (d, J = 8.0 Hz, 1H), 8.80 (s, 1H), 8.90 (s, 2H) and 10.83 (br s, 1H) |
| 160 | 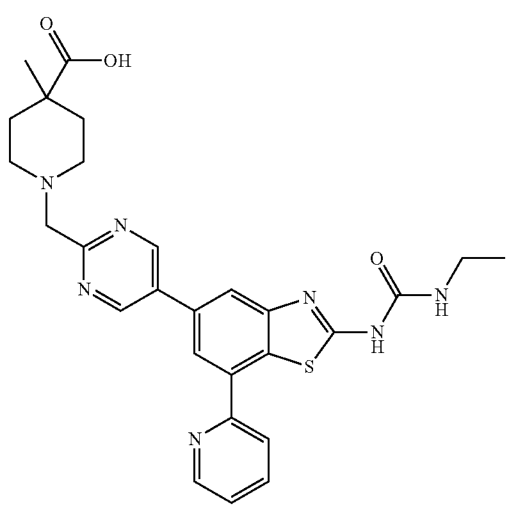 [SMILES: CCNC(=O)Nc1nc2cc(-c3cnc(CN4CCC(C)(C(=O)O)CC4)nc3)cc(-c3ccccn3)c2s1] | 532.19 | (DMSO-d6 + D2O): δ 1.09 (t, J = 7.20 Hz, 3H), 1.19 (s, 3H), 1.84 (m, 2H), 2.20 (m, 2H), 3.09 (m, 2H), 3.20 (m, 2H), 3.35 (m, 2H), 4.71 (s, 2H), 7.46 (m, 1H), 8.01 (t, J = 7.60 Hz, 1H), 8.16 (s, 1H), 8.38 (s, 1H), 8.46 (d, (J = 8.0 Hz, 1H), 8.80 (d, J = 4.0 Hz, 1H) and 9.42 (s, 2H) |

-continued

| Cpd No. | Structure | LCMS data [M + H]+ | 1H NMR data |
|---|---|---|---|
| 36 | 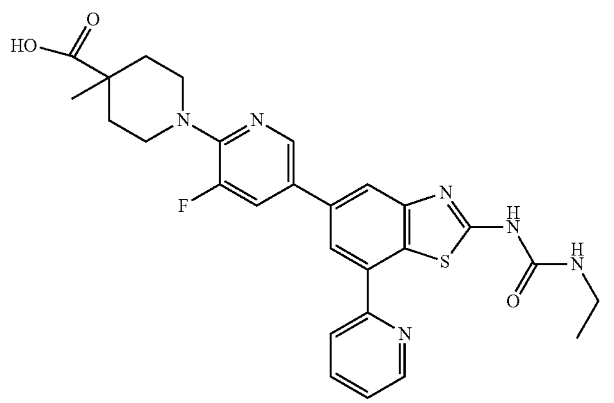 [SMILES: CCNC(=O)Nc1nc2cc(-c3cnc(N4CCC(C)(C(=O)O)CC4)c(F)c3)cc(-c3ccccn3)c2s1] | 535.1 | (MeOD) δ 8.78-8.75 (m, 1H), 8.34 (d, J = 1.3 Hz, 1H), 8.22 (d, J = 8.2 Hz, 1H), 8.07 (d, J = 1.6 Hz, 1H), 7.96 (m, 1H), 7.90 (d, J = 1.5 Hz, 1H), 7.86 (m, 1H), 7.42-7.37 (m, 1H), 3.88 (m, 2H), 3.40-3.32 (m, 2H), 3.28-3.22 (m, 2H), 2.28-2.20 (m, 2H), 1.67-1.58 (m, 2H), 1.29 (s, 3H), 1.23 (t, J = 7.2 Hz, 3H). |
| 182 | 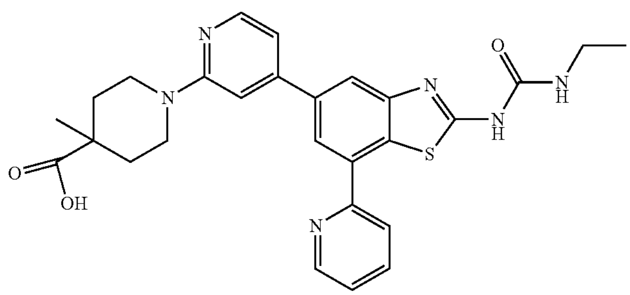 [SMILES: CCNC(=O)Nc1nc2cc(-c3ccnc(N4CCC(C)(C(=O)O)CC4)c3)cc(-c3ccccn3)c2s1] | 517 | ((MeOD) δ 8.71 (d, J = 4.0 Hz, 1H), 8.17 (d, J = 8.1 Hz, 1H), 8.10 (d, J = 5.4 Hz, 1H), 8.06 (d, J = 1.2 Hz, 1H), 7.97-7.83 (m, 2H), 7.34 (dd, J = 7.2, 5.0 Hz, 1H), 7.10 (s, 1H), 7.00 (d, J = 5.4 Hz, 1H), 4.00 (dt, J = 13.3, 4.0 Hz, 2H), 3.39-3.33 (m, 2H), 3.27-3.16 (m, 2H), 2.25-2.16 (m, 2H), 1.59-1.49 (m, 2H), 1.31 (t, J = 7.3 Hz, 3H), 1.23 (t, J = 7.2 Hz, 3H). |
| 214 | 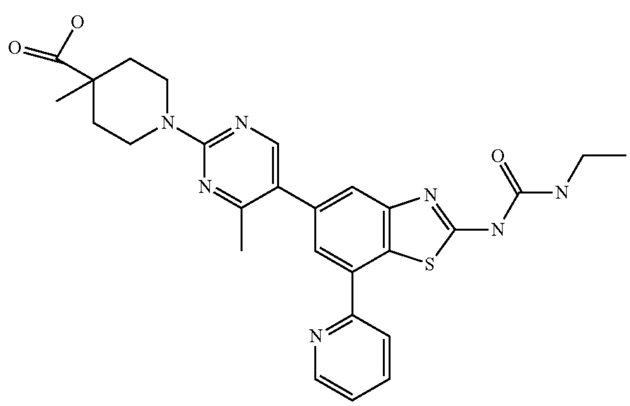 [SMILES: CCNC(=O)Nc1nc2cc(-c3cnc(N4CCC(C)(C(=O)O)CC4)nc3C)cc(-c3ccccn3)c2s1] | 532.2 | (DMSO) δ 10.56 (s, 1H), 8.83 (ddd, J = 4.9, 1.8, 0.9 Hz, 1H), 8.36 (s, 1H), 8.34 (s, 1H), 8.01-7.94 (m, 2H), 7.68 (s, 1H), 7.47-7.41 (m, 1H), 6.88 (t, J = 5.4 Hz, 1H), 4.50-4.19 (m, 2H), 2.47 (td, J = 3.8, 2.0 Hz, 4H), 2.40 (s, 2H), 2.03 (d, J = 13.6 Hz, 2H), 1.40 (t, J = 9.8 Hz, 2H), 1.22 (s, 2H), 1.13 (t, J = 7.2 Hz, 3H). |
| 220 | 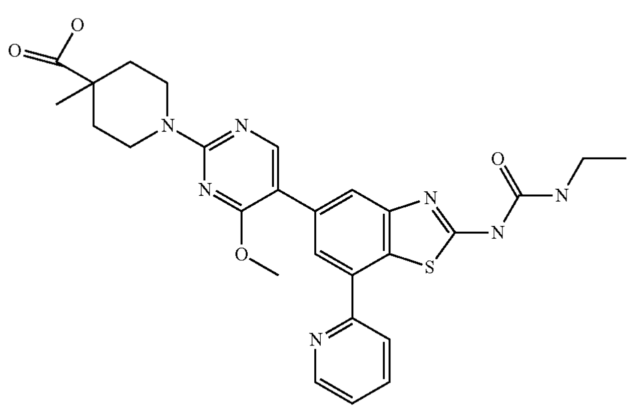 [SMILES: CCNC(=O)Nc1nc2cc(-c3cnc(N4CCC(C)(C(=O)O)CC4)nc3OC)cc(-c3ccccn3)c2s1] | 548.2 | (DMSO) δ 10.60 (s, 1H), 8.82 (ddd, J = 4.9, 1.7, 0.9 Hz, 1H), 8.41 (s, 1H), 8.31 (d, J = 8.4 Hz, 1H), 8.07 (d, J = 1.5 Hz, 1H), 8.04-7.96 (m, 1H), 7.83 (d, J = 1.5 Hz, 1H), 7.46 (ddd, J = 7.5, 4.9, 0.9 Hz, 1H), 6.96 (t, J = 5.4 Hz, 1H), 4.38-4.19 (m, 3H), 4.00 (s, 4H), 3.28-3.15 (m, 4H), 2.14-1.98 (m, 2H), 1.57-1.40 (m, 2H), 1.23 (s, 3H), 1.13 (t, J = 7.2 Hz, 3H). |

-continued

| Cpd No. | Structure | LCMS data [M + H]+ | 1H NMR data |
|---|---|---|---|
| 192 | 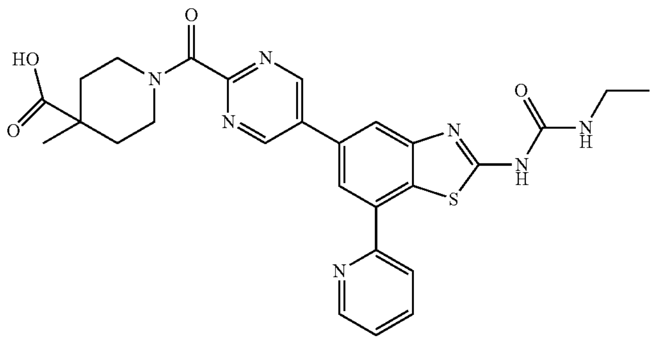 [SMILES: CCNC(=O)Nc1nc2cc(-c3cnc(C(=O)N4CCC(C)(C(=O)O)CC4)nc3)cc(-c3ccccn3)c2s1] | 546.15 | δ 12.49 (br, s, 1H), 10.69 (br s, 1H), 9.44 (s, 2H), 8.83 (d, J = 4.0 Hz, 1H), 8.55 (d, J = 8.4 Hz, 1H), 8.45 (s, 1H), 8.20 (s, 1H), 8.03 (t, J = 7.6 Hz, 1H), 7.45-7.48 (m, 1H), 6.86 (br s, 1H), 4.08-4.12 (m, 1H), 3.20-3.23 (m, 3H), 3.07-3.13 (m, 1H), 2.53 (m, 1H), 2.03-2.07 (m, 1H), 1.91-1.94 (m, 1H), 1.38-1.48 (m, 2H), 1.20 (s, 3H) and 1.11 (t, J = 7.2 Hz, 3H). |
| 222 | 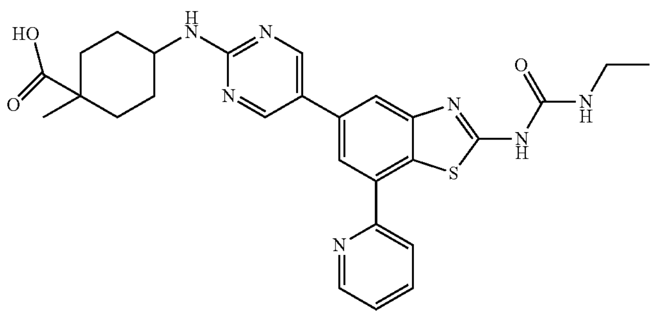 [SMILES: CCNC(=O)Nc1nc2cc(-c3cnc(NC4CCC(C)(C(=O)O)CC4)nc3)cc(-c3ccccn3)c2s1] | 532.2 | δ 12.17 (br s, 1H), 10.55 (s, 1H), 8.80-8.83 (m, 3H), 8.47 (d, J = 8.0 Hz, 1H), 8.20 (s, 1H), 7.99 (t, J = 8.0 Hz, 1H), 7.92 (s, 1H), 7.44 (t, J = 6.0 Hz, 1H), 7.28 (d, J = 8.0 Hz, 1H), 6.86 (br s, 1H), 3.74 (br s, 1H), 3.17-3.24 (m, 2H), 2.10 (d, J = 12 Hz, 2H), 1.84 (d, J = 10 Hz, 2H), 1.31-1.40 (m, 2H), 1.17-1.28 (m, 2H), 1.09-1.12 (m, 6H). |
| 218 | 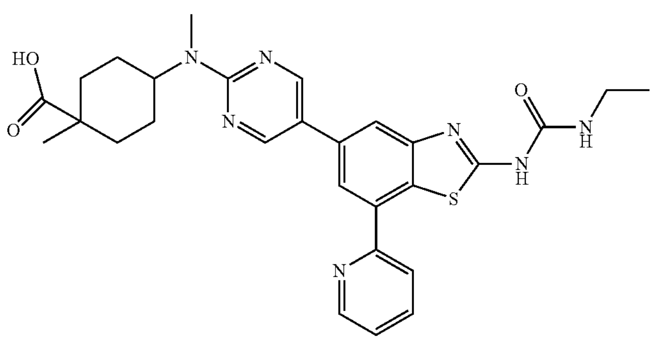 [SMILES: CCNC(=O)Nc1nc2cc(-c3cnc(N(C)C4CCC(C)(C(=O)O)CC4)nc3)cc(-c3ccccn3)c2s1] | 546.26 | δ 12.32 (br s, 1H), 10.56 (s, 1H), 8.90 (s, 2H), 8.81 (d, J = 4.4 Hz, 1H), 8.48 (d, J = 8.0 Hz, 1H), 8.22 (s, 1H), 7.99 (t, J = 8.0 Hz, 1H), 7.95 (s, 1H), 7.42-7.45 (m, 1H), 6.88 (br s, 1H), 4.68-4.71 (m, 1H), 3.19-3.24 (m, 2H), 2.98 (s, 3H), 2.16 (d, J = 12.4 Hz, 2H), 1.59-1.65 (m, 4H), 1.31-1.36 (m, 2H), 1.15 (s, 3H), 1.13 (t, J = 7.2 Hz, 3H). |
| 206 | 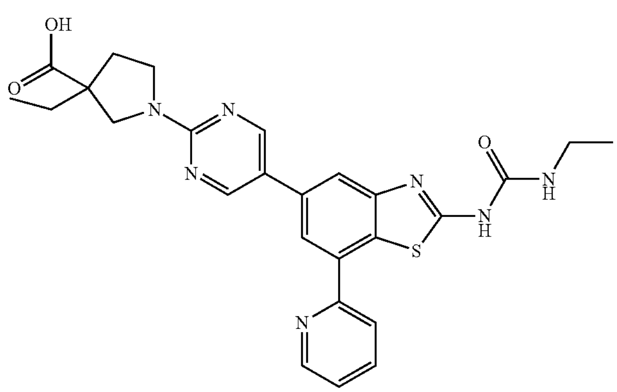 [SMILES: CCNC(=O)Nc1nc2cc(-c3cnc(N4CCC(CC)(C(=O)O)C4)nc3)cc(-c3ccccn3)c2s1] | 518.22 | δ 12.57 (br s, 1H, D2O exchangeable), 10.66 (br s, 1H, D2O exchangeable), 8.89 (s, 2H), 8.81 (m, 1H), 8.48 (d, J = 8.40 Hz, 1H), 8.22 (s, 1H), 7.95 (s, 1H), 7.99 (t, J = 7.20 Hz, 1H), 7.44 (m, 1H), 6.99 (br s, 1H, D2O exchangeable), 4.10 (t, J = 11.20 Hz, 1H), 3.68 (m, 1H), 3.53 (m, 1H), 3.37 (m, 1H), 3.22 (m, 2H), 2.40 (m, 1H), 1.95 (m, 1H), 1.76 (m, 2H), 1.11 (t, J = 7.20 Hz, 3H) and 0.90 (t, J = 7.20 Hz, 3H). |

-continued

| Cpd No. | Structure | LCMS data [M + H]⁺ | ¹H NMR data |
|---|---|---|---|
| 201 | 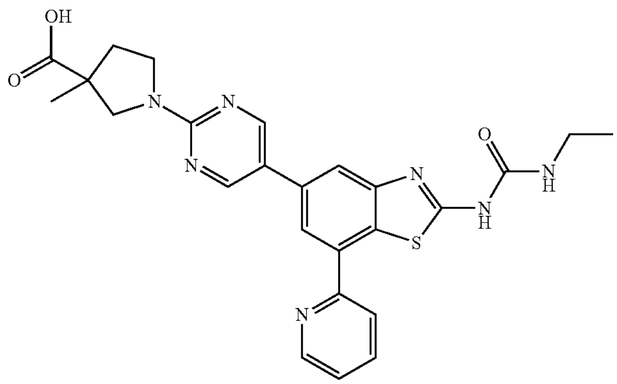 [SMILES: CCNC(=O)Nc1nc2cc(-c3cnc(N4CCC(C)(C(=O)O)C4)nc3)cc(-c3ccccn3)c2s1] | 504.19 | δ 10.74 (br s, 1H), 8.90 (s, 2H), 8.81 (m, 1H), 8.49 (d, J = 8.0 Hz, 1H), 8.22 (s, 1H), 7.99 (t, J = 8.0 Hz, 1H), 7.95 (s, 1H), 7.44 (m, 1H), 7.03 (br s, 1H), 4.04 (m, 1H), 3.58-3.65 (m, 2H), 3.22 (m, 2H), 2.38 (m, 2H), 1.90 (m, 1H), 1.34 (s, 3H) and 1.11 (t, J = 7.20 Hz, 3H). |
| 219 | 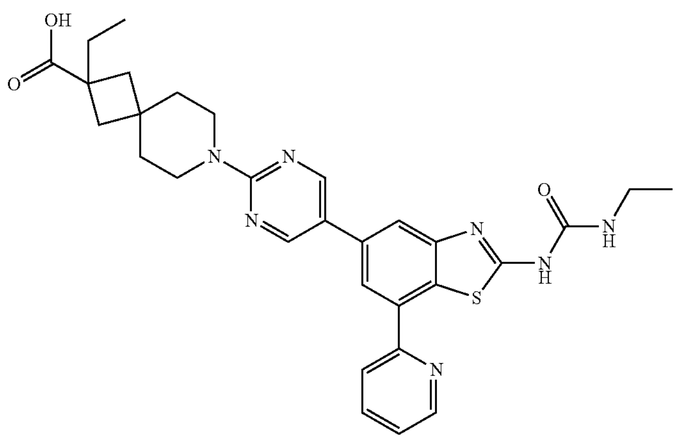 [SMILES: CCNC(=O)Nc1nc2cc(-c3cnc(N4CCC5(CC4)CC(CC)(C(=O)O)C5)nc3)cc(-c3ccccn3)c2s1] | 572.16 | δ 12.15 (br s, 1H), 10.71 (br s, 1H), 8.88 (s, 2H), 8.81 (m, 1H), 8.48 (d, J = 7.60 Hz, 1H), 8.21 (s, 1H), 7.99 (t, J = 7.20 Hz, 1H), 7.94 (s, 1H), 7.44 (m, 1H), 7.05 (br s, 1H), 3.75 (br s, 4H), 3.20 (m, 2H), 2.25 (d, J = 12.40 Hz, 2H), 1.72-1.75 (m, 4H), 1.55 (m, 4H), 1.11 (t, J = 7.20 Hz, 3H) and 0.76 (t, J = 7.60 Hz, 3H). |
| 212 | 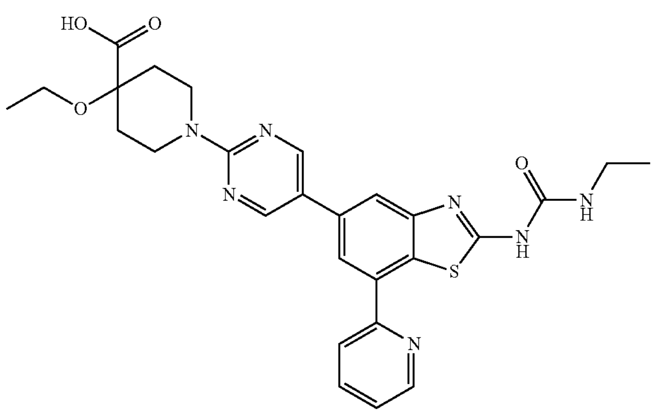 [SMILES: CCNC(=O)Nc1nc2cc(-c3cnc(N4CCC(OCC)(C(=O)O)CC4)nc3)cc(-c3ccccn3)c2s1] | 546.22 | δ 2.83 (br s, 1H), 10.56 (br s, 1H), 8.92 (s, 2H), 8.81 (d, J = 4.80 Hz, 1H), 8.49 (m, 1H), 8.24 (s, 1H), 7.97-8.01 (m, 2H), 7.44 (m, 1H), 6.86 (br s, 1H), 4.36 (m, 2H), 3.39-3.47 (m, 4H), 3.21 (m, 2H), 1.89-1.92 (m, 4H), 1.16 (t, J = 7.20 Hz, 3H) and 1.11 (t, J = 7.20 Hz, 3H). |
| 196 | 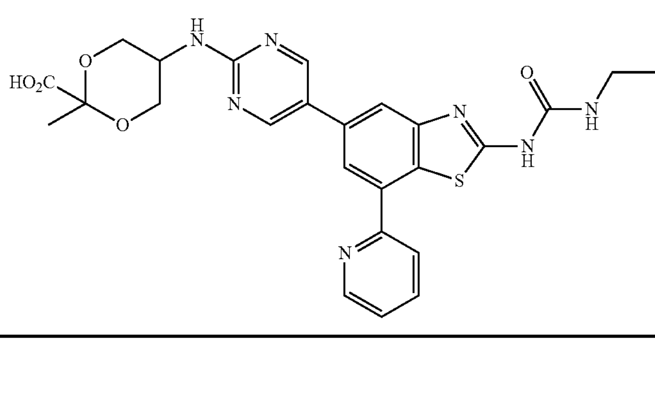 | 536.1 | (MeOD) δ 8.75 (d, J = 4.1 Hz, 1H), 8.67 (s, 2H), 8.10 (d, J = 8.1 Hz, 1H), 7.93 (d, J = 1.5 Hz, 1H), 7.89 (m, 1H), 7.82 (d, J = 1.5 Hz, 1H), 7.33 (dd, J = 6.6, 4.8 Hz, 1H), 4.21 (d, J = 11.8 Hz, 2H), 4.04-3.91 (m, 3H), 3.39-3.33 (m, 2H, partially obscured by solvent), 1.55 (s, 3H), 1.22 (t, J = 7.3 Hz, 3H). |

Compound 6: 1-[5-[2-(ethylcarbamoylamino)-7-(4-methyl-2-pyridyl)-1,3-benzothiazol-5-yl]pyrimidin-2-yl]-4-methyl-piperidine-4-carboxylic acid

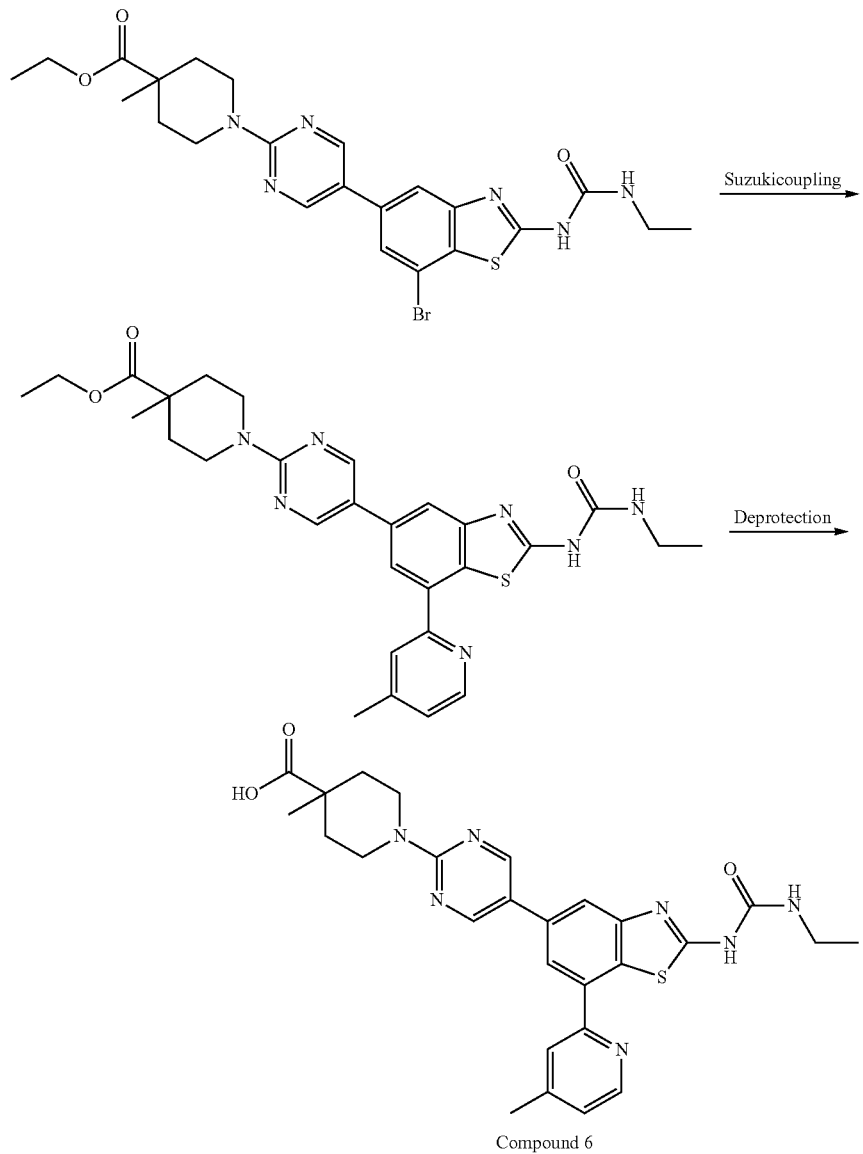

Compound 6

Ethyl 1-[5-[2-(ethylcarbamoylamino)-7-(4-methyl-2-pyridyl)-1,3-benzothiazol-5-yl]pyrimidin-2-yl]-4-methyl-piperidine-4-carboxylate: To a solution of ethyl 1-(5-(7-bromo-2-(3-ethylureido)benzothiazol-5-yl)pyrimidin-2-yl)-4-methylpiperidine-4-carboxylate (Intermediate 4) (0.5 g, 0.91 mmol) in DMSO (5 mL) was added bis(neopentylglycolato)diboron (0.41 g, 1.82 mmol) and potassium acetate (0.18 g, 1.82 mmol). The reaction was degassed by purging $N_2$ for 15 min followed by addition of dichloro(1,1-bis(diphenylphosphino)ferrocene)palladium (II) (0.07 g, 0.091 mmol) and again degassed for 10-15 min then heated up to 80° C. for 2 h. After completion of reaction (TLC as well as MS monitoring), the reaction was cooled to rt followed by addition of 2-chloro-4-methylpyridine (0.23 g, 1.37 mmol) and an aqueous solution of $Cs_2CO_3$ (0.45 g, 1.37 mmol, dissolved in minimum amount of water). The reaction was degassed by purging $N_2$ for 15 min followed by addition of tetrakis (triphenylphosphine)palladium(0) (0.11 g, 0.091 mmol) and again degassed for 10-15 min then heated up to 80° C. for 16 h. After reaction completion, 100 mL of ice-cold water was added then extracted with EtOAc (3×150 mL) and the combined organic layer was washed with brine, dried over $Na_2SO_4$, filtered and evaporated under reduced pressure. The crude residue was purified over 100-200 M silica-gel using 1.50% MeOH: DCM to obtain a beige solid, which was further purified through preperative-HPLC to obtain the desired product as an off-white solid (0.016 g, 3%).

1-[5-[2-(Ethylcarbamoylamino)-7-(4-methyl-2-pyridyl)-1,3-benzothiazol-5-yl]pyrimidin-2-yl]-4-methyl-piperidine-4-carboxylic acid (6): To an ice-cold solution of ethyl 1-(5-(2-(3-ethylureido)-7-(4-methylpyridin-2-yl)benzothiazol-5-yl)pyrimidin-2-yl)-4-methylpiperidine-4-carboxylate (0.015 g, 0.026 mmol) in THF was added aqueous LiOH (0.006 g, 0.134 mmol dissolved in minimum amount of $H_2O$) and the mixture heated up to 65° C. for 3 h. After reaction completion (by TLC), the solvent was concentrated and 10 mL of water added and washed with EtOAc (2×50 mL). The organic layer was discarded and the pH of the aqueous layer was adjusted up to 4-5 then extracted with hot EtOAc (3×50 mL) and the combined organic layer dried over $Na_2SO_4$ and solvent evaporated under reduced pressure. The residue thus obtained was triturated with ether to afford the desired product as an off-white solid (0.005 g, 35%). $^1$H NMR (DMSO-$d_6$): δ 1.11 (t, J=7.20 Hz, 3H), 1.19 (s, 3H), 1.41 (m, 2H), 2.07 (m, 2H), 2.45 (s, 3H), 3.17-3.24 (m, 4H), 4.32 (m, 2H), 6.93 (br s, 1H), 7.27 (d, J=4.80, 1H), 7.94 (s, 1H), 8.23 (s, 1H), 8.35 (s, 1H), 8.65 (d, J=4.8 Hz, 1H), 8.91 (s, 2H) and 10.60 (br s, 1H). MS: 530.21 [M−H]$^-$.

The following compounds were similarly prepared.

| Cpd No. | Structure | LCMS data [M + H]$^+$ | $^1$H NMR data |
|---|---|---|---|
| 8 | 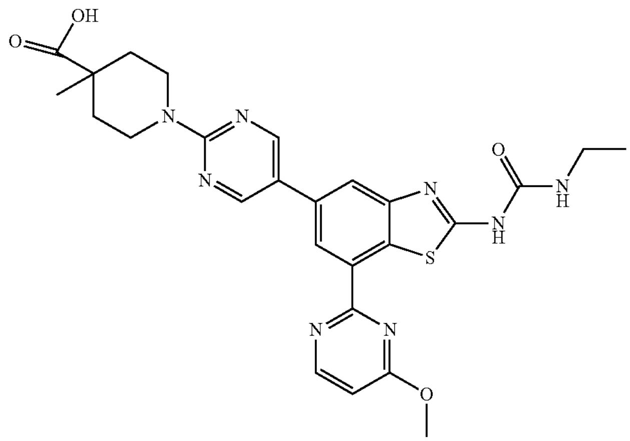 [SMILES: CCNC(=O)Nc1nc2cc(-c3cnc(N4CCC(C)(C(=O)O)CC4)nc3)cc(-c3nccc(OC)n3)c2s1] | 549.14 | δ 1.09 (t, J = 7.20 Hz, 3H), 1.19 (s, 3H), 1.40 (m, 2H), 2.0 (m, 2H), 3.21 (m, 2H), 3.37 (m, 2H), 4.19 (s, 3H), 4.28 (m, 2H), 6.82 (br s, 1H), 6.97 (d, J = 6.0 Hz, 1H), 8.04 (s, 1H), 8.58 (s, 1H), 8.75 (d, J = 6.0 Hz, 1H), 8.81 (s, 2H), 10.62 (br s, 1H) and 12.45 (br s, 1H). |
| 10 | 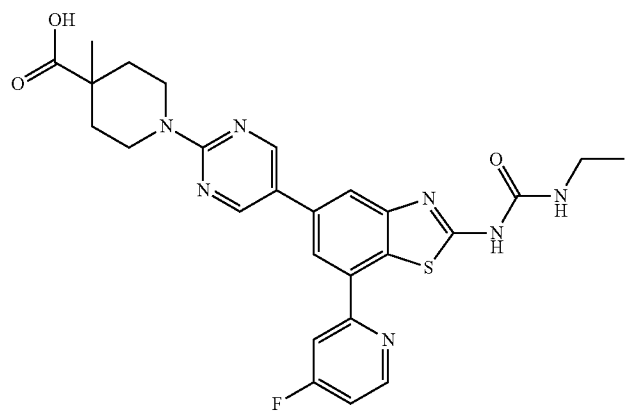 [SMILES: CCNC(=O)Nc1nc2cc(-c3cnc(N4CCC(C)(C(=O)O)CC4)nc3)cc(-c3cc(F)ccn3)c2s1] | 536.33 | δ 1.09 (t, J = 7.20 Hz, 3H), 1.19 (s, 3H), 1.40 (m, 2H), 2.0 (m, 2H), 3.20 (m, 2H), 4.28 (m, 2H), 4.28 (m, 2H), 6.94 (br s, 1H), 7.40 (m, 1H), 8.0 (s, 1H), 8.29 (s, 1H), 8.50 (m, 1H), 8.85 (m, 1H), 8.93 (s, 2H), 10.63 (br s, 1H) and 12.46 (br s, 1H). |
| 11 | 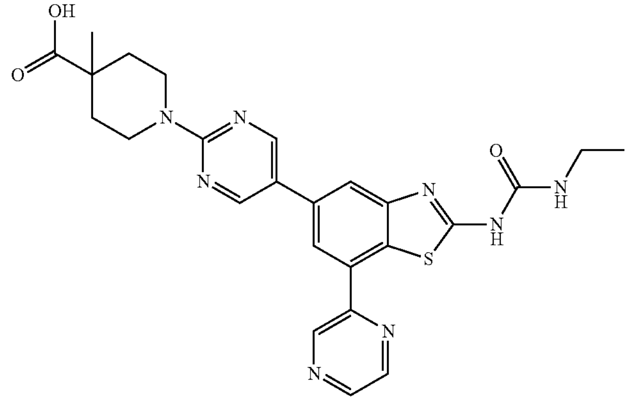 [SMILES: CCNC(=O)Nc1nc2cc(-c3cnc(N4CCC(C)(C(=O)O)CC4)nc3)cc(-c3cnccn3)c2s1] | 517.13 [M − H]$^-$ | δ 1.11 (t, J = 7.20 Hz, 3H), 1.19 (s, 3H), 1.40 (m, 2H), 2.0 (m, 2H), 3.20 (m, 2H), 3.38 (m, 2H), 4.31 (m, 2H), 6.92 (br s, 1H), 8.03 (s, 1H), 8.40 (s, 1H), 8.68 (d, J = 2.40 Hz, 1H), 8.87 (s, 1H), 8.94 (s, 2H), 9.76 (s, 1H), 10.71 (br s, 1H) and 12.47 (br s, 1H). |

-continued

| Cpd No. | Structure | LCMS data [M + H]+ | 1H NMR data |
|---|---|---|---|
| 12 | 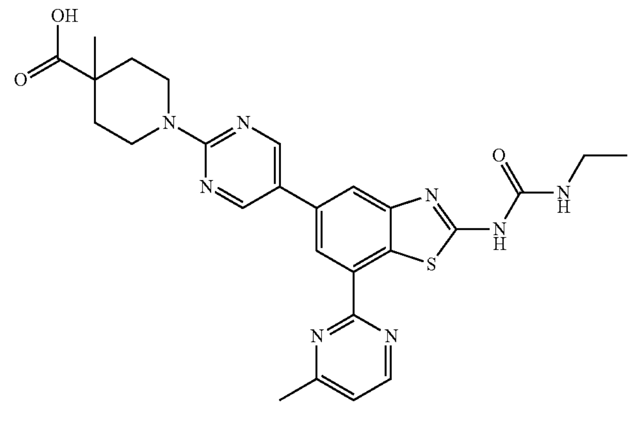 [SMILES: CCNC(=O)Nc1nc2cc(-c3cnc(N4CCC(C)(C(=O)O)CC4)nc3)cc(-c3nccc(C)n3)c2s1] | 533.13 | δ 1.11 (t, J = 7.20 Hz, 3H), 1.19 (s, 3H), 1.40 (m, 2H), 2.0 (m, 2H), 2.64 (s, 3H), 3.20 (m, 2H), 3.33 (m, 2H), 4.29 (m, 2H), 6.85 (br s, 1H), 7.42 (d, J = 5.20 Hz, 1H), 8.03 (s, 1H), 8.57 (d, J = 1.60 Hz, 1H), 8.80 (s, 2H), 8.90 (d, J = 4.80 Hz, 1H), 10.62 (br s, 1H) and 12.41 (br s, 1H). |
| 15 | 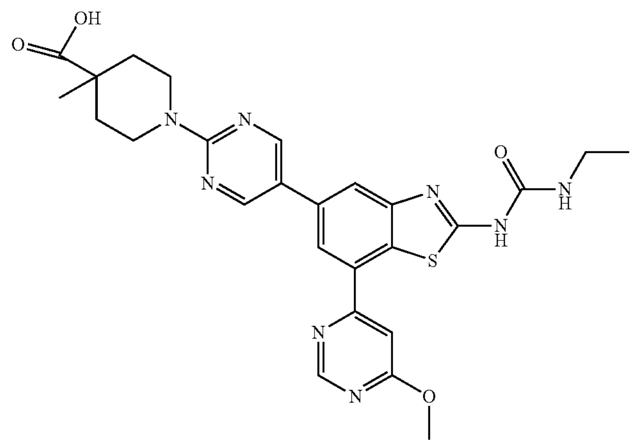 [SMILES: CCNC(=O)Nc1nc2cc(-c3cnc(N4CCC(C)(C(=O)O)CC4)nc3)cc(-c3cc(OC)ncn3)c2s1] | 549.30 | δ 1.10 (t, J = 7.20 Hz, 3H), 1.16 (s, 3H), 1.34 (m, 2H), 2.0 (m, 2H), 3.20 (m, 2H), 3.33 (m, 2H), 4.02 (s, 3H), 4.29 (m, 2H), 7.18 (br s, 1H, D2O exchangeable), 7.98 (s, 1H), 8.03 (s, 1H), 8.31 (s, 1H), 8.91 (s, 2H), 9.02 (s, 1H) and 10.47 (br s, 1H, D2O exchangeable). |
| 99 | 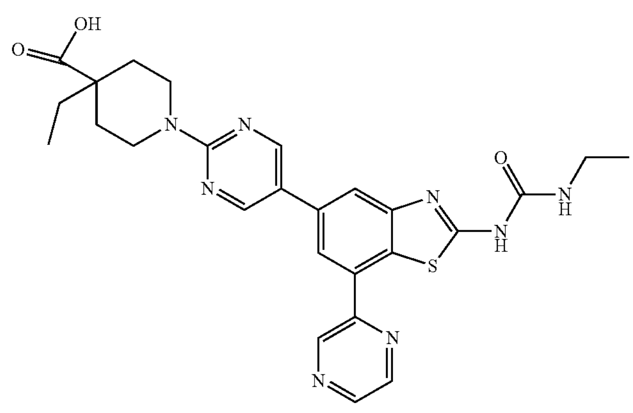 [SMILES: CCNC(=O)Nc1nc2cc(-c3cnc(N4CCC(CC)(C(=O)O)CC4)nc3)cc(-c3cnccn3)c2s1] | 533.27 | δ 0.83 (t, 7.20 Hz, 3H), 1.11 (t, J = 7.20 Hz, 3H), 1.35 (m, 2H), 1.55 (m, 2H), 2.05 (m, 2H), 3.13-3.24 (m, 4H), 4.50 (m, 2H), 6.86 (br s, 1H), 8.03 (s, 1H), 8.40 (s, 1H), 8.68 (d, J = 2.40 Hz, 1H), 8.87 (s, 1H), 8.94 (s, 2H), 9.76 (s, 1H), 10.68 (br s, 1H) and 12.50 (br s, 1H). |

| Cpd No. | Structure | LCMS data [M + H]+ | ¹H NMR data |
|---|---|---|---|
| 100 | 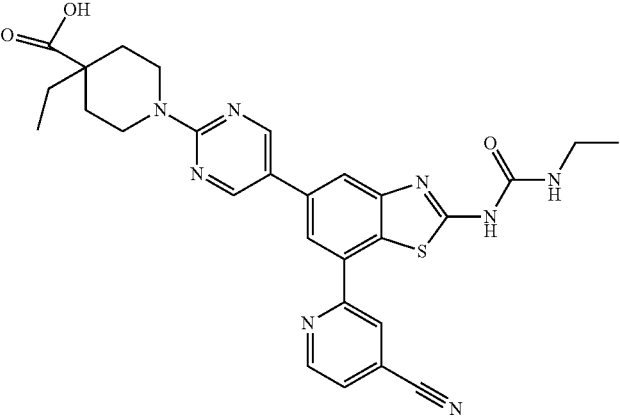 [SMILES: CCNC(=O)Nc1nc2cc(-c3cnc(N4CCC(CC)(C(=O)O)CC4)nc3)cc(-c3cc(C#N)ccn3)c2s1] | 555.34 [M − H]⁻ | δ 0.83 (t, 7.20 Hz, 3H), 1.11 (t, J = 7.20 Hz, 3H), 1.36 (m, 2H), 1.55 (m, 2H), 2.05 (m, 2H), 3.14-3.22 (m, 4H), 4.50 (m, 2H), 6.83 (br s, 1H), 7.89 (dd, J = 0.80 and 5.20 Hz, 1H), 8.03 (s, 1H), 8.41 (s, 1H), 8.96 (s, 2H), 9.05 (d, J = 5.20 Hz, 1H), 9.09 (s, 1H), 10.61 (br s, 1H) and 12.49 (br s, 1H). |
| 101 | 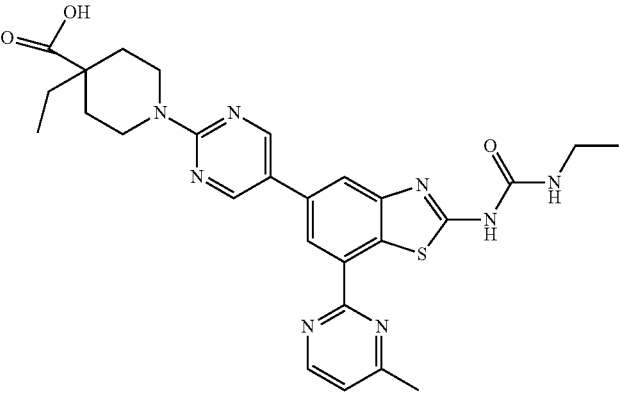 [SMILES: CCNC(=O)Nc1nc2cc(-c3cnc(N4CCC(CC)(C(=O)O)CC4)nc3)cc(-c3nccc(C)n3)c2s1] | 547.24 | δ 0.83 (t, J = 7.20 Hz, 3H), 1.09 (t, J = 7.20 Hz, 3H), 1.35 (m, 2H), 1.54 (m, 2H), 2.04 (m, 2H), 2.64 (s, 3H), 3.12-3.23 (m, 4H), 4.49 (m, 2H), 6.84 (br s, 1H), 7.42 (d, J = 4.80 Hz, 1H), 8.03 (s, 1H), 8.57 (d, J = 1.60 Hz, 1H), 8.79 (s, 2H), 8.90 (d, J = 5.20 Hz, 1H), 10.62 (br s, 1H) and 12.50 (br s, 1H). |
| 102 | 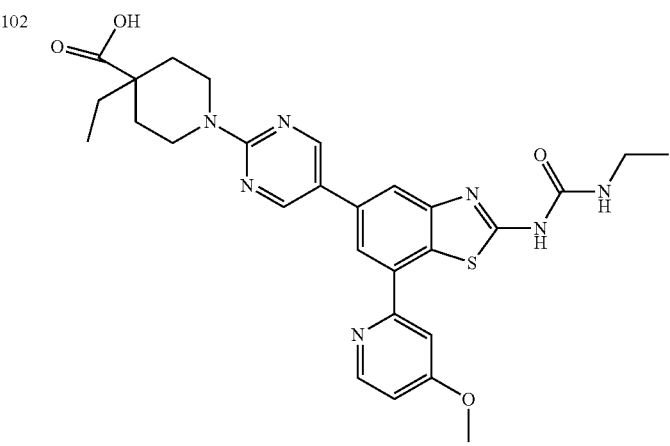 | 562.33 | δ 0.83 (t, J = 7.20 Hz, 3H), 1.09 (t, J = 7.20 Hz, 3H), 1.35 (m, 2H), 1.54 (m, 2H), 2.04 (m, 2H), 3.13-3.22 (m, 4H), 3.97 (s, 3H), 4.49 (m, 2H), 6.90 (br s, 1H), 7.02 (d, J = 5.20 Hz, 1H), 7.96 (m, 2H), 8.22 (s, 1H), 8.59 (m, 1H), 8.91 (s, 2H), 10.54 (br s, 1H) and 12.50 (br s, 1H). |

-continued

| Cpd No. | Structure | LCMS data [M + H]+ | 1H NMR data |
|---|---|---|---|
| 103 | 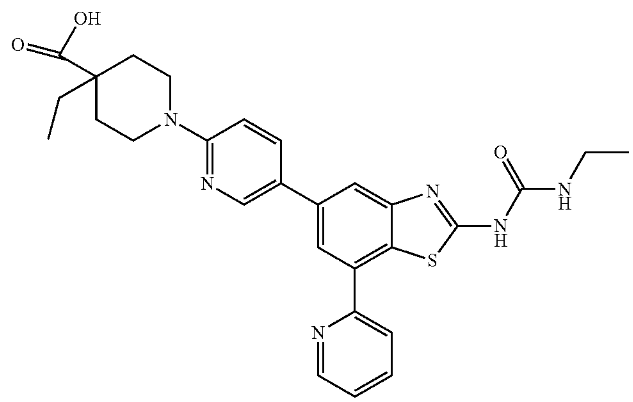 [SMILES: CCNC(=O)Nc1nc2cc(-c3ccc(N4CCC(CC)(C(=O)O)CC4)nc3)cc(-c3ccccn3)c2s1] | 531.16 | δ 0.83 (t, J = 7.20 Hz, 3H), 1.09 (t, J = 7.20 Hz, 3H), 1.36 (m, 2H), 1.54 (m, 2H), 2.04 (m, 2H), 3.04 (m, 2H), 3.21 (m, 2H), 4.12 (m, 2H), 6.86 (br s, 1H), 6.94 (d, J = 8.80 Hz, 1H), 7.45 (m, 1H), 7.91 (s, 1H), 7.96-8.0 (m, 1H), 8.06 (d, J = 2.40 and 8.80 Hz, 1H), 8.19 (s, 1H), 8.45 (d, J = 8.40 Hz, 1H), 8.65 (d, J = 2.80 Hz, 1H), 8.80 (m, 1H), 10.54 (br s, 1H) and 12.45 (br s, 1H). |
| 104 | 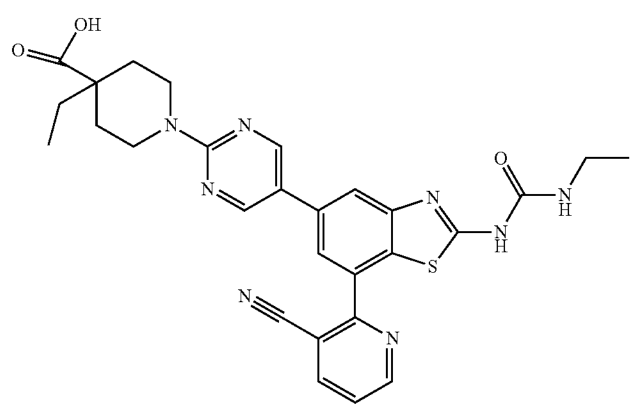 [SMILES: CCNC(=O)Nc1nc2cc(-c3cnc(N4CCC(CC)(C(=O)O)CC4)nc3)cc(-c3ncccc3C#N)c2s1] | 557.16 | δ 0.81 (t, J = 7.20 Hz, 3H), 1.09 (t, J = 7.20 Hz, 3H), 1.33 (m, 2H), 1.52 (m, 2H), 2.04 (m, 2H), 3.12-3.21 (m, 4H), 4.49 (m, 2H), 7.02 (br s, 1H), 7.70 (m, 1H), 8.05 (s, 1H), 8.24 (s, 1H), 8.55 (dd, J = 1.60 and 8.0 Hz, 1H), 8.81 (s, 2H) and 9.05 (m, 1H). |
| 105 | 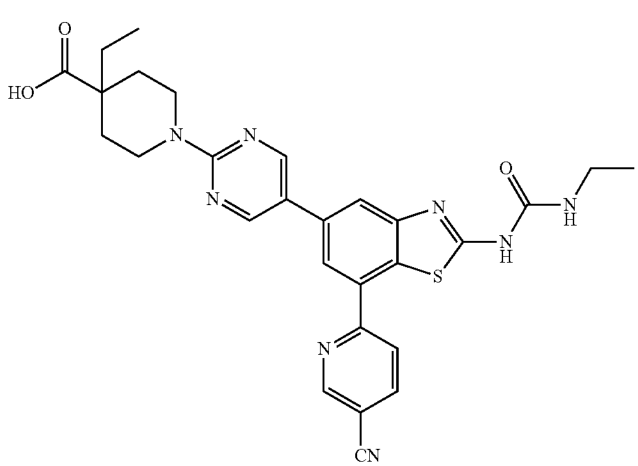 [SMILES: CCNC(=O)Nc1nc2cc(-c3cnc(N4CCC(CC)(C(=O)O)CC4)nc3)cc(-c3ccc(C#N)cn3)c2s1] | 557.16 | δ 0.82 (t, J = 7.20 Hz, 3H), 1.09 (t, J = 7.20 Hz, 3H), 1.23 (m, 2H), 1.49 (m, 2H), 2.07 (m, 2H), 3.19-3.24 (m, 4H), 4.49 (m, 2H), 7.10 (br s, 1H), 7.95 (m, 1H), 8.02 (s, 1H), 8.32 (m, 1H), 8.49 (m 1H), 8.70 (m, 1H), 8.89 (s, 2H) and 9.23 (m, 1H). |

-continued

| Cpd No. | Structure | LCMS data [M + H]+ | 1H NMR data |
|---|---|---|---|
| 106 | 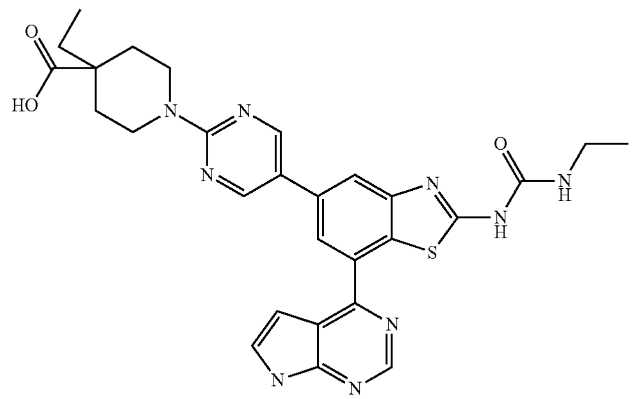 [SMILES: CCNC(=O)Nc1nc2cc(-c3cnc(N4CCC(CC)(C(=O)O)CC4)nc3)cc(-c3ncnc4[nH]ccc34)c2s1] | 572.19 | δ 0.81 (t, J = 6.80 Hz, 3H), 1.09 (t, J = 7.20 Hz, 3H), 1.36 (m, 2H), 1.55 (m, 2H), 2.05 (m, 2H), 3.13-3.21 (m, 4H), 4.50 (m, 2H), 6.87 (br s, 1H), 7.14 (br s, 1H), 7.73 (m, 1H), 8.03 (s, 1H), 8.26 (s, 1H), 8.87 (s 2H), 8.97 (s, 1H), 10.65 (br s, 1H), 12.43 (br s, 1H) and 12.50 (br s, 1H). |
| 109 | 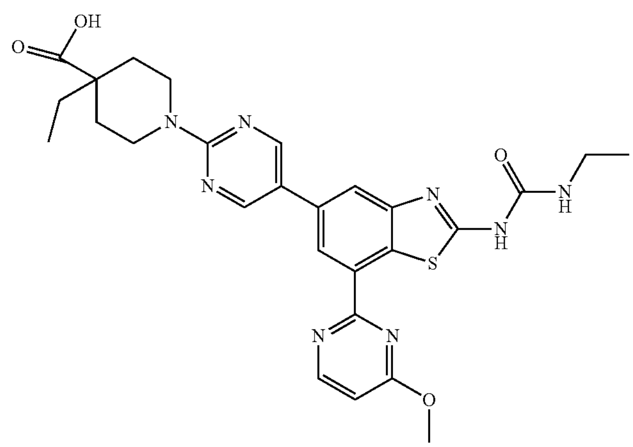 [SMILES: CCNC(=O)Nc1nc2cc(-c3cnc(N4CCC(CC)(C(=O)O)CC4)nc3)cc(-c3nccc(OC)n3)c2s1] | 563.20 | δ 0.81 (t, J = 6.80 Hz, 3H), 1.09 (t, J = 7.20 Hz, 3H), 1.35 (m, 2H), 1.50 (m, 2H), 2.08 (m, 2H), 3.13-3.24 (m, 4H), 4.18 (s, 3H), 4.49 (m, 2H), 6.92 (br s, 1H), 6.95 (d, J = 5.60 Hz, 1H), 8.04 (s, 1H), 8.58 (s, 1H), 8.75 (d, J = 5.60 Hz, 1H), 8.81 (s, 2H) and 10.71 (br s, 1H). |
| 110 | 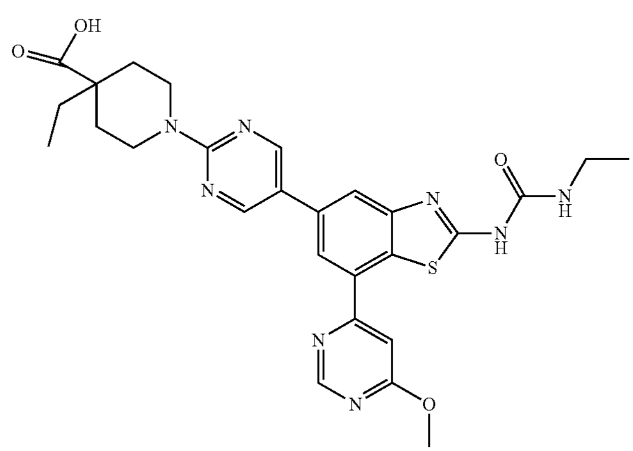 | 563.20 | δ 0.81 (t, J = 6.80 Hz, 3H), 1.11 (t, J = 7.20 Hz, 3H), 1.34 (m, 2H), 1.52 (m, 2H), 2.08 (m, 2H), 3.13-3.22 (m, 4H), 4.03 (s, 3H), 4.49 (m, 2H), 7.01 (br s, 1H), 7.99 (s, 1H), 8.04 (s, 1H), 8.32 (s, 1H), 8.92 (s, 2H) and 9.02 (s, 1H). |

-continued

| Cpd No. | Structure | LCMS data [M + H]⁺ | ¹H NMR data |
|---|---|---|---|
| 111 | 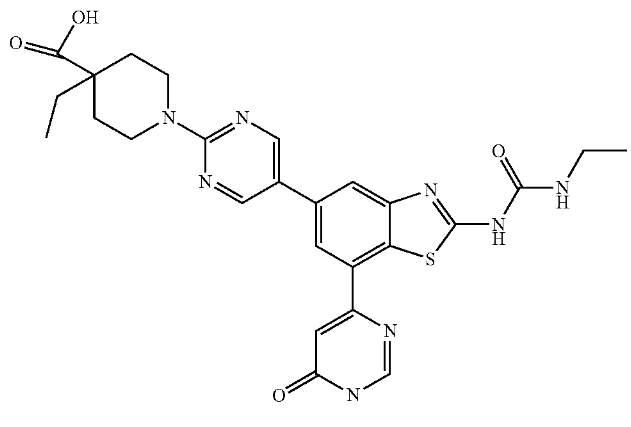 [SMILES: CCNC(=O)Nc1nc2cc(-c3cnc(N4CCC(CC)(C(=O)O)CC4)nc3)cc(-c3cc(=O)[nH]cn3)c2s1] | 547.20 | δ 0.81 (t, J = 7.60 Hz, 3H), 1.10 (t, J = 7.20 Hz, 3H), 1.32 (m, 2H), 1.52 (m, 2H), 2.08 (m, 2H), 3.13-3.19 (m, 4H), 4.49 (m, 2H), 6.93 (br s, 1H), 7.33 (s, 1H), 7.97 (s, 1H), 8.10 (s, 1H), 8.45 (s, 1H) and 8.88 (s, 2H). |
| 112 | 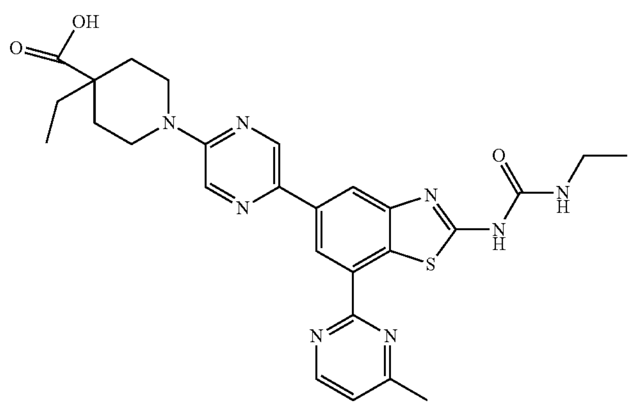 [SMILES: CCNC(=O)Nc1nc2cc(-c3cnc(N4CCC(CC)(C(=O)O)CC4)cn3)cc(-c3nccc(C)n3)c2s1] | 547.17 | δ 0.82 (t, J = 7.60 Hz, 3H), 1.10 (t, J = 7.20 Hz, 3H), 1.40 (m, 2H), 1.54 (m, 2H), 2.07 (m, 2H), 2.65 (s, 3H), 3.11 (m, 2H), 3.22 (m, 2H), 4.17 (m, 2H), 6.84 (br s, 1H), 7.40 (d, J = 4.80 Hz, 1H), 8.32 (s, 1H), 8.46 (s, 1H), 8.81 (s, 1H), 8.90 (d, J = 5.20 Hz, 1H), 9.07 (s, 1H), 10.60 (br s, 1H) and 12.50 (br s, 1H). |
| 118 | 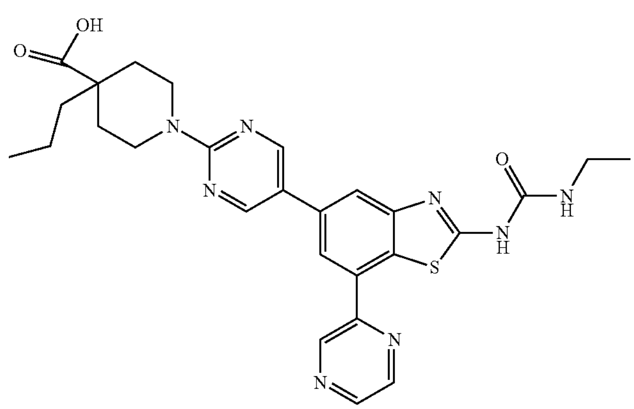 [SMILES: CCCC1(C(=O)O)CCN(c2ncc(-c3cc(-c4cnccn4)c4sc(NC(=O)NCC)nc4c3)cn2)CC1] | 547.18 | δ 0.87 (t, J = 7.60 Hz, 3H), 1.09 (t, J = 7.20 Hz, 3H), 1.20 (m, 2H), 1.37 (m, 2H), 1.49 (m, 2H), 2.08 (m, 2H), 3.13-3.24 (m, 4H), 4.46 (m, 2H), 6.83 (br s, 1H), 8.03 (s, 1H), 8.40 (s, 1H), 8.69 (d, J = 2.40 Hz, 1H), 8.87 (s, 1H), 8.94 (s, 2H), 9.77 (s, 1H), 10.66 (br s, 1H) and 12.55 (br s, 1H). |

-continued

| Cpd No. | Structure | LCMS data [M + H]+ | ¹H NMR data |
|---|---|---|---|
| 120 | 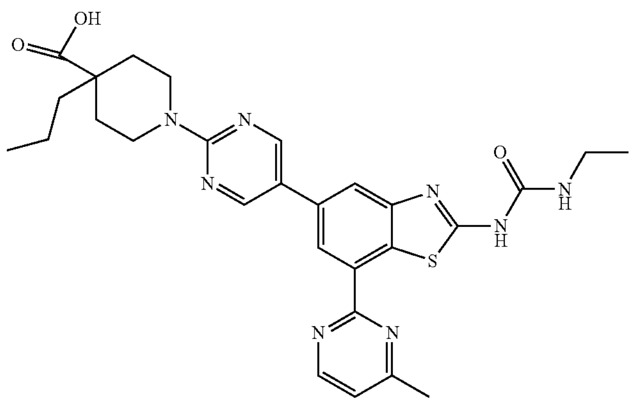 [SMILES: CCCC1(C(=O)O)CCN(c2ncc(-c3cc(-c4nccc(C)n4)c4sc(NC(=O)NCC)nc4c3)cn2)CC1] | 561.10 | δ 0.84 (t, J = 6.80 Hz, 3H), 1.09 (t, J = 7.20 Hz, 3H), 1.20-1.40 (m, 4H), 1.45 (m, 2H), 2.09 (m, 2H), 2.63 (s, 3H), 3.17-3.24 (m, 4H), 4.48 (m, 2H), 7.06 (br s, 1H), 7.41 (m, 1H), 8.01 (s, 1H), 8.55 (br s, 1H), 8.77 (s, 2H) and 8.89 (m, 1H). |
| 121 | 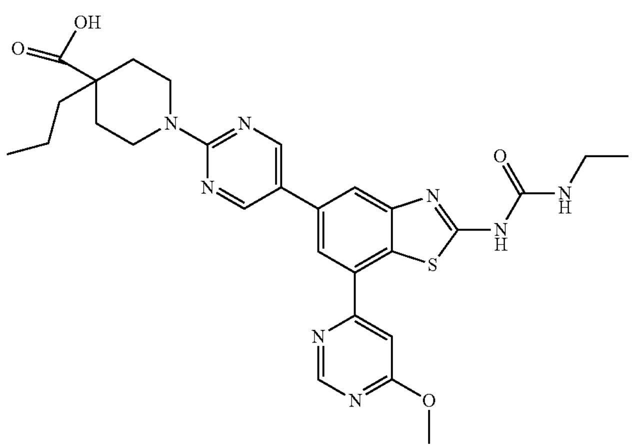 [SMILES: CCCC1(C(=O)O)CCN(c2ncc(-c3cc(-c4cc(OC)ncn4)c4sc(NC(=O)NCC)nc4c3)cn2)CC1] | 577.10 | δ 0.86 (t, J = 7.20 Hz, 3H), 1.09 (t, J = 7.20 Hz, 3H), 1.23 (m, 2H), 1.37 (m, 2H), 1.47 (m, 2H), 2.08 (m, 2H), 3.12-3.22 (m, 4H), 4.03 (s, 3H), 4.48 (m, 2H), 6.83 (br s, 1H), 8.0 (s, 1H), 8.04 (s, 1H), 8.34 (s, 1H), 8.92 (s, 2H), 9.03 (s, 1H), 10.61 (br s, 1H) and 12.49 (br s, 1H). |
| 122 | 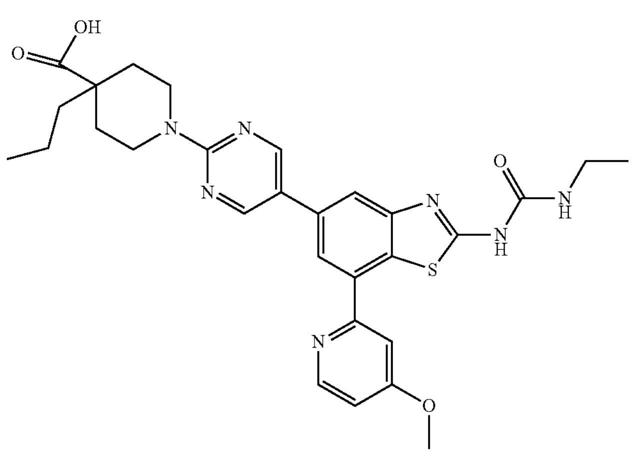 [SMILES: CCCC1(C(=O)O)CCN(c2ncc(-c3cc(-c4cc(OC)ccn4)c4sc(NC(=O)NCC)nc4c3)cn2)CC1] | 576.10 | δ 0.86 (t, J = 7.20 Hz, 3H), 1.09 (t, J = 7.20 Hz, 3H), 1.23 (m, 2H), 1.37 (m, 2H), 1.47 (m, 2H), 2.08 (m, 2H), 3.10-3.20 (m, 4H), 3.95 (s, 3H), 4.42 (m, 2H), 6.88 (br s, 1H), 7.04 (m, 1H), 7.99 (m, 2H), 8.22 (s, 1H), 8.60 (d, J = 6.0 Hz, 1H), 8.92 (s, 2H), 10.54 (br s, 1H) and 12.53 (br s, 1H). |

-continued

| Cpd No. | Structure | LCMS data [M + H]⁺ | ¹H NMR data |
|---|---|---|---|
| 123 | 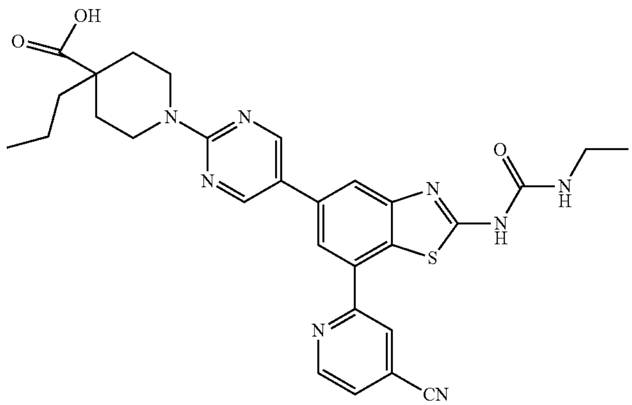 [SMILES: CCCC1(C(=O)O)CCN(c2ncc(-c3cc(-c4cc(C#N)ccn4)c4sc(NC(=O)NCC)nc4c3)cn2)CC1] | 571.16 | δ 0.86 (t, J = 7.20 Hz, 3H), 1.09 (t, J = 7.20 Hz, 3H), 1.23 (m, 2H), 1.38 (m, 2H), 1.46 (m, 2H), 2.08 (m, 2H), 3.20 (m, 4H), 4.49 (m, 2H), 6.84 (br s, 1H), 7.88 (m, 1H), 8.04 (s, 1H), 8.41 (s, 1H), 8.95 (s, 2H), 9.05 (m, 1H), 9.08 (s, 1H), 10.61 (br s, 1H) and 12.45 (br s, 1H). |
| 124 | 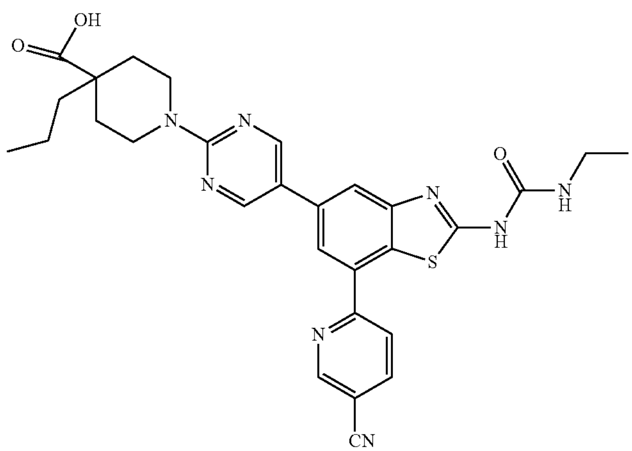 [SMILES: CCCC1(C(=O)O)CCN(c2ncc(-c3cc(-c4ccc(C#N)cn4)c4sc(NC(=O)NCC)nc4c3)cn2)CC1] | 569.20 [M − H]⁻ | δ 0.85 (t, J = 6.80 Hz, 3H), 1.09 (t, J = 7.20 Hz, 3H), 1.23 (m, 2H), 1.37 (m, 2H), 1.45 (m, 2H), 2.08 (m, 2H), 3.12-3.24 (m, 4H), 4.49 (m, 2H), 6.86 (br s, 1H), 8.05 (s, 1H), 8.36 (s, 1H), 8.50 (m, 1H), 8.74 (m, 1H), 8.92 (s, 2H), 9.25 (s, 1H), 10.66 (br s, 1H) and 12.51 (br s, 1H). |
| 125 | 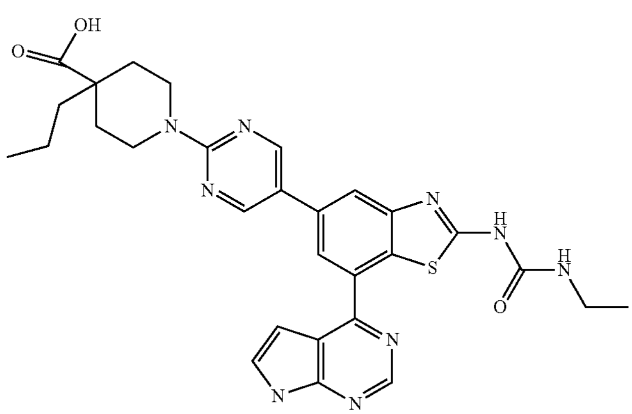 [SMILES: CCCC1(C(=O)O)CCN(c2ncc(-c3cc(-c4ncnc5[nH]ccc45)c4sc(NC(=O)NCC)nc4c3)cn2)CC1] | 586.30 | δ 0.86 (t, J = 7.20 Hz, 3H), 1.09 (t, J = 7.20 Hz, 3H), 1.20 (m, 2H), 1.40 (m, 2H), 1.50 (m, 2H), 2.08 (m, 2H), 3.13-3.22 (m, 4H), 4.50 (m, 2H), 6.87 (br s, 1H), 7.14 (m, 1H), 7.74 (m, 1H), 8.03 (s, 1H), 8.25 (s, 1H), 8.87 (s, 2H), 8.97 (s, 1H), 10.65 (br s, 1H) and 12.48 (br s, 1H). |

-continued

| Cpd No. | Structure | LCMS data [M + H]+ | 1H NMR data |
|---|---|---|---|
| 126 | 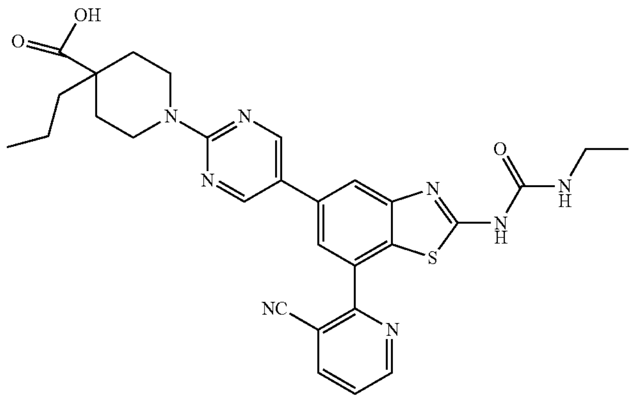 [SMILES: CCCC1(C(=O)O)CCN(c2ncc(-c3cc(-c4ncccc4C#N)c4sc(NC(=O)NCC)nc4c3)cn2)CC1] | 571.14 | δ 0.87 (t, J = 7.20 Hz, 3H), 1.09 (t, J = 7.20 Hz, 3H), 1.20 (m, 2H), 1.36 (m, 2H), 1.48 (m, 2H), 2.08 (m, 2H), 3.11-3.21 (m, 4H), 4.48 (m, 2H), 6.80 (br s, 1H), 7.70 (m, 1H), 8.06 (s, 1H), 8.24 (s, 1H), 8.55 (dd, J = 1.60 and 8.0 Hz, 1H), 8.81 (s, 2H), 9.05 (m, 1H), 10.73 (br s, 1H) and 12.47 (br s, 1H). |
| 127 | 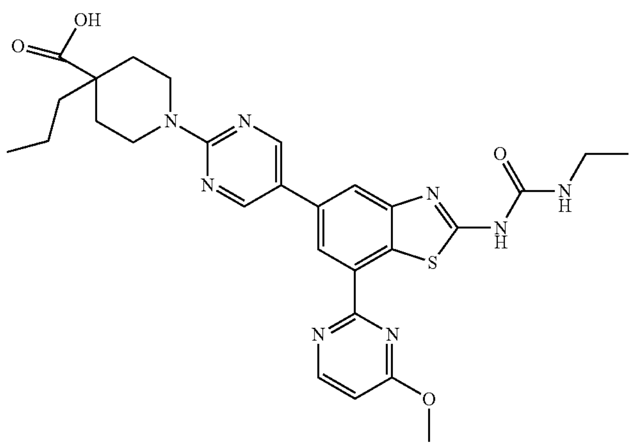 [SMILES: CCCC1(C(=O)O)CCN(c2ncc(-c3cc(-c4nccc(OC)n4)c4sc(NC(=O)NCC)nc4c3)cn2)CC1] | 577.16 | δ 0.85 (t, J = 7.60 Hz, 3H), 1.09 (t, J = 7.20 Hz, 3H), 1.22 (m, 2H), 1.45 (m, 2H), 1.49 (m, 2H), 2.08 (m, 2H), 3.12-3.24 (m, 4H), 4.18 (s, 3H), 4.45 (m, 2H), 6.83 (br s, 1H), 6.95 (d, J = 6.0 Hz, 1H), 8.04 (s, 1H), 8.58 (d, J = 1.20 Hz, 1H), 8.75 (d, J = 5.60 Hz, 1H), 8.81 (s, 2H), 10.63 (br s, 1H) and 12.49 (br s, 1H). |
| 7 | 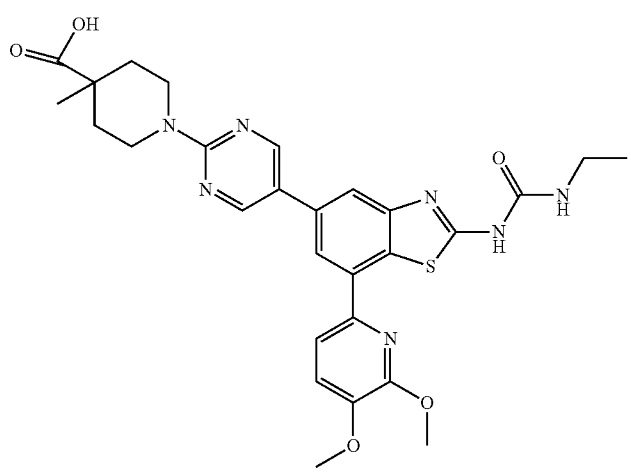 [SMILES: CCNC(=O)Nc1nc2cc(-c3cnc(N4CCC(C)(C(=O)O)CC4)nc3)cc(-c3ccc(OC)c(OC)n3)c2s1] | 578.12 | (DMSO-d$_6$): δ 1.11 (t, J = 7.20 Hz, 3H), 1.19 (s, 3H), 1.39 (m, 2H), 2.07 (m, 2H), 3.20 (q, J = 6.80, 2H), 3.33 (m, 2H), 3.87 (s, 3H), 4.18 (s, 3H), 4.28 (m, 2H), 6.86 (br s, 1H), 7.46 (d, J = 8.0 Hz, 1H), 7.86 (s, 1H), 7.99 (d, J = 8.40 Hz, 1H), 8.06 (s, 1H), 8.87 (s, 2H), 10.57 (br s, 1H) and 12.40 (br s, 1H). |

-continued

| Cpd No. | Structure | LCMS data [M + H]+ | 1H NMR data |
|---|---|---|---|
| 13 | 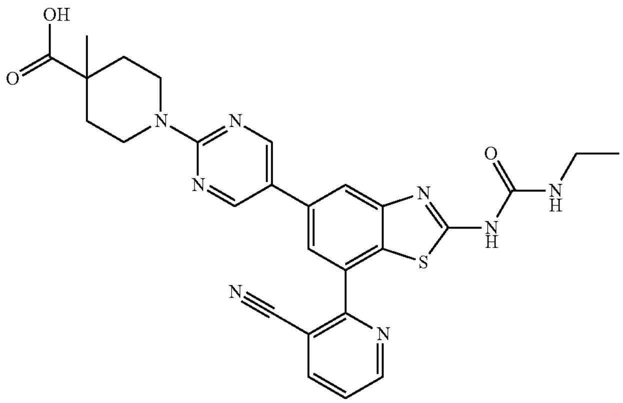 [SMILES: CCNC(=O)Nc1nc2cc(-c3cnc(N4CCC(C)(C(=O)O)CC4)nc3)cc(-c3ncccc3C#N)c2s1] | 543.12 | (DMSO-d6 + D2O): δ 1.09 (t, J = 7.20 Hz, 3H), 1.18 (s, 3H), 1.35 (m, 2H), 2.0 (m, 2H), 3.17 (q, J = 7.20, 2H), 3.30 (m, 2H), 3.87 (s, 3H), 4.25 (m, 2H), 7.66 (m, 1H), 8.01 (s, 1H), 8.20 (s, 1H), 8.51 (m, 1H), 8.76 (s, 2H) and 9.01 (d, J = 3.60 Hz, 1H). |
| 14 | 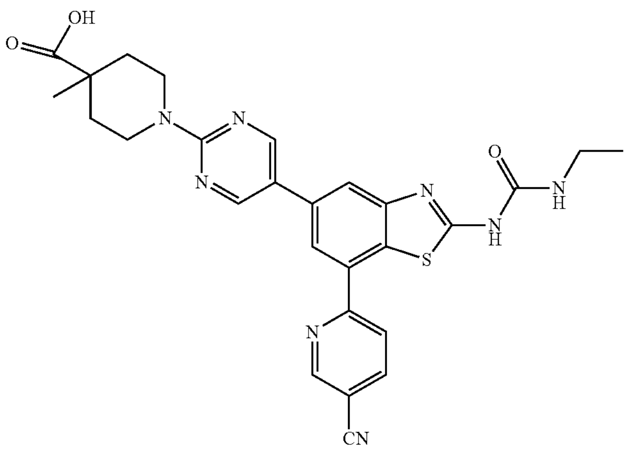 [SMILES: CCNC(=O)Nc1nc2cc(-c3cnc(N4CCC(C)(C(=O)O)CC4)nc3)cc(-c3ccc(C#N)cn3)c2s1] | 543.36 | δ 1.11 (t, J = 7.20 Hz, 3H), 1.18 (s, 3H), 1.42 (m, 2H), 2.0 (m, 2H), 3.20 (m, 2H), 3.35 (m, 2H), 4.32 (m, 2H), 6.90 (br s, 1H), 8.05 (s, 1H), 8.36 (s, 1H), 8.49 (m, 1H), 8.71 (m, 1H), 8.92 (s, 2H) and 9.25 (br s, 1H). |
| 16 | 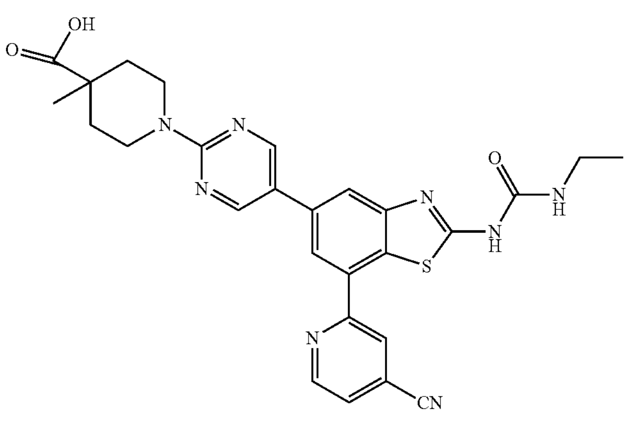 [SMILES: CCNC(=O)Nc1nc2cc(-c3cnc(N4CCC(C)(C(=O)O)CC4)nc3)cc(-c3cc(C#N)ccn3)c2s1] | 541.53 [M − H]− | (DMSO-D2O): δ 1.08 (t, J = 7.20 Hz, 3H), 1.17 (s, 3H), 1.30 (m, 2H), 2.0 (m, 2H), 3.20 (m, 2H), 3.34 (m, 2H), 4.24 (m, 2H), 7.77 (d, J = 4.80 Hz, 1H), 7.93 (s, 1H), 8.27 (s, 1H), 8.83 (s, 2H), 8.91 (s, 1H) and 8.95 (d, J = 5.20 Hz, 1H). |

| Cpd No. | Structure | LCMS data [M + H]+ | 1H NMR data |
|---|---|---|---|
| 17 | 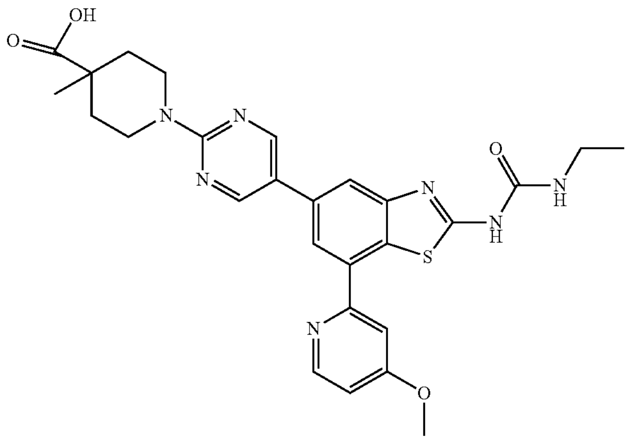 [SMILES: CCNC(=O)Nc1nc2cc(-c3cnc(N4CCC(C)(C(=O)O)CC4)nc3)cc(-c3cc(OC)ccn3)c2s1] | 548.15 | (DMSO-D2O): δ 1.09 (t, J = 7.20 Hz, 3H), 1.17 (s, 3H), 1.37 (m, 2H), 2.0 (m, 2H), 3.20 (m, 2H), 3.34 (m, 2H), 3.95 (s, 3H), 4.24 (m, 2H), 7.05 (d, J = 4.40 Hz, 1H), 7.88 (s, 1H), 7.91 (s, 1H), 8.13 (s, 1H), 8.59 (d, J = 6.0 Hz, 1H) and 8.84 (s, 2H). |
| 18 | 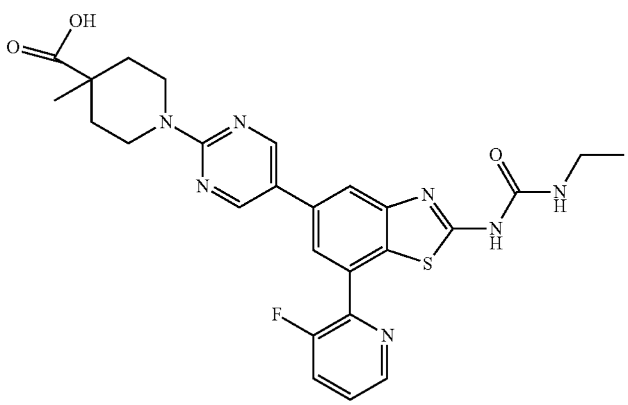 [SMILES: CCNC(=O)Nc1nc2cc(-c3cnc(N4CCC(C)(C(=O)O)CC4)nc3)cc(-c3ncccc3F)c2s1] | 534.22 [M − H]− | (DMSO-D2O): δ 1.09 (m, 6H), 1.25 (m, 2H), 2.0 (m, 2H), 3.20 (d, J = 6.80 Hz, 2H), 3.29 (m, 2H), 4.24 (m, 2H), 7.85-7.88 (m, 2H), 8.10 (s, 1H), 8.48 (m, 1H), 8.74 (d, J = 2.80 Hz, 1H) and 8.80 (s, 2H). |
| 42 | 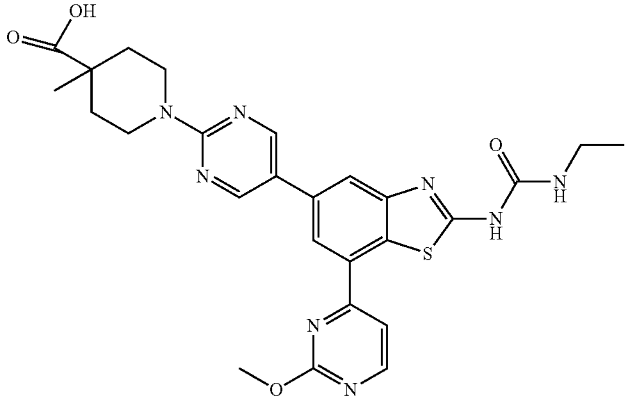 [SMILES: CCNC(=O)Nc1nc2cc(-c3cnc(N4CCC(C)(C(=O)O)CC4)nc3)cc(-c3ccnc(OC)n3)c2s1] | 549.08 | δ 1.11 (t, J = 7.20 Hz, 3H), 1.20 (s, 3H), 1.40 (m, 2H), 2.0 (m, 2H), 3.20 (m, 2H), 3.35 (m, 2H), 4.16 (s, 3H), 4.31 (m, 2H), 6.82 (br s, 1H), 8.08 (s, 1H), 8.18 (d, J = 5.20 Hz, 1H), 8.35 (s, 1H), 8.75 (d, J = 4.80 Hz, 1H), 8.91 (s, 2H), 10.62 (br s, 1H) and 12.42 (br s, 1H). |

-continued

| Cpd No. | Structure | LCMS data [M + H]+ | 1H NMR data |
|---|---|---|---|
| 43 | 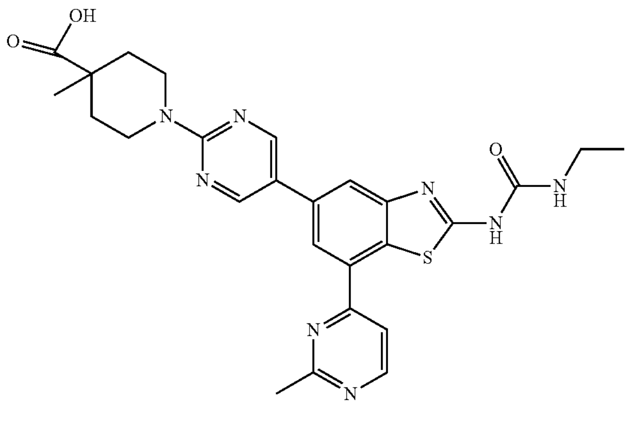 [SMILES: CCNC(=O)Nc1nc2cc(-c3cnc(N4CCC(C)(C(=O)O)CC4)nc3)cc(-c3ccnc(C)n3)c2s1] | 533.14 | δ 1.11 (t, J = 7.20 Hz, 3H), 1.19 (s, 3H), 1.40 (m, 2H), 2.0 (m, 2H), 2.64 (s, 3H), 3.23 (d, J = 6.80 Hz, 2H), 3.35 (m, 2H), 4.28 (m, 2H), 6.84 (br s, 1H), 7.40 (d, J = 5.20 Hz, 1H), 8.02 (s, 1H), 8.57 (s, 1H), 8.79 (s, 2H), 8.90 (d, J = 4.80 Hz, 1H), 10.60 (br s, 1H) and 12.44 (br s, 1H). |
| 44 | 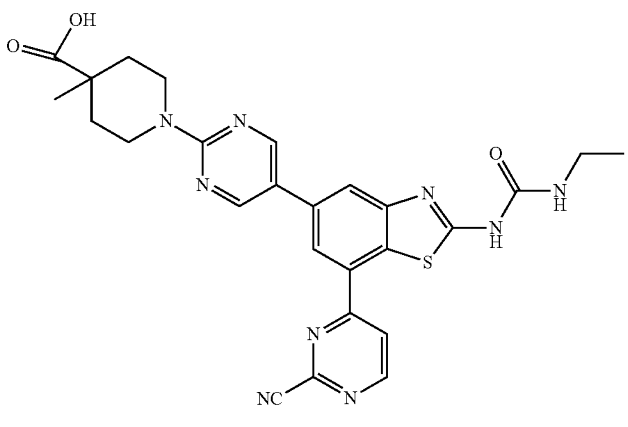 [SMILES: CCNC(=O)Nc1nc2cc(-c3cnc(N4CCC(C)(C(=O)O)CC4)nc3)cc(-c3ccnc(C#N)n3)c2s1] | 542.16 [M − H]− | (DMSO-D$_2$O): δ 1.05-1.12 (m, 6H), 1.22 (m, 2H), 2.03 (m, 2H), 3.14-3.39 (m, 4H), 4.29 (m, 2H), 8.01 (s, 1H), 8.27 (s, 1H), 8.73 (d, J = 5.60 Hz, 1H), 8.78 (s, 2H) and 9.04 (d, J = 5.20 Hz, 1H). |
| 45 | 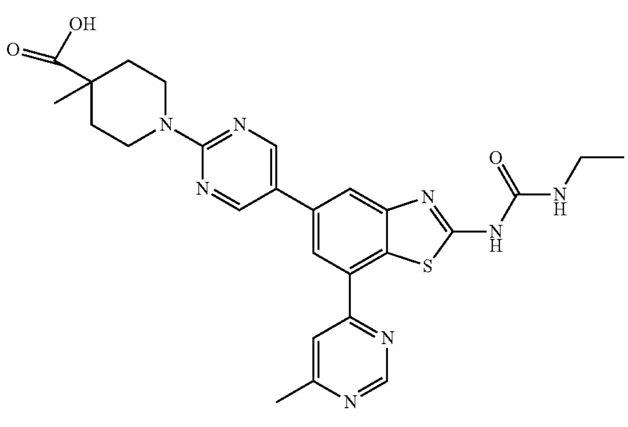 [SMILES: CCNC(=O)Nc1nc2cc(-c3cnc(N4CCC(C)(C(=O)O)CC4)nc3)cc(-c3cc(C)ncn3)c2s1] | 533.13 | δ 1.11 (t, J = 7.20 Hz, 3H), 1.19 (s, 3H), 1.40 (m, 2H), 2.0 (m, 2H), 2.59 (s, 3H), 3.20 (m, 2H), 3.35 (m, 2H), 4.28 (m, 2H), 6.87 (br s, 1H), 8.07 (s, 1H), 8.37 (s, 1H), 8.50 (s, 1H), 8.93 (s, 2H), 9.25 (s, 1H), 10.65 (br s, 1H) and 12.43 (br s, 1H). |

| Cpd No. | Structure | LCMS data [M + H]+ | ¹H NMR data |
|---|---|---|---|
| 73 | 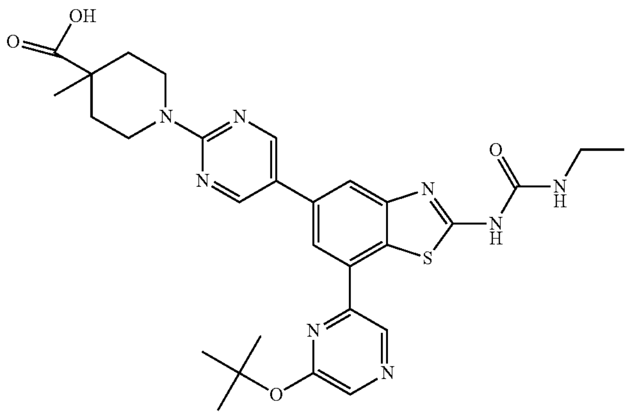 [SMILES: CCNC(=O)Nc1nc2cc(-c3cnc(N4CCC(C)(C(=O)O)CC4)nc3)cc(-c3cncc(OC(C)(C)C)n3)c2s1] | 589.30 [M − H]⁻ | (DMSO-D₂O): δ 1.09 (t, J = 7.20 Hz, 3H), 1.18 (s, 3H), 1.30 (m, 2H), 1.65 (s, 9H), 2.01 (m, 2H), 3.18 (q, J = 7.20 Hz, 2H), 3.35 (m, 2H), 4.22 (m, 2H), 7.92 (s, 1H), 8.06 (s, 1H), 8.13 (s, 1Hz, 1H), 8.78 (s, 2H) and 8.99 (s, 1H). |
| 63 | 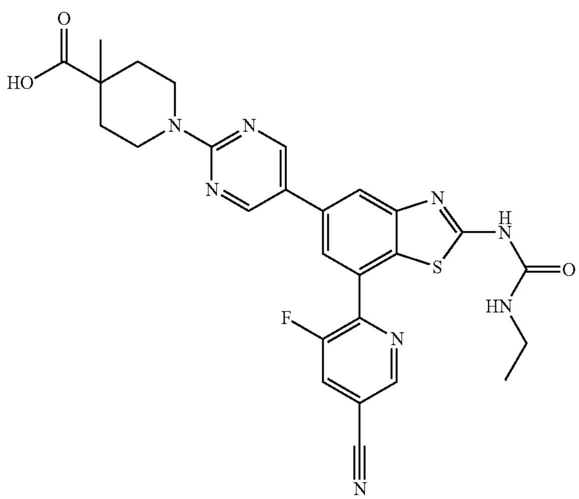 [SMILES: CCNC(=O)Nc1nc2cc(-c3cnc(N4CCC(C)(C(=O)O)CC4)nc3)cc(-c3ncc(C#N)cc3F)c2s1] | 561 | (DMSO-d₆): δ 12.47 (1H, s), 10.82 (1H, s), 9.16 (1H, d, J = 2.81 Hz), 8.83 (2H, s), 8.73 (1H, dd, J = 8.52, 2.83 Hz), 8.21 (1H, d, J = 1.65 Hz), 8.08 (1H, d, J = 1.63 Hz), 6.86 (1H, t, J = 5.51 Hz), 4.34 (2H, dt, J = 13.68, 4.33 Hz), 3.49-3.30 (1H, m), 3.22 (2H, p, J = 6.69 Hz), 2.05 (2H, d, J = 13.28 Hz), 1.43 (2H, ddd, J = 13.31, 10.10, 3.83 Hz), 1.22 (3H, s), 1.13 (3H, t, J = 7.17 Hz). |
| 64 | 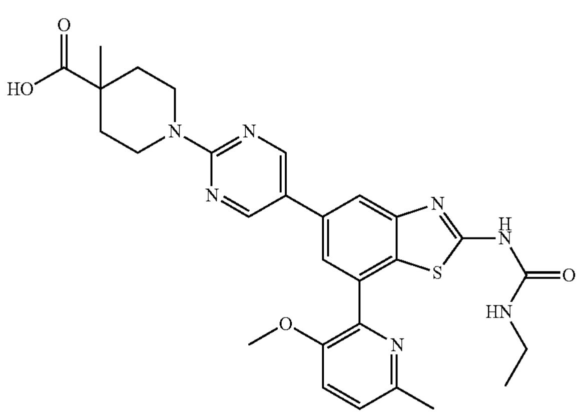 [SMILES: CCNC(=O)Nc1nc2cc(-c3cnc(N4CCC(C)(C(=O)O)CC4)nc3)cc(-c3nc(C)ccc3OC)c2s1] | 562 | (DMSO-d₆): δ 12.47 (1H, s), 10.57 (1H, s), 8.79 (2H, s), 8.34 (1H, d, J = 1.70 Hz), 7.91 (1H, d, J = 1.68 Hz), 7.63 (1H, d, J = 8.51 Hz), 7.34 (1H, d, J = 8.45 Hz), 6.95 (1H, t, J = 5.59 Hz), 4.33 (2H, dt, J = 13.72, 4.45 Hz), 3.96 (3H, s), 3.38 (2H, ddd, J = 13.34, 9.00, 3.23 Hz), 3.24 (2H, p, J = 6.36 Hz), 2.60 (3H, s), 2.06 (2H, dt, J = 13.55, 3.67 Hz), 1.43 (2H, ddd, J = 13.41, 10.09, 3.89 Hz), 1.23 (3H, s), 1.14 (3H, t, J = 7.18 Hz). |

-continued

| Cpd No. | Structure | LCMS data [M + H]+ | 1H NMR data |
|---|---|---|---|
| 65 | 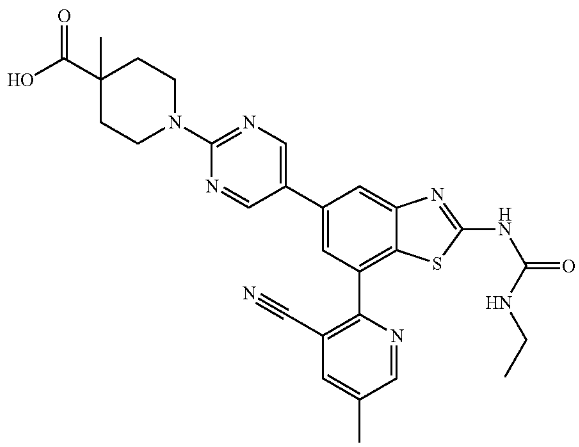 [SMILES: CCNC(=O)Nc1nc2cc(-c3cnc(N4CCC(C)(C(=O)O)CC4)nc3)cc(-c3ncc(C)cc3C#N)c2s1] | 557 | (DMSO-d6): δ 12.47 (1H, s), 10.77 (1H, s), 8.93(1H, d, J = 2.05 Hz), 8.83 (2H, s), 8.41 (1H, d, J = 2.05 Hz), 8.22 (1H, d, J = 1.58 Hz), 8.06 (1H, d, J = 1.57 Hz), 6.87 (1H, t, J = 5.63 Hz), 4.34 (2H, dt, J = 13.73, 4.46 Hz), 3.51-3.29 (2H, m), 3.22 (2H, p, J = 6.68 Hz), 2.48 (3H, s), 2.05 (2H, dt, J = 13.58, 3.67 Hz), 1.43 (2H, ddd, J = 13.43, 10.12, 3.88 Hz), 1.22 (3H, s), 1.13 (3H, t, J = 7.18 Hz). |
| 68 | 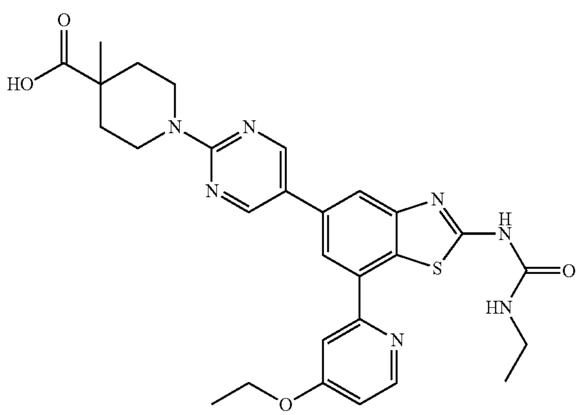 [SMILES: CCNC(=O)Nc1nc2cc(-c3cnc(N4CCC(C)(C(=O)O)CC4)nc3)cc(-c3cc(OCC)ccn3)c2s1] | 562 | (DMSO-d6): δ 8.95 (2H, s), 8.62 (1H, d, J = 5.71 Hz), 8.25 (1H, d, J = 1.61 Hz), 7.98 (1H, d, J = 2.25 Hz), 7.97 (1H, d, J = 1.53 Hz), 7.07 (1H, t, J = 4.86 Hz), 7.04 (1H, dd, J = 5.74, 2.23 Hz), 4.37-4.28 (4H, m), 3.39 (2H, dt, J = 14.44, 5.28 Hz), 3.24 (2H, p, J = 6.77 Hz), 2.07 (2H, dt, J = 13.57, 3.76 Hz), 1.44 (3H, t, J = 6.94 Hz), 1.23 (3H, s), 1.15 (3H, t, J = 7.17 Hz). |
| 69 | 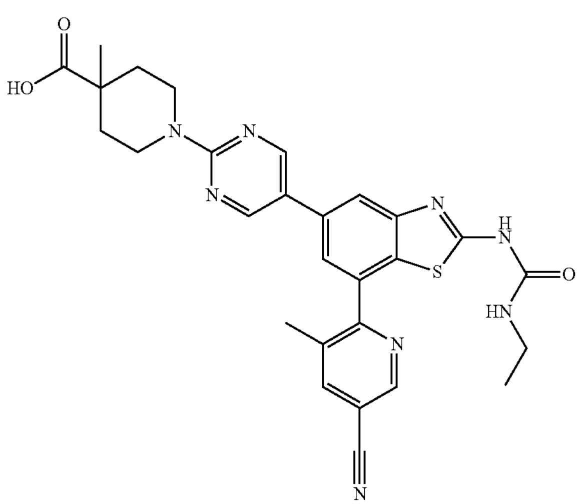 | 557 | (DMS0-d6): δ 9.07 (1H, d, J = 1.96 Hz), 8.83 (2H, s), 8.45 (1H, d, J = 1.97 Hz), 8.01 (1H, d, J = 1.58 Hz), 7.74 (1H, d, J = 1.61 Hz), 7.18 (1H, s), 4.32 (2H, dt, J = 13.65, 4.44 Hz), 3.38 (2H, ddd, J = 13.67, 10.30, 3.53 Hz), 3.20 (2H, p, J = 6.70 Hz), 2.51 (3H, s), 2.06 (2H, dt, J = 13.45, 3.64 Hz), 1.40 (2H, ddd, J = 13.31, 10.04, 3.83 Hz), 1.21 (3H, s), 1.11 (3H, t, J = 7.16 Hz). |

-continued

| Cpd No. | Structure | LCMS data [M + H]+ | ¹H NMR data |
|---|---|---|---|
| 70 | 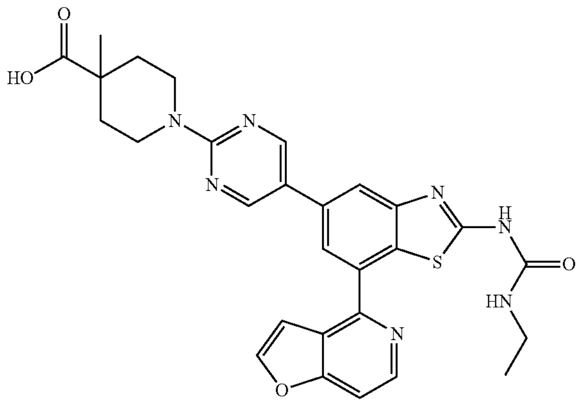 [SMILES: CCNC(=O)Nc1nc2cc(-c3cnc(N4CCC(C)(C(=O)O)CC4)nc3)cc(-c3nccc4occc34)c2s1] | 558 | (DMSO-d₆): δ 10.79 (1H, s), 8.92 (2H, s), 8.73 (1H, d, J = 5.62 Hz), 8.31 (1H, d, J = 2.35 Hz), 8.09 (1H, d, J = 1.71 Hz), 8.01 (1H, d, J = 1.72 Hz), 7.82 (1H, dd, J = 5.63, 1.01 Hz), 7.67 (1H, d, J = 2.31 Hz), 7.04 (1H, t, J = 5.47 Hz), 4.35 (2H, dt, J = 13.67, 4.35 Hz), 3.39 (2H, t, J = 12.61 Hz), 3.24 (2H, p, J = 6.67 Hz), 2.07 (2H, dt, J = 13.50, 3.70 Hz), 1.43 (2H, ddd, J = 13.19, 9.96, 3.80 Hz), 1.23 (3H, s), 1.15 (3H, t, J = 7.14 Hz). |
| 81 | 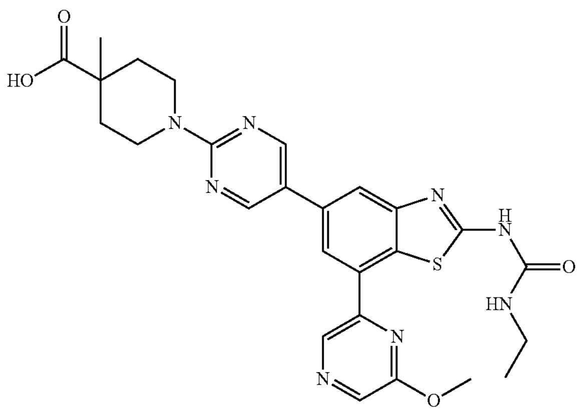 [SMILES: CCNC(=O)Nc1nc2cc(-c3cnc(N4CCC(C)(C(=O)O)CC4)nc3)cc(-c3cncc(OC)n3)c2s1] | 549 | (DMSO-d₆): δ 10.97 (1H, s), 9.34 (1H, s), 8.95 (2H, s), 8.37 (1H, s), 8.36 (1H, d, J = 1.55 Hz), 8.04 (1H, d, J = 1.51 Hz), 7.17 (1H, s), 4.34 (2H, dt, J = 13.65, 4.52 Hz), 4.25 (3H, s), 3.64-3.24 (2H, m), 3.24 (2H, p, J = 6.84 Hz), 2.08 (2H, dt, J = 13.50, 3.84 Hz), 1.40 (2H, ddd, J = 12.89, 8.38, 3.05 Hz), 1.21 (3H, s), 1.14 (3H, t, J = 7.18 Hz). |
| 82 | 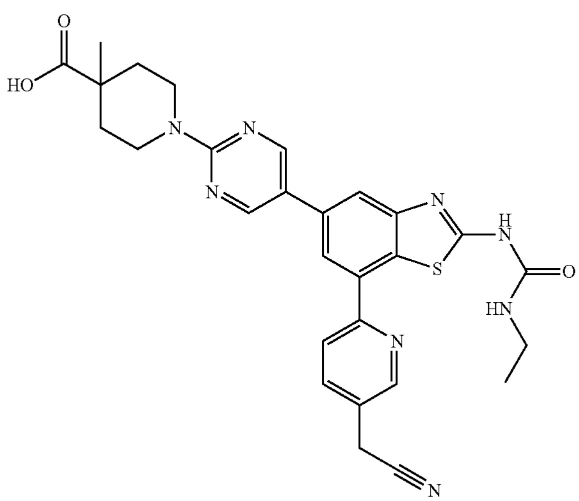 [SMILES: CCNC(=O)Nc1nc2cc(-c3cnc(N4CCC(C)(C(=O)O)CC4)nc3)cc(-c3ccc(CC#N)cn3)c2s1] | 557 | (DMSO-d₆): δ 12.50 (1H, s), 10.68 (1H, s), 8.94 (2H, s), 8.81 (1H, d, J = 2.17 Hz), 8.55 (1H, d, J = 8.42 Hz), 8.27 (1H, d, J = 1.61 Hz), 8.02 (1H, dd, J = 8.26, 2.38 Hz), 8.00 (1H, d, J = 1.44 Hz), 6.99 (1H, t, J = 5.66 Hz), 4.34 (2H, dt, J = 13.70, 4.50 Hz), 4.23 (2H, s), 3.48-3.33 (2H, m), 3.25 (2H, p, J = 6.71 Hz), 2.06 (2H, dt, J = 13.51, 3.74 Hz), 1.44 (2H, ddd, J = 13.39, 9.99, 3.91 Hz), 1.23 (3H, s), 1.15 (3H, t, J = 7.18 Hz). |

-continued

| Cpd No. | Structure | LCMS data [M + H]+ | 1H NMR data |
|---|---|---|---|
| 83 | 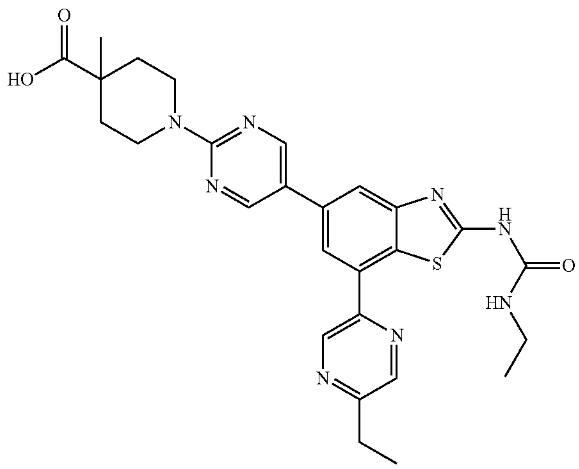 [SMILES: CCNC(=O)Nc1nc2cc(-c3cnc(N4CCC(C)(C(=O)O)CC4)nc3)cc(-c3cnc(CC)cn3)c2s1] | 547 | (DMSO-d6): δ 10.79 (1H, s), 9.65 (1H, s), 8.95 (2H, s), 8.80 (1H, s), 8.35 (1H, s), 8.03 (1H, s), 7.01 (1H, t, J = 5.68 Hz), 4.34 (2H, dt, J = 13.67, 4.43 Hz), 3.24 (2H, p, J = 6.86 Hz), 2.93 (2H, q, J = 7.61 Hz), 2.07 (2H, d, J = 13.01 Hz), 1.43 (2H, ddd, J = 13.65, 9.98, 4.12 Hz), 1.36 (3H, t, J = 7.58 Hz), 1.23 (3H, s), 1.15 (3H, t, J = 7.19 Hz). |
| 84 | 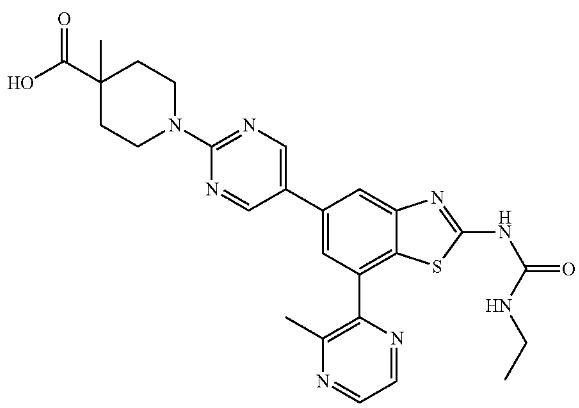 [SMILES: CCNC(=O)Nc1nc2cc(-c3cnc(N4CCC(C)(C(=O)O)CC4)nc3)cc(-c3nccnc3C)c2s1] | 533 | (DMSO-d6): δ 8.85 (2H, s), 8.70 (1H, d, J = 2.45 Hz), 8.66 (1H, d, J = 2.49 Hz), 8.01 (1H, d, J = 1.59 Hz), 7.80(1H, d, J = 1.60 Hz), 7.07 (1H, s), 4.32 (2H, dt, J = 13.74, 4.55 Hz), 3.20 (2H, p, J = 6.87 Hz), 2.70 (3H, s), 2.06 (2H, dt, J = 13.31, 3.62 Hz), 1.40 (2H, ddd, J = 12.87, 9.65, 4.16 Hz), 1.21 (3H, s), 1.11 (3H, t, J = 7.12 Hz). |
| 85 | 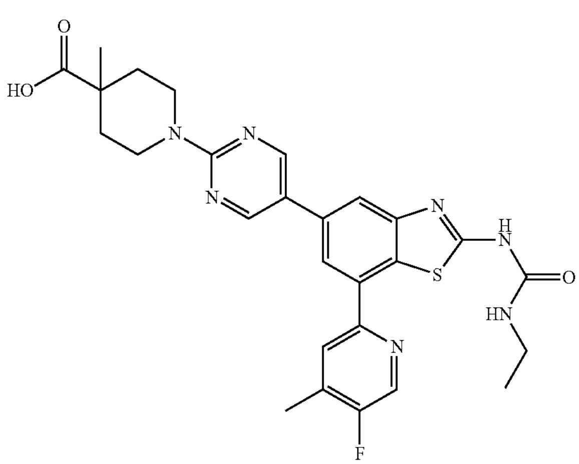 [SMILES: CCNC(=O)Nc1nc2cc(-c3cnc(N4CCC(C)(C(=O)O)CC4)nc3)cc(-c3cc(C)c(F)cn3)c2s1] | 550 | (DMSO-d6): δ 10.76 (1H, s), 8.94 (2H, s), 8.70 (1H, s), 8.54 (1H, d, J = 5.98 Hz), 8.22 (1H, d, J = 1.63 Hz), 7.98 (1H, d, J = 1.54 Hz), 7.05 (1H, t, J = 5.77 Hz), 4.34 (2H, dt, J = 13.73, 4.57 Hz), 3.67-3.21 (2H, m), 3.24 (2H, p, J = 6.89 Hz), 2.45 (3H, s), 2.07 (2H, dt, J = 13.67, 3.87 Hz), 1.43 (2H, ddd, J = 13.56, 10.07, 4.08 Hz), 1.23 (3H, s), 1.15 (3H, t, J = 7.17 Hz). |

-continued

| Cpd No. | Structure | LCMS data [M + H]+ | 1H NMR data |
|---|---|---|---|
| 86 | 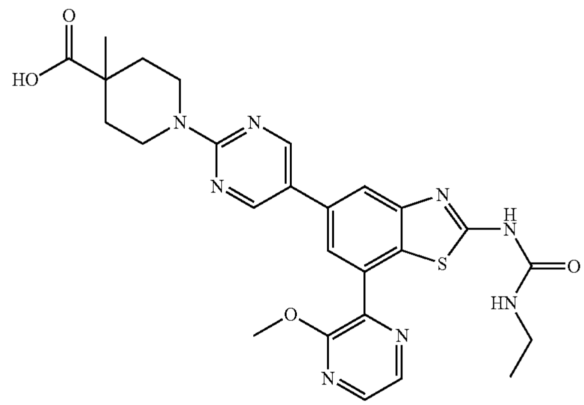 [SMILES: CCNC(=O)Nc1nc2cc(-c3cnc(N4CCC(C)(C(=O)O)CC4)nc3)cc(-c3nccnc3OC)c2s1] | 549 | (DMSO-d6): δ 12.47 (1H, s), 10.71 (1H, s), 8.82 (2H, s), 8.52 (1H, d, J = 2.63 Hz), 8.47 (1H, d, J = 1.69 Hz), 8.39 (2H, dd, J = 7.79, 2.71 Hz), 8.35 (1H, d, J = 2.63 Hz), 8.01 (1H, d, J = 1.73 Hz), 6.97 (1H, t, J = 5.68 Hz), 4.34 (2H, dt, J = 14.68, 9.56 Hz), 4.13 (3H, s), 3.52-3.28 (2H, m), 3.23 (2H, p, J = 6.77 Hz), 2.06 (2H, dt, J = 13.35, 3.78 Hz), 1.43 (2H, ddd, J = 13.48, 10.11, 3.92 Hz), 1.23 (3H, s), 1.14 (3H, t, J = 7.16 Hz). |
| 32 | 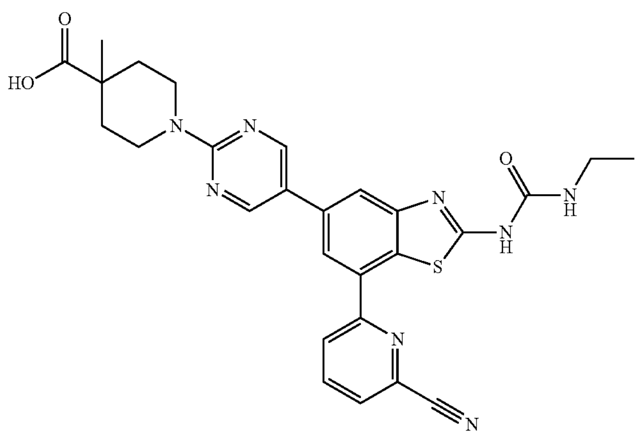 [SMILES: CCNC(=O)Nc1nc2cc(-c3cnc(N4CCC(C)(C(=O)O)CC4)nc3)cc(-c3cccc(C#N)n3)c2s1] | 543 | (DMSO-d6): δ 12.48 (1H, s), 10.69 (1H, s), 8.95 (2H, s), 8.85 (1H, d, J = 8.23 Hz), 8.35 (1H, s), 8.28 (1H, t, J = 7.95 Hz), 8.12 (1H, d, J = 7.60 Hz), 8.08 (1H, s), 6.93 (1H, t, J = 5.67 Hz), 4.34 (2H, dt, J = 13.60, 4.41 Hz), 3.39 (2H, ddd, J = 13.62, 10.00, 3.19 Hz), 3.27 (2H, p, J = 6.70 Hz), 2.06 (2H, d, J = 13.29 Hz), 1.43 (2H, ddd, J = 13.15, 9.83, 3.89 Hz), 1.23 (3H, s), 1.16 (3H, t, J = 7.18 Hz). |
| 34 | 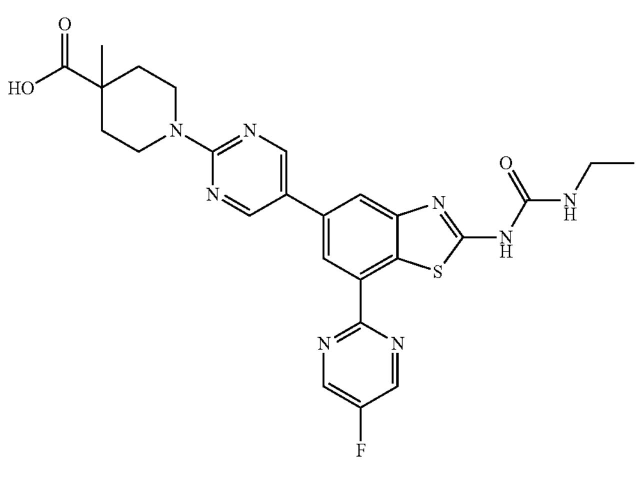 [SMILES: CCNC(=O)Nc1nc2cc(-c3cnc(N4CCC(C)(C(=O)O)CC4)nc3)cc(-c3ncc(F)cn3)c2s1] | 537 | (DMSO-d6): δ 12.50 (1H, s), 10.73 (1H, s), 9.19 (2H, s), 8.83 (2H, s), 8.54 (1H, d, J = 1.72 Hz), 8.07 (1H, d, J = 1.74 Hz), 6.90 (1H, t, J = 5.64 Hz), 4.33 (2H, dt, J = 13.68, 4.43 Hz), 3.40 (2H, dd, J = 11.86, 3.33 Hz), 3.25 (2H, p, J = 6.71 Hz), 2.06 (2H, dt, J = 13.47, 3.69 Hz), 1.44 (2H, ddd, J = 13.39, 9.99, 3.87 Hz), 1.23 (3H, s), 1.15 (3H, t, J = 7.17 Hz). |

-continued

| Cpd No. | Structure | LCMS data [M + H]+ | ¹H NMR data |
|---|---|---|---|
| 35 | 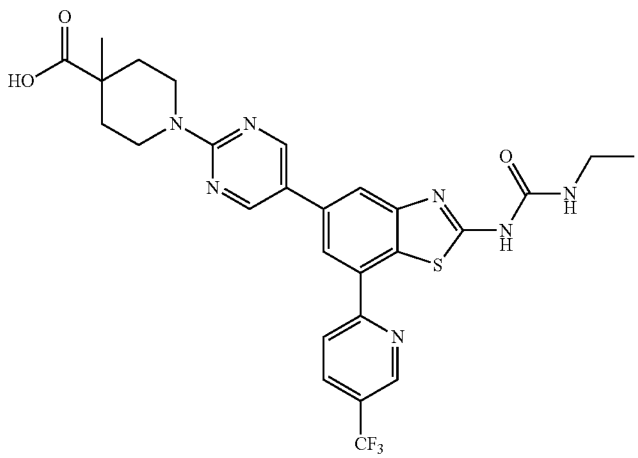 [SMILES: CCNC(=O)Nc1nc2cc(-c3cnc(N4CCC(C)(C(=O)O)CC4)nc3)cc(-c3ccc(C(F)(F)F)cn3)c2s1] | 537 | (DMSO-d₆): δ 12.49 (1H, s), 10.72 (1H, s), 9.23 (1H, s), 8.96 (2H, s), 8.77 (1H, d, J = 8.62 Hz), 8.44 (1H, dd, J = 8.60, 2.34 Hz), 8.39 (1H, s), 8.08 (1H, s), 6.95 (1H, t, J = 5.55 Hz), 4.34 (2H, dt, J = 13.68, 4.44 Hz), 3.61-3.21 (2H, m), 3.25 (2H, p, J = 6.79 Hz), 2.06 (2H, dt, J = 13.25, 3.64 Hz), 1.44 (2H, ddd, J = 13.33, 9.98, 3.96 Hz), 1.23 (3H, s), 1.15 (3H, t, J = 7.17 Hz). |
| 55 | 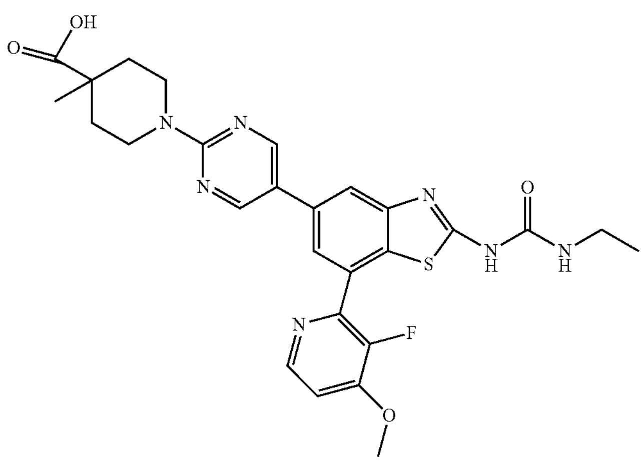 [SMILES: CCNC(=O)Nc1nc2cc(-c3cnc(N4CCC(C)(C(=O)O)CC4)nc3)cc(-c3nccc(OC)c3F)c2s1] | 566 | (DMSO-d₆): δ 12.48 (1H, s), 10.69 (1H, s), 8.81 (2H, s), 8.56 (1H, d, J = 5.45 Hz), 8.00 (2H, d, J = 8.57 Hz), 7.41 (1H, t, J = 5.91 Hz), 6.90 (1H, s), 4.33 (2H, d, J = 13.58 Hz), 4.05 (3H, s), 3.39 (2H, d, J = 12.28 Hz), 3.25 (2H, m), 2.05 (2H, dt, J = 13.52, 3.67 Hz), 1.43 (2H, ddd, J = 13.41, 10.03, 3.87 Hz), 1.23 (3H, s), 1.14 (3H, t, J = 7.16 Hz). |
| 48 | 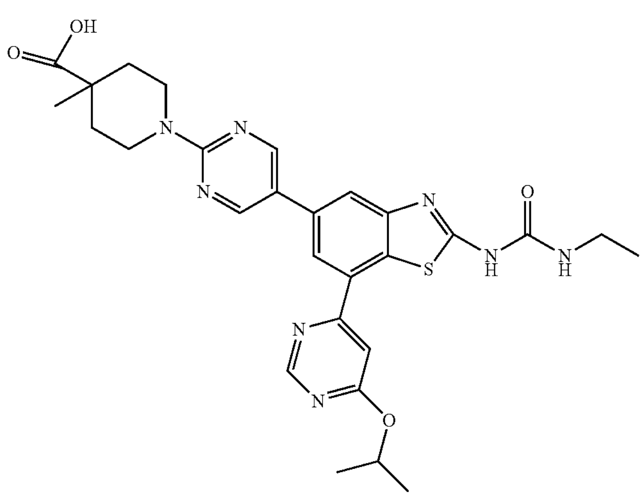 [SMILES: CCNC(=O)Nc1nc2cc(-c3cnc(N4CCC(C)(C(=O)O)CC4)nc3)cc(-c3cc(OC(C)C)ncn3)c2s1] | 577 | (DMSO-d₆): δ 12.51 (1H, s), 10.70 (1H, s), 9.03 (1H, s), 8.96 (2H, s), 8.37 (1H, d, J = 1.63 Hz), 8.07 (1H, d, J = 1.53 Hz), 7.98 (1H, s), 7.03-6.84 (1H, m), 5.51-5.42 (1H, m), 4.33 (2H, td, J = 9.10, 4.61 Hz), 3.40-3.42 (2H, m), 3.30-3.20 (2H, m), 2.06 (2H, dt, J = 13.51, 3.71 Hz), 1.45 (2H, dd, J = 10.64, 3.26 Hz), 1.42 (6H, d, J = 6.17 Hz), 1.23 (3H, s), 1.15 (3H, t, J = 7.17 Hz). |

-continued

| Cpd No. | Structure | LCMS data [M + H]+ | ¹H NMR data |
|---|---|---|---|
| 57 | 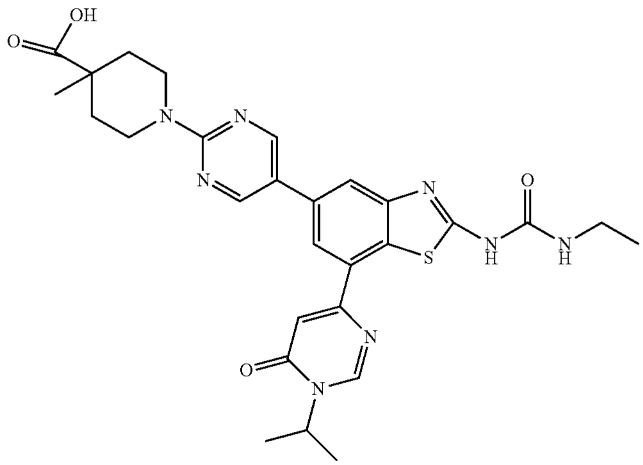 [SMILES: CCNC(=O)Nc1nc2cc(-c3cnc(N4CCC(C)(C(=O)O)CC4)nc3)cc(-c3cc(=O)n(C(C)C)cn3)c2s1] | 577 | (DMSO-d₆): δ 12.54 (1H, s), 10.82 (1H, d, J = 24.95 Hz), 8.93 (2H, s), 8.87 (1H, s), 8.16 (1H, d, J = 1.67 Hz), 8.02 (1H, d, J = 1.58 Hz), 7.43 (1H, s), 7.02 (1H, t, J = 5.89 Hz), 4.98 (1H, p, J = 6.84 Hz), 4.33 (2H, dt, J = 13.74, 4.62 Hz), 3.38 (2H, t, J = 11.18 Hz), 3.23 (2H, p, J = 6.70 Hz), 2.06 (2H, dt, J = 13.59, 3.89 Hz), 1.49 (6 H, d, J = 6.84 Hz), 1.42 (2H, ddd, J = 13.98, 9.85, 4.16 Hz), 1.22 (3H, s), 1.14 (3H, t, J = 7.11 Hz). |
| 49 | 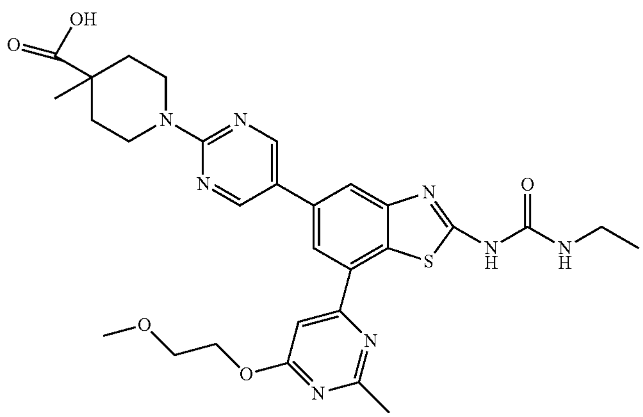 [SMILES: CCNC(=O)Nc1nc2cc(-c3cnc(N4CCC(C)(C(=O)O)CC4)nc3)cc(-c3cc(OCCOC)nc(C)n3)c2s1] | 607 | (DMSO-d₆): δ 12.48 (1H, s), 10.61 (1H, s), 8.96 (2H, s), 8.38 (1H, s), 8.06 (1H, s), 7.88 (1H, s), 6.93 (1H, t, J = 5.50 Hz), 4.57 (2H, dd, J = 5.61, 3.39 Hz), 4.33 (2H, dt, J = 13.77, 4.47 Hz), 3.75 (2H, dd, J = 5.59, 3.34 Hz), 3.41 (2H, dd, J = 11.75, 2.91 Hz), 3.36 (3H, s), 3.26 (2H, p, J = 6.71 Hz), 2.72 (3H, s), 2.06 (2H, dt, J = 13.38, 3.67 Hz), 1.44 (2H, ddd, J = 13.34, 9.95, 3.83 Hz), 1.23 (3H, s), 1.15 (3H, t, J = 7.18 Hz). |
| 80 | 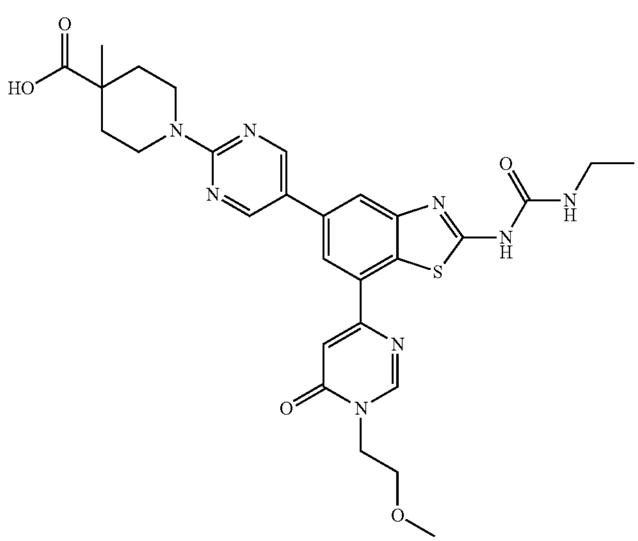 [SMILES: CCNC(=O)Nc1nc2cc(-c3cnc(N4CCC(C)(C(=O)O)CC4)nc3)cc(-c3cc(=O)n(CCOC)cn3)c2s1] | 593 | (DMSO-d₆): δ 11.21 (1H, s), 8.91 (2H, s), 8.66 (1H, s), 8.15 (1H, d, J = 1.65 Hz), 8.02 (1H, d, J = 1.57 Hz), 7.45 (1H, s), 4.32 (2H, dt, J = 13.74, 4.58 Hz), 4.19 (2H, t, J = 5.22 Hz), 3.67 (2H, t, J = 5.28 Hz), 3.33 (3H, s), 3.23 (2H, p, J = 6.89 Hz), 2.07 (2H, dt, J = 13.22, 3.79 Hz), 1.38 (2H, dt, J = 13.30, 5.05 Hz), 1.20 (3H, s), 1.14 (3H, t, J = 7.16 Hz). |

| Cpd No. | Structure | LCMS data [M + H]+ | ¹H NMR data |
|---|---|---|---|
| 71 | 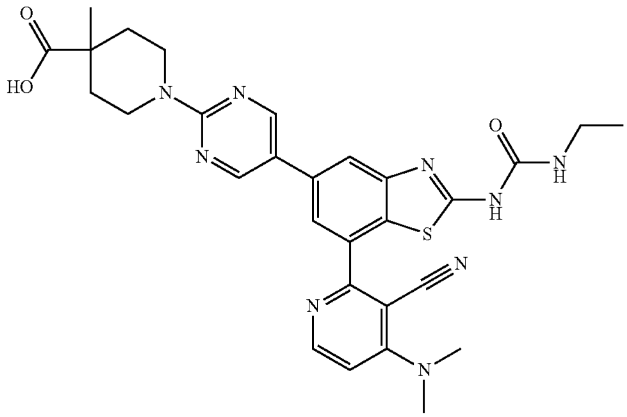 [SMILES: CCNC(=O)Nc1nc2cc(-c3cnc(N4CCC(C)(C(=O)O)CC4)nc3)cc(-c3nccc(N(C)C)c3C#N)c2s1] | 586 | (DMSO-d₆): δ 8.84 (2H, s), 8.45 (1H, d, J = 6.23 Hz), 8.11 (1H, d, J = 1.63 Hz), 8.02 (1H, d, J = 1.62 Hz), 7.25 (1H, s), 7.00 (1H, d, J = 6.37 Hz), 4.34 (2H, dt, J = 13.60, 4.36 Hz), 337 (2H, ddd, J = 14.50, 10.35, 4.68 Hz), 3.30 (6 H, s), 3.21 (2H, p, J = 6.64 Hz), 2.07 (2H, dt, J = 13.26, 3.63 Hz), 1.40 (2H, ddd, J = 13.39, 10.01, 4.00 Hz), 1.20 (3H, s), 1.13 (3H, t, J = 7.17 Hz). |
| 67 | 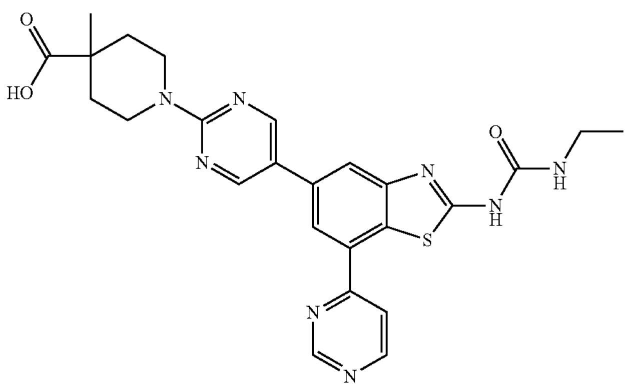 [SMILES: CCNC(=O)Nc1nc2cc(-c3cnc(N4CCC(C)(C(=O)O)CC4)nc3)cc(-c3ccncn3)c2s1] | 519 | (DMSO-d₆): δ 9.79 (1H, d, J = 1.51 Hz), 8.97 (2H, s), 8.90 (1H, dd, J = 2.55, 1.50 Hz), 8.72 (1H, d, J = 2.54 Hz), 8.42 (1H, d, J = 1.60 Hz), 8.06 (1H, d, J = 1.51 Hz), 7.14 (1H, s), 4.34 (2H, dt, J = 13.62, 4.43 Hz), 3.24 (2H, p, J = 6.87 Hz), 2.07 (2H, dt, J = 13.52, 3.69 Hz), 1.42 (2H, ddd, J = 13.33, 10.06, 3.91 Hz), 1.22 (3H, s), 1.15 (3H, t, J = 7.18 Hz). |
| 66 | 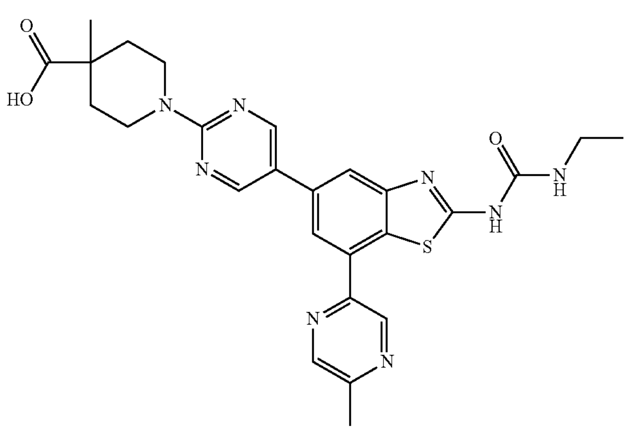 [SMILES: CCNC(=O)Nc1nc2cc(-c3cnc(N4CCC(C)(C(=O)O)CC4)nc3)cc(-c3cnc(C)cn3)c2s1] | 533 | (DMSO-d₆): δ 9.63 (1H, d, J = 1.45 Hz), 8.95 (2H, s), 8.78 (1H, d, J = 1.37 Hz), 8.36 (1H, d, J = 1.58 Hz), 8.03 (1H, d, J = 1.52 Hz), 7.15 (1H, s), 4.34 (2H, dt, J = 13.67, 4.54 Hz), 3.24 (2H, p, J = 6.78 Hz), 2.63 (3H, s), 2.07 (2H, dt, J = 13.59, 3.85 Hz), 1.42 (2H, ddd, J = 13.46, 10.00, 3.99 Hz), 1.22 (3H, s), 1.15 (3H, t, J = 7.18 Hz). |

-continued

| Cpd No. | Structure | LCMS data [M + H]+ | ¹H NMR data |
|---|---|---|---|
| 60 | 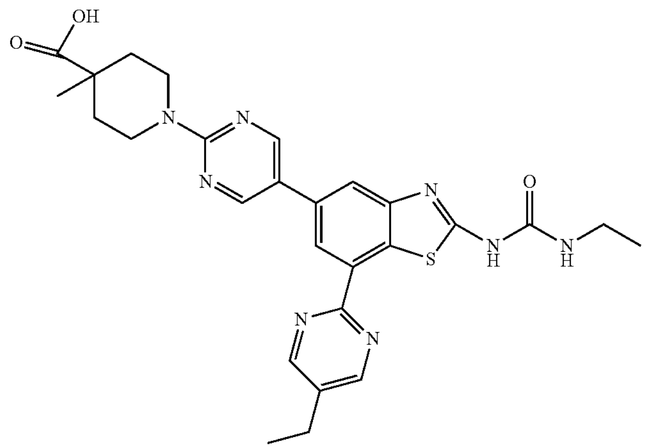 [SMILES: CCNC(=O)Nc1nc2cc(-c3cnc(N4CCC(C)(C(=O)O)CC4)nc3)cc(-c3ncc(CC)cn3)c2s1] | 547 | (DMSO-d$_6$): δ 12.50 (1H, s), 10.83 (1H, s), 8.98 (2H, s), 8.82 (2H, s), 8.57 (1H, d, J = 1.86 Hz), 8.04 (1H, s), 7.07 (1H, t, J = 5.64 Hz), 4.33 (2H, dt, J = 13.71, 4.40 Hz), 3.41-3.32 (2H, m), 3.25 (2H, p, J = 6.72 Hz), 2.76 (2H, q, J = 7.57 Hz), 2.06 (2H, d, J = 13.16 Hz), 1.43 (2H, ddd, J = 13.46, 10.25, 3.96 Hz), 1.32 (3H, t, J = 7.56 Hz), 1.22 (3H, s), 1.15 (3H, t, J = 7.19 Hz). |
| 59 | 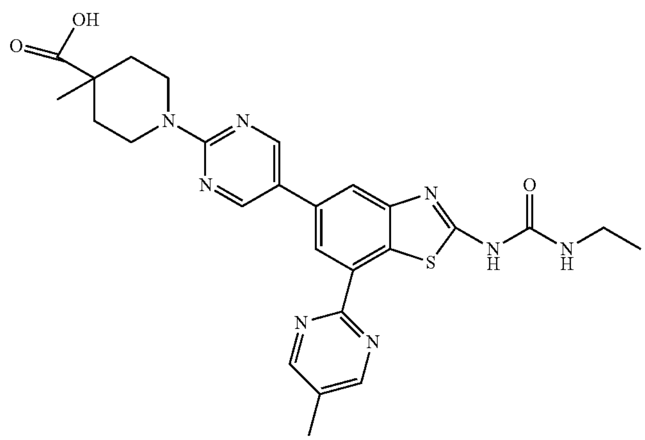 [SMILES: CCNC(=O)Nc1nc2cc(-c3cnc(N4CCC(C)(C(=O)O)CC4)nc3)cc(-c3ncc(C)cn3)c2s1] | 533 | (DMSO-d$_6$): δ 12.40 (1H, s), 10.73 (1H, s), 8.94 (2H, s), 8.82 (2H, s), 8.57 (1H, d, J = 1.75 Hz), 8.04 (1H, d, J = 1.75 Hz), 6.96 (1H, t, J = 5.56 Hz), 4.33 (2H, dt, J = 13.70, 4.47 Hz), 3.39 (2H, ddd, J = 13.88, 9.53, 3.40 Hz), 3.25 (2H, p, J = 6.71 Hz), 2.41 (3H, s), 2.06 (2H, dt, J = 13.50, 3.70 Hz), 1.43 (2H, ddd, J = 13.39, 10.05, 3.89 Hz), 1.23 (3H, s), 1.16 (3H, t, J = 7.18 Hz). |
| 58 | 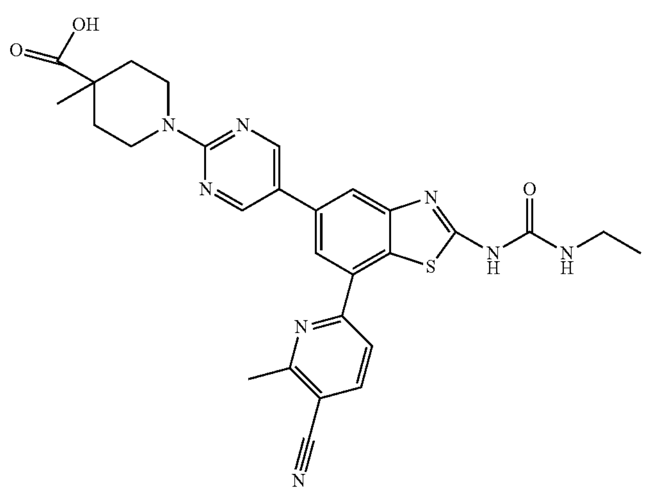 [SMILES: CCNC(=O)Nc1nc2cc(-c3cnc(N4CCC(C)(C(=O)O)CC4)nc3)cc(-c3ccc(C#N)c(C)n3)c2s1] | 557 | (DMSO-d$_6$): δ 12.48 (1H, s), 10.67 (1H, s), 8.94 (2H, s), 8.56 (1H, d, J = 8.46 Hz), 8.43 (1H, d, J = 8.39 Hz), 8.36 (1H, s), 8.05 (1H, d, J = 1.50 Hz), 6.95 (1H, t, J = 5.61 Hz), 4.33 (2H, dt, J = 13.74, 4.49 Hz), 3.39 (2H, ddd, J = 13.82, 10.60, 3.65 Hz), 3.26 (2H, p, J = 6.72 Hz), 2.89 (3H, s), 2.06 (2H, dt, J = 13.56, 3.79 Hz), 1.43 (2H, ddd, J = 13.41, 9.97, 3.95 Hz), 1.23 (3H, s), 1.15 (3H, t, J = 7.20 Hz). |

| Cpd No. | Structure | LCMS data [M + H]+ | 1H NMR data |
|---|---|---|---|
| 56 | 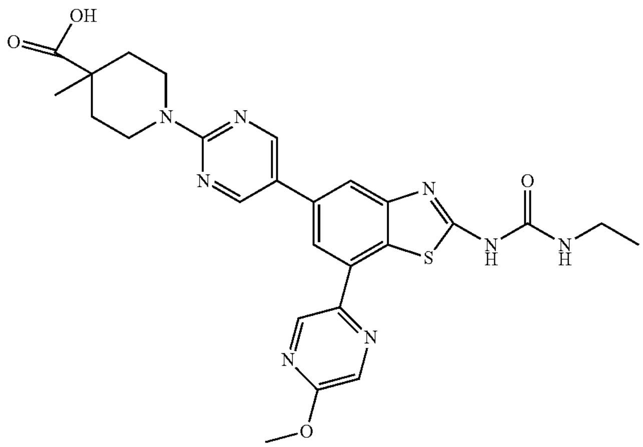 [SMILES: CCNC(=O)Nc1nc2cc(-c3cnc(N4CCC(C)(C(=O)O)CC4)nc3)cc(-c3cnc(OC)cn3)c2s1] | 549 | (DMSO-d6): δ 9.30 (1H, s), 8.93 (2H, s), 8.56 (1H, d, J = 1.38 Hz), 8.23 (1H, s), 7.97 (1H, s), 7.16 (1H, s), 4.34 (2H, dt, J = 13.65, 4.45 Hz), 4.05 (3H, s), 3.39 (2H, ddd, J = 16.43, 9.43, 4.06 Hz), 3.23 (2H, p, J = 6.88 Hz), 2.07 (2H, dt, J = 14.01, 3.95 Hz), 1.42 (2H, ddd, J = 13.31, 9.98, 3.94 Hz), 1.22 (3H, s), 1.14 (3H, t, J = 7.15 Hz). |
| 51 | 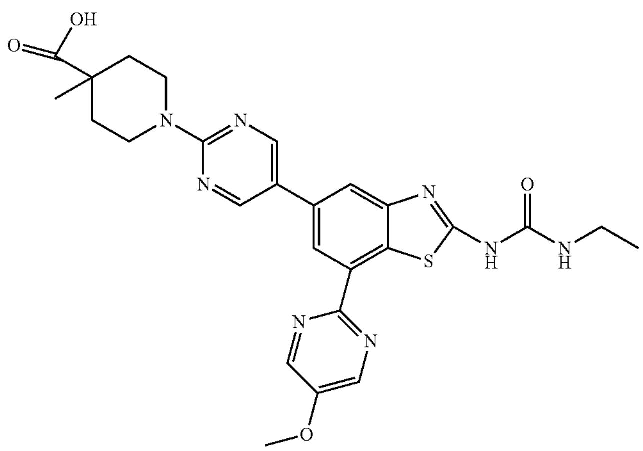 [SMILES: CCNC(=O)Nc1nc2cc(-c3cnc(N4CCC(C)(C(=O)O)CC4)nc3)cc(-c3ncc(OC)cn3)c2s1] | 549 | (DMSO-d6): δ 12.48 (1H, s), 10.70 (1H, s), 8.85 (2H, s), 8.82 (2H, s), 8.49 (1H, d, J = 1.81 Hz), 8.01 (1H, d, J = 1.82Hz), 6.93 (1H, t, J = 5.43 Hz), 4.33 (2H, dt, J = 13.71, 4.43 Hz), 4.05 (3H, s), 3.47-3.33 (2H, m), 3.25 (2H, p, J = 6.70 Hz), 2.06 (2H, dt, J = 13.51, 3.66 Hz), 1.43 (2H, ddd, J = 13.45, 9.96, 3.90 Hz), 1.23 (3H, s), 1.15 (3H, t, J = 7.18 Hz). |
| 31 | 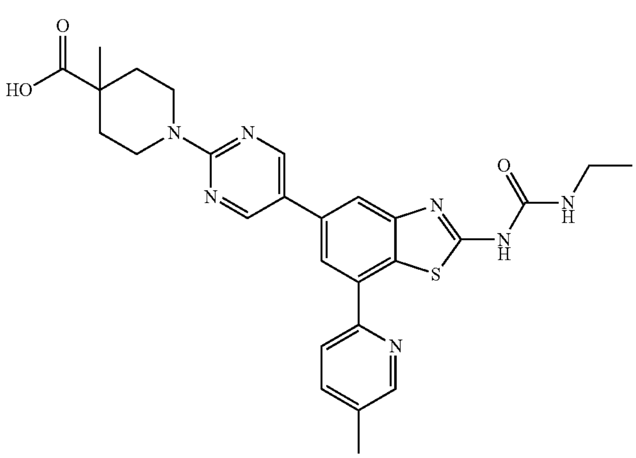 [SMILES: CCNC(=O)Nc1nc2cc(-c3cnc(N4CCC(C)(C(=O)O)CC4)nc3)cc(-c3ccc(C)cn3)c2s1] | 532 | (DMSO-d6): δ 10.82 (1H, s), 8.93 (2H, s), 8.67 (1H, s), 8.40 (1H, d, J = 8.29 Hz), 8.21 (1H, s), 7.96 (1H, s), 7.84 (1H, dd, J = 8.25, 2.17 Hz), 7.08 (1H, t, J = 5.54 Hz), 4.33 (2H, dt, J = 13.68, 4.44 Hz), 3.39 (2H, ddd, J = 12.32, 11.93, 2.43 Hz), 3.23 (2H, p, J = 6.61 Hz), 2.43 (3H, s), 2.06 (2H, d, J = 13.34 Hz), 1.43 (2H, ddd, J = 13.30, 10.01, 3.90 Hz), 1.23 (3H, s), 1.15 (3H, t, J = 7.18 Hz). |

| Cpd No. | Structure | LCMS data [M + H]+ | ¹H NMR data |
|---|---|---|---|
| 92 | 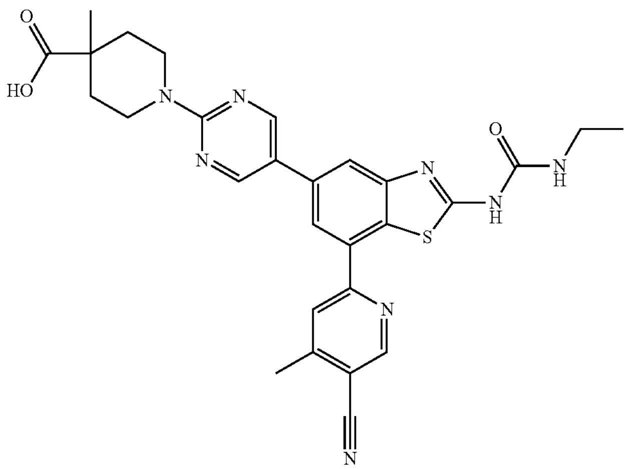 [SMILES: CCNC(=O)Nc1nc2cc(-c3cnc(N4CCC(C)(C(=O)O)CC4)nc3)cc(-c3cc(C)c(C#N)cn3)c2s1] | 557 | (DMSO-d₆): δ 9.17 (1H, s), 8.96 (2H, s), 8.70 (1H, s), 8.36 (1H, s), 8.07 (1H, s), 7.27 (1H, s), 4.34 (2H, d, J = 13.48 Hz), 3.47-3.31 (2H, m), 3.24 (2H, p, J = 7.34 Hz), 2.66 (3H, s), 2.07 (2H, d, J = 13.21 Hz), 1.41 (2H, ddd, J = 13.46, 9.80, 3.42 Hz), 1.22 (3H, s), 1.15 (3H, t, J = 7.19 Hz). |
| 93 | 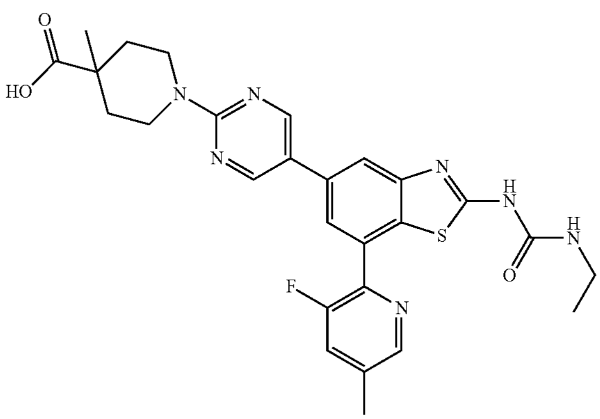 [SMILES: CCNC(=O)Nc1nc2cc(-c3cnc(N4CCC(C)(C(=O)O)CC4)nc3)cc(-c3ncc(C)cc3F)c2s1] | 550 | (DMSO-d₆): δ 11.24 (1H, s), 8.79 (2H, s), 8.57 (1H, s), 8.02 (1H, s), 7.97 (1H, s), 7.84 (1H, d, J = 12.97 Hz), 7.50 (1H, s), 4.32 (2H, d, J = 13.10 Hz), 3.22 (2H, p, J = 7.38 Hz), 2.47 (3H, s), 2.07 (2H, d, J = 13.36 Hz), 1.36 (2H, t, J = 11.08 Hz), 1.18 (3H, s), 1.14 (3H, t, J = 7.16 Hz). |
| 52 | 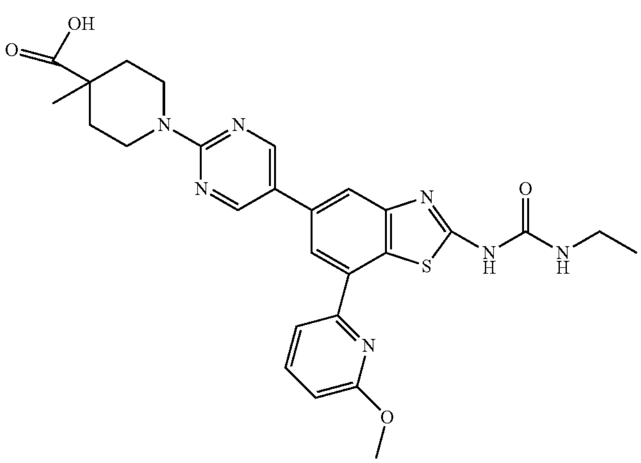 [SMILES: CCNC(=O)Nc1nc2cc(-c3cnc(N4CCC(C)(C(=O)O)CC4)nc3)cc(-c3cccc(OC)n3)c2s1] | 548 | (DMSO-d₆): δ 11.02 (1H, s), 8.91 (2H, s), 8.19 (1H, d, J = 1.62 Hz), 8.06 (1H, d, J = 7.63 Hz), 7.97 (1H, d, J = 1.53 Hz), 7.92 (1H, t, J = 7.87 Hz), 7.31 (1H, s), 6.90 (1H, d, J = 8.13 Hz), 4.34 (2H, dt, J = 13.68, 4.45 Hz), 4.20 (3H, s), 3.39 (6H, ddd, J = 14.44, 10.68, 4.48 Hz), 3.24 (3H, p, J = 6.96 Hz), 2.08 (2H, dt, J = 13.61, 3.77 Hz), 1.40 (2H, ddd, J = 13.25, 10.02, 3.85 Hz), 1.21 (3H, s), 1.14 (3H, t, J = 7.18 Hz). |

| Cpd No. | Structure | LCMS data [M + H]+ | 1H NMR data |
|---|---|---|---|
| 53 | 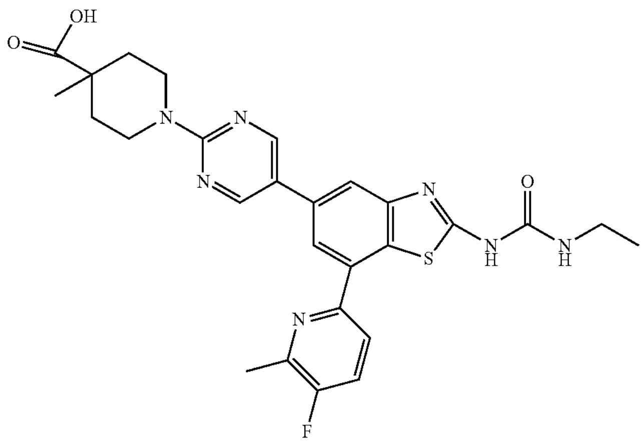 [SMILES: CCNC(=O)Nc1nc2cc(-c3cnc(N4CCC(C)(C(=O)O)CC4)nc3)cc(-c3ccc(F)c(C)n3)c2s1] | 550 | (DMSO-d6): δ 10.89 (1H, s), 8.93 (2H, s), 8.42 (1H, dd, J = 8.76, 3.43 Hz), 8.21 (1H, d, J = 1.63 Hz), 7.97 (1H, d, J = 1.54 Hz), 7.87 (1H, t, J = 9.05 Hz), 7.25 (1H, s), 4.34 (2H, dt, J = 13.66, 4.45 Hz), 3.39 (2H, ddd, J = 13.99, 9.87, 3.85 Hz), 3.25 (2H, p, J = 6.76 Hz), 2.67 (3H, d, J = 2.75 Hz), 2.07 (2H, dt, J = 13.47, 3.71 Hz), 1.41 (2H, ddd, J = 13.32, 10.06, 3.91 Hz), 1.22 (3H, s), 1.15 (3H, t, J = 7.18 Hz). |
| 54 | 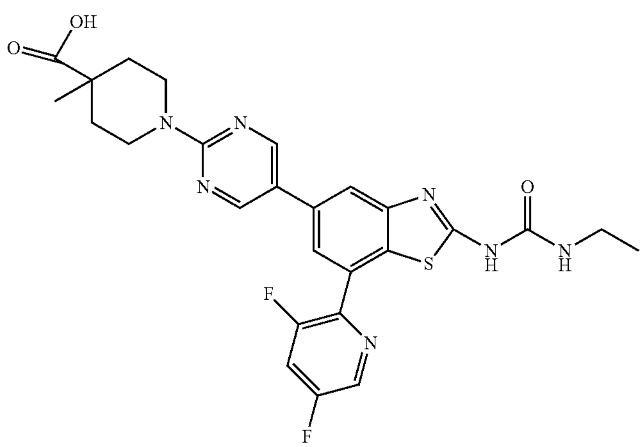 [SMILES: CCNC(=O)Nc1nc2cc(-c3cnc(N4CCC(C)(C(=O)O)CC4)nc3)cc(-c3ncc(F)cc3F)c2s1] | 554 | (DMSO-d6): δ 12.49 (1H, s), 10.88 (1H, s), 8.83 (1H, d, J = 2.39 Hz), 8.81 (2H, s), 8.24 (1H, ddd, J = 11.66, 8.81, 2.40 Hz), 8.02 (2H, dd, J = 6.52, 1.47 Hz), 7.04 (1H, t, J = 6.01 Hz), 4.33 (2H, dt, J = 13.72, 4.59 Hz), 3.40 (2H, dd, J = 10.13, 3.36 Hz), 3.23 (2H, p, J = 6.72 Hz), 2.06 (2H, dt, J = 13.63, 3.89 Hz), 1.42 (2H, ddd, J = 13.50, 10.00, 4.14 Hz), 1.22 (3H, s), 1.14 (3H, t, J = 7.16 Hz). |
| 61 | 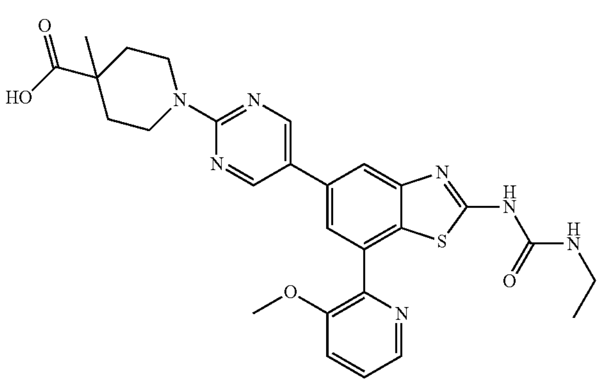 [SMILES: CCNC(=O)Nc1nc2cc(-c3cnc(N4CCC(C)(C(=O)O)CC4)nc3)cc(-c3ncccc3OC)c2s1] | 548 | (DMSO-d6): δ 10.67 (1H, s), 8.80 (2H, s), 8.42 (1H, dd, J = 4.57, 1.23 Hz), 8.28 (1H, d, J = 1.68 Hz), 7.93 (1H, d, J = 1.68 Hz), 7.73 (1H, dd, J = 8.43, 1.26 Hz), 7.51 (1H, dd, J = 8.38, 4.58 Hz), 6.99 (1H, t, J = 5.71 Hz), 4.33 (2H, dt, J = 13.72, 4.49 Hz), 3.99 (3H, s), 3.22 (2H, p, J = 6.70 Hz), 2.06 (2H, dt, J = 13.53, 3.69 Hz), 1.42 (2H, ddd, J = 13.42, 10.06, 3.94 Hz), 1.22 (3H, s), 1.14 (3H, t, J = 7.17 Hz). |

-continued

| Cpd No. | Structure | LCMS data [M + H]+ | ¹H NMR data |
|---|---|---|---|
| 62 | 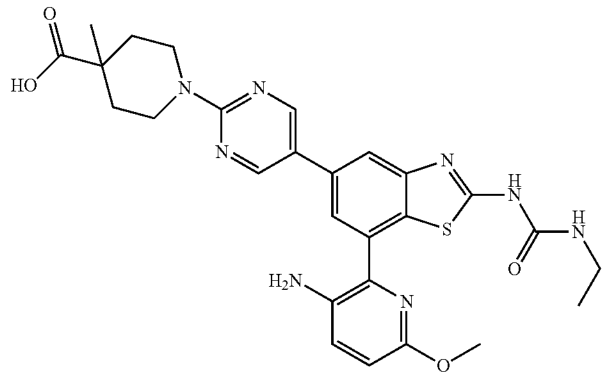 [SMILES: CCNC(=O)Nc1nc2cc(-c3cnc(N4CCC(C)(C(=O)O)CC4)nc3)cc(-c3nc(OC)ccc3N)c2s1] | 563 | (DMSO-d$_6$): δ 12.48 (1H, s), 10.66 (1H, s), 8.80 (2H, s), 7.95 (1H, d, J = 1.67 Hz), 7.85 (1H, d, J = 1.59 Hz), 7.37 (1H, d, J = 8.67 Hz), 6.92 (1H, t, J = 5.58 Hz), 6.72 (1H, d, J = 8.64 Hz), 5.03 (2H, s), 4.32 (2H, dt, J = 13.69, 4.39 Hz), 3.91 (3H, s), 3.22 (2H, p, J = 6.70 Hz), 2.05 (2H, dt, J = 13.44, 3.61 Hz), 1.42 (2H, ddd, J = 13.35, 10.09, 3.84 Hz), 1.22 (3H, s), 1.13 (3H, t, J = 7.18 Hz). |
| 89 | 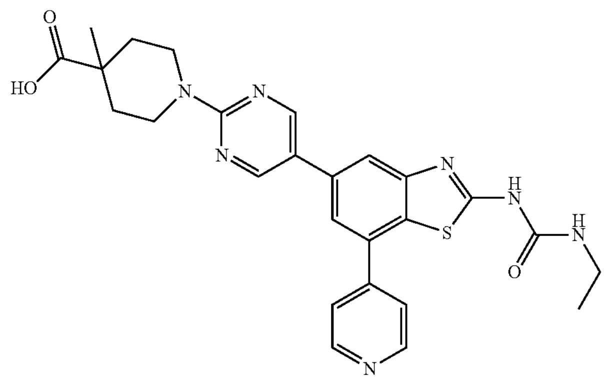 [SMILES: CCNC(=O)Nc1nc2cc(-c3cnc(N4CCC(C)(C(=O)O)CC4)nc3)cc(-c3ccncc3)c2s1] | 518 | (DMSO-d$_6$): δ 11.08 (1H, s), 8.88 (2H, s), 8.79 (2H, d, J = 5.30 Hz), 8.00 (1H, d, J = 1.59 Hz), 7.84 (2H, dd, J = 4.88, 1.51 Hz), 7.70 (1H, d, J = 1.62 Hz), 7.01 (1H, t, J = 5.66 Hz), 4.32 (2H, dt, J = 13.69, 4.44 Hz), 3.21 (2H, p, J = 6.72 Hz), 2.05 (2H, d, J = 13.37 Hz), 1.42 (2H, ddd, J = 13.41, 10.06, 3.87 Hz), 1.22 (3H, s), 1.12 (3H, t, J = 7.16 Hz). |
| 90 | 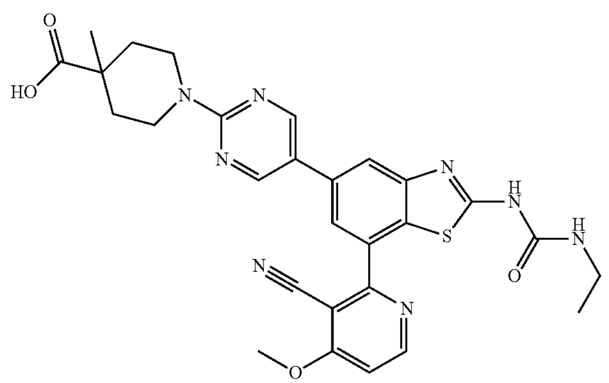 [SMILES: CCNC(=O)Nc1nc2cc(-c3cnc(N4CCC(C)(C(=O)O)CC4)nc3)cc(-c3nccc(OC)c3C#N)c2s1] | 573 | (DMSO-d$_6$): δ 11.30 (1H, s), 8.91 (1H, d, J = 5.94 Hz), 8.83 (2H, s), 8.18 (1H, d, J = 1.56 Hz), 8.06 (1H, s), 7.46 (1H, d, J = 6.03 Hz), 7.41 (1H, s), 4.33 (2H, dt, J = 13.63, 4.33 Hz), 4.14 (3H, s), 3.21 (2H, p, J = 6.82 Hz), 2.08 (2H, d, J = 13.32 Hz), 1.39 (2H, t, J = 11.43 Hz), 1.20 (3H, s), 1.13 (3H, t, J = 7.18 Hz). |
| 27 | 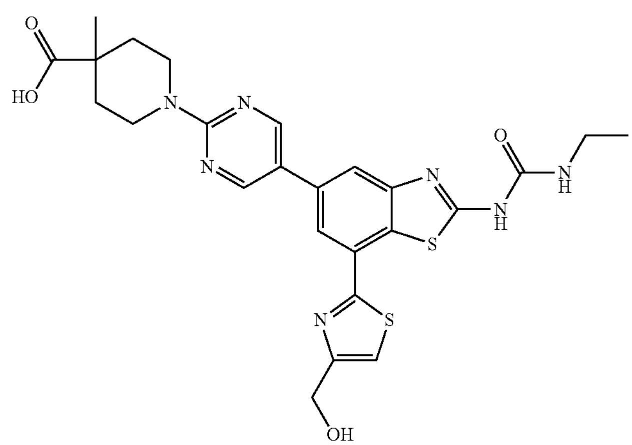 [SMILES: CCNC(=O)Nc1nc2cc(-c3cnc(N4CCC(C)(C(=O)O)CC4)nc3)cc(-c3nc(CO)cs3)c2s1] | 554 | (DMSO-d$_6$): δ 8.84 (2H, s), 7.98 (1H, s), 7.93 (1H, s), 7.62 (1H, s), 7.36 (1H, s), 4.76 (2H, s), 4.34 (2H, dt, J = 13.62, 4.30 Hz), 3.38 (2H, t, J = 12.64 Hz), 3.24 (2H, p, J = 6.90 Hz), 2.08 (2H, d, J = 13.30 Hz), 1.38 (2H, t, J = 11.01 Hz), 1.20 (3H, s), 1.15 (3H, t, J = 7.18 Hz). |

| Cpd No. | Structure | LCMS data [M + H]+ | 1H NMR data |
|---|---|---|---|
| 30 | 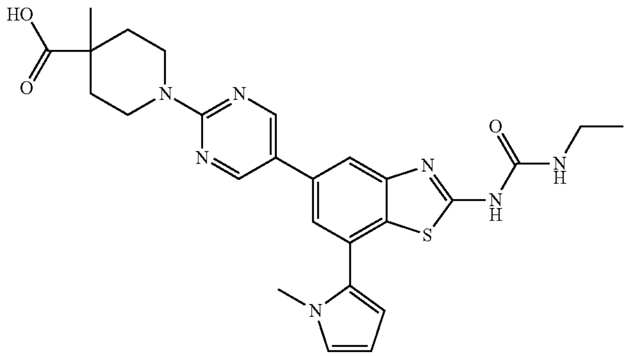 [SMILES: CCNC(=O)Nc1nc2cc(-c3cnc(N4CCC(C)(C(=O)O)CC4)nc3)cc(-c3cccn3C)c2s1] | 520 | (DMSO-d6): δ 8.82 (2H, s), 7.84 (1H, d, J = 1.58 Hz), 7.47 (1H, d, J = 1.60 Hz), 7.01 (1H, t, J = 5.54 Hz), 6.97 (1H, t, J = 2.15 Hz), 6.42 (1H, dd, J = 3.62, 1.74 Hz), 6.21 (1H, t, J = 3.13 Hz), 4.32 (2H, dt, J = 13.69, 4.43 Hz), 3.37 2H, ddd, J = 13.50, 10.33, 3.11 Hz), 3.21 (2H, p, J = 6.70 Hz), 2.05 (2H, dt, J = 13.41, 3.64 Hz), 1.41 (2H, ddd, J = 13.36, 10.08, 3.89 Hz), 1.22 (3H, s), 1.12 (3H, t, J = 7.17 Hz). |
| 25 | 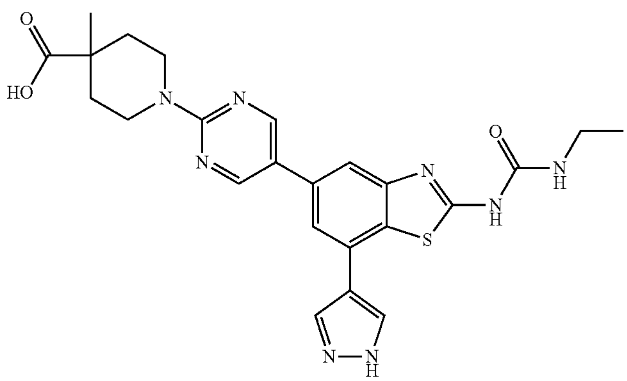 [SMILES: CCNC(=O)Nc1nc2cc(-c3cnc(N4CCC(C)(C(=O)O)CC4)nc3)cc(-c3cn[nH]c3)c2s1] | 507 | (DMSO-d6): δ 13.16 (1H, s), 11.06 (1H, s), 8.85 (2H, s), 8.21 (2H, s), 7.79 (1H, d, J = 1.59 Hz), 7.73 (1H, d, J = 1.63 Hz), 7.13 (1H, t, J = 5.45 Hz), 4.32 (2H, dt, J = 13.67, 4.44 Hz), 3.23 (2H, p, J = 6.78 Hz), 2.06 (2H, dt, J = 13.44, 3.62 Hz), 1.41 (2H, ddd, J = 13.35, 10.16, 3.89 Hz), 1.22 (3H, s), 1.14 (3H, t, J = 7.18 Hz). |
| 24 | 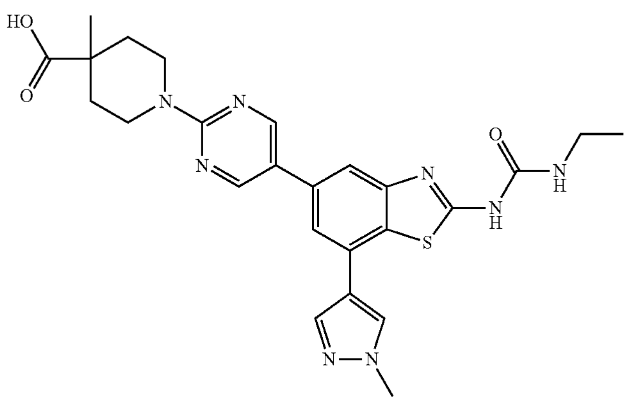 [SMILES: CCNC(=O)Nc1nc2cc(-c3cnc(N4CCC(C)(C(=O)O)CC4)nc3)cc(-c3cnn(C)c3)c2s1] | 521 | (DMSO-d6): δ 8.85 (2H, s), 8.29 (1H, s), 8.06 (1H, d, J = 0.86 Hz), 7.79 (1H, d, J = 1.61 Hz), 7.71 (1H, d, J = 1.65 Hz), 7.08 (1H, t, J = 5.52 Hz), 4.32 (2H, dt, J = 13.69, 4.46 Hz), 3.99 (3H, s), 3.38 (2H, ddd, J = 13.89, 10.28, 3.81 Hz), 3.23 (2H, p, J = 6.68 Hz), 2.06 (2H, dt, J = 13.49, 3.66 Hz), 1.41 (2H, ddd, J = 13.39, 10.10, 3.90 Hz), 1.22 (3H, s), 1.14 (3H, t, J = 7.17 Hz). |
| 33 | 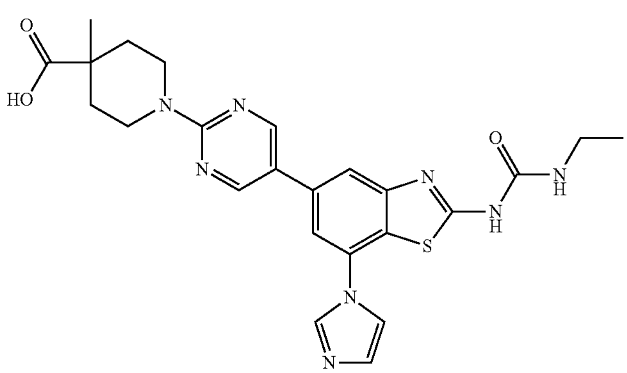 [SMILES: CCNC(=O)Nc1nc2cc(-c3cnc(N4CCC(C)(C(=O)O)CC4)nc3)cc(-n3ccnc3)c2s1] | 507 | (DMSO-d6): δ 8.88 (2H, s), 8.27 (1H, s), 7.97 (1H, d, J = 1.50 Hz), 7.80 (1H, t, J = 1.29 Hz), 7.66 (1H, d, J = 1.51 Hz), 7.45 (1H, s), 7.25(1H, s), 4.31 (2H, dt, J = 13.64, 4.44 Hz), 3.21 (2H, p, J = 6.83 Hz), 2.06 (2H, dt, J = 13.61, 3.68 Hz), 1.39 (2H, ddd, J = 13.35, 9.97, 3.80 Hz), 1.21 (3H, s), 1.12 (3H, t, J = 7.17 Hz). |

-continued

| Cpd No. | Structure | LCMS data [M + H]⁺ | ¹H NMR data |
|---|---|---|---|
| 29 | 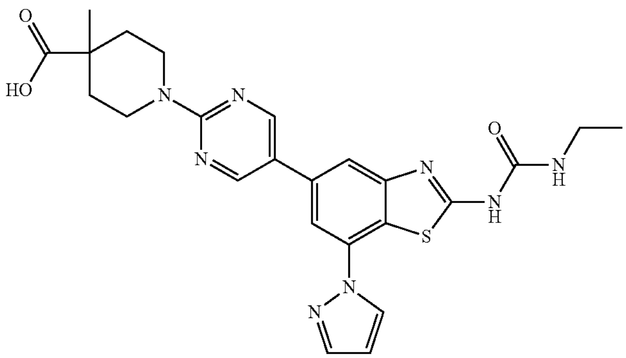 [SMILES: CCNC(=O)Nc1nc2cc(-c3cnc(N4CCC(C)(C(=O)O)CC4)nc3)cc(-n3cccn3)c2s1] | 507 | (DMSO-d₆): δ 10.96 (1H, s), 8.93 (2H, s), 8.91 (1H, d, J = 2.57 Hz), 7.97 (1H, d, J = 1.51 Hz), 7.94 (1H, d, J = 1.71 Hz), 7.85 (1H, d, J = 1.43 Hz), 7.09 (1H, t, J = 5.62 Hz), 6.70 (1H, t, J = 2.10 Hz), 4.33 (2H, dt, J = 13.72, 4.63 Hz), 3.38 (2H, ddd, J = 13.65, 10.07, 5.80 Hz), 3.23 (2H, p, J = 6.81 Hz), 2.06 (2H, dt, J = 13.51, 3.90 Hz), 1.42 (2H, ddd, J = 13.41, 9.92, 3.94 Hz), 1.22 (3H, s), 1.13 (3H, t, J = 7.16 Hz). |
| 75 | 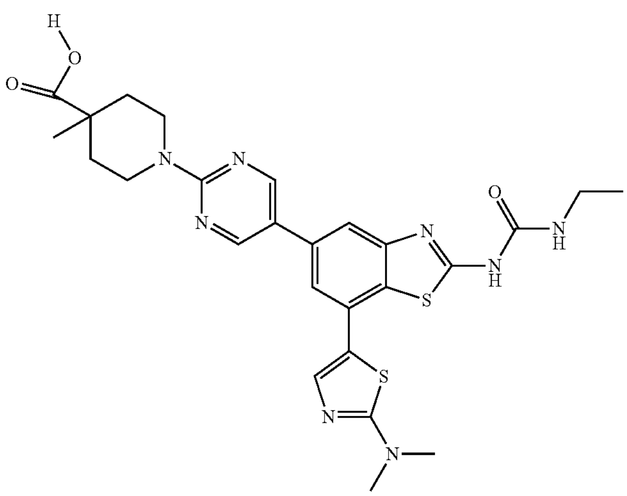 [SMILES: CCNC(=O)Nc1nc2cc(-c3cnc(N4CCC(C)(C(=O)O)CC4)nc3)cc(-c3cnc(N(C)C)s3)c2s1] | 567.1 | (CDCl₃) δ 8.68-8.47 (m, 2H), 7.62 (dd, J = 35.2, 11.7 Hz, 2H), 6.90 (d, J = 5.4 Hz, 1H), 4.24 (d, J = 13.1 Hz, 2H), 3.66 (s, 2H), 3.54-3.36 (m, 2H), 3.24-3.14 (m, 6H), 2.25 (d, J = 13.8 Hz, 2H), 1.53 (dd, J = 21.0, 11.6 Hz, 2H), 1.37 (s, 3H), 1.28 (t, J = 7.2 Hz, 3H) |
| 76 | 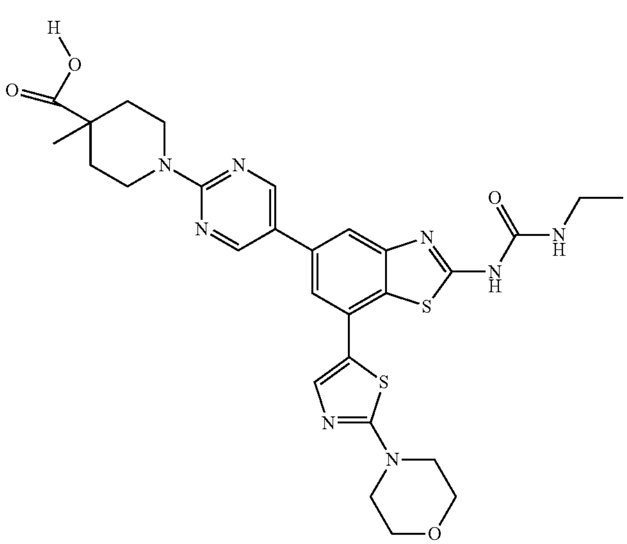 [SMILES: CCNC(=O)Nc1nc2cc(-c3cnc(N4CCC(C)(C(=O)O)CC4)nc3)cc(-c3cnc(N4CCOCC4)s3)c2s1] | 609.1 | (CDCl₃) δ 8.86-8.38 (m, 2H), 7.67 (d, J = 16.5 Hz, 2H), 6.99 (d, J = 9.8 Hz, 1H), 4.33-4.17 (m, 2H), 3.84 (dd, J = 12.3, 7.3 Hz, 4H), 3.74-3.60 (m, 2H), 3.62-3.50 (m, 4H), 3.50-3.35 (m, 2H), 2.25 (d, J = 14.1 Hz, 2H), 1.55 (t, J = 9.5 Hz, 2H), 1.37 (s, 3H), 1.28 (t, J = 7.2 Hz, 3H) |

-continued
| Cpd No. | Structure | LCMS data [M + H]+ | 1H NMR data |
|---|---|---|---|
| 77 | 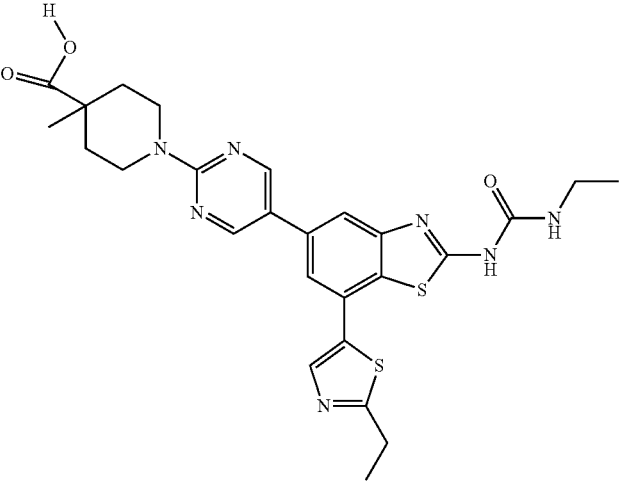 [SMILES: CCNC(=O)Nc1nc2cc(-c3cnc(N4CCC(C)(C(=O)O)CC4)nc3)cc(-c3cnc(CC)s3)c2s1] | 552.1 | (CDCl3) δ 8.64 (s, 2H), 7.78 (d, J = 1.3 Hz, 1H), 7.68 (s, 1H), 7.58 (d, J = 9.3 Hz, 1H), 4.18 (d, J = 13.9 Hz, 2H), 3.76 (s, 2H), 3.55-3.36 (m, 3H), 3.18-3.08 (m, 2H), 2.33-2.18 (m, 2H), 1.57 (t, J = 9.4 Hz, 2H), 1.48 (t, J = 7.5 Hz, 3H), 1.40 (d, J = 7.8 Hz, 3H), 1.29 (t, J = 7.2 Hz, 3H). |
| 78 | 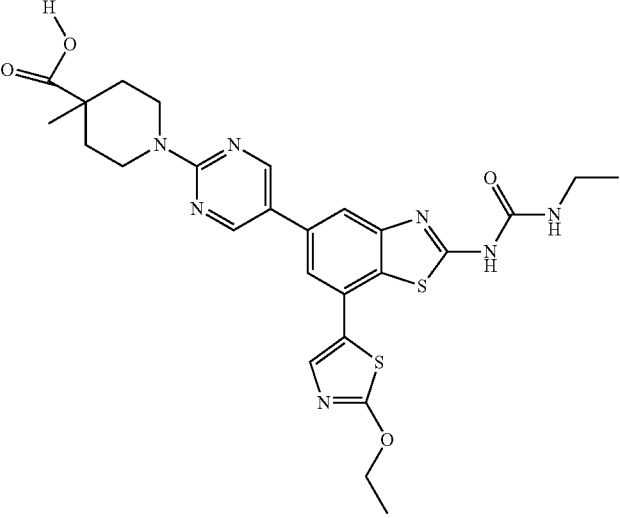 [SMILES: CCNC(=O)Nc1nc2cc(-c3cnc(N4CCC(C)(C(=O)O)CC4)nc3)cc(-c3cnc(OCC)s3)c2s1] | 568.1 | (CDCl3) δ 8.62 (s, 2H), 7.80-7.59 (m, 2H), 7.07 (s, 1H), 4.64 (q, J = 7.0 Hz, 2H), 4.19 (d, J = 14.8 Hz, 2H), 3.74 (s, 3H), 3.51-3.36 (m, 3H), 2.32-2.13 (m, 3H), 1.57 (t, J = 9.6 Hz, 2H), 1.51 (t, J = 7.1 Hz, 3H), 1.38 (s, 3H), 1.29 (t, J = 7.2 Hz, 3H). |
| 79 | 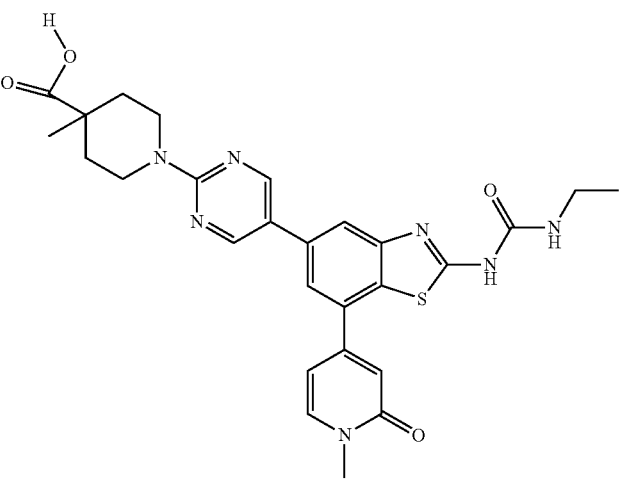 [SMILES: CCNC(=O)Nc1nc2cc(-c3cnc(N4CCC(C)(C(=O)O)CC4)nc3)cc(-c3ccn(C)c(=O)c3)c2s1] | 548.1 | (CDCl3) δ 8.55 (s, 2H), 7.67 (s, 1H), 7.44-7.33 (m, 2H), 6.96 (s, 1H), 6.57 (dd, J = 7.1, 2.0 Hz, 1H), 4.10-4.02 (s, 2H), 3.91-3.84 (s, 2H), 3.63 (s, 3H), 3.51-3.33 (m, 2H), 2.19 (d, J = 18.5 Hz, 2H), 1.53-1.48 (m, 2H), 1.39 (s, 3H), 1.27 (t, J = 7.2 Hz, 3H). |

| Cpd No. | Structure | LCMS data [M + H]+ | 1H NMR data |
|---|---|---|---|
| 115 | 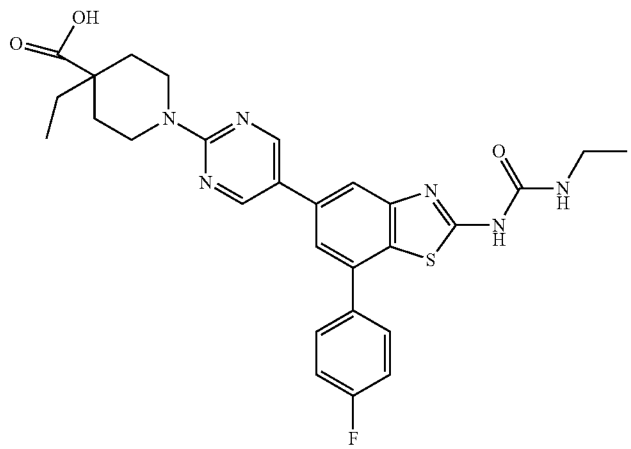 [SMILES: CCNC(=O)Nc1nc2cc(-c3cnc(N4CCC(CC)(C(=O)O)CC4)nc3)cc(-c3ccc(F)cc3)c2s1] | 549.1 | (DMSO) δ 7.81 (s, 2H), 6.92 (d, J = 1.6 Hz, 1H), 6.90-6.86 (m, 2H), 6.54 (d, J = 1.6 Hz, 1H), 6.42-6.37 (m, 2H), 3.74-3.67 (m, 2H), 2.49-2.40 (m, 2H), 1.47-1.40 (m, 2H), 0.86-0.79 (m, 2H), 0.70-0.61 (m, 2H), 0.43 (t, J = 7.4 Hz, 3H), 0.11 (t, J = 7.4 Hz, 3H) |
| 205 | 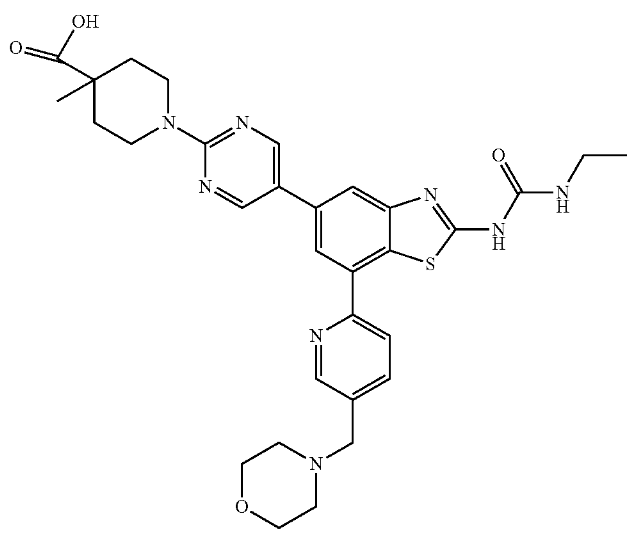 [SMILES: CCNC(=O)Nc1nc2cc(-c3cnc(N4CCC(C)(C(=O)O)CC4)nc3)cc(-c3ccc(CN4CCOCC4)cn3)c2s1] | 617.31 | δ 12.46 (br s, 1H), 10.56 (br s, 1H), 8.90 (s, 2H), 8.71 (s, 1H), 8.45 (d, J = 8.0 Hz, 1H), 8.21 (s, 1H), 7.94 (s, 1H), 7.89 (m, 1H), 6.89 (br s, 1H), 4.32 (m, 2H), 3.60 (br s, 6H), 3.38 (m, 2H), 3.21 (m, 2H), 2.41 (m, 4H), 2.03 (m, 2H), 1.40 (m, 2H), 1.22 (s, 3H) and 1.09 (t, J = 6.80 Hz, 3H). |
| 217 | 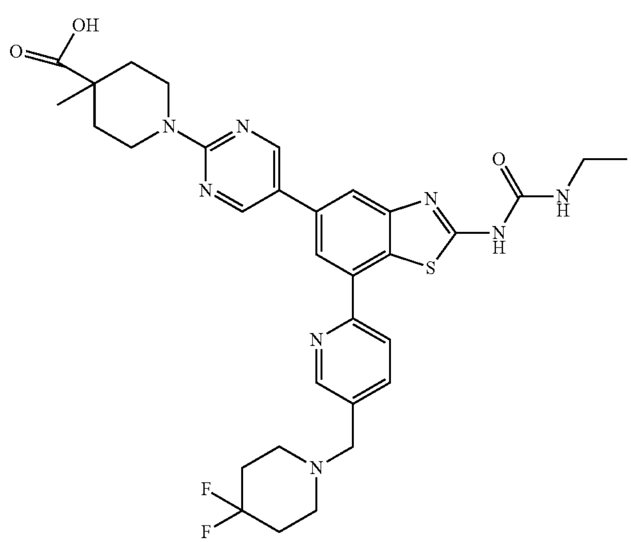 [SMILES: CCNC(=O)Nc1nc2cc(-c3cnc(N4CCC(C)(C(=O)O)CC4)nc3)cc(-c3ccc(CN4CCC(F)(F)CC4)cn3)c2s1] | 649.27 | δ 12.45 (br s, 1H), 10.54 (br s, 1H), 8.90 (s, 2H), 8.72 (s, 1H), 8.45 (m, 1H), 8.21 (s, 1H), 7.90-7.94 (m, 2H), 6.86 (br s, 1H), 4.32 (m, 2H), 3.68 (s, 2H), 3.36 (m, 2H), 3.21 (m, 2H), 2.50 (m, 4H), 2.02 (m, 6H), 1.40 (m, 2H), 1.19 (s, 3H) and 1.09 (t, J = 6.80 Hz, 3H). |

| Cpd No. | Structure | LCMS data [M + H]+ | 1H NMR data |
|---|---|---|---|
| 226 | 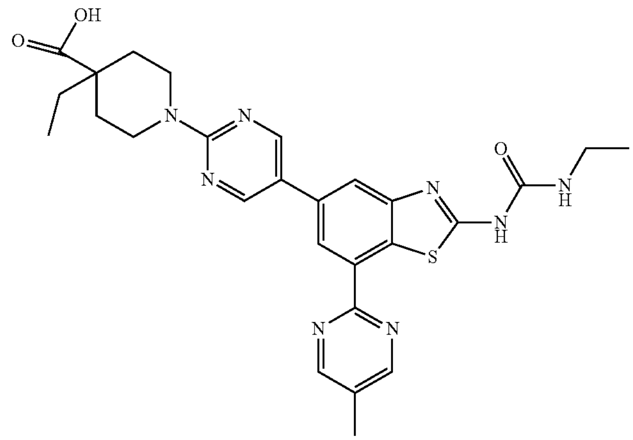 [SMILES: CCNC(=O)Nc1nc2cc(-c3cnc(N4CCC(CC)(C(=O)O)CC4)nc3)cc(-c3ncc(C)cn3)c2s1] | 547.26 | δ 12.68 (br s, 1H), 10.63 (br s, 1H), 8.90 (s, 2H), 8.78 (s, 2H), 8.52 (s, 1H), 7.91 (s, 1H), 6.84 (br s, 1H), 4.49 (m, 2H), 3.12-3.23 (m, 4H), 2.37 (s, 3H), 2.07 (m, 2H), 1.53 (m, 2H), 1.35 (m, 2H), 1.11 (t, J = 7.2 Hz, 3H) and 0.81 (t, J = 7.2 Hz, 3H). |
| 228 | 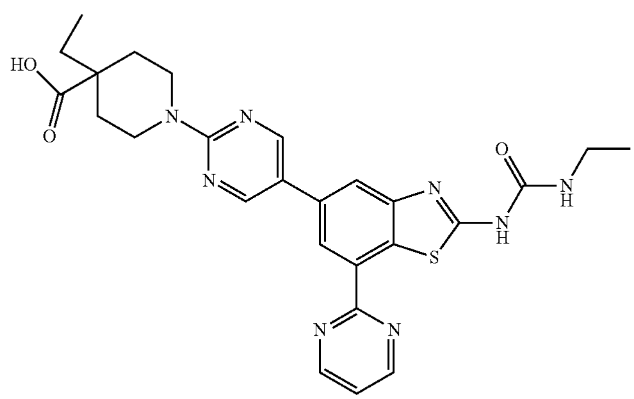 [SMILES: CCNC(=O)Nc1nc2cc(-c3cnc(N4CCC(CC)(C(=O)O)CC4)nc3)cc(-c3ncccn3)c2s1] | 533.25 | δ 12.49 (br s, 1H), 10.64 (br s, 1H), 9.07 (d, J = 8.4 Hz, 2H), 8.79 (s, 2H), 8.58 (s, 1H), 8.04 (s, 1H), 7.54 (t, J = 8.4 Hz, 1H), 6.83 (s, 1H), 4.49 (m, 2H), 3.21 (m, 4H), 2.04-2.07 (m, 2H), 1.53 (m, 2H), 1.35 (m, 2H), 1.10 (t, J = 7.2 Hz, 3H) and 0.81 (t, J = 7.2 Hz, 3H). |

Compound 23: 1-[5-[2-(ethylcarbamoylamino)-7-(2-methoxythiazol-4-yl)-1,3-benzothiazol-5-yl]pyrimidin-2-yl]-4-methyl-piperidine-4-carboxylic acid

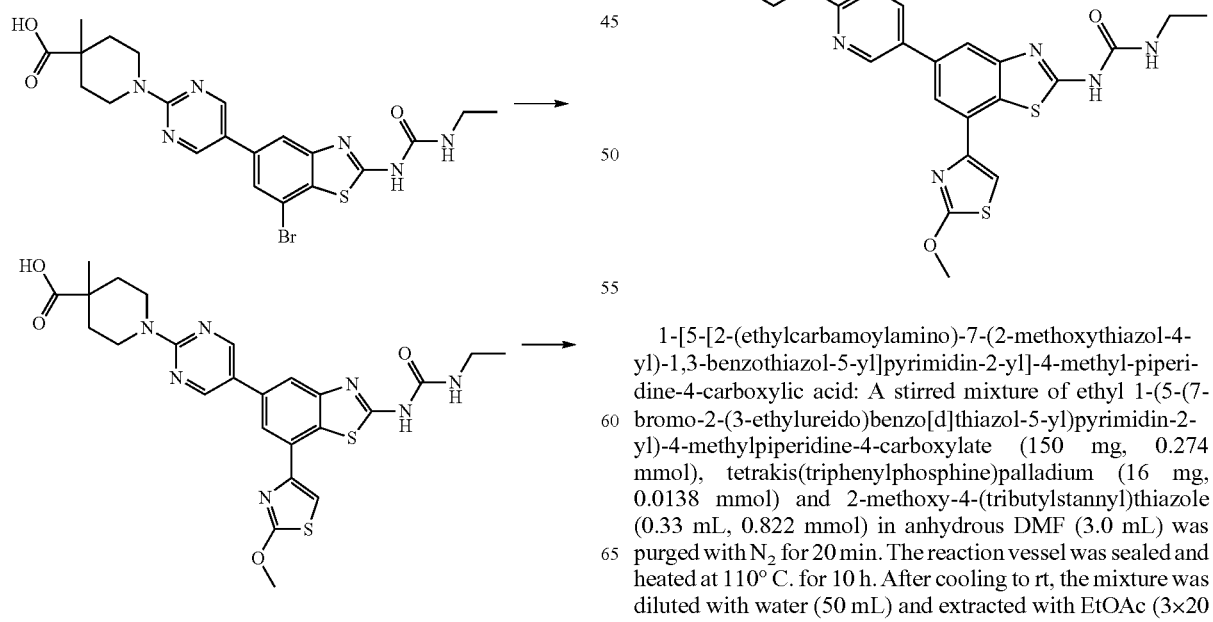

1-[5-[2-(ethylcarbamoylamino)-7-(2-methoxythiazol-4-yl)-1,3-benzothiazol-5-yl]pyrimidin-2-yl]-4-methyl-piperidine-4-carboxylic acid: A stirred mixture of ethyl 1-(5-(7-bromo-2-(3-ethylureido)benzo[d]thiazol-5-yl)pyrimidin-2-yl)-4-methylpiperidine-4-carboxylate (150 mg, 0.274 mmol), tetrakis(triphenylphosphine)palladium (16 mg, 0.0138 mmol) and 2-methoxy-4-(tributylstannyl)thiazole (0.33 mL, 0.822 mmol) in anhydrous DMF (3.0 mL) was purged with N₂ for 20 min. The reaction vessel was sealed and heated at 110° C. for 10 h. After cooling to rt, the mixture was diluted with water (50 mL) and extracted with EtOAc (3×20 mL) which was washed with brine (30 mL) and dried (MgSO₄). The solvent was removed in vacuo and the residue purified by flash silica chromatography eluting with 0 to 100% EtOAc in iso-hexane to give 99 mg of the desired product as an off white gummy solid.

1-[5-[2-(ethylcarbamoylamino)-7-(2-methoxythiazol-4-yl)-1,3-benzothiazol-5-yl]pyrimidin-2-yl]-4-methyl-piperidine-4-carboxylic acid (23): A stirred solution of 1-[5-[2-(ethylcarbamoylamino)-7-(2-methoxythiazol-4-yl)-1,3-benzothiazol-5-yl]pyrimidin-2-yl]-4-methyl-piperidine-4-carboxylic acid (99 mg, 0.17 mmol) in the minimum of DMSO was cooled in an ice bath and treated with potassium tert-butoxide (95 mg, 0.85 mmol). When the addition was complete, the mixture was allowed to come to rt and stirred for 1 h by which time LCMS showed complete reaction. The reaction mixture was then diluted with water (20 mL) and washed with EtOAc (20 mL). The aqueous portion was acidified (pH4) by the addition of dilute hydrochloric acid and concentrated to a small volume in vacuo. The residue was dissolved in DMSO and purified by preparative-HPLC. Compound 23 was obtained as a pale yellow solid (31 mg, 33% yield). ¹HNMR δ (ppm) (DMSO-d₆): 8.88 (2H, s), 8.02 (1H, d, J=1.67 Hz), 7.87 (2H, s), 6.96 (1H, s), 4.32 (2H, dt, J=13.81, 4.49 Hz), 4.25 (3H, s), 3.38 (2H, ddd, J=14.70, 8.77, 3.84 Hz), 3.24 (2H, p, J=6.77 Hz), 2.06 (2H, dt, J=13.42, 3.67 Hz), 1.42 (2H, ddd, J=13.42, 10.03, 3.87 Hz), 1.22 (3H, s), 1.14 (3H, t, J=7.18 Hz). MS 554.0 [M+H]⁺

The following compounds were similarly prepared.

| Cpd No. | Structure | LCMS data [M + H]⁺ | ¹H NMR data |
|---|---|---|---|
| 19 | 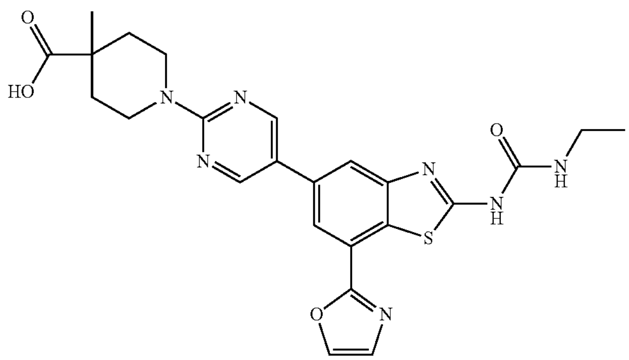 [SMILES: CCNC(=O)Nc1nc2cc(-c3cnc(N4CCC(C)(C(=O)O)CC4)nc3)cc(-c3ncco3)c2s1] | 508 | (DMSO-d₆): δ 8.84 (2 H, s), 8.40 (1 H, d, J = 0.85 Hz), 8.05 (2 H, dd, J = 6.53, 1.67 Hz), 7.60 (1 H, d, J = 0.84 Hz), 7.15 (1 H, t, J = 5.48 Hz), 4.33 (2 H, dt, J = 13.66, 4.50 Hz), 3.38 (2 H, ddd, J = 13.97, 10.30, 4.02 Hz), 3.25 (2 H, p, J = 6.82 Hz), 2.57 (1 H, s), 2.06 (2 H, dt, J = 13.49, 3.81 Hz), 1.42 (2 H, ddd, J = 13.47, 10.01, 4.12 Hz), 1.22 (3 H, s), 1.14 (3 H, q, J = 7.22 Hz). |
| 20 | 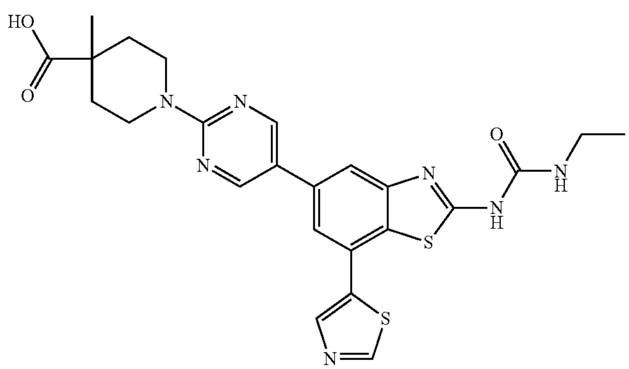 [SMILES: CCNC(=O)Nc1nc2cc(-c3cnc(N4CCC(C)(C(=O)O)CC4)nc3)cc(-c3cncs3)c2s1] | 524 | (DMSO-d₆): δ 9.29 (1 H, s), 8.86 (2 H, s), 8.53 (1 H, s), 7.94 (1 H, d, J = 1.57 Hz), 7.83 (1 H, d, J = 1.59 Hz), 7.27 (1 H, s), 4.32 (2 H, dt, J = 13.67, 4.50 Hz), 3.39 (2 H, ddd, J = 14.69, 10.79, 4.59 Hz), 3.23 (2 H, p, J = 6.89 Hz), 2.06 (2 H, dt, J = 13.48, 3.75 Hz), 1.41 (2 H, ddd, J = 13.34, 9.96, 3.88 Hz), 1.22 (3 H, s), 1.14 (3 H, t, J = 7.17 Hz). |
| 21 | 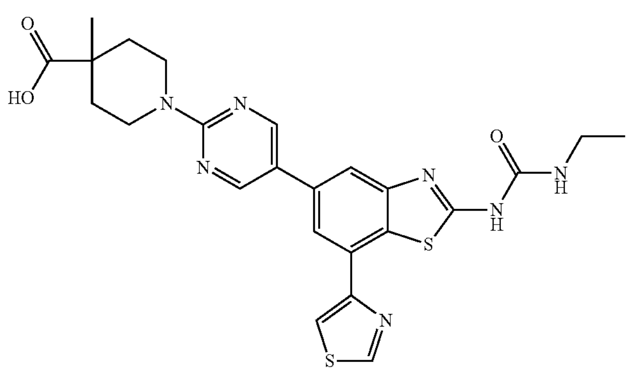 [SMILES: CCNC(=O)Nc1nc2cc(-c3cnc(N4CCC(C)(C(=O)O)CC4)nc3)cc(-c3cscn3)c2s1] | 524 | (DMSO-d₆): δ 10.83 (1 H, s), 9.40 (1 H, d, J = 1.89 Hz), 8.91 (2 H, s), 8.62 (1 H, d, J = 1.96 Hz), 8.15 (1 H, d, J = 1.64 Hz), 7.91 (1 H, d, J = 1.59 Hz), 7.06 (1 H, t, J = 5.41 Hz), 4.33 (2 H, dt, J = 13.75, 4.49 Hz), 3.61-3.19 (4 H, m), 3.24 (4 H, p, J = 6.95 Hz), 2.06 (2 H, dt, J = 13.56, 3.71 Hz), 1.42 (2 H, ddd, J = 13.39, 10.05, 3.92 Hz), 1.22 (3 H, s), 1.15 (3 H, t, J = 7.15 Hz). |

Compound 26: 1-[5-[2-(ethylcarbamoylamino)-7-hydroxy-1,3-benzothiazol-5-yl]pyrimidin-2-yl]-4-methyl-piperidine-4-carboxylic acid

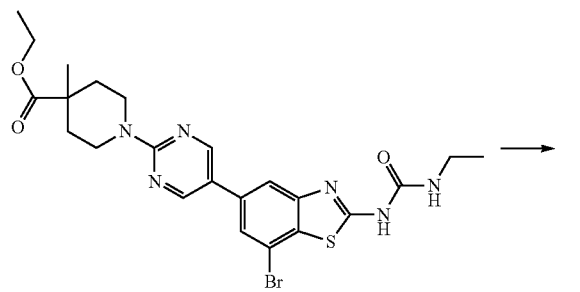

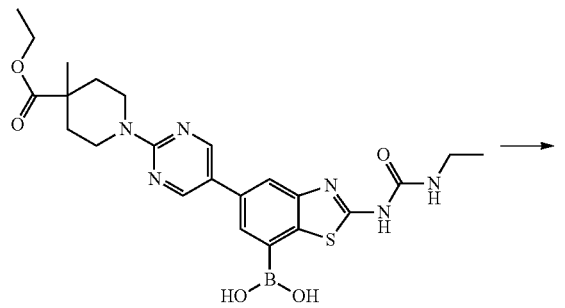

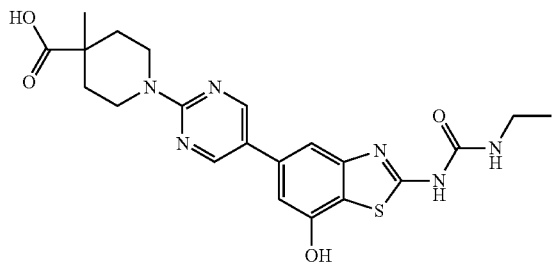

[5-[2-(4-Ethoxycarbonyl-4-methyl-1-piperidyl)pyrimidin-5-yl]-2-(ethylcarbamoylamino)-1,3-benzothiazol-7-yl]boronic acid A stirred mixture ethyl 1-[5-[7-bromo-2-(ethylcarbamoylamino)-1,3-benzothiazol-5-yl]pyrimidin-2-yl]-4-methyl-piperidine-4-carboxylate (513 mg, 0.938 mmol), bis(neopentyl)glycolatodiboron (634 mg, 2.822 mmol), potassium acetate (366 mg, 3.75 mmol) and 1,1'-bis(diphenylphosphino)ferrocene palladium(II)chloride (76 mg, 0.094 mmol) in anhydrous DMF (9.8 mL) was purged with $N_2$ for 15 min, sealed and heated at 80° C. for 16 h, by which time HPLC showed complete reaction. The reaction mixture was cooled to rt, diluted with DCM (100 mL), washed with water (100 mL) followed by brine (100 mL) and dried ($MgSO_4$). The solvent was removed in vacuo and the residue purified by flash silica chromatography eluting with 0 to 100% EtOAc in iso-hexane to give the desired product as an off white solid (316 mg, 60% yield).

1-[5-[2-(Ethylcarbamoylamino)-7-hydroxy-1,3-benzothiazol-5-yl]pyrimidin-2-yl]-4-methyl-piperidine-4-carboxylic acid (26)

A stirred suspension of [5-[2-(4-ethoxycarbonyl-4-methyl-1-piperidyl)pyrimidin-5-yl]-2-(ethylcarbamoylamino)-1,3-benzothiazol-7-yl]boronic acid (166 mg, 0.286 mmol) in aqueous NaOH solution (2 M, 1.3 mL) was treated with excess hydrogen peroxide (27.5% aqueous solution, 0.45 mL) and kept at rt for 3 days by which time LCMS showed complete reaction. The resultant mixture was diluted with water (30 mL) and acidified by the addition of a small amount of conc. sulfuric acid. The precipitated solid was collected by filtration, washed with water (10 mL) and dried in vacuo to give Compound 26 as a white solid (102 mg, 78% yield). $^1$H NMR (DMSO-$d_6$): δ 10.37 (1H, s), 8.67 (2H, s), 7.37 (1H, s), 6.85 (1H, s), 6.77 (1H, t, J=5.86 Hz), 4.30 (2H, dt, J=13.75, 4.56 Hz), 3.36 (2H, ddd, J=13.34, 9.92, 3.07 Hz), 3.22 (2H, p, J=6.69 Hz), 2.04 (2H, dt, J=13.63, 3.69 Hz), 1.42 (2H, ddd, J=13.55, 10.29, 3.91 Hz), 1.22 (3H, s), 1.13 (3H, t, J=7.19 Hz). m/z: 457 [M+H]$^+$.

Compound 37: 1-{5-[7-Ethyl-2-(3-ethyl-ureido)-benzothiazol-5-yl]-pyrimidin-2-yl}-4-methyl-piperidine-4-carboxylic acid (alternatively named 1-[5-[7-ethyl-2-(ethylcarbamoylamino)-1,3-benzothiazol-5-yl]pyrimidin-2-yl]-4-methyl-piperidine-4-carboxylic acid)

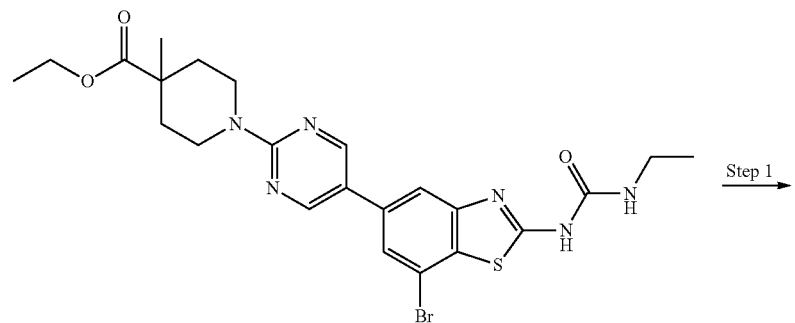

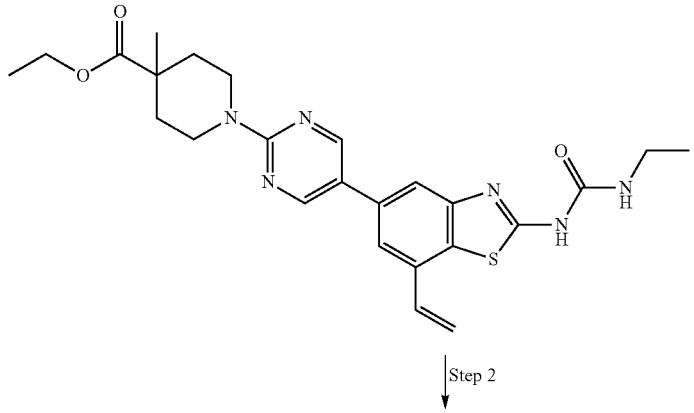

Step 2 ↓

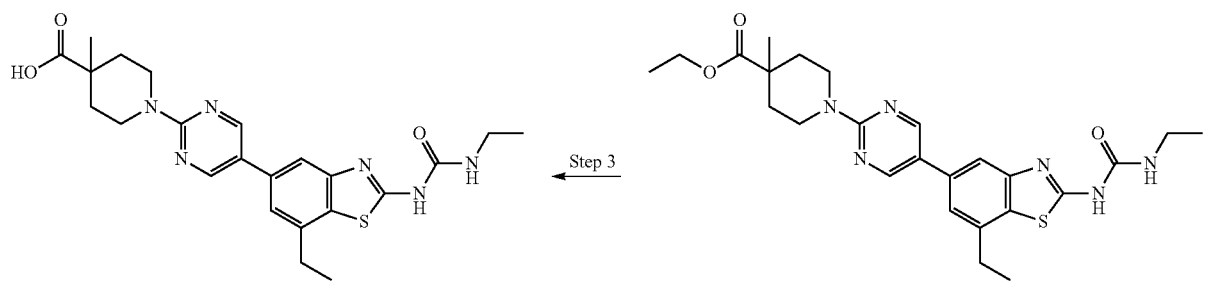

1-{5-[2-(3-Ethyl-ureido)-7-vinyl-benzothiazol-5-yl]-pyrimidin-2-yl}-4-methyl-piperidine-4-carboxylic acid ethyl ester 1-{5-[7-Bromo-2-(3-ethyl-ureido)-benzothiazol-5-yl]-pyrimidin-2-yl}-4-methyl-piperidine-4-carboxylic acid ethyl ester (50 mg), 4,4,5,5-tetramethyl-2-vinyl-1,3,2-dioxaborolane (28 mg), PdCl$_2$(dppf).DCM (4 mg), potassium fluoride (16 mg), 1,4-dioxane (1.5 mL) and water (0.5 mL) were combined in a 0.5-2 mL microwave vial, degassed and heated in a pre-heated oil bath at 90° C. overnight. The mixture was cooled to rt, diluted with water and extracted into EtOAc (4×10 mL). The organic phase was washed with brine, dried over Na$_2$SO$_4$ and concentrated in vacuo. The residue was purified by Biotage Si chromatography, 12 g Grace cartridge, 4-5% MeOH in DCM. The relevant fractions were combined to give a solid (56 mg) which was purified again by Biotage Si chromatography, 12 g Grace cartridge, 2% MeOH in DCM isocratic. The relevant fractions were combined to give the desired product as a light orange solid (27 mg, 60%). m/z: 495 [M+H]$^+$.

1-{5-[7-Ethyl-2-(3-ethyl-ureido)-benzothiazol-5-yl]-pyrimidin-2-yl}-4-methyl-piperidine-4-carboxylic acid ethyl ester 1-{5-[2-(3-Ethyl-ureido)-7-vinyl-benzothiazol-5-yl]-pyrimidin-2-yl}-4-methyl-piperidine-4-carboxylic acid ethyl ester (27 mg) was dissolved in EtOH (5 mL), THF (0.5 mL) and acetic acid (0.5 mL) and 10% palladium on carbon (6 mg) and ammonium formate (168 mg) added. The flask was evacuated and purged with N$_2$ (×2) and stirred at 60° C. for four days. The mixture was cooled to rt and filtered through a PTFE filter. The filter was rinsed with EtOH/DCM and the filtrate concentrated under reduced pressure. The residue was then taken up in EtOAc and washed with Na$_2$CO$_3$ (sat, aq). The aqueous layer was washed with EtOAc. The combined organic layers were washed with brine, dried over Na$_2$SO$_4$ and concentrated in vacuo. The residue was purified by chromatography, Biotage, 12 g Grace cartridge, DCM to 4% MeOH in DCM and the relevant fractions combined and concentrated under reduced pressure to give the desired product as a white solid (19 mg, 70%). m/z: 497 [M+H]$^+$.

1-{5-[7-Ethyl-2-(3-ethyl-ureido)-benzothiazol-5-yl]-pyrimidin-2-yl}-4-methyl-piperidine-4-carboxylic acid (37)

1-{5-[7-Ethyl-2-(3-ethyl-ureido)-benzothiazol-5-yl]-pyrimidin-2-yl}-4-methyl-piperidine-4-carboxylic acid ethyl ester (19 mg) was dissolved in EtOH (1 mL) and 1 M aq NaOH (1 mL) added. The mixture was stirred at 70° C. overnight. The mixture was cooled to rt and acidified to pH 3 with 1 M HCl (aq) then concentrated in vacuo and the residue suspended (sonication) in ~10% MeOH in DCM. The mixture was filtered through a syringe filter (20 micron) and the filtrate concentrated in vacuo. A cream solid was obtained (54 mg) and purified by preperative HPLC (Gilson, 40s-70-100% water/MeCN+0.1% formic acid). The relevant fractions were combined and concentrated in vacuo slightly then freeze-dried to give Compound 37 (2 mg) as a white solid. ¹H NMR (CDCl₃+CD₃OD): δ 1.21 (3H, t, J=7.2 Hz), 1.25 (3H, s), 1.35 (3H, t, J=7.6 Hz), 1.45 (2H, m), 2.17 (2H, br d, J=13.6 Hz), 2.85 (2H, q, J=7.6 Hz), 3.32-3.41 (4H, m), 4.31 (2H, br dt, J=13.8 and 4.0 Hz), 7.14 (1H, s), 7.54 (1H, s), 8.54 (1H, s), 8.54 (1H, s). m/z: 469 [M+H]⁺.

Compound 38 1-{5-[2-(3-Ethyl-ureido)-7-methyl-benzothiazol-5-yl]-pyrimidin-2-yl}-4-methyl-piperidine-4-carboxylic acid (alternatively named 1-[5-[2-(ethylcarbamoylamino)-7-methyl-1,3-benzothiazol-5-yl]pyrimidin-2-yl]-4-methyl-piperidine-4-carboxylic acid)

under reduced pressure. The mixture was purified by chromatography Si 12 g Grace cartridge, DCM to 75% EtOAc in DCM. The relevant fractions were combined to give a cream solid (55 mg) which was shown by ¹H NMR in CDCl₃ plus drop MeOD to be approximately 1:1 mixture of starting material and product. The mixture was used with no further purification. m/z: 483 [M+H]⁺.

1-{5-[2-(3-Ethyl-ureido)-7-methyl-benzothiazol-5-yl]-pyrimidin-2-yl}-4-methyl-piperidine-4-carboxylic acid (38)

1-{5-[2-(3-Ethyl-ureido)-7-methyl-benzothiazol-5-yl]-pyrimidin-2-yl}-4-methyl-piperidine-4-carboxylic acid

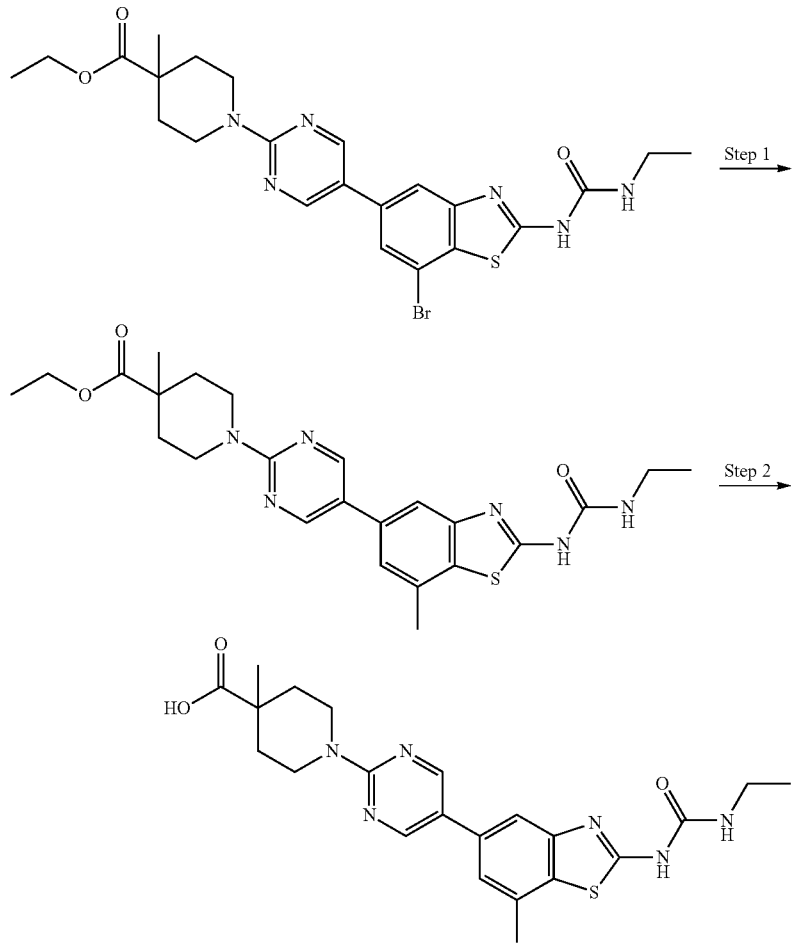

1-{5-[2-(3-Ethyl-ureido)-7-methyl-benzothiazol-5-yl]-pyrimidin-2-yl}-4-methyl-piperidine-4-carboxylic acid ethyl ester 1-{5-[7-Bromo-2-(3-ethyl-ureido)-benzothiazol-5-yl]-pyrimidin-2-yl}-4-methyl-piperidine-4-carboxylic acid ethyl ester (75 mg), 2,4,6-trimethyl-cyclotriboroxane (0.19 mL) and PdCl₂(dppf).DCM (6 mg) were dissolved in 1,4-dioxane (2 mL) in a 2-5 mL microwave vial and a solution of potassium fluoride (24 mg) in water (0.67 mL) added. The mixture was degassed and heated in the microwave at 130° C. for 20 minutes. LCMS showed the reaction to be about 50% conversion to product. The mixture was diluted with water, extracted into EtOAc (4×10 mL) and the organic phase washed with brine, dried over Na₂SO₄ and concentrated ethyl ester (55 mg, ~50% purity) was dissolved in EtOH (1 mL) and 1 M aq NaOH (1 mL) added. The mixture was heated at 70° C. overnight. The mixture was cooled to rt and acidified to pH 3 with 1 M HCl (aq). The mixture was concentrated in vacuo, the residue suspended in MeCN and concentrated to dryness again. The white solid obtained was sonicated in ~10% MeOH in DCM and filtered through celite. The filtrate was concentrated under reduced pressure to give a cream solid (33 mg). The mixture was suspended in MeOH plus drop water and filtered and the filtrate purified by preperative HPLC (Gilson, isocratic 45% water/MeCN+0.1% formic acid). The relevant fractions were combined and freeze dried to afford Compound 38 as a white solid (9 mg). ¹H NMR (CDCl₃+CD₃OD): δ 1.19 (3H, t, J=7.2 Hz), 1.26 (3H, s), 1.46 (2H, m), 2.14 (2H, br d, J=14.0 Hz), 2.49 (3H, s), 3.33 (2H, q, J=7.2 Hz), 3.45 (2H, m), 4.23 (2H, br dt, J=14.0 and 4.5 Hz), 7.07 (1H, s), 7.50 (1H, s), 8.50 (2H, s). m/z: 455 [M+H]$^+$.

Compound 39: 1-{5-[7-Cyclohexyl-2-(3-ethyl-ureido)-benzothiazol-5-yl]-pyrimidin-2-yl}-4-methyl-piperidine-4-carboxylic acid (alternatively named 1-[5-[7-cyclohexyl-2-(ethylcarbamoylamino)-1,3-benzothiazol-5-yl]pyrimidin-2-yl]-4-methyl-piperidine-4-carboxylic acid)

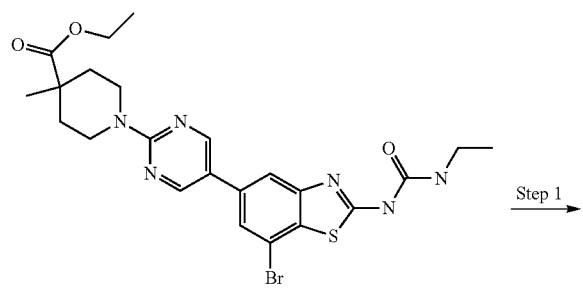

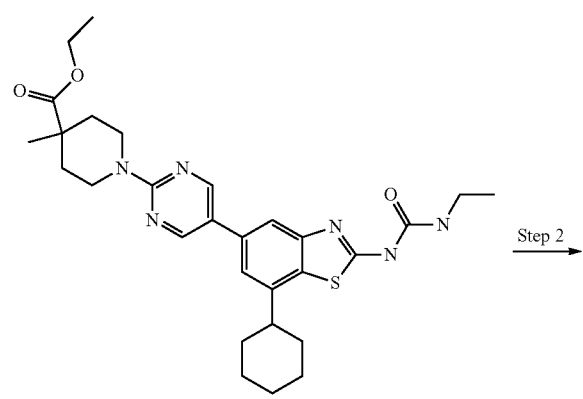

Ethyl 1-[5-[7-cyclohexyl-2-(ethylcarbamoylamino)-1,3-benzothiazol-5-yl]pyrimidin-2-yl]-4-methyl-piperidine-4-carboxylate Cyclohexylmagnesium chloride in Et$_2$O (2.03 mL, 3.65 mmol) was added to a THF (2.5 mL) solution of LiCl (53 mg, 1.25 mmol) and 1M zinc chloride in Et$_2$O (4.38 mL, 4.38 mmol) at rt, after which a grey precipitate immediately formed. After stirring at rt for 15 mins, a THF solution (3 mL) of 1-{5-[7-Bromo-2-(3-ethyl-ureido)-benzothiazol-5-yl]-pyrimidin-2-yl}-4-methyl-piperidine-4-carboxylic acid ethyl ester (100 mg, 182.66 mmol) and Pd(dppf)Cl$_2$.DCM (10 mol %) and was allowed to stir at rt for 30 mins. Subsequent heating at reflux gave minimal formation of the desired product and an equimolar amount of the hydrodebrominated starting material. The reaction mixture was transferred to a microwave vessel and heated at 110° C. for 30 mins. The reaction mixture was quenched with 1M HCl (1×5 mL), extracted with EtOAc (10 mL), dried (MgSO$_4$), concentrated in vacuo and subjected to reverse phase HPLC (60-80% water (0.1% FA):MeOH) to afford 2.7 mg (3% isolated yield) of a white solid.

1-{5-[7-Cyclohexyl-2-(3-ethyl-ureido)-benzothiazol-5-yl]-pyrimidin-2-yl}-4-methyl-piperidine-4-carboxylic acid (39)

The material obtain from the previous step was subsequently dissolved in 3:2 EtOH:1M NaOH (0.5 mL) and irradiated for 30 mins at 120° C. in a microwave reactor. The reaction mixture was diluted with water/EtOH (1 mL), acidified with 1M HCl (1.0 mL), extracted with EtOAc (6 mL) and the organic fraction washed with sat. brine (4 mL), dried (MgSO$_4$) and concentrated in vacuo to afford 2 mg (77%) yield of Compound 39. $^1$H NMR (CDCl$_3$) δ 8.57 (s, 2H), 7.53 (d, J=6.3 Hz, 1H), 7.17 (t, J=8.9 Hz, 1H), 4.11 (dd, J=13.5, 6.9 Hz, 2H), 3.82 (s, 2H), 3.48-3.40 (m, 2H), 2.72 (dd, J=13.4, 10.5 Hz, 1H), 2.30-0.80 (m, 21H). MS: 566.2 [M+H]$^+$.

Compound 41 1-[5-[2-(ethylcarbamoylamino)-7-(1-phenyltriazol-4-yl)-1,3-benzothiazol-5-yl]pyrimidin-2-yl]-4-methyl-piperidine-4-carboxylic acid

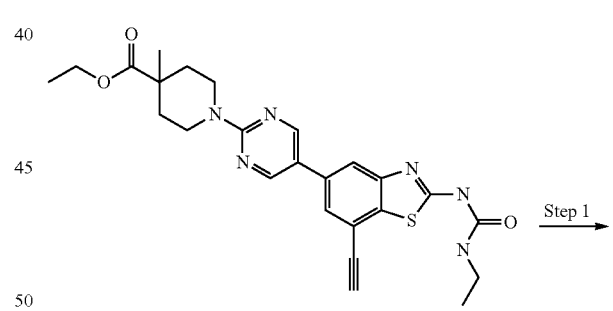

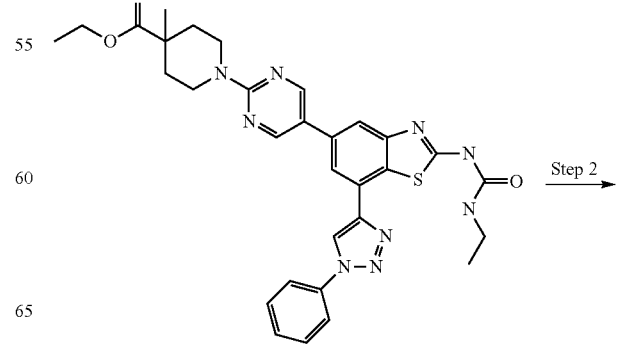

-continued

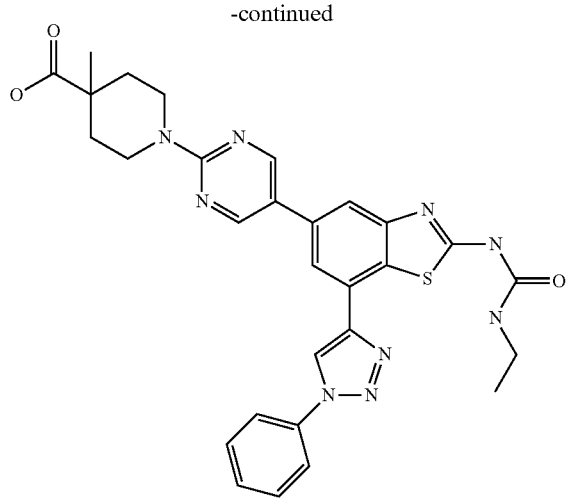

Ethyl 1-[5-[2-(ethylcarbamoylamino)-7-(1-phenyltriazol-4-yl)-1,3-benzothiazol-5-yl]pyrimidin-2-yl]-4-methyl-piperidine-4-carboxylate: Aniline (18.9 mg, 0.203 mmol) in ACN (2 mL) was cooled to 0° C., t-Butyl nitrite (31.4 mg, 0.305 mmol) was added dropwise, the reaction stirred for 5 minutes, then trimethylsilylazide (50.7 mg, 0.244 mmol) was added in one portion and the mixture allowed to warm to rt and stirred for hours. Ethyl 1-[5-[2-(ethylcarbamoylamino)-7-ethynyl-1,3-benzothiazol-5-yl]pyrimidin-2-yl]-4-methyl-piperidine-4-carboxylate (100 mg, 0.203 mmol) and sodium ascorbate (8.1 mg, 0.040 mmol) were added, followed by copper sulphate (1.6 mg, 0.010 mmol) in 0.1 mL of water. The reaction was stirred at rt for 18 hours, filtered through a pad of keiselguhr and the solvent removed under vacuum to yield a brown gum. The crude material was purified by preperative HPLC to give the product as an off white solid 28 mg, 22.6% yield.

1-[5-[2-(Ethylcarbamoylamino)-7-(1-phenyltriazol-4-yl)-1,3-benzothiazol-5-yl]pyrimidin-2-yl]-4-methyl-piperidine-4-carboxylic acid (41): The hydrolysis was carried out using similar conditions to those described for Compound 9 to give Compound 41 as an off white solid 7.9 mg, 29% yield $^1$H NMR (DMSO-$d_6$): δ 12.50 (1H, s), 10.82 (1H, s), 9.68 (1H, s), 8.92 (2H, s), 8.12 (1H, d, J=1.65 Hz), 8.03 (2H, d, J=7.99 Hz), 7.97 (1H, d, J=1.63 Hz), 7.72 (2H, t, J=7.76 Hz), 7.60 (1H, t, J=7.44 Hz), 6.97 (1H, t, J=5.49 Hz), 4.34 (2H, dt, J=13.69, 4.45 Hz), 3.40 (2H, t, J=10.86 Hz), 3.26 (2H, p, J=6.70 Hz), 2.06 (2H, dt, J=13.58, 3.73 Hz), 1.43 (2H, ddd, J=13.68, 9.65, 3.95 Hz), 1.23 (3H, s), 1.16 (3H, t, J=7.18 Hz). MS: 584 [M+H]$^+$.

Compound 46: 1-{5-[2-(3-Ethyl-ureido)-benzothiazol-5-yl]-pyrimidin-2-yl}-4-methyl-piperidine-4-carboxylic acid (alternatively named 1-[5-[2-(ethylcarbamoylamino)-1,3-benzothiazol-5-yl]pyrimidin-2-yl]-4-methyl-piperidine-4-carboxylic acid)

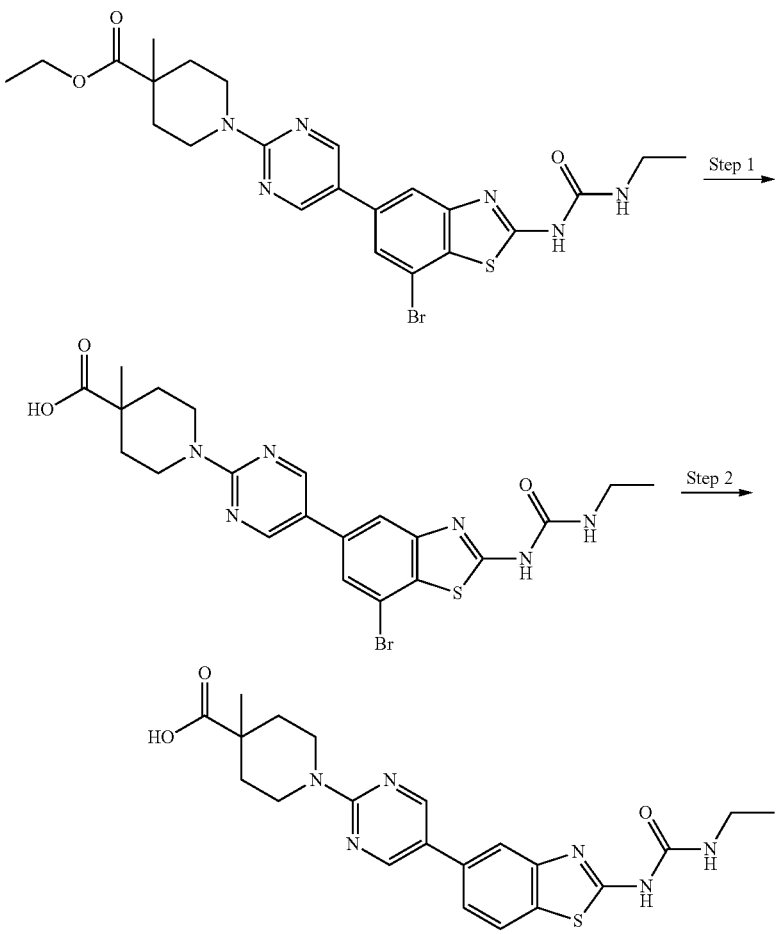

1-{5-[7-Bromo-2-(3-ethyl-ureido)-benzothiazol-5-yl]-pyrimidin-2-yl}-4-methyl-piperidine-4-carboxylic acid 1-{5-[7-Bromo-2-(3-ethyl-ureido)-benzothiazol-5-yl]-pyrimidin-2-yl}-4-methyl-piperidine-4-carboxylic acid ethyl ester (50 mg) was dissolved in THF (1 mL) and 1 M aq NaOH (1 mL) added. The mixture was heated to 70° C. overnight. LCMS showed approx 50% conversion to product. EtOH (0.5 mL) was added and heating continued for a further 6 h. The mixture was acidified to pH 3 with 1 M HCl (aq) and concentrated under reduced pressure. The mixture was suspended in ~10% MeOH in DCM and filtered through a syringe filter. The filtrate was concentrated in vacuo to give the desired product as an off-white solid (16 mg) which was used in the next step with no further purification. m/z: 519/521 [M+H]$^+$.

1-{5-[2-(3-Ethyl-ureido)-benzothiazol-5-yl]-pyrimidin-2-yl}-4-methyl-piperidine-4-carboxylic acid (46)

1-{5-[7-Bromo-2-(3-ethyl-ureido)-benzothiazol-5-yl]-pyrimidin-2-yl}-4-methyl-piperidine-4-carboxylic acid (16 mg) was dissolved in EtOH (5 mL), THF (1 mL) and AcOH (0.5 mL) and 10% palladium on carbon (3 mg) was added followed by ammonium formate (78 mg). The mixture was degassed and heated at 60° C. for four days then cooled to rt. The mixture was filtered through a syringe filter and the filtrate concentrated in vacuo. The material was purified by preperative HPLC (Gilson, 40-60%, water/MeCN+0.1% formic acid). The relevant fractions were combined and freeze-dried overnight to give Compound 46 as a white solid (5.2 mg). $^1$H NMR ((CD$_3$)$_2$SO): δ 1.09 (3H, t, J=7.2 Hz), 1.13 (3H, s), 1.29 (2H, m), 2.03 (2H, br d, J=13.5 Hz), 3.17 (4H, m), 4.1 (1H, br s), 4.23 (2H, br dt, J=13.5 and 4.7 Hz), 7.43 (1H, dd, J=8.2 and 1.5 Hz), 7.6 (1H, br s), 7.83 (1H, d, J=1.5 Hz), 7.88 (1H, d, J=8.2 Hz), 8.71 (2H, s), 11.5 (1H, br s). m/z: 441 [M+H]$^+$.

Compound 47 1-[5-[2-(ethylcarbamoylamino)-7-tetrahydropyran-4-yl-1,3-benzothiazol-5-yl]pyrimidin-2-yl]-4-methyl-piperidine-4-carboxylic acid

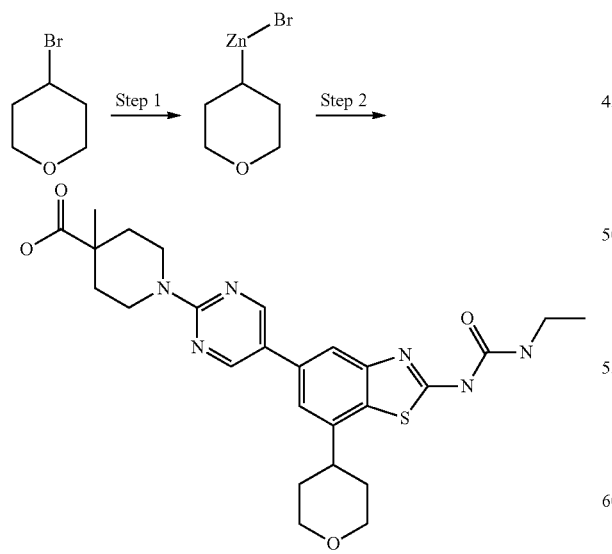

Bromo(tetrahydropyran-4-yl)zinc

Zinc dust (920 mg, 14 mmol) and lithium chloride (420 mg, 10 mmol) in a two-neck round bottom flask were heated under high vacuum with the aid of a heat gun for 15 minutes and allowed to cool to ambient temperature. The reaction vessel was backfilled with argon and evacuated three times, then THF (6 mL) was introduced through a rubber septa. The LiCl/Zn suspension was activated by the addition of trimethylsilyl chloride (18 μL, 140 nmol) and dibromoethane (60 μL, 700 nmol). 4-bromo-tetrahydropyran (1 g, 6.06 mmol) was added, and the reaction was allowed to stir overnight at rt. After this period the resulting organozinc species was iodometrically titrated following the literature procedure (A. Krasovskiy, A. Gavryushin, P. Knochel, *Synlett* (2006), 792) and was typically determined to be 0.65-0.8M.

1-{5-[2-(3-Ethyl-ureido)-7-(tetrahydro-pyran-4-yl)-benzothiazol-5-yl]-pyrimidin-2-yl}-4-methyl-piperidine-4-carboxylic acid ethyl ester (47)

A THF solution of the secondary alkylzinc bromide (0.80M; 0.32 mmol, 0.4 mL) was added to a stirred solution of the aryl bromide (55 mg, 1 mmol), CuI (15 mg, 79 umol) and Pd(dppf)Cl$_2$ (5 mol %) in THF (3 mL) at rt. The reaction was heated to 75° C. (sealed tube) and maintained at this temperature overnight. An additional 3.2 eq of the alkylzinc bromide solution in THF (400 μL, 79 μmol) was added, and allowed to stir at 75° C. for 2 h. The reaction mixture was allowed to cool, and was quenched with 1M HCl (5 mL) and washed with EtOAc (2×10 mL), followed by sat NaHCO$_3$ (10 mL) and sat. brine (1×10 mL). The organic extract was dried (MgSO$_4$), and concentrated in vacuo to afford 49.7 mg of a yellow wax. This was purified via reverse phase HPLC (60-80 MeCN/Water with 0.1% formic acid modifier) to afford 12.2 mg (21% yield) of Compound 47 as a white solid. $^1$H NMR (CDCl$_3$) δ 8.57 (s, 2H), 7.58 (s, 1H), 7.19 (s, 1H), 4.11 (d, J=10.6 Hz, 4H), 3.78 (d, J=20.6 Hz, 2H), 3.56 (t, J=10.3 Hz, 2H), 3.50-3.36 (m, 2H), 2.98 (s, 2H), 2.23 (s, 2H), 1.94 (s, 3H), 1.55 (dd, J=19.5, 10.9 Hz, 2H), 1.38 (s, 3H), 1.26 (dt, J=14.6, 7.1 Hz, 3H). MS: 525.2 [M+H]$^+$.

Compound 74 1-[5-[7-(1-acetyl-4-piperidyl)-2-(ethylcarbamoylamino)-1,3-benzothiazol-5-yl]pyrimidin-2-yl]-4-methyl-piperidine-4-carboxylic acid was similarly prepared

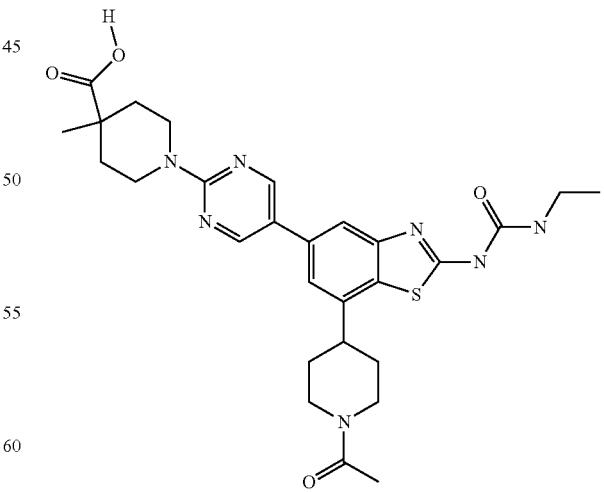

(CDCl$_3$) δ 8.54 (s, 2H), 7.58 (s, 1H), 7.13 (s, 1H), 4.85 (d, J=13.3 Hz, 1H), 4.17 (d, J=14.5 Hz, 2H), 3.97 (d, J=13.0 Hz, 1H), 3.74-3.63 (m, 2H), 3.43 (dd, J=13.1, 7.1 Hz, 2H), 3.20 (t, J=12.1 Hz, 1H), 2.95 (t, J=12.0 Hz, 1H), 2.66 (t, J=13.4 Hz, 1H), 2.28-2.19 (m, 2H), 2.16 (s, 3H), 2.02 (dd, J=19.4, 10.4

Hz, 2H), 1.87-1.70 (m, 2H), 1.54 (dd, J=15.7, 6.5 Hz, 2H), 1.37 (s, 3H), 1.28 (t, J=7.2 Hz, 3H). MS 566.2 [M+H]+.

Compound 50 1-[5-[2-(ethylcarbamoylamino)-7-(1-methyltriazol-4-yl)-1,3-benzothiazol-5-yl]pyrimidin-2-yl]-4-methyl-piperidine-4-carboxylic acid

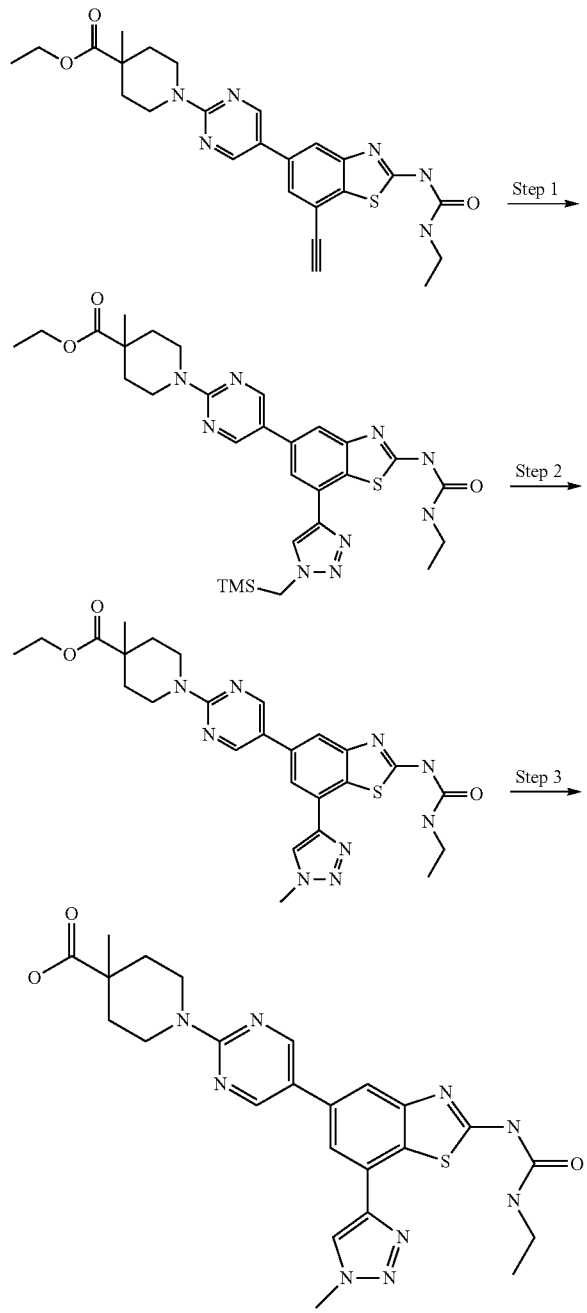

Ethyl 1-[5-[2-(ethylcarbamoylamino)-7-[1-(trimethylsilylmethyl)triazol-4-yl]-1,3-benzothiazol-5-yl]pyrimidin-2-yl]-4-methyl-piperidine-4-carboxylate: Ethyl 1-[5-[2-(ethylcarbamoylamino)-7-ethynyl-1,3-benzothiazol-5-yl]pyrimidin-2-yl]-4-methyl-piperidine-4-carboxylate (115 mg, 0.233 mmol), (azidomethyl)trimethylsilane (150 mg, 1.169 mmol), Copper(I)Iodide (8.9 mg, 0.0467 mmol), N-ethyl-N-isopropylpropan-2-amine (30.1 mg, 0.233 mmol) in 2 mL of DMF were stirred at rt for 24 hours. The reaction was diluted with 10 mL of water, filtered and washed with water then dried to yield the desired compound as a beige solid, 95 mg, 65.5 yield %.

Ethyl 1-[5-[2-(ethylcarbamoylamino)-7-(1-methyltriazol-4-yl)-1,3-benzothiazol-5-yl]pyrimidin-2-yl]-4-methyl-piperidine-4-carboxylate: Ethyl 1-[5-[2-(ethylcarbamoylamino)-7-[1-(trimethylsilylmethyl)triazol-4-yl]-1,3-benzothiazol-5-yl]pyrimidin-2-yl]-4-methyl-piperidine-4-carboxylate (95 mg, 0.1529 mmol) in 1 mL of THF was cooled to 0° C. Water (5 drops) was added followed by tetra butyl ammonium fluoride (0.153 mL, 1.0 M solution in THF). The reaction was stirred at rt for 18 hours, another 0.2 mL of tetra butyl ammonium fluoride solution added and stirred for another 24 hours. The reaction was filtered through a pad of keiselguhr and the solvent removed under vacuum to yield a brown gum. The crude material was purified by preperative HPLC to give the product as a brown gum 63 mg, 75% yield.

1-[5-[2-(Ethylcarbamoylamino)-7-(1-methyltriazol-4-yl)-1,3-benzothiazol-5-yl]pyrimidin-2-yl]-4-methyl-piperidine-4-carboxylic acid (50): The hydrolysis was carried out using similar conditions to those described for Compound 9 to give Compound 50 as an off white solid 22.5 mg, 38% yield. $^1$H NMR (DMSO-d$_6$): δ 10.96 (1H, s), 8.87-8.88 (2H, m), 7.97 (1H, d, J=1.65 Hz), 7.89 (1H, d, J=1.63 Hz), 7.15 (1H, t, J=5.59 Hz), 4.33 (2H, dt, J=13.66, 4.46 Hz), 4.21 (3H, s), 3.45-3.32 (2H, m), 3.24 (2H, p, J=6.75 Hz), 2.06 (2H, ddd, J=13.11, 4.63, 2.99 Hz), 1.42 (2H, ddd, J=13.44, 10.10, 3.98 Hz), 1.22 (3H, s), 1.15 (3H, t, J=7.18 Hz). MS: 522 [M+H]+.

Compound 72: (E)-1-(5-(2-(3-ethylureido)-7-((methoxyimino)methyl)benzo[d]thiazol-5-yl)pyrimidin-2-yl)-4-methylpiperidine-4-carboxylic acid (alternatively named 1-[5-[2-(ethylcarbamoylamino)-7-[(E)-methoxyiminomethyl]-1,3-benzothiazol-5-yl]pyrimidin-2-yl]-4-methyl-piperidine-4-carboxylic acid)

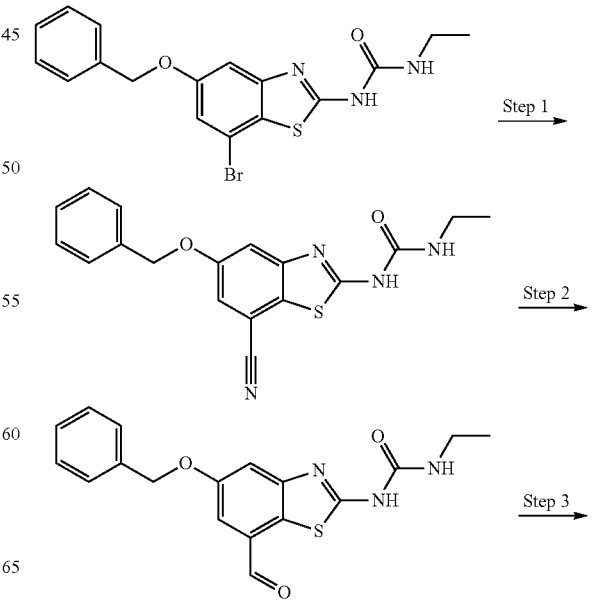

-continued

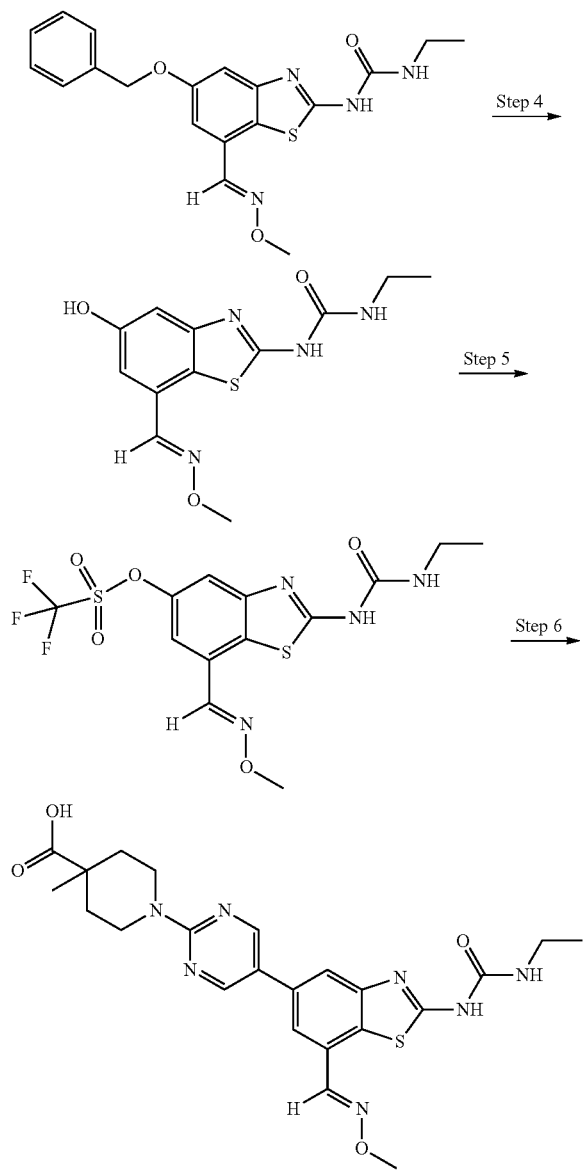

1-(5-(Benzyloxy)-7-cyanobenzo[d]thiazol-2-yl)-3-ethylurea 1-(5-(benzyloxy)-7-bromobenzo[d]thiazol-2-yl)-3-ethylurea (5.00 g, 12.29 mmol), zinc cyanide (1.58 g, 13.49 mmol), 1,1'-bis(diphenylphosphino)ferrocene (20 mg, 0.033 mmol), zinc acetate (90 mg, 0.50 mmol) and zinc dust (33.3 mg, 0.50 mmol) were stirred in a reaction tube in degassed DMF (60 ml) and water (600 ul). Tris(dibenzylideneacetone)dipalladium(0) (113.2 mg, 0.133 mmol) was added and the reaction purged with $N_2$, sealed and heated to 100° C. for 18 h with stirring. LCMS indicated clean conversion to the desired material. The solvents were removed under reduced pressure, the resulting residue triturated with water, the solid collected by filtration and dried in a vacuum oven to afford the desired material as a pale white solid 4.4 g (100%). This material was used directly in the next step with no further purification.

1-(5-(Benzyloxy)-7-formylbenzo[d]thiazol-2-yl)-3-ethylurea 1-(5-(Benzyloxy)-7-cyanobenzo[d]thiazol-2-yl)-3-ethylurea (1.00 g, 2.84 mmol) was stirred in formic acid (75 ml) and water (20 ml). Aluminum Nickel alloy (5.5 g, 64.7 mmol) was added and the reaction was stirred at 95° C. for 5 h under $N_2$. LCMS indicated 60% conversion to the desired aldehyde. The reaction was allowed to cool then the volatiles were removed under reduced pressure. The resulting concentrated solution was neutralized to pH9 with a 2M aqueous solution of sodium hydroxide then extracted with EtOAc, the combined extracts concentrated and the resulting residue purified by column chromatography eluting with EtOAc 50 to 100% in petroleum-ether to afford the aldehyde as a yellow solid (200 mg, 99% purity by LC-MS) (20%).

(E)-1-(5-(benzyloxy)-7-((methoxyimino)methyl)benzo[d]thiazol-2-yl)-3-ethylurea 1-(5-(Benzyloxy)-7-formylbenzo[d]thiazol-2-yl)-3-ethylurea (425 mg, 1.20 mmol), methoxylamine hydrochloride (105.2 mg, 1.26 mmol) and N,N'-diisopropylethylamine (0.77 g, 1.05 ml) were stirred in DMF degassed with $N_2$. The reaction was purged with $N_2$, sealed and heated to 105° C. for 18 h. LCMS after indicated complete consumption of starting material. The solvents were removed under reduced pressure and the resulting residue absorbed onto silica and purified by flash column chromatography eluting with 0 to 100% EtOAc in petroleum-ether to afford the product as a white solid 325 mg (70%) which was used directly in the next step.

(E)-1-ethyl-3-(5-hydroxy-7-((methoxyimino)methyl)benzo[d]thiazol-2-yl)urea (E)-1-(5-(benzyloxy)-7-((methoxyimino)methyl)benzo[d]thiazol-2-yl)-3-ethylurea (325 mg, 0.85 mmol) was stirred in DCM (17 ml) and methanesulfonic acid (2.8 ml) was added. The reaction was allowed to stir at rt for 1 h in a round bottomed flask equipped with a drying tube. LCMS showed a mixture of product and starting material and the reaction was stirred for a further 1 h and LCMS showed no further reaction. Methanesulfonic acid (0.5 ml) was added and the reaction stirred for 18 h, diluted with DCM (30 ml) and extracted with water (2×25 ml). The DCM layer contained mainly starting material and impurities by LCMS. The aqueous portions were combined, and solid sodium hydrogen carbonate was used to adjust the pH to ~10 and then extracted with a 1:1 mixture of DCM-$Et_2O$. The combined organic extracts were washed with water, dried ($MgSO_4$) and concentrated to afford a yellow solid (100 mg, 80% purity by LC-MS) (40%) which was used directly in the next step.

(E)-2-(3-Ethylureido)-7-((methoxyimino)methyl)benzo[d]thiazol-5-yl trifluoromethanesulfonate (E)-1-ethyl-3-(5-hydroxy-7-((methoxyimino)methyl)benzo[d]thiazol-2-yl)urea (100 mg, 0.34 mmol), triethylamine (41.4 mg, 0.41 mmol, 57 ul) and N-phenyl-bis(trifluoromethanesulfonimide) (133 mg, 0.37 mmol) were stirred in DMF (1.5 ml). The reaction was allowed to stir at rt and after 2.5 h LCMS indicated complete consumption of starting material. The reaction was concentrated under reduced pressure and the resulting residue partitioned between EtOAc and water. The layers were separated and the aqueous portion extracted with DCM. The combined organic extracts were dried (MgSO$_4$) and concentrated to afford a crude residue 225 mg (100%) which was used directly in the next step.

(E)-1-(5-(2-(3-Ethylureido)-7-((methoxyimino)methyl)benzo[d]thiazol-5-yl)pyrimidin-2-yl)-4-methylpiperidine-4-carboxylic acid (72)

A stirred solution of (E)-2-(3-ethylureido)-7-((methoxyimino)methyl)benzo[d]thiazol-5-yl trifluoromethanesulfonate (225 mg, 0.34 mmol), bis(neopentyl)glycolatodiboron (180 mg, 0.8 mmol) and potassium acetate (100 mg, 1.02 mmol) in anhydrous DMF (3.5 ml) was purged with N$_2$ for 15 min. 1,1'-bis(diphenylphosphino)ferrocene palladium (II)chloride (30 mg, 0.034 mmol) was added, the reaction vessel was sealed and heated at 80° C. for 2 h. The reaction mixture was cooled to ambient temperature, treated with 1-(5-bromopyrimidin-2-yl)-4-methylpiperidine-4-carboxylic acid (120 mg, 0.4 mmol) followed by aqueous cesium carbonate solution (3.7M 0.5 ml, 0.343 mmol). The reaction mixture was purged with N$_2$ for 5 min, treated with 1,1'-bis(diphenylphosphino)ferrocene palladium(II)chloride (30 mg, 0.034 mmol), sealed and heated at 80° C. for 2 h. The reaction was allowed to cool, filtered and Compound 72 purified by preperative HPLC as a brown solid (40 mg, LC-MS indicated 97% purity) (24%). $^1$H NMR (CH$_3$OH-d$_4$): δ 8.67 (2H, s), 8.40 (1H, s), 7.86 (1H, d, J=1.66 Hz), 7.53 (1H, d, J=1.67 Hz), 4.42 (2H, dt, J=13.74, 4.26 Hz), 4.11 (3H, s), 3.45-3.32 (2H, m), 2.21 (2H, dt, J=13.45, 3.31 Hz), 1.49 (2H, ddd, J=13.45, 10.71, 4.04 Hz), 1.30 (3H, s), 1.26 (3H, t, J=7.28 Hz). MS: 498 [M+H]$^+$ The following compound was similarly prepared.

Compound 87: 1-{5-[7-Cyclopropyl-2-(3-ethyl-ureido)-benzothiazol-5-yl]-pyrimidin-2-yl}-4-methyl-piperidine-4-carboxylic acid (alternatively named 1-[5-[7-cyclopropyl-2-(ethylcarbamoylamino)-1,3-benzothiazol-5-yl]pyrimidin-2-yl]-4-methyl-piperidine-4-carboxylic acid)

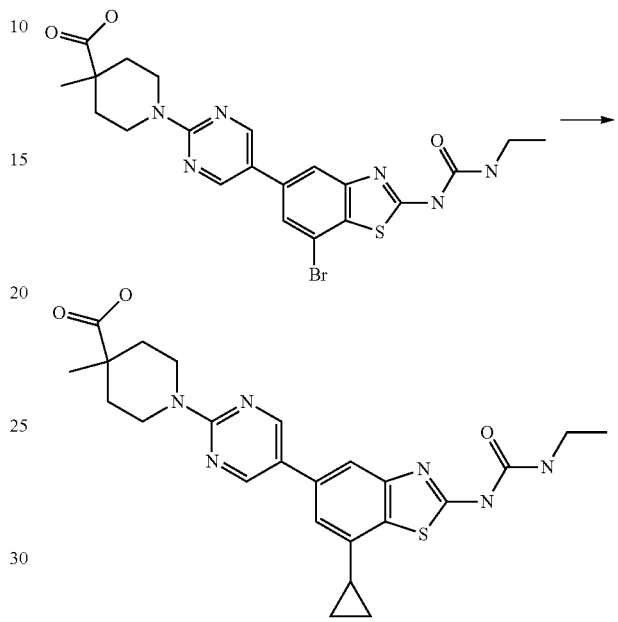

1-[5-[7-bromo-2-(ethylcarbamoylamino)-1,3-benzothiazol-5-yl]pyrimidin-2-yl]-4-methyl-piperidine-4-carboxylic acid (137 mg, 0.25 mmol), potassium cyclopropyl trifluoroborate (666 mg, 4.5 mmol), K$_3$PO$_4$ (1.75 g, 8.25 mmol) and Pd(dppf)Cl$_2$.DCM (20 mol %) were suspended as a heterogeneous mixture in 3:1 toluene/water (10 mL). The reaction was briefly ultrasonicated to aid the dissolution of insolubles and subjected to microwave irradiation at 120° C. for 30 mins after which quantitative consumption of starting material had

| Cpd No. | Structure | LCMS data [M + H]$^+$ | $^1$H NMR data |
|---|---|---|---|
| 204 | | 512 | (DMSO-d$_6$): δ 11.2 (1 H, s), 8.8 (2 H, s), 8.52 (1 H, s), 7.95 (1 H, s), 7.75 (1 H, s), 4.35 (4 H, m), 3.4 (2 H, m), 3.25 (2 H, m), 2.05 (2 H, m), 1.4 (H, m), 1.2 (3 H, s), 1.13 (H, m). | occurred by LCMS analysis (m/z 509 [M+H]$^+$. The organic phase was partitioned, dried (MgSO$_4$) and concentrated in vacuo to give an orange-yellow amorphous solid. This was triturated with MeCN and collected via vacuum filtration to afford a beige solid in 65 mg. This was dissolved in 3:1 EtOH:1M NaOH with the aid of ultrasonication, and irradiated for 30 mins at 100° C. in a microwave reactor. The reaction was diluted with water (10 mL), the volatile components were removed in vacuo and the resulting aqueous phase was washed with EtOAc (2×10 mL). The alkaline, aqueous phase was acidified with 1M HCl (pH~2) and extracted with EtOAc (3×20 mL), and the organic fractions were combined, washed with sat. brine (60 mL) and dried over MgSO$_4$, concenrated and purificated by reverse phase chromatography (SNAP 12 g, 25% to 90% H$_2$O/MeCN) to afford 29 mg (97% purity HPLC, 31% yield over two steps) after freeze drying of Compound 87. $^1$HNMR (CDCl$_3$) δ 8.55 (s, 2H), 7.53 (d, J=11.2 Hz, 1H), 7.00 (d, J=3.5 Hz, 1H), 4.22-4.08 (m, 2H), 3.73 (s, 2H), 3.48-3.36 (m, 2H), 2.22 (s, 2H), 2.05 (d, J=13.3 Hz, 1H), 1.60-1.49 (m, 2H), 1.37 (s, 3H), 1.27 (dd, J=12.4, 5.2 Hz, 3H), 1.05 (d, J=8.3 Hz, 2H), 0.84 (d, J=4.8 Hz, 2H). MS: 481.1 [M+H]$^+$.

Compound 88: 1-[5-[2-(ethylcarbamoylamino)-7-[(E)-N-methoxy-C-methyl-carbonimidoyl]-1,3-benzothiazol-5-yl]pyrimidin-2-yl]-4-methyl-piperidine-4-carboxylic acid

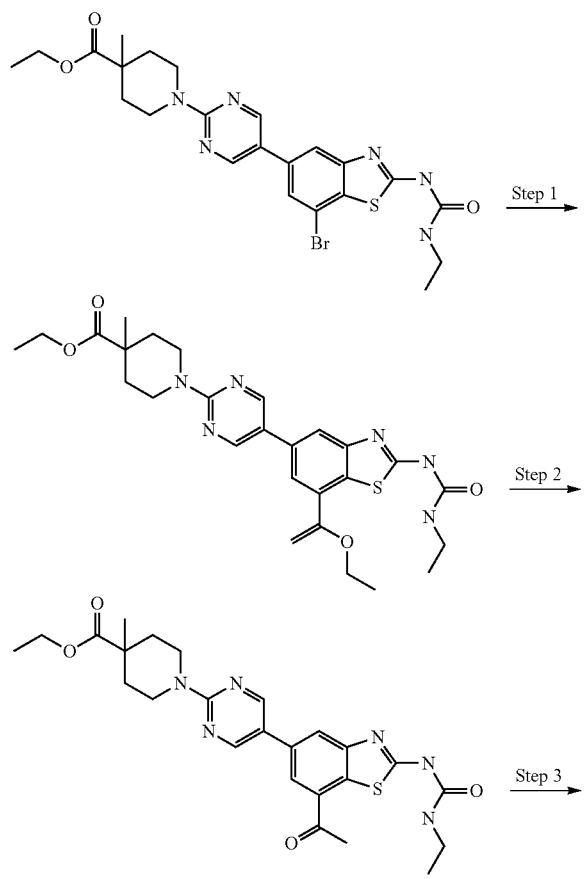

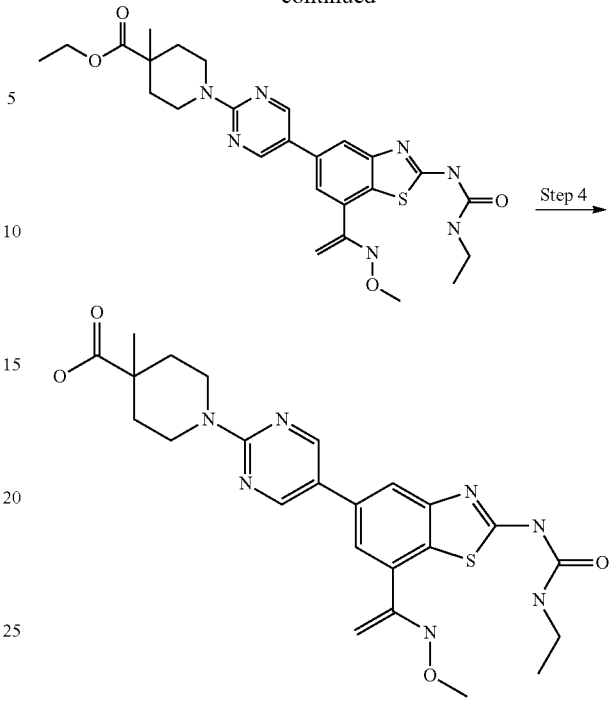

Ethyl 1-[5-[7-(1-ethoxyvinyl)-2-(ethylcarbamoylamino)-1,3-benzothiazol-5-yl]pyrimidin-2-yl]-4-methyl-piperidine-4-carboxylate: The ethyl 1-[5-[7-bromo-2-(ethylcarbamoylamino)-1,3-benzothiazol-5-yl]pyrimidin-2-yl]-4-methyl-piperidine-4-carboxylate (1 g, 1.82 mmol) and tributyl-(1-ethoxy-vinyl)-stannane (1.31 g, 3.64 mmol) were dissolved in DMF (20 mL) and the mixture deoxygenated by bubbling N2 through the solution for 20 min. Pd(PPh3)4, (210 mg, 0.18 mmol) was added and the reaction heated to 100° C. for 4 h under a N2 atmosphere, at the end of which time LCMS indicated clean formation of the vinyl ether. The reaction was concentrated under reduced pressure then diluted with EtOAc, washed with water then brine, the organic layer dried (MgSO4), filtered and the solvent removed in vacuo to give the desired compound.

Ethyl 1-[5-[7-acetyl-2-(ethylcarbamoylamino)-1,3-benzothiazol-5-yl]pyrimidin-2-yl]-4-methyl-piperidine-4-carboxylate Ethyl 1-[5-[7-(1-ethoxyvinyl)-2-(ethylcarbamoylamino)-1,3-benzothiazol-5-yl]pyrimidin-2-yl]-4-methyl-piperidine-4-carboxylate was dissolved in THF (24 mL) and water (6 mL). Sulfonic acid resin MP (200 mg, 3.2 mmol/g) was added and the reaction stirred at rt for 1 h, after which time LCMS indicated clean conversion to the ketone. The reaction mixture was filtered and the solvent removed in vacuo to give a solid which was triturated with Et$_2$O to give the desired product as a yellow solid (600 mg, 64% yield over 2 steps).

Ethyl 1-[5-[2-(ethylcarbamoylamino)-7-[(E)-N-methoxy-C-methyl-carbonimidoyl]-1,3-benzothiazol-5-yl]pyrimidin-2-yl]-4-methyl-piperidine-4-carboxylate O-Methyl hydroxylamine hydrochloride (64 mg, 0.784 mmol) was added to ethyl 1-[5-[7-acetyl-2-(ethylcarbamoylamino)-1,3-benzothiazol-5-yl]pyrimidin-2-yl]-4-methylpiperidine-4-carboxylate (200 mg, 0.39 mmol) in DMF (5 mL). The reaction mixture was heated to 60° C. for 4 h after which time LCMS indicated clean conversion to the desired product. The reaction was diluted with EtOAc, washed with water then brine and the organic layer dried (MgSO$_4$), filtered and the solvent removed in vacuo. The crude product obtained was used in the next step.

1-[5-[2-(ethylcarbamoylamino)-7-[(E)-N-methoxy-C-methyl-carbonimidoyl]-1,3-benzothiazol-5-yl]pyrimidin-2-yl]-4-methyl-piperidine-4-carboxylic acid (88)

tBuOK (124 mg, 1.11 mmol) was added to a solution of ethyl 1-[5-[2-(ethylcarbamoylamino)-7-[(E)-N-methoxy-C-methyl-carbonimidoyl]-1,3-benzothiazol-5-yl]pyrimidin-2-yl]-4-methyl-piperidine-4-carboxylate in DMSO (4 mL). The mixture was stirred at ambient temperature for 2 h after which time LCMS indicated clean conversion to the acid. The mixture was filtered through cotton wool to remove solid particulates and purified by preparative HPLC to give Compound 88 as a white solid, 76 mg, 40% yield over 2 steps. $^1$H NMR (DMSO-d$_6$): δ 10.89 (1H, s), 8.85 (2H, s), 7.95 (1H, d, J=1.62 Hz), 7.76 (1H, d, J=1.69 Hz), 7.16 (1H, t, J=5.50 Hz), 4.32 (2H, dt, J=13.67, 4.40 Hz), 4.09 (3H, s), 3.38 (2H, ddd, J=13.49, 10.48, 3.40 Hz), 3.23 (2H, p, J=6.71 Hz), 2.42 (3H, s), 2.05 (2H, dt, J=13.34, 3.66 Hz), 1.41 (2H, ddd, J=13.34, 10.04, 3.92 Hz), 1.21 (3H, s), 1.14 (3H, t, J=7.15 Hz). MS: 512 [M+H]$^+$.

The following compounds were similarly prepared.

| Cpd No. | Structure | LCMS data [M + H]$^+$ | $^1$H NMR data |
|---|---|---|---|
| 94 | 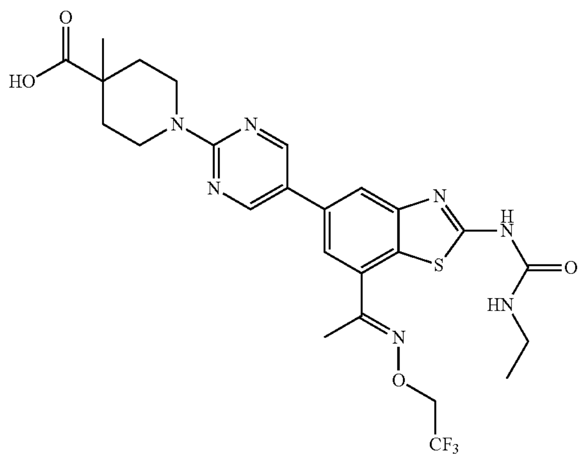 [SMILES: CCNC(=O)Nc1nc2cc(-c3cnc(N4CCC(C)(C(=O)O)CC4)nc3)cc(/C(C)=N/OCC(F)(F)F)c2s1] | 580 | (DMSO-d$_6$): δ 11.74 (1 H, s), 11.00 (1 H, s), 8.84 (2 H, s), 7.90 (1 H, d, J = 1.56 Hz), 7.72 (1 H, d, J = 1.63 Hz), 7.69-7.56 (2 H, m), 7.32 (1 H, t, J = 5.70 Hz), 4.32 (2 H, dt, J = 13.61, 4.39 Hz), 3.22 (2 H, p, J = 7.12 Hz), 2.39 (3 H, s), 2.07 (2 H, dt, J = 13.14, 3.58 Hz), 1.38 (2 H, ddd, J = 13.14, 10.03, 3.76 Hz), 1.20 (3 H, s), 1.13 (3 H, t, J = 7.17 Hz). |
| 95 | 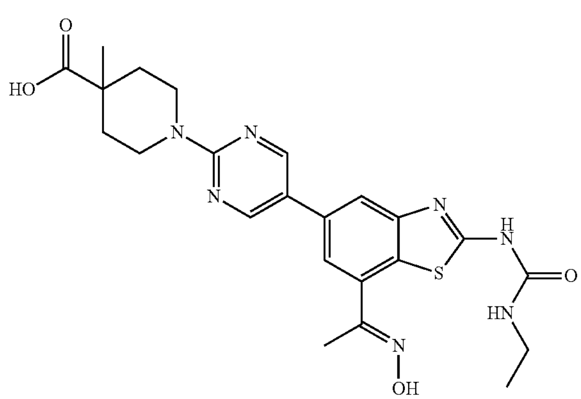 [SMILES: CCNC(=O)Nc1nc2cc(-c3cnc(N4CCC(C)(C(=O)O)CC4)nc3)cc(/C(C)=N/O)c2s1] | 498 | (DMSO-d$_6$): δ 10.79 (1 H, s), 8.86 (2 H, s), 8.00 (1 H, d, J = 1.58 Hz), 7.82 (1 H, d, J = 1.64 Hz), 6.99 (1 H, t, J = 5.59 Hz), 4.92 (2 H, q, J = 9.01 Hz), 4.32 (2 H, dt, J = 13.70, 4.46 Hz), 3.24 (2 H, p, J = 6.74 Hz), 2.50 (3H, s), 2.05 (3 H, d, J = 13.22 Hz), 1.41 (2 H, ddd, J = 13.43, 10.12, 3.91 Hz), 1.22 (3 H, s), 1.14 (3 H, t, J = 7.17 Hz). |

| Cpd No. | Structure | LCMS data [M + H]+ | 1H NMR data |
|---|---|---|---|
| 96 | 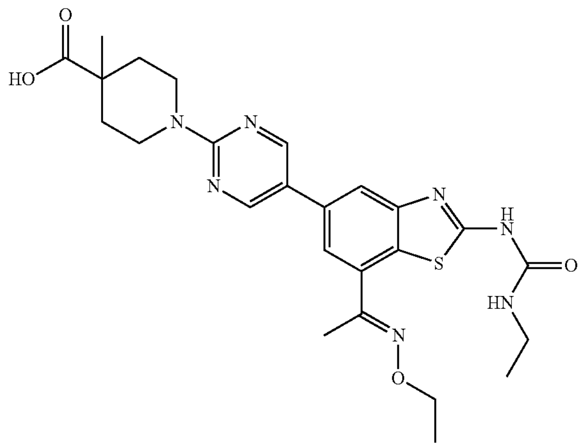 [SMILES: CCNC(=O)Nc1nc2cc(-c3cnc(N4CCC(C)(C(=O)O)CC4)nc3)cc(/C(C)=N/OCC)c2s1] | 526 | (DMSO-d6): δ 10.77 (1 H, s), 8.85 (2 H, s), 7.94 (1 H, d, J = 1.58 Hz), 7.75 (1 H, d, J = 1.65 Hz), 7.06 (1 H, t, J = 5.60 Hz), 4.39-4.27 (4 H, m), 3.24 (2 H, p, J = 6.75 Hz), 2.42 (3 H, s), 2.06 (2 H, dt, J = 13.39, 3.61 Hz), 1.44 (3 H, t, J = 7.03 Hz), 1.39 (2H, dd, J = 9.85, 3.61 Hz), 1.22 (3 H, s), 1.14 (3 H, t, J = 7.17 Hz). |
Compound 97: 1-[5-[7-(Ethylcarbamoyl)-2-(ethylcarbamoylamino)-1,3-benzothiazol-5-yl]pyrimidin-2-yl]-4-methyl-piperidine-4-carboxylic acid
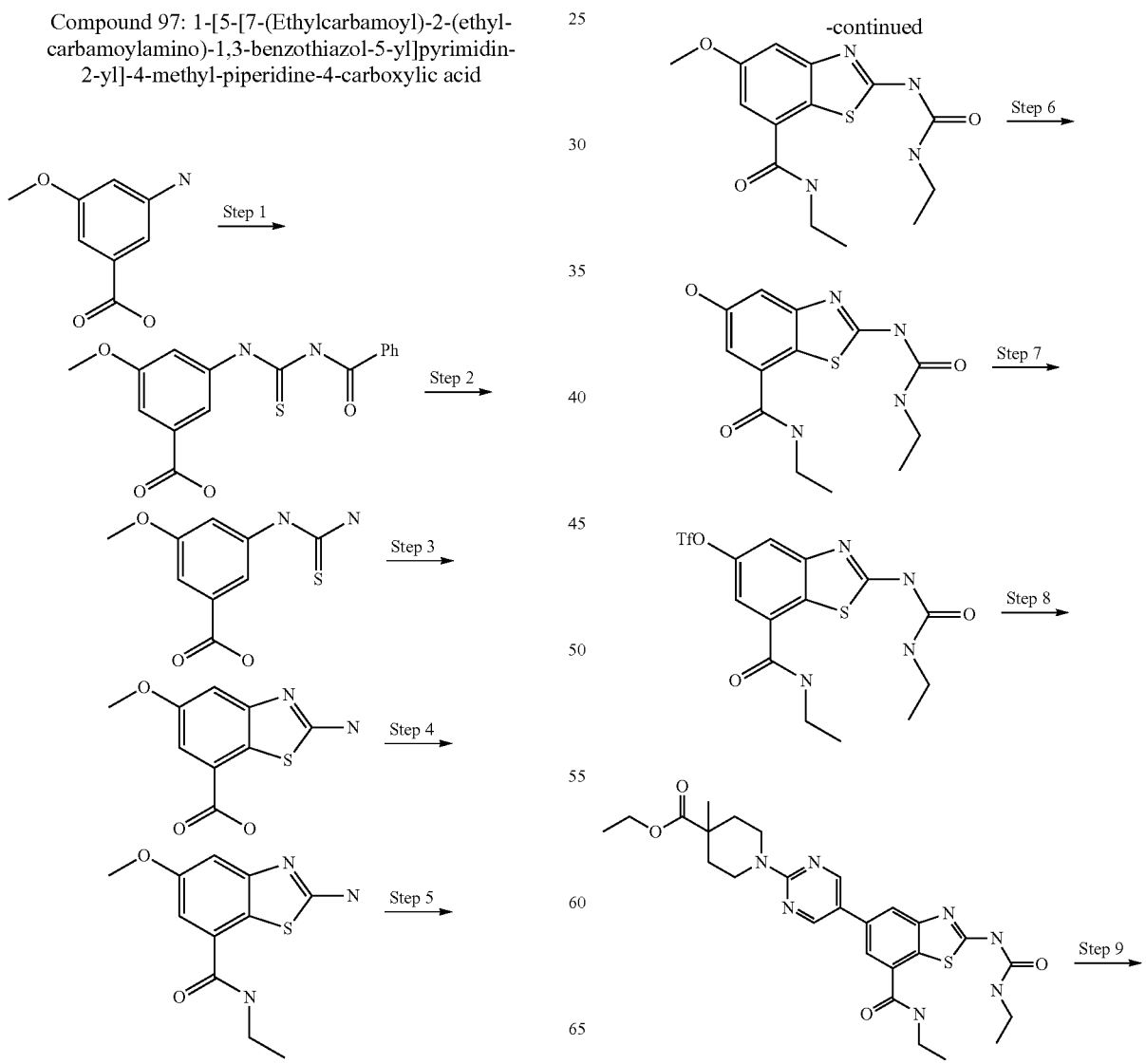

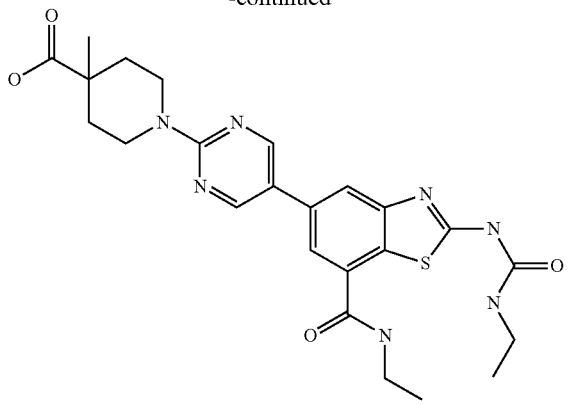

3-(Benzoylcarbamothioylamino)-5-methoxy-benzoic acid

Benzoyl isothiocyanate (169 µl, 1.25 mmol) was added to a solution of 3-amino-5-methoxy-benzoic acid (0.2 g, 1.19 mmol) in acetone (10 mL). The reaction was stirred at ambient temperature and a thick precipitate formed after 10 minutes. LCMS indicated complete conversion of the starting material. The solvent was removed in vacuo and the crude material triturated with iso-hexane, dried under reduced pressure and used directly in the next step.

3-(carbamothioylamino)-5-methoxy-benzoic acid

Sodium methoxide (4.76 mL, 2.38 mmol, 0.5 M solution in methanol) was added to a solution of 3-(benzoylcarbamothioylamino)-5-methoxy-benzoic acid from Step 1 in MeOH (4 mL). The reaction was stirred at ambient temperature for 2 h after which time LCMS indicated complete conversion of the starting material. The solvent was removed in vacuo, the crude partitioned between water and DCM, the organic layer separated and the aqueous layer was acidified to pH 5 with conc HCl resulting in a thick precipitate. The precipitate was extracted into EtOAc which was then washed with brine, dried (MgSO$_4$), filtered and concentrated in vacuo. The product was obtained as an off white solid, 248 mg, 92% yield.

2-amino-5-methoxy-1,3-benzothiazole-7-carboxylic acid

Bromine (56 µl, 1.09 mmol) was added to a suspension of 3-(carbamothioylamino)-5-methoxy-benzoic acid (248 mg, 1.09 mmol) in chloroform (7 mL). The reaction was stirred at ambient temperature resulting in large granules of solid material which were pulverized with a spatula. The chloroform was removed by pipette and the remaining solid was triturated with dichloromethane to give the product as a pale yellow solid, 200 mg, 81% yield.

2-amino-N-ethyl-5-methoxy-1,3-benzothiazole-7-carboxamide

Ethylamine (2 mL, 4.02 mmol, 2M soln in methanol) was added to a solution of 2-amino-5-methoxy-1,3-benzothiazole-7-carboxylic acid (300 mg, 1.34 mmol), diisopropyl ethylamine (0.93 mL, 5.36 mmol) and HATU (560 mg, 1.47 mmol) in DMF (6 mL). The reaction was stirred at ambient temperature for 2 hours after which time LCMS indicated clean conversion to the product. The reaction was diluted with EtOAc, washed with water and brine then dried (MgSO$_4$), filtered and concentrated in vacuo. The crude material was purified by trituration with DCM to give the product as an off white solid, 178 mg, 53% yield.

N-ethyl-2-(ethylcarbamoylamino)-5-methoxy-1,3-benzothiazole-7-carboxamide

Ethyl isocyanate (0.87 mL, 10.9 mmol) was added to a suspension of 2-amino-N-ethyl-5-methoxy-1,3-benzothiazole-7-carboxamide (549 mg, 2.18 mmol) and dibutyl tin diacetate (4 drops, catalytic amount) in dioxane (12 mL). The reaction was heated to 60° C. for 8 hours after which time LCMS indicated clean conversion to the desired product. The reaction solvent was removed in vacuo and the crude material used directly in the next step.

N-ethyl-2-(ethylcarbamoylamino)-5-hydroxy-1,3-benzothiazole-7-carboxamide

Boron tribromide (8.72 mL, 8.72 mmol, 4M solution in DCM was added to a suspension of N-ethyl-2-(ethylcarbamoylamino)-5-methoxy-1,3-benzothiazole-7-carboxamide in dichloromethane (10 mL). The reaction was stirred at ambient temperature overnight then diluted with EtOAc, washed with saturated aqueous sodium hydrogen carbonate and brine and the organic layer dried (MgSO$_4$), filtered and concentrated in vacuo. The crude material was purified by flash chromatography on silica gel using DCM:MeOH 95:5. The product was obtained as a white solid, 212 mg, 31% yield.

[7-(ethylcarbamoyl)-2-(ethylcarbamoylamino)-1,3-benzothiazol-5-yl]trifluoromethanesulfonate N-phenylbis(trifluoromethanesulphonimide (270 mg, 0.757 mmol) was added to a solution of N-ethyl-2-(ethylcarbamoylamino)-5-hydroxy-1,3-benzothiazole-7-carboxamide (212 mg, 0.688 mmol) and triethylamine (0.115 mL, 0.826 mmol) in DMF (4 mL). The reaction mixture was stirred at ambient temperature for 6 hours after which time LCMS indicated clean conversion to the desired product. The reaction was diluted with EtOAc, washed with water and brine then dried (MgSO$_4$), filtered and concentrated in vacuo. The product was used without purification in the next step.

Ethyl 1-[5-[7-(ethylcarbamoyl)-2-(ethylcarbamoylamino)-1,3-benzothiazol-5-yl]pyrimidin-2-yl]-4-methyl-piperidine-4-carboxylate

[7-(Ethylcarbamoyl)-2-(ethylcarbamoylamino)-1,3-benzothiazol-5-yl]trifluoromethanesulfonate (150 mg, 0.344 mmol), bis-(neopentyl glycolato)diboron (155 mg, 0.688 mmol) and potassium acetate (100 mg, 0.89 mmol) were weighed into a Kymax tube. DMF (4 mL) was added and the mixture degassed by bubbling N$_2$ through for 15 min. Pd(dppf)Cl$_2$ (28 mg, 0.0344 mmol) was added and the reaction sealed and heated to 80° C. for 3 h at the end of which time LCMS indicated clean boronate formation. The reaction was allowed to cool to ambient temperature then 1-(5-bromopyrimidin-2-yl)-4-ethyl-piperidine-4-carboxylic acid ethyl ester (169 mg, 0.516 mmol), cesium carbonate solution (185 µl, 0.688 mmol, 3.7M aq. soln.) and Pd(dppf)Cl$_2$ (28 mg, 0.0344 mmol) were added and the reaction sealed and heated to 90° C. for 3 h at the end of which time LCMS indicated formation of the desired product. The reaction mixture was diluted with EtOAc, washed with water then brine and the organic layer dried (MgSO$_4$), filtered and the solvent was removed in vacuo. The crude material obtained was purified by flash chromatography on silica gel using DCM:MeOH 96:4 as eluent. The product was obtained as a pale brown solid, 78 mg, 42% yield.

1-[5-[7-(Ethylcarbamoyl)-2-(ethylcarbamoylamino)-1,3-benzothiazol-5-yl]pyrimidin-2-yl]-4-methyl-piperidine-4-carboxylic acid (97)

Potassium tert butoxide (67 mg, 0.59 mmol) was added to a solution of ethyl 1-[5-[7-(ethylcarbamoyl)-2-(ethylcarbamoylamino)-1,3-benzothiazol-5-yl]pyrimidin-2-yl]-4-methyl-piperidine-4-carboxylate (78 mg, 0.147 mmol) in DMSO (1.5 mL). The mixture was stirred at ambient temperature for 2 h after which time LCMS indicated clean conversion to the acid. The mixture was filtered through cotton wool to remove solid particulates and purified by preparative HPLC. Compound 97 was obtained as a white solid, 44 mg, 75% yield. $^1$H NMR (DMSO-$d_6$): δ 10.86 (1H, s), 8.88 (2H, s), 8.82 (1H, t, J=5.47 Hz), 8.12 (1H, d, J=1.57 Hz), 8.05 (1H, d, J=1.45 Hz), 7.14 (1H, t, J=5.61 Hz), 4.32 (2H, dt, J=13.66, 4.46 Hz), 3.24 (5H, p, J=6.88 Hz), 3.20-3.27 (2H, m), 2.06 (2H, dt, J=13.52, 3.72 Hz), 1.41 (2H, ddd, J=13.42, 10.06, 3.89 Hz), 1.24 (1H, s), 1.22 (3H, t, J=3.29 Hz), 1.21 (3H, s), 1.14 (3H, t, J=7.17 Hz). MS: 512 [M+H]$^+$.

Compound 159: 1-[5-[2-(ethylcarbamoylamino)-7-(morpholine-4-carbonyl)-1,3-benzothiazol-5-yl]pyrimidin-2-yl]-4-methyl-piperidine-4-carboxylic acid was similarly prepared

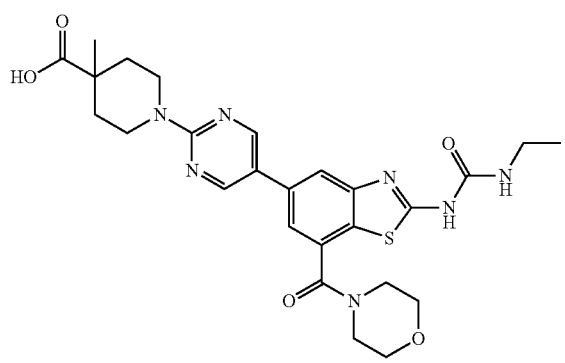 [SMILES: CCNC(=O)Nc1nc2cc(-c3cnc(N4CCC(C)(C(=O)O)CC4)nc3)cc(C(=O)N3CCOCC3)c2s1]

LCMS [M+H]$^+$554.

Compound 114: 4-ethyl-1-[5-[2-(ethylcarbamoylamino)-7-morpholino-1,3-benzothiazol-5-yl]pyrimidin-2-yl]piperidine-4-carboxylic acid

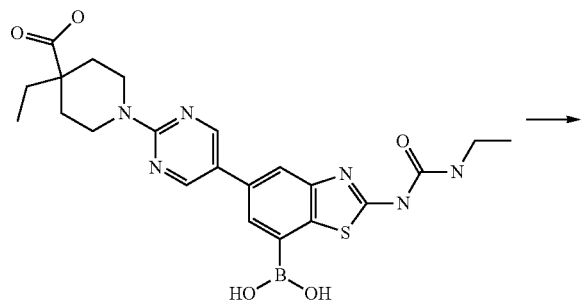

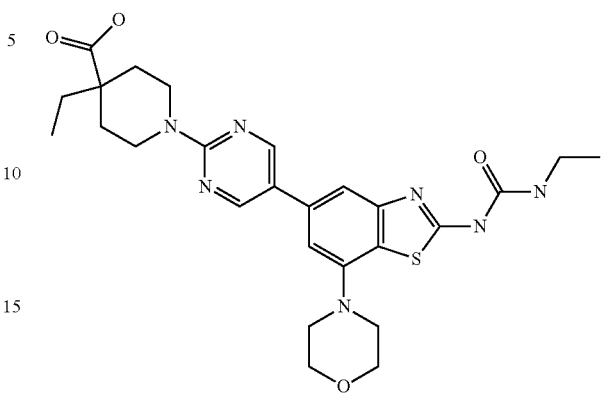

1-[5-[7-borono-2-(ethylcarbamoylamino)-1,3-benzothiazol-5-yl]pyrimidin-2-yl]-4-ethyl-piperidine-4-carboxylic acid (100 mg) was placed in DCM 5 ml and copper acetate 47 mg, triethylamine 122 mg, 4A molecular sieves (powdered) and morpholine 17 mg were added and the mixture stirred at rt over the weekend. LCMS showed that some desired product had formed and a close running 7-H impurity. The mixture was filtered and the solvent removed in vacuo to give a dark gum which was purified by preparative HPLC using a phenyl hexyl column eluting with 65-75% ACN to give Compound 114 as an off white solid (8 mg). $^1$H NMR (CDCl$_3$) δ 8.52 (s, 2H), 7.38 (s, 1H), 6.84 (s, 1H), 4.50-4.42 (m, 2H), 3.89-3.85 (m, 4H), 3.35-3.29 (m, 4H), 3.21-3.17 (m, 4H), 2.22-2.14 (m, 2H), 1.61-1.54 (m, 2H), 1.45-1.35 (m, 2H), 1.19 (t, J=7.2 Hz, 3H), 0.86 (t, J=7.5 Hz, 3H). MS: 540.13 [M+H]$^+$.

Also isolated in this reaction was Compound 113 4-ethyl-1-[5-[2-(ethylcarbamoylamino)-1,3-benzotriazol-5-yl]pyrimidin-2-yl]piperidine-4-carboxylic acid

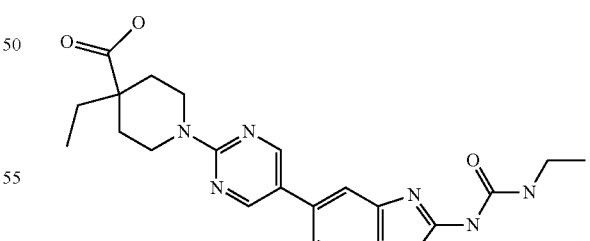

$^1$H NMR (CDCl$_3$) δ 8.55 (s, 2H), 7.76 (d, J=8.3 Hz, 1H), 7.69 (s, 1H), 7.32 (d, J=8.3 Hz, 1H), 4.53-4.45 (m, 2H), 3.38-3.31 (m, 2H), 3.21 (t, J=12 Hz, 2H), 2.21 (d, J=12 Hz, 2H), 1.65-1.56 (m, 2H), 1.48-1.38 (m, 2H), 1.24-1.18 (m, 3H), 0.88 (t, J=7 Hz, 3H). MS: 455.07 [M+H]$^+$.

Compound 116: 4-ethyl-1-[5-[2-(ethylcarbamoylamino)-7-[(E)-N-methoxy-C-methyl-carbonimidoyl]-1,3-benzothiazol-5-yl]pyrimidin-2-yl]piperidine-4-carboxylic acid

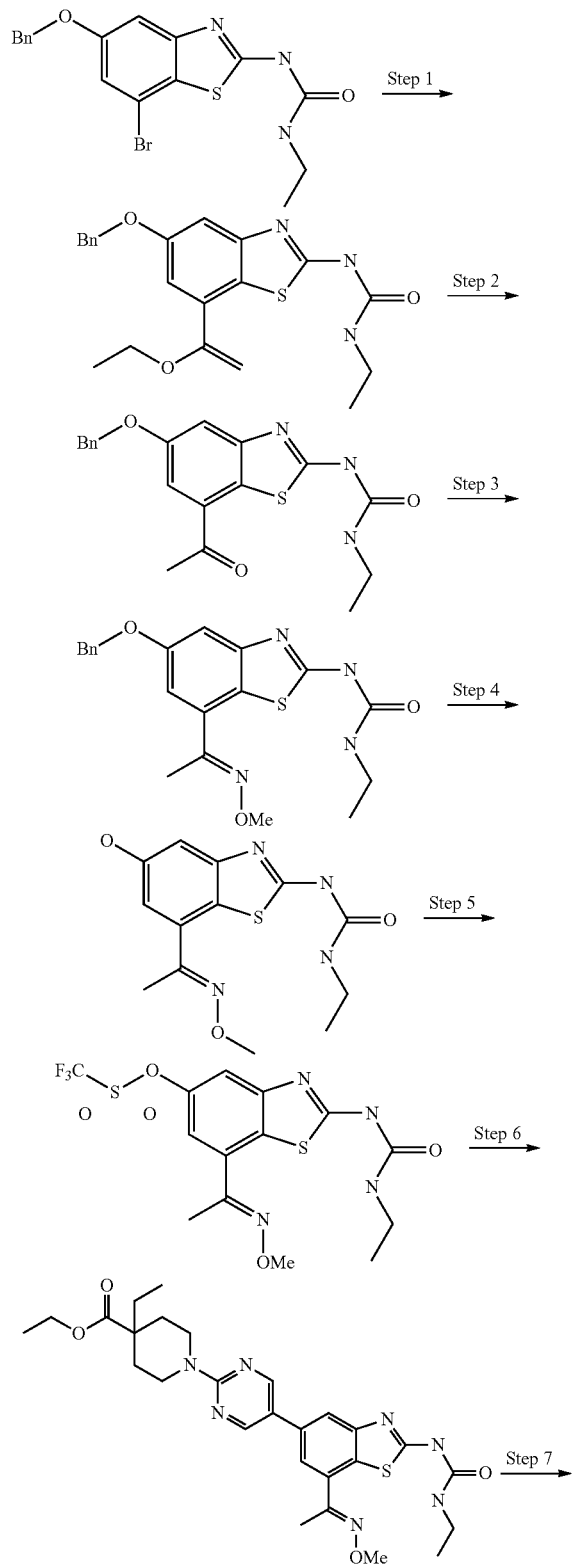

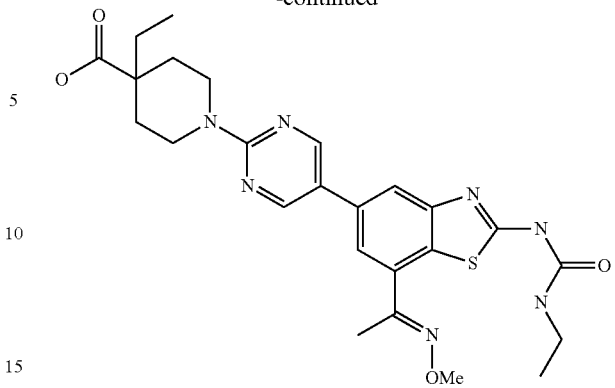

1-[5-Benzyloxy-7-(1-ethoxyvinyl)-1,3-benzothiazol-2-yl]-3-ethyl-urea: 1-(5-benzyloxy-7-bromo-1,3-benzothiazol-2-yl)-3-ethyl-urea (1 g, 2.46 mmol) and tributyl-(1-ethoxy-vinyl)-stannane (1.77 g, 4.92 mmol) were dissolved in DMF (30 mL) and the mixture deoxygenated by bubbling $N_2$ through the solution for 20 min. $Pd(PPh_3)_4$, (284 mg, 0.246 mmol) was added and the reaction heated to 100° C. for 4 h under a $N_2$ atmosphere, at the end of which time LCMS indicated clean formation of the vinyl ether. The reaction was concentrated under reduced pressure, diluted with EtOAc, washed with water then brine and the organic layer dried ($MgSO_4$), filtered and the solvent removed in vacuo to give the desired compound.

1-(7-Acetyl-5-benzyloxy-1,3-benzothiazol-2-yl)-3-ethyl-urea: 1-[5-benzyloxy-7-(1-ethoxyvinyl)-1,3-benzothiazol-2-yl]-3-ethyl-urea was dissolved in THF (24 mL) and 2M aqueous hydrochloric acid (2 mL) was added and the reaction stirred at ambient temperature for 4 h, after which time LCMS indicated clean conversion to the ketone. The reaction solvent was removed in vacuo to give the desired compound (650 mg, 70% yield).

1-[5-Benzyloxy-7-[(E)-N-methoxy-C-methyl-carbonimidoyl]-1,3-benzothiazol-2-yl]-3-ethyl-urea: O-Methyl hydroxylamine hydrochloride (289 mg, 3.46 mmol) was added to 1-(7-acetyl-5-benzyloxy-1,3-benzothiazol-2-yl)-3-ethyl-urea (650 mg, 1.73 mmol) in DMF (7 mL). The reaction mixture was heated to 60° C. for 2 h after which time LCMS indicated clean conversion to the desired product. The reaction was diluted with EtOAc, washed with water then brine and the organic layer dried ($MgSO_4$), filtered and the solvent removed in vacuo to give the desired compound an off white solid, 550 mg, 78% yield.

1-Ethyl-3-[5-hydroxy-7-[(E)-N-methoxy-C-methyl-carbonimidoyl]-1,3-benzothiazol-2-yl]urea: A solution of methanesulfonic acid (6.5 mL) in DCM (32 mL) was added to 1-[5-benzyloxy-7-[(E)-N-methoxy-C-methyl-carbonimidoyl]-1,3-benzothiazol-2-yl]-3-ethyl-urea (718 mg, 1.8 mmol) and the reaction stirred at ambient temperature for 2 h after which time LCMS indicated clean conversion to the desired product. The reaction was diluted with DCM, washed with water and the aqueous layer neutralized with saturated aqueous $Na_2CO_3$ solution and extracted with EtOAc. The organic layer was dried ($MgSO_4$), filtered and the solvent was removed in vacuo. The crude material obtained was purified by flash chromatography on silica gel using MeOH:DCM 3:97 as the eluent to give the desired compound as an off white solid, 300 mg, 54% yield.

[2-(Ethylcarbamoylamino)-7-[(E)-N-methoxy-C-methyl-carbonimidoyl]-1,3-benzothiazol-5-yl]trifluoromethanesulfonate: N-Phenylbis(trifluoromethanesulfonimide (383 mg, 1.07 mmol) was added to a solution of 1-ethyl-3-[5-hydroxy-7-[(E)-N-methoxy-C-methyl-carbonimidoyl]-1,3-benzothiazol-2-yl]urea (300 mg, 0.97 mmol) and triethylamine (162 µl, 1.16 mmol) in DMF (5 mL). The reaction was stirred at ambient temperature for 18 hours then diluted with EtOAc, washed with water then brine and the organic layer dried (MgSO₄), filtered and the solvent removed in vacuo to give the desired compound as an off white solid, 220 mg, 50% yield, Ethyl 4-ethyl-1-[5-[2-(ethylcarbamoylamino)-7-[(E)-N-methoxy-C-methyl-carbonimidoyl]-1,3-benzothiazol-5-yl]pyrimidin-2-yl]piperidine-4-carboxylate [2-(ethylcarbamoylamino)-7-[(E)-N-methoxy-C-methyl-carbonimidoyl]-1,3-benzothiazol-5-yl]trifluoromethanesulfonate (220 mg, 0.5 mmol), bis-(neopentyl glycolato)diboron (226 mg, 1 mmol) and potassium acetate (147 mg, 1.5 mmol) were weighed into a Kymax tube. DMF (4 mL) was added and the mixture degassed by bubbling N₂ through for 15 min. Pd(dppf)Cl₂ (26 mg, 0.05 mmol) was added and the reaction sealed and heated to 80° C. for 3 h at the end of which time LCMS indicated clean boronate formation. The reaction was allowed to cool to ambient temperature then divided into 2 aliquots in reaction tubes. To one of the tubes was added 1-(5-Bromo-pyrimidin-2-yl)-4-ethyl-piperidine-4-carboxylic acid ethyl ester (103 mg, 0.3 mmol), cesium carbonate solution (170 µl, 0.63 mmol, 3.7M aq. soln.) and Pd(dppf)Cl₂ (13 mg, 0.025 mmol) were added and the reaction sealed and heated to 90° C. for 3 h at the end of which time LCMS indicated formation of the desired product. The reaction mixture was diluted with EtOAc, washed with water then brine and the organic layer dried (MgSO₄), filtered and the solvent was removed in vacuo. The crude material obtained was purified by flash chromatography on silica gel using a gradient of petrol-EtOAc 0-100% as the eluent to give the desired compound as an off white solid, 87 mg, 32% yield.

4-Ethyl-1-[5-[2-(ethylcarbamoylamino)-7-[(E)-N-methoxy-C-methyl-carbonimidoyl]-1,3-benzothiazol-5-yl]pyrimidin-2-yl]piperidine-4-carboxylic acid (116): Potassium tertiary butoxide (71 mg, 0.63 mmol) was added to a solution of ethyl 4-ethyl-1-[5-[2-(ethylcarbamoylamino)-7-[(E)-N-methoxy-C-methyl-carbonimidoyl]-1,3-benzothiazol-5-yl]pyrimidin-2-yl]piperidine-4-carboxylate (87 mg, 0.16 mmol) in DMSO (1.5 mL). The mixture was stirred at rt for 2 h after which time LCMS indicated clean conversion to the acid. The mixture was filtered through cotton wool to remove solid particulates and purified by preparative HPLC to give Compound 116 as a white solid, 27 mg, 25% yield. ¹H NMR (DMSO-d₆): δ 12.49 (1H, s), 10.66 (1H, s), 8.85 (2H, s), 7.95 (1H, d, J=1.58 Hz), 7.76 (1H, d, J=1.64 Hz), 6.94 (1H, t, J=5.58 Hz), 4.49 (2H, dt, J=13.57, 3.98 Hz), 4.10 (3H, s), 3.30-3.15 (4H, m), 2.42 (3H, s), 2.10 (2H, dt, J=13.97, 2.91 Hz), 1.57 (2H, q, J=7.49 Hz), 1.38 (2H, ddd, J=13.34, 11.14, 4.02 Hz), 1.14 (3H, t, J=7.17 Hz), 0.85 (3H, t, J=7.43 Hz). MS: 526 [M+H]⁺.

Compound 128: 4-amino-1-[5-[2-(ethylcarbamoylamino)-7-(2-pyridyl)-1,3-benzothiazol-5-yl]pyrimidin-2-yl]piperidine-4-carboxylic acid

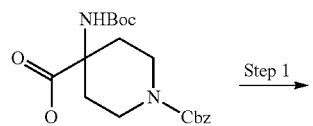

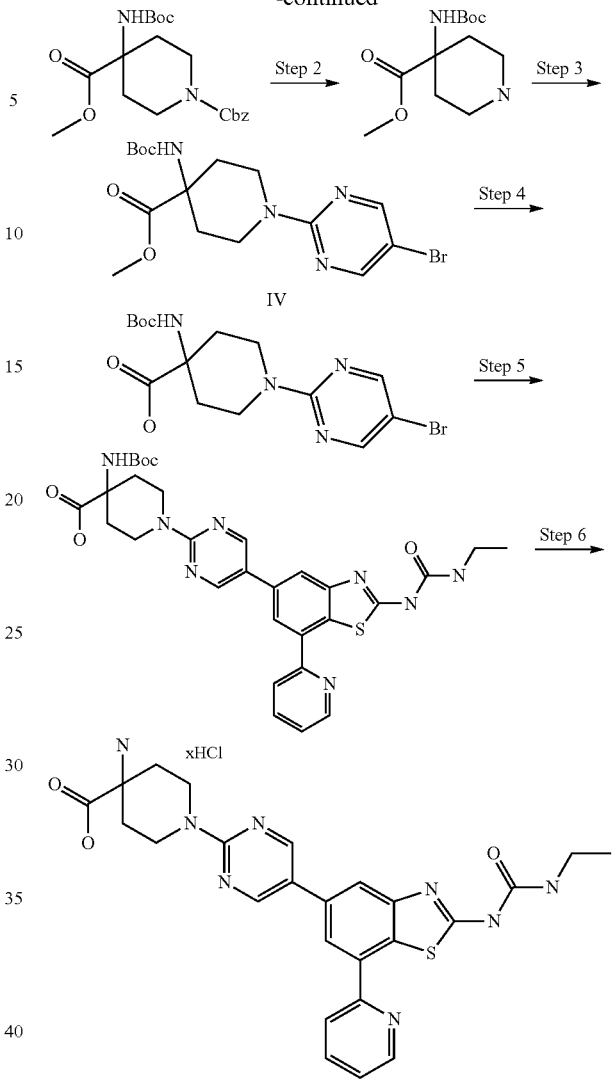

1-Benzyl 4-methyl 4-((tert-butoxycarbonyl)amino) piperidine-1,4-dicarboxylate

To an ice-cold solution of 1-((benzyloxy)carbonyl)-4-((tert-butoxycarbonyl)amino)piperidine-4-carboxylic acid (0.50 g, 1.32 mmol) in ACN (15 mL) was added Cs₂CO₃ (0.52 g, 1.59 mmol) and the resulting reaction mixture stirred at the same temperature for 10 min followed by addition of MeI (0.4 mL, 4.2 mmol). The reaction mixture was stirred for 1 h at rt. After completion of reaction (by TLC), the mixture was passed through celite and solvent was evaporated under reduced pressure to obtain a white solid compound (0.52 g, 96% yield). MS: 393.31 [M+H]⁺.

Methyl 4-((tert-butoxycarbonyl)amino) piperidine-4-carboxylate

To a solution of 1-benzyl 4-methyl 4-((tert-butoxycarbonyl)amino)piperidine-1,4-dicarboxylate (0.50 g, 1.27 mmol) in MeOH (10 mL) was added palladium on charcoal (0.05 g, 10%) at rt. The reaction was stirred under hydrogen atmosphere (atmospheric pressure) for 16 h at rt. After completion (by TLC), the residue was passed through celite and solvent evaporated under reduced pressure to obtain a white solid compound (0.32 g, 98% yield). MS: 259.22 [M+H]$^+$.

Methyl 1-(5-bromopyrimidin-2-yl)-4-((tert-butoxycarbonyl)amino)piperidine-4-carboxylate To a solution of methyl 4-((tert-butoxycarbonyl)amino) piperidine-4-carboxylate (0.11 g, 0.42 mmol) in EtOH (5 mL) was added 5-bromo-2-chloropyrimidine (0.09 g, 0.46 mmol) at rt and the reaction mixture heated up to 70° C. for 1 h. After completion (by TLC), solvent was evaporated and the crude residue purified over 100-200 M silica-gel using 20% EtOAc: hexane to obtain the desired product as a yellow solid (0.09 g, 52% yield). MS: 415.17 [M+H]$^+$.

1-(5-Bromopyrimidin-2-yl)-4-((tert-butoxycarbonyl) amino) piperidine-4-carboxylic acid To an ice-cold solution of methyl 1-(5-bromopyrimidin-2-yl)-4-((tert-butoxycarbonyl)amino) piperidine-4-carboxylate (0.157 g, 0.38 mmol) in THF was added aqueous LiOH (0.08 g, 1.89 mmol dissolved in minimum amount of H$_2$O). The resulting mixture was heated up to 65° C. for 5-6 h. After completion (by TLC), the solvent was concentrated and 10 mL of water was added, the aqueous layer was washed with EtOAc (2×50 mL) and the organic layer discarded. The pH of the aqueous layer was adjusted up to 4-5 then extracted with hot EtOAc (3×100 mL) and the combined organic layer dried over Na$_2$SO$_4$ and solvent was evaporated. The residue thus obtained was triturated with ether to afford the desired product as an off-white solid (0.15 g, 99% yield). MS: 401.16 [M+H]$^+$.

4-((tert-butoxycarbonyl)amino)-1-(5-(2-(3-ethylureido)-7-(pyridin-2-yl)benzothiazol-5-yl)pyrimidin-2-yl)piperidine-4-carboxylic acid To a solution of 1-(5-bromopyrimidin-2-yl)-4-((tert-butoxycarbonyl)amino) piperidine-4-carboxylic acid (0.15 g, 0.38 mmol) in DMF (5.0 mL) was added 2-(3-ethylureido)-7-(pyridin-2-yl)benzothiazol-5-ylboronic acid (0.26 g, 0.75 mmol) and aqueous solution of K$_3$PO$_4$ (0.12 g, 0.57 mmol) and the mixture degassed by purging N$_2$ for 15 min followed by addition of bis(triphenylphosphine)palladium(II)chloride (0.026 g, 0.038 mmol). The reaction mixture was again degassed for 10-15 min then heated up to 80° C. for 2 h. After completion of reaction (by TLC), the mixture was poured into 100 mL of ice-cold water, extracted with EtOAc (3×100 mL) and the combined organics washed with brine, dried over anhydrous Na$_2$SO$_4$, filtered and evaporated under reduced pressure. The crude residue was purified over 100-200 M silica-gel using MeOH: DCM:NH$_3$ in ratio of 6:92:2 to obtain an off white solid compound that was finally triturated with ether (0.02 g, 9% yield). $^1$H NMR (DMSO-d$_6$): δ 1.11 (t, J=7.20 Hz, 3H), 1.40 (s, 9H), 1.83 (m, 2H), 2.05 (m, 2H), 3.19 (q, J=7.20 Hz, 2H), 3.33 (m, 2H), 4.34 (m, 2H), 6.88 (br s, 1H), 7.43 (br, s, 1H), 7.96 (m, 2H), 8.01 (s, 1H), 8.19 (m, 1H), 8.49 (m, 1H), 8.81 (m, 1H), 8.92 (s, 2H) and 10.54 (br s, 1H). MS: 618.99 [M+H]$^+$.

4-Amino-1-(5-(2-(3-ethylureido)-7-(pyridin-2-yl) benzothiazol-5-yl)pyrimidin-2-yl)piperidine-4-carboxylic acid hydrochloride (128)

To an ice-cold solution of 4-((tert-butoxycarbonyl)amino)-1-(5-(2-(3-ethylureido)-7-(pyridin-2-yl)benzothiazol-5-yl) pyrimidin-2-yl)piperidine-4-carboxylic acid (0.02 g, 0.03 mmol) in 1,4-dioxane (2.0 mL) was added HCl-dioxane (4.0 M, 1.0 mL) solution and the reaction mixture was left to stir at rt for 30 min. After completion (by TLC), the solvent was evaporated to obtain a brownish solid material that was finally triturated with ether to afford Compound 128 (0.01 g) as a hydrochloride salt. $^1$H NMR (DMSO-d$_6$): δ 1.11 (t, J=7.20 Hz, 3H), 1.87 (m, 2H), 2.11 (m, 2H), 3.19 (m, 2H), 3.40 (m, 2H), 3.93 (m, 2H), 4.12 (m, 2H), 6.99 (br s, 1H), 7.45 (m, 1H), 7.95 (br s, 2H), 8.25 (s, 1H), 8.49 (d, J=8.0 Hz, 1H), 8.62 (s, 2H), 8.80 (d, J=4.0 Hz, 1H), 8.97 (s, 1H) and 10.65 (br s, 1H). LCMS: 519.30 [M+H]$^+$ Compound 139: 4-allyl-1-[5-[2-(ethylcarbamoylamino)-7-pyrazin-2-yl-1,3-benzothiazol-5-yl]pyrimidin-2-yl]piperidine-4-carboxylic acid

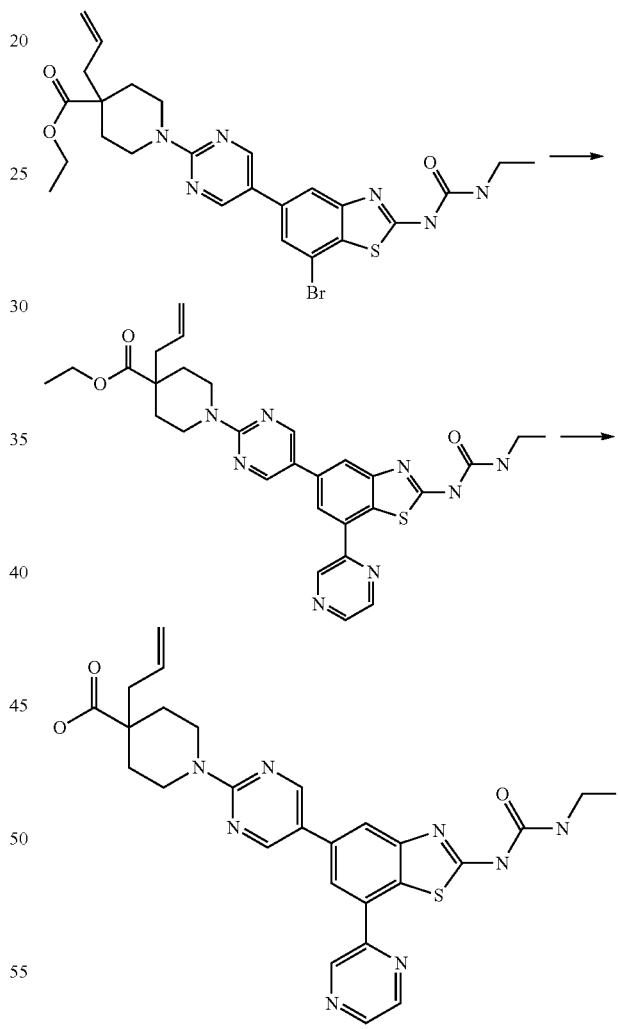

Ethyl 4-allyl-1-[5-[7-bromo-2-(ethylcarbamoylamino)-1,3-benzothiazol-5-yl]pyrimidin-2-yl]piperidine-4-carboxylate To a solution of 1-(7-bromo-5-iodobenzothiazol-2-yl)-3-ethylurea (0.55 g, 1.29 mmol) and ethyl 4-allyl-1-(5-(4,4,5,5-tetramethyl-1,3,2-dioxaborolan-2-yl)pyrimidin-2-yl)piperidine-4-carboxylate (0.79 g, 1.97 mmol) in 1,4-dioxane:

MeOH (30:20 mL) was added potassium phosphate (0.41 g, 1.97 mmol) at rt and the mixture degassed for 15-20 min by purging N$_2$ followed by addition of tetrakis(triphenylphosphine)palladium(0) (0.15 g, 0.13 mmol). The reaction mixture was again degassed for another 15-20 min then heated up to 80° C. for 5 h. After completion of reaction (by TLC), the reaction mixture was cooled to rt, diluted with EtOAc (500 mL) and passed through celite. The filtrate was evaporated and the crude residue was purified over 100-200 M silica-gel using 1.50% MeOH: DCM to obtain the desired product as a beige solid (0.20 g, 27% yield). $^1$H NMR (DMSO-d$_6$): δ 1.09 (t, J=7.20 Hz, 3H), 1.21 (t, J=6.80 Hz, 3H), 1.47 (m, 2H), 2.05 (m, 2H), 2.29 (m, 2H), 3.18 (m, 2H), 3.21 (q, J=7.20, 2H), 4.17 (q, J=6.80 Hz, 2H), 4.46 (m, 2H), 5.05 (m, 2H), 5.72 (m, 1H) 6.74 (br s, 1H), 7.69 (s, 1H), 7.87 (s, 1H); 8.77 (s, 2H) and 10.90 (br s, 1H).

Ethyl 4-allyl-1-[5-[2-(ethylcarbamoylamino)-7-pyrazin-2-yl-1,3-benzothiazol-5-yl]pyrimidin-2-yl]piperidine-4-carboxylate To a solution of 4-allyl-1-(5-(7-bromo-2-(3-ethylureido)benzothiazol-5-yl)pyrimidin-2-yl)piperidine-4-carboxylate (0.45 g, 0.78 mmol) in DMSO (5.0 mL) was added bis(neopentylglycolato)diboron (0.35 g, 1.57 mmol) and potassium acetate (0.11 g, 1.17 mmol) and the mixture degassed by purging N$_2$ for 15 min followed by addition of dichloro(1,1-bis(diphenylphosphino)ferrocene)palladium (II) (0.057 g, 0.078 mmol). The reaction mixture was again degassed for 10-15 min then heated up to 80° C. for 2 h. After reaction completion the mixture was cooled to rt followed by the addition of 2-chloropyrazine (0.20 g, 1.17 mmol) and aqueous solution of Cs$_2$CO$_3$ (0.38 g, 1.17 mmol, dissolved in minimum amount of water) and the mixture degassed by purging N$_2$ for 15 min followed by addition of tetrakis(triphenylphosphine)palladium (0) (0.09 g, 0.078 mmol). The reaction mixture was again degassed for 10-15 min then heated up to 80° C. for 16 h. After reaction completion, the mixture was poured into 100 mL of ice-cold water, extracted with EtOAc (3×150 mL) and the combined organic layer washed with brine, dried over Na$_2$SO$_4$, filtered and evaporated. The crude residue was purified over 100-200 M silica-gel using 1.50% MeOH: DCM to obtain the desired product as a beige solid (0.26 g, 58% yield). $^1$H NMR (DMSO-d$_6$): δ 1.09 (t, J=7.20 Hz, 3H), 1.21 (t, J=6.80 Hz, 3H), 1.47 (m, 2H), 2.05 (m, 2H), 2.29 (m, 2H), 3.18 (m, 2H), 3.21 (q, J=7.20, 2H), 4.17 (q, J=6.80 Hz, 2H), 4.46 (m, 2H), 5.05 (m, 2H), 5.72 (m, 1H) 6.80 (br s, 1H), 8.04 (s, 1H), 8.40 (s, 1H); 8.69 (s, 1H), 8.87 (s, 1H), 8.94 (s, 2H), 9.77 (s, 1H) and 10.64 (br s, 1H).

4-Allyl-1-[5-[2-(ethylcarbamoylamino)-7-pyrazin-2-yl-1,3-benzothiazol-5-yl]pyrimidin-2-yl]piperidine-4-carboxylic acid To an ice-cold solution of ethyl 4-allyl-1-(5-(2-(3-ethylureido)-7-(pyrazin-2-yl)benzothiazol-5-yl)pyrimidin-2-yl) piperidine-4-carboxylate (0.26 g, 0.45 mmol) in DMSO (2.0 mL) was added potassium tert-butoxide (0.25 g, 2.25 mmol). The resulting mixture was stirred at rt for 2 h. After completion of reaction (by TLC), water (10 mL) was added followed by extraction with EtOAc (2×50 mL). The organic layer was discarded and the pH of the aqueous layer was adjusted up to 4-5, then extracted with hot EtOAc (3×100 mL) and the combined organic layer dried over Na$_2$SO$_4$, filtered and evaporated under reduced pressure. The residue thus obtained was triturated with ether to afford Compound 139 as a beige solid (0.13 g, 53% yield). $^1$H NMR (DMSO-d$_6$): δ 1.09 (t, J=7.20 Hz, 3H), 1.44 (m, 2H), 2.05 (m, 2H), 2.29 (m, 2H), 3.17-3.22 (m, 4H), 4.43 (m, 2H), 5.07 (m, 2H), 5.71 (m, 1H), 6.90 (br s, 1H), 8.03 (s, 1H), 8.40 (s, 1H), 8.69 (d, J=2.80 Hz, 1H), 8.87 (d, J=2.0 Hz, 1H), 8.94 (s, 2H), 9.77 (s, 1H), 10.71 (br s, 1H) and 12.69 (br s, 1H). MS: 545.26 [M+H]$^+$.

Compound 142: 1-[5-[2-(ethylcarbamoylamino)-7-(2-pyridyl)-1,3-benzothiazol-5-yl]pyrimidin-2-yl]-4-(trifluoromethyl)piperidine-4-carboxylic acid

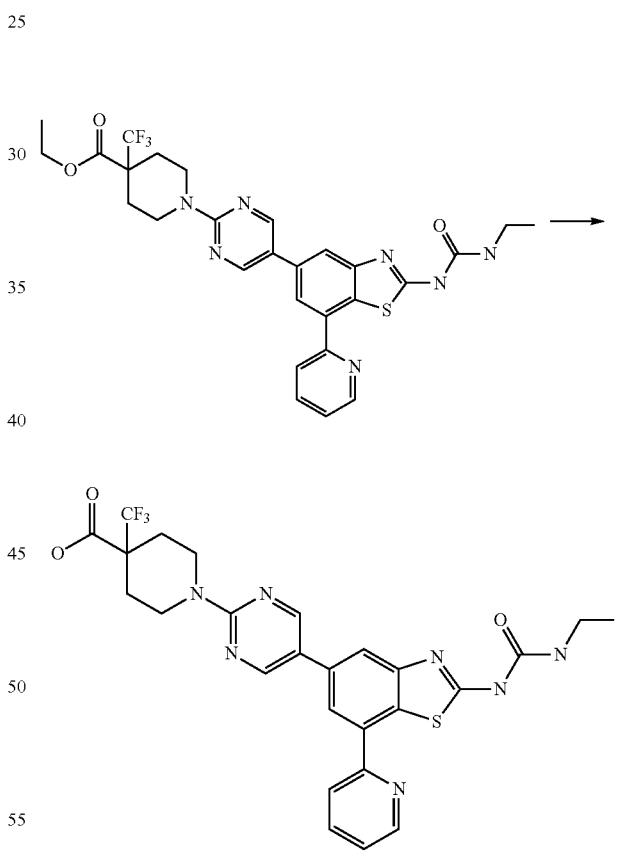

Ethyl 1-(5-(2-(3-ethylureido)-7-(pyridin-2-yl)benzothiazol-5-yl)pyrimidin-2-yl)-4-(trifluoromethyl)piperidine-4-carboxylate To the solution of ethyl 4-(trifluoromethyl)piperidine-4-carboxylate hydrochloride (0.1 g, 0.44 mmol) in DMA (5.0 mL) was added DIPEA (0.25 mL, 1.46 mmol) at rt and the mixture stirred at rt for 10 min followed by addition of 1-(5-(2-chloropyrimidin-5-yl)-7-(pyridin-2-yl)benzothiazol-2-yl)-3-ethylurea (0.12 g, 0.29 mmol). The reaction was heated up to 80° C. for 16 h and after completion (by TLC), the mixture was poured into 50 mL of ice cold water, extracted with EtOAc (3×50 mL) and the combined organics washed with brine, dried (Na$_2$SO$_4$), filtered and concentrated under reduced pressure. The crude residue was purified over 100-200 M silica-gel using 1.50% MeOH: DCM to obtain an off white solid (0.09 g, 51%). $^1$H NMR (DMSO-d$_6$): δ 1.15 (t, J=7.20 Hz, 3H), 1.20 (t, J=6.80 Hz, 3H), 1.45 (m, 2H), 2.06 (m, 2H), 2.54 (m, 2H), 3.21 (q, J=7.20, 2H), 4.15 (q, J=6.80 Hz, 2H), 4.32 (m, 2H), 6.86 (br s, 1H), 7.44 (m, 1H), 7.99 (m, 2H), 8.23 (s, 1H), 8.47 (m, 1H), 8.80 (m, 1H), 8.92 (s, 2H) and 10.56 (br s, 1H).

1-[5-[2-(Ethylcarbamoylamino)-7-(2-pyridyl)-1,3-benzothiazol-5-yl]pyrimidin-2-yl]-4-(trifluoromethyl)piperidine-4-carboxylic acid To an ice-cold solution of ethyl 1-(5-(2-(3-ethylureido)-7-(pyridin-2-yl)benzothiazol-5-yl)pyrimidin-2-yl)-4-(trifluoromethyl)piperidine-4-carboxylate (0.05 g, 0.08 mmol) in DMSO (2.0 mL) was added potassium tert-butoxide (0.046 g, 0.41 mmol) and the mixture stirred at rt for 2 h. After completion of reaction (by TLC), water (10 mL) was added followed by extraction with EtOAc (2×50 mL) and the organic layer discarded. The pH of the aqueous layer was adjusted up to 4-5 then extracted with hot EtOAc (3×75 mL) and the combined organic layer dried over Na$_2$SO$_4$, filtered and evaporated under reduced pressure. The residue thus obtained was triturated with ether to afford Compound 142 as off-white solid (0.04 g, 84% yield). $^1$H NMR (DMSO-d$_6$): δ 1.09 (t, J=7.20 Hz, 3H), 1.65 (m, 2H), 2.31 (m, 2H), 3.01 (m, 2H), 3.20 (q, J=7.20 Hz, 2H), 4.75 (m, 2H), 6.87 (br s, 1H, D$_2$O exchangeable), 7.43 (m, 1H), 7.99 (m, 2H), 8.23 (s, 1H), 8.48 (d, J=7.20 Hz, 1H), 8.80 (d, J=3.60 Hz, 1H), 8.92 (s, 2H), 10.57 (br s, 1H, D$_2$O exchangeable) and 14.06 (br s, 1H, D$_2$O exchangeable). MS: 572.10 [M+H]$^+$.

The following compounds were similarly prepared from their respective precursors.

| Cpd No. | Structure | LCMS data [M + H]$^+$ | $^1$H NMR data |
|---|---|---|---|
| 163 | 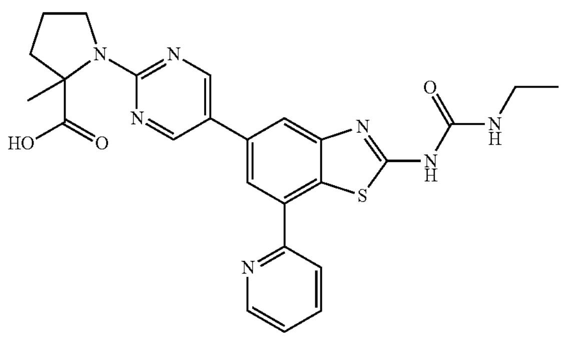 [SMILES: CCNC(=O)Nc1nc2cc(-c3cnc(N4CCCC4(C)C(=O)O)nc3)cc(-c3ccccn3)c2s1] | 504.1 | (Acetone) δ 8.83 (m, 1H), 8.81 (s, 2H), 8.44 (d, J = 8.2 Hz, 1H), 8.21 (d, J = 1.6 Hz, 1H), 7.98 (m, 1H), 7.90 (d, J = 1.6 Hz, 1H), 7.42 (m, 1H), 4.17 (d, J = 11.4 Hz, 1H), 3.79-3.68 (m, 3H), 3.50 (d, J = 11.3 Hz, 1H), 3.41-3.33 (m, 2H), 2.57-2.48 (m, 1H), 1.46 (s, 3H), 1.21 (t, J = 7.2 Hz, 4H). |
| 143 | 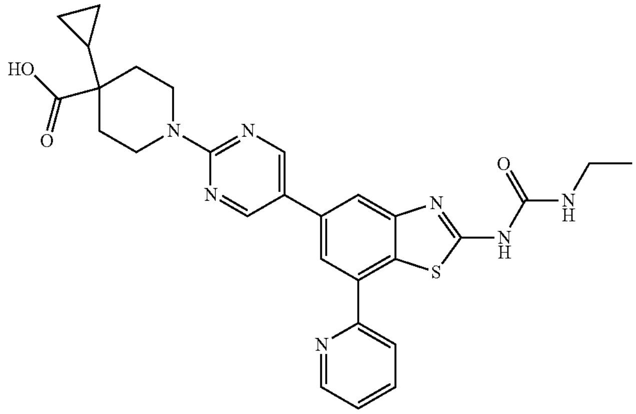 [SMILES: CCNC(=O)Nc1nc2cc(-c3cnc(N4CCC(C(=O)O)(C5CC5)CC4)nc3)cc(-c3ccccn3)c2s1] | 544.1 | (CDCl$_3$) δ 8.74 (d, J = 4.0 Hz, 1H), 8.68 (s, 2H), 8.00 (d, J = 8.1 Hz, 1H), 7.90 (s, 1H), 7.85-7.74 (m, 2H), 7.27-7.24 (M, 1H), 4.75 (d, J = 13.4 Hz, 2H), 3.48 (dt, J = 13.7, 7.0 Hz, 2H), 3.16 (t, J = 12.3 Hz, 2H), 2.22 (d, J = 12.9 Hz, 2H), 1.48 (dd, J = 11.4, 8.1 Hz, 2H), 1.29 (dd, J = 14.5, 7.2 Hz, 3H), 1.18-1.03 (m, 1H), 0.56-0.36 (m, 4H). |

| Cpd No. | Structure | LCMS data [M + H]+ | 1H NMR data |
|---|---|---|---|
| 166 | 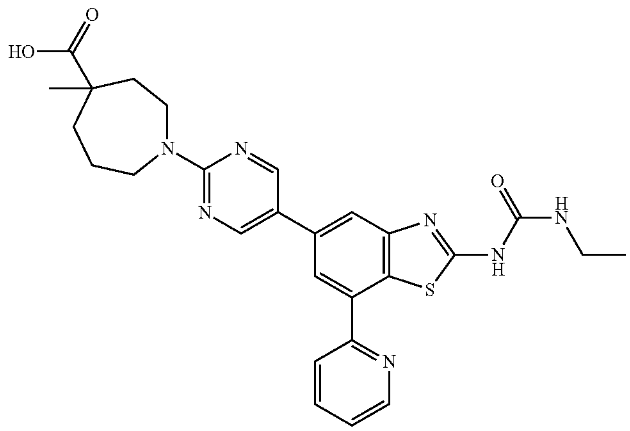 [SMILES: CCNC(=O)Nc1nc2cc(-c3cnc(N4CCCC(C)(C(=O)O)CC4)nc3)cc(-c3ccccn3)c2s1] | 532.16 | (CDCl3) δ 8.59 (s, 2H), 8.48 (d, J = 4.25 Hz, 1H), 7.77 (d, J = 8.4 Hz, 1H), 7.64-7.60 (m, 1H), 7.5 (s, 1H), 7.44 (s, 1H), 7.05-7.02 (m, 1H), 3.53-3.35 (m, 4H), 2.42-2.35 (m 1H), 2.20-2.12 (m, 2H), 1.92-1.78 (m, 2H), 1.53-1.43 (m, 1H), 1.35 (s, 3H), 1.30-1.23 (m, 5H) |

Compound 144: 1-[5-[2-(ethylcarbamoylamino)-7-[2-(3-methylimidazol-4-yl)ethynyl]-1,3-benzothiazol-5-yl]pyrimidin-2-yl]-4-methyl-piperidine-4-carboxylic acid

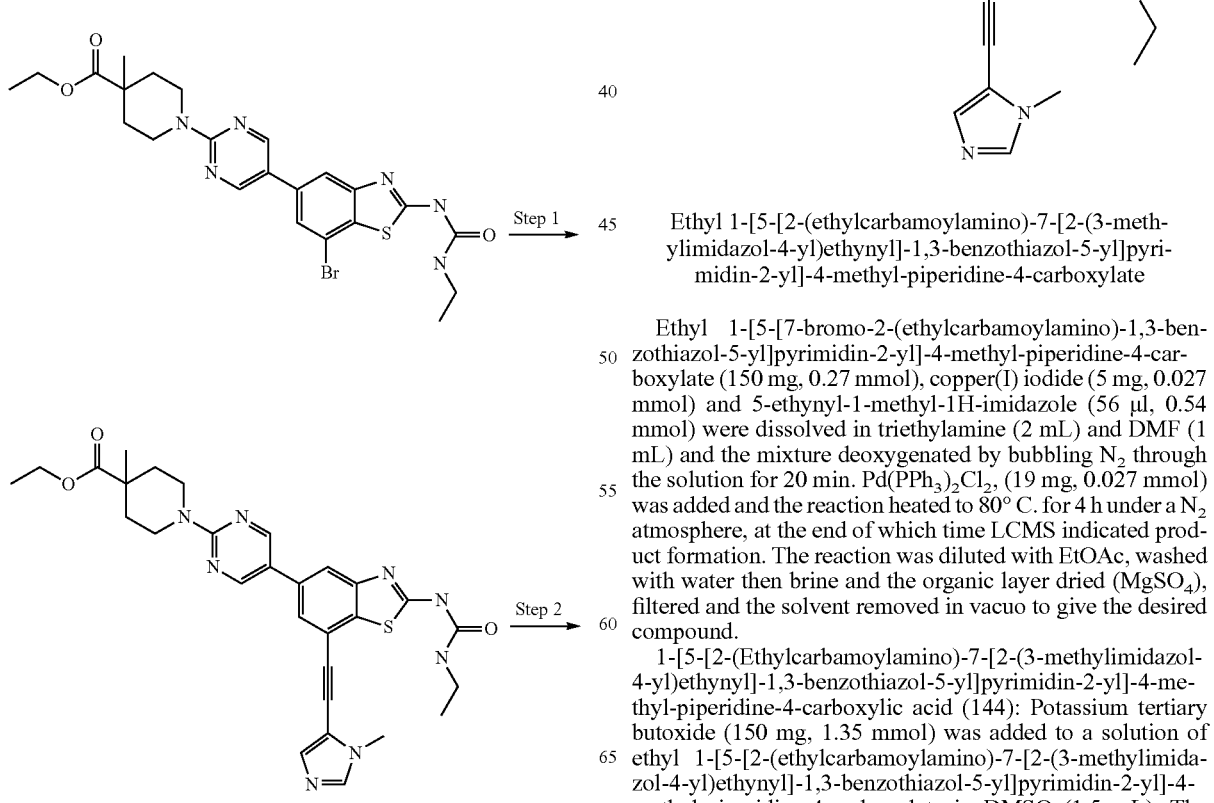

Ethyl 1-[5-[2-(ethylcarbamoylamino)-7-[2-(3-methylimidazol-4-yl)ethynyl]-1,3-benzothiazol-5-yl]pyrimidin-2-yl]-4-methyl-piperidine-4-carboxylate Ethyl 1-[5-[7-bromo-2-(ethylcarbamoylamino)-1,3-benzothiazol-5-yl]pyrimidin-2-yl]-4-methyl-piperidine-4-carboxylate (150 mg, 0.27 mmol), copper(I) iodide (5 mg, 0.027 mmol) and 5-ethynyl-1-methyl-1H-imidazole (56 µl, 0.54 mmol) were dissolved in triethylamine (2 mL) and DMF (1 mL) and the mixture deoxygenated by bubbling N2 through the solution for 20 min. Pd(PPh3)2Cl2, (19 mg, 0.027 mmol) was added and the reaction heated to 80° C. for 4 h under a N2 atmosphere, at the end of which time LCMS indicated product formation. The reaction was diluted with EtOAc, washed with water then brine and the organic layer dried (MgSO4), filtered and the solvent removed in vacuo to give the desired compound.

1-[5-[2-(Ethylcarbamoylamino)-7-[2-(3-methylimidazol-4-yl)ethynyl]-1,3-benzothiazol-5-yl]pyrimidin-2-yl]-4-methyl-piperidine-4-carboxylic acid (144): Potassium tertiary butoxide (150 mg, 1.35 mmol) was added to a solution of ethyl 1-[5-[2-(ethylcarbamoylamino)-7-[2-(3-methylimidazol-4-yl)ethynyl]-1,3-benzothiazol-5-yl]pyrimidin-2-yl]-4-methyl-piperidine-4-carboxylate in DMSO (1.5 mL). The mixture was stirred at rt for 2 h after which time LCMS indicated clean conversion to the acid. The mixture was filtered through cotton wool to remove solid particulates and purified by preparative-HPLC to give Compound 144 as a white solid, 43 mg, 29% yield for 2 steps. $^1$H NMR δ (ppm) (DMSO-d$_6$): 8.81 (2H, s), 7.95 (1H, d, J=1.55 Hz), 7.89 (1H, s), 7.73 (1H, d, J=1.56 Hz), 7.45 (1H, s), 7.27 (1H, t, J=5.58 Hz), 4.32 (2H, dt, J=13.70, 4.46 Hz), 3.83 (3H, s), 3.37 (2H, ddd, J=14.10, 10.43, 4.06 Hz), 3.23 (2H, p, J=6.90 Hz), 2.06 (2H, dt, J=13.39, 3.62 Hz), 1.41 (2H, ddd, J=13.36, 10.05, 3.86 Hz), 1.21 (3H, s), 1.13 (3H, t, J=7.15 Hz). MS: 545 [M+H]$^+$.

The following compounds were similarly prepared

| Cpd No. | Structure | $^1$H NMR data |
|---|---|---|
| 22 | 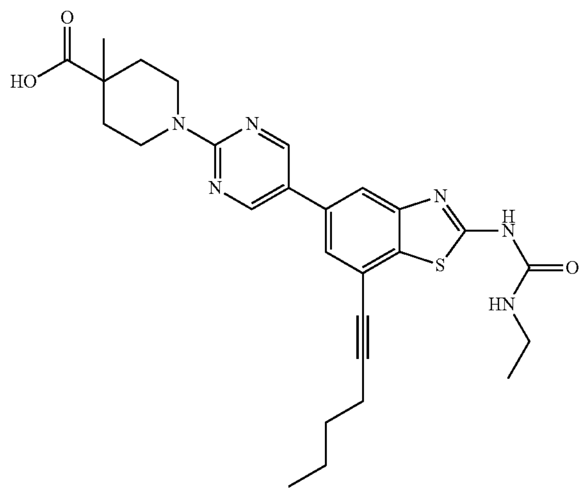 [SMILES: CCCCC#Cc1cc(-c2cnc(N3CCC(C)(C(=O)O)CC3)nc2)cc2nc(NC(=O)NCC)sc12] | (DMSO-d$_6$): δ 8.77 (2 H, s), 7.86 (1 H, d, J = 1.62 Hz), 7.52 (1 H, d, J = 1.55 Hz), 7.01 (1 H, t, J = 5.62 Hz), 4.31 (2 H, dt, J = 13.60, 4.30 Hz), 3.23 (2 H, p, J = 6.71 Hz), 2.58 (2 H, t, J = 6.86 Hz), 2.05 (2 H, d, J = 13.05 Hz), 1.62 (2 H, ddd, J = 14.32, 13.29, 7.10 Hz), 1.53 (2 H, ddd, J = 14.83, 7.55, 7.18 Hz), 1.41 (2 H, t, J = 11.51 Hz), 1.22 (3 H, s), 1.13 (3 H, t, J = 7.17 Hz), 0.99 (3 H, t, J = 7.23 Hz). |
| 150 | 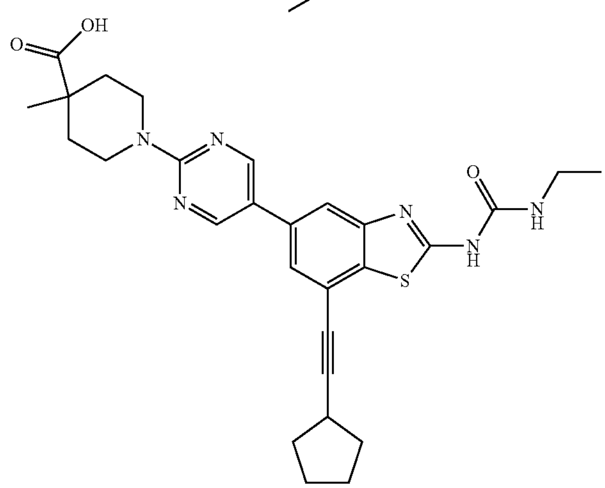 | (DMSO-d$_6$): δ 1.10 (t, J = 7.20 Hz, 3H), 1.18 (s, 3H), 1.40 (m, 2H), 1.62-1.70 (m, 4H), 1.75 (m, 2H), 1.98-2.08 (m, 4H), 3.0 (m, 1H), 3.17 (m, 2H), 3.31 (m, 2H), 4.25 (m, 2H), 6.74 (br s, 1H), 7.48 (s, 1H), 7.82 (s, 1H), 8.79 (s, 2H), 10.80 (br s, 1H) and 12.40 (br s, 1H) |
| 151 | 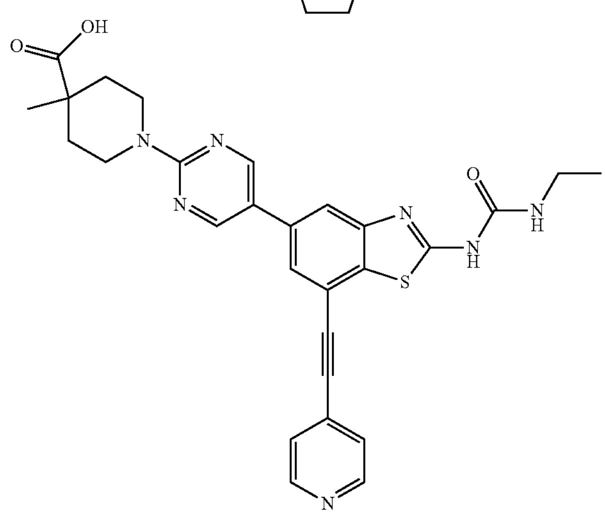 | (DMSO-D$_2$O): δ 1.09 (t, J = 7.20 Hz, 3H), 1.17 (s, 3H), 1.40 (m, 2H), 1.99 (m, 2H), 3.18 (q, J = 6.80 Hz, 2H), 3.36 (m, 2H), 4.21 (m, 2H), 7.57-7.77 (m, 3H), 7.94 (s, 1H), 8.70 (m, 2H) and 8.73 (s, 2H) |

Compound 145 1-[5-[2-(ethylcarbamoylamino)-7-(thiazol-2-ylcarbamoyl)-1,3-benzothiazol-5-yl]pyrimidin-2-yl]-4-methyl-piperidine-4-carboxylic acid

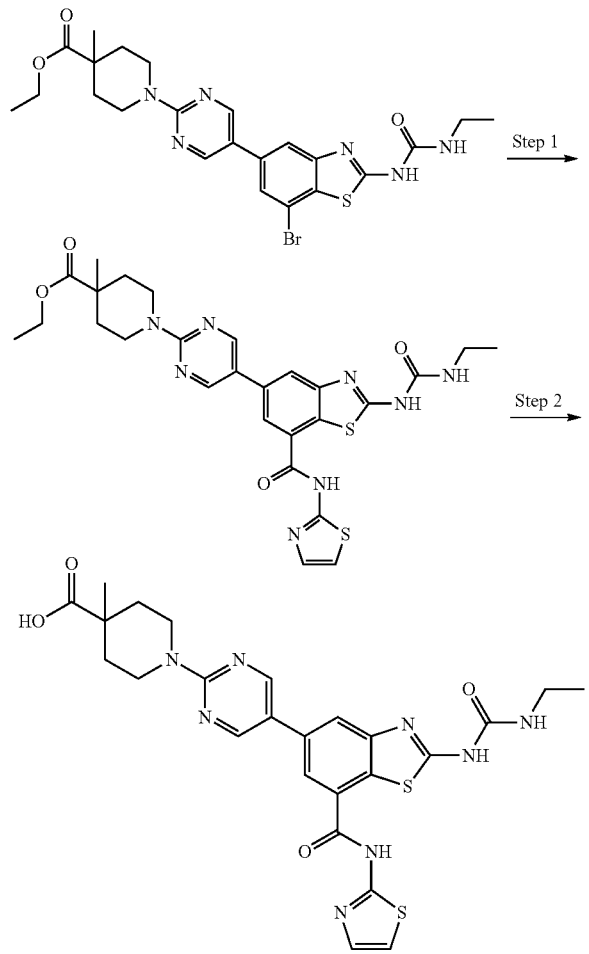

Ethyl 1-(5-(7-(4,5-dihydrothiazol-2-ylcarbamoyl)-2-(3-ethylureido)benzo[d]thiazol-5-yl)pyrimidin-2-yl)-4-methylpiperidine-4-carboxylate: Ethyl 1-(5-(7-bromo-2-(3-ethylureido)benzo[d]thiazol-5-yl)pyrimidin-2-yl)-4-methylpiperidine-4-carboxylate (200 mg, 0.37 mmol) and 2-aminothiazole (111 mg, 1.11 mmol) were stirred in DMF (3 ml) and triethylamine (3 ml) was added. Carbon monoxide was bubbled through the mixture for 10 min. Xantphos (86.3 mg, 0.15 mmol) and palladium (II) acetate (18 mg, 0.08 mmol) were added and the reaction was purged with carbon monoxide, sealed then heated to 90° C. for 18 h. The reaction was allowed to cool and the solvents removed under reduced pressure. The resulting residue was triturated with water causing a solid to precipitate which was isolated by filtration to afford the target material (185 mg, 80% pure by LC-MS) (86%) after drying in a vacuum oven. This material was used directly in the next step with no further purification.

1-(5-(7-(4,5-Dihydrothiazol-2-ylcarbamoyl)-2-(3-ethylureido)benzo[d]thiazol-5-yl)pyrimidin-2-yl)-4-methylpiperidine-4-carboxylic acid (145): Ethyl 1-(5-(2-(3-ethylureido)-7-(thiazole-2-carbonyl)benzo[d]thiazol-5-yl) pyrimidin-2-yl)-4-methylpiperidine-4-carboxylate (185 mg, 0.31 mmol) was dissolved in DMSO (2 ml) with stirring and potassium-t-butoxide (174 mg, 1.56 mmol) was added. The reaction was allowed to stir at rt for 1 h. The reaction was filtered and purified by preparative HPLC to afford Compound 145 as a solid (7 mg, 95% purity by HPCL) (4%) $^1$H NMR (DMSO-d$_6$): δ 9.00-8.95 (2H, m), 8.63 (1H, s), 8.19 (1H, s), 7.65 (1H, d, J=3.59 Hz), 7.37 (1H, d, J=3.57 Hz), 6.93 (1H, t, J=5.58 Hz), 4.34 (2H, dt, J=13.73, 4.50 Hz), 3.41 (2H, dd, J=11.79, 3.40 Hz), 3.25 (2H, p, J=6.76 Hz), 2.06 (2H, dt, J=13.53, 3.67 Hz), 1.44 (2H, ddd, J=13.50, 9.94, 4.01 Hz), 1.23 (3H, s), 1.15 (3H, t, J=7.18 Hz). MS: 567 [M+H]$^+$.

Compound 91 1-[5-[2-(ethylcarbamoylamino)-7-[ethyl(methyl)carbamoyl]-1,3-benzothiazol-5-yl]pyrimidin-2-yl]-4-methyl-piperidine-4-carboxylic acid was similarly prepared

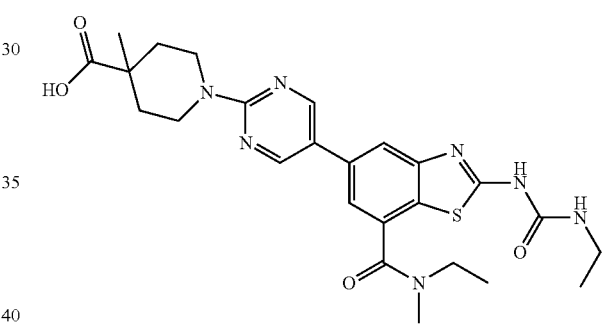

$^1$H NMR (DMSO-d$_6$): δ 8.80 (2H, s), 7.96 (1H, d, J=1.61 Hz), 7.51 (1H, s), 7.17 (1H, t, J=5.70 Hz), 4.31 (2H, dt, J=13.72, 4.50 Hz), 3.37 (2H, ddd, J=14.36, 9.75, 4.17 Hz), 3.22 (2H, p, J=6.87 Hz), 3.03 (3H, s), 2.05 (2H, dt, J=13.49, 3.73 Hz), 1.40 (2H, ddd, J=13.38, 10.04, 4.01 Hz), 1.21 (3H, s), 1.13 (3H, t, J=7.17 Hz). MS: 526[M+H]$^+$.

Compound 146: 1-[5-[2-(ethylcarbamoylamino)-7-(pyrimidine-2-carbonylamino)-1,3-benzothiazol-5-yl]pyrimidin-2-yl]-4-methyl-piperidine-4-carboxylic acid

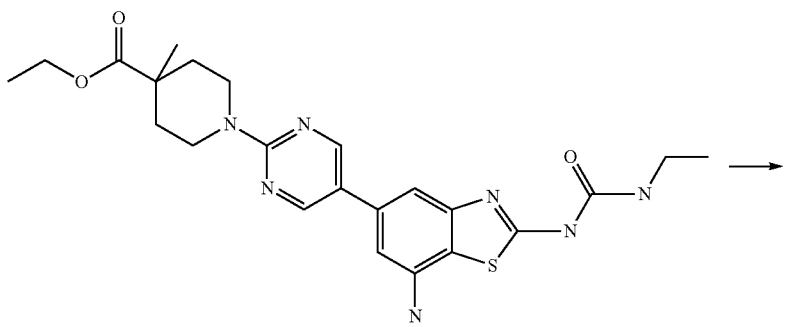

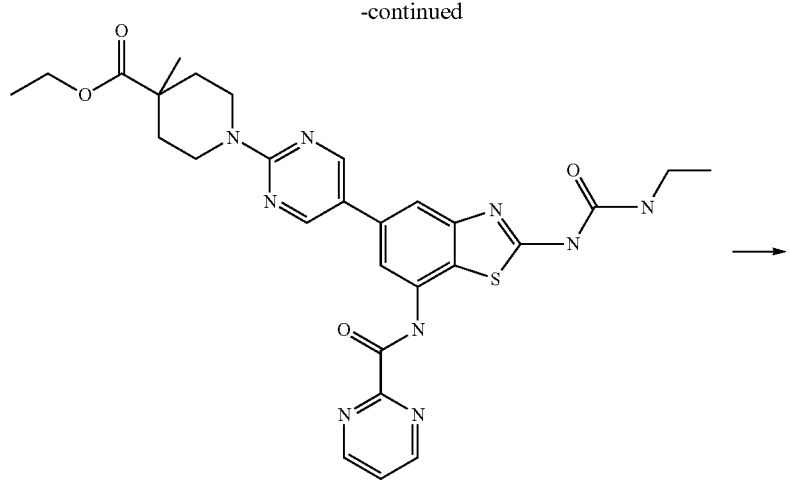

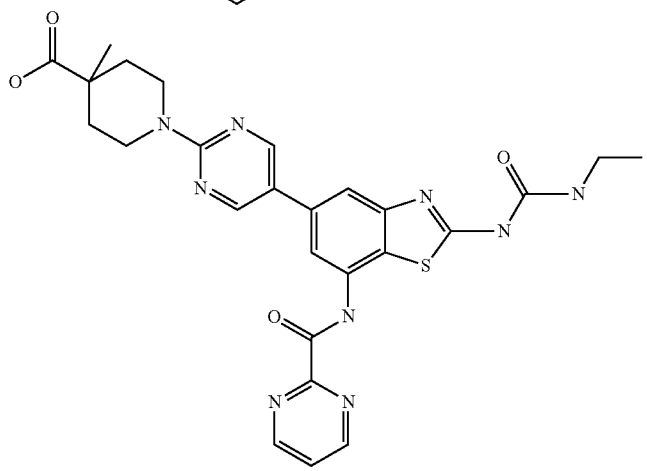

Ethyl 1-[5-[2-(ethylcarbamoylamino)-7-(pyrimidine-2-carbonylamino)-1,3-benzothiazol-5-yl]pyrimidin-2-yl]-4-methyl-piperidine-4-carboxylate: Ethyl 1-[5-[7-amino-2-(ethylcarbamoylamino)-1,3-benzothiazol-5-yl]pyrimidin-2-yl]-4-methyl-piperidine-4-carboxylate (159 mg, 0.27 mmol), pyrimidine-2-carboxylic acid (64.2 mg, 0.52 mmol) and diisopropylethylamine (271 mg, 2.1 mmol) were dissolved in DMF (5 mL). The reaction was purged with $N_2$ then HATU (197 mg, 0.5 2 mmol) was added and the reaction stirred at rt for 18 h. The DMF was removed under reduced pressure and the resulting residue diluted with water and extracted with EtOAc. During the work up a solid precipitated which was collected by filtration and dried in the vacuum oven to provide the crude product (100 mg, 66% yield).

1-[5-[2-(Ethylcarbamoylamino)-7-(pyrimidine-2-carbonylamino)-1,3-benzothiazol-5-yl]pyrimidin-2-yl]-4-methyl-piperidine-4-carboxylic acid (146): Ethyl 1-[5-[2-(ethylcarbamoylamino)-7-(pyrimidine-2-carbonylamino)-1,3-benzothiazol-5-yl]pyrimidin-2-yl]-4-methyl-piperidine-4-carboxylate (100 mg, 0.17 mmol) was dissolved in DMSO (0.5 mL) with stirring and potassium-t-butoxide (40 mg, 0.35 mmol) added. The reaction was allowed to stir at rt for 2 h. The reaction mixture was filtered and purified by preparative HPLC to afford Compound 146 as a solid (5 mg). $^1$H NMR (DMSO-$d_6$): δ 11.01 (1H, s), 9.12 (2H, d, J=4.86 Hz), 8.77 (2H, s), 7.83 (1H, d, J=4.75 Hz), 7.82 (1H, t, J=1.44 Hz), 7.67 (1H, d, J=1.66 Hz), 7.01 (1H, s), 4.32 (2H, d, J=13.32 Hz), 3.22 (2H, p, J=7.59 Hz), 2.05 (2H, dd, J=13.04, 4.48 Hz), 1.42 (2H, t, J=11.27 Hz), 1.22 (3H, s), 1.13 (3H, dd, J=7.16, 7.16 Hz). MS: 562 [M+H]$^+$.

Compound 147 1-[5-[2-(ethylcarbamoylamino)-7-[[methyl(pyrimidin-2-yl)amino]methyl]-1,3-benzothiazol-5-yl]pyrimidin-2-yl]-4-methyl-piperidine-4-carboxylic acid

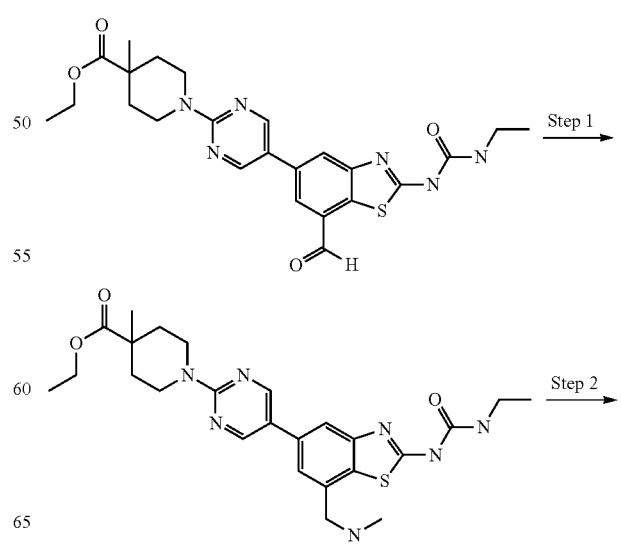

-continued

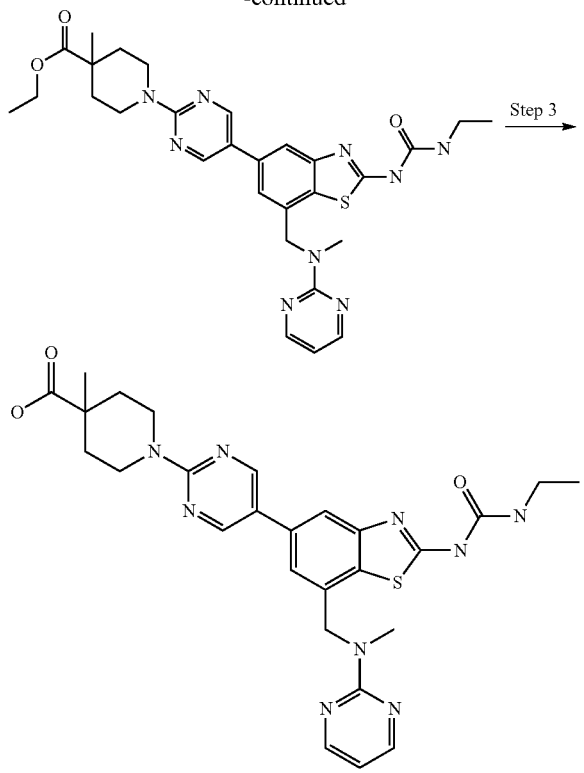

Ethyl 1-[5-[2-(ethylcarbamoylamino)-7-(methylaminomethyl)-1,3-benzothiazol-5-yl]pyrimidin-2-yl]-4-methyl-piperidine-4-carboxylate: Ethyl 1-[5-[2-(ethylcarbamoylamino)-7-formyl-1,3-benzothiazol-5-yl]pyrimidin-2-yl]-4-methyl-piperidine-4-carboxylate (140 mg, 0.28 mmol) was stirred in a 7M solution of methylamine in THF (8 mL) in a microwave tube equipped with a stirrer. The reaction was irradiated to 80° C. for 1 h in a CEM explorer microwave with stirring. After cooling, the solvents were removed under reduced pressure, the resulting residue dissolved in anhydrous MeOH (8 mL) and the reaction transferred to a round bottomed flask equipped with a calcium chloride drying tube. Sodium borohydride (43 mg, 1.12 mmol) was added and the reaction stirred at rt for 18 h. After this time LCMS indicated 70% conversion to the desired material. The reaction was diluted with water (20 mL), extracted with EtOAc (3×20 mL) and the combined organic extracts washed with brine, dried (MgSO$_4$) and concentrated under reduced pressure to afford the crude product as a glassy brown/grey solid 130 mg (91% yield).

Ethyl 1-[5-[2-(ethylcarbamoylamino)-7-[[methyl(pyrimidin-2-yl)amino]methyl]-1,3-benzothiazol-5-yl]pyrimidin-2-yl]-4-methyl-piperidine-4-carboxylate: Ethyl 1-[5-[2-(ethylcarbamoylamino)-7-(methylaminomethyl)-1,3-benzothiazol-5-yl]pyrimidin-2-yl]-4-methyl-piperidine-4-carboxylate (130 mg, 0.25 mmol), N,N'-diisopropylethylamine (3.69 mmol, 477 mg, 324 ul) and 2-chloropyrimidine (1.75 mmol, 200 mg) were combined in isopropanol (2 mL) in a microwave tube equipped with a stirrer. The tube was purged with N$_2$, sealed and irradiated to 110° C. for 1 hr in a CEM explorer microwave with stirring however LCMS indicated only starting material was present and the reaction was diluted with isopropanol (4 mL) and N,N'-diisopropylethylamine (4.19 mmol, 540 mg, 400 ul), then purged with N$_2$, sealed then irradiated to 110° C. for 1 hr in the CEM explorer with stirring. LCMS indicated conversion to the desired product along with the corresponding isopropylester and starting material. The reaction was allowed to cool, the solvents removed under reduced pressure and the resulting residue partitioned between EtOAc and water and the layers separated. The aqueous portion was extracted with EtOAc and the combined organic portions dried (MgSO$_4$) and concentrated to afford the crude product (160 mg). This material was purified by flash silica chromatography eluting with 0 to 50% EtOAc in petroleum-ether then 0 to 10% MeOH in DCM to afford the target material (40 mg, 27% yield).

1-[5-[2-(Ethylcarbamoylamino)-7-[[methyl(pyrimidin-2-yl)amino]methyl]-1,3-benzothiazol-5-yl]pyrimidin-2-yl]-4-methyl-piperidine-4-carboxylic acid (147): A stirred solution of ethyl 1-[5-[2-(ethylcarbamoylamino)-7-[[methyl(pyrimidin-2-yl)amino]methyl]-1,3-benzothiazol-5-yl]pyrimidin-2-yl]-4-methyl-piperidine-4-carboxylate (40 mg, 0.068 mmol) was dissolved in DMSO (1 mL) with stirring and potassium-t-butoxide (31 mg, 0.27 mmol) added. The reaction was allowed to stir at rt for 1 h after which time the reaction was filtered and purified by preparative HPLC to affor Compound 174 as a solid (8 mg, 21% yield). $^1$H NMR (DMSO-d$_6$): δ 8.74 (2H, s), 8.00 (1H, dd, J=4.99, 1.80 Hz), 7.79 (1H, s), 7.48 (1H, s), 7.42 (1H, ddd, J=8.42, 7.00, 1.94 Hz), 7.16 (2H, t, J=5.74 Hz), 6.59 (1H, d, J=8.41 Hz), 6.55 (1H, ddd, J=7.00, 5.02, 0.90 Hz), 4.70 (2H, d, J=5.58 Hz), 4.59 (2H, dt, J=13.29, 3.70 Hz), 3.20 (2H, p, J=6.82 Hz), 3.14 (2H, t, J=12.51 Hz), 1.92 (2H, dd, J=12.80, 3.92 Hz), 1.54 (2H, q, J=11.74 Hz), 1.12 (3H, t, J=7.16 Hz). MS: 562 [M+H]$^+$.

Compound 149 1-(5-(2-(3-ethylureido)-7-(picolinamido)benzo[d]thiazol-5-yl)pyrimidin-2-yl)-4-methylpiperidine-4-carboxylic acid (alternatively named 1-[5-[2-(ethylcarbamoylamino)-7-(pyridine-2-carbonylamino)-1,3-benzothiazol-5-yl]pyrimidin-2-yl]-4-methyl-piperidine-4-carboxylic acid)

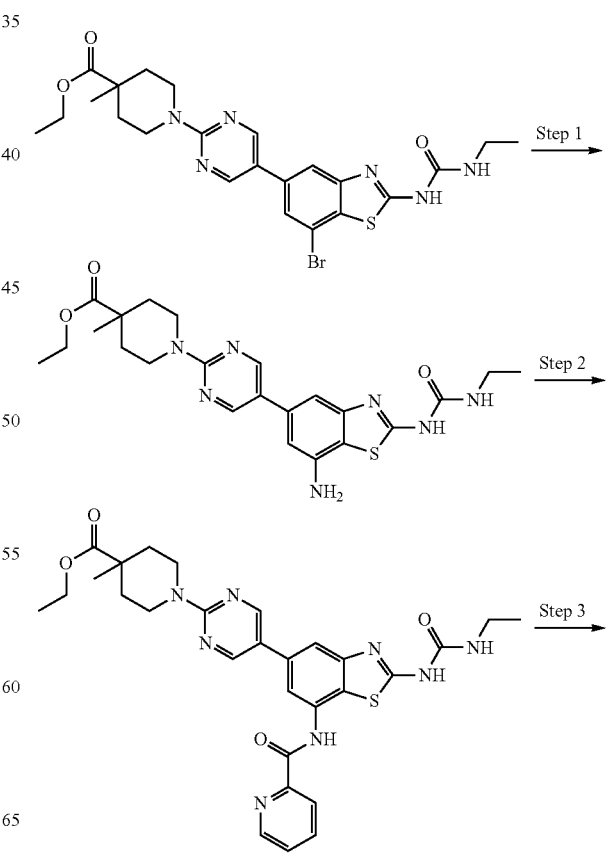

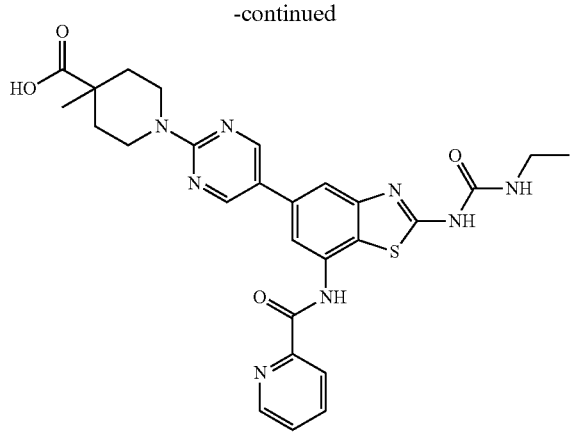

Ethyl 1-(5-(7-amino-2-(3-ethylureido)benzo[d]thiazol-5-yl)pyrimidin-2-yl)-4-methylpiperidine-4-carboxylate: Ethyl 1-(5-(7-bromo-2-(3-ethylureido)benzo[d]thiazol-5-yl)pyrimidin-2-yl)-4-methylpiperidine-4-carboxylate (306 mg, 0.56 mmol), trans-(1R,2R)—N,N'-bismethyl-1,2-cyclohexane (24 mg, 0.17 mmol), sodium azide (73 mg, 1.12 mmol) and sodium ascorbate (6 mg, 0.028 mmol) were stirred in DMSO-water 1:1 (3 ml) which had been degassed with $N_2$. CuI (1.1 mg, 0.0056 mmol) was added and the tube purged with $N_2$, sealed and heated to 110° C. for 2 h. The mixture turned black and evolution of gas was observed. LCMS after this time indicated 34% conversion to the desired amine and starting material remaining. Additional equivalents of all reagents were added and the reaction was heated to 110° C. for a further 2 h. LCMS after this time indicated 75% conversion to the desired material. The solvents were removed under reduced pressure and the resulting residue was triturated with water. The resulting solid was isolated by filtration and dried to afford the crude product (250 mg, 73% purity by LCMS) (92%). This material was used directly in the next step without further purification.

Ethyl 1-(5-(2-(3-ethylureido)-7-(picolinamido)benzo[d]thiazol-5-yl)pyrimidin-2-yl)-4-methylpiperidine-4-carboxylate: Ethyl 1-(5-(7-amino-2-(3-ethylureido)benzo[d]thiazol-5-yl)pyrimidin-2-yl)-4-methylpiperidine-4-carboxylate (119 mg, 0.25 mmol) was dissolved in pyridine (2 ml) then picolinoyl chloride hydrochloride (58 mg, 0.33 mmol) was added with stirring and the reaction stirred at rt for 18 h. The pyridine was removed under reduced pressure and the residue triturated with water. The resulting solid was collected by filtration and dried to afford the crude product 100 mg (68%). This material was used directly in the next step without further purification.

1-(5-(2-(3-Ethylureido)-7-(picolinamido)benzo[d]thiazol-5-yl)pyrimidin-2-yl)-4-methylpiperidine-4-carboxylic acid (149): Ethyl 1-(5-(2-(3-ethylureido)-7-(picolinamido)benzo[d]thiazol-5-yl)pyrimidin-2-yl)-4-methylpiperidine-4-carboxylate (100 mg, 0.17 mmol) was dissolved in DMSO (2 ml) with stirring and potassium-t-butoxide (76 mg, 0.68 mmol) added. The reaction was stirred at rt for 2 h. The reaction mixture was filtered and purified by preparative HPLC to afford Compound 149 as a solid (29 mg, 98% purity by LC-MS) (30%). $^1$H NMR (DMSO-$d_6$): δ 10.87 (1H, s), 8.84 (1H, d, J=4.78 Hz), 8.78 (2H, s), 8.25 (1H, d, J=7.82 Hz), 8.15 (1H, td, J=7.67, 1.67 Hz), 7.81 (1H, s), 7.77 (1H, dd, J=7.65, 4.87 Hz), 7.73 (1H, s), 6.86 (1H, s), 4.32 (2H, dt, J=13.67, 4.43 Hz), 3.22 (2H, p, J=6.69 Hz), 2.05 (2H, dt, J=13.55, 3.74 Hz), 1.43 (2H, ddd, J=13.38, 9.93, 3.91 Hz), 1.22 (3H, s), 1.13 (3H, t, J=7.15 Hz). MS: 561 [M+H]$^+$.

Compound 152: 1-[5-[2-(ethylcarbamoylamino)-7-[2-(6-methoxy-2-pyridyl)ethynyl]-1,3-benzothiazol-5-yl]pyrimidin-2-yl]-4-methyl-piperidine-4-carboxylic acid

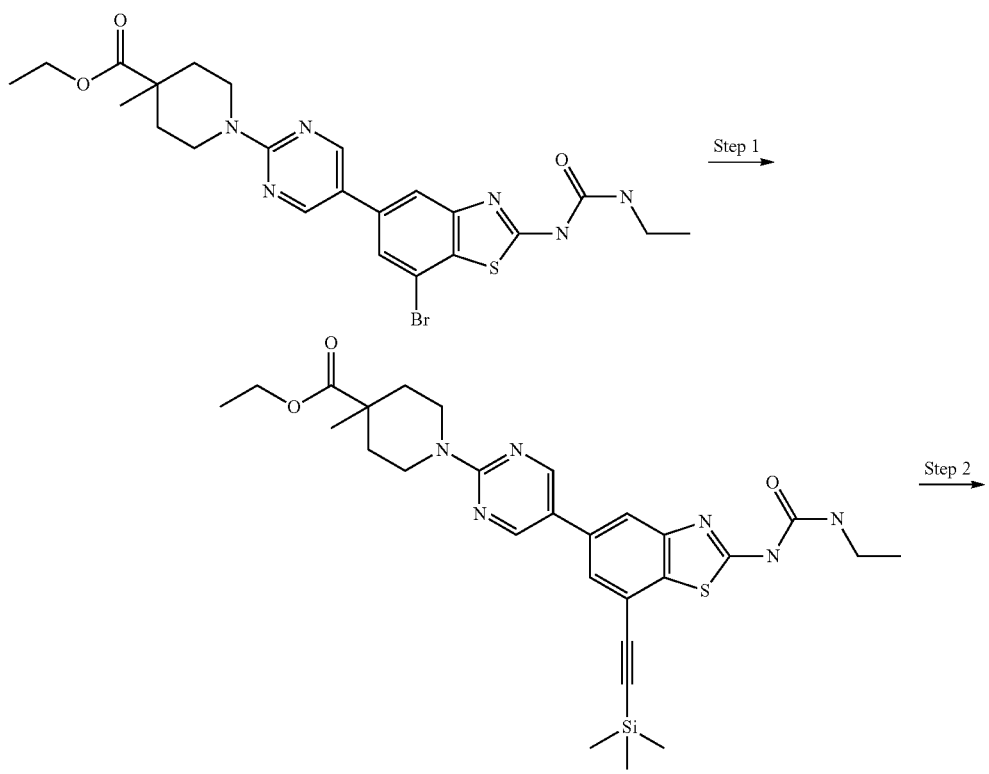

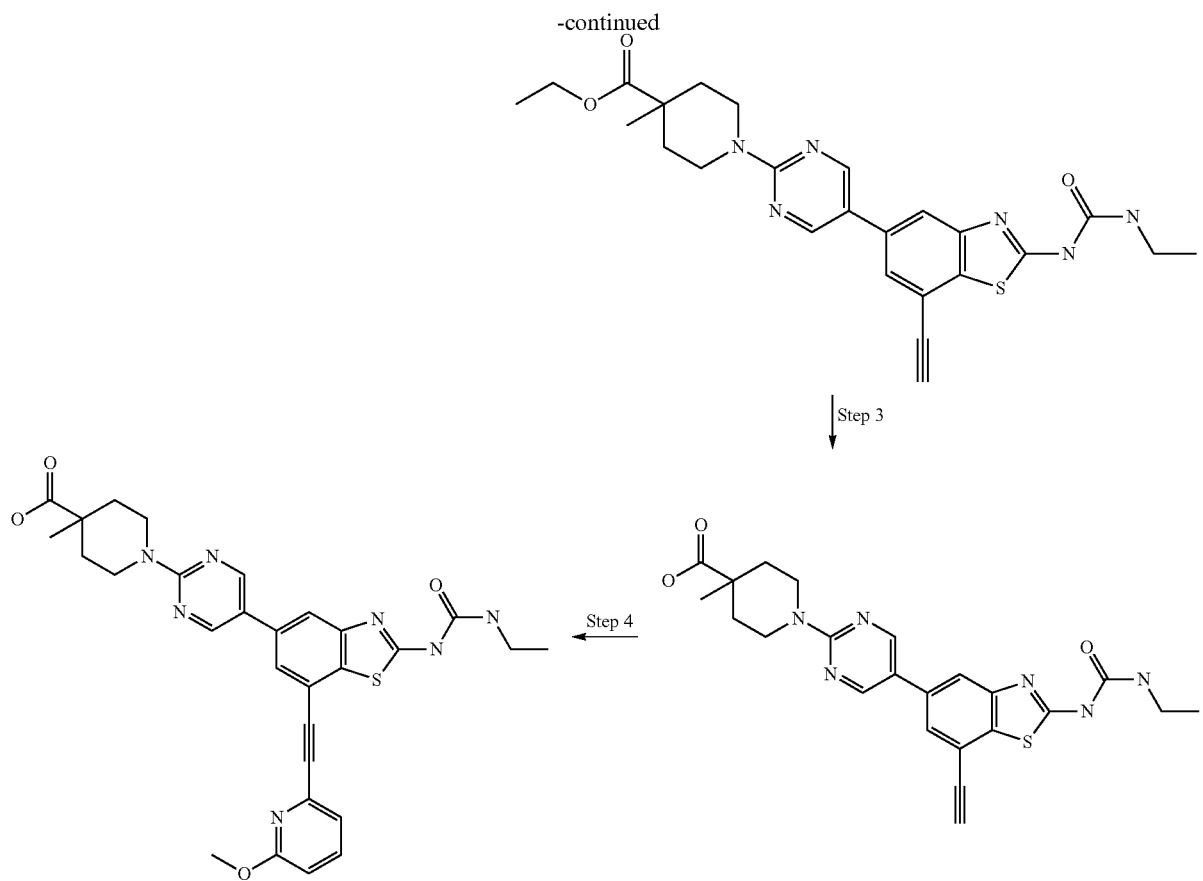

Ethyl 1-[5-[2-(ethylcarbamoylamino)-7-(2-trimethylsilyl-ethynyl)-1,3-benzothiazol-5-yl]pyrimidin-2-yl]-4-methyl-piperidine-4-carboxylate: To a solution of ethyl 1-[5-[7-bromo-2-(ethylcarbamoylamino)-1,3-benzothiazol-5-yl]pyrimidin-2-yl]-4-methyl-piperidine-4-carboxylate (3 g, 5.47 mmol) in DMF (25 mL) was added trimethylsilyl acetylene (0.91 g, 9.3 mmol) and triethyl amine (4.6 mL, 32.8 mmol) and the mixture degassed by purging $N_2$ for 15 min followed by addition of CuI (0.1 g, 0.54 mmol) and tetrakis (triphenylphosphine)palladium (0) (0.38 g, 0.54 mmol). The reaction mixture was again degassed for 10-15 min then heated up to 80° C. for 4 h. After completion of reaction (by TLC), the mixture was poured in 100 mL of ice-cold water, extracted with EtOAc (3×100 mL) and the combined organic layer washed with brine, dried over anhydrous $Na_2SO_4$, filtered and evaporated under reduced pressure. The crude residue was purified over 100-200 M silica-gel using 30% EtOAc:hexane to obtain the product as an off-white solid compound (2.4 g, 77% yield). $^1$H NMR (DMSO-$d_6$): δ 0.29 (s, 9H), 1.09 (t, J=7.20 Hz, 3H), 1.20 (m, 6H), 1.42 (m, 2H), 2.04 (m, 2H), 3.19 (m, 2H), 3.33 (q, J=7.20 Hz, 2H), 4.13 (q, J=6.80 Hz, 2H), 4.25 (m, 2H), 6.74 (br s, 1H), 7.58 (s, 1H), 7.90 (s, 1H); 8.76 (s, 2H) and 10.86 (br s, 1H). MS: 565.26 [M+H]$^+$.

Ethyl 1-[5-[2-(ethylcarbamoylamino)-7-ethynyl-1,3-benzothiazol-5-yl]pyrimidin-2-yl]-4-methyl-piperidine-4-carboxylate: To an ice-cold solution of ethyl 1-[5-[2-(ethylcarbamoylamino)-7-(2-trimethylsilylethynyl)-1,3-benzothiazol-5-yl]pyrimidin-2-yl]-4-methyl-piperidine-4-carboxylate (1.1 g, 1.94 mmol) in EtOH (40 mL) was added powdered KOH (0.24 g, 4.21 mmol) and the mixture stirred at rt for 4 h. After completion of reaction (by TLC), the solvent was evaporated under reduced pressure, water added and extracted with EtOAc (3×100 mL). The combined organic layer was washed with brine and water then dried over anhydrous $Na_2SO_4$. Solvent was evaporated under reduced pressure to obtain the product as a pale yellow solid (0.8 g, 83% yield). $^1$H NMR (DMSO-$d_6$): δ 1.11 (t, J=7.20 Hz, 3H), 1.21 (m, 6H), 1.42 (m, 2H), 2.04 (m, 2H), 3.20 (m, 2H), 3.33 (q, J=7.20 Hz, 2H), 4.13 (q, J=6.80 Hz, 2H), 4.25 (m, 2H), 4.67 (s, 1H), 6.80 (br s, 1H), 7.61 (s, 1H), 7.94 (s, 1H); 8.78 (s, 2H) and 10.86 (br s, 1H). MS: 493.12 [M+H]$^+$.

1-[5-[2-(Ethylcarbamoylamino)-7-ethynyl-1,3-benzothiazol-5-yl]pyrimidin-2-yl]-4-methyl-piperidine-4-carboxylic acid: To an ice-cold solution of ethyl 1-[5-[2-(ethylcarbamoylamino)-7-ethynyl-1,3-benzothiazol-5-yl]pyrimidin-2-yl]-4-methyl-piperidine-4-carboxylate (1.1 g, 2.23 mmol) in DMSO (10 mL) was added potassium tert-butoxide (1.25 g, 11.1 mmol) and the mixture stirred at rt for 1 h. After completion of reaction (by TLC), water (100 mL) was added, followed by extraction with EtOAc (2×100 mL) and the organic layer then discarded. The pH of the aqueous layer was adjusted up to 4-5, extracted with hot EtOAc (3×100 mL) and the combined organic layer dried over $Na_2SO_4$, filtered and evaporated under reduced pressure. The residue thus obtained was triturated with ether to obtain the desired product as off-white solid (0.9 g, 87% yield). $^1$H NMR (DMSO-$d_6$): δ 1.14 (t, J=7.20 Hz, 3H), 1.21 (s, 3H), 1.42 (m, 2H), 2.04 (m, 2H), 3.20 (m, 2H), 3.33 (q, J=7.20 Hz, 2H), 4.25 (m, 2H), 4.67 (s, 1H), 6.80 (br s, 1H), 7.61 (s, 1H), 7.94 (s, 1H); 8.86 (s, 2H), 10.78 (br s, 1H) and 12.46 (br, s, 1H).

1-[5-[2-(Ethylcarbamoylamino)-7-[2-(6-methoxy-2-pyridyl)ethynyl]-1,3-benzothiazol-5-yl]pyrimidin-2-yl]-4-methyl-piperidine-4-carboxylic acid (152): To a solution of 1-[5-[2-(ethylcarbamoylamino)-7-ethynyl-1,3-benzothiazol-5-yl]pyrimidin-2-yl]-4-methyl-piperidine-4-carboxylic acid (0.18 g, 0.39 mmol) in DMF (5 mL) was added 2-bromo-6-methoxy pyridine (0.15 g, 0.77 mmol) and DIPEA (0.16 mL, 1.16 mmol). The reaction mass was degassed by purging $N_2$ for 15 min followed by addition of CuI (0.015 g, 0.077 mmol) and tetrakis(triphenylphosphine)palladium (0) (0.067 g, 0.058 mmol). The reaction mixture was again degassed for 10-15 min then heated up to 80° C. for 30 min under microwave irradiation. The mixture was then poured in 100 mL of ice-cold water, extracted with EtOAc (3×100 mL) and the combined organic layer washed with brine, dried over anhydrous $Na_2SO_4$, filtered and evaporated under reduced pressure. The crude residue was purified over 100-200 M silica-gel using 30% EtOAc:hexane to obtain Compound 152 as an off-white solid (0.01 g, 5% yield). $^1$H NMR (DMSO-$d_6$): δ 1.09 (t, J=7.20 Hz, 3H), 1.19 (s, 3H), 1.41 (m, 2H), 2.02 (m, 2H), 3.19 (m, 2H), 3.30 (m, 2H), 3.90 (s, 3H), 4.30 (m, 2H), 6.77 (br s, 1H), 6.93 (d, J=8.40 Hz, 1H), 7.34 (d, J=7.20 Hz, 1H), 7.66-7.82 (m, 2H), 7.97 (s, 1H), 8.81 (s, 2H), 10.91 (br s, 1H) and 12.46 (br s, 1H). MS: 572.05 [M+H]$^+$.

The following compounds were similarly prepared.

| Cpd No. | Structure | LCMS data [M + H]$^+$ | $^1$H NMR data |
|---|---|---|---|
| 153 | 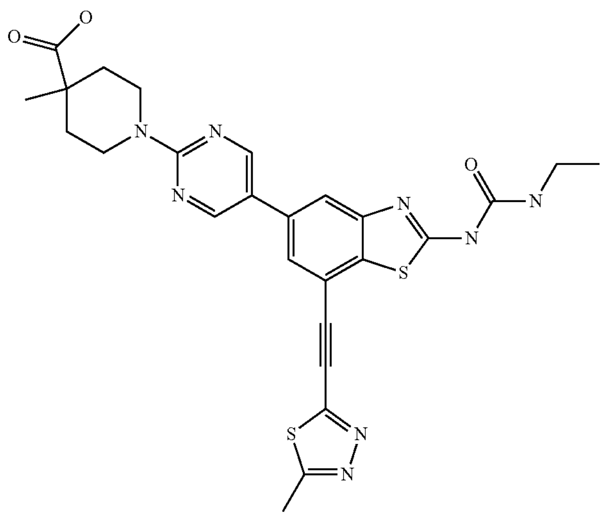 [SMILES: CCNC(=O)Nc1nc2cc(-c3cnc(N4CCC(C)(C(=O)O)CC4)nc3)cc(C#Cc3nnc(C)s3)c2s1] | 563.14 | δ 1.09 (t, J = 7.20 Hz, 3H), 1.22 (s, 3H), 1.38 (m, 2H), 1.98 (m, 2H), 2.82 (s, 3H), 3.20 (m, 2H), 3.33 (m, 2H), 4.27 (m, 2H), 6.77 (br s, 1H), 7.88 (s, 1H), 8.04 (s, 1H), 8.81 (s, 2H), 10.98 (br s, 1H) and 12.47 (br s, 1H) |
| 154 | 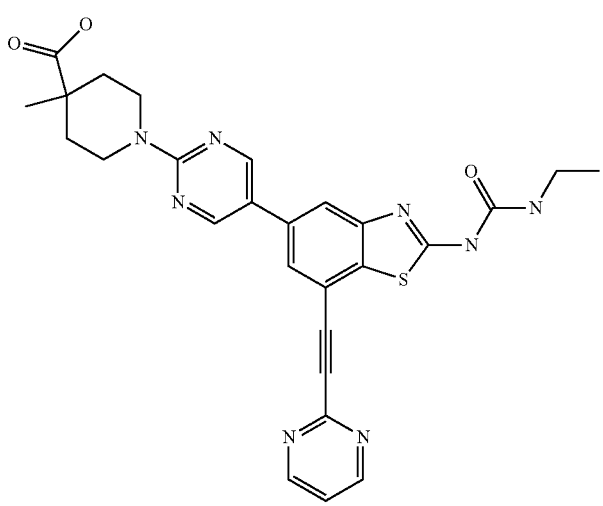 [SMILES: CCNC(=O)Nc1nc2cc(-c3cnc(N4CCC(C)(C(=O)O)CC4)nc3)cc(C#Cc3ncccn3)c2s1] | 543.12 | δ 1.10 (t, J = 7.20 Hz, 3H), 1.19 (s, 3H), 1.36 (m, 2H), 1.99 (m, 2H), 3.20 (m, 2H), 3.38 (m, 2H), 4.30 (m, 2H), 6.81 (br s, 1H), 7.57 (t, J = 4.80 Hz, 1H), 7.81 (s, 1H), 8.01 (s, 1H), 8.81 (s, 2H), 8.89 (m, 2H), 10.95 (br s, 1H) and 12.46 (br s, 1H) |

| Cpd No. | Structure | LCMS data [M + H]+ | 1H NMR data |
|---|---|---|---|
| 155 | 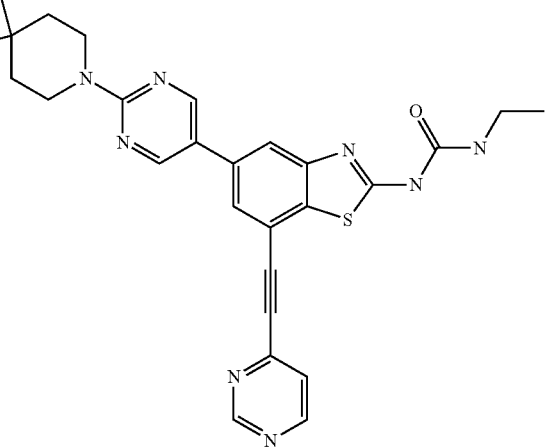 | 543.13 | δ 1.10 (t, J = 7.20 Hz, 3H), 1.18 (s, 3H), 1.38 (m, 2H), 1.99 (m, 2H), 3.20 (m, 2H), 3.32 (m, 2H), 4.30 (m, 2H), 6.81 (br s, 1H), 7.78 (m, 1H), 7.82 (s, 1H), 8.02 (s, 1H), 8.80 (s, 2H), 8.93 (br s, 1H), 9.27 (s, 1H), 10.99 (br s, 1H) and 12.45 (br s, 1H) |
| 156 | 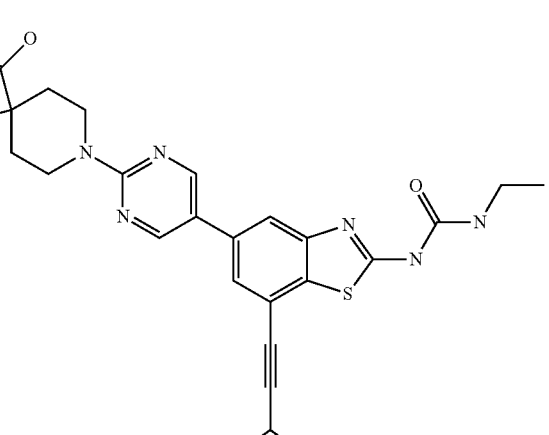 | 548.15 | δ 1.10 (t, J = 7.20 Hz, 3H), 1.18 (s, 3H), 1.38 (m, 2H), 1.99 (m, 2H), 3.15 (m, 2H), 3.20 (m, 2H), 4.31 (m, 2H), 6.79 (br s, 1H), 7.83 (s, 1H), 8.01 (m, 3H), 8.81 (s, 2H), 10.97 (br s, 1H) and 12.47 (br s, 1H) |
| 157 | 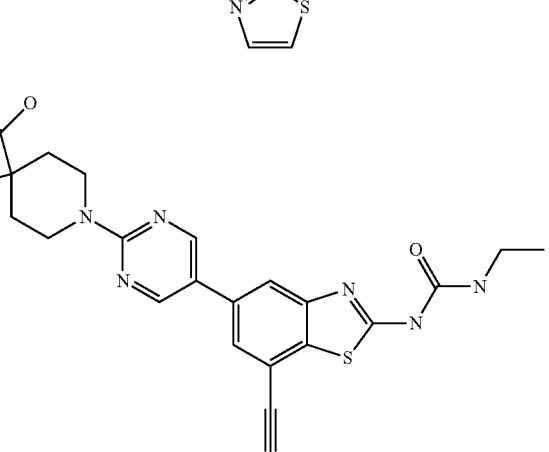 | 543.11 | δ 1.10 (t, J = 7.20 Hz, 3H), 1.18 (s, 3H), 1.38 (m, 2H), 1.99 (m, 2H), 3.20 (m, 2H), 3.33 (m, 2H), 4.30 (m, 2H), 6.81 (br s, 1H), 7.80 (s, 1H), 8.0 (s, 1H), 8.70 (d, J = 2.40 Hz, 1H), 8.75 (t, J = 2.40 Hz, 1H), 8.80 (s, 2H), 8.93 (d, J = 1.20 Hz, 1H), 10.99 (br s, 1H) and 12.45 (br s, 1H) |

| Cpd No. | Structure | LCMS data [M + H]+ | 1H NMR data |
|---|---|---|---|
| 148 | 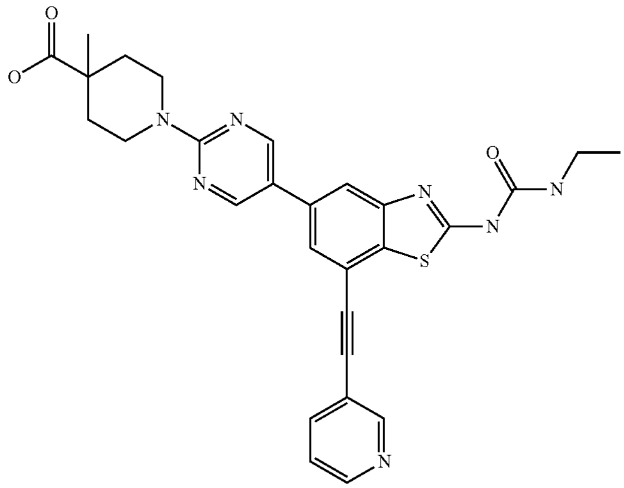 [SMILES: CCNC(=O)Nc1nc2cc(-c3cnc(N4CCC(C)(C(=O)O)CC4)nc3)cc(C#Cc3cccnc3)c2s1] | 542 | δ (ppm)(CHCl3-d): 8.78 (1 H, s), 8.59 (2 H, d, J = 2.77 Hz), 8.54 (1 H, s), 7.96 (1 H, dd, J = 7.77, 2.74 Hz), 7.73 (1 H, s), 7.53 (1 H, s), 7.41 (1 H, s), 4.36 (2 H, d, J = 13.44 Hz), 3.41 (2 H, s), 2.20 (2 H, d, J = 12.96 Hz), 1.48 (2 H, t, J = 11.88 Hz), 1.28 (3 H, s), 1.24 (3 H, td, J = 7.41, 2.94 Hz). |
| 28 | 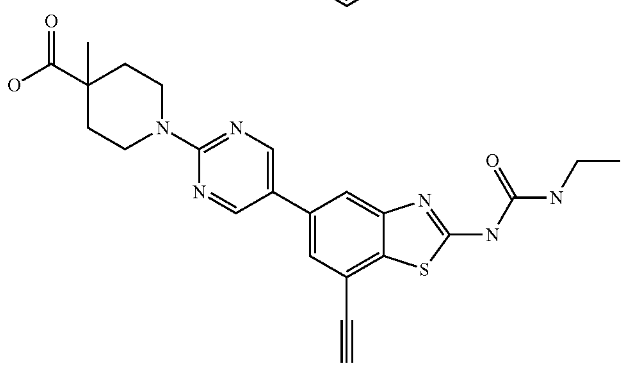 | 465 | δ (ppm)(CHCl3-d): 8.56 (2 H, s), 7.71 (1 H, d, J = 1.61 Hz), 7.47 (1 H, d, J = 1.61 Hz), 4.36 (2 H, dt, J = 13.82, 4.38 Hz), 3.52 (1 H, s), 3.44-3.38 (2 H, m), 3.37 (3 H, s), 3.39-3.33 (2 H, m), 2.20 (2 H, d, J = 13.68 Hz), 1.49 (2 H, ddd, J = 13.60, 10.61, 4.07 Hz), 1.29 (3 H, s), 1.24 (3 H, t, J = 7.26 Hz). |

Compound 158 1-[5-[2-(ethylcarbamoylamino)-7-(morpholinomethyl)-1,3-benzothiazol-5-yl]pyrimidin-2-yl]-4-methyl-piperidine-4-carboxylic acid

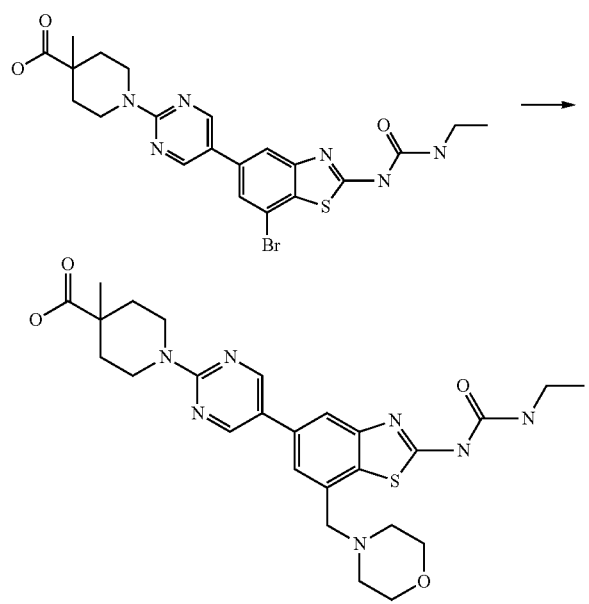

1-[5-[7-bromo-2-(ethylcarbamoylamino)-1,3-benzothiazol-5-yl]pyrimidin-2-yl]-4-methyl-piperidine-4-carboxylic acid (138 mg, 0.27 mmol), potassium(morpholin-4-yl)methyl trifluoroborate (54 mg, 0.27 mmol), X-phos (13 mg, 0.0265 mmol) and cesium carbonate (0.26 g, 0.80 mmol) were stirred in a mixture of THF-water (10:1) degassed with N2. Palladium (II) acetate (3 mg, 0.0133 mmol) was added and the mixture purged with N2, sealed and heated to 90° C. for 18 h. LCMS indicated 3% conversion to the desired material. A further 2 equivalents of the borate salt, 10 mol % of X-phos and 5 mol % of palladium acetate were added and the mixture purged with N2, sealed and heated to 90° C. for 18 h. LCMS indicated a 30% conversion to the desired material. The reaction was allowed to cool, filtered then purified by preparative HPLC to afford Compound 158 as a solid (3.5 mg,). 1H NMR (DMSO-d6): δ 10.81 (1H, s), 8.76 (2H, s), 7.79 (1H, s), 7.39 (1H, s), 7.09 (1H, s), 4.31 (2H, dt, J=13.55, 4.31 Hz), 3.74 (2H, s), 3.66 (4H, t, J=4.25 Hz), 3.23 (2H, p, J=6.75 Hz), 2.45 (4H, t, J=4.16 Hz), 2.05 (2H, dt, J=13.32, 3.59 Hz), 1.39 (2H, dt, J=12.77, 5.07 Hz), 1.20 (3H, s), 1.13 (3H, t, J=7.17 Hz). MS: 540 [M+H]+.

Compound 161: 1-[5-[2-(ethylcarbamoylamino)-4-fluoro-7-(2-pyridyl)-1,3-benzothiazol-5-yl]pyrimidin-2-yl]-4-methyl-piperidine-4-carboxylic acid

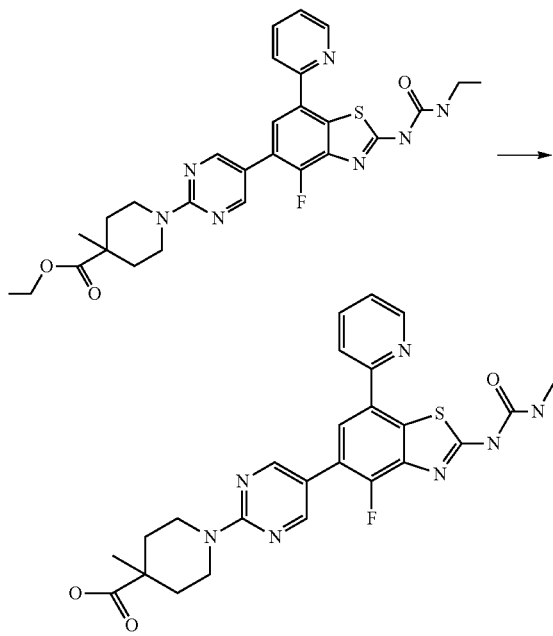

Ethyl 1-(5-(2-(3-ethylureido)-4-fluoro-7-(pyridin-2-ylbenzothiazol-5-ylpyrimidin-2-yl)-4-methylpiperidine-4-carboxylate To a solution of 1-(5-bromo-4-fluoro-7-(pyridin-2-ylbenzothiazol-2-yl)-3-ethylurea (Intermediate 7) (0.095 g, 0.24 mmol) in DMF (4.0 mL) was added the boronate ester of (0.18 g, 0.48 mmol, and aqueous solution of $K_3PO_4$ (0.102 g, 0.48 mmol) and the mixture degassed by purging $N_2$ for 15 min followed by addition of bis(triphenylphosphine)palladium (II)chloride (0.016 g, 0.024 mmol). The reaction mixture was again degassed for 10 min then heated up to 80° C. for 2 h. After completion of reaction (by TLC), the mixture was poured into 25 mL of ice-cold water, extracted with EtOAc (3×25 mL) and the combined organics washed with brine, dried over anhydrous $Na_2SO_4$, filtered and evaporated under reduced pressure. The crude residue was purified over 100-200 M silica-gel using 1.50% MeOH: DCM to obtain the desired product as an off white solid that was finally triturated with ether (0.070 g, 55% yield). $^1$H NMR (DMSO-$d_6$): δ 1.10 (t, J=7.20 Hz, 3H), 1.20 (m, 6H), 1.45 (m, 2H), 2.06 (m, 2H), 3.20 (q, J=7.20 Hz, 2H), 3.33 (m, 2H), 4.16 (q, J=6.80 Hz, 2H), 4.29 (m, 2H), 6.74 (br, s, 1H), 7.44 (m, 1H), 7.97 (m, 1H), 8.12 (d, J=8.80 Hz, 1H), 8.40 (d, J=8.40 Hz, 1H), 8.74 (s, 2H), 8.80 (d, J=4.40 Hz, 1H) and 10.88 (br s, 1H).

1-(5-(2-(3-ethylureido)-4-fluoro-7-(pyridin-2-yl) benzothiazol-5-yl)pyrimidin-2-yl)-4-methylpiperidine-4-carboxylic acid (161)

To an ice-cold solution of ethyl 1-(5-(2-(3-ethylureido)-4-fluoro-7-(pyridin-2-ylbenzothiazol-5-ylpyrimidin-2-yl)-4-methylpiperidine-4-carboxylate (0.060 g, 0.10 mmol) in DMSO (3.0 mL) was added potassium tert-butoxide (0.059 g, 0.532 mmol) and the mixture stirred at rt for 20 min. After completion of reaction (by TLC), water (10 mL) was added, followed by extraction with EtOAc (3×25 mL) and the organic layer discarded. The pH of the aqueous layer was adjusted up to 4-5 then extracted with hot EtOAc (3×100 mL) and the combined organic layer dried over $Na_2SO_4$, filtered and evaporated under reduced pressure. The residue thus obtained was triturated with ether to afford Compound 161 as an off-white solid (0.050 g, 88%). $^1$H NMR (DMSO-$d_6$): δ 1.11 (t, J=7.20 Hz, 3H), 1.20 (s, 3H), 1.44 (m, 2H), 2.01 (m, 2H), 3.21 (m, 2H), 3.37 (m, 2H), 4.30 (m, 2H), 6.75 (br, s, 1H), 7.44 (m, 1H), 7.97 (m, 1H), 8.11 (d, J=6.40 Hz, 1H), 8.41 (d, J=8.0 Hz, 1H), 8.73 (s, 2H), 8.80 (d, J=4.40 Hz, 1H), 10.86 (br s, 1H) and 12.50 (br s, 1H). MS: 536.37 [M+H]$^+$.

Compound 162: 1-[5-[2-(ethylcarbamoylamino)-4-(2-pyridyl)thiazolo[5,4-c]pyridin-6-yl]pyrimidin-2-yl]-4-methyl-piperidine-4-carboxylic acid

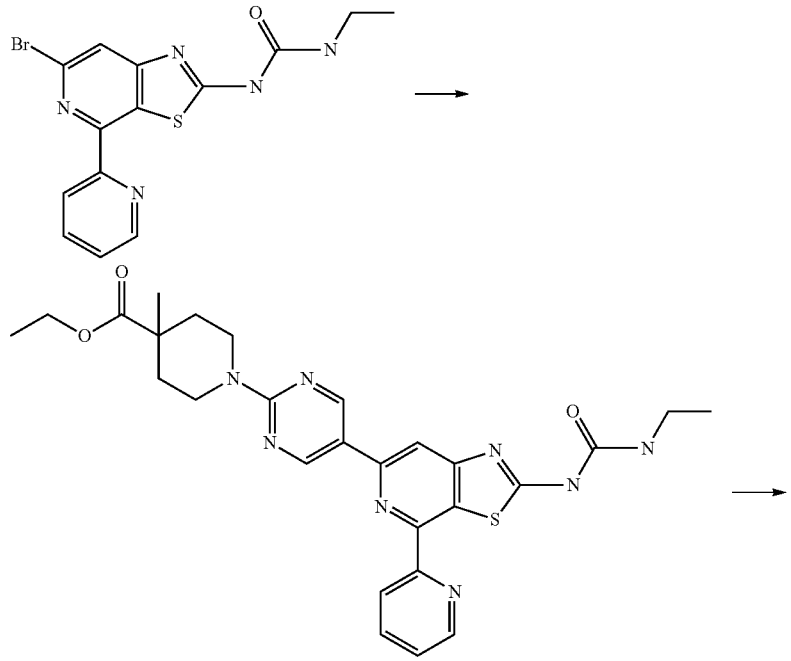

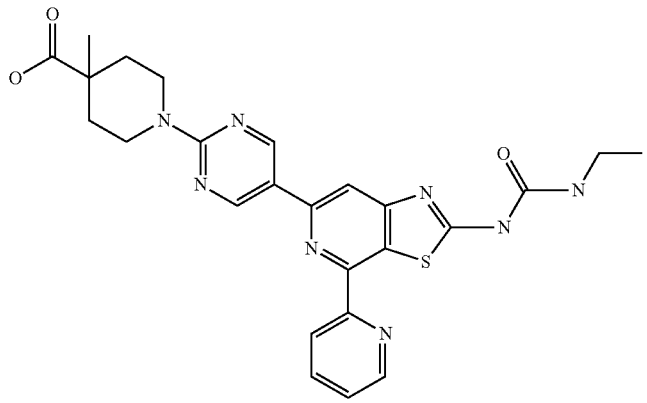

1-(6-Bromo-4-(pyridin-2-yl)thiazolo[5,4-c]pyridin-2-yl)-3-ethylurea

A solution of 1-(4,6-dibromothiazolo[5,4-c]pyridin-2-yl)-3-ethylurea (Intermediate 8) (0.25 g, 0.65 mmol) and 2-(tributylstannyl)pyridine (0.21 mL, 0.65 mmol) in DMF (10 mL) was purged with $N_2$ for 15 min followed by addition of tetrakis(triphenylphosphine)palladium (0) (0.075 g, 0.065 mmol). The reaction mixture was again degassed by purging $N_2$ for 15 min then heated to 80° C. for 16 h. The solvent was distilled under reduced pressure, water (25 mL) added and extracted with EtOAc (3×100 mL). The combined organics were dried over anhydrous $Na_2SO_4$, filtered and concentrated under reduced pressure. The residue was purified over silica gel (100-200M, 2.50% MeOH-DCM) to afford the desired product that was finally triturated with ether (0.10 g, 40%). The regio chemistry was ascertained by NOE experiments.

Ethyl 1-(5-(2-(3-ethylureido)-4-(pyridin-2-yl)thiazolo[5,4-c]pyridin-6-yl)pyrimidin-2-yl)-4-methylpiperidine-4-carboxylate To a solution of 1-(6-bromo-4-(pyridin-2-yl)thiazolo[5,4-c]pyridin-2-yl)-3-ethylurea (0.075 g, 0.20 mmol) in DMF-$H_2O$ (6:4 mL) was added the boronate ester of (0.075 g, 0.20 mmol), and potassium phosphate (0.085 g, 0.40 mmol) and the mixture degassed by purging $N_2$ for 15 min followed by addition of bis(triphenylphosphine)palladium (II)chloride (0.015 g, 0.02 mmol). The reaction mixture was again degassed by puriging $N_2$ for 15 min then heated to 80° C. for 16 h. The reaction was then distilled under reduced pressure, water (50 mL) added and extracted with EtOAc (3×50 mL). The combined organics were washed with brine, dried ($Na_2SO_4$), filtered and concentrated under reduced pressure. The residue was purified over silica gel (60-120 M, 70% EtOAc-hexane) to afford the desired product that was finally triturated with ether (0.06 g, 55%). $^1$H NMR (DMSO-$d_6$): δ 1.10 (t, J=7.20 Hz, 3H), 1.22 (m, 6H), 1.46 (m, 2H), 2.03 (m, 2H), 3.21 (m, 2H), 3.38 (m, 2H), 4.16 (q, J=7.20 Hz, 2H), 4.34 (m, 2H), 6.85 (br s, 1H), 7.56 (m, 1H), 8.05 (m, 1H), 8.16 (s, 1H), 8.78-8.84 (m, 2H), 9.26 (s, 2H) and 10.93 (br s, 1H). LCMS: 547.18 [M+H]$^+$

1-(5-(2-(3-Ethylureido)-4-(pyridin-2-yl)thiazolo[5,4-c]pyridin-6-yl)pyrimidin-2-yl)-4-methylpiperidine-4-carboxylic acid (162)

To a solution of ethyl 1-(5-(2-(3-ethylureido)-4-(pyridin-2-yl)thiazolo[5,4-c]pyridin-6-yl)pyrimidin-2-yl)-4-methylpiperidine-4-carboxylate (0.050 g, 0.091 mmol) in DMSO (2.0 mL) at rt was added potassium tert-butoxide (0.052 g, 0.45 mmol) and the mixture stirred at rt for 15-20 min. After completion of reaction (by TLC), water (25 mL) was added, followed by extraction with EtOAc (3×50 mL) and the organic layer was discarded. The pH of the aqueous layer was adjusted up to 4-5, extracted with hot EtOAc (3×50 mL) and the combined organic layer washed with brine, dried over $Na_2SO_4$, filtered and evaporated under reduced pressure. The residue thus obtained was triturated with ether to afford Compound 162 (0.030 g, 64%). $^1$H NMR (DMSO-$d_6$): δ 1.10 (t, J=7.20 Hz, 3H), 1.20 (s, 3H), 1.44 (m, 2H), 2.04 (m, 2H), 3.22 (m, 2H), 3.37 (m, 2H), 4.35 (m, 2H), 6.86 (br s, 1H), 7.53 (m, 1H), 8.05 (m, 1H), 8.16 (s, 1H), 8.80 (d, J=8.40 Hz, 1H), 8.84 (d, J=4.40 Hz, 1H), 9.26 (s, 2H), 10.93 (br s, 1H) and 12.45 (br s, 1H). MS: 519.28 [M+H]$^+$.

The following compound was similarly prepared:

| Cpd No. | Structure | LCMS data [M + H]+ | 1H NMR data |
|---|---|---|---|
| 210 | 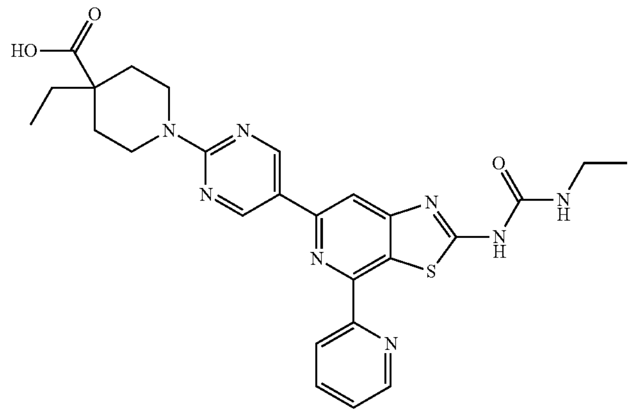 [SMILES: CCNC(=O)Nc1nc2cc(-c3cnc(N4CCC(CC)(C(=O)O)CC4)nc3)nc(-c3ccccn3)c2s1] | 533.27 | δ12.57 (br s, 1H) 10.98 (br s, 1H), 9.26 (m, 2H), 8.86 (m, 2H), 8.15 (s, 1H), 8.06 (m, 1H), 7.53 (m, 1H), 6.91 (br s, 1H), 4.52 (m, 2H), 3.21 (m, 4H), 2.06 (m, 2H), 1.54 (m, 2H), 1.36 (m, 2H), 1.11 (m, 3H) and 0.81 (m, 3H). |

Compound 190 7-[2-(ethylcarbamoylamino)-7-(2-pyridyl)-1,3-benzothiazol-5-yl]-2-methyl-3-oxo-4H-pyrido[3,2-b][1,4]oxazine-2-carboxylic acid

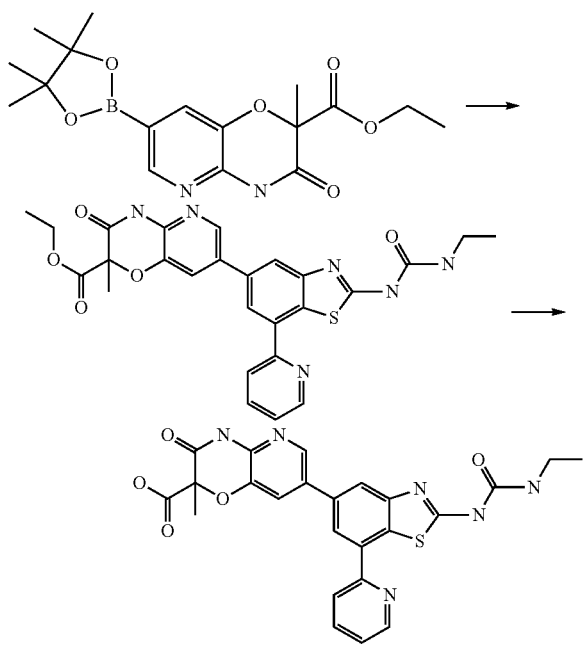

Ethyl 2-methyl-3-oxo-7-(4,4,5,5-tetramethyl-1,3,2-dioxaborolan-2-yl)-3,4-dihydro-2H-pyrido[3,2-b][1,4]oxazine-2-carboxylate To a solution of ethyl 7-bromo-2-methyl-3-oxo-3,4-dihydro-2H-pyrido[3,2-b][1,4]oxazine-2-carboxylate (0.5 g, 1.59 mmol) in 1,4-dioxane (10 mL) was added potassium acetate (0.23 g, 2.38 mmol) and bispinacolatodiboron (0.6 g, 2.38 mmol) at rt and the mixture degassed for 15-20 min by purging $N_2$ followed by the addition of tris(dibenzylideneacetone) dipalladium(0) (0.082 g, 0.08 mmol) and tricyclohexyl phosphine (0.053 gm, 0.19 mmol). The reaction was degassed for another 15-20 min then heated to 80° C. for 3 h. After completion of reaction (by TLC), the reaction mixture was cooled to rt, diluted with 500 mL of EtOAc, passed through celite and the filtrate evaporated to obtain the crude material (0.4 g, 70%), which was used in the next step without further purification. MS: 363.25 [M+H]+.

Ethyl 7-(2-(3-ethylureido)-7-(pyridin-2-yl)benzothiazol-5-yl)-2-methyl-3-oxo-3,4-dihydro-2H-pyrido[3,2-b][1,4]oxazine-2-carboxylate: To the solution of 2-(3-ethylureido)-7-(pyridin-2-yl)benzothiazol-5-yl trifluoromethanesulfonate (0.5 g, 1.12 mmol) and ethyl 2-methyl-3-oxo-7-(4,4,5,5-tetramethyl-1,3,2-dioxaborolan-2-yl)-3,4-dihydro-2H-pyrido[3,2-b][1,4]oxazine-2-carboxylate (0.4 g, 1.12 mmol) in 1,4-dioxane:MeOH (5:3 mL) was added potassium phosphate (0.36 g, 1.68 mmol) at rt and the mixture degassed for 15-20 min by purging $N_2$ followed by the addition of dichloro(1,1-bis(diphenylphosphino)(ferrocene)palladium (II) (0.091 g, 0.11 mmol). The reaction was degassed for another 15-20 min then heated to 80° C. for 5 h. After completion of reaction (by TLC), the reaction was cooled to rt, diluted with EtOAc (500 mL), passed through celite, the filtrate concentrated under reduced pressure and the crude residue purified over 100-200 M silica-gel using eluent 2.3% MeOH: DCM to obtain the desired product as an off-white solid (0.25 g, 42%). 1H NMR (DMSO-d6): δ 1.06-1.13 (m, 6H), 1.77 (s, 3H), 3.21 (q, J=7.20, 2H), 4.14 (m, 2H), 6.87 (br s, 1H), 7.45 (m, 1H), 7.97-8.03 (m, 2H), 8.09 (s, 1H), 8.29 (s, 1H), 8.55 (s, 2H), 8.80 (d, J=4.0 Hz, 1H), 10.62 (br s, 1H) and 11.73 (br s, 1H). MS: 533.24 [M+H]+.

7-[2-(Ethylcarbamoylamino)-7-(2-pyridyl)-1,3-benzothiazol-5-yl]-2-methyl-3-oxo-4H-pyrido[3,2-b][1,4]oxazine-2-carboxylic acid (190)

To an ice-cold solution of ethyl 7-(2-(3-ethylureido)-7-(pyridin-2-yl)benzothiazol-5-yl)-2-methyl-3-oxo-3,4-dihydro-2H-pyrido[3,2-b][1,4]oxazine-2-carboxylate (0.10 g, 0.19 mmol) in THF was added LiOH (0.023 g, 0.57 mmol dissolved in minimum amount of $H_2O$) and the mixture stirred at rt for 3 h. After completion of reaction (by TLC), the solvent was concentrated and 10 mL of water added to the reaction. The aqueous layer was washed with EtOAc (2×50 mL) and the organic layer discarded. The pH of the aqueous layer was adjusted up to 4-5, extracted with hot EtOAc (3×50 mL) and the combined organic layer dried over Na$_2$SO$_4$, filtered and concentrated under reduced pressure. The residue thus obtained was triturated with ether to afford Compound 190 as an off-white solid (0.06 g, 63%). $^1$H NMR (DMSO-d$_6$): δ 1.11 (t, J=7.20 Hz, 3H), 1.74 (s, 3H), 3.21 (m, 2H), 6.86 (br s, 1H), 7.44 (m, 1H), 7.97-8.06 (m, 3H), 8.28 (s, 1H), 8.50 (s, 1H), 8.56 (d, J=8.0 Hz, 1H), 8.81 (d, J=4.0 Hz, 1H), 10.63 (br s, 1H) and 11.57 (br s, 1H). MS: 505.29 [M+H]$^+$.

The following compounds were similarly prepared using the general methods and/or examples described herein.

| Cpd No. | Structure | LCMS data [M + H]$^+$ | $^1$H NMR data |
|---|---|---|---|
| 107 | 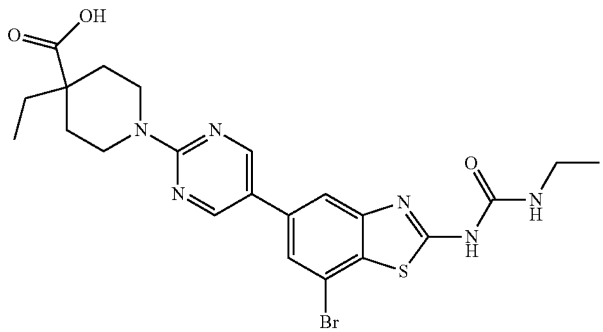 [SMILES: CCNC(=O)Nc1nc2cc(-c3cnc(N4CCC(CC)(C(=O)O)CC4)nc3)cc(Br)c2s1] | 559.33 [M − H]$^-$ | δ 0.79 (t, J = 5.60 Hz, 3H), 1.09 (t, J = 7.20 Hz, 3H), 1.22 (t, J = 7.20 Hz, 3H), 1.38 (m, 2H), 1.55 (m, 2H), 2.09 (m, 2H), 3.08 (m, 2H), 3.21 (m, 2H), 4.17 (q, J = 6.80 Hz, 2H), 4.47 (m, 2H), 6.74 (br s, 1H), 7.70 (s, 1H), 7.87 (s, 1H), 8.81 (s, 2H) and 10.91 (br s, 1H). |
| 119 | 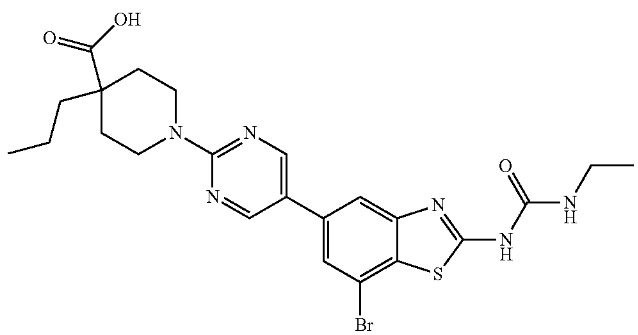 [SMILES: CCCC1(C(=O)O)CCN(c2ncc(-c3cc(Br)c4sc(NC(=O)NCC)nc4c3)cn2)CC1] | 575.26 | δ 0.84 (t, J = 7.20 Hz, 3H), 1.09 (t, J = 7.20 Hz, 3H), 1.15-1.36 (m, 5H), 1.40 (m, 2H), 1.50 (m, 2H), 2.06 (m, 2H), 3.07 (m, 2H), 3.21 (m, 2H), 4.16 (q, J = 7.20 Hz, 2H), 4.45 (m, 2H), 6.74 (br s, 1H), 7.70 (s, 1H), 7.87 (s, 1H), 8.76 (s, 2H) and 10.91 (br s, 1H). |
| 167 | 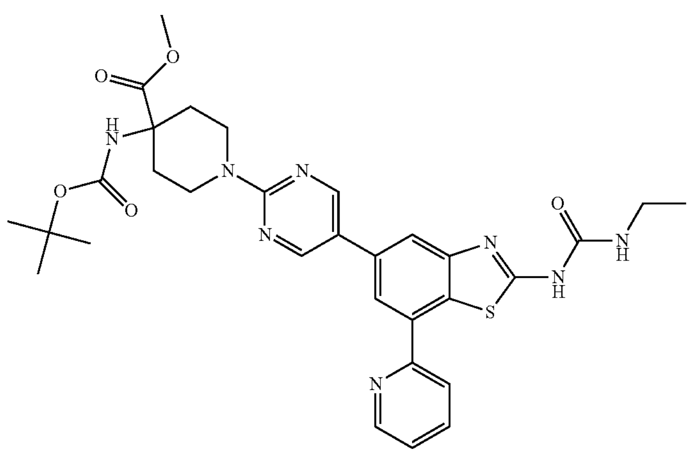 [SMILES: CCNC(=O)Nc1nc2cc(-c3cnc(N4CCC(NC(=O)OC(C)(C)C)(C(=O)OC)CC4)nc3)cc(-c3ccccn3)c2s1] | 633.03 | (DMSO-d$_6$): δ 1.09 (t, J = 7.20 Hz, 3H), 1.40 (s, 9H), 1.88 (m, 2H), 2.07 (m, 2H), 3.21 (m, 2H), 3.32 (m, 2H), 3.61 (s, 3H), 4.34 (m, 2H), 6.86 (br s, 1H), 7.43-7.49 (m, 2H), 7.97-8.01 (m, 2H), 8.24 (s, 1H), 8.49 (d, J = 8.40 Hz, 1H), 8.81 (d, J = 5.20 Hz, 1H), 8.92 (s, 2H) and 10.54 (br s, 1H). |

| Cpd No. | Structure | LCMS data [M + H]+ | 1H NMR data |
|---|---|---|---|
| 168 | 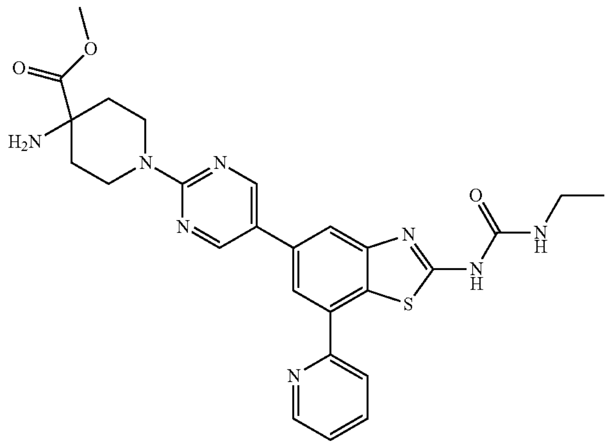 [SMILES: CCNC(=O)Nc1nc2cc(-c3cnc(N4CCC(N)(C(=O)OC)CC4)nc3)cc(-c3ccccn3)c2s1] | 533.52 | |
| 169 | 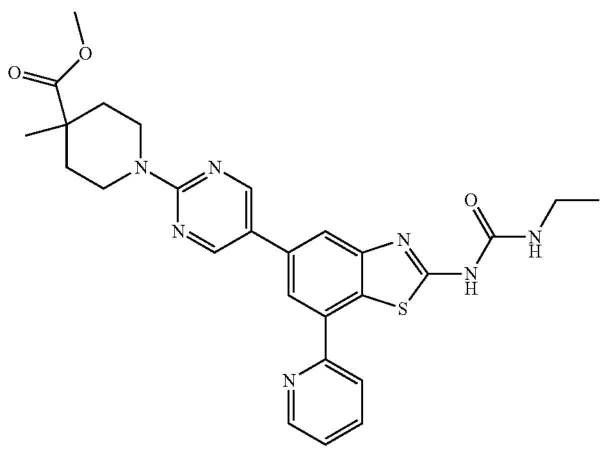 [SMILES: CCNC(=O)Nc1nc2cc(-c3cnc(N4CCC(C)(C(=O)OC)CC4)nc3)cc(-c3ccccn3)c2s1] | 532.10 | (DMSO-d6): δ 1.11 (t, J = 7.20 Hz, 3H), 1.21 (s, 3H), 1.45 (m, 2H), 2.02 (m, 2H), 3.21 (m, 2H), 3.32 (m, 2H), 3.68 (s, 3H), 4.30 (m, 2H), 6.86 (br s, 1H), 7.44 (m, 1H), 7.96-8.01 (m, 2H), 8.23 (s, 1H), 8.49 (d, J = 8.0 Hz, 1H), 8.81 (d, J = 4.0 Hz, 1H), 8.91 (s, 2H) and 10.55 (br s, 1H). |
| 170 | 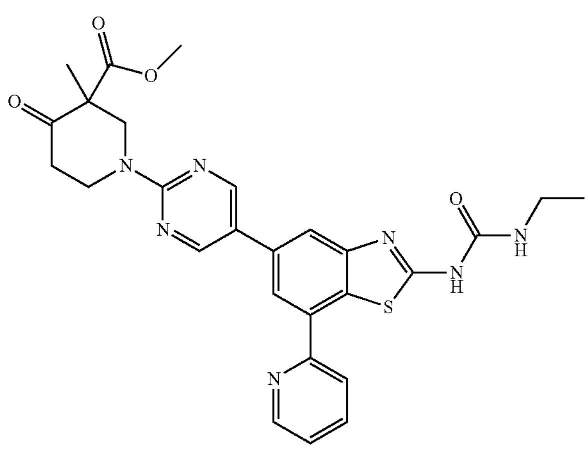 [SMILES: CCNC(=O)Nc1nc2cc(-c3cnc(N4CCC(=O)C(C)(C(=O)OC)C4)nc3)cc(-c3ccccn3)c2s1] | 546.21 | (DMSO-d6): δ 1.11 (t, J = 7.20 Hz, 3H), 1.28 (s, 3H), 2.59-2.63 (m, 1H), 2.74-2.82 (m, 1H), 3.21 (m, 2H), 3.53 (s, 3H), 3.56-3.59 (m, 1H), 3.68-3.74 (m, 1H), 4.59 (m, 1H), 5.08 (m, 1H), 6.86 (br s, 1H), 7.44 (m, 1H), 7.98-8.02 (m, 2H), 8.26 (s, 1H), 8.51 (d, J = 8.40 Hz, 1H), 8.81 (d, J = 4.40 Hz, 1H), 8.98 (s, 2H) and 10.55 (br s, 1H). |

-continued

| Cpd No. | Structure | LCMS data [M + H]+ | 1H NMR data |
|---|---|---|---|
| 171 | 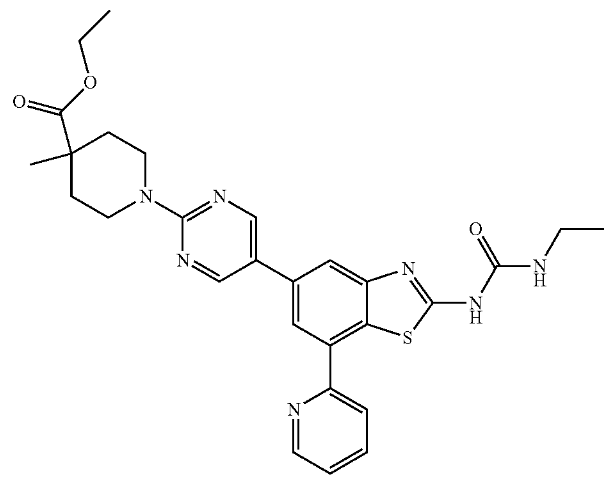 [SMILES: CCNC(=O)Nc1nc2cc(-c3cnc(N4CCC(C)(C(=O)OCC)CC4)nc3)cc(-c3ccccn3)c2s1] | 546.12 | (DMSO-d6): δ 1.15 (t, J = 7.20 Hz, 3H), 1.20 (m, 6H), 1.45 (m, 2H), 2.06 (m, 2H), 2.54 (m, 2H), 3.21 (q, J = 7.20, 2H), 4.15 (q, J = 6.80 Hz, 2H), 4.32 (m, 2H), 6.86 (br s, 1H), 7.44 (m, 1H), 7.99 (m, 2H), 8.23 (s, 1H), 8.47 (m, 1H), 8.80 (m, 1H), 8.92 (s, 2H) and 10.55 (br s, 1H). |
| 172 | 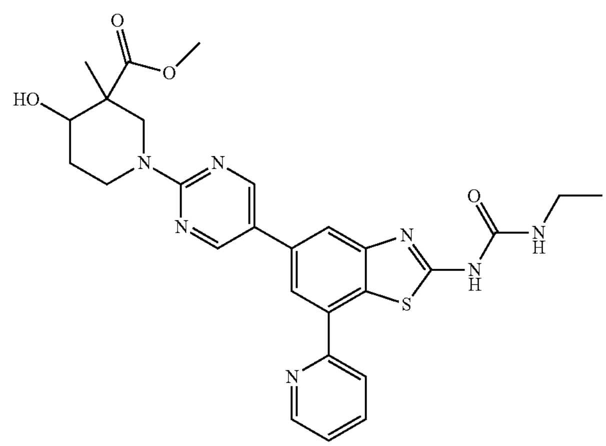 [SMILES: CCNC(=O)Nc1nc2cc(-c3cnc(N4CCC(O)C(C)(C(=O)OC)C4)nc3)cc(-c3ccccn3)c2s1] | 548.24 | |
| 173 | 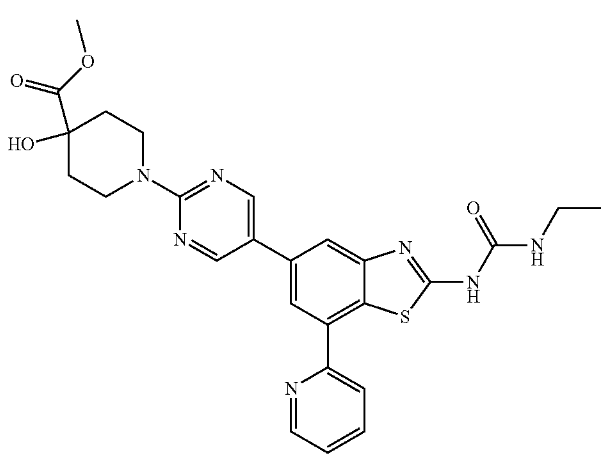 [SMILES: CCNC(=O)Nc1nc2cc(-c3cnc(N4CCC(O)(C(=O)OC)CC4)nc3)cc(-c3ccccn3)c2s1] | 534.13 | (DMSO-d6): δ 1.11 (t, J = 7.20 Hz, 3H), 1.72 (m, 2H), 1.88 (m, 2H), 3.23 (q, J = 7.20 Hz, 2H), 3.44 (m, 2H), 3.65 (s, 3H), 4.43 (m, 2H), 5.64 (s, 1H), 6.86 (br s, 1H), 7.44 (m, 1H), 7.99 (m, 2H), 8.24 (s, 1H), 8.49 (d, J = 8.0 Hz, 1H), 8.81 (d, J = 4.0 Hz, 1H), 8.92 (s, 2H) and 10.55 (br s, 1H). |

| Cpd No. | Structure | LCMS data [M + H]+ | 1H NMR data |
|---|---|---|---|
| 174 | 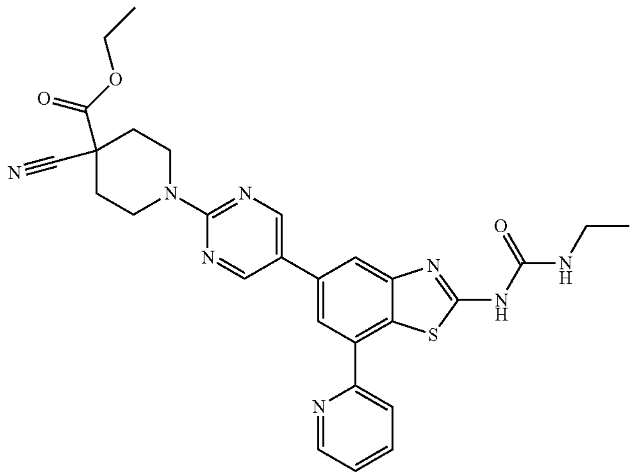 [SMILES: CCNC(=O)Nc1nc2cc(-c3cnc(N4CCC(C#N)(C(=O)OCC)CC4)nc3)cc(-c3ccccn3)c2s1] | 557.05. | (DMSO-d6): δ 1.11 (t, J = 7.20 Hz, 3H), 1.25 (t, J = 7.20 Hz, 3H), 1.97 (m, 2H), 2.20 (m, 2H), 3.19-3.24 (m, 4H), 4.26 (q, J = 6.80 Hz, 2H), 4.77 (m, 2H), 6.86 (br s, 1H), 7.44 (m, 1H), 7.99 (m, 2H), 8.25 (s, 1H), 8.49 (d, J = 8.40 Hz, 1H), 8.81 (m, 1H), 8.97 (s, 2H) and 10.55 (br s, 1H). |
| 175 | 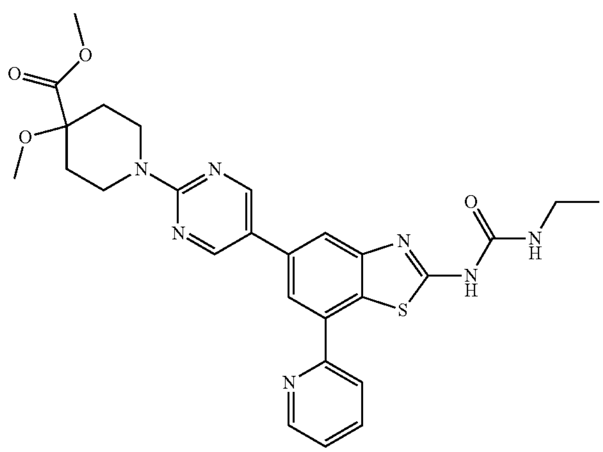 [SMILES: CCNC(=O)Nc1nc2cc(-c3cnc(N4CCC(OC)(C(=O)OC)CC4)nc3)cc(-c3ccccn3)c2s1] | 548.12 | δ (DMSO-d6): δ 1.11 (t, J = 7.20 Hz, 3H), 1.84 (m, 2H), 1.92 (m, 2H), 3.19 (m, 2H), 3.23 (s, 3H), 3.40 (m, 2H), 3.70 (s, 3H), 4.36 (m, 2H), 6.86 (br s, 1H), 7.44 (m, 1H), 7.99 (m, 2H), 8.24 (s, 1H), 8.49 (d, J = 8.40 Hz, 1H), 8.81 (d, J = 4.40 Hz, 1H), 8.93 (s, 2H) and 10.55 (br s, 1H). . |
| 176 | 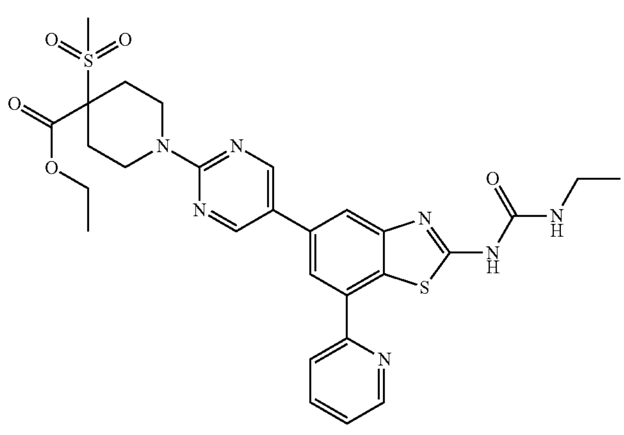 [SMILES: CCNC(=O)Nc1nc2cc(-c3cnc(N4CCC(C(=O)OCC)(S(C)(=O)=O)CC4)nc3)cc(-c3ccccn3)c2s1] | 610.33 | (DMSO-d6): δ 1.11 (t, J = 7.20 Hz, 3H), 1.23 (m, 3H), 1.94 (m, 2H), 2.43 (m, 2H), 2.98 (m, 2H), 3.08 (s, 3H), 3.19 (m, 2H), 4.36 (q, J = 6.80 Hz, 2H), 4.89 (m, 2H), 6.86 (br s, 1H), 7.44 (m, 1H), 8.01 (m, 2H), 8.25 (s, 1H), 8.47 (d, J = 8.0 Hz, 1H), 8.81 (d, J = 3.60 Hz, 1H), 8.96 (s, 2H) and 10.55 (br s, 1H). |

| Cpd No. | Structure | LCMS data [M + H]+ | 1H NMR data |
|---|---|---|---|
| 177 | 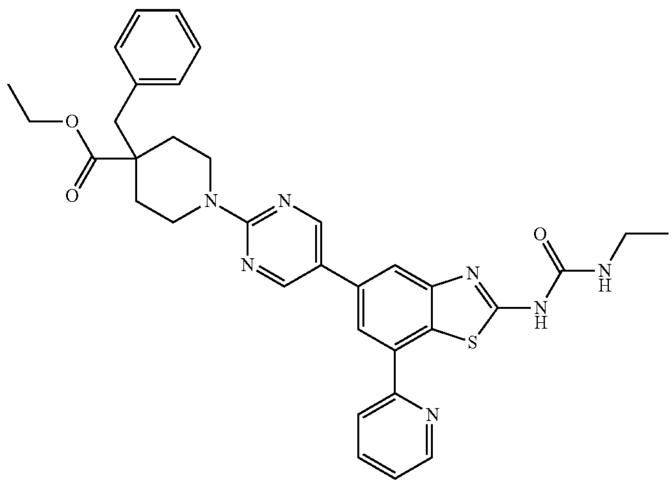 [SMILES: CCNC(=O)Nc1nc2cc(-c3cnc(N4CCC(Cc5ccccc5)(C(=O)OCC)CC4)nc3)cc(-c3ccccn3)c2s1] | 622.19 | (DMSO-d6): δ 1.15 (t, J = 7.20 Hz, 3H), 1.19 (t, J = 6.80 Hz, 3H), 1.53 (m, 2H), 2.06 (m, 2H), 2.85 (s, 2H), 3.04 (m, 2H), 3.21 (q, J = 7.20 Hz, 2H), 4.12 (q, J = 6.80 Hz, 2H), 4.54 (m, 2H), 6.86 (br s, 1H), 7.07 to 7.29 (m, 5H), 7.44 (m, 1H), 7.99 (m, 2H), 8.23 (s, 1H), 8.48 (m, 1H), 8.81 (m, 1H), 8.91 (s, 2H) and 10.54 (br s, 1H). |
| 178 | 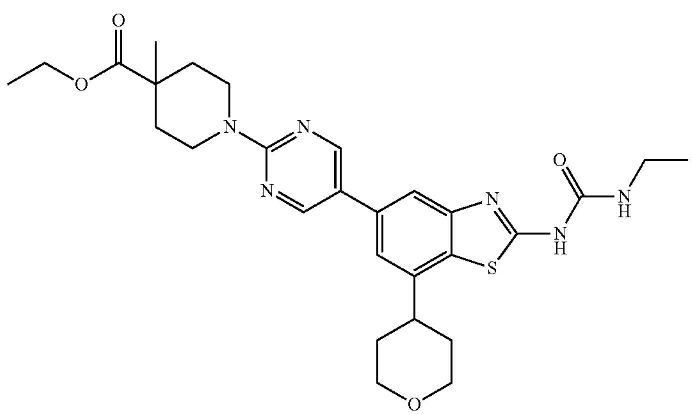 [SMILES: CCNC(=O)Nc1nc2cc(-c3cnc(N4CCC(C)(C(=O)OCC)CC4)nc3)cc(C3CCOCC3)c2s1] | 594.1 | (CDCl3) δ 8.51 (s, 2H), 7.71 (s, 1H), 7.13 (s, 1H), 4.82 (d, J = 13.3 Hz, 1H), 4.35 (dt, J = 13.6, 4.1 Hz, 2H), 4.20 (q, J = 7.1 Hz, 2H), 3.93 (d, J = 13.2 Hz, 1H), 3.50-3.40 (m, 2H), 3.40-3.25 (m, 2H), 3.16 (t, J = 12.2 Hz, 1H), 2.90 (t, J = 12.0 Hz, 1H), 2.64 (t, J = 12.1 Hz, 1H), 2.22-2.16 (m, 2H), 2.15 (s, 3H), 2.06 (dd, J = 19.1, 10.9 Hz, 2H), 1.84-1.70 (m, 2H), 1.52-1.40 (m, 2H), 1.31-1.23 (m, 9H). |
| 179 | 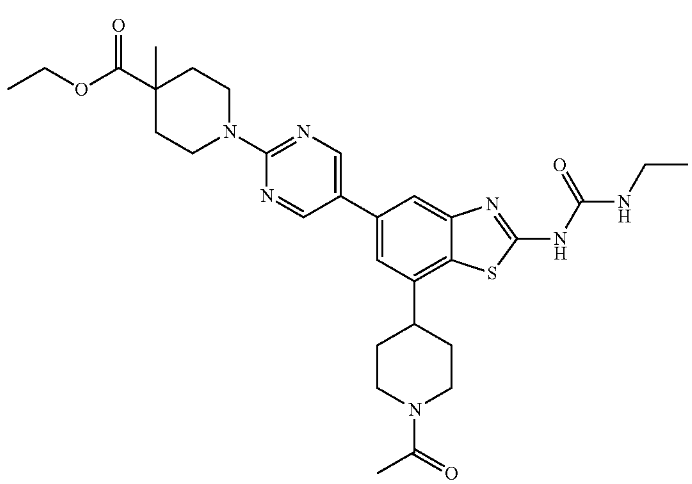 [SMILES: CCNC(=O)Nc1nc2cc(-c3cnc(N4CCC(C)(C(=O)OCC)CC4)nc3)cc(C3CCN(C(C)=O)CC3)c2s1] | 595.15 | (CDCl3) δ 8.59 (d, J = 5.7 Hz, 2H), 7.75 (dd, J = 14.2, 4.8 Hz, 1H), 7.21 (d, J = 1.4 Hz, 1H), 4.38 (dt, J = 13.7, 4.2 Hz, 2H), 4.21 (q, J = 7.1 Hz, 2H), 4.09 (dd, J = 10.5, 3.0 Hz, 2H), 3.58-3.42 (m, 4H), 3.34 (ddd, J = 13.7, 10.7, 3.0 Hz, 2H), 2.91 (ddd, J = 15.2, 10.4, 4.5 Hz, 1H), 2.21 (d, J = 13.6 Hz, 2H), 2.05-1.93 (m, 4H), 1.49 (ddd, J = 14.1, 10.2, 4.9 Hz, 2H), 1.33-1.26 (m, 6H), 1.26 (s, 3H). |

-continued

| Cpd No. | Structure | LCMS data [M + H]+ | 1H NMR data |
|---|---|---|---|
| 180 | 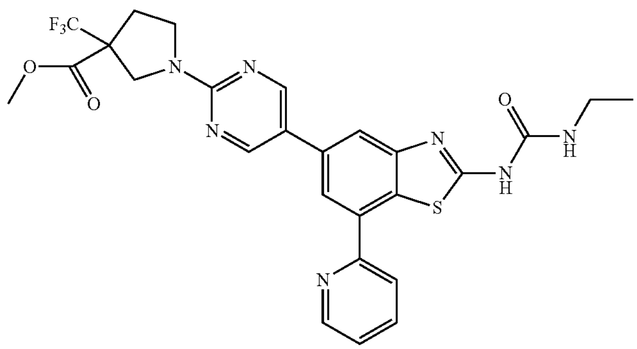 [SMILES: CCNC(=O)Nc1nc2cc(-c3cnc(N4CCC(C(=O)OC)(C(F)(F)F)C4)nc3)cc(-c3ccccn3)c2s1] | 572.20 | (DMSO-d6): δ 1.11 (t, J = 7.20 Hz, 3H), 2.56 (m, 1H), 2.70 (m, 1H), 3.19 (m, 2H), 3.67 (m, 1H), 3.80 (m, 4H), 4.0 (m, 1H), 4.25 (m, 1H), 6.86 (br s, 1H), 7.44 (m, 1H), 7.98-8.01 (m, 2H), 8.24 (s, 1H), 8.49 (d, J = 8.0 Hz, 1H), 8.81 (d, (J = 4.0 Hz, 1H), 8.96 (s, 2H) and 10.54 (br s, 1H). |
| 184 | 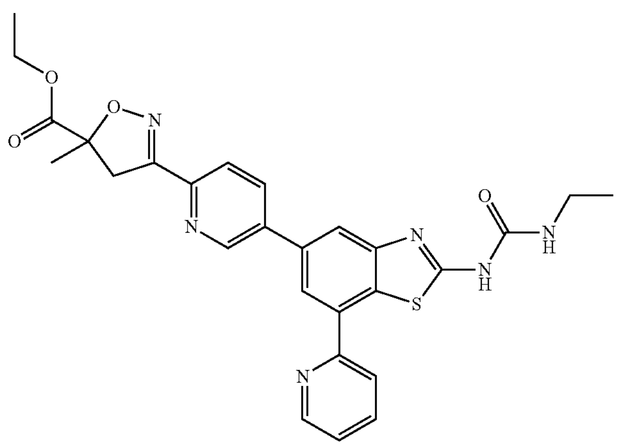 [SMILES: CCNC(=O)Nc1nc2cc(-c3ccc(C4=NOC(C)(C(=O)OCC)C4)nc3)cc(-c3ccccn3)c2s1] | 531.03. | (DMSO-d6): δ 1.11 (t, J = 7.20 Hz, 3H), 1.23 (t, J = 6.80 Hz, 3H), 1.64 (s, 3H), 3.20 (m, 2H), 3.54 (d, J = 17.60 Hz, 1H), 3.96 (d, J = 17.60 Hz, 1H), 4.20 (q, J = 7.20 Hz, 2H), 6.88 (br s, 1H), 7.46 (m, 1H), 8.0-8.04 (m, 2H), 8.12 (s, 1H), 8.38 (s, 1H), 8.45 (dd, J = 2.40 and 8.40 Hz respectively, 1H), 8.53 (d, J = 8.0 Hz, 1H), 8.83 (d, J = 4.40 Hz, 1H), 9.22 (s, 1H) and 10.64 (br s, 1H). |
| 185 | 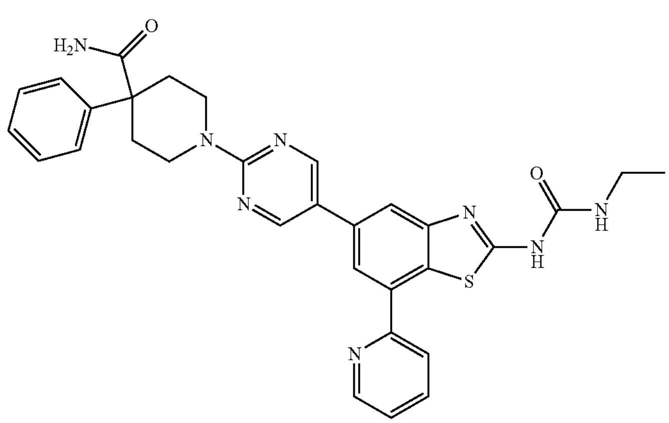 [SMILES: CCNC(=O)Nc1nc2cc(-c3cnc(N4CCC(C(N)=O)(c5ccccc5)CC4)nc3)cc(-c3ccccn3)c2s1] | 579.29 | (DMSO-d6): δ 1.09 (t, J = 7.20 Hz, 3H), 1.80 (m, 2H), 2.58 (m, 2H), 3.20 (m, 2H), 3.31 (m, 2H), 4.50 (m, 2H), 6.86 (br s, 1H), 7.20 (s, 1H), 7.25 (m, 1H), 7.30-7.38 (m, 3H), 7.40-7.50 (m, 3H), 7.96-8.01 (m, 2H), 8.23 (s, 1H), 8.49 (d, J = 8.0 Hz, 1H), 8.81 (d, J = 4.0 Hz, 1H), 9.06 (s, 2H) and 10.57 (br s, 1H). |

| Cpd No. | Structure | LCMS data [M + H]+ | 1H NMR data |
|---|---|---|---|
| 186 | 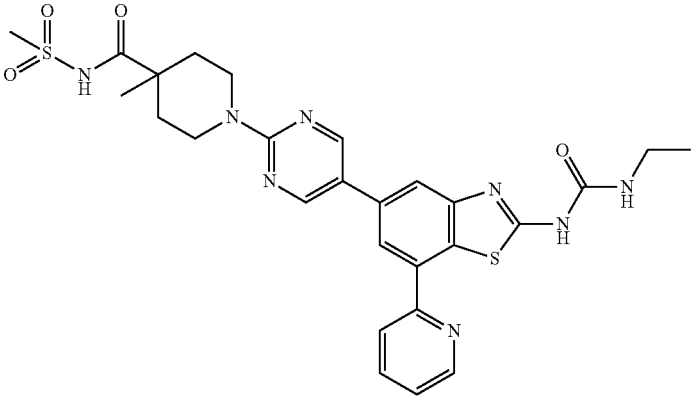 [SMILES: CCNC(=O)Nc1nc2cc(-c3cnc(N4CCC(C)(C(=O)NS(C)(=O)=O)CC4)nc3)cc(-c3ccccn3)c2s1] | | (CDCl3) δ 11.56-11.55 (m, 1H), 11.47 (s, 1H), 11.42-11.40 (m, 1H), 10.59 (s, 1H), 8.97 (s, 2H), 8.86 (dd, J = 4.8, 0.9 Hz, 1H), 8.53 (d, J = 8.4 Hz, 1H), 8.28 (d, J = 1.5 Hz, 1H), 8.09-7.98 (m, 2H), 7.52-7.46 (m, 1H), 6.98-6.85 (m, 1H), 4.31-4.16 (m, 2H), 2.21-2.10 (m, 2H), 1.62-1.44 (m, 2H), 1.30 (s, 5H), 1.17 (t, J = 7.2 Hz, 3H). |
| 187 | 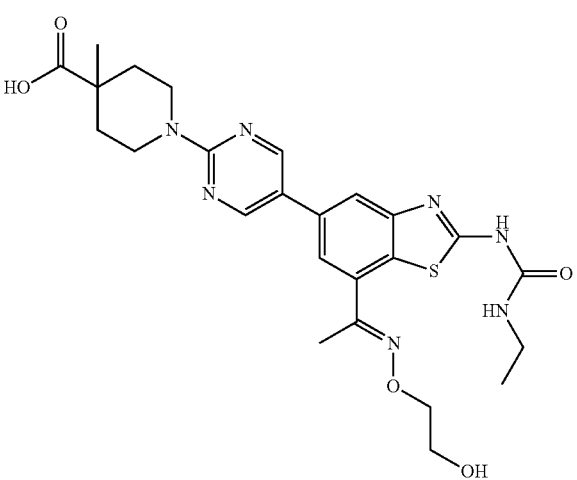 [SMILES: CCNC(=O)Nc1nc2cc(-c3cnc(N4CCC(C)(C(=O)O)CC4)nc3)cc(/C(C)=N/OCCO)c2s1] | 542 | (DMSO-d6): δ 10.82 (1 H, s), 8.85 (2 H, s), 7.95 (1 H, d, J = 1.53 Hz), 7.76 (1 H, s), 7.10 (1 H, t, J = 5.83 Hz), 4.80 (1 H, s), 4.34 (1 H, t, J = 5.45 Hz), 4.31 (2 H, t, J = 4.98 Hz), 3.84 (2 H, t, J = 5.14 Hz), 3.38 (2 H, ddd, J = 22.19, 11.49, 9.13 Hz), 2.44 (3 H, s), 2.05 (2 H, d, J = 13.34 Hz), 1.41 (2 H, ddd, J = 13.34, 10.09, 3.85 Hz), 1.22 (3 H, s), 1.14 (3 H, t, J = 7.17 Hz). |
| 188 | 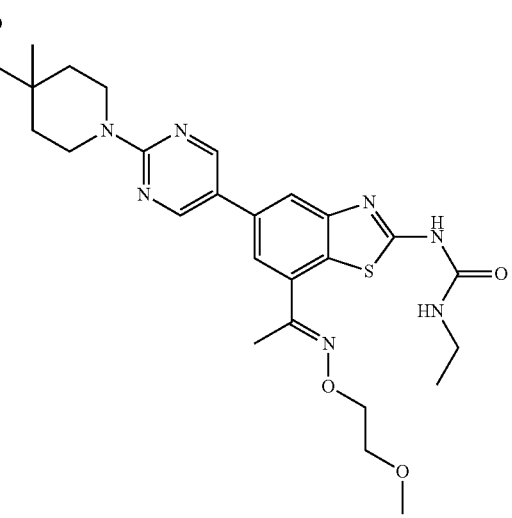 | 556 | (DMSO-d6): δ 11.23 (1 H, s), 8.85 (2 H, s), 7.95 (1 H, d, J = 1.55 Hz), 7.76 (1 H, d, J = 1.62 Hz), 7.53 (1 H, s), 4.40 (2 H, t, J = 4.74 Hz), 4.32 (2 H, dt, J = 13.67, 4.43 Hz), 3.81 (2 H, t, J = 4.79 Hz), 3.36 (3 H, s), 3.58-3.09 (1 H, m), 3.22 (2 H, p, J = 6.80 Hz), 2.43 (3 H, s), 2.07 (2 H, d, J = 13.16 Hz), 1.38 (2 H, ddd, J = 13.15, 10.05, 3.75 Hz), 1.20 (3 H, s), 1.13 (3 H, t, J = 7.18 Hz). |

-continued

| Cpd No. | Structure | LCMS data [M + H]+ | 1H NMR data |
|---|---|---|---|
| 215 | 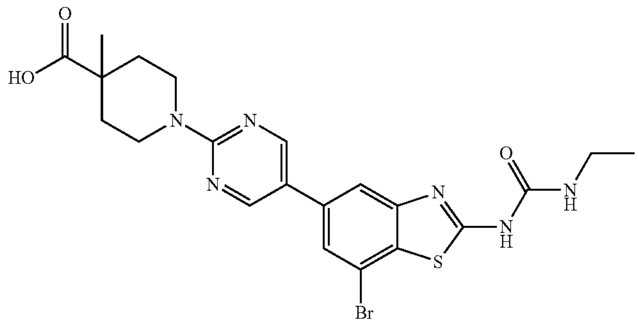 [SMILES: CCNC(=O)Nc1nc2cc(-c3cnc(N4CCC(C)(C(=O)O)CC4)nc3)cc(Br)c2s1] | 519 | δ 12.52 (br s, 1H), 10.88 (br s, 1H), 8.75 (s, 2H), 7.87 (s, 1H), 7.69 (s, 1H), 6.81 (s, 1H), 4.26-4.29 (m, 2H), 3.16-3.21 (m, 4H), 1.98-2.02 (m, 2H), 1.35-1.41 (m, 2H), 3.18 (s, 3H) and 1.09 (t, J = 7.2 Hz, 3H). |
| 216 | 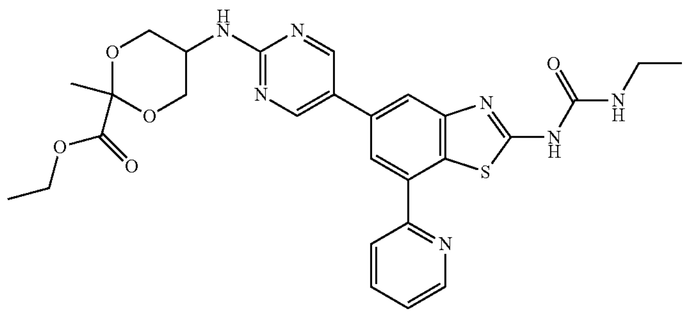 [SMILES: CCNC(=O)Nc1nc2cc(-c3cnc(NC4COC(C)(C(=O)OCC)OC4)nc3)cc(-c3ccccn3)c2s1] | 564.2 | (CDCl$_3$) δ 8.74 (d, J = 4.9, 1H), 8.66 (s, 2H), 8.06 (d, J = 8.2 Hz, 1H), 7.95-7.81 (m, 3H), 7.34-7.27 (m, 1H), 6.17 (d, J = 8.7 Hz, 1H), 4.35 (q, J = 7.1 Hz, 2H), 4.15 (dd, J = 11.6, 1.5 Hz, 2H), 4.10-3.97 (m, 3H), 3.55-3.35 (m, 2H), 1.59 (s, 3H), 1.37 (t, J = 7.1 Hz, 3H), 1.32 (t, J = 7.3 Hz, 3H). |

Compound 193: 1-[5-[7-carbamoyl-2-(ethylcarbamoylamino)-1,3-benzothiazol-5-yl]pyrimidin-2-yl]-4-ethyl-piperidine-4-carboxylic acid

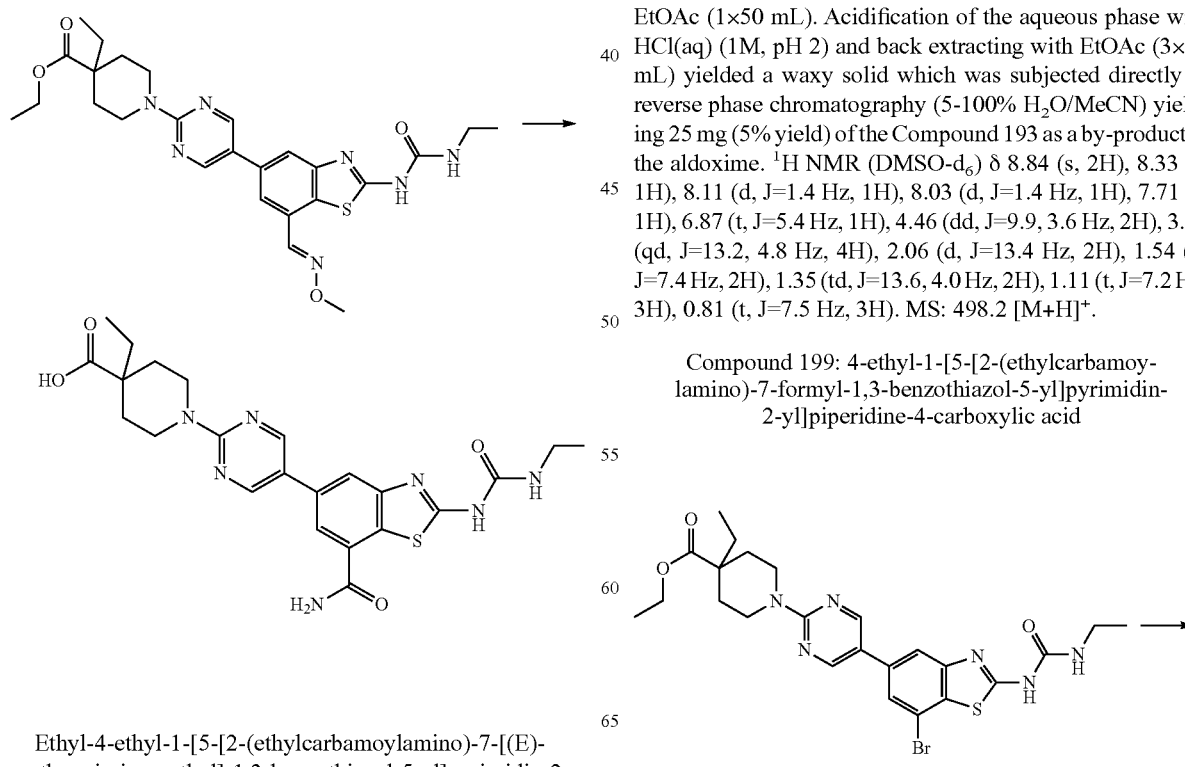

Ethyl-4-ethyl-1-[5-[2-(ethylcarbamoylamino)-7-[(E)-methoxyiminomethyl]-1,3-benzothiazol-5-yl]pyrimidin-2-yl]piperidine-4-carboxylate (619 mg, 1.147 mmol) 100 was suspended in MeOH (9 mL) and NaOH(aq) (1M, 9 mL), sealed in a microwave vessel, irradiated at 85° C. for 1 h, followed by conventionally heating overnight at 65° C. The reaction was diluted with water (40 mL) and washed with EtOAc (1×50 mL). Acidification of the aqueous phase with HCl(aq) (1M, pH 2) and back extracting with EtOAc (3×60 mL) yielded a waxy solid which was subjected directly to reverse phase chromatography (5-100% H$_2$O/MeCN) yielding 25 mg (5% yield) of the Compound 193 as a by-product to the aldoxime. $^1$H NMR (DMSO-d$_6$) δ 8.84 (s, 2H), 8.33 (s, 1H), 8.11 (d, J=1.4 Hz, 1H), 8.03 (d, J=1.4 Hz, 1H), 7.71 (s, 1H), 6.87 (t, J=5.4 Hz, 1H), 4.46 (dd, J=9.9, 3.6 Hz, 2H), 3.18 (qd, J=13.2, 4.8 Hz, 4H), 2.06 (d, J=13.4 Hz, 2H), 1.54 (q, J=7.4 Hz, 2H), 1.35 (td, J=13.6, 4.0 Hz, 2H), 1.11 (t, J=7.2 Hz, 3H), 0.81 (t, J=7.5 Hz, 3H). MS: 498.2 [M+H]$^+$.

Compound 199: 4-ethyl-1-[5-[2-(ethylcarbamoylamino)-7-formyl-1,3-benzothiazol-5-yl]pyrimidin-2-yl]piperidine-4-carboxylic acid

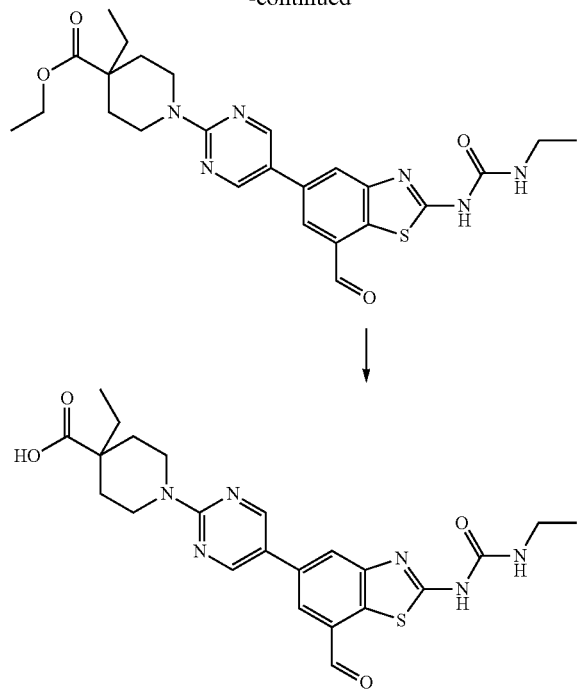

Ethyl-4-ethyl-1-[5-[2-(ethylcarbamoylamino)-7-formyl-1,3-benzothiazol-5-yl]pyrimidin-2-yl]piperidine-4-carboxylate A medium pressure reaction vessel was charged with the following reagents and solvent(s): Ethyl 1-[5-[7-bromo-2-(ethylcarbamoylamino)-1,3-benzothiazol-5-yl]pyrimidin-2-yl]-4-ethyl-piperidine-4-carboxylate (2.54 g, 4.52 mmol), palladium acetate (102 mg, 0.452 mmol), Pd(dppf)Cl$_2$.CH$_2$Cl$_2$ (200 mg, 0.2 mmol), 3-diphenylphosphanylpropyl(diphenyl)phosphane (200 mg, 0.5 mmol), triethylsilane (2.3 mL, 14 mmol), triethylamine (1.3 mL, 9.05 mmol) in DMF (35 mL). The mixture was pressurised to 100 psi of carbon monoxide and heated at 75° C. overnight. The reaction was filtered through a 0.4 micron filter, and the majority of the DMF was removed in vacuo. Partitioning the crude mixture between DCM (100 mL) and washing with water (100 mL) followed by sat. aq. brine (100 mL) afforded a dark red syrup upon drying over MgSO$_4$ and removal of the volatiles. Subjecting the residue to flash chromatography (Grace 80 g, 0-10% DCM/MeOH) yielded 1.85 g (80% yield) of the product as a yellow solid. $^1$HNMR (CDCl$_3$) δ 10.20 (d, J=12.8 Hz, 1H), 8.65 (d, J=9.9 Hz, 2H), 8.11 (d, J=1.6 Hz, 1H), 7.86 (d, J=1.7 Hz, 1H), 4.58 (dt, J=13.7, 3.4 Hz, 2H), 4.23 (qd, J=7.1, 3.4 Hz, 2H), 3.57-3.41 (m, 2H), 3.28-3.10 (m, 2H), 2.26 (d, J=13.2 Hz, 2H), 1.61 (dt, J=7.5, 5.7 Hz, 4H), 1.52-1.39 (m, 2H), 1.31 (td, J=7.2, 3.6 Hz, 6H), 0.91-0.84 (m, 3H). MS: 511.0 [M+H]$^+$.

4-Ethyl-1-[5-[2-(ethylcarbamoylamino)-7-formyl-1,3-benzothiazol-5-yl]pyrimidin-2-yl]piperidine-4-carboxylic acid Ethyl-4-ethyl-1-[5-[2-(ethylcarbamoylamino)-7-formyl-1,3-benzothiazol-5-yl]pyrimidin-2-yl]piperidine-4-carboxylate (1.75 g, 3.43 mmol) was dissolved in THF (60 mL) and MeOH (125 mL) and an aqueous solution of KOH (125 mL; 1 mol/L) was introduced and refluxed overnight. After this period the mixture was diluted with water (150 mL), washed with Et$_2$O/EtOAc (1:1, 100 mL) and the residual aqueous acidified to pH 1 (3M HCl) and back extracted with EtOAc (3×100 mL). The organic fractions were combined, dried (MgSO$_4$) and concentrated in vacuo affording 1.05 g (64% yield) of the product as a light yellow solid after flash column chromatography on silica gel (0-10% DCM/MeOH). $^1$HNMR (CDCl$_3$): δ 10.16 (s, 1H), 8.56 (d, J=20.7 Hz, 2H), 7.95 (d, J=1.5 Hz, 1H), 7.81 (d, J=1.6 Hz, 1H), 4.51 (d, J=13.9 Hz, 2H), 3.39-3.32 (m, 2H), 3.26-3.15 (m, 2H), 2.20 (d, J=13.4 Hz, 2H), 1.59 (q, J=7.5 Hz, 2H), 1.48-1.34 (m, 2H), 1.21 (t, J=7.2 Hz, 3H), 0.87 (t, J=7.5 Hz, 3H). MS: 483.1 [M+H]$^+$.

Compound 202 1-[5-[2-(Ethylcarbamoylamino)-7-(methoxymethyl)-1,3-benzothiazol-5-yl]pyrimidin-2-yl]-4-methyl-piperidine-4-carboxylic acid

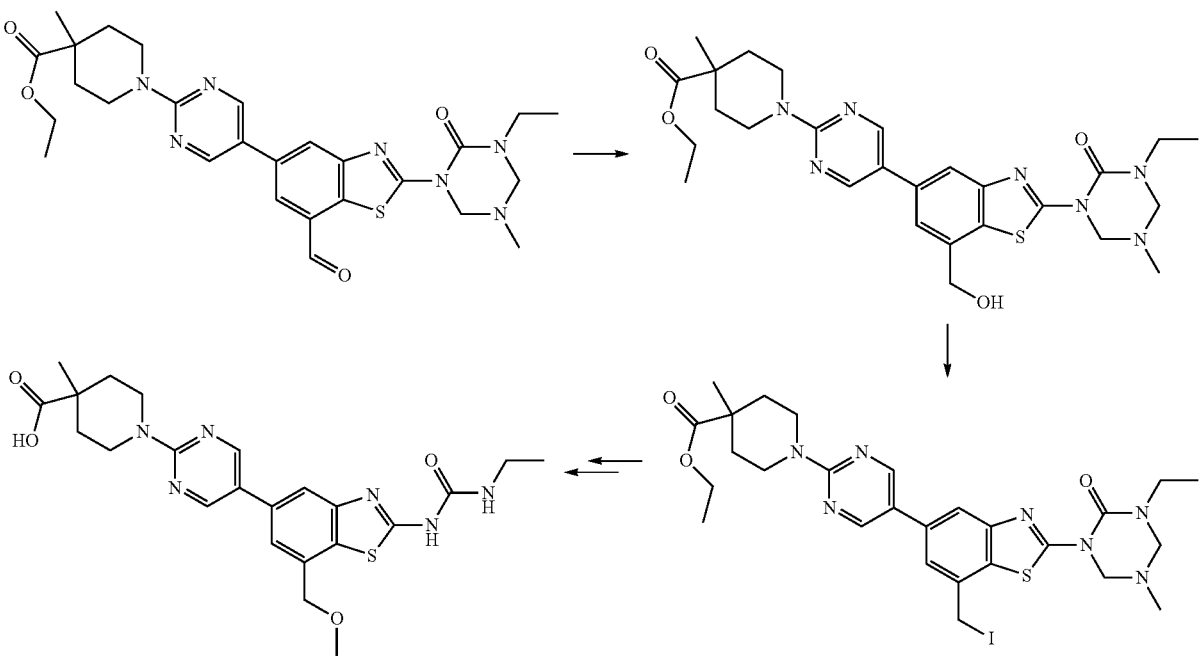

Ethyl 1-[5-[2-(3-ethyl-5-methyl-2-oxo-1,3,5-triazinan-1-yl)-7-formyl-1,3-benzothiazol-5-yl]pyrimidin-2-yl]-4-methyl-piperidine-4-carboxylate: Ethyl 1-[5-[7-bromo-2-(3-ethyl-5-methyl-2-oxo-1,3,5-triazinan-1-yl)-1,3-benzothiazol-5-yl]pyrimidin-2-yl]-4-methyl-piperidine-4-carboxylate (Intermediate 9) (2.58 g, 4.28 mmol) was dissolved in DMF (50 mL). Triethylamine (1.19 mL, 8.56 mmol), 1,3-bis(diphenylphosphino)propane (200 mg, 0.4 mmol), triethylsilane (2.05 mL, 12.8 mmol), Pd(OAc)$_2$ (100 mg, 0.4 mmol) and Pd(dppf)Cl$_2$DCM (200 mg, 0.2 mmol) were added and the mixture stirred at 75° C. for 32 h under an atmosphere of carbon monoxide (160 psi). The reaction mixture was cooled to rt, concentrated to dryness and the solid residue purified by flash column chromatography (80 g GraceResolv silica cartridge—dry loaded) eluting with 0-20% MeOH/CH$_2$Cl$_2$ to afford a brown solid. This solid was washed with EtOAc to afford the desired compound (690 mg, 29%) as an off-white solid. MS: 552.08 [M+H]$^+$.

Ethyl 1-[5-[2-(3-ethyl-5-methyl-2-oxo-1,3,5-triazinan-1-yl)-7-(hydroxymethyl)-1,3-benzothiazol-5-yl]pyrimidin-2-yl]-4-methyl-piperidine-4-carboxylate: Ethyl 1-[5-[2-(3-ethyl-5-methyl-2-oxo-1,3,5-triazinan-1-yl)-7-formyl-1,3-benzothiazol-5-yl]pyrimidin-2-yl]-4-methyl-piperidine-4-carboxylate (560 mg, 1.02 mmol) was dissolved in 1:1 EtOH/CH$_2$Cl$_2$ (40 mL) and cooled to 0° C. NaBH$_4$ (77 mg, 2.03 mmol) was added and the mixture allowed to warm to rt with stirring for 2 h. The mixture was diluted with EtOAc (200 mL), washed with water, brine and separated. The organic fraction was dried (Na$_2$SO$_4$) and concentrated under reduced pressure to afford the desired compound (484 mg, 86%) as a white solid. MS: 554.12 [M+H]$^+$.

Ethyl 1-[5-[2-(3-ethyl-5-methyl-2-oxo-1,3,5-triazinan-1-yl)-7-(iodomethyl)-1,3-benzothiazol-5-yl]pyrimidin-2-yl]-4-methyl-piperidine-4-carboxylate: Imidazole (75 mg, 1.09 mmol), triphenylphosphine (276 mg, 1.05 mmol) and iodine (267 mg, 1.05 mmol) were dissolved in CH$_2$Cl$_2$ (15 mL) and stirred at rt for 5 mins. A solution of ethyl 1-[5-[2-(3-ethyl-5-methyl-2-oxo-1,3,5-triazinan-1-yl)-7-(hydroxymethyl)-1,3-benzothiazol-5-yl]pyrimidin-2-yl]-4-methyl-piperidine-4-carboxylate (485 mg, 0.88 mmol) in CH$_2$Cl$_2$ (10 mL) was then added and the mixture stirred at rt for 2 h. The mixture was pre-adsorbed onto silica gel and purified by flash column chromatography (80 g GraceResolv silica cartridge—dry loaded) eluting with 25-100% EtOAc/heptane to afford the desired compound (323 mg, 56%) as a pale yellow foam. MS: 664.02 [M+H]$^+$.

Ethyl 1-[5-[2-(3-ethyl-5-methyl-2-oxo-1,3,5-triazinan-1-yl)-7-(2-methoxyethoxymethyl)-1,3-benzothiazol-5-yl]pyrimidin-2-yl]-4-methyl-piperidine-4-carboxylate: Ethyl 1-[5-[2-(3-ethyl-5-methyl-2-oxo-1,3,5-triazinan-1-yl)-7-(iodomethyl)-1,3-benzothiazol-5-yl]pyrimidin-2-yl]-4-methyl-piperidine-4-carboxylate (160 mg, 0.241 mmol) and 2-methoxyethanol (95 μL, 1.21 mmol) were dissolved in THF (10 mL). Sodium hydride (96 mg, 2.41 mmol) was added portionwise and the mixture stirred under argon at rt for 1 h. The mixture was then diluted with EtOAc (50 mL), carefully quenched with saturated aqueous NH$_4$Cl, washed with water, brine and separated. The organic fraction was dried (Na$_2$SO$_4$), concentrated under reduced pressure and the resulting solid residue purified by flash column chromatography (40 g GraceResolv, silica cartridge) eluting with 50-100% EtOAc/heptane to afford the desired compound (86 mg, 58%) as a colourless resin. MS: 612.16 [M+H]$^+$.

1-[5-[2-(Ethylcarbamoylamino)-7-(2-methoxyethoxymethyl)-1,3-benzothiazol-5-yl]pyrimidin-2-yl]-4-methyl-piperidine-4-carboxylic acid (202): Ethyl 1-[5-[2-(3-ethyl-5-methyl-2-oxo-1,3,5-triazinan-1-yl)-7-(2-methoxyethoxymethyl)-1,3-benzothiazol-5-yl]pyrimidin-2-yl]-4-methyl-piperidine-4-carboxylate (86 mg, 0.141 mmol) was dissolved in EtOH (15 mL) and 2M aqueous NaOH (5 mL) added. The reaction was then stirred at 70° C. for 2 h then cooled to rt, 2M HCl (10 mL) was added and the mixture was stirred for 1 h. The mixture was then extracted with EtOAc (3×25 mL) and the combined organic fractions, washed with brine, separated, dried (Na$_2$SO$_4$) and concentrated under reduced pressure to afford Compound 202 (60 mg, 81%) as an off-white solid. $^1$H NMR (DMSO-d$_6$): δ=12.40 (bs, 1H), 10.76 (bs, 1H), 8.75 (s, 2H), 7.82 (d, J=1.5 Hz, 1H), 7.41 (d, J=1.4 Hz, 1H), 6.84 (bt, J=5.4 Hz, 1H), 4.68 (s, 2H), 4.28 (dt, J=13.8 and 4.2 Hz, 2H), 3.39-3.30 (m, 2H), 3.35 (s, 3H), 3.25-3.17 (m, 2H), 2.05-2.00 (m, 2H), 1.39 (ddd, J=13.8, 10.2 and 3.9 Hz, 2H), 1.20 (s, 3H), 1.12 (t, J=7.2 Hz, 3H). MS: 529.16 [M+H]$^+$.

The following compound(s) were similarly prepared.

| Cpd No. | Structure | LCMS data [M + H]$^+$ | $^1$H NMR data |
|---|---|---|---|
| 194 | (structure) | 529.16 | d6-DMSO: d = 8.78 (s, 2H), 7.85 (d, J = 1.6 Hz, 1H), 7.49-7.45 (m, 1H), 7.45 (d, J = 1.4 Hz, 1H), 4.75 (s, 2H), 4.30 (dt, J = 13.9 and 4.1 Hz, 2H), 3.61 (dd, J = 5.9 and 3.3 Hz, 2H), 3.54 (dd, J = 5.9 and 3.3 Hz, 2H), 3.34-3.33 (m, 2H), 3.29 (s, 3H), 3.30-3.11 (m, 2H), 2.10-2.00 (m, 2H), 1.39 (ddd, J = 13.8, 10.2 and 3.8 Hz, 2H), 1.20 (s, 3H), 1.11 (t, J = 7.2 Hz, 3H) |

$^1$H NMR (DMSO-d$_6$): δ=8.78 (s, 2H), 7.85 (d, J=1.6 Hz, 1H), 7.49-7.45 (m, 1H), 7.45 (d, J=1.4 Hz, 1H), 4.75 (s, 2H), 4.30 (dt, J=13.9 and 4.1 Hz, 2H), 3.61 (dd, J=5.9 and 3.3 Hz, 2H), 3.54 (dd, J=5.9 and 3.3 Hz, 2H), 3.34-3.33 (m, 2H), 3.29 (s, 3H), 3.30-3.11 (m, 2H), 2.10-2.00 (m, 2H), 1.39 (ddd, J=13.8, 10.2 and 3.8 Hz, 2H), 1.20 (s, 3H), 1.11 (t, J=7.2 Hz, 3H). MS: 485.12 [M+H]$^+$.

257

Compound 195: 1-(5-(2-(3-Ethylureido)-7-(pyridin-2-yl benzothiazol-5-yl pyridazin-3-yl)-4-methylpiperidine-4-carboxylic acid (alternatively named 1-[5-[2-(ethylcarbamoylamino)-7-(2-pyridyl)-1,3-benzothiazol-5-yl]pyridazin-3-yl]-4-methyl-piperidine-4-carboxylic acid)

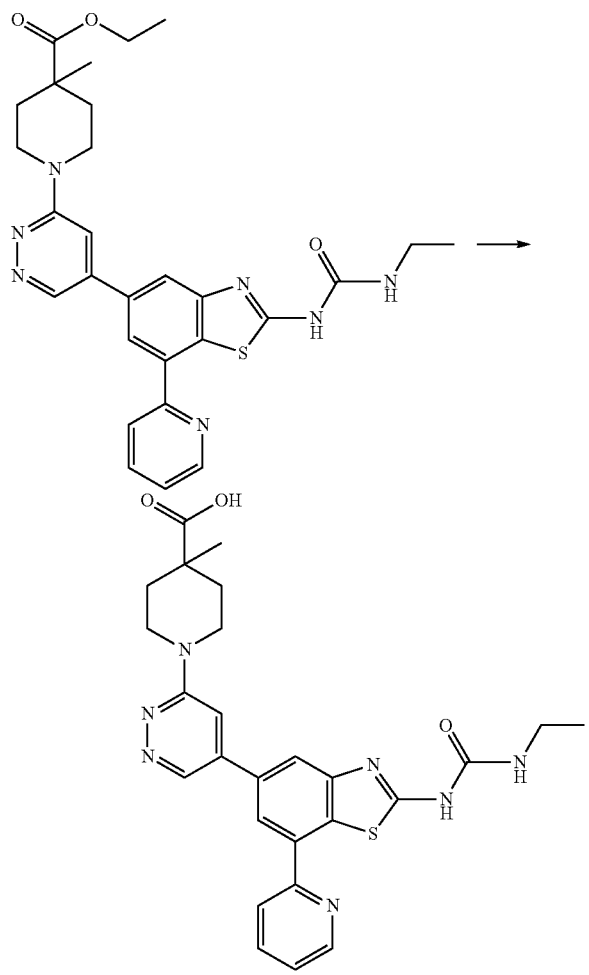

258

Ethyl 1-(5-(2-(3-ethylureido)-7-(pyridin-2-yl)benzo[d]thiazol-5-yl)pyridazin-3-yl)-4-methylpiperidine-4-carboxylate To a solution of 1-(5-(6-bromopyridazin-4-yl)-7-(pyridin-2-yl)benzothiazol-2-yl)-3-ethylurea (Intermediate 10) (0.090 g, 0.19 mmol) in DMF (2 mL) was added Et₃N (0.08 mL, 0.57 mmol) followed by the addition of ethyl 4-methylpiperidine-4-carboxylate hydrochloride (0.06 g, 0.29 mmol) and the mixture heated to 90° C. for 20 h then cooled to rt, water added and extracted with EtOAc (3×75 mL). The combined organics were washed with brine, dried over anhydrous Na₂SO₄, filtered and evaporated under reduced pressure. The crude residue was purified over 100-200 M silica-gel using 3% MeOH: DCM to obtain the desired product as yellow solid (0.05 g, 47%). MS: 546.40 [M+H]⁺.

1-(5-(2-(3-Ethylureido)-7-(pyridin-2-yl)benzothiazol-5-yl)pyridazin-3-yl)-4-methylpiperidine-4-carboxylic acid (195)

To an ice-cold solution of ethyl 1-(5-(2-(3-ethylureido)-7-(pyridin-2-yl)benzo[d]thiazol-5-yl)pyridazin-3-yl)-4-methylpiperidine-4-carboxylate (0.05 g, 0.092 mmol) in DMSO (2 mL) was added potassium tert-butoxide (0.051 g, 0.45 mmol) and the mixture stirred at rt for 2 h. After completion of reaction (by TLC), water (10 mL) was added followed by extraction with EtOAc (3×50 mL) and the organic layer discarded. The pH of the aqueous layer was adjusted up to 4-5, extracted with EtOAc (3×50 mL) and the combined organic layer dried over Na₂SO₄, filtered and evaporated under reduced pressure. The residue thus obtained was triturated with ether to obtain Compound 195 as an off-white solid (0.025 g, 53%). ¹H NMR (DMSO-d₆): δ 9.15 (s, 1H), 8.82 (m, 1H), 8.55 (d, J=8.0 Hz, 1H), 8.38 (s, 1H), 8.21 (s, 1H), 8.02 (t, J=8.0 Hz, 1H), 7.90 (m, 1H), 7.64 (s, 1H), 7.46 (m, 1H), 7.17 (br s, 1H), 4.20 (m, 2H), 3.19-3.24 (m, 4H), 2.10 (m, 2H), 1.43 (m, 2H), 1.22 (s, 3H) and 1.01 (t, J=7.2 Hz, 3H). MS: 518.29 [M+H]⁺.

Compound 197 1-[5-[7-(4,5-dihydroisoxazol-3-yl)-2-(ethylcarbamoylamino)-1,3-benzothiazol-5-yl]pyrimidin-2-yl]-4-ethyl-piperidine-4-carboxylic acid

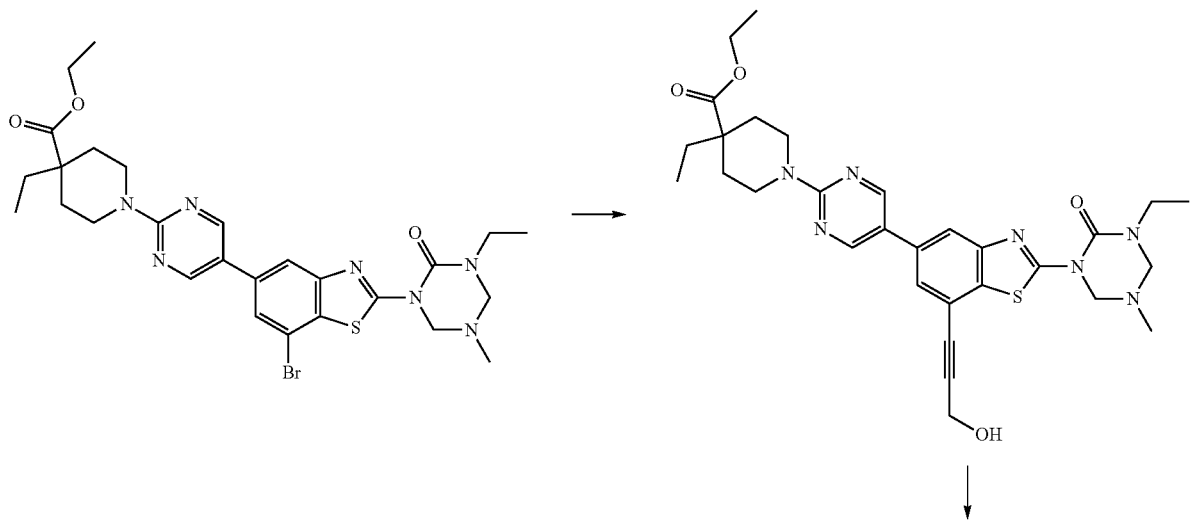

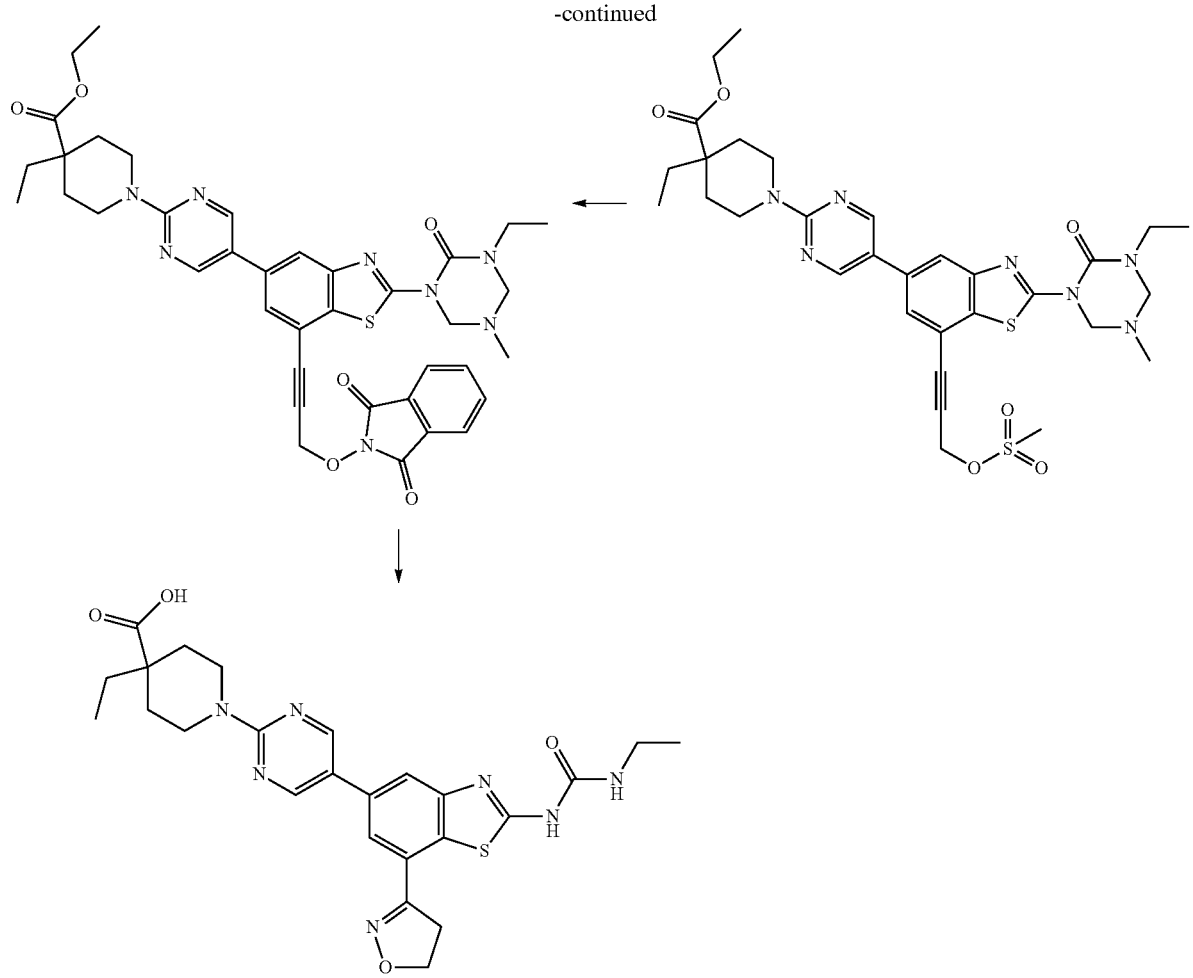

Ethyl 4-ethyl-1-[5-[2-(3-ethyl-5-methyl-2-oxo-1,3,5-triazinan-1-yl)-7-(3-hydroxyprop-1-ynyl)-1,3-benzothiazol-5-yl]pyrimidin-2-yl]piperidine-4-carboxylate: Ethyl 1-[5-[7-bromo-2-(3-ethyl-5-methyl-2-oxo-1,3,5-triazinan-1-yl)-1,3-benzothiazol-5-yl]pyrimidin-2-yl]-4-ethyl-piperidine-4-carboxylate (700 mg, 1.14 mmol), PdCl$_2$(PPh$_3$)$_2$ (32 mg, 0.05 mmol) and triphenylphosphine (3 mg, 0.01 mmol) were placed in a 10-20 mL microwave vial and anhydrous DMF (14 mL) added, quickly followed by triethylamine (0.95 mL, 6.81 mmol) and propargyl alcohol (0.13 mL, 2.27 mmol). The solution was bubbled with argon for ~3 minutes then CuI (4 mg, 0.02 mmol) was added. The vial was capped and mixture degassed then heated in the microwave at 100° C. for 30 minutes. More PdCl$_2$(PPh$_3$)$_2$ (11 mg) and propargyl alcohol (0.05 mL) were added and argon was bubbled through the mixture then CuI (1.5 mg) added. The vial was capped and mixture degassed then heated in the microwave again at 100° C. for 15 minutes. The crude reaction mixture was filtered through a PTFE filter. The filter was rinsed with EtOAc and then water. The filtrate was diluted with water, extracted into EtOAc (4×60 mL) and the combined organic layers washed with water (2×50 mL) and brine, dried over Na$_2$SO$_4$ and concentrated to dryness under reduced pressure to give a brown solid. The mixture was purified by chromatography, Biotage SP4, 40 g Si cartridge, 50-80% EtOAc in cyclohexane and the relevant fractions combined to give the desired product as an off-white solid, 247 mg (37%). MS: 592.13 [M+H]$^+$.

Ethyl 4-ethyl-1-[5-[2-(3-ethyl-5-methyl-2-oxo-1,3,5-triazinan-1-yl)-7-(3-methylsulfonyloxyprop-1-ynyl)-1,3-benzothiazol-5-yl]pyrimidin-2-yl]piperidine-4-carboxylate:
Ethyl 4-ethyl-1-[5-[2-(3-ethyl-5-methyl-2-oxo-1,3,5-triazinan-1-yl)-7-(3-hydroxyprop-1-ynyl)-1,3-benzothiazol-5-yl]pyrimidin-2-yl]piperidine-4-carboxylate (325 mg, 0.55 mmol) was dissolved in anhydrous DCM (32 mL) under argon and the solution cooled to 0° C. Triethylamine (0.19 mL, 1.40 mmol) was added followed by methanesulfonyl chloride (0.064 mL, 0.82 mmol) and the mixture allowed to warm to rt and stirred for 45 minutes. The mixture was diluted with water, extracted into DCM (3×20 mL) and the combined organic layer washed with brine, dried over Na$_2$SO$_4$ and concentrated to dryness under reduced pressure. The desired compound was obtained as a yellow oil which was used without further purification in the next step. MS: 670.09 [M+H]$^+$.

Ethyl 1-[5-[7-[3-(1,3-dioxoisoindolin-2-yl)oxyprop-1-ynyl]-2-(3-ethyl-5-methyl-2-oxo-1,3,5-triazinan-1-yl)-1,3-benzothiazol-5-yl]pyrimidin-2-yl]-4-ethyl-piperidine-4-carboxylate: Ethyl 4-ethyl-1-[5-[2-(3-ethyl-5-methyl-2-oxo-1,3,5-triazinan-1-yl)-7-(3-methylsulfonyloxyprop-1-ynyl)-1,3-benzothiazol-5-yl]pyrimidin-2-yl]piperidine-4-carboxylate (368 mg, 0.55 mmol), N-hydroxyphthalimide (134 mg, 0.82 mmol), potassium iodide (9 mg, 0.05 mmol) and potassium carbonate (152 mg, 1.10 mmol) were dissolved in anhydrous DMF (5 mL) under argon and heated to 60° C. for 3 h. The cooled mixture was diluted with water, extracted into EtOAc (4×30 mL) and the organic phase washed with water then brine, dried over Na₂SO₄ and concentrated to dryness under reduced pressure. A yellow solid was obtained and the mixture was purified by chromatography, Biotage SP4, 40 g Si cartridge, 50-80% EtOAc in cyclohexane. The relevant fractions were combined to give the desired compound as a pale yellow oil, 233 mg (58%). MS: 737.13 [M+H]⁺.

1-[5-[7-(4,5-Dihydroisoxazol-3-yl)-2-(ethylcarbamoylamino)-1,3-benzothiazol-5-yl]pyrimidin-2-yl]-4-ethyl-piperidine-4-carboxylic acid (197): Ethyl 1-[5-[7-[3-(1,3-dioxoisoindolin-2-yl)oxyprop-1-ynyl]-2-(3-ethyl-5-methyl-2-oxo-1,3,5-triazinan-1-yl)-1,3-benzothiazol-5-yl]pyrimidin-2-yl]-4-ethyl-piperidine-4-carboxylate (233 mg, 0.32 mmol) was suspended in EtOH (20 mL) and sodium hydroxide solution (10 mL, 1 M, aq) was added to give a light yellow solution. The solution was heated at 100° C. then cooled to rt after 48 h. The mixture was concentrated to dryness under reduced pressure and remaining water azeotroped with MeCN. The resulting yellow residue was suspended in MeOH with sonication and warming then filtered through a PTFE filter cup. A white (salt-like) solid was obtained (discarded) and a yellow filtrate. The yellow filtrate was concentrated to dryness under reduced pressure to give a yellow solid which was suspended in water, sonicated, DCM added and the mixture filtered through a PTFE filter cup leaving a pale yellow solid. This solid was dissolved in MeOH, passed through the filter cup and the solution concentrated to dryness under reduced pressure to give a pale yellow solid which was purified by chromatography, Biotage SP4, 40 g Si cartridge, 0-5% MeOH in DCM. The relevant fractions were combined to afford Compound 197 as a pale yellow solid, 9 mg. ¹H NMR (MeOD): δ 8.67 (2H, s), 7.85 (1H, d, J=1.6 Hz), 7.51 (1H, d, J=1.6 Hz), 4.57 (2H, t, J=10.2 Hz), 4.57 (2H, m), 3.60 (2H, t, J=10.2 Hz), 3.36 (2H, q, J=7.2 Hz), 3.24 (2H, m), 2.22 (2H, dm, J=13.4 Hz), 1.64 (2H, J=7.5 Hz), 1.45 (2H, m), 1.24 (3H, t, J=7.2 Hz), 0.93 (3H, t, J=7.5 Hz). MS: 524.14 [M+H]⁺.

Compound 191 Ethyl 1-[5-[2-(ethylcarbamoylamino)-6-methoxy-1,3-benzothiazol-5-yl]pyrimidin-2-yl]-4-methyl-piperidine-4-carboxylate; and Compound 198 1-[5-[2-(Ethylcarbamoylamino)-6-methoxy-1,3-benzothiazol-5-yl]pyrimidin-2-yl]-4-methyl-piperidine-4-carboxylic acid

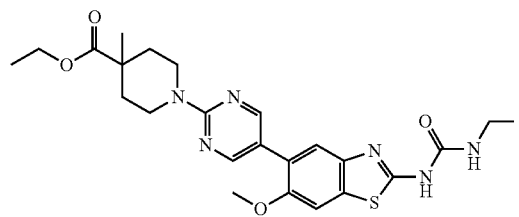

Ethyl 1-[5-[2-(ethylcarbamoylamino)-6-methoxy-1,3-benzothiazol-5-yl]pyrimidin-2-yl]-4-methyl-piperidine-4-carboxylate (191)

1-(5-Bromo-6-methoxy-1,3-benzothiazol-2-yl)-3-ethyl-urea (Intermediate 11) (200 mg, 66 mass %, 0.40 mmol),
ethyl 4-methyl-1-[5-(4,4,5,5-tetramethyl-1,3,2-dioxaborolan-2-yl)pyrimidin-2-yl]piperidine-4-carboxylate (crude, 638 mg, 47 mass %, 0.80 mmol) and Pd(dppf)Cl₂.DCM (16 mg, 0.02 mmol) were dissolved in dioxane (7.5 mL) in a microwave vial and a solution of cesium carbonate (391 mg, 1.20 mmol) in water (2.5 mL) was added. The vial was capped, the mixture degassed and heated in the microwave at 110° C. for 30 minutes. The mixture was poured into water, extracted into EtOAc (4×20 mL) and the organic layers washed with brine, dried over Na₂SO₄ and concentrated to dryness in vacuo. A yellow solid was obtained and the mixture purified by chromatography, Biotage SP4, 12 g Si cartridge, 0-5% MeOH in DCM. The relevant fractions were combined to give a brown solid which was further purified by chromatography, Biotage SP4, 12 g Si cartridge, 50% EtOAc in hexane (isocratic) then the column flushed with EtOAc. The relevant fractions were combined to give Compound 191 as a white solid, 110 mg (55%). ¹H NMR (MeCN-d3): δ 1.19 (3H, t, J=7.2 Hz), 1.26 (3H, s), 1.29 (3H, t, J=7.1 Hz), 1.49 (2H, ddd, J=14.0, 10.5 and 4.1 Hz), 2.14 (2H, m), 3.32 (4H, m), 3.87 (3H, s), 4.20 (2H, q, J=7.1 Hz), 4.37 (2H, dt, J=14.0 and 4.1 Hz), 6.16 (1H, br s), 7.51 (1H, s), 7.61 (1H, s), 8.55 (2H, s), 8.77 (1H, br s). MS: 499.12 [M+H]⁺.

1-[5-[2-(Ethylcarbamoylamino)-6-methoxy-1,3-benzothiazol-5-yl]pyrimidin-2-yl]-4-methyl-piperidine-4-carboxylic acid (198)

Ethyl 1-[5-[2-(ethylcarbamoylamino)-6-methoxy-1,3-benzothiazol-5-yl]pyrimidin-2-yl]-4-methyl-piperidine-4-carboxylate (101 mg, 0.20 mmol) was suspended in ethanol (2 mL) and sodium hydroxide solution (2 mL, 1 M, aq) was added to give a pale yellow solution and the mixture heated to 60° C. for 1 h 40 minutes then left to cool to rt overnight. The mixture was acidified to pH 3 with HCl solution (1 M, aq) and diluted with water. DCM was added but the material did not dissolve so the mixture was concentrated under reduced pressure to remove the DCM then filtered through a PTFE filter (the filter was treated with ~2 mL DCM to make it more permeable to aqueous suspensions) and rinsed with water (2 mL). A white solid was obtained which was dried in a vacuum oven at 40° C. to give Compound 198, 75 mg (79%). ¹H NMR (DMSO): δ 1.11 (3H, t, J=7.1 Hz), 1.21 (3H, s), 1.40 (2H, ddd, J=13.8, 9.9 and 3.8 Hz), 2.02 (2H, dt, J=13.8 and 3.8 Hz), 3.20 (2H, dt, J=12.8 and 7.1 Hz), 3.33 (2H, m), 3.83 (3H, s), 4.28 (2H, dt, J=13.8 and 4.5 Hz), 6.71 (1H, br t, J=5.7 Hz), 7.56 (1H, s), 7.65 (1H, s), 8.53 (2H, s), 10.56 (1H, br s), 12.44 (1H, br s). MS: 471.13 [M+H]⁺.

Compound 200: 1-[5-[2-(Ethylcarbamoylamino)-7-methoxy-1,3-benzothiazol-5-yl]pyrimidin-2-yl]-4-methyl-piperidine-4-carboxylic acid

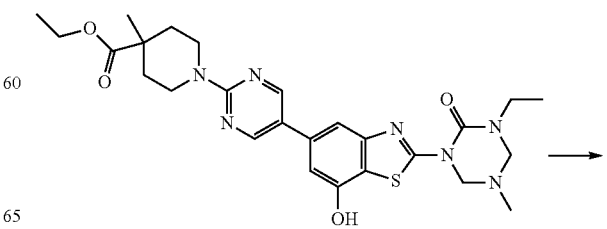

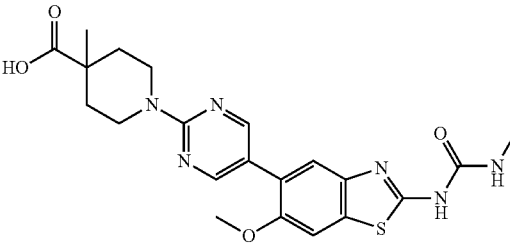

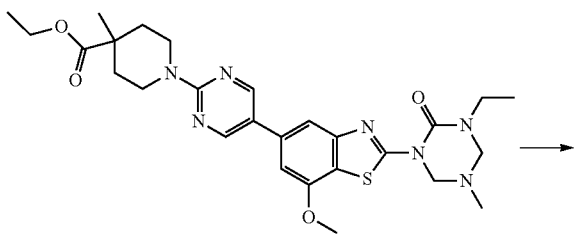

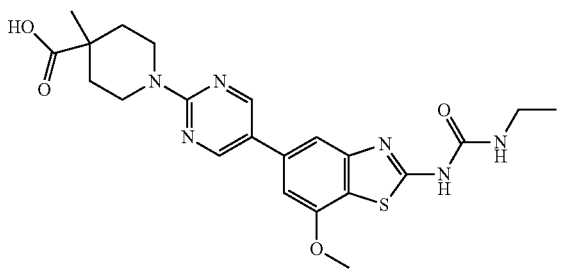

Ethyl 1-[5-[2-(3-ethyl-5-methyl-2-oxo-1,3,5-triazinan-1-yl)-7-hydroxy-1,3-benzothiazol-5-yl]pyrimidin-2-yl]-4-methyl-piperidine-4-carboxylate: [5-[2-(4-Ethoxycarbonyl-4-methyl-1-piperidyl)pyrimidin-5-yl]-2-(3-ethyl-5-methyl-2-oxo-1,3,5-triazinan-1-yl)-1,3-benzothiazol-7-yl]boronic acid (Intermediate 12) (1.88 g, 3.32 mmol) was dissolved in acetone (60 mL) and cooled to 0° C. Oxone (2.45 g, 3.98 mmol), dissolved in sodium hydrogen carbonate (sat aq) (40 mL), was added dropwise to the reaction mixture, resulting in a dark red solution. After addition, the mixture was stirred for 5 min at 0° C. before 1M HCl was added, bring the reaction mixture to ~pH 2. The reaction mixture was diluted with water (100 mL) and EtOAc (100 mL). The organic layer was removed, and the aqueous layer was extracted twice more with EtOAc (2×100 mL). The organic fractions were dried and concentrated in vacuo to give a dark brown solid. Flash chromatography (40 g silica column), eluting with 0-100% EtOAc gradient in n-heptane, gave desired product (2.1 g, dark red solid). $^1$H NMR (MeOD) δ 8.61 (s, 2H), 7.41 (d, J=1.4 Hz, 1H), 6.84 (d, J=1.5 Hz, 1H), 5.21 (s, 2H), 4.47-4.36 (m, 4H), 4.28-4.20 (m, 2H), 3.53-3.44 (m, 2H), 3.35-3.25 (m, 2H, obscured under solvent), 2.67 (s, 3H), 2.19 (d, J=13.5 Hz, 2H), 1.56-1.46 (m, 2H), 1.36-1.21 (m, 9H). MS: [M−H]$^-$ 538.1.

Ethyl 1-[5-[2-(3-ethyl-5-methyl-2-oxo-1,3,5-triazinan-1-yl)-7-methoxy-1,3-benzothiazol-5-yl]pyrimidin-2-yl]-4-methyl-piperidine-4-carboxylate: To a solution of ethyl 1-[5-[2-(3-ethyl-5-methyl-2-oxo-1,3,5-triazinan-1-yl)-7-hydroxy-1,3-benzothiazol-5-yl]pyrimidin-2-yl]-4-methyl-piperidine-4-carboxylate (533 mg, 0.593 mmol), dicesium carbonate (390 mg, 1.19 mmol) and N,N-dimethylformamide (10 mL) at 0° C. was added MeI (55 μL, 0.89 mmol) and the reaction mixture was allowed to warm to rt before stirring for 1 hr. A further portion of MeI (110 μL, 1.78 mmol) was added and the mixture stirred at rt for a further 18 hrs. The reaction was diluted with ammonium chloride solution (50 mL) and EtOAc (50 mL). The organic layer was separated and the aqueous layer washed with further portions of EtOAc (2×50 mL). The organic layers were combined, dried (MgSO$_4$) and concentrated in vacuo to give crude product mixture followed by flash chromatography (12 g silica column), eluting with 0-100% EtOAc gradient in n-heptane to give the desired product (226 mg, light brown solid). $^1$H NMR (CDCl$_3$) δ 8.63 (s, 2H), 7.51 (d, J=1.3 Hz, 1H), 6.82 (d, J=1.3 Hz, 1H), 5.23 (s, 2H), 4.42 (dt, J=13.6, 4.0 Hz, 2H), 4.35 (s, 2H), 4.25 (q, J=7.1 Hz, 2H), 4.04 (s, 3H), 3.56-3.50 (m, 2H), 3.43-3.34 (m, 2H), 2.70 (s, 3H), 2.25 (d, J=13.6 Hz, 2H), 1.58-1.48 (m, 2H), 1.38-1.24 (m, 9H). MS: 554.1 [M+H]$^+$.

1-[5-[2-(Ethylcarbamoylamino)-7-methoxy-1,3-benzothiazol-5-yl]pyrimidin-2-yl]-4-methyl-piperidine-4-carboxylic acid (200): Ethyl 1-[5-[2-(3-ethyl-5-methyl-2-oxo-1,3,5-triazinan-1-yl)-7-methoxy-1,3-benzothiazol-5-yl]pyrimidin-2-yl]-4-methyl-piperidine-4-carboxylate (225 mg, 0.41 mmol) was dissolved in a mixture of NaOH (1M) (1 mL) and THF (3 mL) and the mixture stirred at rt for 3 hrs. A further portion of NaOH (1M) (1 mL) was added and stirring at rt continued for a further 1 hr. The reaction was heated at 60° C. for 16 hrs then at 100 C for 2 hrs and then with a further portion of NaOH (1 M, 1 mL) for 4 hrs. 5 M NaOH solution (1 mL, 5 mmol) was added and stirring continued at rt overnight, followed by 60° C. for 2 hrs. The reaction mixture was concentrated by freeze-drying then purified using reverse-phase chromatography (C18 column), eluting with 20-60% ACN gradient in water (with 0.1% formic acid), to give Compound 200 (60 mg, light yellow solid). $^1$H NMR (MeOD) δ 8.63 (s, 2H), 7.43 (s, 1H), 6.94 (s, 1H), 4.45-4.35 (m, 2H), 4.05 (s, 3H), 3.46-3.35 (m, 4H, obscured by solvent), 2.23-2.16 (m, 2H), 1.53-1.42 (m, 2H), 1.28 (s, 3H), 1.24 (t, J=7.2 Hz, 3H). [M+H]$^+$471.1.

Compound 203 4-Ethyl-1-[5-[2-(ethylcarbamoylamino)-7-(methoxymethyl)-1,3-benzothiazol-5-yl]pyrimidin-2-yl]piperidine-4-carboxylic acid

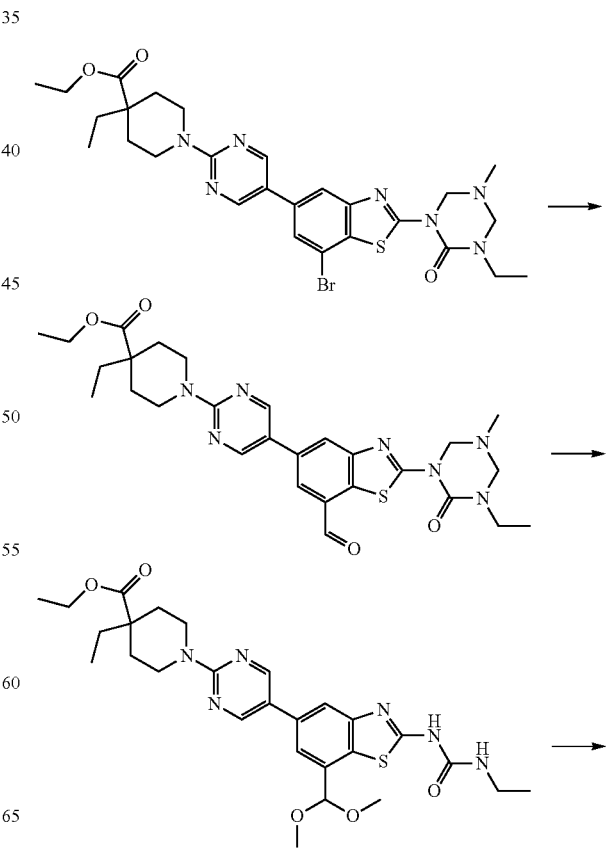

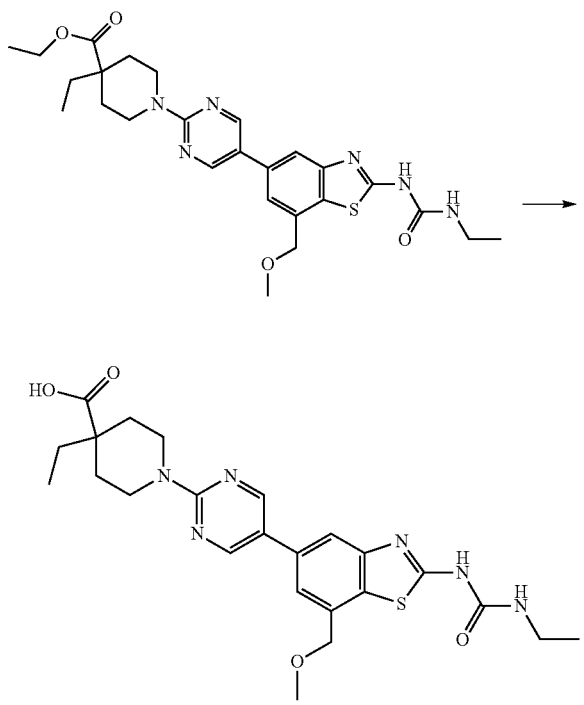

Ethyl 4-ethyl-1-[5-[2-(3-ethyl-5-methyl-2-oxo-1,3,5-triazinan-1-yl)-7-formyl-1,3-benzothiazol-5-yl]pyrimidin-2-yl]piperidine-4-carboxylate: 1.4M BuLi (600 μL, 0.84 mmol) was added to ethyl 1-[5-[7-bromo-2-(3-ethyl-5-methyl-2-oxo-1,3,5-triazinan-1-yl)-1,3-benzothiazol-5-yl]pyrimidin-2-yl]-4-ethyl-piperidine-4-carboxylate (250 mg, 0.41 mmol) in THF (10 mL) at −90° C. and the reaction stirred for 10 mins before DMF (300 μL) was added and the mixture stirred for a further 20 mins. The reaction was quenched with sat. NH$_4$Cl (aq) then allowed to warm to rt before extraction with EtOAc (3×). Combined EtOAc extracts were dried and the solvent evaporated to yield the crude product which was purified by flash chromatography on 12 g SiO$_2$ using EtOAc/Cyclohexane gradient 0-0% 3CV, 0-100% 20CV, 100-100% 5CV to yield the desired product (105 mg, 46%). $^1$H NMR (CDCl$_3$) δ 10.22 (s, 1H), 8.63 (s, 2H), 8.06 (d, J=1.7 Hz, 1H), 7.83 (d, J=1.7 Hz, 1H), 5.21 (s, 2H), 4.56 (dt, J=13.8, 3.5 Hz, 2H), 4.33 (s, 2H), 4.23 (q, J=7.1 Hz, 2H), 3.51 (q, J=7.2 Hz, 2H), 3.23-3.13 (m, 2H), 2.67 (s, 3H), 2.25 (bd, J=13.4 Hz, 2H), 1.61 (q, J=7.6 Hz, 2H), 1.45 (ddd, J=13.5, 11.9, 4.2 Hz, 2H), 1.30 (t, J=7.1 Hz, 3H), 1.25 (t, J=7.2 Hz, 3H), 0.86 (t, J=7.5 Hz, 3H).

Ethyl 1-[5-[7-(dimethoxymethyl)-2-(ethylcarbamoylamino)-1,3-benzothiazol-5-yl]pyrimidin-2-yl]-4-ethyl-piperidine-4-carboxylate: Ethyl 4-ethyl-1-[5-[2-(3-ethyl-5-methyl-2-oxo-1,3,5-triazinan-1-yl)-7-formyl-1,3-benzothiazol-5-yl]pyrimidin-2-yl]piperidine-4-carboxylate (33 mg, 0.058 mmol) was suspended in MeOH (2 mL) and treated with conc. H$_2$SO$_4$ (~5 μL). The reaction was heated to 50° C. for 1.5 h then diluted with DCM and sat.NaHCO$_3$(aq). The organic layer was separated and the aqueous layer extracted further with DCM (2×) before the combined DCM extracts were dried and the solvent evaporated to yield the crude product (35 mg). Crude product was used in the next step without further purification. MS: 557.16 [M+H]$^+$.

Ethyl 4-ethyl-1-[5-[2-(ethylcarbamoylamino)-7-(methoxymethyl)-1,3-benzothiazol-5-yl]pyrimidin-2-yl]piperidine-4-carboxylate: Ethyl 1-[5-[7-(dimethoxymethyl)-2-(ethylcarbamoylamino)-1,3-benzothiazol-5-yl]pyrimidin-2-yl]-4-ethyl-piperidine-4-carboxylate (35 mg, 0.063 mmol) was dissolved in DCM (2 mL), cooled to 0° C. and treated sequentially with Et$_3$SiH (50 μL, 0.313 mmol) and BF$_3$:OEt$_2$ (15 μL, 0.119 mmol) and the mixture stirred for 10 mins then allowed to warm to rt. After 40 mins additional Et$_3$SiH (50 μL, 0.313 mmol) was added at rt followed by BF$_3$:OEt$_2$ (15 μL, 0.119 mmol) and the mixture stirred for 2.5 h after which time the reaction was diluted with sat. NaHCO$_3$ (aq), extracted with DCM (3×), dried and the solvent evaporated to yield the crude product (31.7 mg). The crude product was purified on 12 g SiO$_2$ using EtOAc/Cyclohexane gradient 0-0% 3CV, 0-100% 30CV, 100-100% 5CV to yield the desired compound (22.3 mg, 73%). $^1$H NMR (CDCl$_3$) δ 8.59 (s, 2H), 7.79 (d, J=1.2 Hz, 1H), 7.25 (d, J=0.9 Hz, 1H), 4.66 (s, 2H), 4.53 (dt, J=13.7, 3.5 Hz, 2H), 4.22 (q, J=7.1 Hz, 2H), 3.51-3.40 (m, 2H), 3.38 (s, 3H), 3.22-3.07 (m, 2H), 2.23 (d, J=13.4 Hz, 2H), 1.59 (q, J=7.5 Hz, 2H), 1.48-1.43 (m, 2H), 1.29 (dd, J=10.0, 4.1 Hz, 6H), 0.85 (t, J=7.5 Hz, 3H). MS: 527.15 [M+H]$^+$ 4-Ethyl-1-[5-[2-(ethylcarbamoylamino)-7-(methoxymethyl)-1,3-benzothiazol-5-yl]pyrimidin-2-yl]piperidine-4-carboxylic acid (203): Ethyl 4-ethyl-1-[5-[2-(ethylcarbamoylamino)-7-(methoxymethyl)-1,3-benzothiazol-5-yl]pyrimidin-2-yl]piperidine-4-carboxylate (23 mg, 0.042 mmol) was dissolved in EtOH (1 mL) and 2M aqueous NaOH (330 μL, 0.66 mmol) added. The reaction mixture was stirred at 70° C. for 15 mins before additional 2M NaOH (670 μL, 1.34 mmol) was added and the reaction continued for 1.5 h then temperature increased to 100° C. and reaction continued for 4 h after which time the reaction was allowed to cool to rt overnight. After this time LCMS indicated small amount of starting material still present and the reaction was completed by heating to 100° C. for a further 2 h after which time the reaction was cooled to rt, diluted with water and extracted with DCM (3×). The aqueous layer was acidified with 10% HCl (aq) before extracting with EtOAc (3×) and the combined EtOAc extracts dried and the solvent evaporated to yield the Compound 203 (13.5 mg, 64%). $^1$H NMR (MeOD) δ 8.54 (s, 2H), 7.66 (bd, J=1.4 Hz, 1H), 7.28 (s, 1H), 4.68 (s, 2H), 4.48 (dt, J=13.7, 3.6 Hz, 2H), 3.35-3.28 (m, 2H), 3.22-3.11 (m, 2H), 2.20-2.13 (m, 2H), 1.60 (q, J=7.5 Hz, 2H), 1.44-1.34 (m, 2H), 1.21 (t, J=7.2 Hz, 3H), 0.89 (t, J=7.5 Hz, 3H). MS: 499.12 [M+H]$^+$

Compound 207: 4-Ethyl-1-(5-(2-(3-ethylureido)-7-propionylbenzo[d]thiazol-5-yl pyrimidin-2-yl)piperidine-4-carboxylic acid (alternatively named 4-ethyl-1-[5-[2-(ethylcarbamoylamino)-7-propanoyl-1,3-benzothiazol-5-yl]pyrimidin-2-yl]piperidine-4-carboxylic acid)

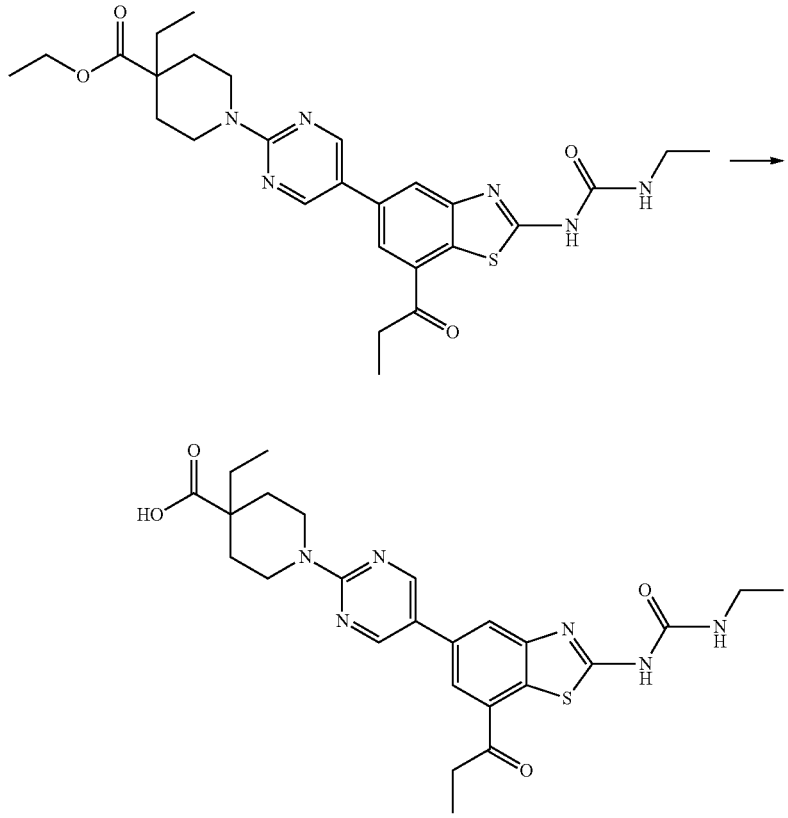 [SMILES: CCNC(=O)Nc1nc2cc(-c3cnc(N4CCC(CC)(C(=O)OCC)CC4)nc3)cc(C(=O)CC)c2s1 ; CCNC(=O)Nc1nc2cc(-c3cnc(N4CCC(CC)(C(=O)O)CC4)nc3)cc(C(=O)CC)c2s1]

Ethyl 4-ethyl-1-(5-(2-(3-ethylureido)-7-propionylbenzo[d]thiazol-5-yl)pyrimidin-2-yl)piperidine-4-carboxylate To a solution of 2-(3-ethylureido)-7-propionylbenzo[d]thiazol-5-yl trifluoromethanesulfonate (Intermediate 13) (0.25 g, 0.587 mmol) in 1,4-dioxane:MeOH (21 mL: 14 mL) were added ethyl 4-methyl-1-(5-(4,4,5,5-tetramethyl-1,3,2-dioxaborolan-2-yl)pyrimidin-2-yl)piperidine-4-carboxylate (0.46 g, 1.17 mmol) and potassium phosphate (0.19 g, 0.88 mmol) at rt under $N_2$ atmosphere. The reaction mixture was degassed by $N_2$ for 15 min followed by addition of tetrakis(triphenylphosphine)palladium(0) (0.068 g, 0.058 mmol). The reaction mixture was further degassed by $N_2$ for 15 min then stirred for 2 h at 80° C. After the completion of reaction (by TLC), water (50 mL) was added, extracted with EtOAc (3×50 mL) and the combined organic layers washed with water, brine, dried over anhydrous $Na_2SO_4$, filtered then concentrated under reduced pressure. The residue was purified by column chromatography (silica gel 100-200 M, 70% EtOAc-hexane) to afford the desired product as an off-white solid (0.110 g, 35%). $^1$H NMR (DMSO-$d_6$): δ 10.70 (br s, 1H), 8.87 (s, 2H), 8.23 (s, 1H), 8.14 (s, 1H), 6.80 (br s, 1H), 4.47 (m, 2H), 4.17 (q, J=7.20 Hz, 2H), 3.33 (m, 2H), 3.12-3.22 (m, 4H), 2.09 (m, 2H), 1.56 (q, J=7.60 Hz, 2H), 1.39 (m, 2H), 1.22 (t, J=7.20 Hz, 3H), 1.16 (t, J=7.2 Hz, 3H), 1.10 (t, J=7.2 Hz, 3H) and 0.75 (t, J=7.2 Hz, 3H). MS: 539.52 [M+H]$^+$

4-Ethyl-1-(5-(2-(3-ethylureido)-7-propionylbenzo[d]thiazol-5-yl)pyrimidin-2-yl)piperidine-4-carboxylic acid (207)

To a solution of ethyl 4-ethyl-1-(5-(2-(3-ethylureido)-7-propionylbenzo[d]thiazol-5-yl)pyrimidin-2-yl)piperidine-4-carboxylate (0.025 g, 0.046 mmol) in EtOH (5 mL) was added an aqueous solution (1 mL) of NaOH (0.0092 g, 0.232 mmol) and the mixture stirred overnight at 80° C. After reaction completion (by TLC), the EtOH was evaporated under reduced pressure, water (10 mL) was added to the residue and extracted with EtOAc (3×25 mL) and the organic layers discarded. The aqueous layer was acidified to pH 4-5 with 1N HCl, extracted with EtOAc (3×25 mL) and the combined organic layers washed with brine, dried over anhydrous $Na_2SO_4$, filtered then concentrated under reduced pressure. The residue was purified by preparative TLC (5% MeOH in DCM) to obtain Compound 207 as white solid (0.007 g, 30%). $^1$H NMR (DMSO-$d_6$): δ 10.82 (br s, 1H), 8.86 (s, 2H), 8.23 (s, 1H), 8.14 (s, 1H), 6.95 (br s, 1H), 4.46 (m, 2H), 3.36 (m, 2H), 3.13-3.24 (m, 4H), 2.08 (m, 2H), 1.51-1.53 (m, 2H), 1.32 (m, 2H), 1.16 (t, J=7.2 Hz, 3H), 1.10 (t, J=7.2 Hz, 3H) and 0.81 (t, J=7.2 Hz, 3H). MS: 511.24 [M+H]$^+$.

Compound 223: (E/Z)-4-ethyl-1-(5-(2-(3-ethylureido)-7-(1-(methoxyimino)propyl)benzo[d]thiazol-5-yl)pyrimidin-2-yl)piperidine-4-carboxylic acid (alternatively named 4-ethyl-1-[5-[2-(ethylcarbamoylamino)-7-(C-ethyl-N-methoxycarbonimidoyl)-1,3-benzothiazol-5-yl]pyrimidin-2-yl]piperidine-4-carboxylic acid)

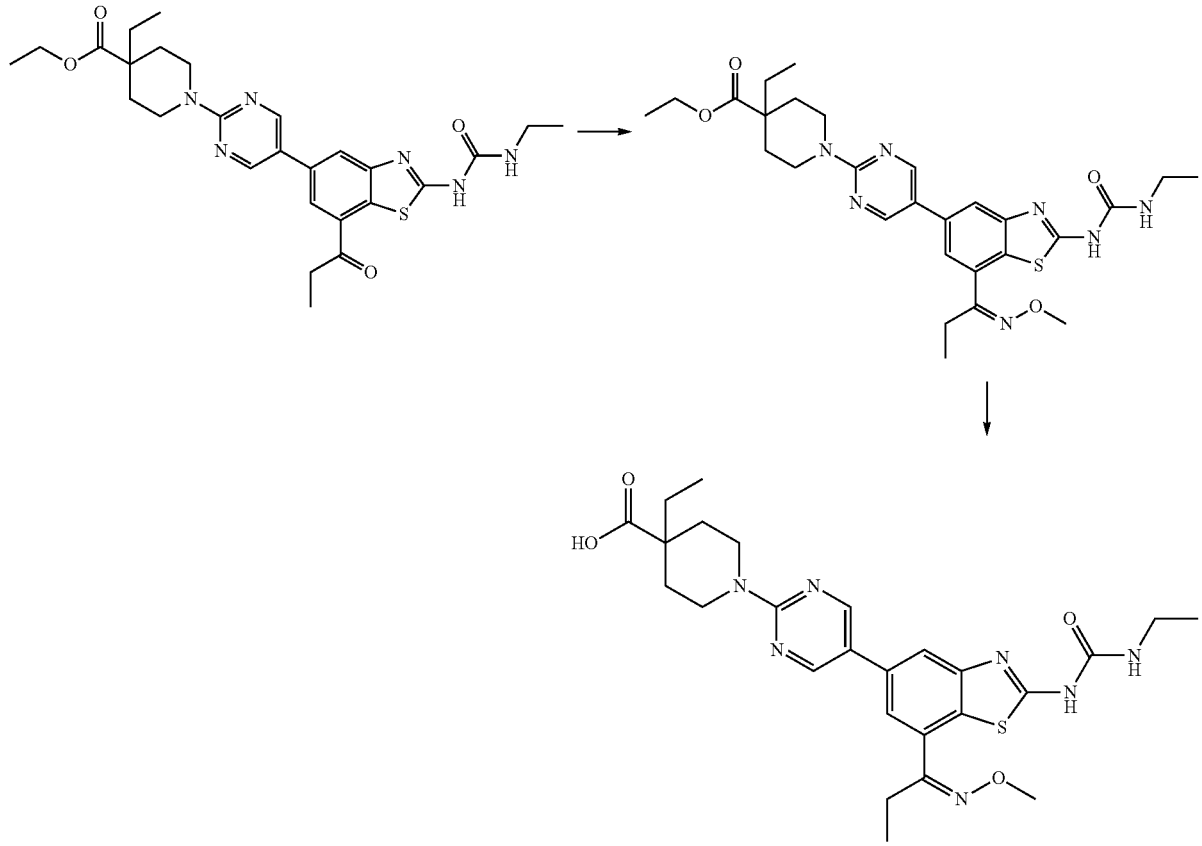 [SMILES: CCNC(=O)Nc1nc2cc(-c3cnc(N4CCC(CC)(C(=O)OCC)CC4)nc3)cc(C(=O)CC)c2s1 ; CCNC(=O)Nc1nc2cc(-c3cnc(N4CCC(CC)(C(=O)OCC)CC4)nc3)cc(/C(CC)=N\OC)c2s1 ; CCNC(=O)Nc1nc2cc(-c3cnc(N4CCC(CC)(C(=O)O)CC4)nc3)cc(/C(CC)=N\OC)c2s1]

(E/Z)-ethyl 4-ethyl-1-(5-(2-(3-ethylureido)-7-(1-(methoxyimino)propyl)benzo[d]thiazol-5-yl)pyrimidin-2-yl)piperidine-4-carboxylate: To a solution of ethyl 4-ethyl-1-(5-(2-(3-ethylureido)-7-propionylbenzo[d]thiazol-5-yl)pyrimidin-2-yl)piperidine-4-carboxylate (0.25 g, 0.464 mmol) in anhydrous DMF was added O-methoxylamine hydrochloride (0.078 g, 0.928 mmol) at rt under $N_2$ atmosphere and the mixture stirred for 2 h at 80° C. After the completion of reaction (by TLC), the reaction was quenched by addition of ice-cold water (50 mL) followed by extraction with EtOAc (3×25 mL) and the combined organic layers washed with water, brine, dried over anhydrous $Na_2SO_4$ and concentrated under reduced pressure. The residue was purified by ether washing to obtain the desired product as a beige solid (0.22 g, 84%). $^1$H NMR (DMSO-$d_6$): δ 10.56 (br s, 1H), 8.81 (s, 2H), 7.92 (br s, 1H), 7.71 (br s, 1H), 6.80 (br s 1H), 4.46 (d, J=13.6 Hz, 2H), 4.14-4.19 (m, 2H), 4.058 (s, 3H), 3.18-3.23 (m, 2H), 3.09-3.15 (m, 2H), 2.90-2.95 (m, 2H), 2.08 (d, J=15.2 Hz, 2H), 1.54-1.57 (m, 2H), 1.36-1.41 m, 2H), 1.22 (t, J=7.2 Hz, 3H), 1.09-1.14 (m, 6H) and 0.75 (t, J=7.2 Hz, 3H). MS: 568.2 [M+H]$^+$.

(E/Z)-4-Ethyl-1-(5-(2-(3-ethylureido)-7-(1-(methoxyimino)propyebenzo[d]thiazol-5-yl)pyrimidin-2-yl)piperidine-4-carboxylic acid (223): To a solution of (E/Z)-ethyl 4-ethyl-1-(5-(2-(3-ethylureido)-7-(1-(methoxyimino)propyebenzo[d]thiazol-5-yl)pyrimidin-2-yl)piperidine-4-carboxylate (0.25 g, 0.440 mmol) in EtOH (10 mL) was added aqueous solution (2 ml) of NaOH (0.088 g, 2.20 mmol) and the mixture stirred overnight at 80° C. After the completion of reaction (by TLC), EtOH was evaporated under reduced pressure, water (20 mL) added, extracted with EtOAc (3×50 mL) and the combined organic layer discarded. The aqueous layer was acidified with 1N HCl (pH ~4.0-5.0), extracted with EtOAc (3×50 mL) and the combined organic layer washed with brine, dried over anhydrous $Na_2SO_4$, filtered then concentrated under reduced pressure. The residue was purified by column chromatography (silica gel 100-200 M, 5% MeOH in DCM) to obtain Compound 223 as off white solid (0.12 g, 51%). $^1$H NMR (DMSO-$d_6$): δ 10.66 (br s, 1H), 8.82 (s, 2H), 7.92 (s, 1H), 7.72 (s, 1H), 6.88 (br s, 1H), 4.45 (d, J=12.8 Hz, 2H), 4.05 (s, 3H), 3.16-3.18 (m, 4H), 2.05 (d, J=13.2 Hz, 2H), 1.52-1.54 (m, 2H), 1.33-1.37 (m, 2H), 1.22-1.23 (m, 2H), 1.07-1.14 (m, 6H), 0.80 (t, J=7.2 Hz, 3H). LCMS: 540.29 [M+H]$^+$ Compound 224: (E)-4-Ethyl-1-(5-(2-(3-ethylureido)-7-(1-(methoxyimino)propyl)benzo thiazol-5-yl)pyrimidin-2-yl)piperidine-4-carboxylic acid (alternatively named 4-ethyl-1-[5-[2-(ethylcarbamoylamino)-7-[(E)-C-ethyl-N-methoxy-carbonimidoyl]-1,3-benzothiazol-5-yl]pyrimidin-2-yl]piperidine-4-carboxylic acid); and Compound 211: (Z)-4-Ethyl-1-(5-(2-(3-ethylureido)-7-(1-(methoxyimino)propyl)benzo[d]thiazol-5-yl)pyrimidin-2-yl)piperidine-4-carboxylic acid (alternatively named 4-ethyl-1-[5-[2-(ethylcarbamoylamino)-7-[(Z)—C-ethyl-N-methoxy-carbonimidoyl]-1,3-benzothiazol-5-yl]pyrimidin-2-yl]piperidine-4-carboxylic acid)

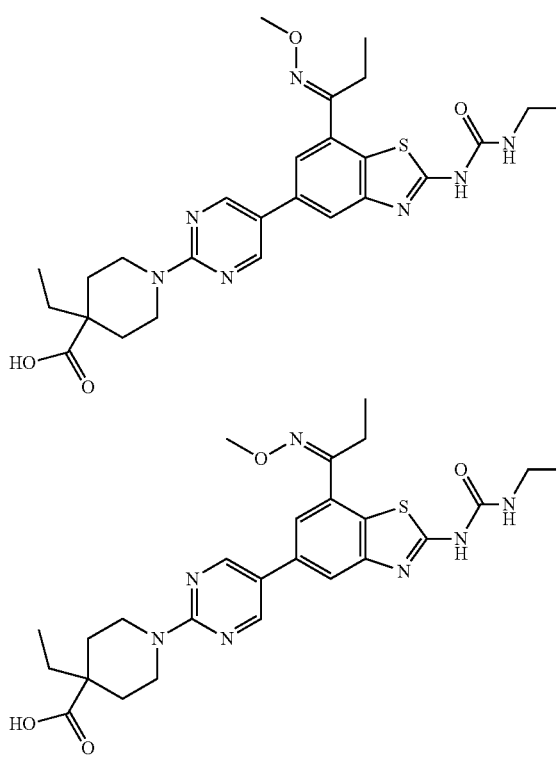

(E/Z)-4-ethyl-1-(5-(2-(3-ethylureido)-7-(1-(methoxyimino)propyl)benzo[d]thiazol-5-yl)pyrimidin-2-yl)piperidine-4-carboxylic acid was purified by preparative-HPLC
Method: Column: X-Selectfluorophenyl (19×250) mm, 5μ.
Mobile Phase: A—5 mM Ammoniumacetate
  B—Methanol
Flow: 15 mL/min
Mode: Gradient
Diluent: Mix of ACN/MeOH, DMF and water.
to give: (E)-4-Ethyl-1-(5-(2-(3-ethylureido)-7-(1-(methoxyimino)propyebenzo[d]thiazol-5-yl)pyrimidin-2-yl)piperidine-4-carboxylic acid. $^1$H NMR (DMSO-d$_6$): δ 8.81 (s, 2H), 7.92 (s, 1H), 7.72 (s, 1H), 6.81 (br s, 1H), 4.46 (d, J=14.0 Hz, 2H), 4.05 (s, 3H), 3.11-3.21 (m, 4H), 2.93 (q, J=7.2 Hz, 2H), 2.05 (d, J=15.2 Hz, 2H), 1.52-1.54 (m, 2H), 1.34-1.36 (m, 2H), 1.04-1.14 (m, 6H), 0.81 (t, J=7.2 Hz, 3H). MS: 540.33 [M+H]$^+$ and (Z)-4-Ethyl-1-(5-(2-(3-ethylureido)-7-(1-(methoxyimino)propyl)benzo[d]thiazol-5-yl)pyrimidin-2-yl)piperidine-4-carboxylic acid. $^1$H NMR (DMSO-d$_6$): δ 8.76 (s, 2H), 7.86 (s, 1H), 7.40 (s, 1H), 6.78 (br s, 1H), 4.44-4.47 (m, 2H), 3.75 (s, 3H), 3.13-3.16 (m, 4H), 2.61-2.62 (m, 2H), 2.04 (d, J=10.0 Hz, 2H), 1.53 (m, 2H), 1.27-1.32 (m, 2H), 1.09 (m, 3H), 0.98 (m, 3H), 0.81 (m, 3H). MS: 540.32 [M+H]$^+$ Compound 189: 4-Ethyl-1-[5-[2-(ethylcarbamoylamino)-7-[(E)-methoximinomethl]-1,3-benzothiazol-5-yl]pyrimidin-2-yl]piperidine-4-carboxylic acid; and Compound 225: 4-Ethyl-1-[5-[2-(ethylcarbamoylamino)-7-[(Z)-methoxyiminomethyl]-1,3-benzothiazol-5-yl]pyrimidin-2-yl]piperidine-4-carboxylic acid

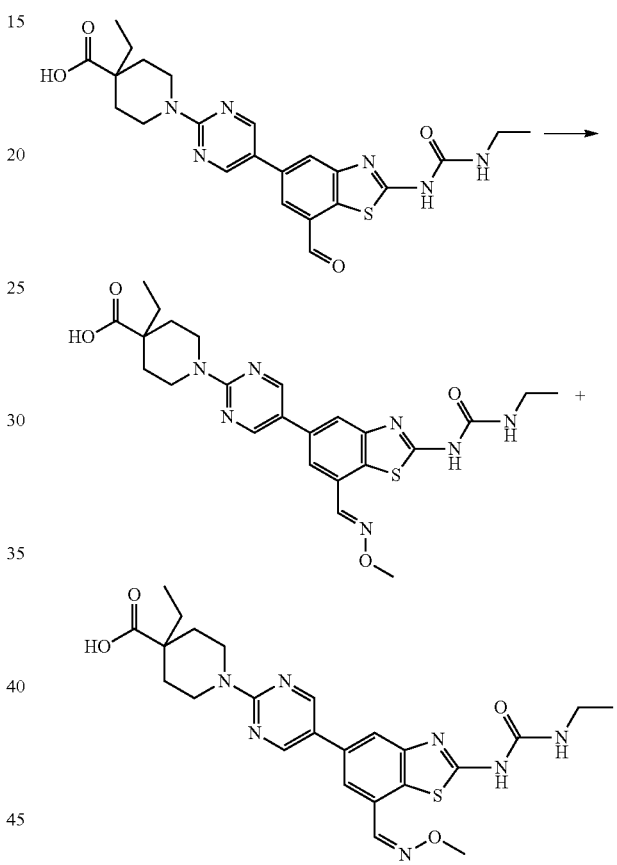

O-methylhydroxylamine hydrochloride (545 mg, 6.53 mmol) was added to a solution of 4-ethyl-1-[5-[2-(ethylcarbamoylamino)-7-formyl-1,3-benzothiazol-5-yl]pyrimidin-2-yl]piperidine-4-carboxylic acid (1.05 g; 2.18 mmol) and diisopropylethylamine (1.2 mL, 7.0 mmol) in DMF (25 mL) and heated to 70° C. for 3.5 hours, after which LCMS analysis confirmed quantitative consumption of the starting aldehyde. The DMF was concentrated in vacuo and crude residue taken up in DCM (100 mL), washed with sat. NaHCO$_3$(aq) (75 mL) followed by sat. brine(aq) (75 mL), dried (MgSO$_4$) and concentrated in vacuo followed by flash column chromatography (0-10% DCM/MeOH) to afford 860 mg (77% yield) of a yellow solid. Purification by reverse-phase chromatography (Revelerais C18, 80 g; 25-75% 0.1% Aq. FA/MeCN) gave Compound 189 as a white solid (627 mg). Preparative reverse phase HPLC of the mixed fractions gave Compound 225 (25 mg).

Compound 189: $^1$HNMR (DMSO) δ 10.61 (d, J=90.5 Hz, 1H), 8.76 (s, 2H), 8.50 (s, 1H), 7.95 (s, 1H), 7.73 (d, J=12.6

Hz, 1H), 6.84 (s, 1H), 4.45 (d, J=13.3 Hz, 2H), 4.00 (d, J=13.8 Hz, 3H), 3.25-3.10 (m, 5H), 2.05 (d, J=13.7 Hz, 2H), 1.53 (q, J=7.1 Hz, 2H), 1.43-1.26 (m, 2H), 1.10 (t, J=7.1 Hz, 3H), 0.81 (t, J=7.4 Hz, 3H). MS: m/z 512.1 [M+H]⁺.

Compound 225: ¹HNMR (DMSO) δ 10.61 (d, J=90.5 Hz, 1H), 8.72 (s, 2H), 7.94 (t, J=4.1 Hz, 1H), 7.89 (d, J=1.6 Hz, 1H), 7.75 (s, 1H), 6.94 (s, 1H), 4.50-4.39 (m, 2H), 3.97 (s, 3H), 3.24-3.10 (m, 5H), 2.05 (d, J=13.2 Hz, 2H), 1.53 (q, J=7.4 Hz, 2H), 1.33 (td, J=13.5, 4.0 Hz, 2H), 1.10 (td, J=7.2, 2.5 Hz, 3H), 0.81 (t, J=7.5 Hz, 3H). MS: m/z 512.1 [M+H]⁺.

Compound 208 1-[5-[7-bromo-2-(ethylcarbamoylamino)-6-methoxy-1,3-benzothiazol-5-yl]pyrimidin-2-yl]-4-methyl-piperidine-4-carboxylic acid

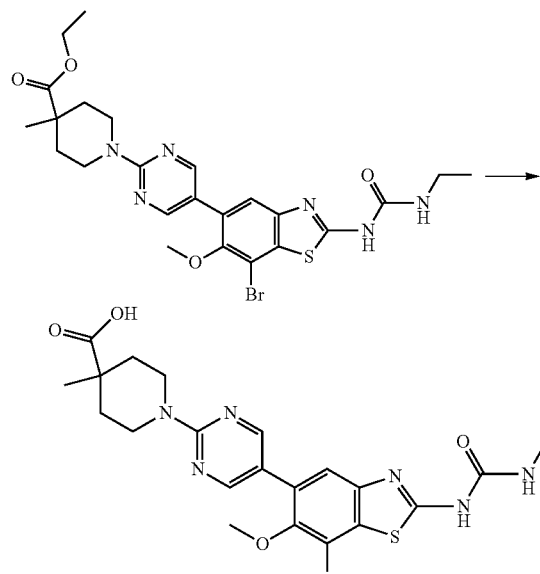

Ethyl 1-[5-[7-bromo-2-(ethylcarbamoylamino)-6-methoxy-1,3-benzothiazol-5-yl]pyrimidin-2-yl]-4-methyl-piperidine-4-carboxylate 1-(5,7-Dibromo-6-methoxy-1,3-benzothiazol-2-yl)-3-ethyl-urea (Intermediate 14) (234 mg, 0.57 mmol), ethyl 4-methyl-1-[5-(4,4,5,5-tetramethyl-1,3,2-dioxaborolan-2-yl)pyrimidin-2-yl]piperidine-4-carboxylate (716 mg, 1.14 mmol, 60 mass %) and PdCl₂(dppf).DCM (23 mg, 0.03 mmol) were dissolved in dioxane (7.5 mL) in a 10-20 mL microwave vial and a solution of cesium carbonate (559 mg, 1.72 mmol) in water (2.5 mL) was added. The vial was capped, the mixture degassed and heated in the microwave at 110° C. for 30 minutes. The mixture was poured into water and extracted into EtOAc (4×40 mL). The organic layers were washed with brine, dried over Na₂SO₄ and concentrated to dryness in vacuo. The mixture was purified by chromatography, Biotage SP4, 40 g Si cartridge, 10-100% EtOAc in heptane. Two compounds were detected with the same mass ion (m/z) and retention time by LCMS but were distinct by TLC (60% EtOAc in heptane) so were assumed to be two regioisomers. The relevant fractions were combined to give the desired compound as a pale yellow oil, 47 mg (14%). MS: 577.04/579.07 [M+H]⁺.

1-[5-[7-Bromo-2-(ethylcarbamoylamino)-6-methoxy-1,3-benzothiazol-5-yl]pyrimidin-2-yl]-4-methyl-piperidine-4-carboxylic acid (208)

Ethyl 1-[5-[7-bromo-2-(ethylcarbamoylamino)-6-methoxy-1,3-benzothiazol-5-yl]pyrimidin-2-yl]-4-methyl-piperidine-4-carboxylate (47 mg, 0.081 mmol) was dissolved in EtOH (3 mL) and NaOH solution (1 mL, 1 M, aq) was added to give a pale yellow solution. The mixture was heated to 60° C. overnight then cooled to rt, the EtOH removed under reduced pressure and the residue acidified with HCl solution (1 M, aq) to pH 3. The mixture was extracted into EtOAc (3×15 mL) and the combined organic layer washed with brine, dried over Na₂SO₄ and concentrated to dryness under reduced pressure. The mixture was purified by chromatography, Biotage SP4, 4 g Si cartridge, 50-100% EtOAc in heptane. The relevant fractions were combined to give Compound 208 as an off white solid, 8 mg (18%). ¹H NMR (CDCl₃): δ 1.31 (3H, t, J=7.2 Hz), 1.42 (3H, s), 1.61 (2H, m), 2.27 (2H, m), 3.47 (2H, m), 3.64 (3H, s), 3.84 (2H, m), 4.15 (2H, q, J=7.2 Hz), 4.2-7.2 (3H, br s), 7.48 (1H, s), 8.62 (2H, s). MS: 549.07/551.06 [M+H]⁺.

Compound 209: 4-Ethyl-1-[4-[2-(ethylcarbamoylamino)-7-(2-pyridyl)-1,3-benzothiazol-5-yl]thiazol-2-yl]piperidine-4-carboxylic acid

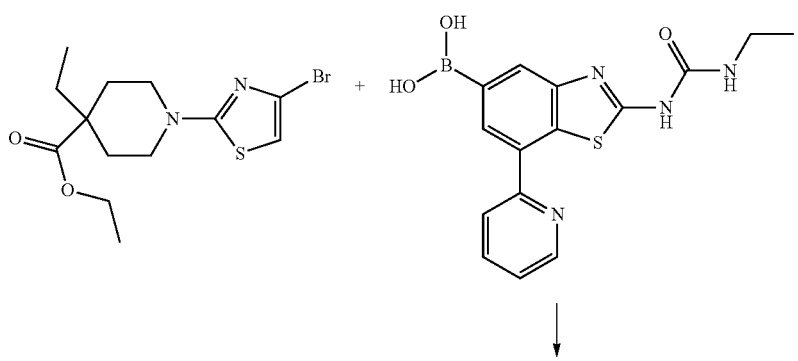

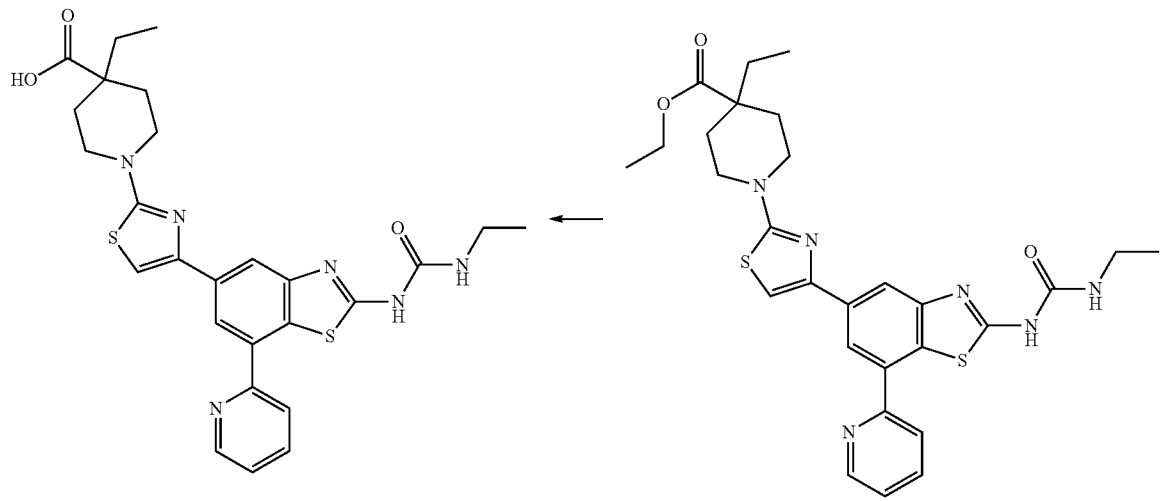

Ethyl 4-ethyl-1-[4-[2-(ethylcarbamoylamino)-7-(2-pyridyl)-1,3-benzothiazol-5-yl]thiazol-2-yl]piperidine-4-carboxylate Ethyl 1-(4-bromothiazol-2-yl)-4-ethyl-piperidine-4-carboxylate (56 mg, 0.16 mmol), 2-(ethylcarbamoylamino)-7-(2-pyridyl)-1,3-benzothiazol-5-yl-boronic acid (50 mg, 0.15 mmol), and cesium carbonate (42 mg, 0.22 mmol) were suspended in DMF (1 mL) in a 5 mL microwave vessel. The resulting mixture was degassed with Ar for 5 min. [1,1'-Bis(diphenylphosphino)ferrocene]dichloropalladium(II), complex with dichloromethane (10 mg, 0.01 mmol), was added to the mixture, then the vessel sealed and heated at 120° C. for 60 min in a microwave. The mixture was cooled to rt then evaporated to dryness and the crude residue purified over a 12 g silica-gel column using a MeOH: DCM elution gradient (0-5%) to obtain the product as a viscous oil (30 mg, 36% yield). MS: 565.13 [M+H]$^+$.

4-Ethyl-1-[4-[2-(ethylcarbamoylamino)-7-(2-pyridyl)-1,3-benzothiazol-5-yl]thiazol-2-yl]piperidine-4-carboxylic acid (209)

To a solution of ethyl 4-ethyl-1-[4-[2-(ethylcarbamoylamino)-7-(2-pyridyl)-1,3-benzothiazol-5-yl]thiazol-2-yl]piperidine-4-carboxylate (20 mg, 0.035 mmol) in EtOH (1 mL) was added aqueous NaOH (0.3 mL, 3.5 M). The solution was heated to 70° C. for 22 h then cooled to rt and the pH of the solution adjusted to 4-5. The mixture was extracted with EtOAc (3×1 mL) and the combined organic layer combined, dried over Na$_2$SO$_4$, filtered then evaporated under reduced pressure. The residue was adsorbed to a 0.5 g silica plug then purified using a 4 g silica column and a MeOH:DCM elution gradient. Compound 209 was isolated as an off-white solid (3.4 mg, 18% yield). $^1$H NMR (MeOD) δ 8.75 (ddd, J=4.8, 1.8, 0.9 Hz, 1H), 8.38 (d, J=1.5 Hz, 1H), 8.22 (d, J=8.2 Hz, 1H), 8.18 (d, J=1.4 Hz, 1H), 7.97-7.91 (m, 1H), 7.37 (ddd, J=7.5, 4.9, 0.9 Hz, 1H), 7.16 (s, 1H), 3.95 (dt, J=13.1, 3.7 Hz, 2H), 3.36 (t, J=7.2 Hz, 2H), 3.25 (td, J=13.3, 2.9 Hz, 2H), 2.24 (d, J=13.2 Hz, 2H), 1.70-1.53 (m, 4H), 1.24 (td, J=7.2, 2.0 Hz, 3H), 0.92 (td, J=7.5, 4.2 Hz, 3H). MS: 537.12 [M+H]$^+$.

Compound 213 1-[5-[2-(Ethylcarbamoylamino)-7-(5-methyl-1,2,4-oxadiazol-3-yl)-1,3-benzothiazol-5-yl]pyrimidin-2-yl]-4-methyl-piperidine-4-carboxylic acid

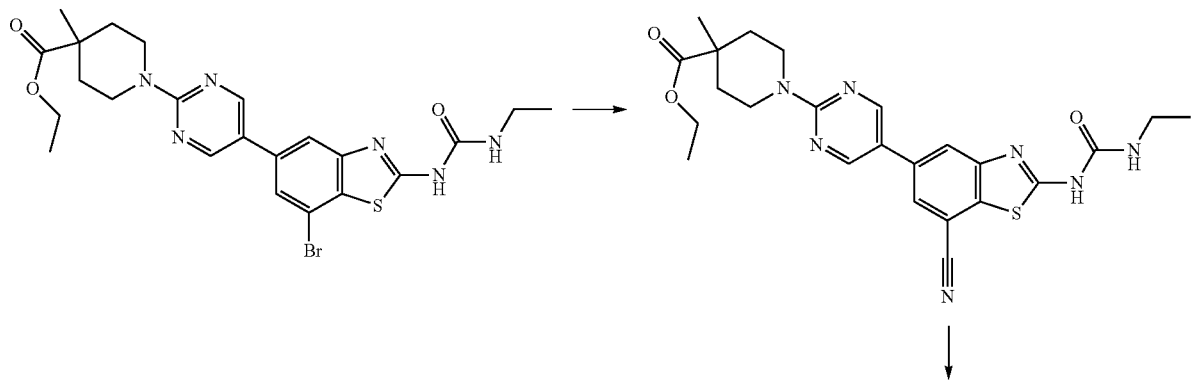

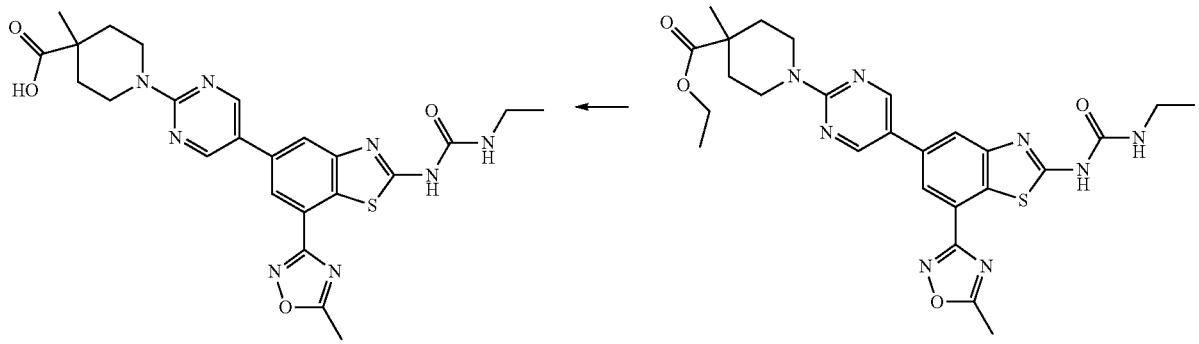

Ethyl 1-[5-[7-cyano-2-(ethylcarbamoylamino)-1,3-benzothiazol-5-yl]pyrimidin-2-yl]-4-methyl-piperidine-4-carboxylate Ethyl 1-[5-[7-bromo-2-(ethylcarbamoylamino)-1,3-benzothiazol-5-yl]pyrimidin-2-yl]-4-methyl-piperidine-4-carboxylate (600 mg, 0.658 mmol), zinc cyanide (96 mg, 0.822 mmol) and Pd(PPh$_3$)$_4$ (76 mg, 0.066 mmol) were suspended in DMF (10 mL) and degassed/purged (×3) with Ar. The reaction mixture was then heated at 100° C. under microwave irradiation for 40 mins, cooled to rt, diluted with EtOAc (50 mL), washed with water, brine and separated. The organic fraction was dried (Na$_2$SO$_4$) and concentrated under reduced pressure and the resulting solid purified by flash column chromatography (40 g GraceResolv silica cartridge—dry loaded), eluting with 0-10% MeOH/CH$_2$Cl$_2$. The resulting residue was washed with MeOH to afford desired compound (327 mg, ~100%) as an off-white solid. MS: 494.14 [M+H]$^+$.

Ethyl 1-[5-[2-(ethylcarbamoylamino)-7-(5-methyl-1,2,4-oxadiazol-3-yl)-1,3-benzothiazol-5-yl]pyrimidin-2-yl]-4-methyl-piperidine-4-carboxylate Ethyl 1-[5-[7-cyano-2-(ethylcarbamoylamino)-1,3-benzothiazol-5-yl]pyrimidin-2-yl]-4-methyl-piperidine-4-carboxylate (327 mg, 0.66 mmol) and hydroxylamine hydrochloride (230 mg, 3.31 mmol) were suspended in pyridine (20 mL) and the mixture stirred at 80° C. for 4 h. The reaction was cooled to rt and acetyl chloride (565 μL, 7.95 mmol) was added then stirred at 80° C. for 9 h. The reaction was diluted with EtOAc (100 mL), washed with dilute HCl (2×100 mL), brine and separated. The organic fraction was dried (Na$_2$SO$_4$) and concentrated under reduced pressure and the oily residue purified by flash column chromatography (40 g GraceResolv silica cartridge—dry loaded), eluting with 50-100% EtOAc/heptane to afford the desired compound (192 mg, 53%) as a white solid. MS: 551.13 [M+H]$^+$.

1-[5-[2-(Ethylcarbamoylamino)-7-(5-methyl-1,2,4-oxadiazol-3-yl)-1,3-benzothiazol-5-yl]pyrimidin-2-yl]-4-methyl-piperidine-4-carboxylic acid (213)

Ethyl 1-[5-[2-(ethylcarbamoylamino)-7-(5-methyl-1,2,4-oxadiazol-3-yl)-1,3-benzothiazol-5-yl]pyrimidin-2-yl]-4-methyl-piperidine-4-carboxylate (192 mg, 0.349 mmol) was dissolved in EtOH (20 mL) and 2M aqueous NaOH (10 mL) added. The reaction mixture was stirred at 70° C. for 2 h then cooled to rt and 2M HCl (20 mL) added. The mixture was extracted with hot EtOAc (3×50 mL), the aqueous phase saturated with NaCl and further extracted with EtOAc (50 mL) and the combined organic fractions washed with brine, separated, dried (Na$_2$SO$_4$) and concentrated under reduced pressure. The solid residue was washed with MeCN then Et$_2$O to afford Compound 213 (163 mg, 89%) as a pale-yellow solid. $^1$H NMR (DMSO-d$_6$): δ10.98 (bs, 1H), 8.81 (s, 2H), 8.11 (d, J=1.8 Hz, 1H), 8.10 (d, J=1.8 Hz, 1H), 7.06 (bt, J=5.4 Hz, 1H), 4.31 (dt, J=13.9 and 4.4 Hz, 2H), 3.37 (ddd, J=13.3, 10.2 and 2.9 Hz, 2H), 3.26-3.19 (m, 2H), 2.76 (s, 3H), 2.09-2.02 (m, 2H), 1.43 (ddd, J=13.8, 10.2 and 3.9 Hz, 2H), 1.21 (s, 3H), 1.13 (t, J=7.2 Hz, 3H). MS: 523.13 [M+H]$^+$.

Compound 221: 4-Ethyl-1-[5-[2-(ethylcarbamoylamino)-7-(2-pyridyl)-1,3-benzothiazol-5-yl]thiazol-2-yl]piperidine-4-carboxylic acid

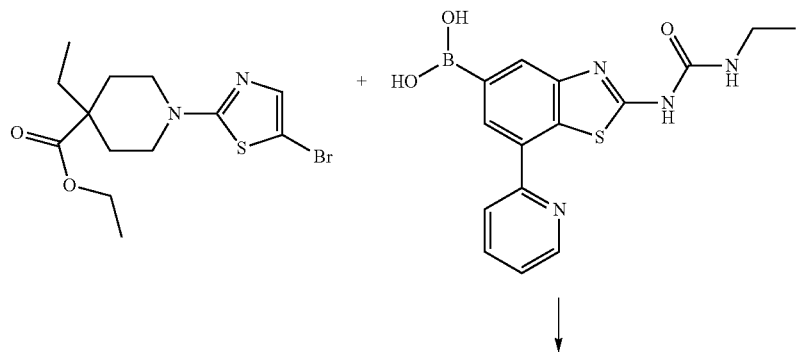

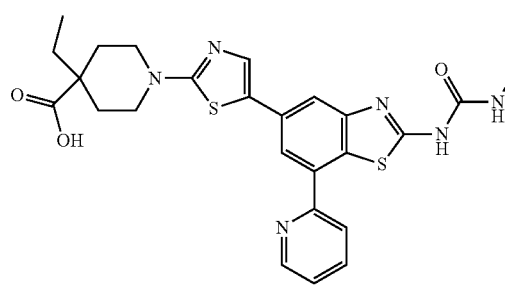
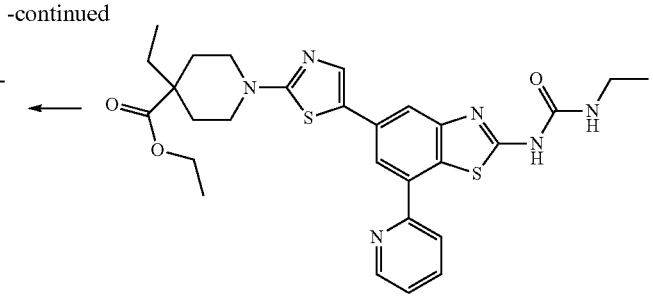

Ethyl 4-ethyl-1-[5-[2-(ethylcarbamoylamino)-7-(2-pyridyl)-1,3-benzothiazol-5-yl]thiazol-2-yl]piperidine-4-carboxylate Ethyl 1-(5-bromothiazol-2-yl)-4-ethyl-piperidine-4-carboxylate (66 mg, 0.19 mmol), 2-(ethylcarbamoylamino)-7-(2-pyridyl)-1,3-benzothiazol-5-yl-boronic acid (50 mg, 0.15 mmol) and cesium carbonate (42 mg, 0.22 mmol) were suspended in DMF (1 mL) in a 5 mL microwave vessel and the mixture degassed with Ar for 5 min. [1,1'-Bis(diphenylphosphino)ferrocene]dichloropalladium(II), complex with DCM (10 mg, 0.01 mmol) was added to the mixture, then the vessel was sealed and heated at 120° C. for 60 min in a microwave. The mixture was cooled to rt then evaporated to dryness and the crude residue purified over a 12 g silica-gel column using a MeOH: DCM elution gradient (0-5%) to obtain the product as a viscous oil (30 mg, 36% yield). MS: 565.17 [M+H]$^+$.

4-Ethyl-1-[5-[2-(ethylcarbamoylamino)-7-(2-pyridyl)-1,3-benzothiazol-5-yl]thiazol-2-yl]piperidine-4-carboxylic acid (221)

To a solution of ethyl 4-ethyl-1-[5-[2-(ethylcarbamoylamino)-7-(2-pyridyl)-1,3-benzothiazol-5-yl]thiazol-2-yl]piperidine-4-carboxylate (30 mg, 0.053 mmol) in EtOH (1 mL) was added aqueous NaOH (0.3 mL, 3.5 M). The solution was heated to 70° C. for 22 h then cooled to rt and the pH of the solution adjusted to 4-5. The mixture was extracted with EtOAc (3×1 mL) and the combined organic layer dried over Na$_2$SO$_4$, filtered then evaporated under reduced pressure. The residue was adsorbed to a 0.5 g silica plug then purified using a 4 g silica column, using a MeOH:DCM elution gradient. Compound 221 was isolated as an off-white solid (2.0 mg, 11% yield). $^1$H NMR (MeOD) δ 8.75 (ddd, J=4.8, 1.8, 0.9 Hz, 1H), 8.20 (d, J=8.3 Hz, 1H), 8.00 (d, J=1.6 Hz, 1H), 7.97-7.90 (m, 1H), 7.73 (d, J=1.6 Hz, 1H), 7.59 (s, 1H), 7.38 (ddd, J=7.5, 4.9, 0.9 Hz, 1H), 3.87 (dd, J=9.6, 3.7 Hz, 2H), 3.39-3.32 (m, 2H), 3.25 (td, J=13.3, 2.9 Hz, 2H), 2.23 (d, J=13.3 Hz, 2H), 1.64 (q, J=7.5 Hz, 2H), 1.61-1.52 (m, 2H), 1.23 (t, J=7.2 Hz, 3H), 0.92 (t, J=7.5 Hz, 3H). MS: 537.13 [M+H]$^+$.

Compound 229: 4-Ethyl-1-(5-(2-(3-ethylureido)-7-(pyridin-2-yl)-1H-benzoimidazol-5-yl)pyrimidin-2-yl)piperidine-4-carboxylic acid (alternatively named 4-ethyl-1-[5-[2-(ethylcarbamoylamino)-7-(2-pyridyl)-1H-benzimidazol-5-yl]pyrimidin-2-yl]piperidine-4-carboxylic acid)

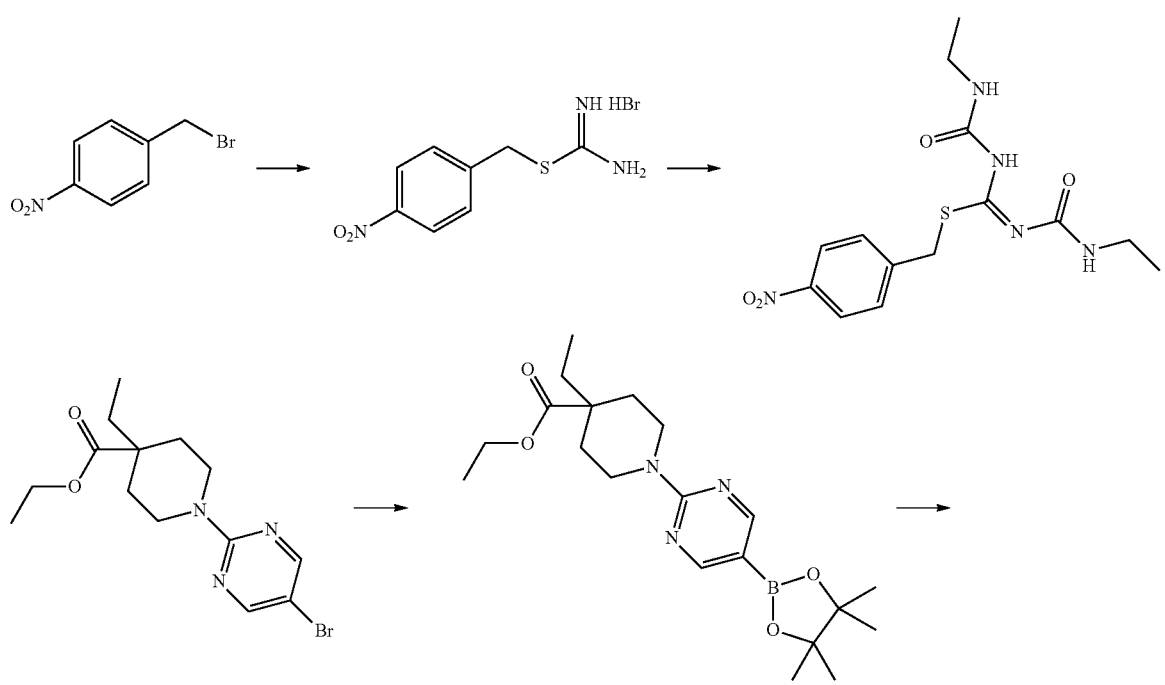

281 282
-continued
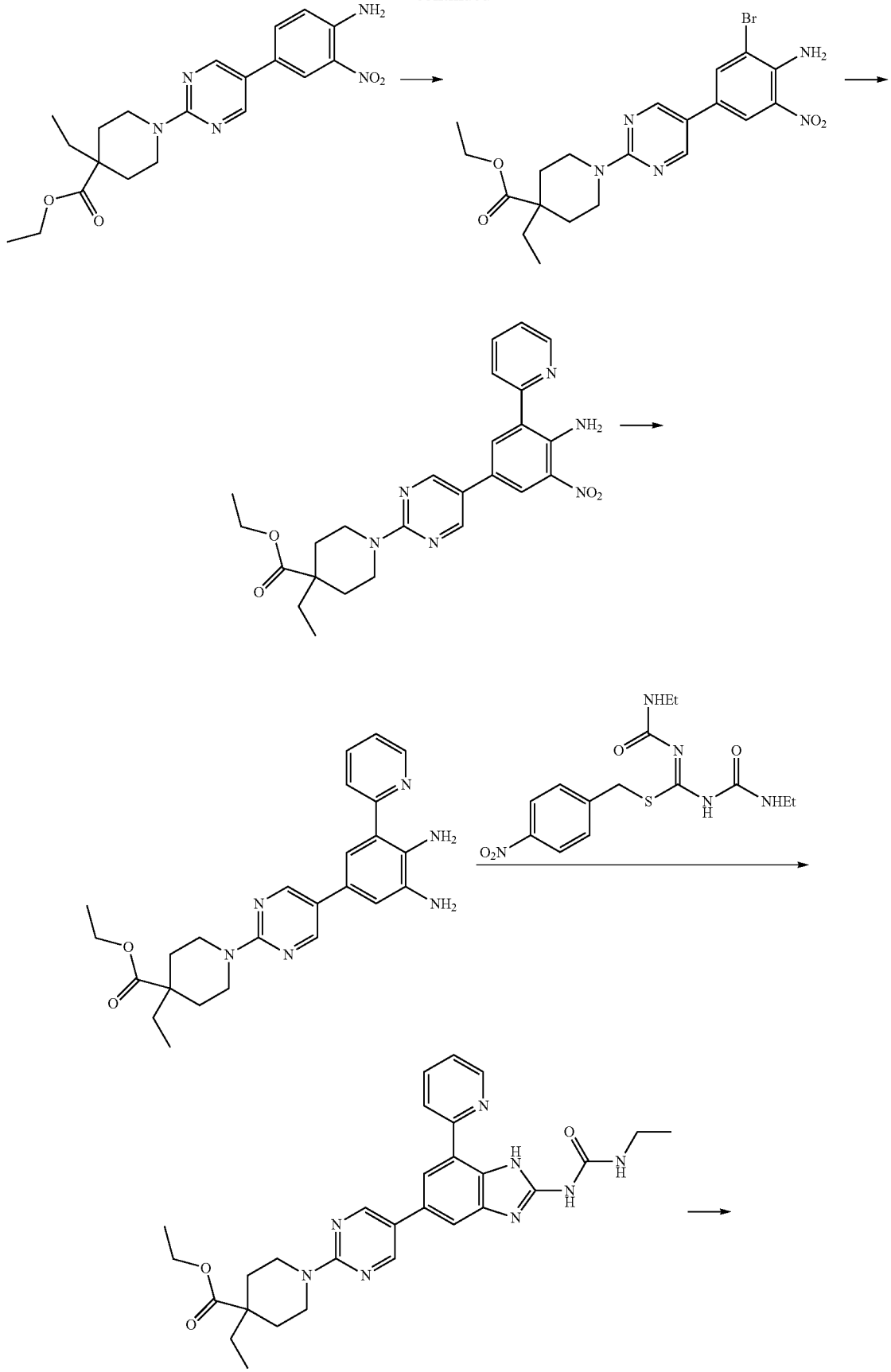

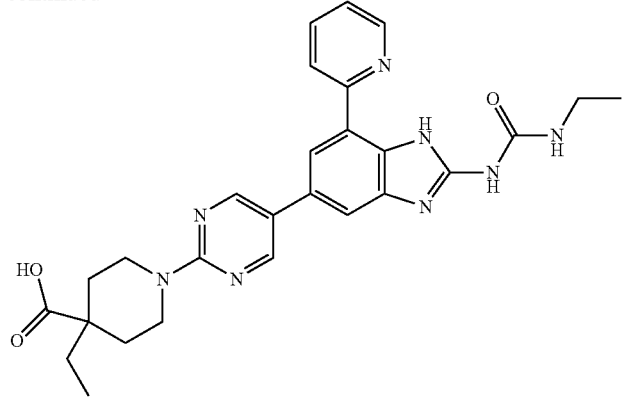

4-Nitrobenzyl carbamimidothioate hydrobromide

To a solution of thiourea (3.87 g, 50.92 mmol) in acetone (15 mL) was added a solution of 1-(bromomethyl)-4-nitrobenzene (10 g, 46.29 mmol) in acetone (15 mL) and the mixture stirred at rt for 2 h upon which a white precipitate formed. After completion of reaction (by TLC), the mixture was filtered and solid washed with EtOAc and acetone respectively to afford the desired product as off-white solid (12.0 g, 89%). $^1$H NMR (DMSO-$d_6$): δ 9.17 (br s, 4H), 8.24 (d, J=8.40 Hz, 2H), 7.70 (d, J=8.40 Hz, 2H) and 4.66 (s, 2H). MS: 212.08 [M+H]$^+$

N,N-diethylurea-2-(4-nitrobenzyl)-2-thiopseudourea

To a solution of 4-nitrobenzyl carbamimidothioate hydrobromide (2.5 g, 8.55 mmol) in DMF (10 mL) was added aqueous buffer solution of ammonium acetate (pH ~7, 4.0 mL) followed by addition of ethyl isocyanate (10 mL. 85.57 mmol) at rt and the mixture stirred at rt for 48 h. After completion of reaction (by TLC), water (10 mL) was added and a white precipitate formed. The reaction mixture was filtered and solid was washed with water to obtain the desired product as white solid (1.40 g, 41%). MS: 354.18 [M+H]$^+$

Ethyl 4-ethyl-1-(5-(4,4,5,5-tetramethyl-1,3,2-dioxaborolan-2-yl)pyrimidin-2-yl)piperidine-4-carboxylate To the solution of ethyl 1-(5-bromopyrimidin-2-yl)-4-ethylpiperidine-4-carboxylate (10.0 g, 29.22 mmol) in 1,4-dioxane (250 mL) was added bis(pinacolato)diboron (8.16 g, 32.14 mmol) and KOAc (4.30 g, 43.83 mmol). The mixture was degassed by purging $N_2$ for 15 min followed by addition of tris(dibenzylyideneacetone) dipalladium (0) (1.51 g, 1.46 mmol) and tricyclohexylphosphine (0.98 g, 3.50 mmol). The mixture was again degassed for 10 min and then heated up to 80° C. for 2 h. After completion of reaction, the mixture was cooled to rt, filtered through celite and the filtrate concentrated under reduced pressure to obtain crude product (21.59 g, crude yield) which was used in the next step without purification.

Ethyl 1-(5-(4-amino-3-nitrophenyl)pyrimidin-2-yl)-4-ethylpiperidine-4-carboxylate To a solution of 4-bromo-2-nitroaniline (10.0 g, 46.07 mmol) in 1,4-dioxane (240 mL) and MeOH (140 mL) was added ethyl 4-ethyl-1-(5-(4,4,5,5-tetramethyl-1,3,2-dioxaborolan-2-yl)pyrimidin-2-yl)piperidine-4-carboxylate (21.59 g, 55.28 mmol) and potassium phosphate (14.69 g, 69.10 mmol) and the mixture degassed by purging $N_2$ for 15 min 1,1-Bis (diphenylphosphino) ferrocene-palladium (II) dichloride (3.75 g, 6.91 mmol) was then added to the reaction mixture that was again degassed for 10 min. The reaction was heated up to 80° C. for 16 h. After completion, solvent was evaporated and diluted with water (150 mL), extracted with EtOAc (4×150 mL) and the combined organic layer washed with brine, dried over anhydrous $Na_2SO_4$, filtered and concentrated under reduced pressure. The crude residue was purified over 100-200 M silica-gel column chromatography by using 20% EtOAc:Hexane to obtain the product as a beige solid (6.0 g, 51% over 2 steps). $^1$H NMR (CDCl$_3$): δ 8.49 (s, 2H), 8.23 (s, 1H), 7.48 (d, J=8.4 Hz, 1H), 6.88 (d, J=8.4 Hz, 1H), 6.11 (br s, 2H), 4.52 (m, 2H), 4.19 (m, 2H), 3.11 (m, 2H), 2.22 (m, 2H), 1.56-1.58 (m, 2H), 1.40-1.42 (m, 2H), 1.29 (t, J=7.20 Hz, 3H) and 0.83 (t, J=7.20 Hz, 3H). MS: 400.25 [M+H]

Ethyl 1-(5-(4-amino-3-bromo-5-nitrophenyl)pyrimidin-2-yl)-4-ethylpiperidine-4-carboxylate To solution of ethyl 1-(5-(4-amino-3-nitrophenyl)pyrimidin-2-yl)-4-ethylpiperidine-4-carboxylate (6.0 g, 15.02 mmol) in acetic acid (60.0 mL) was added bromine (0.85 mL, 16.52 mmol) dropwise at rt and the mixture then stirred at rt for 16 h. After completion of reaction the mixture was poured into 100 mL of ice-cold water, extracted with EtOAc (3×150 mL) and the combined organic layer washed with brine, dried over anhydrous $Na_2SO_4$, filtered and evaporated under reduced pressure. The crude residue was purified over 100-200 M silica-gel column chromatography using 10% EtOAc: Hexane to obtain the product as a beige solid (5.60 g, 78%). $^1$H NMR (CDCl$_3$): δ 8.66 (s, 2H), 8.18 (s, 2H), 7.21 (br s, 2H), 4.39-4.43 (m, 2H), 4.13-4.18 (m, 2H), 3.06-3.11 (m, 2H), 2.04-2.08 (m, 2H), 1.50-1.52 (m, 2H), 1.38-1.39 (m, 2H), 1.21 (t, J=7.60 Hz, 3H) and 0.75 (t, J=7.60 Hz, 3H). MS: 478.11 [M+H]$^+$, 81%.

Ethyl 1-(5-(4-amino-3-nitro-5-(pyridin-2-yl)phenyl) pyrimidin-2-yl)-4-ethylpiperidine-4-carboxylate To a solution of ethyl 1-(5-(4-amino-3-bromo-5-nitrophenyl)pyrimidin-2-yl)-4-ethylpiperidine-4-carboxylate (1.5 g, 3.14 mmol) in DMF (10.0 mL) was added 2-(tributylstannyl) pyridine (1.73 g, 4.72 mmol) and the mixture degassed by purging $N_2$ for 15 min followed by addition of tetrakis(triphenylphosphine)palladium(0) (0.36 g, 0.314 mmol). The reaction mixture was again degassed for 10 min then heated up to 120° C. for 5 h. After completion of reaction, 100 mL ice-cold water was added, extracted with EtOAc (4×100 mL) and the combined organic layer washed with ice-cold water, brine solution respectively, dried over $Na_2SO_4$, filtered and evaporated under reduced pressure. The crude residue was purified over neutral alumina using 15% EtOAc:Hexane to obtain the desired product (0.712 g, 47%). $^1$H NMR (CDCl$_3$): δ 8.68-8.69 (m, 1H), 8.63 (s, 2H), 8.38 (s, 1H), 7.89 (s, 1H), 7.84 (s, 1H), 7.69 (d, J=8.4 Hz, 1H), 7.34-7.36 (m, 1H), 4.65-4.67 (m, 2H), 4.20-4.22 (m, 2H), 3.21-3.25 (m, 2H), 2.30-2.34 (m, 2H), 1.58-1.60 (m, 2H), 1.44-1.46 (m, 2H), 1.30 (t, J=7.20 Hz, 3H) and 0.86 (t, J=7.60 Hz, 3H). MS: 477.44 [M+H]$^+$.

Ethyl 1-(5-(3,4-diamino-5-(pyridin-2-yl)phenyl)pyrimidin-2-yl)-4-ethylpiperidine-4-carboxylate To a solution of ethyl 1-(5-(4-amino-3-nitro-5-(pyridin-2-yl)phenyl)pyrimidin-2-yl)-4-ethylpiperidine-4-carboxylate (0.70 g, 1.46 mmol) in EtOAc (20.0 mmol) was added Pd/C (0.14 g, 20% w/w) and the mixture stirred at rt under hydrogen for 16 h. After completion the reaction (by TLC), the mixture was filtered through celite, the filtrate concentrated under reduced pressure and triturated with $Et_2O$ to afford the desired product (0.65 g, 99%). $^1$H NMR (DMSO-d$_6$): δ 8.61-8.62 (m, 1H), 8.58 (s, 2H), 7.86-7.88 (m, 2H), 7.28-7.30 (m, 1H), 7.11 (s, 1H), 6.84 (s, 1H), 6.16 (s, 2H), 4.78 (br s, 2H), 4.38-4.42 (m, 2H), 4.13-4.18 (m, 2H), 3.04-3.10 (m, 2H), 2.04-2.08 (m, 2H), 1.55-1.57 (m, 2H), 1.37-1.39 (m, 2H), 1.19 (t, J=7.20 Hz, 3H) and 0.83 (t, J=7.20 Hz, 3H). MS: 447.35 [M+H]$^+$ Ethyl 4-ethyl-1-(5-(2-(3-ethylureido)-7-(pyridin-2-yl)-1H-benzo[d]imidazol-5-yl)pyrimidin-2-yl)piperidine-4-carboxylate To a solution of sodium acetate (0.606 g, 7.38 mmol) in water (8.0 mL), concentrated sulphuric acid was added dropwise till pH ~3.5 followed by addition of ethyl 1-(5-(3,4-diamino-5-(pyridin-2-yl)phenyl)pyrimidin-2-yl)-4-ethylpiperidine-4-carboxylate (0.55 g, 1.23 mmol) to get a yellow suspension. The solution of N,N-diethylurea-2-(4-nitrobenzyl)-2-thiopseudourea (0.454 g, 1.23 mmol) in DME (15.0 mL) was added to the resulting mixture. The homogenous mixture was stirred and heated to 80° C. for 5 h. After completion the reaction (by TLC), the mixture was filtered and the filtrate was concentrated under reduced pressure. The residue thus obtained was triturated with water, EtOAc and $Et_2O$ respectively obtain the product (0.40 g, 60%). $^1$H NMR (TFA-d$_1$): δ 10.03 (br s, 1H), 9.91 (s, 1H), 9.86 (m, 1H), 9.47 (m, 1H), 9.27 (m, 2H), 8.96 (s, 1H), 5.57 (m, 2H), 5.43 (q, J=7.20 Hz, 2H), 5.09 (m, 4H), 4.84 (m, 2H), 4.62 (q, J=7.20 Hz, 2H), 3.59 (m, 2H), 2.76-2.83 (m, 4H), 2.44 (t, J=7.20 Hz, 3H), 2.32 (t, J=7.20 Hz, 3H) and 1.98 (t, J=7.60 Hz, 3H).

4-Ethyl-1-(5-(2-(3-ethylureido)-7-(pyridin-2-yl)-1H-benzoimidazol-5-yl)pyrimidin-2-yl)piperidine-4-carboxylic acid (229)

To an ice-cold solution of ethyl 4-ethyl-1-(5-(2-(3-ethylureido)-7-(pyridin-2-yl)-1H-benzo[d]imidazol-5-yl)pyrimidin-2-yl)piperidine-4-carboxylate (0.20 g, 0.37 mmol) in DMSO (3.0 mL) was added potassium tert-butoxide (0.2.06 g, 1.84 mmol) and the mixture stirred at rt for 16 h. After completion of reaction (by TLC), water (10 mL) was added followed by extraction with EtOAc (3×25 mL) and the organic layer discarded. The pH of the aqueous layer was adjusted up to 4-5, extracted with EtOAc (3×25 mL) and the combined organic layer dried over $Na_2SO_4$, filtered and evaporated under reduced pressure. The residue thus obtained was triturated with n-pentane to afford Compound 229 as yellow solid (0.10 g, 53%). $^1$H NMR (DMSO-d6+D2O): δ 8.78 (m, 3H), 8.38 (m, 1H), 7.95-8.0 (m, 2H), 7.69 (s, 1H), 7.39 (br s, 1H), 4.44 (m, 2H), 3.22 (m, 2H), 3.13 (m, 2H), 2.06 (m, 2H), 1.51 (m, 2H), 1.34 (m, 2H), 1.11 (t, J=7.20 Hz, 3H) and 0.80 (t, J=7.20 Hz, 3H). LCMS: 515.19 [M+H]$^+$ Compound 227 1-(5-{2-[(ethylcarbamoyl)amino]-1-5-(1H-pyrazol-1-yl)[1,2,4]triazolo[1,5-a]pyridin-7-yl}pyrimidin-2-yl)-4-methylpiperidine-4-carboxylic acid (alternatively named 1-[5-[2-(ethylcarbamoylamino)-5-pyrazol-1-yl-[1,2,4]triazolo[1,5-a]pyridin-7-yl]pyrimidin-2-yl]-4-methyl-piperidine-4-carboxylic acid)

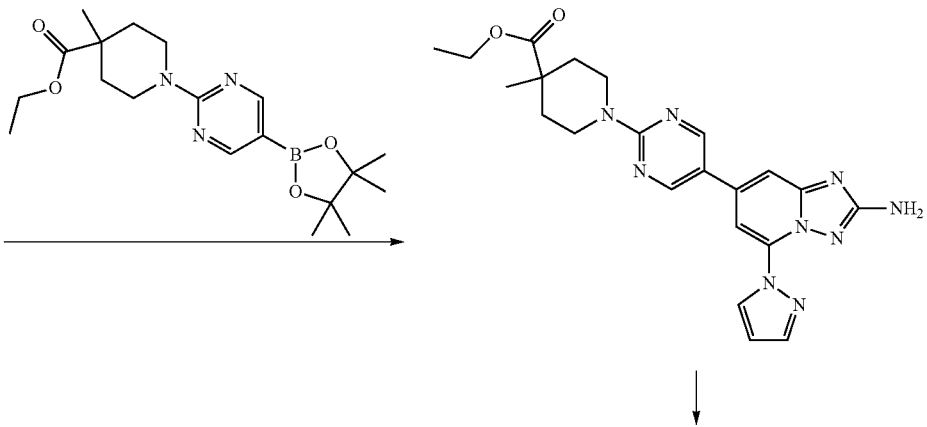

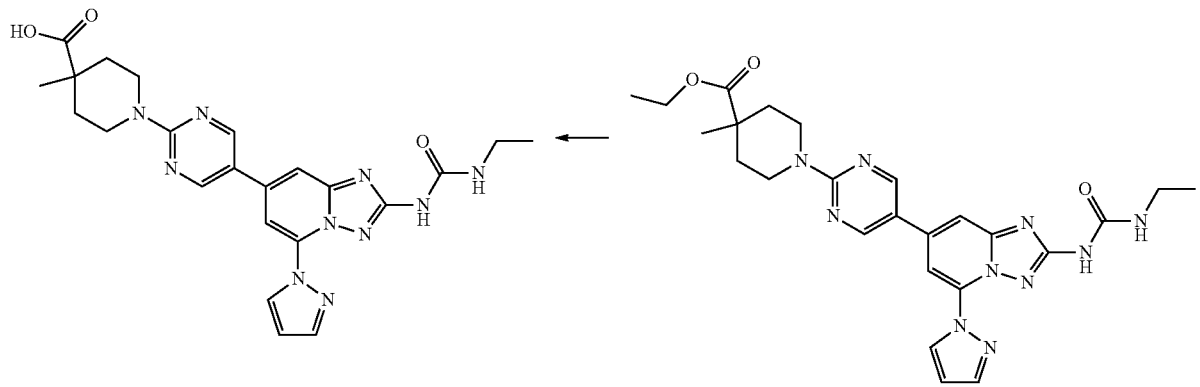

7-Chloro-5-(1H-pyrazol-1-yl) [1,2,4]triazolo[1,5-a]pyridin-2-amine 5,7-Dichloro[1,2,4]triazolo[1,5-a]pyridin-2-amine (Intermediate 15) (0.5 g, 2.46 mmol), cesium carbonate (1.6 g, 4.93 mmol) and pyrazole (0.5 g, 7.39 mmol) was suspended in DMF (10 mL) and stirred at 70° C. for 2 h after which time LCMS showed desired product formation. The reaction mixture was filtered through celite, which was washed with further DMF and the resultant green/brown solution was concentrated in vacuo to give a brown residue, which was partitioned between 10% IPA/DCM (20 mL) and water (10 mL), the organic layer was separated and the aqueous extracted with further 10% IPA/DCM (2×10 mL). The organic layers were combined and dried (MgSO₄), filtered and concentrated in vacuo to give the desired product as a brown solid (0.4 g, 69%). ¹H NMR (DMSO) δ 9.16 (d, J=2.6 Hz, 1H), 7.99 (d, J=1.4 Hz, 1H), 7.54 (d, J=2.1 Hz, 1H), 7.36 (d, J=2.1 Hz, 1H), 6.72 (dd, J=2.4, 1.9 Hz, 1H), 6.46 (s, 2H). MS: 235.12 [M+H]⁺.

Ethyl 1-{5-[2-amino-5-(1H-pyrazol-1-yl)[1,2,4]triazolo[1,5-a]pyridin-7-yl]pyrimidin-2-yl}-4-methylpiperidine-4-carboxylate A suspension of ethyl 4-methyl-1-[5-(4,4,5,5-tetramethyl-1,3,2-dioxaborolan-2-yl)pyrimidin-2-yl]piperidine-4-carboxylate (360 mg, 0.97 mmol), 7-chloro-5-(1H-pyrazol-1-yl)[1,2,4]triazolo[1,5-a]pyridin-2-amine (190 mg, 0.81 mmol), cesium carbonate (400 mg, 1.2 mmol) and Pd(dppf)₂Cl2 (60 mg, 0.08 mmol) in 1,4-dioxane (4.5 mL) and water (0.5 mL) was added to a microwave vial and degassed with N₂. The vessel was then heated at 110° C. in a microwave reactor for 60 mins. The resultant solution was concentrated in vacuo and the residue purified by flash column chromatography (Biotage SP4, 40 g 0-10% MeOH/DCM) and (Biotage SP4, 12 g 2% MeOH/DCM, then flush with 10% MeOH/DCM) to give the desired product as a cream solid (200 mg, 55%) MS: 448.27 [M+H]⁺.

Ethyl 1-(5-{2-[(ethylcarbamoyl)amino]-5-(1H-pyrazol-1-yl)[1,2,4]triazolo[1,5-a]pyridin-7-yl}pyrimidin-2-yl)-4-methylpiperidine-4-carboxylate Ethyl isocyanate (143 mg, 2.01 mmol) was added to solution of ethyl 1-{5-[2-amino-5-(1H-pyrazol-1-yl)[1,2,4]triazolo[1,5-a]pyridin-7-yl]pyrimidin-2-yl}-4-methylpiperidine-4-carboxylate (180 mg, 0.40 mmol) in 1,4-dioxane (15 mL) and stirred at 80° C. for 22 h. LCMS showed desired product formation. The resultant black reaction mixture was concentrated in vacuo to give a brown tarry solid which was triturated with EtOAc (10 mL) to give the desired product as a grey solid (88 mg, 42%) MS: 519.23 [M+H]⁺.

1-(5-{2-[(ethylcarbamoyl)amino]-5-(1H-pyrazol-1-yl)[1,2,4]triazolo[1,5-a]pyridin-7-yl}pyrimidin-2-yl)-4-methylpiperidine-4-carboxylic acid (227)

A 2N aqueous solution of NaOH (5 mL) was added to a solution of ethyl 1-(5-{2-[(ethylcarbamoyl)amino]-5-(1H-pyrazol-1-yl)[1,2,4]triazolo[1,5-a]pyridin-7-yl}pyrimidin-2-yl)-4-methylpiperidine-4-carboxylate (88 mg, 0.17 mmol) in EtOH (15 mL) at rt and was heated at 70° C. After 2 h the reaction mixture was cooled to rt and concentrated in vacuo to ~⅓ volume. Water (10 mL) was added and the resultant solution extracted with EtOAc (2×10 mL). The aqueous was then acidified to pH 1-2 and extracted with 10% IPA/DCM (3×10 mL). The organic layers were combined and dried (MgSO₄), filtered and concentrated in vacuo to give a off white solid which was purified by semi preparative HPLC to give Compound 227 as a cream solid (20 mg, 24%). ¹H NMR (DMSO) δ 10.01 (s, 1H), 9.00 (d, J=2.4 Hz, 1H), 8.94 (s, 2H), 8.16-8.06 (m, 1H), 8.01 (s, 2H), 7.81 (s, 1H), 6.77-6.73 (m, 1H), 4.35 (d, J=13.5 Hz, 2H), 3.25 (s, 2H), 2.05 (d, J=12.9 Hz, 2H), 1.38 (s, 2H), 1.25 (s, 2H), 1.19 (s, 3H), 1.14 (d, J=7.2 Hz, 3H). MS: 491.1 [M+H]⁺.

Compound 230 4-ethyl-1-[5-[2-(ethylcarbamoylamino)-5-pyrazol-1-yl-imidazo[1,2-a]pyridin-7-yl]pyrimidin-2-yl]piperidine-4-carboxylic acid
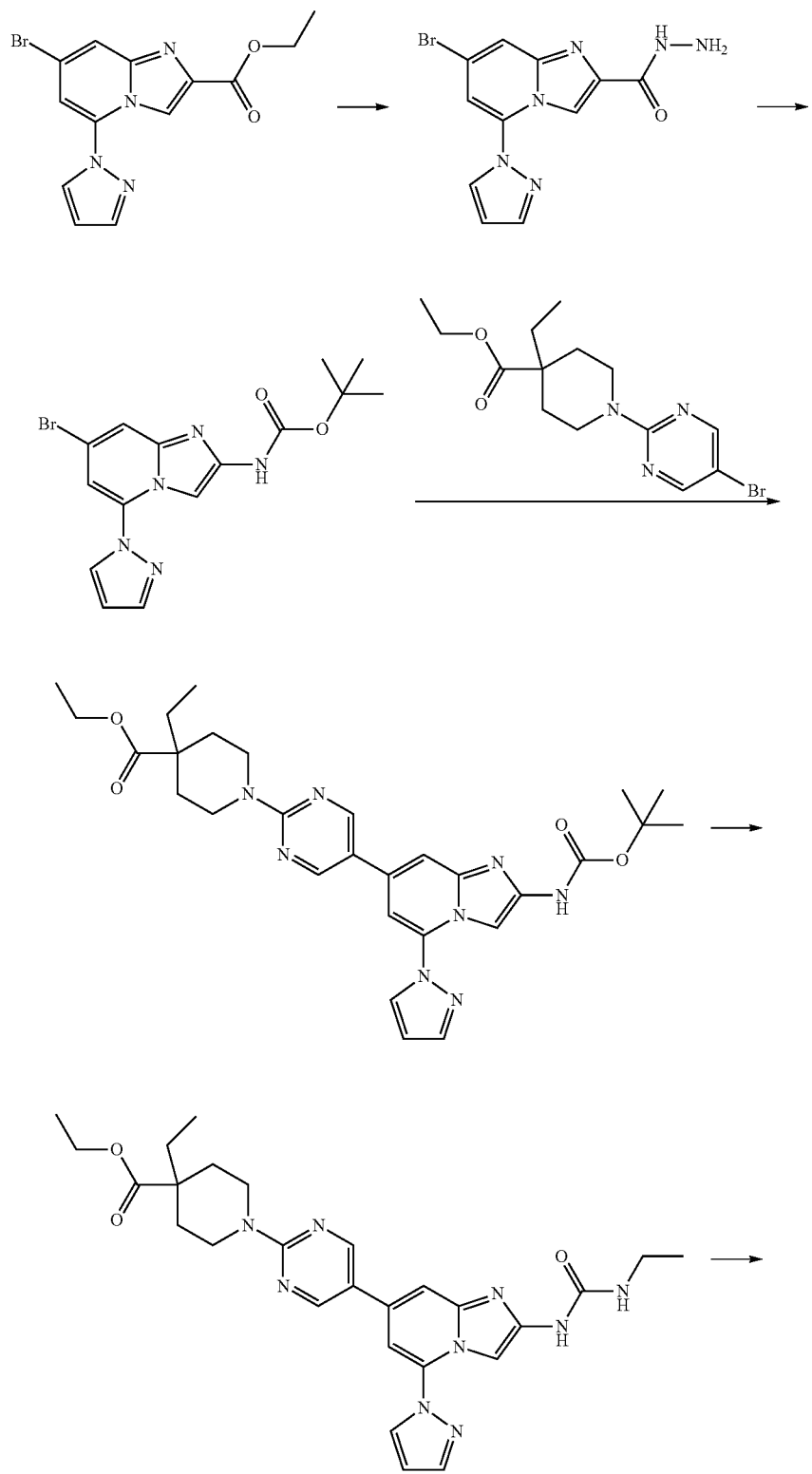

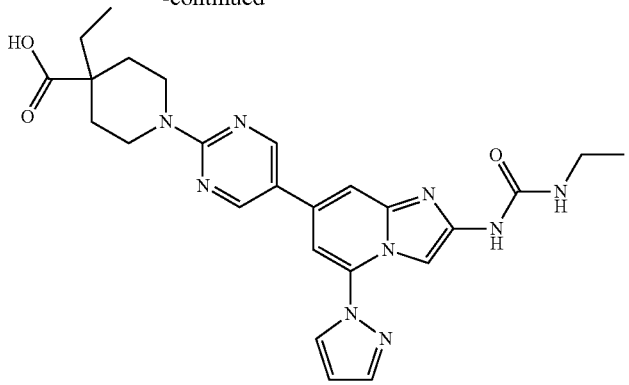

Ethyl 7-bromo-5-pyrazol-1-yl-imidazo[1,2-a]pyridine-2-carboxylate

A mixture of 7-bromo-5-chloro-imidazo[1,2-a]pyridine-2-carboxylate (Intermediate 16) (0.867 g, 2.86 mmol) and pyrazole (0.194 g, 2.86 mmol) was dissolved in DMF (15 mL). Cesium carbonate (1.95 g, 2.1 eq.) was added and the mixture stirred at rt. After 16 hours TLC indicated clean but incomplete reaction and stirring was continued over the weekend. Saturated aqueous NH$_4$Cl (50 mL) was added, resulting in effervescence and a gelatinous precipitate which was then broken up, water (30 mL) added and the solid filtered in vacuo. This material was washed with water and sucked dry to give a tan paste. The filtrate was extracted with EtOAc (100 mL), washed with water (30 mL), brine (30 mL), and set aside. The tan paste was dissolved in EtOAc (200 mL), combined with the filtrate, dried over MgSO$_4$, filtered and evaporated to give a brown residue that crystallized upon standing. Trituration with EtOAc (15 mL) and heptane (50 mL) yielded a yellow powder, 0.363 g (38%). MS: 335, 337 [M+H]$^+$.

7-bromo-5-pyrazol-1-yl-imidazo[1,2-a]pyridine-2-carbohydrazide: To a suspension of ethyl 7-bromo-5-pyrazol-1-yl-imidazo[1,2-a]pyridine-2-carboxylate (3.96 g, 11.8 mmol) in EtOH (100 mL) was added hydrazine hydrate (5.91 mL, 0.118 mmol) and the mixture stirred overnight at rt. After 3 days, the reaction was almost complete by LCMS so stirring was maintained for 1 more night. The mixture was diluted with EtOH (50 mL), filtered and the solids washed with EtOH (2×50 mL), EtOAc (2×50 mL) and heptane (50 mL) before being air dried. The yield was 3.56 g (94%) LCMS MS: 321.01, 322.98 [M+H]$^+$.

tert-butyl N-(7-bromo-5-pyrazol-1-yl-imidazo[1,2-a]pyridin-2-yl)carbamate 7-bromo-5-pyrazol-1-yl-imidazo[1,2-a]pyridine-2-carbohydrazide (3.56 g, 11.1 mmol) was suspended in 1M HCl (50 mL) and stirred overnight. The reaction was cooled in an ice/water bath and a solution of sodium nitrite in water (918 mg, 13.3 mmol in 10 mL) was added. The mixture was stirred for 2.5 hours. 1M NaOH (40 mL) and saturated NaHCO$_3$ (15 mL) were carefully added and the mixture extracted with EtOAc (3×100 mL), dried over MgSO$_4$, and evaporated (water bath temp <25° C.) to give an off-white solid, which upon trituration with DCM (10 mL) and filtration, yielded 1.06 g of a crystalline material. TLC (Rf=0.7, 50% EtOAc/DCM) indicated complete consumption of starting material. The aqueous layers and solid matter were retained further filtration yielded another 2.5 grams of solid, which upon washing with water, air drying, trituration with DCM and heptane, gave additional crops (1.5 g) of azide. 1.06 g of azide was suspended in dioxane (20 mL) and t-butanol (20 mL) and heated at 80° C. for 3 hours then at 90° C. for 5 hours. LCMS indicated conversion to the desired Boc-protected amine. The solution was then cooled and concentrated in vacuo and the residue was triturated in cold MeOH (10 mL) then filtered to give a gray solid, weight 650 mg (MS: 377.8, 379.8 [M+H]$^+$) (54% yield from azide, yield of azide from hydrazide=68%).

Ethyl 1-[5-[2-(tert-butoxycarbonylamino)-5-pyrazol-1-yl-imidazo[1,2-a]pyridin-7-yl]pyrimidin-2-yl]-4-ethyl-piperidine-4-carboxylate A solution of 1-(5-bromopyrimidin-2-yl)-4-ethyl-piperidine-4-carboxylate (0.882 g, 2.58 mmol), bis(pinacolato)diboron, (0.818 g, 2.58 mmol), potassium acetate (0.379 g, 3.87 mmol) and tricyclohexylphosphine, 43 mg, 0.15 mmol in dioxane (10 mL) was degassed with N$_2$ for 10 mins. Pd$_2$(dba)$_3$ (71 mg, 0.077 mmol) was introduced and the reaction heated to 95° C. for 2 hours. TLC indicated complete consumption of tarting material. The solution was filtered through celite, the solids washed with 10 mL of dioxane and the combined filtrate added to a separate flask containing N-(7-bromo-5-pyrazol-1-yl-imidazo[1,2-a]pyridin-2-yl)carbamate (0.650 g, 1.72 mmol) and K$_3$PO$_4$ (0.694 g; 3.27 mmol) in dioxane (10 mL) and water (2 mL). The mixture was degassed with N$_2$ for 10 mins then PdCl$_2$(PPh$_3$)$_2$ (92 mg, 0.131 mmol) was added. The mixture was heated under N$_2$ to 85° C. for 3 hours then cooled and diluted with EtOAc (50 mL). The suspension was filtered, yielding a slightly greenish white solid with the requisite molecular ion (MS: 561.05 [M+H]$^+$). The crude was suspended in EtOAc (30 mL) to which was added DCM (20 mL) and MeOH (10 mL), heated until partial dissolution then cooled overnight. The solid was once again filtered, washed with a small amount of EtOAc, then heptane, and dried, giving 0.530 g (55%) of product, which was used directly in the next step without further purification.

Ethyl 4-ethyl-1-[5-[2-(ethylcarbamoylamino)-5-pyrazol-1-yl-imidazo[1,2-a]pyridin-7-yl]pyrimidin-2-yl]piperidine-4-carboxylate Material from the previous step was suspended in CH$_2$Cl$_2$ (5 mL) and treated with 4M HCl/dioxane (2.35 mL of a 4M solution) at rt for 60 minutes. CH$_2$Cl$_2$ (50 mL) was then added and the mixture stirred vigorously, then diluted with heptane (100 mL). The mixture was stirred overnight, filtered, washed with 1:1 CH$_2$Cl$_2$/heptane (30 mL), then heptane (30 mL), and air dried to give 0.550 g (quantitative mass recovery) of product. MS: 461.3 [M+H]$^+$. The amine salt (500 mg, 1.086 mmol) was treated with excess ethyl isocyanate (1.5 mL) and triethylamine (1.5 mL) in dioxane for 2 days. The mixture was evaporated to dryness, triturated in DCM, and filtered, giving an off-white solid, MS: 532.19 [M+H]$^+$.

4-Ethyl-1-[5-[2-(ethylcarbamoylamino)-5-pyrazol-1-yl-imidazo[1,2-a]pyridin-7-yl]pyrimidin-2-yl]piperidine-4-carboxylic acid (230)

Material from the previous step was suspended in EtOH (5 mL) and NaOH (1 mL, 1M) added. The mixture was heated at 70° C. for 3 days. MeOH (2 mL) was added to increase the reaction rate and heating continued for another 2 days. The mixture was concentrated, acidified to pH 3 with 1M HCl, filtered and the residue washed with MeOH, giving an insoluble yellow solid, which was filtered. The filtrate was concentrated and purified by preparative HPLC (30-50% ACN/0.1% aq. formic acid) to afford 14.6 mg of Compound 230 (2.7%). $^1$H NMR (DMSO-d$_6$): δ 9.06 (1H, s); 8.92 (2H, s); 8.50 (1H, dd, J=2.4, 0.4 Hz); 8.04 (1H, dd, J=1.6, 0.4 Hz); 7.87 (1H, s); 7.83 (1H, d, J=1.2 Hz); 7.48 (1H, d, J=1.6 Hz); 6.72 (1H, dd, J=2.4, 2 Hz); 6.70 (1H, br s); 4.48 (2H, d, J=13 Hz); 3.15 (4H, m); 2.07 (2H, d, J=13 Hz); 1.53 (2H, q, J=7 Hz); 1.33 (2H, m); 1.07 (3H, t, J=7 Hz); 0.82 (3H, t, J=7 Hz). MS: 504.14 [M+H]$^+$.

Compound 231 1-[5-[2-(ethylcarbamoylamino)-5-pyrazol-1-yl-imidazo[1,2-a]pyridin-7-yl]pyrimidin-2-yl]-4-methyl-piperidine-4-carboxylic acid 1-(7-bromo-5-pyrazol-1-yl-imidazo[1,2-a]pyridin-2-yl)-3-ethyl-urea To a solution of tert-butyl N-(7-bromo-5-pyrazol-1-yl-imidazo[1,2-a]pyridin-2-yl)carbamate (1.096 g, 2.90 mmol) in DCM (15 mL) was added 4M HCl/dioxane (2.35 mL of a 4M solution) and the mixture stirred at rt for 60 minutes. An additional 5 mL of HCl/dioxane was added and stirring continued overnight. After 24 hours, ether (200 mL) was added and a dark brown solid filtered. The solid was washed with ether (50 mL) and heptane (50 mL) to give 1.03 g of the amine salt. This material was suspended in dioxane (10 mL), treated with ethyl isocyanate (2 ml) and because the mixture was not homogeneous, triethylamine (1 mL) was added. Stirring was maintained at rt for 36 hours. The mixture was diluted with EtOAc (80 mL), filtered, the grayish solid washed with EtOAc (30 mL), heptane (20 mL) and dried. An additional swish with THF (10 mL) and EtOAc (60 mL), followed by filtration, heptane wash, and drying gave 0.833 g (82% for two steps) product. MS: 348.9, 350.9 [M+H]$^+$.

Ethyl 1-[5-[2-(ethylcarbamoylamino)-5-pyrazol-1-yl-imidazo[1,2-a]pyridin-7-yl]pyrimidin-2-yl]-4-methyl-piperidine-4-carboxylate 1-(5-bromopyrimidin-2-yl)-4-ethyl-piperidine-4-carboxylate (0.469 g, 1.25 mmol), bis(pinacolato)diboron (0.397 g, 1.56 mmol) potassium acetate (0.184 g, 1.87 mmol) and tricyclohexylphosphine (21 mg, 0.075 mmol) was dissolved in dioxane (10 mL) and degassed with N$_2$ for 10 mins. Pd$_2$(dba)$_3$ (34 mg, 0.037 mmol) was added and the reaction heated to 90° C. for 2 hours. An additional 21 mg of tricyclohexylphosphine and 34 mg of Pd2(dba)$_3$ were added and heating maintained for a further 4 hours. The solution was filtered through celite, the solids washed with 2×10 mL of dioxane and the mother liquor collected for the next step.

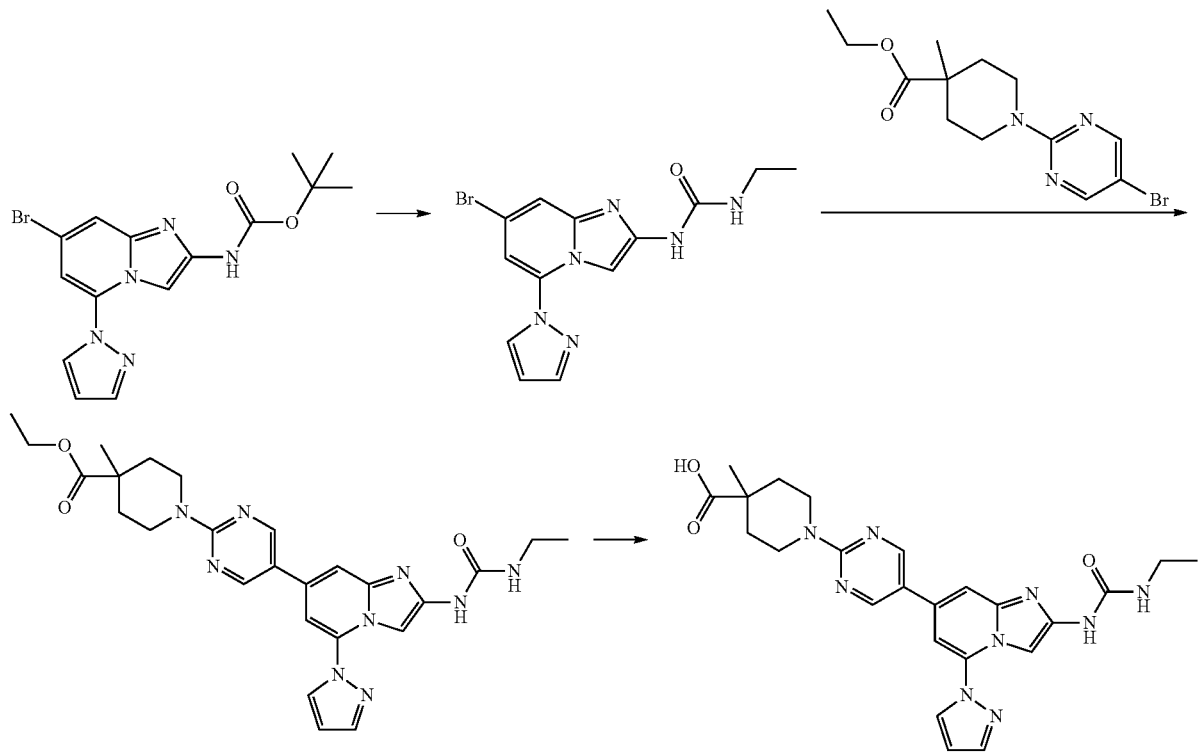

A solution of the boronate was added to a separate flask containing N-(7-bromo-5-pyrazol-1-yl-imidazo[1,2-a]pyridin-2-yl)carbamate (0.349 g, 1.00 mmol), K$_3$PO$_4$ (0.694 g; 3.27 mmol) and water (3 mL). PdCl$_2$(PPh$_3$)$_2$ (92 mg; 0.1311 mmol was added and the mixture heated under N$_2$ to 85° C. for 3 hours. An additional 92 mg of PdCl$_2$(PPh$_3$)$_2$ was added and the mixture heated overnight at 80° C. The solution was cooled, diluted with EtOAc (50 mL) and the suspension filtered, yielding a dark brown solid which was washed with water, dissolved in DCM and plugged through silica (20-50% EtOAc/DCM then 5% MeOH/DCM). The product-containing fractions were concentrated then suspended in cold EtOAc (50 mL) and filtered to give 50.1 mg (8%) of the coupled ester as a greenish powder. MS: 518.6 [M+H]$^+$.

1-[5-[2-(ethylcarbamoylamino)-5-pyrazol-1-yl-imidazo[1,2-a]pyridin-7-yl]pyrimidin-2-yl]-4-methyl-piperidine-4-carboxylic acid (231)

The ester (50 mg, 0.097 mmol) from the previous step was dissolved in MeOH (5 mL) and treated with 1M NaOH (2 mL) at 55° C. overnight. A total of 72 hours was required to effect complete conversion. MeOH (10 mL) was added and the mixture filtered then concentrated to give an orange solid which was dissolved in water (5 mL), acidified to pH 3 with 1M HCl, filtered, and the solid purified on a short plug of silica gel (5-15% MeOH/CH$_2$Cl$_2$) to afford Compound 231. $^1$H NMR (MeOD-d$_4$): δ 8.77 (2H, s); 8.31 (1H, s); 7.99 (1H, s); 7.85 (1H, s); 7.68 (1H, s); 7.36 (1H, s); 6.70 (1H, s); 4.43 (2H, d, J=15 Hz); 3.29 (4H, m); 2.10 (2H, d, J=10 Hz); 1.47 (2H, t, J=10.8 Hz); 1.32 (3H, s); 1.20 (3H, t, J=7 Hz). MS: 490.15 [M+H]$^+$.

Compound 232 4-ethyl-1-(3-{2-[(ethylcarbamoyl)amino]-7-(pyridin-2-yl)-1,3-benzothiazol-5-yl}-1,2,4-thiadiazol-5-yl)piperidine-4-carboxylic acid

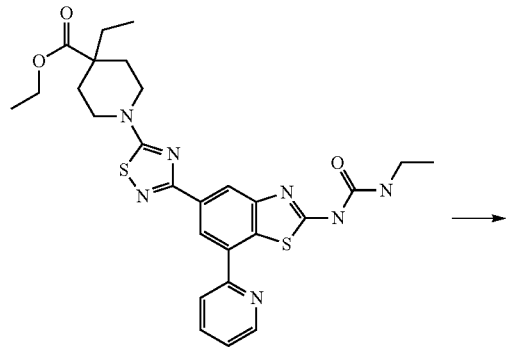

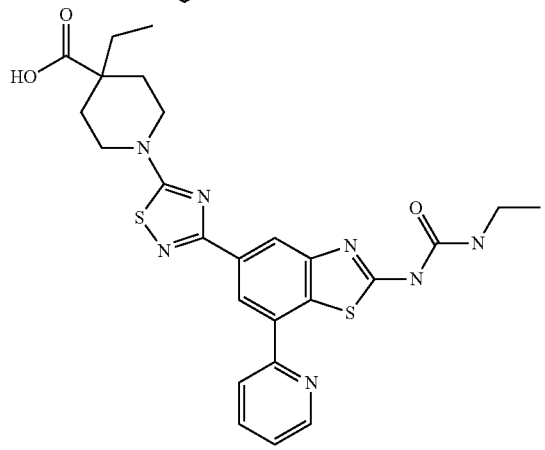

Ethyl 4-ethyl-1-(3-{2-[(ethylcarbamoyl)amino]-7-(pyridin-2-yl)-1,3-benzothiazol-5-yl}-1,2,4-thiadiazol-5-yl)piperidine-4-carboxylate: Ethyl 1-(3-chloro-1,2,4-thiadiazol-5-yl)-4-ethylpiperidine-4-carboxylate (110 mg, 0.35 mmol), cesium carbonate (285.6 mg, 0.88 mmol), Pd(dppf)$_2$Cl$_2$ (20 mg, 0.03 mmol) and {2-[(ethylcarbamoyl)amino]-7-(pyridin-2-yl)-1,3-benzothiazol-5-yl}boronic acid (100 mg, 0.29 mmol) was suspended in a mixture of THF (9 mL) and water (1 mL) and heated in the microwave at 110° C. for 50 min. The reaction mixture was concentrated in vacuo and the residue partitioned between 10% IPA/DCM (10 mL) and water (10 mL). The organic layer was separated and the aqueous extracted with further 10% IPA/DCM (3×10 mL), the organic layers were combined, dried (MgSO$_4$), filtered and concentrated to give a black solid which was pre-absorbed onto silica and purified by flash column chromatography (Biotage SP4 12 g, 2% MeOH/DCM-5% MeOH/DCM-8% MeOH/DCM) to give the desired product as a brown solid. MS: 566.11 [M+H]$^+$.

4-ethyl-1-(3-{2-[(ethylcarbamoyl)amino]-7-(pyridin-2-yl)-1,3-benzothiazol-5-yl}-1,2,4-thiadiazol-5-yl)piperidine-4-carboxylic acid (232): Ethyl 4-ethyl-1-(3-{2-[(ethylcarbamoyl)amino]-7-(pyridin-2-yl)-1,3-benzothiazol-5-yl}-1,2,4-thiadiazol-5-yl)piperidine-4-carboxylate (70 mg, 0.09 mmol) was dissolved in EtOH (15 mL) and 2M aqueous NaOH (5 mL) and stirred at 90° C. for 18 h. The reaction was cooled to rt and concentrated to ~⅕ volume. Water (10 mL) and DCM (10 mL) were added and the aqueous layer separated, the organic layer discarded and the aqueous layer acidified to pH~2 and extracted with DCM (3×10 mL). The organic layers were combined, dried (MgSO$_4$), filtered and concentrated in vacuo to give a brown solid, which was purified by flash column chromatography (Biotage, SP4, 12 g, 2-8% MeOH, DCM) to afford Compound 232 as a cream solid (18 mg, 38%).

$^1$H NMR (CDCl$_3$) δ 8.70 (dd, J=4.8, 0.8 Hz, 1H), 8.62 (d, J=1.4 Hz, 1H), 8.44 (d, J=1.3 Hz, 1H), 8.09 (d, J=8.2 Hz, 1H), 7.78 (td, J=7.8, 1.8 Hz, 1H), 7.22 (ddd, J=7.4, 4.9, 0.8 Hz, 1H), 3.83 (brs, 2H), 3.39-3.29 (m, 5H), 2.22 (d, J=13.3 Hz, 2H), 1.70-1.40 (m, 4H), 1.19 (t, J=7.3 Hz, 4H), 0.86 (t, J=7.5 Hz, 3H). MS: 538.08 [M+H]$^+$.

Compound 233 1-(5-{2-[(ethylcarbamoyl)amino]-7-(pyridin-2-yl)-1,3-benzothiazol-5-yl}-1,2,4-thiadiazol-3-yl)-4-methylpiperidine-4-carboxylic acid

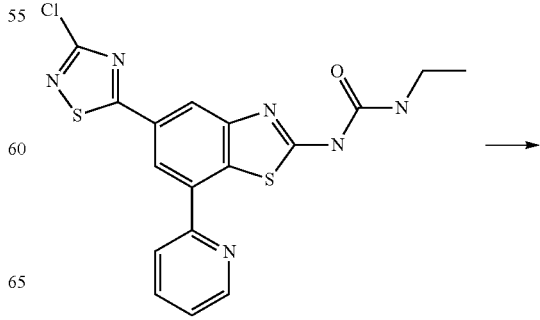

-continued

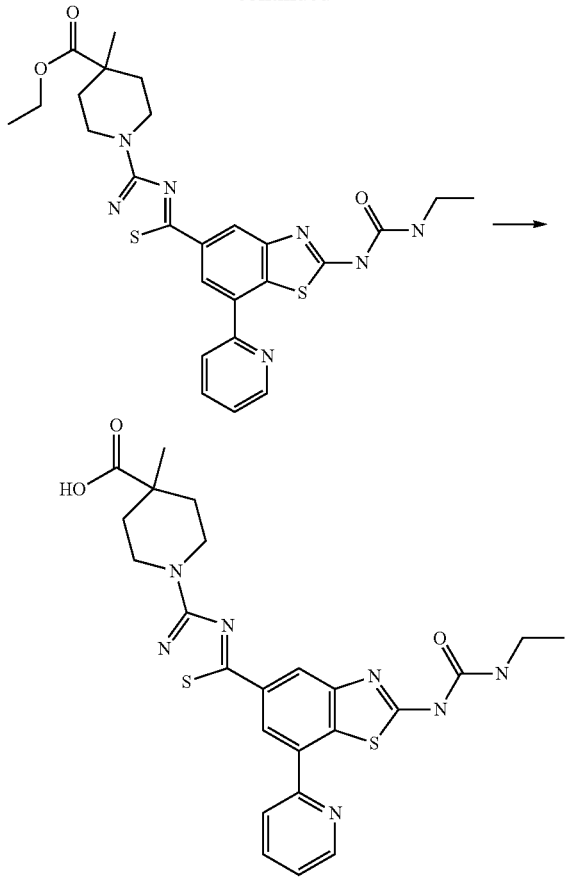

1-[5-(3-chloro-1,2,4-thiadiazol-5-yl)-7-(pyridin-2-yl)-1,3-benzothiazol-2-yl]-3-ethylurea 3,5-dichloro-1,2,4-thiadiazole (50 mg, 0.32 mmol), Cesium carbonate (285.6 mg, 0.88 mmol), Pd(dppf)$_2$Cl2 (20 mg, 0.03 mmol) and {2-[(ethylcarbamoyl)amino]-7-(pyridin-2-yl)-1,3-benzothiazol-5-yl}boronic acid (100 mg, 0.29 mmol) was suspended in a mixture of THF (9 mL) and water (1 mL) and heated in the microwave at 110° C. for 50 min. The reaction mixture was concentrated in vacuo and the residue partitioned between 10% IPA/DCM (10 mL) and water (10 mL). The organic layer was separated and the aqueous extracted with further 10% IPA/DCM (3×10 mL), the organic layers were combined, dried (MgSO$_4$), filtered and concentrated, then pre-absorbed onto silica and purified by flash column chromatography (Biotage SP4 12 g, 2% MeOH/DCM-5% MeOH/DCM-8% MeOH/DCM) to give 1-[5-(3-chloro-1,2,4-thiadiazol-5-yl)-7-(pyridin-2-yl)-1,3-benzothiazol-2-yl]-3-ethylurea as a brown solid. (100 mg, 81%) MS: 416.92 [M+H]$^+$.

Ethyl 1-(5-{2-[(ethylcarbamoyl)amino]-7-(pyridin-2-yl)-1,3-benzothiazol-5-yl}-1,2,4-thiadiazol-3-yl)-4-methylpiperidine-4-carboxylate To a solution of 1-[5-(3-chloro-1,2,4-thiadiazol-5-yl)-7-(pyridin-2-yl)-1,3-benzothiazol-2-yl]-3-ethylurea (100 mg, 0.24 mmol) and Triethylamine (73 mg, 0.72 mmol) in DMF (10 mL) was added ethyl 4-ethylpiperidine-4-carboxylate hydrochloride (100 mg, 0.48 mmol) and the mixture stirred at rt for 1 h giving a suspension. LCMS showed only SM so the reaction was heated at 90° C. for 3 days after which time LCMS showed a major product peak. The reaction mixture was concentrated in vacuo to give an orange gum, which was purified by flash column chromatography (Biotage SP4, 12 g 2-10% MeOH/DCM)) to give the desired product as a cream solid (100 mg, 52%) MS: 552.11 [M+H]$^+$.

1-(5-{2-[(ethylcarbamoyl)amino]-7-(pyridin-2-yl)-1,3-benzothiazol-5-yl}-1,2,4-thiadiazol-3-yl)-4-methylpiperidine-4-carboxylic acid Ethyl 1-(5-{2-[(ethylcarbamoyl)amino]-7-(pyridin-2-yl)-1,3-benzothiazol-5-yl}-1,2,4-thiadiazol-3-yl)-4-methylpiperidine-4-carboxylate (100 mg, 0.13 mmol) was dissolved in EtOH (10 mL) and 2M aqueous NaOH (2.5 mL) was added and the mixture stirred at 90° C. for 18 h, cooled to rt and concentrated to ~⅕ volume water (10 mL) and DCM (10 mL) added. The aqueous layer was separated and the organic layer discarded. The resultant aqueous layer was acidified to pH~2 and extracted with DCM (3×10 mL), the combined organic layers were dried (MgSO$_4$), filtered and concentrated in vacuo to give a brown solid which was purified by flash column chromatography (2× Biotage, SP4, 12 g, 2-8% MeOH, DCM) to afford Compound 233 as a cream solid (23 mg, 34%). $^1$H NMR (CDCl$_3$) δ 8.70 (dd, J=4.8, 0.8 Hz, 1H), 8.62 (d, J=1.4 Hz, 1H), 8.44 (d, J=1.3 Hz, 1H), 8.09 (d, J=8.2 Hz, 1H), 7.78 (td, J=7.8, 1.8 Hz, 1H), 7.22 (ddd, J=7.4, 4.9, 0.8 Hz, 1H), 3.83 (brs, 2H), 3.39-3.29 (m, 5H), 2.22 (d, J=13.3 Hz, 2H), 1.70-1.40 (m, 4H), 1.19 (t, J=7.3 Hz, 4H), 0.86 (t, J=7.5 Hz, 3H). MS: 524.06 [M+H]$^+$.

Compound 234 Diethyl 1,1'-({2-[(ethylcarbamoyl)amino]-1,3-benzoxazole-5,7-diyl}dipyrimidine-5,2-diyl)bis(4-ethylpiperidine-4-carboxylate)

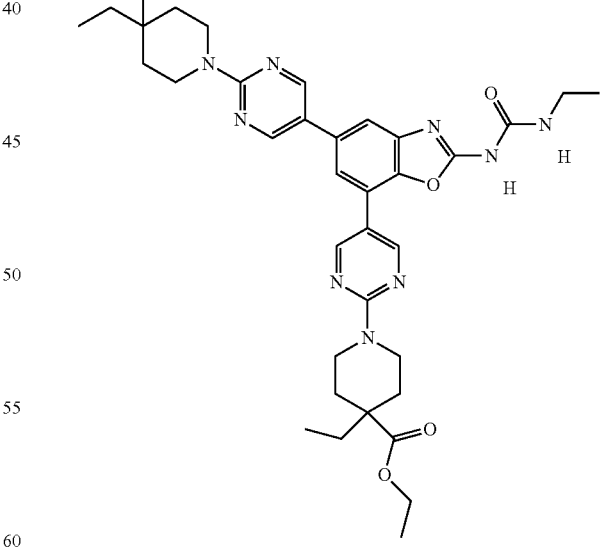

The reaction mixture was split evenly between 4 microwave vessels and recombined for work-up. In each vessel ethyl 4-ethyl-1-[5-(4,4,5,5-tetramethyl-1,3,2-dioxaborolan-2-yl)pyrimidin-2-yl]piperidine-4-carboxylate (300 mg, 0.77 mmol) was mixed with 1-(5,7-dibromo-1,3-benzoxazol-2-yl)-3-ethylurea (Intermediate 17) (200 mg, 0.55 mmol) in 1,4-dioxane; 11.4 mL. The microwave vessel was freeze-dried, vacuumed down and filled back with Ar (3 times). The mixture was then let to come back to rt and the catalyst [1,1'Bis(diphenylphosphino)ferrocene]dichloropalladium (II) (22 mg, 0.027 mmol) was added. The mixture was then freeze-dried, vacuumed down and filled back with Ar (3 times) then heated at 110° C. for 30 minutes in the microwave. The recombined reaction mixture was then filtrated on celite and the pad of celite rinsed with 1,4-dioxane. The filtrate was concentrated in vacuo, dissolved with EtOAc (40 mL) and the mixture washed with water (30 mL). The organics were concentrated in vacuo to give a residue that was purified by flash chromatography using the biotage SP4 (EtOAc gradient in heptane; 40 g cartridge). A large amount of both starting materials was recovered. Fractions containing the product were collected and concentrated in vacuo and purified using preparative LCMS (ACN gradient in water containing 0.1% formic acid). Compound 234 was isolated (2.3 mg, yield: 1%). $^1$H NMR (DMSO) δ 11.11 (br s, J=53.9 Hz, 1H), 8.34-8.27 (m, 1H), 8.15 (d, J=4.1 Hz, 4H), 7.65 (s, 1H), 7.52 (s, 1H), 4.41-4.29 (m, 4H), 4.15 (q, J=7.1 Hz, 4H), 3.30-3.24 (m, 2H), 3.10-2.98 (m, 4H), 2.05 (br d, J=13.2 Hz, 4H), 1.53 (br q, J=7.1 Hz, 4H), 1.36 (dd, J=24.2, 11.1 Hz, 4H), 1.21 (t, J=7.1 Hz, 6H), 1.15 (t, J=7.2 Hz, 3H), 0.77 (t, J=7.4 Hz, 6H). MS: 728.33 [M+H]$^+$.

Solubility Data

Turbimetric Assay: Determination of Solubility

The solubility of the compounds was measured using a turbidimetric method. A series of doubling dilutions of compounds were prepared in neat dimethyl sulfoxide (DMSO). 5 μl samples were diluted twenty-fold into 95 μl volumes of 100 mM citrate buffer (pH 4), phosphate buffered saline (PBS, pH 7.4) or carbonate-bicarbonate buffer (pH 9) in microtitre assay plates and allowed to reach equilibrium at room temperature for 24 hours. The absorbance within each well of the plate was read spectrophotometrically at a wavelength of 620 nm. A precipitate forms when the maximum aqueous solubility level is reached. The value quoted is the highest concentration where the compound was in solution i.e. where no measurable precipitate was present. L="Low" solubility <12.5 μg/mL; M="Moderate" solubility ≥12.5 μg/mL to <400 μg/mL; H="High" solubility ≥400 μg/mL to <800 μg/mL; and VH="Very High" solubility≥800 μg/mL. ND=not determined Biological Data On-Target Enzyme Assay: Determination of Gyrase ATPase Activity Gyrase converts ATP into ADP and inorganic phosphate. The released phosphate can be detected by the addition of malachite green solution and measured by monitoring the increase in absorbance at 600 nm. The ATPase assay is carried out in a buffer containing 2 mU/μl Gyrase enzyme (A$_2$B$_2$ complex from *Staphylococcus aureus*), 0.08 mg/ml double-stranded DNA, 8 mM HEPES.KOH pH 7.6, 100 mM K glutamate, 2 mM Mg acetate, 2 mM DTT, 0.01 mg/ml BSA, and 5% DMSO solution containing the inhibitor. Alternatively, the ATPase assay is carried out in a buffer containing 4.8 μg/mL Gyrase enzyme (A$_2$B$_2$ complex from *Escherichia coli*), 0.08 μg/mL ssDNA, 35 mM Tris pH 7.5, 24 mM KCl, 2 mM MgCl$_2$, 6.5% Glycerol, 2 mM DTT, 1.8 mM Spermidine, 0.5 mg/mL BSA and 5% DMSO solution containing the inhibitor. The reaction is started by adding ATP to a final concentration of 1 mM and allowed to incubate at 30° C. for 60 minutes. The reaction is stopped by adding 200 of malachite green solution (0.034% malachite green, 10 mM ammonium molybdate, 1 M HCl, 3.4% ethanol, 0.01% tween 20). Colour is allowed to develop for 5 minutes and the absorbance at 600 nm is measured spectrophotometrically. The IC$_{50}$ values are determined from the absorbance readings using no compound and no enzyme controls. The compounds of the invention generally demonstrated Gyrase ATPase activity values equal to or less than 0.1 μg/mL with compounds 18, 22, 26, 39, 44, 91, 146, 159, 178 demonstrating activity equal to or less than 0.3 μg/mL, compound 232 demonstrating activity of 0.5 μg/mL, compound 179 demonstrating activity of 0.6 μg/mL and compound 234 demonstrating activity of >1 μg/mL, Bacterial Assay: Determination of Antibacterial Activity Compounds of the invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. Methods for Dilution Antimicrobial Susceptibility Tests for Bacteria That Grow Aerobically; Approved Standard—Seventh Edition. Document M7-A7. CLSI, Wayne, Pa., 2006; Clinical Laboratories and Standards Institute. The gram positive bacterial strains tested include *S. aureus* (*Staphylococcus aureus* (Isolate ID ATCC 29213)), *E. faecalis* (*Enterococcus faecalis* (Isolate ID ATCC 29212)) and *S. pyogenes* (*Streptococcus pyogenes* (Isolate ID ATCC 51339)). The gram negative bacterial strains tested include *H. influenzae* (*Haemophilus influenzae* (Isolate ID ATCC 49247))

TABLE 5

Antibacterial Activity

| | Gram Positive Bacterial Strains | | | Gram Negative Bacterial Strains |
|---|---|---|---|---|
| Cpd No | S. aureus (ATCC 29213) | E. faecalis (ATCC 29212) | S. pyogenes (ATCC 51339) | H. influenzae (ATCC 49247) |
| 1 | A | A | A | C |
| 2 | B | B | B | C |
| 3 | C | B | A | C |
| 4 | B | A | A | C |
| 5 | A | A | A | D |
| 6 | A | A | A | C |
| 7 | A | A | A | B |
| 8 | A | A | A | C |
| 9 | A | A | A | C |
| 10 | A | A | A | C |
| 11 | A | A | A | C |
| 12 | A | A | A | C |
| 13 | A | A | A | C |
| 14 | A | A | A | B |
| 15 | A | A | A | B |
| 16 | A | A | A | C |
| 17 | A | A | A | B |
| 18 | A | A | A | C |
| 19 | B | A | A | C |
| 20 | B | A | A | C |
| 21 | A | A | B | C |
| 22 | B | A | C | D |
| 23 | A | A | A | C |
| 24 | C | A | B | C |
| 25 | D | B | B | D |
| 26 | D | C | C | D |
| 27 | C | A | A | C |
| 28 | B | A | B | C |
| 29 | B | A | B | C |
| 30 | B | A | B | C |
| 31 | A | A | A | B |
| 32 | A | A | A | C |
| 33 | D | C | C | D |
| 34 | A | A | A | C |
| 35 | A | A | B | C |
| 36 | A | A | A | C |

TABLE 5-continued

Antibacterial Activity

| Cpd No | Gram Positive Bacterial Strains ||| Gram Negative Bacterial Strains |
|---|---|---|---|---|
| | S. aureus (ATCC 29213) | E. faecalis (ATCC 29212) | S. pyogenes (ATCC 51339) | H. influenzae (ATCC 49247) |
| 37 | B | A | C | D |
| 38 | B | A | B | D |
| 39 | C | A | D | D |
| 40 | B | A | A | C |
| 41 | A | A | A | C |
| 42 | B | A | A | C |
| 43 | A | A | A | B |
| 44 | C | A | A | D |
| 45 | A | A | A | B |
| 46 | C | B | C | D |
| 47 | C | B | C | D |
| 48 | A | A | A | C |
| 49 | A | A | A | C |
| 50 | D | B | B | C |
| 51 | A | A | A | B |
| 52 | A | A | A | C |
| 53 | A | A | A | C |
| 54 | A | A | A | C |
| 55 | A | A | A | B |
| 56 | A | A | A | B |
| 57 | C | B | B | C |
| 58 | A | A | A | C |
| 59 | A | A | A | A |
| 60 | A | A | A | B |
| 61 | A | A | A | C |
| 62 | B | A | B | C |
| 63 | A | A | A | C |
| 64 | A | A | A | C |
| 65 | A | A | A | C |
| 66 | A | A | A | B |
| 67 | A | A | A | C |
| 68 | A | A | A | B |
| 69 | C | A | B | C |
| 70 | A | A | A | C |
| 71 | B | A | A | B |
| 72 | A | A | A | B |
| 73 | B | A | C | D |
| 74 | D | C | C | D |
| 75 | B | A | B | C |
| 76 | C | A | B | D |
| 77 | A | A | A | C |
| 78 | B | A | B | D |
| 79 | D | C | C | D |
| 80 | D | C | C | C |
| 81 | A | A | A | C |
| 82 | A | A | A | B |
| 83 | A | A | A | B |
| 84 | C | A | B | C |
| 85 | A | A | A | B |
| 86 | A | A | A | C |
| 87 | B | A | B | C |
| 88 | A | A | A | C |
| 89 | B | A | B | C |
| 90 | A | A | A | B |
| 91 | D | C | D | D |
| 92 | A | A | A | B |
| 93 | A | ND | A | C |
| 94 | C | ND | C | D |
| 95 | C | ND | B | D |
| 96 | A | ND | B | C |
| 97 | D | ND | C | D |
| 98 | A | A | A | C |
| 99 | A | A | A | C |
| 100 | A | A | A | C |
| 101 | A | A | A | C |
| 102 | A | A | A | C |
| 103 | A | A | A | C |
| 104 | A | A | A | C |
| 105 | A | A | A | C |
| 106 | B | A | A | C |
| 107 | A | A | B | D |
| 108 | A | A | A | C |
| 109 | A | A | A | D |
| 110 | A | A | A | B |
| 111 | D | C | C | D |
| 112 | B | A | A | C |
| 113 | C | B | C | D |
| 114 | C | A | C | D |
| 115 | A | A | C | D |
| 116 | A | ND | A | C |
| 117 | A | A | A | C |
| 118 | A | A | A | C |
| 119 | A | A | C | D |
| 120 | A | A | A | D |
| 121 | A | A | A | C |
| 122 | A | A | A | C |
| 123 | A | A | A | D |
| 124 | A | A | A | C |
| 125 | B | A | A | D |
| 126 | A | A | A | C |
| 127 | A | A | A | D |
| 128 | D | D | C | D |
| 129 | B | A | B | D |
| 130 | D | C | C | D |
| 131 | C | B | A | C |
| 132 | B | A | A | C |
| 133 | D | C | C | D |
| 134 | A | A | B | D |
| 135 | C | A | A | C |
| 136 | A | A | A | C |
| 137 | A | A | A | C |
| 138 | A | A | A | C |
| 139 | A | A | A | C |
| 140 | B | A | A | C |
| 141 | A | A | A | C |
| 142 | C | A | A | C |
| 143 | A | A | A | C |
| 144 | B | A | A | B |
| 145 | D | B | C | D |
| 146 | D | D | D | D |
| 147 | C | A | B | C |
| 148 | A | A | A | B |
| 149 | C | A | B | C |
| 150 | B | A | D | D |
| 151 | B | A | B | C |
| 152 | A | A | A | C |
| 153 | B | A | B | C |
| 154 | C | A | B | C |
| 155 | C | A | B | C |
| 156 | A | A | A | C |
| 157 | A | A | A | B |
| 158 | C | ND | C | D |
| 159 | D | ND | D | D |
| 160 | C | C | C | C |
| 161 | A | A | A | B |
| 162 | A | ND | A | C |
| 163 | B | A | A | B |
| 164 | C | C | B | D |
| 165 | A | A | A | C |
| 166 | A | ND | A | C |
| 167 | C | A | A | D |
| 168 | B | A | C | D |
| 169 | C | B | A | C |
| 170 | B | A | B | D |
| 171 | D | B | A | C |
| 172 | C | A | A | C |
| 173 | B | A | A | C |
| 174 | D | B | B | D |
| 175 | B | A | A | C |
| 176 | D | D | B | D |
| 177 | D | D | D | D |
| 178 | D | D | C | D |
| 179 | D | C | C | D |
| 180 | C | B | B | D |

TABLE 5-continued

Antibacterial Activity

| Cpd No | Gram Positive Bacterial Strains | | | Gram Negative Bacterial Strains |
|---|---|---|---|---|
| | S. aureus (ATCC 29213) | E. faecalis (ATCC 29212) | S. pyogenes (ATCC 51339) | H. influenzae (ATCC 49247) |
| 181 | B | A | A | C |
| 182 | C | ND | A | D |
| 183 | C | B | A | C |
| 184 | A | A | A | C |
| 185 | B | A | C | D |
| 186 | C | ND | A | C |
| 187 | C | ND | B | C |
| 188 | C | ND | C | D |
| 189 | A | ND | A | C |
| 190 | B | ND | B | D |
| 191 | C | ND | C | C |
| 192 | C | ND | C | C |
| 193 | C | ND | C | C |
| 194 | C | ND | C | C |
| 195 | C | ND | A | C |
| 196 | C | ND | C | C |
| 197 | C | ND | B | C |
| 198 | C | ND | C | C |
| 199 | C | ND | B | C |
| 200 | C | ND | C | C |
| 201 | C | ND | B | C |
| 202 | C | ND | C | B |
| 203 | C | ND | C | C |
| 204 | B | ND | B | C |
| 205 | B | ND | B | C |
| 206 | B | ND | A | C |
| 207 | B | ND | B | C |
| 208 | B | ND | C | C |
| 209 | B | ND | B | C |
| 210 | B | ND | A | C |
| 211 | B | ND | B | C |
| 212 | B | ND | A | C |
| 213 | B | ND | B | B |
| 214 | B | ND | B | C |
| 215 | A | ND | B | C |
| 216 | A | ND | C | C |
| 217 | A | ND | B | C |
| 218 | A | ND | A | C |
| 219 | A | ND | B | C |
| 220 | A | ND | A | C |
| 221 | A | ND | A | C |
| 222 | A | ND | A | B |
| 223 | A | ND | A | C |
| 224 | A | ND | A | C |
| 225 | A | ND | A | B |
| 226 | A | ND | A | B |
| 227 | C | ND | C | C |
| 228 | A | ND | A | C |
| 229 | A | ND | A | C |
| 230 | C | ND | C | D |
| 231 | D | ND | C | ND |
| 232 | C | ND | D | D |
| 233 | B | ND | B | D |
| 234 | D | ND | D | ND |

"A" activity ≤0.25 µg/mL;
"B" activity >0.25 µg/mL-1.0 µg/mL;
"C" activity >1.0 µg/mL-16 µg/mL;
"D" activity >16 µg/mL and
ND = not determined Pharmacokinetic Assays: Determination of PK Profile The pharmacokinetic profiles of compounds were determined by measuring the compound concentration in plasma by LC/MS/MS following a single intravenous or peroral administration of the compounds at a dose of 3 mg/kg. The concentrations described are the mean plasma concentrations at each time point from three animals. Intravenous dose formulation was administered as a single bolus dose through the tail vein. Oral dose formulation was administered to animals by an oral gavage needle. In both cases the dose volume was 5.0 mL/kg. Blood was collected from rats using a jugular vein catheter and from anesthetized mice through a capillary guided into the retro-orbital plexus. The collected blood was centrifuged to obtain plasma and the compounds extracted into methanol prior to determining the compound concentration by LC/MS/MS. The results for selected compounds of the invention are shown in FIGS. 2 to 8 where the X axis denotes time (hours) and the Y axis denotes plasma concentration (ng/mL). The $C_{max}$oral (µg/mL), $AUC_{iv}$ (µg·hr/mL), $AUC_{oral}$ (µg·hr/mL) and F(%) values are provided in the following table where $C_{max}$oral is the maximum oral concentration, AUC is area under the curve for intraveneous (IV) and oral and F (%) represents compound bioavailability as calculated by $[AUC_{oral}/AUC_{iv}] \times 100\%$.

TABLE 6

Maximum oral concentration ($C_{max}$) and compound bioavailability (F(%)) values for selected compounds against non-alpha substituted comparator compounds A and B in the rat and/or mouse assay.

| Cpd No. | Assay (mouse/rat) | $C_{max}$oral (µg/mL) | $AUC_{iv}$ (µg · hr/mL) | $AUC_{oral}$ (µg · hr/mL) | F (%) |
|---|---|---|---|---|---|
| A | Mouse | 0.07 | 0.9 | 0.08 | 8 |
| B | Mouse | 0.003 | 0.5 | 0.002 | 0.4 |
| 1 | Rat | 1.8 | 17.4 | 8.3 | 48 |
| 4 | Mouse | 1.7 | 7.6 | 2.5 | 33 |
| 4 | Rat | 0.6 | 6.6 | 2.1 | 31 |
| 21 | Rat | 0.4 | 7.1 | 1.0 | 14.3 |
| 88 | Mouse | 2 | 6.1 | 3.4 | 56 |
| 98 | Mouse | 6.1 | 14.3 | 12.5 | 87 |
| 98 | Rat | 3.5 | 27.7 | 22.2 | 80.4 |
| 103 | Rat | 5.7 | 29 | 22.2 | 76.5 |
| 136 | Mouse | 4.4 | 20 | 16.5 | 83 |
| 136 | Rat | 5.5 | 36.3 | 34.8 | 95.9 |
| 141 | Rat | 0.3 | 8.3 | 0.7 | 8.9 |
| 143 | Rat | 0.7 | 46.9 | 4.7 | 10 |
| 161 | Rat | 0.7 | 4.8 | 4.2 | 87 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

The invention claimed is:

1. A compound of the following general formula or salt thereof:

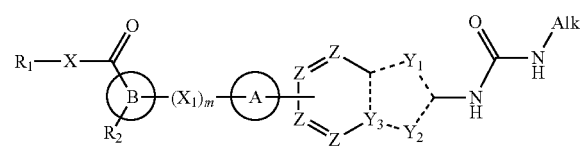

wherein
$R_1$ is selected from H, $C_{1-6}$alkyl, $C_{2-6}$alkenyl, $C_{2-6}$alkynyl, $S(O)_2OH$, $S(O)_2$—$C_{1-6}$alkyl, and M where M represents a monovalent or divalent cation;
$R_2$ is joined to the same ring B atom as the —C(=O)—X—$R_1$ moiety and is selected from $C_{1-6}$ alkyl, $C_{2-6}$ alkenyl, $C_{2-6}$ alkynyl, $(C_{1-6}$ alkyl)$_t C_{3-7}$ cycloalkyl, $(C_{1-6}$ alkyl)$_t$ aryl, $(C_{1-6}$alkyl)$_t$heterocyclyl, $(C_{1-6}$alkyl)$_t$heteroaryl, $NH_2$, $NH(C_{1-6}$alkyl), $N(C_{1-6}$alkyl)$_2$, CN, OH, $C_{1-6}$alkoxy, $SO_2H$, $SO_2C_{1-6}$alkyl, SH, $SC_{1-6}$alkyl, halo, halo$C_{1-6}$alkyl, —NH(C═O)O$C_{1-6}$alkyl, —NH(C═O)OC($C_{1-3}$alkyl)$_3$, and wherein $C_{1-3}$alkyl, $C_{1-6}$alkyl, $C_{2-6}$alkenyl, $C_{2-6}$alkynyl, $C_{3-7}$cycloalkyl, aryl and heterocyclyl in each case may be further optionally substituted, in particular, with one or more substituents selected from $NH_2$, $NH(C_{1-6}$alkyl), $N(C_{1-6}$alkyl)$_2$, CN, OH, $C_{1-6}$alkoxy, $SO_2H$, $SO_2C_{1-6}$alkyl, SH, $SC_{1-6}$alkyl and halo or $R_2$ is a chain of 3 or 4 carbon atoms or carbon and heteroatoms which joins with an adjacent B ring atom to form a fused carbocyclylic or heterocycylic ring which is optionally further substituted;

ring "A" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered-heterocyclyl, $C_{6-10}$aryl and 5-10 membered heteroaryl;

ring "B" is optionally substituted and is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-12 membered heterocyclyl, $C_{6-10}$aryl, 5-10 membered heteroaryl, and a Spiro bicyclic 8-12 membered heterocyclic ring system;

or ring "A" and ring "B" may join together to form a saturated or unsaturated fused bicyclic $C_{8-10}$cycloalkyl, a saturated or unsaturated fused bicyclic 8-10 membered heterocyclyl and a spiro bicyclic 8-12 membered heterocyclic ring system;

Each Z is independently selected from C—H, C—$C_{1-3}$ alkyl, C—OH, C—O$C_{1-3}$alkyl, C-halo, C-halo$C_{1-3}$ alkyl, C—CN, or C—$(X_2)_n R_3$ wherein $R_3$ is H, halo, OH, CN, $C_{1-6}$alkyl, $C_{1-6}$alkoxy, halo$C_{1-6}$alkyl, $C_{2-6}$alkenyl, $C_{2-6}$alkenyl, saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl wherein each $R_3$ may be optionally substituted; provided that one Z is C substituted with ring "A";

X is O, NH or $N(C_{1-6}$alkyl);

m, n and t are each independently an integer 0 or 1;

$X_1$ is a covalent bond, a spiro ring centre, or a fused ring bond when m is 0 or when m is 1 is selected from optionally substituted $C_{1-3}$alkylene, optionally substituted $C_{2-3}$alkenylene and optionally substituted $C_{2-3}$alkynylene and wherein each carbon atom in $C_{1-3}$alkylene may be optionally replaced by an oxygen or nitrogen heteroatom or C(═O);

$X_2$ is a covalent bond when n is 0 or when n is 1 is selected from optionally substituted $C_{1-4}$alkylene, optionally substituted $C_{2-3}$alkenylene and optionally substituted $C_{2-3}$alkynylene and wherein each carbon atom in $C_{1-3}$alkylene and $C_{2-3}$alkenylene may be optionally replaced by an oxygen or nitrogen heteroatom (wherein the nitrogen atom may be substituted with H or $C_{1-3}$alkyl) or C(═O);

$Y_1$ and $Y_2$ are each independently selected from C, N, O or S;

$Y_3$ is selected from C;

------indicates a double or a single bond as the case may be; and

Alk is $C_{1-6}$alkyl, $C_{2-6}$alkenyl, $C_{2-6}$alkynyl, $C_{3-6}$cycloalkyl.

2. A compound according to claim 1 of Formula I or a salt thereof

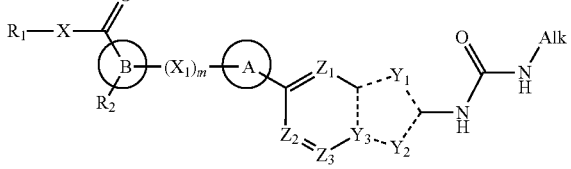

Formula I wherein $Z_1$, $Z_2$ and $Z_3$ are each independently selected from C—H, C—$C_{1-3}$alkyl, C—OH, C—O$C_{1-3}$alkyl, C-halo, C-halo$C_{1-3}$alkyl, C—CN, or C—$(X_2)_n$—$R_3$ wherein $R_3$ is H, halo, OH, CN, $C_{1-6}$alkyl, $C_{1-6}$alkoxy, halo$C_{1-6}$alkyl, $C_{2-6}$alkenyl, $C_{2-6}$alkenyl, saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered heterocyclyl, $C_{6-10}$aryl and 5-10 membered heteroaryl wherein each $R_3$ may be optionally substituted;

and wherein $R_1$, $R_2$, ring "A", ring "B", X, $Y_1$, $Y_2$, $Y_3$, m, ------ and Alk are as previously defined in claim 1.

3. A compound of claim 2 of Formula Ia or a salt thereof

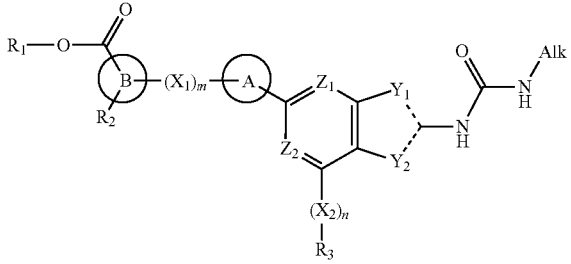

Formula Ia wherein $R_1$, $R_2$, $R_3$, $X_1$, $X_2$, $Z_1$, $Z_2$, $Y_1$, $Y_2$, ring A, ring B, Alk, m and n are as defined in claim 2.

4. A compound according to claim 3 of Formula Ia-(i) or a salt thereof

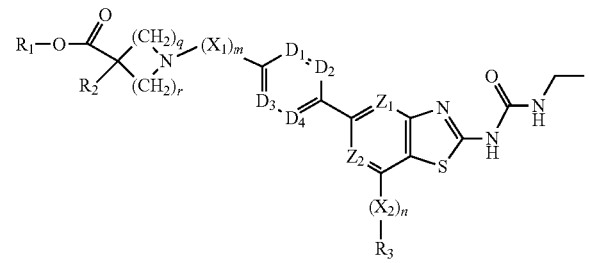

Formula Ia-(i)

wherein
- $D_1, D_2, D_3$ and $D_4$ are each independently selected from C—H, C—$C_{1-3}$alkyl, C—$C_{1-3}$alkoxy, C-halo and N;
- each —($CH_2$)— moiety is optionally substituted with one or more substituents independently selected from $C_{1-3}$alkyl, $C_{1-3}$alkoxy, halo, halo$C_{1-3}$alkoxy, halo$C_{1-3}$alkyl, OH and =O;
- q and r are each an integer independently selected from 0, 1, 2, 3, 4 and 5 provided that q and r together are at least 1 and no more than 6; and
- $R_1, R_2, R_3, X_1, X_2, Z_1, Z_2$, m and n are as defined in claim 2.

5. A compound according to claim 4 of formula Ia-(iv) and salts thereof

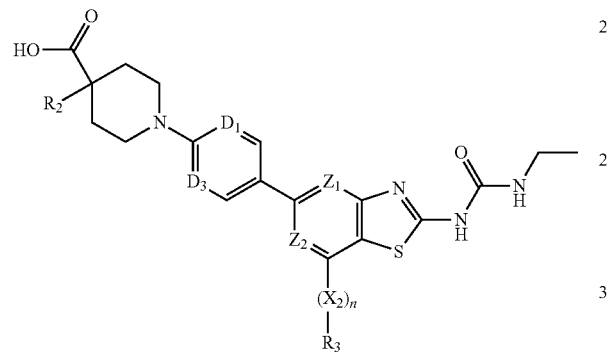

Formula Ia-(iv)

wherein $R_2, R_3, Z_1, Z_2, X_2$, n, $D_1$ and $D_2$ are as defined in claim 4.

6. A compound according to claim 3 of Formula Ia-(ii) or a salt thereof

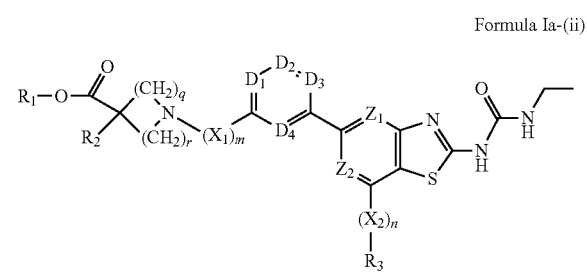

Formula Ia-(ii)

wherein
- $D_1, D_2, D_3$ and $D_4$ are each independently selected from C—H, C—$C_{1-3}$alkyl, $C_{1-3}$alkoxy, C-halo and N;
- each —($CH_2$)— moiety is optionally substituted with one or more substituents selected from $C_{1-3}$alkyl, $C_{1-3}$alkoxy, halo, halo$C_{1-3}$alkoxy, halo$C_{1-3}$alkyl, OH and =O;
- q and r are each an integer independently selected from 0, 1, 2, 3, 4 and 5 provided that q and r together are at least 1 and no more than 6; and
- $R_1, R_2, R_3, X_1, X_2, Z_1, Z_2$, m and n are as defined in claim 2.

7. A compound according to claim 3 of Formula Ia-(iii) and salts thereof

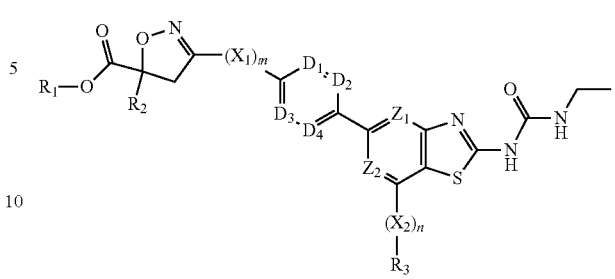

Formula Ia-(iii)

wherein
- $D_1, D_2, D_3$ and $D_4$ are each independently selected from C—H, C—$C_{1-3}$alkyl, $C_{1-3}$alkoxy, C-halo and N; and
- $R_1, R_2, R_3, X_1, X_2, Z_1, Z_2$, m and n are as defined in claim 2.

8. A compound according to claim 2 of Formula Ib and salts thereof

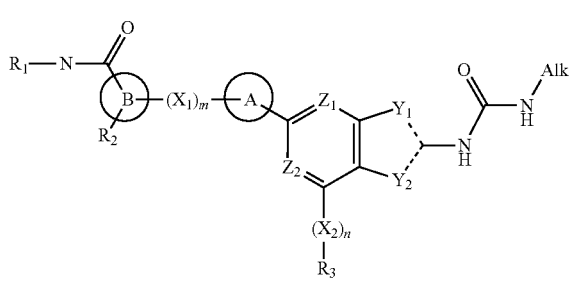

Formula Ib wherein $R_1, R_2, R_3, X_1, X_2, Z_1, Z_2, Y_1, Y_2$, ring A, ring B, Alk, m and n are as defined in claim 2.

9. A compound according to claim 1 or salt thereof selected from the group consisting of:
1) 1-[5-[2-(ethylcarbamoylamino)-7-(2-pyridyl)-1,3-benzothiazol-5-yl]pyrimidin-2-yl]-4-methyl-piperidine-4-carboxylic acid;
2) 1-[5-[2-(ethylcarbamoylamino)-7-(2-pyridyl)-1,3-benzothiazol-5-yl]pyrimidin-2-yl]-2-methyl-piperidine-2-carboxylic acid;
3) 1-[5-[2-(ethylcarbamoylamino)-7-(2-pyridyl)-1,3-benzothiazol-5-yl]pyrimidin-2-yl]-4-hydroxy-3-methyl-piperidine-3-carboxylic acid;
4) 1-[5-[2-(ethylcarbamoylamino)-7-(2-pyridyl)-1,3-benzothiazol-5-yl]-2-pyridyl]-4-methyl-piperidine-4-carboxylic acid;
5) 1-[5-[2-(ethylcarbamoylamino)-7-(2-pyridyl)-1,3-benzothiazol-5-yl]-3-methyl-2-pyridyl]-4-methyl-piperidine-4-carboxylic acid;
6) 1-[5-[2-(ethylcarbamoylamino)-7-(4-methyl-2-pyridyl)-1,3-benzothiazol-5-yl]pyrimidin-2-yl]-4-methyl-piperidine-4-carboxylic acid;
7) 1-[5-[7-(5,6-dimethoxy-2-pyridyl)-2-(ethylcarbamoylamino)-1,3-benzothiazol-5-yl]pyrimidin-2-yl]-4-methyl-piperidine-4-carboxylic acid;
8) 1-[5-[2-(ethylcarbamoylamino)-7-(4-methoxypyrimidin-2-yl)-1,3-benzothiazol-5-yl]pyrimidin-2-yl]-4-methyl-piperidine-4-carboxylic acid;
9) 1-[5-[2-(ethylcarbamoylamino)-7-(2-pyridyl)-1,3-benzothiazol-5-yl]pyrimidin-2-yl]-3,4-dimethyl-piperidine-4-carboxylic acid;

10) 1-[5-[2-(ethylcarbamoylamino)-7-(4-fluoro-2-pyridyl)-1,3-benzothiazol-5-yl]pyrimidin-2-yl]-4-methyl-piperidine-4-carboxylic acid;
11) 1-[5-[2-(ethylcarbamoylamino)-7-pyrazin-2-yl-1,3-benzothiazol-5-yl]pyrimidin-2-yl]-4-methyl-piperidine-4-carboxylic acid;
12) 1-[5-[2-(ethylcarbamoylamino)-7-(4-methylpyrimidin-2-yl)-1,3-benzothiazol-5-yl]pyrimidin-2-yl]-4-methyl-piperidine-4-carboxylic acid;
13) 1-[5-[7-(3-cyano-2-pyridyl)-2-(ethylcarbamoylamino)-1,3-benzothiazol-5-yl]pyrimidin-2-yl]-4-methyl-piperidine-4-carboxylic acid;
14) 1-[5-[7-(5-cyano-2-pyridyl)-2-(ethylcarbamoylamino)-1,3-benzothiazol-5-yl]pyrimidin-2-yl]-4-methyl-piperidine-4-carboxylic acid;
15) 1-[5-[2-(ethylcarbamoylamino)-7-(6-methoxypyrimidin-4-yl)-1,3-benzothiazol-5-yl]pyrimidin-2-yl]-4-methyl-piperidine-4-carboxylic acid;
16) 1-[5-[7-(4-cyano-2-pyridyl)-2-(ethylcarbamoylamino)-1,3-benzothiazol-5-yl]pyrimidin-2-yl]-4-methyl-piperidine-4-carboxylic acid;
17) 1-[5-[2-(ethylcarbamoylamino)-7-(4-methoxy-2-pyridyl)-1,3-benzothiazol-5-yl]pyrimidin-2-yl]-4-methyl-piperidine-4-carboxylic acid;
18) 1-[5-[2-(ethylcarbamoylamino)-7-(3-fluoro-2-pyridyl)-1,3-benzothiazol-5-yl]pyrimidin-2-yl]-4-methyl-piperidine-4-carboxylic acid;
19) 1-[5-[2-(ethylcarbamoylamino)-7-oxazol-2-yl-1,3-benzothiazol-5-yl]pyrimidin-2-yl]-4-methyl-piperidine-4-carboxylic acid;
20) 1-[5-[2-(ethylcarbamoylamino)-7-thiazol-5-yl-1,3-benzothiazol-5-yl]pyrimidin-2-yl]-4-methyl-piperidine-4-carboxylic acid;
21) 1-[5-[2-(ethylcarbamoylamino)-7-thiazol-4-yl-1,3-benzothiazol-5-yl]pyrimidin-2-yl]-4-methyl-piperidine-4-carboxylic acid;
22) 1-[5-[2-(ethylcarbamoylamino)-7-hex-1-ynyl-1,3-benzothiazol-5-yl]pyrimidin-2-yl]-4-methyl-piperidine-4-carboxylic acid;
23) 1-[5-[2-(ethylcarbamoylamino)-7-(2-methoxythiazol-4-yl)-1,3-benzothiazol-5-yl]pyrimidin-2-yl]-4-methyl-piperidine-4-carboxylic acid;
24) 1-[5-[2-(ethylcarbamoylamino)-7-(1-methylpyrazol-4-yl)-1,3-benzothiazol-5-yl]pyrimidin-2-yl]-4-methyl-piperidine-4-carboxylic acid;
25) 1-[5-[2-(ethylcarbamoylamino)-7-(1H-pyrazol-4-yl)-1,3-benzothiazol-5-yl]pyrimidin-2-yl]-4-methyl-piperidine-4-carboxylic acid;
26) 1-[5-[2-(ethylcarbamoylamino)-7-hydroxy-1,3-benzothiazol-5-yl]pyrimidin-2-yl]-4-methyl-piperidine-4-carboxylic acid;
27) 1-[5-[2-(ethylcarbamoylamino)-7-[4-(hydroxymethyl)thiazol-2-yl]-1,3-benzothiazol-5-yl]pyrimidin-2-yl]-4-methyl-piperidine-4-carboxylic acid;
28) 1-[5-[2-(ethylcarbamoylamino)-7-ethynyl-1,3-benzothiazol-5-yl]pyrimidin-2-yl]-4-methyl-piperidine-4-carboxylic acid;
29) 1-[5-[2-(ethylcarbamoylamino)-7-pyrazol-1-yl-1,3-benzothiazol-5-yl]pyrimidin-2-yl]-4-methyl-piperidine-4-carboxylic acid;
30) 1-[5-[2-(ethylcarbamoylamino)-7-(1-methylpyrrol-2-yl)-1,3-benzothiazol-5-yl]pyrimidin-2-yl]-4-methyl-piperidine-4-carboxylic acid;
31) 1-[5-[2-(ethylcarbamoylamino)-7-(5-methyl-2-pyridyl)-1,3-benzothiazol-5-yl]pyrimidin-2-yl]-4-methyl-piperidine-4-carboxylic acid;
32) 1-[5-[7-(6-cyano-2-pyridyl)-2-(ethylcarbamoylamino)-1,3-benzothiazol-5-yl]pyrimidin-2-yl]-4-methyl-piperidine-4-carboxylic acid;
33) 1-[5-[2-(ethylcarbamoylamino)-7-imidazol-1-yl-1,3-benzothiazol-5-yl]pyrimidin-2-yl]-4-methyl-piperidine-4-carboxylic acid;
34) 1-[5-[2-(ethylcarbamoylamino)-7-(5-fluoropyrimidin-2-yl)-1,3-benzothiazol-5-yl]pyrimidin-2-yl]-4-methyl-piperidine-4-carboxylic acid;
35) 1-[5-[2-(ethylcarbamoylamino)-7-[5-(trifluoromethyl)-2-pyridyl]-1,3-benzothiazol-5-yl]pyrimidin-2-yl]-4-methyl-piperidine-4-carboxylic acid;
36) 1-[5-[2-(ethylcarbamoylamino)-7-(2-pyridyl)-1,3-benzothiazol-5-yl]-3-fluoro-2-pyridyl]-4-methyl-piperidine-4-carboxylic acid;
37) 1-[5-[7-ethyl-2-(ethylcarbamoylamino)-1,3-benzothiazol-5-yl]pyrimidin-2-yl]-4-methyl-piperidine-4-carboxylic acid;
38) 1-[5-[2-(ethylcarbamoylamino)-7-methyl-1,3-benzothiazol-5-yl]pyrimidin-2-yl]-4-methyl-piperidine-4-carboxylic acid;
39) 1-[5-[7-cyclohexyl-2-(ethylcarbamoylamino)-1,3-benzothiazol-5-yl]pyrimidin-2-yl]-4-methyl-piperidine-4-carboxylic acid;
40) 1-[5-[2-(ethylcarbamoylamino)-7-(2-pyridyl)-1,3-benzothiazol-5-yl]pyrazin-2-yl]-4-methyl-piperidine-4-carboxylic acid;
41) 1-[5-[2-(ethylcarbamoylamino)-7-(1-phenyltriazol-4-yl)-1,3-benzothiazol-5-yl]pyrimidin-2-yl]-4-methyl-piperidine-4-carboxylic acid;
42) 1-[5-[2-(ethylcarbamoylamino)-7-(2-methoxypyrimidin-4-yl)-1,3-benzothiazol-5-yl]pyrimidin-2-yl]-4-methyl-piperidine-4-carboxylic acid;
43) 1-[5-[2-(ethylcarbamoylamino)-7-(2-methylpyrimidin-4-yl)-1,3-benzothiazol-5-yl]pyrimidin-2-yl]-4-methyl-piperidine-4-carboxylic acid;
44) 1-[5-[7-(2-cyanopyrimidin-4-yl)-2-(ethylcarbamoylamino)-1,3-benzothiazol-5-yl]pyrimidin-2-yl]-4-methyl-piperidine-4-carboxylic acid;
45) 1-[5-[2-(ethylcarbamoylamino)-7-(6-methylpyrimidin-4-yl)-1,3-benzothiazol-5-yl]pyrimidin-2-yl]-4-methyl-piperidine-4-carboxylic acid;
46) 1-[5-[2-(ethylcarbamoylamino)-1,3-benzothiazol-5-yl]pyrimidin-2-yl]-4-methyl-piperidine-4-carboxylic acid;
47) 1-[5-[2-(ethylcarbamoylamino)-7-tetrahydropyran-4-yl-1,3-benzothiazol-5-yl]pyrimidin-2-yl]-4-methyl-piperidine-4-carboxylic acid;
48) 1-[5-[2-(ethylcarbamoylamino)-7-(6-isopropoxypyrimidin-4-yl)-1,3-benzothiazol-5-yl]pyrimidin-2-yl]-4-methyl-piperidine-4-carboxylic acid;
49) 1-[5-[2-(ethylcarbamoylamino)-7-[6-(2-methoxyethoxy)-2-methyl-pyrimidin-4-yl]-1,3-benzothiazol-5-yl]pyrimidin-2-yl]-4-methyl-piperidine-4-carboxylic acid;
50) 1-[5-[2-(ethylcarbamoylamino)-7-(1-methyltriazol-4-yl)-1,3-benzothiazol-5-yl]pyrimidin-2-yl]-4-methyl-piperidine-4-carboxylic acid;
51) 1-[5-[2-(ethylcarbamoylamino)-7-(5-methoxypyrimidin-2-yl)-1,3-benzothiazol-5-yl]pyrimidin-2-yl]-4-methyl-piperidine-4-carboxylic acid;
52) 1-[5-[2-(ethylcarbamoylamino)-7-(6-methoxy-2-pyridyl)-1,3-benzothiazol-5-yl]pyrimidin-2-yl]-4-methyl-piperidine-4-carboxylic acid;
53) 1-[5-[2-(ethylcarbamoylamino)-7-(5-fluoro-6-methyl-2-pyridyl)-1,3-benzothiazol-5-yl]pyrimidin-2-yl]-4-methyl-piperidine-4-carboxylic acid;

54) 1-[5-[7-(3,5-difluoro-2-pyridyl)-2-(ethylcarbamoylamino)-1,3-benzothiazol-5-yl]pyrimidin-2-yl]-4-methyl-piperidine-4-carboxylic acid;
55) 1-[5-[2-(ethylcarbamoylamino)-7-(3-fluoro-4-methoxy-2-pyridyl)-1,3-benzothiazol-5-yl]pyrimidin-2-yl]-4-methyl-piperidine-4-carboxylic acid;
56) 1-[5-[2-(ethylcarbamoylamino)-7-(5-methoxypyrazin-2-yl)-1,3-benzothiazol-5-yl]pyrimidin-2-yl]-4-methyl-piperidine-4-carboxylic acid;
57) 1-[5-[2-(ethylcarbamoylamino)-7-(1-isopropyl-6-oxo-pyrimidin-4-yl)-1,3-benzothiazol-5-yl]pyrimidin-2-yl]-4-methyl-piperidine-4-carboxylic acid;
58) 1-[5-[7-(5-cyano-6-methyl-2-pyridyl)-2-(ethylcarbamoylamino)-1,3-benzothiazol-5-yl]pyrimidin-2-yl]-4-methyl-piperidine-4-carboxylic acid;
59) 1-[5-[2-(ethylcarbamoylamino)-7-(5-methylpyrimidin-2-yl)-1,3-benzothiazol-5-yl]pyrimidin-2-yl]-4-methyl-piperidine-4-carboxylic acid;
60) 1-[5-[2-(ethylcarbamoylamino)-7-(5-ethylpyrimidin-2-yl)-1,3-benzothiazol-5-yl]pyrimidin-2-yl]-4-methyl-piperidine-4-carboxylic acid;
61) 1-[5-[2-(ethylcarbamoylamino)-7-(3-methoxy-2-pyridyl)-1,3-benzothiazol-5-yl]pyrimidin-2-yl]-4-methyl-piperidine-4-carboxylic acid;
62) 1-[5-[7-(3-amino-6-methoxy-2-pyridyl)-2-(ethylcarbamoylamino)-1,3-benzothiazol-5-yl]pyrimidin-2-yl]-4-methyl-piperidine-4-carboxylic acid;
63) 1-[5-[7-(5-cyano-3-fluoro-2-pyridyl)-2-(ethylcarbamoylamino)-1,3-benzothiazol-5-yl]pyrimidin-2-yl]-4-methyl-piperidine-4-carboxylic acid;
64) 1-[5-[2-(ethylcarbamoylamino)-7-(3-methoxy-6-methyl-2-pyridyl)-1,3-benzothiazol-5-yl]pyrimidin-2-yl]-4-methyl-piperidine-4-carboxylic acid;
65) 1-[5-[7-(3-cyano-5-methyl-2-pyridyl)-2-(ethylcarbamoylamino)-1,3-benzothiazol-5-yl]pyrimidin-2-yl]-4-methyl-piperidine-4-carboxylic acid;
66) 1-[5-[2-(ethylcarbamoylamino)-7-(5-methylpyrazin-2-yl)-1,3-benzothiazol-5-yl]pyrimidin-2-yl]-4-methyl-piperidine-4-carboxylic acid;
67) 1-[5-[2-(ethylcarbamoylamino)-7-pyrimidin-4-yl-1,3-benzothiazol-5-yl]pyrimidin-2-yl]-4-methyl-piperidine-4-carboxylic acid;
68) 1-[5-[7-(4-ethoxy-2-pyridyl)-2-(ethylcarbamoylamino)-1,3-benzothiazol-5-yl]pyrimidin-2-yl]-4-methyl-piperidine-4-carboxylic acid;
69) 1-[5-[7-(5-cyano-3-methyl-2-pyridyl)-2-(ethylcarbamoylamino)-1,3-benzothiazol-5-yl]pyrimidin-2-yl]-4-methyl-piperidine-4-carboxylic acid;
70) 1-[5-[2-(ethylcarbamoylamino)-7-furo[3,2-c]pyridin-4-yl-1,3-benzothiazol-5-yl]pyrimidin-2-yl]-4-methyl-piperidine-4-carboxylic acid;
71) 1-[5-[7-[3-cyano-4-(dimethylamino)-2-pyridyl]-2-(ethylcarbamoylamino)-1,3-benzothiazol-5-yl]pyrimidin-2-yl]-4-methyl-piperidine-4-carboxylic acid;
72) 1-[5-[2-(ethylcarbamoylamino)-7-[(E)-methoxyiminomethyl]-1,3-benzothiazol-5-yl]pyrimidin-2-yl]-4-methyl-piperidine-4-carboxylic acid;
73) 1-[5-[7-(6-tert-butoxypyrazin-2-yl)-2-(ethylcarbamoylamino)-1,3-benzothiazol-5-yl]pyrimidin-2-yl]-4-methyl-piperidine-4-carboxylic acid;
74) 1-[5-[7-(1-acetyl-4-piperidyl)-2-(ethylcarbamoylamino)-1,3-benzothiazol-5-yl]pyrimidin-2-yl]-4-methyl-piperidine-4-carboxylic acid;
75) 1-[5-[7-[2-(dimethylamino)thiazol-5-yl]-2-(ethylcarbamoylamino)-1,3-benzothiazol-5-yl]pyrimidin-2-yl]-4-methyl-piperidine-4-carboxylic acid;
76) 1-[5-[2-(ethylcarbamoylamino)-7-(2-morpholinothiazol-5-yl)-1,3-benzothiazol-5-yl]pyrimidin-2-yl]-4-methyl-piperidine-4-carboxylic acid;
77) 1-[5-[2-(ethylcarbamoylamino)-7-(2-ethylthiazol-5-yl)-1,3-benzothiazol-5-yl]pyrimidin-2-yl]-4-methyl-piperidine-4-carboxylic acid;
78) 1-[5-[7-(2-ethoxythiazol-5-yl)-2-(ethylcarbamoylamino)-1,3-benzothiazol-5-yl]pyrimidin-2-yl]-4-methyl-piperidine-4-carboxylic acid;
79) 1-[5-[2-(ethylcarbamoylamino)-7-(1-methyl-2-oxo-4-pyridyl)-1,3-benzothiazol-5-yl]pyrimidin-2-yl]-4-methyl-piperidine-4-carboxylic acid;
80) 1-[5-[2-(ethylcarbamoylamino)-7-[1-(2-methoxyethyl)-6-oxo-pyrimidin-4-yl]-1,3-benzothiazol-5-yl]pyrimidin-2-yl]-4-methyl-piperidine-4-carboxylic acid;
81) 1-[5-[2-(ethylcarbamoylamino)-7-(6-methoxypyrazin-2-yl)-1,3-benzothiazol-5-yl]pyrimidin-2-yl]-4-methyl-piperidine-4-carboxylic acid;
82) 1-[5-[7-[5-(cyanomethyl)-2-pyridyl]-2-(ethylcarbamoylamino)-1,3-benzothiazol-5-yl]pyrimidin-2-yl]-4-methyl-piperidine-4-carboxylic acid;
83) 1-[5-[2-(ethylcarbamoylamino)-7-(5-ethylpyrazin-2-yl)-1,3-benzothiazol-5-yl]pyrimidin-2-yl]-4-methyl-piperidine-4-carboxylic acid
84) 1-[5-[2-(ethylcarbamoylamino)-7-(3-methylpyrazin-2-yl)-1,3-benzothiazol-5-yl]pyrimidin-2-yl]-4-methyl-piperidine-4-carboxylic acid;
85) 1-[5-[2-(ethylcarbamoylamino)-7-(5-fluoro-4-methyl-2-pyridyl)-1,3-benzothiazol-5-yl]pyrimidin-2-yl]-4-methyl-piperidine-4-carboxylic acid;
86) 1-[5-[2-(ethylcarbamoylamino)-7-(3-methoxypyrazin-2-yl)-1,3-benzothiazol-5-yl]pyrimidin-2-yl]-4-methyl-piperidine-4-carboxylic acid;
87) 1-[5-[7-cyclopropyl-2-(ethylcarbamoylamino)-1,3-benzothiazol-5-yl]pyrimidin-2-yl]-4-methyl-piperidine-4-carboxylic acid;
88) 1-[5-[2-(ethylcarbamoylamino)-7-[(E)-N-methoxy-C-methyl-carbonimidoyl]-1,3-benzothiazol-5-yl]pyrimidin-2-yl]-4-methyl-piperidine-4-carboxylic acid;
89) 1-[5-[2-(ethylcarbamoylamino)-7-(4-pyridyl)-1,3-benzothiazol-5-yl]pyrimidin-2-yl]-4-methyl-piperidine-4-carboxylic acid;
90) 1-[5-[7-(3-cyano-4-methoxy-2-pyridyl)-2-(ethylcarbamoylamino)-1,3-benzothiazol-5-yl]pyrimidin-2-yl]-4-methyl-piperidine-4-carboxylic acid;
91) 1-[5-[2-(ethylcarbamoylamino)-7-[ethyl(methyl)carbamoyl]-1,3-benzothiazol-5-yl]pyrimidin-2-yl]-4-methyl-piperidine-4-carboxylic acid;
92) 1-[5-[7-(5-cyano-4-methyl-2-pyridyl)-2-(ethylcarbamoylamino)-1,3-benzothiazol-5-yl]pyrimidin-2-yl]-4-methyl-piperidine-4-carboxylic acid;
93) 1-[5-[2-(ethylcarbamoylamino)-7-(3-fluoro-5-methyl-2-pyridyl)-1,3-benzothiazol-5-yl]pyrimidin-2-yl]-4-methyl-piperidine-4-carboxylic acid;
94) 1-[5-[2-(ethylcarbamoylamino)-7-[(E)-C-methyl-N-(2,2,2-trifluoroethoxyl)carbonimidoyl]-1,3-benzothiazol-5-yl]pyrimidin-2-yl]-4-methyl-piperidine-4-carboxylic acid;
95) 1-[5-[2-(ethylcarbamoylamino)-7-[(E)-N-hydroxy-C-methyl-carbonimidoyl]-1,3-benzothiazol-5-yl]pyrimidin-2-yl]-4-methyl-piperidine-4-carboxylic acid;
96) 1-[5-[7-[(E)-N-ethoxy-C-methyl-carbonimidoyl]-2-(ethylcarbamoylamino)-1,3-benzothiazol-5-yl]pyrimidin-2-yl]-4-methyl-piperidine-4-carboxylic acid;

97) 1-[5-[7-(ethylcarbamoyl)-2-(ethylcarbamoylamino)-1,3-benzothiazol-5-yl]pyrimidin-2-yl]-4-methyl-piperidine-4-carboxylic acid;
98) 4-ethyl-1-[5-[2-(ethylcarbamoylamino)-7-(2-pyridyl)-1,3-benzothiazol-5-yl]pyrimidin-2-yl]piperidine-4-carboxylic acid;
99) 4-ethyl-1-[5-[2-(ethylcarbamoylamino)-7-pyrazin-2-yl-1,3-benzothiazol-5-yl]pyrimidin-2-yl]piperidine-4-carboxylic acid;
100) 1-[5-[7-(4-cyano-2-pyridyl)-2-(ethylcarbamoylamino)-1,3-benzothiazol-5-yl]pyrimidin-2-yl]-4-ethyl-piperidine-4-carboxylic acid;
101) 4-ethyl-1-[5-[2-(ethylcarbamoylamino)-7-(4-methylpyrimidin-2-yl)-1,3-benzothiazol-5-yl]pyrimidin-2-yl]piperidine-4-carboxylic acid;
102) 4-ethyl-1-[5-[2-(ethylcarbamoylamino)-7-(4-methoxy-2-pyridyl)-1,3-benzothiazol-5-yl]pyrimidin-2-yl]piperidine-4-carboxylic acid;
103) 4-ethyl-1-[5-[2-(ethylcarbamoylamino)-7-(2-pyridyl)-1,3-benzothiazol-5-yl]-2-pyridyl]piperidine-4-carboxylic acid;
104) 1-[5-[7-(3-cyano-2-pyridyl)-2-(ethylcarbamoylamino)-1,3-benzothiazol-5-yl]pyrimidin-2-yl]-4-ethyl-piperidine-4-carboxylic acid;
105) 1-[5-[7-(5-cyano-2-pyridyl)-2-(ethylcarbamoylamino)-1,3-benzothiazol-5-yl]pyrimidin-2-yl]-4-ethyl-piperidine-4-carboxylic acid;
106) 4-ethyl-1-[5-[2-(ethylcarbamoylamino)-7-(7H-pyrrolo[2,3-d]pyrimidin-4-yl)-1,3-benzothiazol-5-yl]pyrimidin-2-yl]piperidine-4-carboxylic acid;
107) 1-[5-[7-bromo-2-(ethylcarbamoylamino)-1,3-benzothiazol-5-yl]pyrimidin-2-yl]-4-ethyl-piperidine-4-carboxylic acid;
108) 4-ethyl-1-[5-[2-(ethylcarbamoylamino)-7-(2-pyridyl)-1,3-benzothiazol-5-yl]pyrazin-2-yl]piperidine-4-carboxylic acid;
109) 4-ethyl-1-[5-[2-(ethylcarbamoylamino)-7-(4-methoxypyrimidin-2-yl)-1,3-benzothiazol-5-yl]pyrimidin-2-yl]piperidine-4-carboxylic acid;
110) 4-ethyl-1-[5-[2-(ethylcarbamoylamino)-7-(6-methoxypyrimidin-4-yl)-1,3-benzothiazol-5-yl]pyrimidin-2-yl]piperidine-4-carboxylic acid;
111) 4-ethyl-1-[5-[2-(ethylcarbamoylamino)-7-(6-oxo-1H-pyrimidin-4-yl)-1,3-benzothiazol-5-yl]pyrimidin-2-yl]piperidine-4-carboxylic acid;
112) 4-ethyl-1-[5-[2-(ethylcarbamoylamino)-7-(4-methylpyrimidin-2-yl)-1,3-benzothiazol-5-yl]pyrazin-2-yl]piperidine-4-carboxylic acid;
113) 4-ethyl-1-[5-[2-(ethylcarbamoylamino)-1,3-benzothiazol-5-yl]pyrimidin-2-yl]piperidine-4-carboxylic acid;
114) 4-ethyl-1-[5-[2-(ethylcarbamoylamino)-7-morpholino-1,3-benzothiazol-5-yl]pyrimidin-2-yl]piperidine-4-carboxylic acid;
115) 4-ethyl-1-[5-[2-(ethylcarbamoylamino)-7-(4-fluorophenyl)-1,3-benzothiazol-5-yl]pyrimidin-2-yl]piperidine-4-carboxylic acid;
116) 4-ethyl-1-[5-[2-(ethylcarbamoylamino)-7-[(E)-N-methoxy-C-methyl-carbonimidoyl]-1,3-benzothiazol-5-yl]pyrimidin-2-yl]piperidine-4-carboxylic acid;
117) 1-[5-[2-(ethylcarbamoylamino)-7-(2-pyridyl)-1,3-benzothiazol-5-yl]pyrimidin-2-yl]-4-propyl-piperidine-4-carboxylic acid;
118) 1-[5-[2-(ethylcarbamoylamino)-7-pyrazin-2-yl-1,3-benzothiazol-5-yl]pyrimidin-2-yl]-4-propyl-piperidine-4-carboxylic acid;
119) 1-[5-[7-bromo-2-(ethylcarbamoylamino)-1,3-benzothiazol-5-yl]pyrimidin-2-yl]-4-propyl-piperidine-4-carboxylic acid;
120) 1-[5-[2-(ethylcarbamoylamino)-7-(4-methylpyrimidin-2-yl)-1,3-benzothiazol-5-yl]pyrimidin-2-yl]-4-propyl-piperidine-4-carboxylic acid;
121) 1-[5-[2-(ethylcarbamoylamino)-7-(6-methoxypyrimidin-4-yl)-1,3-benzothiazol-5-yl]pyrimidin-2-yl]-4-propyl-piperidine-4-carboxylic acid;
122) 1-[5-[2-(ethylcarbamoylamino)-7-(4-methoxy-2-pyridyl)-1,3-benzothiazol-5-yl]pyrimidin-2-yl]-4-propyl-piperidine-4-carboxylic acid;
123) 1-[5-[7-(4-cyano-2-pyridyl)-2-(ethylcarbamoylamino)-1,3-benzothiazol-5-yl]pyrimidin-2-yl]-4-propyl-piperidine-4-carboxylic acid;
124) 1-[5-[7-(5-cyano-2-pyridyl)-2-(ethylcarbamoylamino)-1,3-benzothiazol-5-yl]pyrimidin-2-yl]-4-propyl-piperidine-4-carboxylic acid;
125) 1-[5-[2-(ethylcarbamoylamino)-7-(7H-pyrrolo[2,3-d]pyrimidin-4-yl)-1,3-benzothiazol-5-yl]pyrimidin-2-yl]-4-propyl-piperidine-4-carboxylic acid;
126) 1-[5-[7-(3-cyano-2-pyridyl)-2-(ethylcarbamoylamino)-1,3-benzothiazol-5-yl]pyrimidin-2-yl]-4-propyl-piperidine-4-carboxylic acid;
127) 1-[5-[2-(ethylcarbamoylamino)-7-(4-methoxypyrimidin-2-yl)-1,3-benzothiazol-5-yl]pyrimidin-2-yl]-4-propyl-piperidine-4-carboxylic acid;
128) 4-amino-1-[5-[2-(ethylcarbamoylamino)-7-(2-pyridyl)-1,3-benzothiazol-5-yl]pyrimidin-2-yl]piperidine-4-carboxylic acid;
129) 1-[5-[2-(ethylcarbamoylamino)-7-(2-pyridyl)-1,3-benzothiazol-5-yl]pyrimidin-2-yl]-4-phenyl-piperidine-4-carboxylic acid;
130) 4-cyano-1-[5-[2-(ethylcarbamoylamino)-7-(2-pyridyl)-1,3-benzothiazol-5-yl]pyrimidin-2-yl]piperidine-4-carboxylic acid;
131) 1-[5-[2-(ethylcarbamoylamino)-7-(2-pyridyl)-1,3-benzothiazol-5-yl]pyrimidin-2-yl]-4-hydroxy-piperidine-4-carboxylic acid;
132) 1-[5-[2-(ethylcarbamoylamino)-7-(2-pyridyl)-1,3-benzothiazol-5-yl]pyrimidin-2-yl]-4-methoxy-piperidine-4-carboxylic acid;
133) 1-[5-[2-(ethylcarbamoylamino)-7-(2-pyridyl)-1,3-benzothiazol-5-yl]pyrimidin-2-yl]-4-methylsulfonyl-piperidine-4-carboxylic acid;
134) 4-benzyl-1-[5-[2-(ethylcarbamoylamino)-7-(2-pyridyl)-1,3-benzothiazol-5-yl]pyrimidin-2-yl]piperidine-4-carboxylic acid;
135) 1-[5-[2-(ethylcarbamoylamino)-7-(2-pyridyl)-1,3-benzothiazol-5-yl]pyrimidin-2-yl]-4-fluoro-piperidine-4-carboxylic acid;
136) 4-allyl-1-[5-[2-(ethylcarbamoylamino)-7-(2-pyridyl)-1,3-benzothiazol-5-yl]pyrimidin-2-yl]piperidine-4-carboxylic acid;
137) 1-[5-[2-(ethylcarbamoylamino)-7-(2-pyridyl)-1,3-benzothiazol-5-yl]pyrimidin-2-yl]-4-isopropyl-piperidine-4-carboxylic acid;
138) 1-[5-[2-(ethylcarbamoylamino)-7-(2-pyridyl)-1,3-benzothiazol-5-yl]pyrimidin-2-yl]-4-methylsulfanyl-piperidine-4-carboxylic acid;
139) 4-allyl-1-[5-[2-(ethylcarbamoylamino)-7-pyrazin-2-yl-1,3-benzothiazol-5-yl]pyrimidin-2-yl]piperidine-4-carboxylic acid;
140) 1-[5-[2-(ethylcarbamoylamino)-7-(2-pyridyl)-1,3-benzothiazol-5-yl]pyrimidin-2-yl]-4-(2,2,2-trifluoroethyl)piperidine-4-carboxylic acid;

141) 1-[5-[2-(ethylcarbamoylamino)-7-(2-pyridyl)-1,3-benzothiazol-5-yl]pyrimidin-2-yl]-4-(methoxymethyl)piperidine-4-carboxylic acid;
142) 1-[5-[2-(ethylcarbamoylamino)-7-(2-pyridyl)-1,3-benzothiazol-5-yl]pyrimidin-2-yl]-4-(trifluoromethyl)piperidine-4-carboxylic acid;
143) 4-cyclopropyl-1-[5-[2-(ethylcarbamoylamino)-7-(2-pyridyl)-1,3-benzothiazol-5-yl]pyrimidin-2-yl]piperidine-4-carboxylic acid;
144) 1-[5-[2-(ethylcarbamoylamino)-7-[2-(3-methylimidazol-4-yl)ethynyl]-1,3-benzothiazol-5-yl]pyrimidin-2-yl]-4-methyl-piperidine-4-carboxylic acid;
145) 1-[5-[2-(ethylcarbamoylamino)-7-(thiazol-2-ylcarbamoyl)-1,3-benzothiazol-5-yl]pyrimidin-2-yl]-4-methyl-piperidine-4-carboxylic acid;
146) 1-[5-[2-(ethylcarbamoylamino)-7-(pyrimidine-2-carbonylamino)-1,3-benzothiazol-5-yl]pyrimidin-2-yl]-4-methyl-piperidine-4-carboxylic acid;
147) 1-[5-[2-(ethylcarbamoylamino)-7-[[methyl(pyrimidin-2-yl)amino]methyl]-1,3-benzothiazol-5-yl]pyrimidin-2-yl]-4-methyl-piperidine-4-carboxylic acid;
148) 1-[5-[2-(ethylcarbamoylamino)-7-[2-(3-pyridyl)ethynyl]-1,3-benzothiazol-5-yl]pyrimidin-2-yl]-4-methyl-piperidine-4-carboxylic acid;
149) 1-[5-[2-(ethylcarbamoylamino)-7-(pyridine-2-carbonylamino)-1,3-benzothiazol-5-yl]pyrimidin-2-yl]-4-methyl-piperidine-4-carboxylic acid;
150) 1-[5-[7-(2-cyclopentylethynyl)-2-(ethylcarbamoylamino)-1,3-benzothiazol-5-yl]pyrimidin-2-yl]-4-methyl-piperidine-4-carboxylic acid;
151) 1-[5-[2-(ethylcarbamoylamino)-7-[2-(4-pyridyl)ethynyl]-1,3-benzothiazol-5-yl]pyrimidin-2-yl]-4-methyl-piperidine-4-carboxylic acid;
152) 1-[5-[2-(ethylcarbamoylamino)-7-[2-(6-methoxy-2-pyridyl)ethynyl]-1,3-benzothiazol-5-yl]pyrimidin-2-yl]-4-methyl-piperidine-4-carboxylic acid;
153) 1-[5-[2-(ethylcarbamoylamino)-7-[2-(5-methyl-1,3,4-thiadiazol-2-yl)ethynyl]-1,3-benzothiazol-5-yl]pyrimidin-2-yl]-4-methyl-piperidine-4-carboxylic acid;
154) 1-[5-[2-(ethylcarbamoylamino)-7-(2-pyrimidin-2-ylethynyl)-1,3-benzothiazol-5-yl]pyrimidin-2-yl]-4-methyl-piperidine-4-carboxylic acid;
155) 1-[5-[2-(ethylcarbamoylamino)-7-(2-pyrimidin-4-ylethynyl)-1,3-benzothiazol-5-yl]pyrimidin-2-yl]-4-methyl-piperidine-4-carboxylic acid;
156) 1-[5-[2-(ethylcarbamoylamino)-7-(2-thiazol-2-ylethynyl)-1,3-benzothiazol-5-yl]pyrimidin-2-yl]-4-methyl-piperidine-4-carboxylic acid;
157) 1-[5-[2-(ethylcarbamoylamino)-7-(2-pyrazin-2-ylethynyl)-1,3-benzothiazol-5-yl]pyrimidin-2-yl]-4-methyl-piperidine-4-carboxylic acid;
158) 1-[5-[2-(ethylcarbamoylamino)-7-(morpholinomethyl)-1,3-benzothiazol-5-yl]pyrimidin-2-yl]-4-methyl-piperidine-4-carboxylic acid;
159) 1-[5-[2-(ethylcarbamoylamino)-7-(morpholine-4-carbonyl)-1,3-benzothiazol-5-yl]pyrimidin-2-yl]-4-methyl-piperidine-4-carboxylic acid;
160) 1-[[5-[2-(ethylcarbamoylamino)-7-(2-pyridyl)-1,3-benzothiazol-5-yl]pyrimidin-2-yl]methyl]-4-methyl-piperidine-4-carboxylic acid;
161) 1-[5-[2-(ethylcarbamoylamino)-4-fluoro-7-(2-pyridyl)-1,3-benzothiazol-5-yl]pyrimidin-2-yl]-4-methyl-piperidine-4-carboxylic acid;
163) 1-[5-[2-(ethylcarbamoylamino)-7-(2-pyridyl)-1,3-benzothiazol-5-yl]pyrimidin-2-yl]-2-methyl-pyrrolidine-2-carboxylic acid;
164) 1-[5-[2-(ethylcarbamoylamino)-7-(2-pyridyl)-1,3-benzothiazol-5-yl]pyrimidin-2-yl]-3-(trifluoromethyl)pyrrolidine-3-carboxylic acid;
165) 2-[5-[2-(ethylcarbamoylamino)-7-(2-pyridyl)-1,3-benzothiazol-5-yl]pyrimidin-2-yl]-1,3,4,5,6,6a-hexahydrocyclopenta[c]pyrrole-3a-carboxylic acid;
166) 1-[5-[2-(ethylcarbamoylamino)-7-(2-pyridyl)-1,3-benzothiazol-5-yl]pyrimidin-2-yl]-4-methyl-azepane-4-carboxylic acid;
167) methyl 4-(tert-butoxycarbonylamino)-1-[5-[2-(ethylcarbamoylamino)-7-(2-pyridyl)-1,3-benzothiazol-5-yl]pyrimidin-2-yl]piperidine-4-carboxylate;
168) methyl 4-amino-1-[5-[2-(ethylcarbamoylamino)-7-(2-pyridyl)-1,3-benzothiazol-5-yl]pyrimidin-2-yl]piperidine-4-carboxylate;
169) methyl 1-[5-[2-(ethylcarbamoylamino)-7-(2-pyridyl)-1,3-benzothiazol-5-yl]pyrimidin-2-yl]-4-methyl-piperidine-4-carboxylate;
170) methyl 1-[5-[2-(ethylcarbamoylamino)-7-(2-pyridyl)-1,3-benzothiazol-5-yl]pyrimidin-2-yl]-3-methyl-4-oxo-piperidine-3-carboxylate;
171) ethyl 1-[5-[2-(ethylcarbamoylamino)-7-(2-pyridyl)-1,3-benzothiazol-5-yl]pyrimidin-2-yl]-4-methyl-piperidine-4-carboxylate;
172) methyl 1-[5-[2-(ethylcarbamoylamino)-7-(2-pyridyl)-1,3-benzothiazol-5-yl]pyrimidin-2-yl]-4-hydroxy-3-methyl-piperidine-3-carboxylate;
173) methyl 1-[5-[2-(ethylcarbamoylamino)-7-(2-pyridyl)-1,3-benzothiazol-5-yl]pyrimidin-2-yl]-4-hydroxy-piperidine-4-carboxylate;
174) ethyl 4-cyano-1-[5-[2-(ethylcarbamoylamino)-7-(2-pyridyl)-1,3-benzothiazol-5-yl]pyrimidin-2-yl]piperidine-4-carboxylate;
175) methyl 1-[5-[2-(ethylcarbamoylamino)-7-(2-pyridyl)-1,3-benzothiazol-5-yl]pyrimidin-2-yl]-4-methoxy-piperidine-4-carboxylate;
176) ethyl 1-[5-[2-(ethylcarbamoylamino)-7-(2-pyridyl)-1,3-benzothiazol-5-yl]pyrimidin-2-yl]-4-methylsulfonyl-piperidine-4-carboxylate;
177) ethyl 4-benzyl-1-[5-[2-(ethylcarbamoylamino)-7-(2-pyridyl)-1,3-benzothiazol-5-yl]pyrimidin-2-yl]piperidine-4-carboxylate;
178) ethyl 1-[5-[2-(ethylcarbamoylamino)-7-tetrahydropyran-4-yl-1,3-benzothiazol-5-yl]pyrimidin-2-yl]-4-methyl-piperidine-4-carboxylate;
179) ethyl 1-[5-[7-(1-acetyl-4-piperidyl)-2-(ethylcarbamoylamino)-1,3-benzothiazol-5-yl]pyrimidin-2-yl]-4-methyl-piperidine-4-carboxylate;
180) methyl 1-[5-[2-(ethylcarbamoylamino)-7-(2-pyridyl)-1,3-benzothiazol-5-yl]pyrimidin-2-yl]-3-(trifluoromethyl)pyrrolidine-3-carboxylate;
181) 1-[5-[2-(ethylcarbamoylamino)-7-(2-pyridyl)-1,3-benzothiazol-5-yl]-3-pyridyl]-4-methyl-piperidine-4-carboxylic acid;
182) 1-[4-[2-(ethylcarbamoylamino)-7-(2-pyridyl)-1,3-benzothiazol-5-yl]-2-pyridyl]-4-methyl-piperidine-4-carboxylic acid;
183) 3-[5-[2-(ethylcarbamoylamino)-7-(2-pyridyl)-1,3-benzothiazol-5-yl]-2-pyridyl]-5-methyl-4H-isoxazole-5-carboxylic acid;
184) ethyl 3-[5-[2-(ethylcarbamoylamino)-7-(2-pyridyl)-1,3-benzothiazol-5-yl]-2-pyridyl]-5-methyl-4H-isoxazole-5-carboxylate;
185) 1-[5-[2-(ethylcarbamoylamino)-7-(2-pyridyl)-1,3-benzothiazol-5-yl]pyrimidin-2-yl]-4-phenyl-piperidine-4-carboxamide;

186) 1-[5-[2-(ethylcarbamoylamino)-7-(2-pyridyl)-1,3-benzothiazol-5-yl]pyrimidin-2-yl]-4-methyl-N-methylsulfonyl-piperidine-4-carboxamide;
187) 1-[5-[2-(ethylcarbamoylamino)-7-[(E)-N-(2-hydroxyethoxy)-C-methyl-carbonimidoyl]-1,3-benzothiazol-5-yl]pyrimidin-2-yl]-4-methyl-piperidine-4-carboxylic acid;
188) 1-[5-[2-(ethylcarbamoylamino)-7-[(E)-N-(2-methoxyethoxy)-C-methyl-carbonimidoyl]-1,3-benzothiazol-5-yl]pyrimidin-2-yl]-4-methyl-piperidine-4-carboxylic acid;
189) 4-ethyl-1-[5-[2-(ethylcarbamoylamino)-7-[(E)-methoxyiminomethyl]-1,3-benzothiazol-5-yl]pyrimidin-2-yl]piperidine-4-carboxylic acid;
190) 7-[2-(ethylcarbamoylamino)-7-(2-pyridyl)-1,3-benzothiazol-5-yl]-2-methyl-3-oxo-4H-pyrido[3,2-b][1,4]oxazine-2-carboxylic acid;
191) ethyl 1-[5-[2-(ethylcarbamoylamino)-6-methoxy-1,3-benzothiazol-5-yl]pyrimidin-2-yl]-4-methyl-piperidine-4-carboxylate
192) 1-[5-[2-(ethylcarbamoylamino)-7-(2-pyridyl)-1,3-benzothiazol-5-yl]pyrimidine-2-carbonyl]-4-methyl-piperidine-4-carboxylic acid
193) 1-[5-[7-carbamoyl-2-(ethylcarbamoylamino)-1,3-benzothiazol-5-yl]pyrimidin-2-yl]-4-ethyl-piperidine-4-carboxylic acid
194) 1-[5-[2-(ethylcarbamoylamino)-7-(2-methoxyethoxymethyl)-1,3-benzothiazol-5-yl]pyrimidin-2-yl]-4-methyl-piperidine-4-carboxylic acid
195) 1-[5-[2-(ethylcarbamoylamino)-7-(2-pyridyl)-1,3-benzothiazol-5-yl]pyridazin-3-yl]-4-methyl-piperidine-4-carboxylic acid
196) 5-[[5-[2-(ethylcarbamoylamino)-7-(2-pyridyl)-1,3-benzothiazol-5-yl]pyrimidin-2-yl]amino]-2-methyl-1,3-dioxane-2-carboxylic acid
197) 1-[5-[7-(4,5-dihydroisoxazol-3-yl)-2-(ethylcarbamoylamino)-1,3-benzothiazol-5-yl]pyrimidin-2-yl]-4-ethyl-piperidine-4-carboxylic acid
198) 1-[5-[2-(ethylcarbamoylamino)-6-methoxy-1,3-benzothiazol-5-yl]pyrimidin-2-yl]-4-methyl-piperidine-4-carboxylic acid
199) 4-ethyl-1-[5-[2-(ethylcarbamoylamino)-7-formyl-1,3-benzothiazol-5-yl]pyrimidin-2-yl]piperidine-4-carboxylic acid
200) 1-[5-[2-(ethylcarbamoylamino)-7-methoxy-1,3-benzothiazol-5-yl]pyrimidin-2-yl]-4-methyl-piperidine-4-carboxylic acid
201) 1-[5-[2-(ethylcarbamoylamino)-7-(2-pyridyl)-1,3-benzothiazol-5-yl]pyrimidin-2-yl]-3-methyl-pyrrolidine-3-carboxylic acid
202) 1-[5-[2-(ethylcarbamoylamino)-7-(methoxymethyl)-1,3-benzothiazol-5-yl]pyrimidin-2-yl]-4-methyl-piperidine-4-carboxylic acid
203) 4-ethyl-1-[5-[2-(ethylcarbamoylamino)-7-(methoxymethyl)-1,3-benzothiazol-5-yl]pyrimidin-2-yl]piperidine-4-carboxylic acid
204) 1-[5-[7-[(E)-ethoxyiminomethyl]-2-(ethylcarbamoylamino)-1,3-benzothiazol-5-yl]pyrimidin-2-yl]-4-methyl-piperidine-4-carboxylic acid
205) 1-[5-[2-(ethylcarbamoylamino)-7-[5-(morpholinomethyl)-2-pyridyl]-1,3-benzothiazol-5-yl]pyrimidin-2-yl]-4-methyl-piperidine-4-carboxylic acid
206) 3-ethyl-1-[5-[2-(ethylcarbamoylamino)-7-(2-pyridyl)-1,3-benzothiazol-5-yl]pyrimidin-2-yl]pyrrolidine-3-carboxylic acid
207) 4-ethyl-1-[5-[2-(ethylcarbamoylamino)-7-propanoyl-1,3-benzothiazol-5-yl]pyrimidin-2-yl]piperidine-4-carboxylic acid
208) 1-[5-[7-bromo-2-(ethylcarbamoylamino)-6-methoxy-1,3-benzothiazol-5-yl]pyrimidin-2-yl]-4-methyl-piperidine-4-carboxylic acid
209) 4-ethyl-1-[4-[2-(ethylcarbamoylamino)-7-(2-pyridyl)-1,3-benzothiazol-5-yl]thiazol-2-yl]piperidine-4-carboxylic acid
211) 4-ethyl-1-[5-[2-(ethylcarbamoylamino)-7-[(Z)—C-ethyl-N-methoxy-carbonimidoyl]-1,3-benzothiazol-5-yl]pyrimidin-2-yl]piperidine-4-carboxylic acid
212) 4-ethoxy-1-[5-[2-(ethylcarbamoylamino)-7-(2-pyridyl)-1,3-benzothiazol-5-yl]pyrimidin-2-yl]piperidine-4-carboxylic acid
213) 1-[5-[2-(ethylcarbamoylamino)-7-(5-methyl-1,2,4-oxadiazol-3-yl)-1,3-benzothiazol-5-yl]pyrimidin-2-yl]-4-methyl-piperidine-4-carboxylic acid
214) 1-[5-[2-(ethylcarbamoylamino)-7-(2-pyridyl)-1,3-benzothiazol-5-yl]-4-methyl-pyrimidin-2-yl]-4-methyl-piperidine-4-carboxylic acid
215) 1-[5-[7-bromo-2-(ethylcarbamoylamino)-1,3-benzothiazol-5-yl]pyrimidin-2-yl]-4-methyl-piperidine-4-carboxylic acid
216) ethyl 5-[[5-[2-(ethylcarbamoylamino)-7-(2-pyridyl)-1,3-benzothiazol-5-yl]pyrimidin-2-yl]amino]-2-methyl-1,3-dioxane-2-carboxylate
217) 1-[5-[7-[5-[(4,4-difluoro-1-piperidyl)methyl]-2-pyridyl]-2-(ethylcarbamoylamino)-1,3-benzothiazol-5-yl]pyrimidin-2-yl]-4-methyl-piperidine-4-carboxylic acid
218) 4-[[5-[2-(ethylcarbamoylamino)-7-(2-pyridyl)-1,3-benzothiazol-5-yl]pyrimidin-2-yl]-methyl-amino]-1-methyl-cyclohexanecarboxylic acid
219) 2-ethyl-7-[5-[2-(ethylcarbamoylamino)-7-(2-pyridyl)-1,3-benzothiazol-5-yl]pyrimidin-2-yl]-7-azaspiro[3.5]nonane-2-carboxylic acid
220) 1-[5-[2-(ethylcarbamoylamino)-7-(2-pyridyl)-1,3-benzothiazol-5-yl]-4-methoxy-pyrimidin-2-yl]-4-methyl-piperidine-4-carboxylic acid
221) 4-Ethyl-1-[5-[2-(ethylcarbamoylamino)-7-(2-pyridyl)-1,3-benzothiazol-5-yl]thiazol-2-yl]piperidine-4-carboxylic acid
222) 4-[[5-[2-(ethylcarbamoylamino)-7-(2-pyridyl)-1,3-benzothiazol-5-yl]pyrimidin-2-yl]amino]-1-methyl-cyclohexanecarboxylic acid
223) 4-ethyl-1-[5-[2-(ethylcarbamoylamino)-7-(C-ethyl-N-methoxy-carbonimidoyl)-1,3-benzothiazol-5-yl]pyrimidin-2-yl]piperidine-4-carboxylic acid
224) 4-ethyl-1-[5-[2-(ethylcarbamoylamino)-7-[(E)-C-ethyl-N-methoxy-carbonimidoyl]-1,3-benzothiazol-5-yl]pyrimidin-2-yl]piperidine-4-carboxylic acid
225) 4-ethyl-1-[5-[2-(ethylcarbamoylamino)-7-[(Z)-methoxyiminomethyl]-1,3-benzothiazol-5-yl]pyrimidin-2-yl]piperidine-4-carboxylic acid
226) 4-ethyl-1-[5-[2-(ethylcarbamoylamino)-7-(5-methylpyrimidin-2-yl)-1,3-benzothiazol-5-yl]pyrimidin-2-yl]piperidine-4-carboxylic acid
228) 4-ethyl-1-[5-[2-(ethylcarbamoylamino)-7-pyrimidin-2-yl-1,3-benzothiazol-5-yl]pyrimidin-2-yl]piperidine-4-carboxylic acid
229) 4-ethyl-1-[5-[2-(ethylcarbamoylamino)-7-(2-pyridyl)-1H-benzimidazol-5-yl]pyrimidin-2-yl]piperidine-4-carboxylic acid
232) 4-ethyl-1-(3-{2-[(ethylcarbamoyl)amino]-7-(pyridin-2-yl)-1,3-benzothiazol-5-yl}-1,2,4-thiadiazol-5-yl)piperidine-4-carboxylic acid 233) 1-(5-{2-[(ethylcarbamoyl)amino]-7-(pyridin-2-yl)-1,3-benzothiazol-5-yl}-1,2,4-thiadiazol-3-yl)-4-methylpiperidine-4-carboxylic acid; and 234) Diethyl 1,1'-({2-[(ethylcarbamoyl)amino]-1,3-benzoxazole-5,7-diyl}dipyrimidine-5,2-diyl)bis(4-ethylpiperidine-4-carboxylate).

10. A compound according to claim 1 or a pharmaceutically acceptable salt thereof for use in the treatment of a bacterial infection.

11. A compound according to claim 1 or a pharmaceutically acceptable salt thereof for use as a gyrase inhibitor.

12. An antibacterial agent comprising a compound according to claim 1 or a pharmaceutically acceptable salt thereof.

13. A composition comprising a compound according to claim 1 or a salt thereof.

14. A process for the manufacture of a compound of Formula I according to claim 2 comprising the step of coupling an intermediate of Formula IIa with an L-$(X_2)_n$—$R_3$ precursor moiety;

Formula IIa

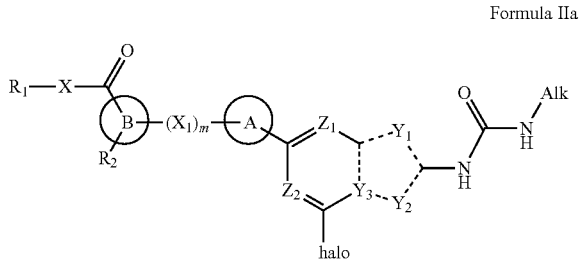

or alternatively comprising the step of coupling an intermediate of Formula IIb

Formula IIb

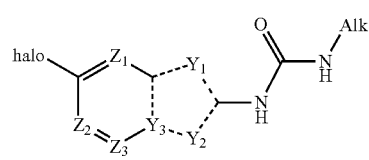

with a precursor moiety of general formula

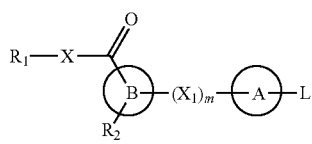

to form a compound of Formula I;
wherein $R_1$, X, $R_2$, $(X_1)_m$, ring A, ring B, $Z_1$, $Z_2$, $Y_1$, $Y_2$, Alk, $(X_2)_n$ and $R_3$ are as defined in claim 2 and L is a suitable reactive group.

15. A process for the manufacture of a compound of Formula I according to claim 2 comprising the step of coupling a precursor of Formula IIIa with a boronic acid intermediate of Formula IVa Formula IIIa

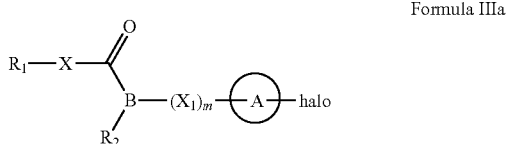

Formula IVa

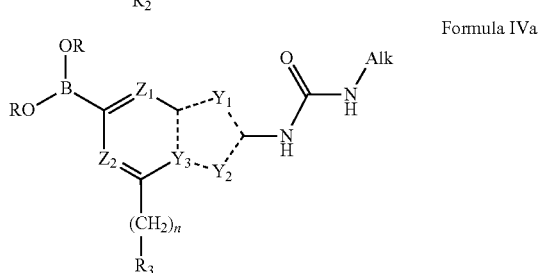

or alternatively comprising the step of coupling a boronic acid intermediate of Formula IVb with a halo-$(X_2)_n$—$R_3$ precursor moiety Formula IVb

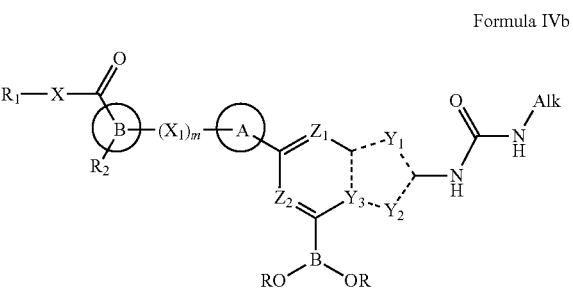

to form a compound of Formula I;
wherein $R_1$, X, $R_2$, $(X_1)_m$, ring A, ring B, $Z_1$, $Z_2$, $Y_1$, $Y_2$, Alk, $(X_2)_n$ and $R_3$ are as defined in claim 2 and $B(OR)_2$ is a boronic acid $(B(OH)_2)$ or a pinacolborane.

16. A method for the treatment of a bacterial infection comprising administration of a compound according to claim 1 or a pharmaceutically acceptable salt thereof to a subject suffering from said infection, wherein the bacterial infection is caused by (i) a Gram positive bacteria selected from the group consisting of *Staphylococci, Enterococci*, and *Streptococci*, or (ii) a Gram negative bacteria selected from the group *Haemophili*.

17. A method of treating bacterial contamination of a substrate comprising applying to the site of such contamination an amount of a compound according claim 1 or pharmaceutically acceptable salt thereof sufficient to inhibit bacterial growth, wherein the bacterial infection is caused by (i) a Gram positive bacteria selected from the group consisting of *Staphylococci, Enterococci*, and *Streptococci*, or (ii) a Gram negative bacteria selected from the group Haemophili.

* * * * *